`US006759536B2`

(12) United States Patent
Reeves et al.

(10) Patent No.: US 6,759,536 B2
(45) Date of Patent: Jul. 6, 2004

(54) POLYNUCLEOTIDES ENCODING THE FKBA GENE OF THE FK-520 POLYKETIDE SYNTHASE GENE CLUSTER

(75) Inventors: Christopher Reeves, Orinda, CA (US); Daniel Chu, Santa Clara, CA (US); Chaitan Khosla, Palo Alto, CA (US); Daniel Santi, San Francisco, CA (US); Kai Wu, Foster City, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 226 days.

(21) Appl. No.: 09/940,316

(22) Filed: Aug. 27, 2001

(65) Prior Publication Data

US 2003/0175901 A1 Sep. 18, 2003

Related U.S. Application Data

(62) Division of application No. 09/410,551, filed on Oct. 1, 1999, now Pat. No. 6,503,737.
(60) Provisional application No. 60/139,650, filed on Jun. 17, 1999, provisional application No. 60/123,810, filed on Mar. 11, 1999, and provisional application No. 60/102,748, filed on Oct. 2, 1998.

(51) Int. Cl.$^7$ .......................................... C07D 221/18
(52) U.S. Cl. ......................................................... 546/71
(58) Field of Search ................................... 546/71, 115

(56) References Cited

U.S. PATENT DOCUMENTS

| | | | |
|---|---|---|---|
| 4,874,748 A | 10/1989 | Katz et al. | 514/29 |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,189,042 A | 2/1993 | Goulet et al. | 514/291 |
| 5,672,491 A | 9/1997 | Khosla et al. | 435/148 |
| 5,712,146 A | 1/1998 | Khosla et al. | 435/252.35 |
| 5,824,513 A | 10/1998 | Katz et al. | 435/76 |
| 5,830,750 A | 11/1998 | Khosla et al. | |
| 5,843,718 A | 12/1998 | Khosla et al. | |
| 5,962,290 A | 10/1999 | Khosla et al. | |
| 5,968,921 A | 10/1999 | Gold | 514/183 |
| 6,022,731 A | 2/2000 | Khosla et al. | |
| 6,077,696 A | 6/2000 | Khosla et al. | |
| 6,150,513 A | 11/2000 | Wu | 536/23.2 |
| 6,210,974 B1 | 4/2001 | Gold | 436/501 |

FOREIGN PATENT DOCUMENTS

| | | |
|---|---|---|
| EP | 0 184 162 * | 6/1986 |
| EP | 0323042 A | 7/1989 |
| EP | 0356399 A | 2/1990 |
| EP | 0463690 A | 1/1992 |
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 98/27203 | 6/1998 |
| WO | WO 98/49315 | 11/1998 |
| WO | WO 00/20601 | 4/2000 |

OTHER PUBLICATIONS

Caffrey et al., FEBS Letters (1992) 304:205.
Fu et al., Biochemistry (1994) 33:9321–9326.
McDaniel et al., Science (1993) 262:1546–1550.
Rohr, Angew. Chem. Int. Ed. Engl. (1995) 34(8):881–888.
Chen T.S. et al. (1992). "Microbial Transformation of Immunosupressive Compounds. II. Specific desmethylation of 13–methoxy group of FK 506 and FR 9500520 by Actinomycete sp. ATCC 53828," *J Antibit* 45(4):577–580.
Dumont F.J. et al. (1992). "The Immunosupressive and Toxic Effects of FK–506 Are Mechanically Related: Pharmacology of a Novel Antagonist of FK–506 and Rapamycin," *J of Exp Medicine* 176(3):751–760.
Gold et al., (1995) Journal of Neuroscience 15:7509–7516.
Gold et al., (1999) J. Pharm. Exp. Ther. 289(3):1202–1210.
Harrison's Principles of Internal Medicine, 14th Edition, 1998, McGraw Hill, Chapters 14,20,21,64–67.
Iwasaki et al., (1993) Drug Metabolism and Disposition 21:971–977.
Iwasaki et al., (1995) Drug Metabolism and Disposition 23:28–34.
Kawai et al., (1993) FEBS Letters 316(2):107–113.
Khosla C. (1997). "Harnessing the Biosynthetic Potential of Modular Polyketide Synthases," *Chemical Reviews* 97(7):2577–2590.
Lyons et al., (1994) Proc. Natl. Acad. Sci. USA 91:3191–3195.
Motamedi et al., (1996) J. Bacteriol. 178:5243–5248.
Motamedi et al., (1997) Eur. J. Biochem. 244:78–80.
Motamedi and Shafiee, (1998) Eur. J. Biochem. 256:528.
Reynolds K.A. et al. (1997). "Rapamycin, FK506, and Ascomycin–related Compounds," *Drugs Pharm Sci* 82:497–520.
Shafiee A. et al. (1993). "Enzymatic synthesis and Immunosupressive Activity of Novel Desmethylated Immunomycins (Ascomycins)," *J Antibiot* 46(9):1397–1405.
Shiraga et al., (1994) Biochem. Pharmacol. 47:727–735.
Stassi D.L. et al. (1998). "Ethyl–substituted Erythromycin Derivatives Produced by Directed Metabolic Engineering," *Proc Natl Acad Sci USA* 95 (13):7305–7309.
Steiner et al., (1997) Proc. Natl. Acad. Sci. USA 94:2019–2024.
Vincent et al., (1992) Arch. Biochem. Biophys. 294:454–460.
Wu et al., (2000) Gene 251:81–90.

* cited by examiner

*Primary Examiner*—Elli Peselev
(74) *Attorney, Agent, or Firm*—Morrison & Foerster LLP

(57) ABSTRACT

Host cells comprising recombinant vectors encoding the FK-520 polyketide synthase and FK-520 modification enzymes can be used to produce the FK-520 polyketide. Recombinant DNA constructs comprising one or more FK-520 polyketide synthase domains, modules, open reading frames, and variants thereof can be used to produce recombinant polyketide synthases and a variety of different polyketides with application as pharmaceutical and veterinary products.

10 Claims, 9 Drawing Sheets

SEQUENCE LISTING

```
<160> NUMBER OF SEQ ID NOS: 72
<210> SEQ ID NO 1
<211> LENGTH: 77536
<212> TYPE: DNA
<213> ORGANISM: Streptomyces hygroscopicus
<220> FEATURE:
<221> NAME/KEY: CDS
<222> LOCATION: (52275)...(71465)

<400> SEQUENCE: 1
gatctcaggc atgaagtcct ccaggcgagg cgccgaggtg gtgaacacct cgccgctgct      60
tgtacggacc acttcagtca gcggcgattg cggaaccaag tcatccggaa taaagggcgg    120
ttacaagatc ctcacattgc gcgaccgcca gcatacgctg agttgcctca gaggcaaacc    180
gaaagggcgc gggcggtccg caccaggcg gagtacgcga cgagagtggc gcacccgcgc    240
accgtcacct ctctccccg ccggcgggat gcccggcgtg acacggttgg gctctcctcg    300
acgctgaaca cccgcgcggt gtggcgtcgg ggacaccgcc tggcatcggc cgggtgacgg    360
```

-continued

```
tacggggagg gcgtacggcg gccgtggctc gtgctcacgg ccgccgggcg gtcatccgtc    420
gagacggcac tcggcgagca gggacgcctg gtcggcacct gcgggccgga cgaccgtgtg    480
gttcgcgggc gggcggtggc cggtggtgag ccagctctcc agggcggtga aggctgagcg    540
gtgacacggc agcaaaggcc ggagtcggtc ggggaaggtg tcgacgaggg cgtcggtgtg    600
cgtgccgtcc tcgatgcggt agtagcggta ccggccgcca ggccgctgcc ggacatacgc    660
gcgtacacgt cggagcccgg gcggcaggca gcagcacgtc gagagtgcct ggatggtgat    720
cagcggcttg ccgatacgac cggtcaacgc gatgcgttcc acggccgcgt ggacgccgga    780
ggagcgggtg gcgtagtcgt agtcggcatc gcagcccggg accgtccccg gggcgcaata    840
cggtgtgccg gcttccttct ccccatcgaa gccggggtcg aactcctcgc ggtagacgcg    900
ctgcgtcaga tcccagtaga cctcgtggtg gtacggccac aagaactcgg agtcggccgg    960
gaacccggcg cggagcagcg cctcgcgcgc ctggccggct gcggggccgc ctgccgcgta   1020
ggtggggtag tcgcgcaggg cggccggcag gaaggtgaag aggttgggac cctccgcgcg   1080 ccacaggggtg ccttcccagt cgactcctcc gtcgtacagc tcgggatggt tctccagctg   1140
ccagcgcacg aggtagccgc cgttggacat cccggtgacc agggtgcgct cgagcggccg   1200
gtggtagcgc tgggcgaccg acgcgcgggc ggcccgggtc agctgggtga ggcgggtgtt   1260
ccactcggcg acggcgtcgc ccggccggga gccatcacgg tagaacgcgg ggccggtgtt   1320
gcccttgtcg gtggcggcgt aggcgtaacc gcgggcgagc acccagtcgg cgatggcccg   1380
gtcgttggcg tactgctcgc ggttaccggg ggtgccggcc acgaccaggc caccgttcca   1440
gcggtcgggc agccggatga cgaactgggc gtcgtggttc cacccgtggt tggtgttggt   1500
ggtggaggtg tcggggaagt agccgtcgat ctggatcccg ggcactccgg tgggagtggc   1560
caggttcttg ggcgtcagcc ctgcccagtc cgccgggtcg gtgtggccgg tggccgccgt   1620
tcccgccgtg gtcagctcgt ccaggcagtc ggcctgctga cgtgccgccg ccgggacacg   1680
cagctgggac agacgggcgc agtgaccgtc cggggcatcg ggagcaggcc gggccgtggc   1740
cggtgagggg agcaggacgg cgactgcggc caggtgaga cgccgaggc cggtgcgtct   1800 tctcggggcc cgtccgacac cgaggggcag aaccatggag agcctccaga cgtgcggatg   1860
gatgacggac tggaggctag gtcgcgcacg gtggagacga acatgggtgc gcccgccatg   1920
actgaggccc ctcagaggtg ggccgccgcc atgacgggcg cgggaccgcg ggcgctccgg   1980
ggcggtgccc gcggccgcca ccggttccgg gtccccgggt cagggacagg tgtcgttcgc   2040
gacggtgaag tagccggtcg gcgactcttt caaggtggtc gtgacgaagg tgttgtacag   2100
gcccatgttc tggccggagc ccttggcgta ggtgtaaccg cgctcgtcg tggcgcggcc   2160 cgcctggacg tgagcgtagt tgccggcggt ccagcagacg gccgtggcac cggtcgtctg   2220
cgcggtgacc gcgcccgaga gcggtccggc cttgccgtcc gcgtcccggg cggcgaccgc   2280
gtaggtgtgc gatgtgcccg ccctcaggcc ggtgtccgtg tacgacgtcg tggcggacgt   2340
ggtgatctgg gcaccgtcgc ggtggacggc gtagtcggtg gcgccgtcga cgggtttcca   2400
ggtcaggctg atggtggtgt cggtggcgcc ggtggcggcc aggccggacg gagcgggcag   2460
cgaaccgggg tcgaggcgg atccgctcag gccgaagaac tgcgtgatcc agtagctgga   2520
acagatcgag tccaggaagt aggcggcgcc ggtgctgccg cactgctgtg ctccggtgcc   2580
gggatcgacc ggggtgccgt gcccgatgcc cggcacccgg ttcacctcca cggccaccga   2640
tccgtccgcg gccaggtact cctcgtgccg ggtggagttc gggccgatca ccgaggtacg   2700
```

```
gtccggcgtc tgggacacgc cgtgcacagc ggtccactgg tcgcgcaact cgtcggcgtt    2760
gcgcggcgcg acggtggtgt ccttgtcgcc gtgccagatg gccacgcgcg gccacgggcc    2820
cgaccacgag gggtagccgt cacggacccg ccgcgcccac tggtccgcgg tcaggtcggt    2880
cccggggttc atgcacaggt acgcgctgct gacgtcggtg gcacagccga agggcaggcc    2940
ggcgacgacc gcgccggcct ggaagacgtc cggataggtg gcgagcatca ccgacgtcat    3000
ggcaccgccg gcggacagcc cggtgatgta gtgcgctgg gggtccgcgc cgtaggcgga    3060
gacggtgtga gcggccatct gccggatcga cgcggcttcg ccctggcccc tgcggttgtc    3120
gctgctctgg aaccagttga agcacctgtt cgcgttgttc gacgacgtgg tctcggcgaa    3180
cacgagcagg aagccatagc ggtccgcgaa tgagagcagg ccggagttgt cggcgtagcc    3240
ctgggcgtcc tgggtgcaac cgtgcagggc gaacaccacc gccggctccg cgggcaggga    3300
cgcgggccgg tagacgtaca tgttcagccg gcccgggttc gtgccgaagt ccgcgacctc    3360
ggtcaggtcc gccttggtca gaccgggctt ggccaggccc gccgcggcgt gggccgtcgg    3420
cgccgggccg agcagggccg ctccgagtac gagggccacg acggccacga gacgggtgag    3480 cacccccgc cgtcccggac gcgacaacga cccgaccggc ggcgaggagg agaggggaa    3540 cagcggggtg aggattcccc ggaacggcgg cggctgcatg gcggctccct cgatgtcgtg    3600 gggggacac ggagggctcc ctgacgtcga tcagtgggag cgccccggtg cccggcaccg    3660
taggggtggt tcaacccgca acggtatggc ccggagcacc acaccccgca ccgcgcgatg    3720
tgcgcccgga cggattgtgt cgccttgcgg aatctgatac ccggacgcga cgaacgcccc    3780
acccgacacg ggtagggcgt catggtgtcc gactcggccg gtcggccttg cctgccctgg    3840
acggaccggg cgtcggcgga ccgggcgtcg cgggctggg cggtatggcg gccgaggacg    3900
ccagccgcgt ggggcggccg cgcccaagtg cagtacgccg accgtggccg gcgggagggc    3960
cggaccggtc agtgcagtcc cgcggccctg cgggaccgct cgtcccagac gggttccacc    4020
gcggcgaacc ggggtccgtg tccgcggcgg tagaccatca gtgtccgctc gaaggtgatg    4080
acgatgacac cgtcctggtt gtagccgatg gtgcgcacgc tgatgatgcc tacgtcaggt    4140
cggctggcgg actcccgggt gttcaggacc tcggactgcg agtagatggt gtcgccctcg    4200
aagaccgggt tcggcagcct gacccggtcc cagccgaggt tggccatcac atgctgggag    4260
atgtcggtga cgctctgccc ggtgaccagg gcgagggtga aggtggagtc caccagcggc    4320
ttgccccagg tggtgcccgc cgagtagtgg cggtcgaagt gcagcggcgc ggtgttctgc    4380
gtcaggagcg tgagccagga gttgtcggtc tccaggaccg tgcggcccag ggggtggcgg    4440
tacacgtcgc cggtggtgaa gtcctcgaag tagcggccct gccagccctc gaccacagcg    4500
gtgcgggtgg cgtcctggtc cgggttctca gtcgtcatgg cgctcattct gggaagtccc    4560
cggtccgctg tgaaatgccg aaccttcacc gggctcatac gtgcggcgca tgagccctgg    4620
accgtacgta gtcgtagaac ctcgccacca ctggcgcgcg tggtcctccg gcgagtgtga    4680
ccacgccgac cgtgcgccgc gcctgcgggt cgtcgagcgg cacggcgacg gcgtggtcac    4740
cgggcccgga cgggctgccg gtgagggggg cgacggccac accgaggccg gcggcgacca    4800
gggcccgcag cgtgctcagc tcggtgctct ccaggacgac ccgcggcacg aatccggccg    4860
cggcgcacag ccggtcggtg atctggcgca gtccgaagac cggctccagt gccacgaacg    4920
cctcatcggc cagctccgcg gtccgcaccc ggcggcgtct ggccagccgg tgtccgggtg    4980
ggacgagcag gcacagtgcc tcgtcccgca gtggtgtcca ctccacatcg tccccggcgg    5040
gtcgtgggct ggtcagcccc aggtccagcc tgctgttgcg gacgtcgtcg accacggcgt    5100
```

-continued

```
cggcggcgtc gccgcgcagt tcgaaggtgg tgccgggagc cagccggcgg tacccggcga    5160
ggaggtcggg caccagccag gtgccgtagg agtgcaggaa acccagtgcc acggtgccgg    5220
tgtcggggtc gatcagggcg gtgatgcgct gctcggcgcc ggagacctca ctgatcgcgc    5280
gcagggcgtg ggcgcggaag acctcgccgt acttgttgag ccggagccgg ttctggtgcc    5340
ggtcgaacag cggcacgccc actcgtcgct ccagccgccg gatggccctg gacagggtcg    5400
gctgggagat gttgagccgt tccgcggtga tcgtcacgtg ctcgtgctcg gccaaggccg    5460
tgaaccactg caactcccgt atctccatgc agggactata cgtaccgggc atggtcctgg    5520
cgaggtttcg tcatttcaca gcggccgggc ggcggcccac agtgagtcct caccaaccag    5580
gaccccatgg gagggacccc atgtccgagc cgcatcctcg ccctgaacag gaacgccccg    5640
ccgggcccct gtccggtctg ctcgtggttt ctttggagca ggccgtcgcc gctccgttcg    5700
ccacccgcca cctggcggac ctgggcgccc gtgtcatcaa gatcgaacgc cccggcagcg    5760
gcgacctcgc ccgcggctac gaccgcacgg tgcgtggcat gtccagccac ttcgtctggc    5820
tgaaccgggg gaaggagagc gtccagctcg atgtgcgctc gccggagggc aaccggcacc    5880
tgcacgcctt ggtggaccgg gccgatgtcc tggtgcagaa tctggcaccc ggcgccgcgg    5940
gccgcctggc atcggccacc aggtcctcgc gcggagccac cgaggctgat cacctgcgga    6000
catatccggc tacggcagta ccggctgcta ccgcggaccg caaggcgtac gacctcctgg    6060
tccagtgcga agcggggctg gtctccatca ccggcacccc cgagacccg tccaaggtgg    6120
gcctgtccat cgcggacatc tgtgcgggga tgtacgcgta ctccggcatc ctcacggccc    6180
tgctgaagcg ggcccgcacc ggccggggct cgcagttgga ggtctcgatg ctcgaagccc    6240
tcggtgaatg gatgggatac gccgagtact acacgcgcta cggcggcacc gctccggccc    6300
gcgccggcgc cagccacgcg acgatcgccc ctacggcccc gttcaccacg cgcgacgggc    6360
agacgatcaa tctcgggctc cagaacgagc gggagtgggc ttccttctgc ggtgtcgtgc    6420
tacaacgccc cggtctctgc gacgacccgc gcttttccgg caacgccgac cgggtggcgc    6480
accgcaccga gctcgacgcc ctggtgagcg aggtgacggg cacgctcacc ggcgaggaac    6540
tggtggcgcg gctggaggag gcgtcgatcg cctacgcacg ccagcgcacc gtgcgggagt    6600
tcagcgaaca ccccaactg cgtgaccgtg gacgctgggc tccgttcgac agcccggtcg    6660
gtgcgctgga gggcctgatc ccccggtca ccttccacgg cgagcacccg cggcggctgg    6720
gccgggtccc ggagctgggc gagcataccg agtccgtcct ggcgtggctg gccgcgcccc    6780
acagcgccga ccgcgaagag gccggccatg ccgaatgaac tcaccggagt cctgatcctg    6840
gccgccgtgt tcctgctcgc cggcgtacgg gggctgaaca tgggcctgct cgcgctggtc    6900
gccacctttc tgctcggggt ggtcgcactc gaccgaacgc cggacgaggt gctggcgggt    6960
ttccccgcga gcatgttcct ggtgctggtc gccgtcacgt tcctcttcgg gatcgcccgc    7020
gtcaacggca cggtggactg gctggtacgt gtcgcggtgc gggcggtggg ggcccgggtg    7080
ggagccgtcc cctgggtgct cttcggcctg gcggcactgc tctgcgcgac aggcgcggcc    7140
tcgcccgcgg cggtggcgat cgtggcgccg atcagcgtcg cgttcgccgt caggcaccgc    7200
atcgatccgc tgtacgccgg actgatggcg gtgaacgggg ccgcagccgg cagtttcgcc    7260
ccctccggga tcctgggcgg catcgtccac tcggcgctgg agaagaacca tctgcccgtc    7320
agcggcgggc tgctcttcgc aggcaccttc gccttcaacc tggcggtcgc cgcggtgtca    7380
tggctcgtcc tcgggcgcag gcgcctcgaa ccacatgacc tggacgagga caccgatccc    7440
```

-continued

```
acggaagggg acccggcttc ccgccccggc gcggaacacg tgatgacgct gaccgcgatg    7500
gccgcgctgg tgctgggaac cacggtcctc tccctggaca ccggcttcct ggccctcacc    7560
ttggcggcgt tgctggcgct gctcttcccg cgcacctccc agcaggccac caaggagatc    7620
gcctggcccg tggtgctgct ggtatgcggg atcgtgacct acgtcgccct gctccaggag    7680
ctgggcatcg tggactccct ggggaagatg atcgcggcga tcggcacccc gctgctggcc    7740
gccctggtga tctgctacgt gggcggtgtc gtctcggcct tcgcctcgac caccgggatc    7800
ctcggtgccc tgatgccgct gtccgagccg ttcctgaagt ccggtgccat cgggacgacc    7860
ggcatggtga tggccctggc ggccgcgcg accgtggtgg acgcgagtcc cttctccacc    7920
aatggtgctc tggtggtggc caacgctccc gagcggctgc ggcccggcgt gtaccagggg    7980
ttgctgtggt ggggcgccgg ggtgtgcgca ctggctcccg cggccgcctg gcggccttc     8040 gtggtggcgt gagcgcagcg gagcgggaat cccctggagc ccgtttcccg tgctgtgtcg    8100
ctgacgtagc gtcaagtcca cgtgccgggc gggcagtacg cctagcatgt cgggcatggc    8160
taatcagata accctgtccg acacgctgct cgcttacgta cggaaggtgt ccctgcgcga    8220
tgacgaggtg ctgagccggc tgcgcgcgca cggccgag ctgccgggcg gtggcgtact      8280
gccggtgcag gccgaggagg acagttcct cgagttcctg gtgcggttga ccggcgcgcg    8340
tcaggtgctg gagatcggga cgtacaccgg ctacagcacg ctctgcctgg cccgcggatt    8400
ggcgcccggg ggccgtgtgg tgacgtgcga tgtcatgccg aagtggcccg aggtgggcga    8460
gcggtactgg gaggaggccg gggttgccga ccggatcgac gtccggatcg gcgacgcccg    8520
gaccgtcctc accgggctgc tcgacgaggc gggcgcgggg ccggagtcgt tcgacatggt    8580
gttcatcgac gccgacaagg ccggctaccc cgcctactac gaggcggcgc tgccgctggt    8640
acgccgcggc gggctgatcg tcgtcgacaa cacgctgttc ttcggccggg tggccgacga    8700
agcggtgcag gacccggaca cggtcgcggt acgcgaactc aacgcggcac tgcgcgacga    8760
cgaccgggtg gacctggcga tgctgacgac ggccgacggc gtcaccctgc tgcggaaacg    8820
gtgaccgggg cgatgtcggc ggcggtcagc gtcagcgtcg tcggcgcggg cctcgcggag    8880
ggctccagat gcaggcgttc gacgccggcg gcggaagcgc ccgccacctc ggacacgcag    8940
gggcagtcgg agtccgcgaa gcccgcgaac cggtaggcga tctccatcat gcggttgcgg    9000
tccgtacgcc ggaagtccgc caccaggtgc gcccccgcgc gggcgccctg gtccgtgagc    9060
cagttcagga tcgtcgcacc ggcaccgaac gacacgaccc ggcaggacgt ggcgagcagt    9120
ttcaggtgcc acgtcgacgg cttcttctcc agcaggatga tgccgacggc gccgtgcggg    9180
ccgaagcggt cgcccatggt gacgacgagg acctcatggg cgggatcggt gagcacgcgc    9240
gcaggtcggc gtcggagtag tgcacgccgg tcgcgttcat ctggctggtc cgcagcgtca    9300
gttcctcgac gcggctgagt tcctcctccc ccgcgggtgc gatcgtcatg gagaggtcga    9360
gcgagcgcag gaagtcctcg tcgggaccgg agtacgcctc ccgggcctgg tcgcgcgcga    9420
aacccgcctg gtacatcagg cggcgccgac gcgagtcgac cgtggacacc ggcgggctga    9480
actccggcag cgacaggagc gtggccgcct gctcggccgg gtagcaccgc acctcgggca    9540
ggtggaacgc cacctcggca cgctcggcgg gctggtcgtc gatgaacgcg atcgtggtcg    9600
gtgcgaagtt cagctccgtg gcgatctcgc ggacggactg cgacttcggc ccccatccga    9660
tgcgggccag cacgaagtac tccgccacac cgaggcgttc cagacgctcc cacgcgaggt    9720
cgtggtcgtt cttgctcgcc accgcctgga ggatgccgcg gtcgtcgagc gtggtgatca    9780
cctcgcggat ctcgtcggtg aggaccacct cgtcgtcctc cagcacggtg cccgccaca     9840
```

```
aggtgttgtc caggtcccag accagacact tgacaatggt catggctgtc ctctcaagcc    9900
gggagcgcca gcgcgtgctg ggccagcatc acccggcaca tctcgctgct gccctcgatg    9960
atctccatga gcttggcgtc gcggtacgcc cgttcgacga cgtgtccctc tctcgcgcct   10020
gccgacgcga gcacctgtgc ggcggtcgcg gccccggcgg cggctcgttc ggcggcgacg   10080
tgcttggcca ggatcgtcgc gggcaccatc tcgggcgagc cctcgtccca gtggtcgctg   10140
gcgtactcgc acacgcgggc cgcgatctgc tccgcggtcc acaggtcggc gatgtgcccg   10200
gcgacgagtt ggtggtcgcc gagcggccgg ccgaactgct cccgggtccg ggcgtggggcc   10260
accgcggcgg tgcggcaggc ccgcaggatc ccgacgcagc cccaggcgac cgacttgcgc   10320
ccgtaggcga gtgacgccgc gaccagcatc ggcagtgacg cgccggagcc ggccaggacc   10380
gcgccggccg gcacacgcac ctggtccagg tgcagatcgg cgtggccggc ggcgcggcag   10440
ccggacgggct tcgggacgcg ctcgacgcgt acgccggggg tgtcggcggg cacgaccacc   10500
accgcaccgg aaccatcctc ctggagaccg aagacgacca ggtggtccgc gtaggcggcg   10560
gcagtcgtcc agaccttgtg gccgtcgacg acagcggtgt ccccgtcgag ccgaacccgc   10620
gtccgcatcg ccgacagatc gctgcccgcc tgccgctcac tgaagccgac ggccgcgagt   10680
ttcccgctgg tcagctcctt caggaaggtc gcccgctgac cggcgtcgcc gagccgctgc   10740
acggtccacg cggccatgcc ctgcgacgtc atgacactgc gcagcgaact gcagaggctg   10800
ccgacgtgtg cggtgaactc gccgttctcc cggctgccga gtcccagacc gccgtgctcg   10860
gccgccactt ccgcgcagag caggccgtcg gcgccgagcc ggacgagcag gtcgcgcggc   10920
agttcgccgg acgtgtccca ctcggcggcc cggtcaccga caaggtcggt cagcagcgcg   10980
tcacgctcag gcatcgacgg cccgcagccg gtggacgagt gcgaccatgg actcgacggt   11040
acggaagttc gcgagctgga ggtccgggcc ggcgatcgtg acgtcgaacg tcttctccag   11100
gtacacgacc agttccatcg cgaacagcga cgtgaggccg ccctccgcga acaggtcgcg   11160
gtccacgggc cagtccgacc tggtcttcgt cttgaggaac gcgaccaacg cgtgcgcgac   11220
ggggtcgtcc ttgacgggtg cggtcatgag aacaccttct cgtattcgta gaagcccgg   11280
ccggtcttcc ggccgtggtg tccctcgcgg accttgccca gcagcaggtc acaggggcgg   11340
ctgcgctcgt cgccggtgcg tttgtgcagc acccacagcg cgtcgacgag gttgtcgatg   11400
ccgatcaggt ccgcggtgcg cagcggcccg gtcggatggc cgaggcaccc cgtcatgagc   11460
gcgtcgacgt cctcgacgga cgcggtgccc tcctgcacga tccgcgccgc gtcgttgatc   11520
atcgggtgga gcagccggct cgtgacgaag ccgggcgcgt cccggacgac gatcggcttg   11580
cgccgcagcg ccgcgagcag gtccccggcg cggccatgg ccttctcacc ggtccggggt   11640
ccgcggatca cctcgaccgt cgggatcagg tacgacgggt tcatgaagtg cgtgccgagc   11700
aggtcctcgg gccgggccac ggagtcggcc agttcgtcaa ccgggatcga cgacgtgttc   11760
gtgatgaccg ggataccggg cgccgctgcc gagaccgtgg cgagtacctc cgccttgacc   11820
tcggcgtcct cgacgacggc ctcgatcacc gcggtggccg taccgatcgc gggcagcgcg   11880
gacgtggccg tccgcagcac accggggtcg gcctcggcgg gccggccac gagttgtgcc   11940
gtccgcagtt cggtggcgat ccgcgcccgc gccgccgtaa ggatctcctc ggacgtgtcg   12000
acgagtgtca ccgggacgcc gtggcgcagc gcgagcgtgg tgatgccggt gcccatcact   12060
cccgcgccga gcacgatcag ctggtggtcc acgctgtttc ctcccctccgg ggtcaccatg   12120
gcagcgagta cgggtcgagg acgtcttccg gggtcgaccc gatcgcgtcc ttgcggccga   12180
```

```
ggccgagttc gtcggcgaag ccgagcagca cgtcgaacgc gatgtggtcg gcgaacgcgc    12240
tgcccgtcga gtcgaggacg ctcaggctgt cccggtggtc cgccgcggtg tccggtgccg    12300
cgcacagggc cgccagcgac gggccgagct cgcggtccgg cagttgctgg tactcgccct    12360
cggcgcgggc ctgccccgga tggtcgacgc agatgaacgc gtcgtcgagc agggtcttcg    12420
gcagttcggt cttgcccggc tcgtcggcgc cgatggcgtt cacatgcagg tgcggcagcc    12480
gcggctcggc gggcagcacc ggcccttgc ccgagggcac cgaggtgacg gtggacagga    12540
catccgcggc ggcggcggcc tccgccggat cggtcacctt gaccggcagt ccgaggaacg    12600
cgatgcggtc cgcgaacgac gccgcgtggc cggggtcggt gtcgctgacc aggatccgct    12660
cgatgggcag gaccctgctg agcgcgtgcg cctgggtcac cgcctgtgcg cccgcgccga    12720
tcagcgtgag cgtggcgctg tcggaccggg ccagcagccg gctcgcgacg gcggcgaccg    12780
cgccggtccg catcgcggtg atcacgcctg cgtcggcgag ggcggtcaga ctgccgctgt    12840
cgtcgtcgag gcgcgacatc gtgccgacga tcgtcggcag ccggaagcgc ggatagttgt    12900
gcggactgta cgaaaccgtc ttcatggtca cgccgacacc ggggacccgg tacggcatga    12960
actcgatgac gccgggaatg tcgccgccgc ggacgaatcc ggtacgcggc ggcgcctcgg    13020
cgaactcgcc gcggccgagc gcggcgaacc cgtcgtgcag ctcgctgatc agccggtcca    13080
tcatcacgtc gcggccgatc acggagagaa tccgcttgat gtcacgttgg cgcaggaccc    13140
tggtctgcat gtgtcacctc cctttcgtgg ccggagctgt cttggtggtg ccgctcgggg    13200
cggcttccgt tctcatcgca gctccctgtc gatgaggtcg aaaatctcgt ccgcggtcgc    13260
gtccgcggac agcacgccgg ccggcgtggt cgggcgggtc tcccgccgcc agcggttgag    13320
cagggcgtcc agccgggttc cgatcgcgtc cgcctggcgg gcgccgggt cgacaccggc    13380 aacgagtgct tccagccggt cgagctgcgc gagcaccacg gtcaccgggt cgtccgggga    13440
cagcagttca ccgatgcggt cggcgagtgc gcgcggcgac gggtagtcga agacgagcgt    13500
ggcggacagt cgcagaccgg tcgcctcgtt gaggccgttg cgcagctgca ccgcgatgag    13560
cgagtccaca ccgagttccc ggaacgccgc gtcctccggg atgtcctccg ggtcggcgtg    13620
gcccaggacg gccgctgcct tctgccggac gagggcgagc aggtcggtgg ggcgttcctg    13680
ctcgttgcgg gcgctccggc gggccgacgg cttgggccgg ccacgcagca gcgggaggtc    13740
cggcggcagg tcgcccgcca cggcgacgac actgcccgtt ccggtgtgga cggcggcgtc    13800
gtacatgcgc atgccctgtt cggcggtgag cgcgctcgcc ccaccccttgc gcatacggcg    13860 ccggtcggcg tcggtcaggt ccgcggtcag gccactcgcc tggtcccaca gccccacgc    13920 gatcgacagc cctggcagcc cttgtgcacg ccggtgttcg gcgagcgcgt cgaggaacgc    13980
gttcgccgcc gcgtagttgc cctgaccggg ggtgcccagc acaccggccg ccgacgagta    14040
gacgacgaat gcggcgaggt cggtgtcgcg ggtgagccgg tgcaggtgcc aggcggcgtc    14100
ggccttgggt ttgaggacgg tgtcgatgcg gtcgggggtg aggttgtcga gcagggcgtc    14160
gtcgagggtt ccggcggtgt ggaagacggc ggtgagggt tgaggatgt gggcgagggt    14220 ggtggcgagt tggtgggggt cgccgacgtc gcagggggag tgggtgccgg gggtggtgtc    14280 gggggggtggg gtgcgggaga ggaggtaggt gtgggggtgg ttcaggtggc gggcgaggat    14340
gccggcgagg gtgccggagc cgccggtgat gacgacggcc ccctcgggg t ccagcggccg    14400 cgggaccgtg aggacgatct tgccggtgtg ctcgccgcgg ctcatggtcg ccagcgcctc    14460
gcggacctgc cgcatgtcgt gcaccgtcac cggcagcggg tgcagcacac cgcgcgcgaa    14520
caggccgagc agctccgcga tgatctcctt gagccggtcg ggccccgcgt ccatcaggtc    14580
```

-continued

```
gaacggtcgc tggacggcgt gccggatgtc cgtcttcccc atctcgatga accggccacc   14640
cggcgcgagc aggccgacgg acgcgtcgag gagttcaccg gtgagcgagt tgagcacgac   14700
gtcgaccggc gggaacgcgt cggcgaacgc ggtgctgcgg gaatcggcca gatgcgctcc   14760
gtccaggtcc accagatggc gcttcgcggc gctggtggtc gcgtacacct ccgcgcccag   14820
gtgccgcgcg atctgccggg cggcggaacc gacaccgccg gtggccgcgt ggatcaggac   14880
cttctcgccg gggcgcagcc cggcgaggtc gaccaggccg taccacgcgg tcgcgaacgc   14940
ggtcatcacg gacgccgcct gcgggaacgt ccagccgtcc ggcatccggc cgagcatccg   15000
gtggtcggcg atgaccgtgg ggccgaagcc ggtgccgacg aggccgaaga cgcggtcgcc   15060
cggtgccaga ccgagacgt cggcgccggt ctccaggacg atgcccgcgg cctcgccgcc   15120
gagcacgccc tgaccggggt aggtgccgag cgcgatcagc acatcgcgga agttgaggcc   15180
cgccgcacgc acaccgatcc ggacctcggc cggggcgagg gggcgccggg gctccgccga   15240
gtcggccgcg gtgaggccgt cgagggtgcc cgtccgcgcc ggccggatca gccacgtgtc   15300
gctgtccggc acggtgagcg gctccggcac ccgggtgagg cggccgcct cgaaccggcc   15360 gccgcgcagc cgcagacgcg gctcgccgag tgcgacggca tgcgctgct gctcgggggc   15420 gagcgtgacg ccggactcgg tctcgacgtg gacgaaccgg ccgggctgct cggcctgggc   15480
ggcgcgcagc agtccggccg ccgcgccggt ggcgaggccc gcggtggtgt gcacgagcag   15540
atccccgccg gagccggtca gggcggtcag cagccgggtg gtgagcgcac gcgtctcggc   15600
caccgggtcg tcgccatcag cggcaggcaa cgtgatgacg tccacgtcgg tcgcggggac   15660
atccgtgggt gcggcgacct cgatccaggt gagacgcatc aggccggtgc cgacgggtgg   15720
ggacagcggg cgggtgcgga ccgtccggat ctcggcgacg agttggccgg cggagtcggc   15780
gacgcgcaga ctcagctcgt cgccgtcacg agtgatcacg gctcggagca tggccgagcc   15840
cgtggcgacg aaccgggccc ccttccaggc gaacggcaga cccgcagcgc tgtcgtccgg   15900
cgtggtgagg gcgacggcgt gcagggccgc gtcgagcagc gccggatgca caccgaaacc   15960
gtccgcctcg gcgcctgct cgtcgggcag cgccacctcg gcatacacgg tgtcaccatc   16020
acgccaggca gcccgcaacc cctggaacgc cgacccgtac tcataaccgg catcccgcag   16080
ttcgtcatag aaccccgaga cgtcgacggc cacggccgtg accggcggcc actgcgagaa   16140
cggctccaca ccgacaacac cgggggtgtc gggggtgtcg ggggtcaggg tgccgctggc   16200
gtgccgggtc cagctgcccg tgccctcggt acgcgcgtgg acggtcaccg gccgccgtcc   16260
ggcctcatca gccccttcca cggtcaccga cacatccacc gctgcggtca ccggcaccac   16320
aaggggggat tcgatgacca gctcgtccac tatcccgcaa ccggtctcgt caccggcccg   16380
gatgaccagc tccacaaacg ccgtacccgg cagcaggacc gtgccccgca ccgcgtgatc   16440
agccagccag gggtgagtgc gcaatgagat ccggccagtg agaacaacac caccatcgtc   16500
ggcgggcagc gctgtgacag cggccagcat cggatgcgcc gcacccgtca ccccgccgc   16560 cgacagatcg gtggcaccgg ccgcctccag ccagtaccgc ctgtgctcga acgcgtacgt   16620
gggcagatcc agcagccgtc ccggcaccgg ttcgaccacc gtgtcccagt ccactgccgt   16680
gcccagggtc cacgcctgcg ccaacgccgt cagccaccgc tcccagccgc cgtcaccggt   16740
ccgcaacgac gccaccgtgt gagcctgctc catcgccggc agcagcaccg gatgggcact   16800
gcactccacg aacaccgacc catccagctc cgccaccgcc gcgtccaacg ccaccggacg   16860
acgcagattc cggtaccagt accctcatc caccggctcc gtcacccagg cgctgtccac   16920
```

```
ggtcgaccac cacgccaccg acgcggcctt ccctgccacc ccctccagta ccttggccag   16980
ttcatcctcg atggcttcca cgtggggcgt gtgggaggcg tagtcgaccg cgatacgacg   17040
cacccgcacg ccttcggcct cataccgcgc caccacctcc tccaccgccg acgggtcccc   17100
cgccaccacc gtcgaagccg ggccgttacg cgccgcgatc cacacaccct cgaccagacc   17160
gacctcaccg gccggcaacg ccaccgaagc catcgctccc cgcccggcca gtcgcgccgc   17220
gatgacctga ctgcgcaatg ccaccacgcg ggcggcgtcc tcgaggctga gggctccggc   17280
cacgcacgcc gccgcgatct cgccctggga gtgtccgatc accgcgtccg gcacgacccc   17340
atgcgcctgc cacagcgcgg ccaggctcac cgcgaccgcc cagctggccg gctggaccac   17400
ctccacccgc tccgccacat ccggccgcgc caacatctcc cgcacatccc agcccgtgtg   17460
cggcagcaac gcctgagcgc actcctccat acgcgcggcg aacaccgcgg agtgggccat   17520
gagttccacg cccatgccga cccactgggc gccctggccg gggaagacga acaccgtacg   17580
cggctggtcc accgccacac ccgtcacccg ggcatcgccc agcagcaccg cacggtgacc   17640
gaagacagca cgctcccgca ccaacccctg cgcgaccgcg ccacatccca ccaccccc    17700 gcgcagatac ccctccagcc gctccacctg cccccgcaga ctcacctcac cacgagccga   17760
caccggcaac ggcaccaacc cgtcaacaac cgactcccca cgcgacggcc caggaacacc   17820
ctcaaggatc acgtgcgcgt tcgtaccgct caccccgaac gacgacacac ccgcatgcgg   17880
tgcccgatcc gactcgggcc acggcctcgc ctcggtgagc agctccaccg caccggccga   17940
ccagtccaca tgcgacgacg gctcgtccac atgcagcgtc ttcggcgcga tcccgtaccg   18000
catcgccatg accatcttga tcacaccggc gacacccgcc gccgcctgcg catgaccgat   18060
gttcgacttc aacgaaccca gcagcagcgg aacctcacgc tcctgcccgt acgtcgccaa   18120
aatggcctgc gcctcgatgg gatcgcccag cgtcgtcccc gtcccgtgcg cctccaccac   18180
gtccacatcg gcggcgcgca gtccggcgtt caccaacgcc tgctggatga cacgctgctg   18240
ggacgggccg ttgggggcgg acagcccgtt ggaggcaccg tcctggttca ccgccgaccc   18300
gcggacgacc gcgagaacgg tgtgtccgtt gcgctcggcg tcggagagcc gctccagcac   18360
aagaacgccg gcgccctccg cccagccggt gccgttggcg gcgtccgcga acgcgcggca   18420
gcggccgtcg ggggagagtc cgccctgctg ctggaattcc acgaacccgg tcggggtcgc   18480
catgacggtg acaccgccga ccagcgccag cgagcactcc ccgtggcgca gtgcgtgccc   18540
ggcctggtgc agcgcgacca cgacgacga gcacgccgtg tccaccgtga acgccggtcc   18600
ctggagccca tagaagtacg agatccggcc ggtgagcacg ctgggctgca tgccgatcga   18660
gccgaacccg tccaggtccg cgccgacgcc gtacccgtac gagaaggcgc ccatgaacac   18720
gccggtgtcg ctgccgcgca gtgtgcccgg cacgatgccc gcgctctcga acgcctccca   18780
tgtcgtttcc agcaggatcc gctgctgggg gtccatggcc cgtgcctcac gggggctgat   18840
gccgaagaac gcggcatcga agccggcggc gtcggagagg aagccgccgc ggtccgtgtc   18900
cgatccgccg gtgaggccgg acgggtccca gccacggtcg gccgggaagc cggtgaccgc   18960
gtcgccgcca ctgtccacca tgcgccacag gtcgtcgggc gaggtgacgc cgcccggcag   19020
tcggcaggcc atgcccacga tggccagcgg ttcgtcacgg gtcgcggcgg ctgtgggaac   19080
agcgaccggt gcggcaccac cgaccagagc ctcgtccaac cgcgacgcga tggcccgcgg   19140
cgtcgggtag tcgaagacaa gcgtggcggg cagtcggaca ccggtcgccg cggcgagtcg   19200
gttccgcagt tcgacggcgg tcagcgagtc gatacccagt tccttgaagg ccgcgtccgc   19260
ggacacgtcc gcggcgtccg cgtggccgag caccgccgcc gcgttgtcgc ggaccagtgc   19320
```

```
cagcagcgcg gtgtcccgct cagcgccgga catggtgccg agccggtcgg cgagcggaac   19380
ggcggtggcc gccgccgggc gcgatacggc gcggcgcaga tcggcgaaaa gcggcgatgt   19440
gtgcgcggtg aggtccatcg tggccgccac ggcgaacgcg gtgccggttc cggccgcggc   19500
ttccagcagg cgcatgccca caccggccga catggggcgg aaaccgccgc ggcggacacg   19560
ggtgcggttg gtgccgctca tgctgccggt gagtccgctg tcatcggccc agaggcccca   19620
ggccagcgac agcgcgggca gtccttcggc atggcgcagc gtcgcgagtc cgtcgaggaa   19680
cccgttcgcc gccgagtagt tgccctggcc gcggccgccc atgatgcccg cgacggacga   19740
gtagaggacg aacgagcgca ggtccgcgtc ccgggtcagc tcgtgcaggt gccaggcgcc   19800
gtcggctttg gggcgcagtg tggtggcgag ccgctcccgg gtgagtgccg tggtcacgcc   19860
gtcgtcgagc acggctgccg tgtggaagac cgccgtgagc ggcctgccgg cggcggcgag   19920
cgcggcggcg agctggtccc ggtcggcgac gtcacagcgg atgtggacac cgggagtgtc   19980
cgccggcggt tcgctgcgcg acagcaacag gaggtggcgg gcgccatgct cggcgacgag   20040
atgccgggcg aggagacctg ccagcacacc cgagccgccg gtgatgacca ccgtgccgtc   20100
cgggtcgagc agcggttcgg gcgtttccgc ggcggccgtg cgggtgaacc gcggcgcttc   20160
gtaccggccg tcggtgacgc ggacgtacgg ctcggccagt gtcgtggcgg cggccagcgc   20220
ctcgatgggg gtgtcggtgc cggtctccac cagcacgaac cggcccgggt gctcggcctg   20280
ggcggaccgg acgaggccgg cgaccgctcc tccgaccggt cccgcgtcga tccggacgac   20340
gagggtggtc tccgcagggc cgtcctcggc gatcacccgg tgcagctcgc cgagcacgaa   20400
ctcggtgagc cggtacgtct cgtcgaggac atccgcgccc ggttccggga gcgcggagac   20460
gatgtggacc gcgtccgcag gaccgggccc gggagtgggc agctcggtcc aggagaggcc   20520
gtacaaggag ttccgtacga cggcggcgtc gccgtcgacg ttcaccggtc gcgcggtcag   20580
cgcggcgacg gtcaccaccg gttggccgac cgggtccgtc gcatgcacgg cagcgccgtc   20640
cgggccctga gtgatcgtga cgcgcagcgt ggtggccccg gtcgtgtgga accgcacgcc   20700
gctccacgag aacggcagcc gcacctccgc ttcctgttcc gcgagcagcg gcaggcaggt   20760
gacgtgcaag gccgcgtcga acagcgccgg gtggacgcca tagtgcggcg tgtcgtccgc   20820
ctgttccccg gcgatctcca cctcggcgta cagggtttcg ccgtcgcgcc aggcggtgcg   20880
cagtccctgg aacgctgggc cgtagctgta gccggtctcg gccagccgct cgtagaacgc   20940
gctcacgtcg acgcgtcgcg cgcccggcgg cggccacgcg ggcggcggga ccgccgcgac   21000
gcttccggcc cggccgaggg tgccgctggc gtgccgggtc cagctgtccg tgccctcggt   21060
acgcgcgtgg acggtcactc gccgccgtcc ggcctcatcg gcccttcga cggtcaccga   21120 cacatccacc gcgccggtca ccggcaccac gagcggggtc tcgatgacca gttcatccac   21180
caccccgcaa ccggtctcgt caccggcccg gatgaccagc tccacaaacg ccgtacccgg   21240
cagcagaacc gtgccccgca ccgcgtgatc agccagccag ggatgcgtac gcaacgagat   21300
ccggccagtg agaacaacac caccaccgtc gtcggcgggc agtgctgtga cggcggccag   21360
catcggatgc gccgccccgg tcagcccggc cgcggacaga tcggtggcac cggccgcctc   21420
cagccagtac cgcctgtgct cgaacgcgta ggtgggcaga tcgagcagcc gtcccggcac   21480
cggttcgacc accgtgtccc agtccactgc cgtgcccagg gtccacgcct gcgccaacgc   21540
cgtcagccac cgctcccagc cgccgtcacc ggtccgcaac gacgccaccg tgtgagcctg   21600
ttccatcgcc ggcagcagca ccggatgggc gctgcactcc acgaacacgg acccgtccag   21660
```

```
ctccgccacc gccgcgtcca gcgcgacggg gcgacgcagg ttccggtacc agtagccctc  21720
atccaccggc tcggtcaccc aggcgctgtc caccgtggac caccaggcca ccgacccggt  21780
cccgccggaa atcccctcca gtacctcggc caactcgtcc tcgatggctt ccacgtgggg  21840
cgtgtgggag gcgtagtcga ccgcgatacg gcgcactcgc acgccttcgg cctcgtaccg  21900
cgtcaccact tcttccaccg cggacgggtc ccccgccacc acagtcgaag acgggccgtt  21960
acgcgccgcg atccacacgc cctcgaccag gtccacctca ccggccggca acgccaccga  22020
agccatcgcc ccccgcccgg ccagccgccc ggcgatcacc tggctgcgca aggccaccac  22080
gcgggcggcg tcctcaaggc tgagggctcc ggccacacac gccgccgcga tctcgccctg  22140
ggagtgtccg accaccgcgt ccggcacgac cccatgcgcc tgccacagcg cggccaggct  22200
caccgcgacc gcccagctgg ccggctggac cacctccacc cgctccgcca catccggccg  22260
cgccaacatc tcccgcacat cccagcccgt gtgcggcaac aacgcccgcg cacactcctc  22320
catacgagcc gcgaacaccg cagaacacgc catcaactcc acacccatgc ccacccactg  22380
agcaccctgc ccgggaaaga cgaacaccgt acgcggctga tccaccgcca cacccatcac  22440
ccgggcatcg cccaacaaca ccgcacggtg accgaagaca gcacgctcac gcaccaaccc  22500
ctgcgcgacc gcggccacat ccacaccacc cccgcgcaga taccctcca gccgctccac  22560
ctgccccgc agactcacct cactccgagc cgacaccggc aacggcacca acccatcgac  22620
agccgactcc ccacgcgacg gcccgggaac accctcaagg atcacgtgcg cgttcgtacc  22680
gctcaccccg aaagcggaga caccggcccg gcgcggacgt cccgcgtcgg gccacgcccg  22740
cgcctcggtg agcagttcca ccgcgccctc ggtccagtcc acatgcgacg acggctcgtc  22800
cacatgcagc gtcttcggcg cgatgccata ccgcatcgcc atgaccatct tgatgacacc  22860
ggcgacaccc gcagccgcct gcgcatgacc gatgttcgac ttcaacgaac ccagcagcag  22920
cggaaccctca cgctcctgcc cgtacgtcgc cagaatcgcg tgcgcctcga tgggatcgcc  22980
cagcgtcgtc cccgtcccgt gcgcctccac cacgtccacg tcggcggggg cgagccccgc  23040
cttgtggagg gcctggcgga tgacgcgctg ctgggagggg ccgttgggtg cggagatgcc  23100
gttggaggcg ccgtcctggt tgacggcgga ggagcggacg accgcgagga cggtgtgtcc  23160
gttgcgctcg gcgtcggaga gcttttcgac gacgaggacg ccggcccccct cggcgaaacc  23220
ggtgccgtcc gccgcgtcag cgaacgcctt gcaccgtccg tccggcgcga cgccgccctg  23280
ccgggagaac tccacgaagg tctgtggtga tgccatcact gtgacaccac cgaccagcgc  23340
cagcgagcac tccccggtcc gcagcgcctg cccggcctgg tgcagcgcga ccagcgacga  23400
cgaacacgcc gtgtcgaccg tgaccgccgg accctccatg ccgaagaagt acgacagccg  23460
tccggcgagc accgcgggct gtgtgctgta ggcgccgaat ccgcccaggt ccgcgcccgt  23520
gccgtagccg tagtagaagc cgccgacgaa gacgccggtg tcgctgccgc gcagggtgtc  23580
cggcacgatg ccggcgtgtt cgagcgcctc ccaggcgatt tcgaggagga tccgctgctg  23640
cgggtcgagt gcggtggcct cgcgcggact gatgccgaag aacgcggcat cgaagtcggc  23700
ggcgcccgcg agtgcgccgg cccgcccggt ggcggactcg gcggcggcgt gcagcgcggc  23760
cacgtcccag ccgcggtcgg tggggaagtc gccgatcgcg tcgcggccgt ccgcgacgag  23820
ctgccacagc tcttccggtg aggtgacgcc gcccggcagt cggcaggcca tgccgacgac  23880
ggcgagcggc tcgttcgccg cggcgcgcag cgcggtgttc tcccggcgga gctgcgcgtt  23940
gtccttgacc gacgtccgca gcgcctcgat caggtcgttc tcggcatcg cctcatccct  24000
tcagcacgtg cgcgatgagc gcgtctgcgt ccatgtcgtc gaacagttcg tcgtccggct  24060
```

```
ccgcggtcgt ggtgctcgcg ggtgcctgtg ccggtggttc accgccgtcc ggggtcccgt     24120
tgtcgtccgg ggtcccgttg acgtccgggg ccaggagggt cagcagatga cgggtgagcg     24180
cgccggcggc gggatagtcg aagacgagcg tggccggcag cggaatgccg agggcctcgg     24240
agagccggtt gcgcaggccg agcgcggtga gcgagtcgac cccgaggtcc ttgaacgccg     24300
tggtggccgt gaccgccgcc gcgtcggtgt ggcccagcag ggtggcggcg gtgtcgcgga     24360
cgacgccgag cagcacctgt tcccgttcct tgtggggcag gtccggcagg cgttccagca     24420
gggagccgcc gtcggtcgcg gagcgccggg tggggcgctg gatcggtcgc cacagcggtg     24480
acgggtcgcc gggcccgggt ggggcggtcg ccacgaccac ggcttccccg gtggcgcacg     24540
cggcgtcgag gaggtcggtc agccggtccg ccgcggcggt gaacgccacg gccggcaggc     24600
cttgtgcccg gcgcaggtcg gccagggcct ggagcggtcc ggccgcctcg ccggacggaa     24660
cggcgagaac gaacgcggtc aggtcgaggt cgcgggtcag gcggtgcagt tcccaggccg     24720
actcggcggt gccgtccgcg tggacgaccg cggtcaccgg ggtttccggc actgtgcccg     24780
gctcgtaccg gatcacttcg gcgccgtgtc cgccgaggtg tccggcgagt tcctccgaac     24840
cgcccgcgag gaggacggtg tcgccgtacg aggccgcggc cgtggtgggc gcggcgggga     24900
cgaggcgggg cgcttcgagg cgcccgtcgg ccaggcgcag gtgcggttcg tcgaggcggg     24960
agagggcggc ggcgcggcgg ggggtgaccg tgtcggtggt ctccacgagc acgagccggc     25020
ccggttccgc ggtgtcgagc agtgcggcga cggcaccggc gacgggcccg gcctcggcgg     25080
acaccaccag cgtggcgccg gcggtcctcg ggtcgtccag tgcggtacgg acctcgtcgg     25140
gaccggatac cgggacgacg atgacgtcgg gcgtggcgtc gtcgccgagg tcggtgtacc     25200
ggcgggccgt ggtgccgggt gccgccgggg cccggacgcc ggtccaggtg cgccggaaca     25260
gccgcacgtc cccgtccggg cccgtcgtgg cgggggccg ggtgatgagc gagccgatct     25320
gagccaccgg ccgtcccagt tcgtcggcga ggtgcacgcg ggcgccgccc tcgccctcgc     25380
cgtggacgaa ggtgacgcgc agtttcgtgg cgccgctggt gtggacacgg acgccggtga     25440
acgcgaacgg caaccgtacc cccgcgttct cggcggccgc gccgatgctg cccgcttgca     25500
gcgcggtgac gagcagcgcc gggtgcagtg tgtagcgggc ggcgtccctg gcgagggcgc     25560
cgtcgagggc gacttcggcg cagacggtgt ctccgtggct ccacgcggcg acatgccgc     25620 ggaactcggg gccgaactcg tatcccgcgt cgtcgagtcg ctggtagaag ccgcgacgt     25680 cgaccggttc cgcgtgctcg ggcggccagg gccccggcgt ggtggccggt tcggtggtgg     25740
cgatgccggc gaagccggag gcgtggcggg tccatgtccg gtcgccgtcc gtccgggcgt     25800
ggacgcgcac ggcacggcgt ccggtgtcgt cgggcgcggc gacggtcacg cgcacctgga     25860
cggcgccggt ggcgggcagg accagcggtg tctcgacgac cagttcgtcg agcaggtcgc     25920
agcctgcctc gtcggcgccg cgtccggcca attccaggaa ggcgggtccg ggcagcagta     25980
cggcgccgtc gacggagtga ccggccagcc atgggtgggt ggccagcgag aaccggccgg     26040
tgagcagcac ctcgtcggag tcggggagcg ccaccgacgc ggcgagcagc gggtggtcga     26100
cggcgtcgag tccgaggccg gaagcgtccg tgccggccgc ggtctcgatc cagtagcgct     26160
catggtggaa ggcgtatgtg ggcaggtcgt gtgccgtcgc cgtcgcgggg acgaccgccg     26220
cccagtcgac gggcacgccg gttgtgtgcg cctcggccag cgcggtgagc agccggtgga     26280
ctcccccgcc gcggcggagc gtggcgacgg tcgcgccgtc gatcgcgggc agcagcacgg     26340
ggtgcgcgct gacctcgacg aacacggtgt cacccggctc gcgggcagcg gtcacggccg     26400
```

```
tggcgaagcc tacggggtgg cgcatgttgc ggaaccagta ctcgtcgtcg agcggcgcgt   26460
cgatccagcg ttcgtcggcg gtggagaacc acgggatctc gggcgtgcgc gaggtggtgt   26520
ccgcgacgat ccgctggagt tcgtcgtaca gcgggtcgac gaacggggtg tgggtcgggc   26580
agtcgacggc gatgcggcgc acccagacgc cgcgggcctc gtagtcggcg atcagcgttt   26640
cgacggcgtc cgggcgcccg cgacggtcg tggtggtggc gccgttgcgg cccgcgaccc    26700
agacgccgtc gatccgggcg gcatccgcct cgacgtcggc ggccgggagc gcgaccgagc   26760
ccatcgcgcc gcgtccggcg agttcgcgca ggagcaggag aacgctgcgc agcgcgacga   26820
ggcgggcacc gtcctccagg gtgagcgctc cggcgacaca ggccgcggcg atctcgccct   26880
gggagtgtcc gatgacggcg tccgggcgta cgcccgcggc ctcccacacg gcggccagcg   26940
acaccatgac ggcccagcag acgggtgca cgacgtcgac gcggcgggtc acctccgggt    27000
cgtcgagcat ggcgatgggg tcccagcccg tgtgcgggat cagcgcgtcg gcgcattggc   27060
gcatcctggc ggcgaacacc ggggaggccg ccatcagttc gacgcccatg ccgcgccact   27120
gcggtccttg tccggggaag acgaagacgg tgcgcggctc ggtgagcgcc gtgccggtga   27180
cgacgtcgtc gtcgagcagc acggcgcggt gcgggaacgt cgtacgcctg gcgagcaggc   27240
ccgcggcgat ggcgcgcggg tcgtggccgg gacgggcggc gaggtgctcg cggagtcggc   27300
ggacctggcc gtcgagggcc gtggcggtcc gcgccgagac gggcagtggt gtgagcggcg   27360
tggcgatcag cggctcaccg ggcttcgagg ccgacggctc ctcggccggc ggctccccgg   27420
ccgggtgggc ttccagcagg acgtgggcgt tggtgccgct gacgccgaag gaggacacac   27480
cggcgcgccg cgggcggtcg gtctcgggcc agggccgggc atcggtgagg agttcgacgg   27540
cgccggccgt ccagtcgacg tgcgaggacg gcgtgtccac gtgcagggtg cgcggcaggg   27600
tgccgtgccg catggcgagg accatcttga tgacaccggc gacacccgcg gcggcctgag   27660
tgtggccgat gttggacttc agcgagccca gcagcaccgg ggtgtcgcgc ccctgcccgt   27720
aggtggccag caccgcctgt gcctcgatgg gatcgcccag cctggtgccg gtgccgtgcg   27780
cctccacggc gtccacgtcc gccggggtga gccggcgttt ggccagggcc tgccggatca   27840
cccgctcctg cgagggcccg ttcggcgccg acaacccgtt ggaagcaccg tcctggttga   27900
ccgccgaacc ccggacaacc gccagcacac ggtggccgtt gcgctcggca tcggagagcc   27960
tctcgacgat cagcacaccg gacccctcgg cgaaaccggt gccgtcagcc gcatccgcga   28020
acgccttgca gcgcgcgtcg ggcgcgagac cccgctgctg ggagaactcg acgaagccgg   28080
acggcgaggc catcaccgtg acgccgccga ccagggcgag cgagcattcg ccggagcgca   28140
gtgactgccc ggcctggtgc agcgccacca gcgacgacga acacgccgtg tcgaccgtga   28200
ccgccggacc ctcagaccg tagaagtacg acagccgacc ggacagcaca ctggtctggg    28260
tgccggtcgc gccgaaaccg cccaggtcgg tgccgagtcc gtaccgtcg gagaaggcgc     28320
ccatgaacac gccggtgtcg cttccgcgca gcgactccgg gaggatcccg gcgtgttcca   28380
gcgcctccca cgaggtctcc aggaccagac gctgctgcgg gtccatcgcc agcgcctcac   28440
gcggactgat cccgaagaac gccgcgtcga agtccgccac cccggcgagg aagccaccat   28500
gacgcacggt cgacgtgccc ggatgatccg gatcgggatc gtacagcccg tccacgtccc   28560
aaccacggtc cgtcggaaac gccgtgatcc cgtcaccacc cgactccagc agccgccaca   28620
agtcctccgg cgacgcgacc ccacccggca gccggcaggc catcccacg atcgccaacg     28680
gctcgtcctg ccggacggcc gcggtcgtgg tgcgggtcgg cgatgccgtc cggcgggaca   28740
gcgccgcggt gagcttcgcc gcgacggcgc gcggcgtcgg gaagtcgaag accgcggtgg   28800
```

```
cgggcagccg tacgcccgtc gcctcggtga aggcgttgcg cagccggatc gccatgagcg   28860
agtcgacgcc gagttccttg aacgtggcgg tcgcctcgac ccgtgcggca ccgtcgtggc   28920
cgagtacggc cgcggtgcac tgccggacga cggcgagcac gtccttttcg gcgtccgcgg   28980
cggagagccg cgcgatccgg tcggcgaggg tggtggcgcc ggccgcccgg cgccgcggct   29040
cccgcgcggg tgcgcgcagc aggggcgagc tgccgaggcc ggccgggtcg gcggcgacca   29100
gcgccgggtc cgaggaccgc aacgccgcgt cgaacagcgt cagtccgcct tcggcggtca   29160
gcgccgtcac gccgtcgcgg cgcatgcggg cgccggtgcc gaccgtcagc ccgctctccg   29220
gttcccacag gccccaggcc acggacaacg cgggcagtcc ggctgccgg cgctgttcgg   29280 ccagcgcgtc gaggaacgcg ttcgcggccg cgtagttgcc ctgtccgggg ctgccgagca   29340
caccggcggc cgacgagtag aggacgaacg cggccagttc cgtgtcctgg gtgagttcgt   29400
gcaggtgcca cgcggcgtcc accttcgggc gcagcaccgt ctcgagccgg tcggggggtga  29460 gcgcggtgag gacgccgtcg tcgaggacgg ccgcggtgtg cacgacggcc gtgagcgggt   29520
gcgccgggtc gatccccgcc agtacgagg cgagttcgtc ccggtcggcg acgtcgcagg   29580
cgatcgccgt gacctcggcg ccgggcacgt cgctcgccgt gccgctgcgc gacagcatca   29640
gcagccggcg cacgccgtgg cgttcgacga ggtggcggct gatgatgccg gccagcgtcc   29700
cggagccacc ggtgacgagc acggtgccgt ccgggtcgag cgccggagcg tcacccgccg   29760
ggaccgccgg ggccagacgg cgggcgtaca cctggccgtc acgcagcacc acctggggct   29820
catcgagcgc ggtggccgct gcgagcagcg gctcggcggt gtccggggcg cgtcgacga   29880 ggacgatccg gccggggtgt tcggcctgcg cggtccgcac cagtccggcg ccgcgggccg   29940
acgcgagacc gggcccggtg tggacggcca ggaccgcgtc ggcgtaccgg tcgtcggtga   30000
ggaagcgctg cacggcggtc aggacgccgg cgcccagttc gcgggtgtcg tcgagcgggg   30060
caccgccgcc gccgtgcgcg gggaggatca ccacgtccgg gaccgtcggg tcgtcgaggc   30120
ggccggtcgt cgcggtcgtg ggcggcagct ccgggagctc ggccagcacc gggcgcagca   30180
ggcccggaac ggctcccgtg atcgtcaggg ggcgcctgcg cacggcgccg atggtggcga   30240
cgggcccgcc ggtctcgtcc gcgaggtgta cgccgtcagc ggtgacggcg acgcgtaccg   30300
ccgtggcgcc ggtggcgtgg acgcggacgt cgtcgaacgc gtacggaagg tggtcccctt   30360
ccgcggcgag gcggagtgcg gcgccgagca gcgccgggtg caggccgtac cgtccggcgt   30420
cggcgagctg tccgtcggcg agggccactt ccgcccagac ggcgtcgtcg tcggcccaga   30480
cggcgcgcgg gcggggcagc gcgggcccgt ccgtgtaccc ggctcgggcc agacggtcgg   30540
cgatgtcgtc ggggtccacc ggccgggccg tgcggggcgg ccacgtcgac ggcatctccc   30600
gcacggccgg ggccgtccgc gggtcggggg cgaggattcc gtgcgcgtgc tcggtccact   30660
cccccgccgc gtgccgcgtg tgcacggtga ccgcgcggcg gccgtccgcc ccgggcgcgc   30720
tcaccgtgac ggagagcgcg agcgcaccgg accgcggcag cgtgaggggg gtgtccacgg   30780
tgaacgtgtc gagggcgccg cagccggctt cgtcgcccgc ccggatcgcc agatccagga   30840
gggccgcggc gggcagcacc gcgaggccgt gcagggagtg cgccagcgga tcggcggcgt   30900
cgacccggcc ggtgagcacc aggtcgccgg tgccgggcag ggtgaccgcc gcggtcagcg   30960
ccgggtgcgc gaccggcgtc tgtccggccg gggccgcgtc gcccgcggtc tgggtgccga   31020
gccagtagcg gacccgctcg aacgggtacg tcgcgggtg cgaggcgcgt gccggcgcgg   31080
ggtcgatgac cttcggccag tcgaccgtga cgccgtcggt gtgcagccgg gcgagcgcgg   31140
```

```
tcagggcgga tcgcggttcg tcgtcggcgt gcagcatcgg gatgccgtcg acgagtcggg    31200
tcaggctccg gtccgggccg atctccagga gcaccgcccc gtcgtgcgcg gcgacctgtt    31260
ccccgaaccg gacggtgtcg cggacctgtc gtacccagta ctccggcgtg gtgcaggcgg    31320
cgcccgcggc catcgggatc ctcggctcgt ggtacgtcag gctctccgcg accttgcgga    31380
actcctcgag catcggctcc atccgcgccg agtggaacgc gtggctggtc cgcaggcggg    31440
tgaagcggcc gagccgggcc gcgacgtcga gcaccgcctc ctcgtcaccg gagagcacga    31500
tcgacgcggg cccgttgacc gcggcgatct ccacgccgtc ccgcagcagc ggcagcgcgt    31560
cccgttccga cgcgatcacg gcggccatcg ccccgccgga cggcagcgcc tgcatcaggc    31620
gggcccgtgc ggacaccagc ctgcacgcgt cctccaggga ccagacgccg gcgacgtacg    31680
cggcggccag ctcgccgatc gaatggccca cgaaggcgtc cgggcgtacg ccccacgcct    31740
cgagctgtgc gccgagtgcg acctggagcg cgaacaccgc gggctgggcg tacccggtgt    31800
cgtggaggtc gagcccggcg ggcacgtcga gggcgtccag cacctcgcgg cgagtgcggg    31860
cgaagacgtc gtaggcggcg gccagtccgt cgcccatgcc gggacgttgt gagccctgtc    31920
cggagaagag ccacacgagg cggcggtccg gttctgcggc gccggtgacc gtgtcggtgc    31980
cgatcagcgc ggcccggtgc gggaaggccg tgcgggcgag cagggccgcg gccaccgcgc    32040
gctcgtcctc ctcgccggtg gcgaggtggg cgcgcaggcg gtgtacctgt gcgtcgagtg    32100
cctgcggggt gcgtgccgag agcagcaggg gcagcggtcc ggtgtcgggt gccggggcgg    32160
gttcgggggc cggtcggggg tggctttcga ggatgatgtg agcgttggtg ccgctaacgc    32220
cgaaggagga caccccggcg cgccgtgggc ggtcggtttc gggccagggg cgggcgtcgg    32280
tgaggagttc gacggcgccg gccgtccagt cgacgtgcga ggacggcgtg tccacgtgca    32340
gggtgcgcgg cagggtgccg tgccgcatgg cgaggaccat cttgatgaca ccggcgacgc    32400
ccgcggcggc ctgagtgtgg ccgatgttgg acttcagcga gcccagcagc accggggtgt    32460
cgcgatgctg cccgtaggtg gccagtaccg cctgcgcctc gatgggtcg cccagcctgg    32520 tcccggtgcc atgcgcctcg acagcgtcca catccgccgg ggtgagcccg gcgttggcca    32580
gcgcctgccg gatcacccgc tcctgcgacg gcccgttcgg cgccgacaac ccgttggaag    32640
caccgtcctg gttgaccgcc gaaccacgca cgaccgccag gacattgtgg ccgtgccgct    32700
cggcgtcgga gagcctctcg acgatcagca caccggatcc ctcggcgaaa ccggtgccat    32760
cagccgcatc cgcgaacgcc ttgcagcggc cgtccgggga gaggccccgc tgctgggaga    32820
agtccacgaa gccggacggc gaggccatca ccgtgacgcc gccgaccacg gcgagcgagc    32880
actcccccga gcgcagcgac tgcccggcct ggtgcagcgc caccagcgac gacgaacacg    32940
ccgtgtccac cgtgaccgcc ggaccctcca aaccgtagaa gtacgacagc cgaccggaca    33000
gcacactggt ctgggtgctg gtggcaccga aaccgccgcg gtcggctcca gtgccgtacc    33060
cgtagaagta gccgcccatg aacacgccgg tgtcgcttcc gcgcagcgac tccgggagga    33120
tcccggcgtg ttccagcgcc tcccacgagg tctccaggac cagacgctgc tgcgggtcca    33180
tcgccagcgc ctcacgcgga ctgatcccga agaacgccgc gtcgaagtcc gccaccccgg    33240
cgaggaagcc accatgacgc acggtcgacg tgcccggatg atccggatcg ggatcgtaca    33300
gcccgtccac gtcccaacca cggtccgtcg gaaacgccgt gatcccgtca ccacccgact    33360
ccagcagccg ccacaagtcc tccggcgacg cgaccccacc cggcagccgg caggccatcc    33420
ccacgatcgc caacgcctcg tcctgccgga cggccgcggt cggggtacgc cgccgggtgg    33480
tggcccgcgc gccggccagt tcgtccaggt gggcggcgag cgcctgcgcc gtggggtggt    33540
```

-continued

```
cgaagacgag cgtagcgggc agcgtcaggc ccgtcgcgtc ggccagccgg ttgcgcagtt    33600
cgacgccggt cagcgagtcg aagcccactt ccctgaacgc gcgcgcgggt gcgatggcgt    33660
gggcgtcgcg gtggccgagc accgcggcag cgctggtacg gacgaggtcg agcatgtcgc    33720
gcgcggccgg aggtgcggac gtgcgccgga cggccggcac gagggtgcgt aggaccggcg    33780
ggacccggtc ggacgcggcg acggcggcga ggtcgagccg gatcggcacg agcgcgggcc    33840
ggtcggtgtg cagggccgcg tcgaacaggg cgagcccctg tgcggccgtc atcggggtca    33900
tgccgttgcg ggcgatgcgg gccaggtcgg tggcggtcag ccgcccgccc atcccgtccg    33960
ccgcgtccca cagtccccag gcgagcgaga cggcgggcag ccctggtgg tgccggtggc      34020 gggcgagcgc gtcgaggaac gcgttgccgg tcgcgtagtt ggcctgaccc cgccgccga    34080 acgtggcgga tatggacgag tacaggacga acgcggccag gtcgagatcg cgcgtcagct    34140
cgtgcaggtg ccaggcgacg tccgccttga cccgcagcac ggcgtccac tgctccggcc      34200 gcatggtcgt cacggccgcg tcgtcgacga tcccggccat gtgcacgacg gcgcgcagcc    34260
gctgggcgac gtcggcgacg actgcggcca gtcgtcgcg gtcgacgacg tcggcggcca      34320
cgtaccgcac gcggtcgtcc tccggcgtgt cgccgggccg gccgttgcgg gacaccacga    34380
cgacctcggc ggcctcgtgc acggtgagca ggtggtccac gaggaggcgg ccgagcccgc    34440
cggtgccgcc ggtgacgagg acggtcccgc cggtcagcgg ggaggttccg gtggccgcgg    34500
cgacacggcg cagacgggcc gcacgcgctg tgccgtcggc gacccggacg tgcggctcgt    34560
cgccggcggc gagcccggcc gctatggcgg cgggcgtgat ctcgtccgct tcgatcaggg    34620
cgacgcggcc gggatgctcc gtctccgccg tccggaccag ccgccgagc gcttcctgcg      34680 cgggatcgcc ggtacgggtg gccacgatga gccgggatcg cgcccagcgc ggctcggcga    34740
gccaggtctg cacggtggtg agcaggtcgc ggcccagctc ccgggtccgg gcgccgggcg    34800
aggtgcccgg gtcgccgggt tccacggcca ggaccacgac cggggggtgc tcgccgtcgg    34860
gcacgtcggc gaggtacgtc cagtcgggga cgggtgacgc gggcacgggc acccaggcga    34920
tctcgaacag cgcctcggca tcggggtcgg cggcccgcac ggtcaggctg tcgacgtcaa    34980
ggaccggtga gccgtgctcg tccgtggcga cgatgcggac catgtcgggg ccgacgcgtt    35040
ccagcagcac gcgcagcgcg gtcgcggcgc gcgcgtggat cctcacgccg gaccaggaga    35100
acgccagccg gcgccgctcc gggtccgtga agaccgtccc gagggcgtgc agggccgcgt    35160
cgagcagcac ggggtgcagc ccgtaccggg cgtcggtgag ctgttcggcg aggcggaccg    35220
acgcgtaggc gcggccctcc cccgtccaca tcgcggtcat ggcccggaac gcgggcccgt    35280
acgagagcgg cagcgcgtcg tagaagccgg tcaggtcggc cgggtcggcg tcggcgggcg    35340
gccagtccac gggctccgcc ggaccgccag tgtccacgct cagcgctccg gtcgcactga    35400
gcgcccaggg gcccgtgccg gtacggctgt gcagactcac cgaccgccgt ccggacacct    35460
cggttccgac ggtggcctgg atctccgtgt cgccgtcgcc gtcgaccacc accggcgcga    35520
cgatggtcag ctccgcgatc tccggcgtgc cgagccgggc tcccgcttcg gcagcagtt      35580 ccacgagcgc cgagccgggc acgatgaccc ggccgtccac ctcgtggtcg gcgagccagg    35640
gctgacggcg taccgagaca ccgcggtggc cagcgcgccc tcgccgtcgg gcgaggtcga    35700
cccacgagcc gagcagcggg tggccggacg ttccgccgg ttccgcgtcg atccagtagc      35760
ggtcacggcg gaacgggtac gtgggcagcg gcaccaccg acgcgtcgcg aacgaccagg      35820
tgacgggcac gccccggacc cagagcgcgg cgagcgaccg agtgaagcgg tccaggccgc    35880
```

-continued

| | |
|---|---|
| cctcgcctcg ccgcagtgtg ccggtgacga ccgtatgcgc atgcccggcg agcgtgtcct | 35940 |
| ccagtgcggt ggtgagcacg ggatgcgcgc tgacctcgac gaacgcgcgg tatccgcggt | 36000 |
| ccgccaggtg gccggtcgcg gcggcgaacc gaacggtgcg gcgcaggttg tcgtaccagt | 36060 |
| aggcggcgtc cgcgggccgg tccagccacg cctcgtccac ggtggagaag aacgggacgt | 36120 |
| ccggcgtgcg cggagtgatg ccggcgagag cgtcgagcag cgcgccgcgg atcgtttcga | 36180 |
| catgcgcggt gtgcgacgcg tagtcgacgg cgatccggcg ggcgcggggg gtggcggcca | 36240 |
| gcagctcctc cacggcgtcg gccgcaccgg cgacaacgat cgacgcgggt ccgttgaccg | 36300 |
| cggcgacctc caggcgcccg gcccacacgg cggcgtcgaa gtcggcgggc ggcaccgaga | 36360 |
| ccatgccgcc ctgcccggcc agttcggtgg cgacgagtcg gctgcgcacc gcgacgacct | 36420 |
| tcgcggcgtc gtccagggtg agcaccccgg cgacgcaggc cgcggcgact cgccctgggg | 36480 |
| agtggccgac gaccgcggcc ggggcgaccc cgtgcgcacg ccacagctcc gccagcgcca | 36540 |
| ccatcaccgc gaacgacgcg ggctgcacga catcgacccg gtcgaacgcg ggcgctccgg | 36600 |
| gccgctgggc gatgacgtcc agcaggtccc atccggtgtg cggggcgagc gccgtggcgc | 36660 |
| actcgcggag ccgccgggcg aacacgggct cggtggcgag cagttcggca cccatgccgg | 36720 |
| cccactggga gccctgcccg gggaacgcga acacgacacg tgtgtcggtg acgtcggcgg | 36780 |
| ttcccgtcac ggcccccggc acttcggcac cacgggcgaa cgcctccgcc tctcgggccg | 36840 |
| gcacgaccgc ccggtggcgc atggccgtcc gggtggtggc gagcgagtgg ccgaccgcgg | 36900 |
| ccgcggcgcg agtgagcggg gccagctgtc ccgcgacgtc ccgcagtccc tccgggtcc | 36960 |
| gggccgacat cggccagacc acgtcctcgg gcaccggctc ggcttcgggt gcggacacgg | 37020 |
| gtgcgggcgc ggcgggggc ccggcctcca ggacgacatg ggcgttggtg ccgctgatgc | 37080 |
| cgaacgacga gacacccgca cgccgggcgc gcccggtgac cggccacggc tcactgcggt | 37140 |
| gcagcagccg gatgtcgccg tcccagtcga cgtgccggga cggctcgtcg acgtgcagcg | 37200 |
| tgcgcggcag gacgccgtgc cgcatcgcca tgaccatctt gatgacgccg gcgacgccgg | 37260 |
| ccgcggcctg ggtgtggccg atgttcgact tgagcgagcc gatcagcagc ggatgcacgc | 37320 |
| gttcgcgccc gtaggccact tgcagggcct gggcctcgac ggggtcgccg agacgggtgc | 37380 |
| cggtgccgtg tgcctccacg gcgtcgacgt cacccggcgc caggccggcg tcggcgagcg | 37440 |
| cacgctggat gacgcgctgc tgcgcaggcc cgttcggggc ggacagcccg ttcgacgcgc | 37500 |
| cgtcggagtt gaccgcggag ccgcgcacca gcgccagcac ggggtggccg tggcgggtgg | 37560 |
| cgtcggagag ccgctccagc accaggacac cggcgccctc ggcgaagctc gtgccgtccg | 37620 |
| cggtgtccgc gaaggccttg gcacggccgt cgggggcgag cccgcgctgc cgggagaact | 37680 |
| cgacgaaccc ggtcgtcgtc gccatcaccg tgacaccgcc gaccagggcg agcgagcact | 37740 |
| cccccgagcg cagcgaccgc gcggcctggt gcagcgccac cagcgacgac gaacacgccg | 37800 |
| tgtcgacggt gaccgacggg ccctccagac cgaagtagta cgagagccgc ccggagagaa | 37860 |
| cgctggtcgg cgtgccggtc gccccgaaac cgcccaggtc cacgcccgcg ccgtagccct | 37920 |
| gggtgaacgc gcccatgaat acgccggtgt cgctgccgcg gacgctttcg ggcaggatgc | 37980 |
| ccgctcgttc gaacgcctcc cacgacgctt cgaggaccag acgctgctgc gggtccatcg | 38040 |
| ccagcgcctc acgcgggctg atcccgaaga acgcggcgtc gaagtcggcg cgccggtga | 38100 |
| ggaagccgcc gtgacgcacg gaaaccttgc cgaccgcgtc ggggttcggg tcgtagagcg | 38160 |
| cggcgaggtc ccagccgcgg tcggcgggga actcggtgat cgcgtccccg ccggagtcga | 38220 |
| ccagccgcca caggtcctcc ggtgaccgca cgccaccggg catccggcac gccatggcca | 38280 |

```
cgatcgccag cggctcgttc cccgccaccg tcggtgcggg cactgtcgcc gccggagcgg    38340
caggggccgg ctcaccccgc cgttcctcat ccaggcgggc ggcgagcgcg ccggtgtcg     38400 ggtggtcgaa gacggccgtc gcggagagcc gtaccccgt cgtctcggcg aggctgttgc    38460
gcaaccggac accgctgagc gagtcgatgc cgaggtcctt gaacgccgtc gtgggcgtga    38520
tctcggaggc gtcggcgtgg ccgagcacgg cggccgtggc cgcacacacg atggccagca    38580
ggtcacgatc gcggtcgcgg tcgcggtcgc ggttgtcctc cgcacgggcg gcgatgcggc    38640
gctcggtccg ctgccggacg ggctcggtgg gaatcgccgc gaccatgaac ggcacgtccg    38700
cggcgaggct cgcgtcgatg aagtgggtgc cctcggcctc ggtgagcggc cggaacccgt    38760
cgcgcacccg ctgccggtcg gcgtcgtcaa gttgtccggt gagggtgctg gtggtgtgcc    38820
acatgcccca ggcgatggag gtggcgggtt ggccgagggt gtggcggtgg gtggcgaggg    38880
cgtcgaggaa ggcgttggcg gcggcgtagt ttccttgtcc ggggctgccg aggacgcgg    38940 cggcgctgga gtagaggacg aagtgggtga ggggttggtt ttgggtgagg tggtgcaggt    39000
gccaggcggc gttggctttg gggtggagga cggtggtgag gcggtcgggg gtgagggcgt    39060
cgaggatgcc gtcgtcgagg gtggcggcgg tgtggaagac ggcggtgagg ggttgggga    39120 tgtgggcgag ggtggtggcg agttggtggg ggtcgccgac gtcgcagggg aggtgggtgc    39180 cggggggtggt gtcgggggt ggggtgcggg agaggaggta ggtgtggggg tggttcaggt    39240
ggcgggcgag gatgccggcg agggtgccgg agccgccggt gatgatgatg gcgtgttcgg    39300
ggttgagggg ggtggtggtg ggtgggtgg tggtgtggag ggggtgagg tggggtcggt    39360 ggagggtgtg gtgggtgagg cggaggtggg ggtggtcgag ggtggcgagt tgggccaggg    39420
ggagggaagt gtggggtgg tcggtttcga tgaggcggat gcggtggggg tgttcgttct    39480
gggcggtgcg ggtgaggccg gtgacggtgg cgccggcggg gtcggtggtg gtgtggacga    39540
tgagggtgtg gtcggtggtg gtgaggtggt gttgcagggc ggtcaggacg cgggtggcgc    39600
gggtgtgggc gcgggtgggt atgtcctcgg ggtcgtcggg gtgggcggcg gtgatcagga    39660
cgtgtccctc gggcaggtca ccgtcgtaga ccgcctcggc gaccgcgagc cactccaacc    39720
ggagcgggtt cggccccgac ggggtgtcgg cccgctccct cagcaccagc gagtccaccg    39780
acacgacagg acgccatcc gggtcggcca cgcgcacggc gacgccggcc tcccccggg     39840 tgagggcgac gcgcaccgcg gcggccccgg tggcgttcag gcgcacgccc gtccaggaga    39900
acggcagctc gatcccgccg cccgcgtcga ggcgcccggc gtgcagggcc gcgtcgagca    39960
gtgccggatg cacaccgaaa ccgtccgcct cggcggcctg ctcgtcgggc agcgccacct    40020
cggcatacac ggtgtcacca tcacgccagg cagcccgcaa cccctggaac gccgacccgt    40080
actcataacc ggcatcccgc agttcgtcat agaacccga gacgtcgacg ccgcggccg     40140 tggccggcgg ccactgcgag aacggctcac cggaagcgtt ggaggtatcc ggggtgtcgg    40200
gggtcagggt gccgctggcg tgccgggtcc agctgcccgt gccctcggta cgcgcgtgga    40260
cggtcaccgg ccgccgtccg gcctcatcgg ccccttccac ggtcaccgac acatccaccg    40320
ctgcggtcac cggcaccacg agcggggatt cgatgaccag ttcatccacc accccgcaac    40380
cggtctcgtc accggcccgg atgaccagct ccacaaacgc cgtacccggc agcagaaccg    40440
tgccccgcac cgcgtgatca gccagccagg gatgcgtacg caatgagatc cggccggtga    40500
gaacaacacc accaccgtcg tcggcgggca gtgctgtgac ggcggccagc atcggatgcg    40560
ccgccccggt cagcccggcc gcggacaggt cggtggcacc ggccgcctcc agccagtacc    40620
```

-continued

```
gcctgtgctc gaacgcgtag gtgggcagat ccagcagccg ccccggcacc ggttcgacca    40680
ccgtgcccca gtccaccccc gcacccagag tccacgcctg cgccaacgcc cccagccacc    40740
gctcccagcc accgtcacca gtccgcaacg acgccaccgt gcgggcctgt tccatcgccg    40800
gcagcagcac cggatgggca ctgcactcca cgaacaccga cccgtccagc tccgccaccg    40860
ccgcatccag cgcgacaggg cgacgcaggt tccggtacca gtaccctca tccaccggct    40920 cggtcaccca ggcgctgtcc acggtcgacc accacgccac cgacccggtc ccgccggaaa    40980
ttcccttcag tacctcagcg agttcgtcct cgatggcctc cacgtgaggc gtgtgggagg    41040
cgtagtcgac cgcgatacga cgcacccgca ccccatcagc ctcataccgc gccaccacct    41100
cctccaccgc cgacgggtcc cccgccacca ccgtcgaagc cggaccatta cgcgccgcga    41160
tccacacacc ctcgaccaga cccacctcac cggccggcaa cgccaccgaa gccatcgccc    41220
cccggccggc cagccgcgcc gcgatcaccc gactgcgcaa cgccaccacg cgggcggcgt    41280
cctccaggct gagggctccg gccacacacg ccgccgcgat ctcccctgc gagtgtccga    41340 ccacagcgtc cggcacgacc ccatgcgcct gccacagcgc ggccaggctc accgcgaccg    41400
cccagctggc cggctggacc acctccaccc gctccgccac atccgaccgc gacaacatct    41460
cccgcacatc ccagcccgtg tgcggcaaca cgcccgcgc acactcctcc atacgagccg    41520
cgaacaccgg ggaacggtcc atgagttcca cgcccatgcc cacccactgg gcaccctgcc    41580
cggggaagac gaacaccgta cgcggctgat ccaccgccac acccatcacc cgggcatcac    41640
ccagcagcac cgcacggtga ccgaagacag cacgctcacg caccaacccc tgcgcgaccg    41700
cggccacatc caccccaccc ccgcgcagat acccctccag ccgctccacc tgccccgca    41760 gactcacctc accacgagcc gacaccggca acggcaccaa cccatcacca cccgactcca    41820
cacgcgacgg cccaggaaca ccctccagga tcacgtgcgc gttcgtaccg ctcaccccga    41880
acgacgacac acccgcatgc ggtgcccgat ccgactcggg ccacggcctc gcctcggtga    41940
gcagctccac cgcaccggcc gaccagtcca catgcgacga cggctcgtcc acgtgcagcg    42000
tcttcggcgc gatcccatgc cgcatcgcca tgaccatctt gatgacaccg gcgacacccg    42060
cagccgcctg cgcatgaccg atgttcgact tgaccgaacc gaggtagagc ggcgtgtcgc    42120
ggtcctgccc gtaggccgcg aggacggcct gcgcctcgat cgggtcgccc agccgcgtgc    42180
cggtgccgtg cgcctccacc acgtccacat cggcggcgcg cagtccggcg ttgaccaacg    42240
cctgccggat cacgcgctgc tgggcgacgc cgttggggc ggacagtccg ttggaggcac    42300
cgtcctggtt caccgccgag ccgcggacga ccgcgagaac ggtgtgcccg ttgcgctcgg    42360
cgtcggagag ccgctccagc acgagaacgc cgacgccctc ggcgaagccg gtcccgtccg    42420
ccgcgtcggc gaacgccttg caccgtccgt ccggggagag tccgcgctgc cgggagaact    42480
ccacgagctc tgcggtgttc gccatgacgg tgacaccgcc gaccagcgcc agggagcact    42540
ccccggcccg cagtgcctgt gccgcctggt gcagggcgac cagcgacgac gagcacgccg    42600
tgtcgaccgt gaccgccggg ccctgaagtc cgtacacgta cgagaggcgc ccggacagga    42660
cgctcgtctg cgtcgccgtg acaccgagcc cgcccaggtc ccggccgacg ccgtagccct    42720
ggttgaacgc gccatgaac acgccggtgt cgctctcccg gagcctgtcc ggcacgatgc    42780
cggcgttctc gaacgcctcc caggaggtct ccaggatcag gcgctgctgg gggtccatcg    42840
ccagcgcctc gttcggactg atgccgaaga acgcggcgtc gaacccggcg ccggccagga    42900
atccgccgtg gcgtgtcgtg gagcggccgg ccgcgtccgg gtccgggtcg tacagcgcgt    42960
cgacgtccca gccccggtcg gtggggaact cggtgatcgc ctcggtaccg gcggcgacga    43020
```

```
gccgccacag gtcctccggc gaggcgaccc cgccgggcag tcggcacgcc atgccgacga   43080
tcgcgacggg gtcgccggag ccgagggtct gggcggtcgc gggtgccgct gtcgcggagc   43140
cggcgaggtg ggcggcgaac gcacgcggag tggggtggtc gaacgcggtt gacgcgggca   43200
cccgcagacc cgtccgcgcg cgacggtgt tggtgaactc gacggtggtg agcgagtcga   43260
ggccgttctc gcggaacgtg cggtccgggg agcagtgtcc ggcgcccggc aggcccagga   43320
cggtggcgac gctgtcgcgg accaggtcga gcagtacgtc ctcccggccc gcacgggccg   43380
cggcgaggcg gttcgcccac tcctgttccg tggcgtcggg ctcggccggt ccggtcagtg   43440
cggtgaggat cggcggcgtg gcgcccgcca tcgtcgcggc ccgcgccccg gcggaaccgg   43500
tccgggccac gatgtacgag ccgccgcccg cgatggcctt ctcgatcagg tcgccggtga   43560
gcgccggccg ttcgatgccg ggcagcgcgc ggacggtgac ggtggggagt ccctccgcgg   43620
cccgtggccg ggtgtgggcg tcggcgccgg ccgggccgtc gagcaggacg tgcacgagcg   43680
cgccggggtt cgcggcttcc tcggctgcgg tggtcacgtg ggtgaggccg gtctcgtcgc   43740
ggagcaggcc ggcgacggtg tcggcgtcct ccccggtgac caggaccggc gcgtccgggc   43800
cgatcggagg cggcacggtg aggaccatct tgccggtgtg ccgggcgtgg ctcatccacg   43860
cgaacgcgtc ccgcgcacgg cggatgtccc acggctgcac cggcagcggg cacagctcac   43920
cgcggtcgaa caggtcgagg agcagttcga ggatctcccg caggcgcgcg ggatccacgt   43980
cggccaggtc gaacggctgc tgggcggcgt ggcggatgtc ggtcttgccc atctcgacga   44040
accggccgcc cggtgcgagc aggccgatgg acgcgtcgag gagttcaccg gtgagcgagt   44100
tgagcacgac gtcgaccggc gggaaggtgt cggcgaacgc ggcgctgcgg gagttcgcca   44160
catggtcggt gtcgaagccg tcggcgtgca gcaggtgttg tttggcggga ctggcggtgg   44220
cgtacacctc ggcgccgagg tggcgggcga tccgggtcgc cgccatgccg acaccgcccg   44280
tcgcggcgtg gaccaggacc ttctggccgg gtcgcagctc gcccgcgtcg acgaggccgt   44340
accaggcggt ggcgaacacg atgggcacgg acgcggcgat ggggaacgac catccccgtg   44400
ggatccgtgc gaccagccgc cggtccgcga ccacgctgcg ccggaacgcg tcctgcacga   44460
gaccgaacac gcggtcgccg ggggccaggt cgtcgacgcc gggtccgact tcggtcacga   44520
tgcccgcggc ctccccgccc atctcgccct cgcccgggta ggtgccgagc gcatcagca   44580
cgtcgcggaa gttcagcccc gcggcgcgga cgtcgatgcg gacctcgccg gcggccaggg   44640
gcgcggcggg acgtcgagcg gggcgacgac gaggtcgcgg agcgttccgg aggcgggcgg   44700
gcgcagcgcc cactggcgcg gtcggcaggg gggtggtgtc cgcgcgtacc agccggggca   44760
cgtaggccac gccggcccgc agcgcgatct ggggttcgcc gagcgaggcc gcggcgggga   44820
cgaggtcgtc atcgccgtcc gtgtccacca gcacgaacga tccgggttcg gcggcctggc   44880
ggcgcagcgc ctcgtcccag agccgggcct ggtccgcgtc cgggatctcg gccgggccga   44940
cgcccaccgc gcggcgggtg acgaccgtcc ggcggggtga cggggtgccg ggcaggtcgc   45000
gccgctccca gaccagttcg cacagcgtgg cctcgccact gccggtggcg accagatggg   45060
ccggcagccc cgcgagccgc gcgcgctgga ccttgcccga cgcggtgcgg gggatcgtgg   45120
tgacgtgcca gatctcgtcg ggcaccttga agtaggcgag ccggcggcgg cactcggcga   45180
ggatcgcctc ggcggggacg cggggccgt cggaaacgac gtagagcacg ggtatgtcgc   45240
cgaggacggg gtgcgggcgg cccgccgcgg cggcgtccg acaccggcc acctcctggg   45300
cgacggtctc gatctcccgg gggtggatgt tctccccgcc gcggatgatc agctccttga   45360
```

```
cccggccggt gatcgtcacg tgtccggtct cggcctgacg tgcgaggtcc ccggtgcggt    45420
accagccgtc cacgagcacc tgggcggtcg cctccggctg ggcgtggtag ccgagcatga    45480
ggctcggccc gctcgcccac agctcgccct cctcgccggg tgccacgtcg gcgccggaca    45540
ccgggtcgac gaaccgcagc gacaggcccg gcacgggcag cccgcacgag ccgggaaccc    45600
gcgcatcctc caggtgttg gcggtgagcg agccggtcgt ctcggtgcag ccgtacgtgt    45660
cgagcagggg cacgccgaac gtcgcctcga aatccctggt gagcgacgcc ggcgaggtgg    45720
atccggcgac cagcgccacg cgcagcgcgc gagcccgcgg ctcgccggac acggcgccga    45780
ggaggtagcg gtacatcgtc ggcacgccga cgagcacggt gctggagtgt tcggccaggg    45840
cgtcgaggac gtcacgcgcg acgaagccgc ccaggatacg gcggacgcg ccgaccgtga    45900
ggacggcgag caggcagagg tggtggccga ggctgtggaa cagcggggcg ggccagagca    45960
gttcgtcgtc ctcggtcagc cgccaggacg gcacgtcgca gtgcatcgcg gaccacaggc    46020
cgctgcgctg tgcggaaacc acgcccttgg gacggccggt ggtgccggag gtgtagagca    46080
tccaggcggg ttcgtccagg ccgaggtcgt cgcggggcgg gcacggcggc tcggtcccgg    46140
cgaggtcctc gtaggagacg cagtccggtg cccggcgccc gacgagcacg acggtggcgt    46200
cggtgccggt gcggcgcacc tggtcgaggt gggtttcgtc ggtgaccagc acggtcgcgc    46260
cggagtccgt caggaagtgg gcgagttcgg cgtcggcggc gtccgggttg agcgggacgg    46320
cgacggcggc ggcgcgggcg gcggcgaggt agacctcgat ggtctcgatc cggttgccga    46380
gcagcatcgc gacccggtcg ccgcggtcga cgccggacgc ggcgaggtgt ccggcgagcc    46440
ggccggcccg gagccggagt tgcgtgtacg tcacggcgcg ttgggaatcc gtgtaggcga    46500
tccggtcgcc gcgtcgctcg gcatggatgc ggagcaattc gtgcaacggc cggattggtt    46560
ccacacgcgc catggaaaca cctttctctc gaccaaccgc acaacagcac ggaaccggcc    46620
acgagtagac gccggcgacg ctagcagcgt tttccggacc gccaccccct gaagatcccc    46680
ctaccgtggc cggcctcccc ggacgctcat ctagggggtt gcacgcatac cgccgtgcgt    46740
aattgccttc ctgatgaccg atgccggacg ccagggaagg gtggaggcgt tgtccatatc    46800
tgtcacggcg ccgtattgcc gcttcgagaa gaccggatca ccggacctcg agggtgacga    46860
gacggtgctc ggcctgatcg agcacggcac cggccacacc gacgtgtcgc tggtggacgg    46920
tgctccccgg accgccgtgc acaccacgac ccgtgacgac gaggcgttca ccgaggtctg    46980
gcacgcacag cgccctgtcg agtccggcat ggacaacggc atcgcctggg cccgcaccga    47040
cgcgtacctg ttcggtgtcg tgcgcaccgg cgagagcggc aggtacgccg atgccaccgc    47100
ggccctctac acgaacgtct tccagctcac ccggtcgctg ggtatcccc tgctcgcccg    47160
gacctggaac tacgtcagcg gtatcaacac gacgaacgcg gacgggctgg aggtgtaccg    47220
ggacttctgc gtgggccgcg cccaggcgct cgacgagggc gggatcgacc cggccaccat    47280
gcccgcggcc accggtatcg gcgcccacg gggcggcatc acctgcgtgt tcctcgccgc    47340
ccggggcgga gtgcggatca acatcgagaa ccccgccgtc ctcacggccc accactaccc    47400
gacgacgtac ggtccgcggc ccccggtctt cgcacgggcc acctggctgg gccgccgga    47460
gggggggccgg ctgttcatct ccgcgacggc cggcatcctc ggacaccgaa cggtgcacca    47520
cggtgatgtg accggccagt gcgaggtcgc cctcgacaac atggcccggg tcatcggcgc    47580
ggagaacctg cggcgccacg gcgtccagcg ggggcacgtc ctcgccgacg tggaccacct    47640
caaggtctac gtccgccgcc gcgaggatct cgatacggtc cgccgggtct cgccgcacg    47700
cctgtcgagc accgcggccg tcgccctttt gcacaccgac atagcccgcg aggatctgct    47760
```

```
cgtcgaaatc gaaggcatgg tggcgtgaca atacccggta aaaggcccgc gacgctgcgc   47820
ctcggcggat ccgcgaagag aaagaagagc gtcaccgcac agcgcggcag cccggtcctt   47880
tcgtccttcg cacagcggcg gatctggttt ctccagcaat tggacccgga gagcaacgcc   47940
tataatctcc cgctcgtgca acgcctgcgc ggtctattgg acgcgccggc cctggagcgt   48000
gcgctggcgc tcgtcgtcgc gcgccacgag gcgttgcgga cggtgttcga caccgccgac   48060
ggcgagcccc tccagcgggt gcttcccgcc ccggaacacc tcctgcgcca cgcgcgggcg   48120
ggcagcgagg aggacgccgc ccggctcgtc cgcgacgaga tcgccgcgcc gttcgacctc   48180
gccaccgggc cgttgatcag ggccctgctg atccgcctcg gtgacgacga ccacgttctc   48240
gcggtgaccg tgcaccatgt cgccggcgac ggctggtcgt tcgggctcct ccaacatgaa   48300
ctcgcagccc actacacggc gctgcgcgac actgcccgcc ctgccgaact gccgccgttg   48360
ccggtgcagt acgccgactt cgccgcctgg gagcggcgcg aactcaccgg cgccggactg   48420
gacaggcgtc tggcctactg gcgcgagcaa ctccggggcg ccccggcgcg gctcgccctc   48480
cccaccgacc gtccccgccc gccggtcgcc gacgcggacg cgggcatggc cgagtggcgg   48540
ccgccggccg cgctggccac cgcggtcctc acgctcgcgc gcgactccgg tgcgtccgtg   48600
ttcatgaccc tgctggcggc cttccaagcg gtcctcgccc ggcaggcggg cacgcgggac   48660
gtgctggtcg gcacgcccgt ggcgaaccgt acgcgggcgg cgtacgaggg cctgatcggc   48720
atgttcgtca acacgctcgc gctgcgcggc gacctctcgg gcgatccgtc gttccgggaa   48780
ctcctcgacc gctgccgggc cacgaccacg gacgcgttcg cccacgccga cctgccgttc   48840
gagaacgtca tcgaactcgt cgcaccggaa cgcgacctgt cggtcaaccc ggtcgtccag   48900
gtgctgttgc aggtgctgcg gcgcgacgcg gcgacgccg cgctgcccgg catcgcggcc   48960
gaaccgttcc gcaccggacg ctggttcacc cgcttcgacc tcgaattcca tgtgtacgag   49020
gagccgggtg gcgcgctgac cggcgaactg ctctacagcc gtgcgctgtt cgacgagcca   49080
cggatcacgg ggttgctgga ggagttcacg gcggtgcttc aggcggtcac cgccgacccg   49140
gacgtacggc tgtcgcggct gccggccggc gacgcgacgg cggcagcgcc cgtggtgccc   49200
tcgaacgaca cggcgcggga cctgcccgtc gacacgctgc cgggcctgct ggcccggtac   49260
gccgcacgca cccccggcgc cgtggccgtc accgacccgc acatctccct cacctacgcg   49320
cagctggacc ggcgggcgaa ccgcctcgcg cacctgctcc gcgcgcgcgg caccgccacc   49380
ggcgacctgg tcgggatctg cgccgatcgc ggcgccgacc tgatcgtcgg catcgtgggg   49440
atcctcaagg cgggcgccgc ttatgtgccg ctggaccccg aacatcctcc ggagcgcacg   49500
gcgttcgtgc tggccgacgc gcagctgacc acggtggtgg cgcacgaggt ctaccgttcc   49560
cggttccccg atgtgccgca cgtggtggcg ttggacgacc cggagctgga ccggcagccg   49620
gacgacacgg cgccggacgt cgagctggac cgggacagcc tcgcctacgc gatctacacg   49680
tccgggtcga ccggcaggcc gaaggccgtg ctcatgccgg gtgtcagcgc cgtcaacctg   49740
ctgctctggc aggagcgcac gatgggccgc gagccggcca ccgcaccgt ccagttcgtg   49800 acgcccacgt tcgactactc ggtgcaggag atctttttccg cgctgctggg cggcacgctc   49860
gtcatcccgc cggacgaggt gcggttcgac ccgccgggac tcgcccggtg gatggacgaa   49920
caggcgatta cccggatcta cgccgccacg gccgtactgc gcgcgctgat cgagcacgtc   49980
gatccgcaca gcgaccagct cgccgccctg cggcacctgt gccagggcgg cgaggcgctg   50040
atcctcgacg cgcggttgcg cgagctgtgc cggcaccggc cccacctgcg cgtgcacaat   50100
```

```
cactacggtc cggccgaaag ccagctcatc accgggtaca cgctgcccgc cgaccccgac   50160
gcgtggcccg ccaccgcacc gatcggcccg ccgatcgaca cacccgcat ccatctgctc    50220 gacgaggcga tgcggccggt tccggacggt atgccggggc agctctgcgt cgccggcgtc   50280
ggcctcgccc gtgggtacct ggcccgtccc gagctgaccg ccgagcgctg ggtgccggga   50340
gatgcggtcg gcgaggagcg catgtacctc accggcgacc tggcccgccg cgcgcccgac   50400
ggcgacctgg aattcctcgg ccggatcgac gaccaggtca agatccgcgg catccgcgtc   50460
gaaccgggtg agatcgagag cctgctcgcc gaggacgccc gcgtcacgca ggcggcggtg   50520
tccgtgcgcg aggaccggcg gggcgagaag ttcctggccg cgtacgtcgt accggtggcc   50580
ggccggcacg gcgacgactt cgccgcgtcg ctgcgcgcgg gactggccgc ccggctgccc   50640
gccgcgctcg tgcctccgc cgtcgtcctg gtggagcgac tgccgaggac cacgagcggc    50700
aaggtggacc ggcgcgcgct gcccgacccg gagccgggcc cggcgtcgac cggggcggtt   50760
acgccccgca ccgatgccga gcggacggtg tgccggatct tccaggaggt gctcgacgtc   50820
ccgcgggtcg gtgccgacga cgacttcttc acgctcggcg ggcactccct gctcgccacc   50880
cgggtcgtct cccgcatccg cgccgagctg ggtgccgatg tcccgctgcg tacgctcttc   50940
gacgggcgga cgcccgccgc gctcgcccgt gcggcggacg aggccggccc ggccgccctg   51000
cccccgatcg cgccctccgc ggagaacggg ccggccccc tcaccgcggc acaggaacag    51060
atgctgcact cgcacggctc gctgctcgcc gcgccctcct acacggtcgc cccgtacggg   51120
ttccggctgc gcgggccact cgaccgcgaa gcgctcgacg cggcactgac ccggatcgcc   51180
gcgcgccacg agccgctgcg gaccgggttc cgcgatcggg aacaggtcgt ccggccgccc   51240
gctccggtgc gcgccgaggt ggttccggtg ccggtcggcg acgtcgacgc cgcggtccgg   51300
gtcgcccacc gggagctgac ccggccgttc gacctcgtga acgggtcgtt gctgcgtgcc   51360
gtgctgctgc cgctgggcgc cgaggatcac gtgctgctgc tgatgctgca ccacctcgcc   51420
ggtgacggat ggtccttcga cctcctggtc cgggagttgt cggggacgca accggacctt   51480
ccggtgtcct acacggacgt ggcccggtgg aacggagtc cggccgtgat cgcggccagg    51540
gagaacgacc gggcctactg gcgccggcgg ctggggggcg ccaccgcgcc ggagctgccc   51600
gcggtccggc ccggcggggc accgaccggg cgggcgttcc tgtggacgct caaggacacc   51660
gccgtcctgg cggcacgccg ggtcgcggac gcccacgacg cgacgttgca cgaaaccgtg   51720
ctcggcgcct tcgccctggt cgtggcggag accgccgaca ccgacgacgt gctcgtcgcg   51780
acgccgttcg cggaccgggg gtacgccggg accgaccacc tcatcggctt cttcgcgaag   51840
gtcctcgcgc tgcgcctcga cctcggcggc acgccgtcgt tccccgaggt gctgcgccgg   51900
gtgcacaccg cgatggtggg cgcgcacgcc caccaggcgg tgccctactc cgcgctgcgc   51960
gccgaggacc ccgcgctgcc gccggccccc gtgtcgttcc agctcatcag cgcgctcagc   52020
gcggaactgc ggctgcccgg catgcacacc gagccgttcc ccgtcgtcgc cgagaccgtc   52080
gacgagatga ccggcgaact gtcgatcaac ctcttcgacg acggtcgcac cgtctccggc   52140
gcggtggtcc acgatccgcc gctgctcgac cgtgccaccg tcgacgattt gctcacccgg   52200
gtggaggcga cgctgcgtgc cgccgcgggc gacctcaccg tacgcgtcac cggttacgtg   52260
gaaagcgagt agcc atg ccc gag cag gac aag aca gtc gag tac ctt cgc    52310
              Met Pro Glu Gln Asp Lys Thr Val Glu Tyr Leu Arg
                1               5                  10 tgg gcg acc gcg gaa ctc cag aag acc cgt gcg gaa ctc gcc gcg cac    52358
Trp Ala Thr Ala Glu Leu Gln Lys Thr Arg Ala Glu Leu Ala Ala His
        15                  20                  25
```

| | | | | | | | | | | | | | | | |
|---|---|---|---|---|---|---|---|---|---|---|---|---|---|---|---|
| agc | gag | ccg | ttg | gcg | atc | gtg | ggg | atg | gcc | tgc | cgg | ctg | ccc | ggc | ggg | 52406
| Ser | Glu | Pro | Leu | Ala | Ile | Val | Gly | Met | Ala | Cys | Arg | Leu | Pro | Gly | Gly |
| | 30 | | | | 35 | | | | 40 | | | | | | |
| gtc | gcg | tcg | ccg | gag | gac | ctg | tgg | cag | ttg | ctg | gag | tcc | ggt | ggc | gac | 52454
| Val | Ala | Ser | Pro | Glu | Asp | Leu | Trp | Gln | Leu | Leu | Glu | Ser | Gly | Gly | Asp |
| 45 | | | | | 50 | | | | | 55 | | | | | 60 |
| ggc | atc | acc | gcg | ttc | ccc | acg | gac | cgg | ggc | tgg | gag | acc | acc | gcc | gac | 52502
| Gly | Ile | Thr | Ala | Phe | Pro | Thr | Asp | Arg | Gly | Trp | Glu | Thr | Thr | Ala | Asp |
| | | | | 65 | | | | | 70 | | | | | 75 | |
| ggt | cgc | ggc | ggc | ttc | ctc | acc | ggg | gcg | gcc | ggc | ttc | gac | gcg | gcg | ttc | 52550
| Gly | Arg | Gly | Gly | Phe | Leu | Thr | Gly | Ala | Ala | Gly | Phe | Asp | Ala | Ala | Phe |
| | | | 80 | | | | | 85 | | | | | 90 | | |
| ttc | ggc | atc | agc | ccg | cgc | gag | gcg | ctg | gcg | atg | gac | ccg | cag | cag | cgc | 52598
| Phe | Gly | Ile | Ser | Pro | Arg | Glu | Ala | Leu | Ala | Met | Asp | Pro | Gln | Gln | Arg |
| | | 95 | | | | | 100 | | | | | 105 | | | |
| ctg | gcc | ctg | gag | acc | tcg | tgg | gag | gcc | ttc | gag | cac | gcg | ggc | atc | gat | 52646
| Leu | Ala | Leu | Glu | Thr | Ser | Trp | Glu | Ala | Phe | Glu | His | Ala | Gly | Ile | Asp |
| | 110 | | | | | 115 | | | | | 120 | | | | |
| ccg | cag | acg | ctg | cgg | ggc | agt | gac | acg | ggg | gtg | ttc | ctc | ggc | gcg | ttc | 52694
| Pro | Gln | Thr | Leu | Arg | Gly | Ser | Asp | Thr | Gly | Val | Phe | Leu | Gly | Ala | Phe |
| 125 | | | | | 130 | | | | | 135 | | | | | 140 |
| ttc | cag | ggg | tac | ggc | atc | ggc | gcc | gac | ttc | gac | ggt | tac | ggc | acc | acg | 52742
| Phe | Gln | Gly | Tyr | Gly | Ile | Gly | Ala | Asp | Phe | Asp | Gly | Tyr | Gly | Thr | Thr |
| | | | | 145 | | | | | 150 | | | | | 155 | |
| agc | att | cac | acg | agc | gtg | ctc | tcc | ggc | cgc | ctc | gcg | tac | ttc | tac | ggt | 52790
| Ser | Ile | His | Thr | Ser | Val | Leu | Ser | Gly | Arg | Leu | Ala | Tyr | Phe | Tyr | Gly |
| | | | 160 | | | | | 165 | | | | | 170 | | |
| ctg | gag | ggt | ccg | gcg | gtc | acg | gtc | gac | acg | gcg | tgt | tcg | tcg | tcg | ctg | 52838
| Leu | Glu | Gly | Pro | Ala | Val | Thr | Val | Asp | Thr | Ala | Cys | Ser | Ser | Ser | Leu |
| | | 175 | | | | | 180 | | | | | 185 | | | |
| gtg | gcg | ctg | cac | cag | gcc | ggg | cag | tcg | ctg | cgc | tcc | ggc | gaa | tgc | tcg | 52886
| Val | Ala | Leu | His | Gln | Ala | Gly | Gln | Ser | Leu | Arg | Ser | Gly | Glu | Cys | Ser |
| | 190 | | | | | 195 | | | | | 200 | | | | |
| ctc | gcc | ctg | gtc | ggc | ggc | gtc | acg | gtg | atg | gcc | tcg | ccg | gcg | ggg | ttc | 52934
| Leu | Ala | Leu | Val | Gly | Gly | Val | Thr | Val | Met | Ala | Ser | Pro | Ala | Gly | Phe |
| 205 | | | | | 210 | | | | | 215 | | | | | 220 |
| gcg | gac | ttc | tcc | gag | cag | ggc | ggc | ctg | gcc | ccc | gac | gcg | cgc | tgc | aag | 52982
| Ala | Asp | Phe | Ser | Glu | Gln | Gly | Gly | Leu | Ala | Pro | Asp | Ala | Arg | Cys | Lys |
| | | | | 225 | | | | | 230 | | | | | 235 | |
| gcc | ttc | gcg | gaa | gcg | gct | gac | ggc | acc | ggt | ttc | gcc | gag | ggg | tcc | ggc | 53030
| Ala | Phe | Ala | Glu | Ala | Ala | Asp | Gly | Thr | Gly | Phe | Ala | Glu | Gly | Ser | Gly |
| | | | 240 | | | | | 245 | | | | | 250 | | |
| gtc | ctg | atc | gtc | gag | aag | ctc | tcc | gac | gcc | gag | cgc | aac | ggc | cac | cgc | 53078
| Val | Leu | Ile | Val | Glu | Lys | Leu | Ser | Asp | Ala | Glu | Arg | Asn | Gly | His | Arg |
| | | 255 | | | | | 260 | | | | | 265 | | | |
| gtg | ctg | gcg | gtc | gtc | cgg | ggt | tcc | gcc | gtc | aac | cag | gac | ggt | gcc | tcc | 53126
| Val | Leu | Ala | Val | Val | Arg | Gly | Ser | Ala | Val | Asn | Gln | Asp | Gly | Ala | Ser |
| | 270 | | | | | 275 | | | | | 280 | | | | |
| aac | ggg | ctg | tcc | gcg | ccg | aac | ggg | ccg | tcg | cag | gag | cgg | gtg | atc | cgg | 53174
| Asn | Gly | Leu | Ser | Ala | Pro | Asn | Gly | Pro | Ser | Gln | Glu | Arg | Val | Ile | Arg |
| 285 | | | | | 290 | | | | | 295 | | | | | 300 |
| cag | gcc | ctg | gcc | aac | gcc | gga | ctc | acc | ccg | gcg | gac | gtg | gac | gcc | gtc | 53222
| Gln | Ala | Leu | Ala | Asn | Ala | Gly | Leu | Thr | Pro | Ala | Asp | Val | Asp | Ala | Val |
| | | | | 305 | | | | | 310 | | | | | 315 | |
| gag | gcc | cac | ggc | acc | ggc | acc | agg | ctg | ggc | gac | ccc | atc | gag | gca | cag | 53270
| Glu | Ala | His | Gly | Thr | Gly | Thr | Arg | Leu | Gly | Asp | Pro | Ile | Glu | Ala | Gln |
| | | | 320 | | | | | 325 | | | | | 330 | | |
| gcc | gtg | ctg | gcc | acc | tac | ggg | cag | ggg | cgc | gac | acc | cct | gtg | ctg | ctg | 53318
| Ala | Val | Leu | Ala | Thr | Tyr | Gly | Gln | Gly | Arg | Asp | Thr | Pro | Val | Leu | Leu |

-continued

| | | | | | | | | | | | | | | | | |
|---|---|---|---|---|---|---|---|---|---|---|---|---|---|---|---|---|
| | | 335 | | | | | 340 | | | | | 345 | | | | |
| ggc | tcg | ctg | aag | tcc | aac | atc | ggc | cac | acc | cag | gcc | gcc | gcg | ggc | gtc | 53366 |
| Gly | Ser | Leu | Lys | Ser | Asn | Ile | Gly | His | Thr | Gln | Ala | Ala | Ala | Gly | Val | |
| | | 350 | | | | | 355 | | | | | 360 | | | | |
| gcc | ggt | gtc | atc | aag | atg | gtc | ctc | gcc | atg | cgg | cac | ggc | acc | ctg | ccc | 53414 |
| Ala | Gly | Val | Ile | Lys | Met | Val | Leu | Ala | Met | Arg | His | Gly | Thr | Leu | Pro | |
| 365 | | | | | 370 | | | | | 375 | | | | | 380 | |
| cgc | acc | ctg | cac | gtg | gac | acg | ccg | tcc | tcg | cac | gtc | gac | tgg | acg | gcc | 53462 |
| Arg | Thr | Leu | His | Val | Asp | Thr | Pro | Ser | Ser | His | Val | Asp | Trp | Thr | Ala | |
| | | | | 385 | | | | | 390 | | | | | 395 | | |
| ggc | gcc | gtc | gaa | ctc | ctc | acc | gac | gcc | cgg | ccc | tgg | ccc | gaa | acc | gac | 53510 |
| Gly | Ala | Val | Glu | Leu | Leu | Thr | Asp | Ala | Arg | Pro | Trp | Pro | Glu | Thr | Asp | |
| | | | 400 | | | | | 405 | | | | | 410 | | | |
| cgc | cca | cgg | cgc | gcc | ggt | gtc | tcc | tcc | ttc | ggc | gtc | agc | ggc | acc | aac | 53558 |
| Arg | Pro | Arg | Arg | Ala | Gly | Val | Ser | Ser | Phe | Gly | Val | Ser | Gly | Thr | Asn | |
| | | 415 | | | | | 420 | | | | | 425 | | | | |
| gcc | cac | atc | atc | ctc | gaa | agc | cac | ccc | cga | ccg | gcc | ccc | gaa | ccc | gcc | 53606 |
| Ala | His | Ile | Ile | Leu | Glu | Ser | His | Pro | Arg | Pro | Ala | Pro | Glu | Pro | Ala | |
| | 430 | | | | | 435 | | | | | 440 | | | | | |
| ccg | gca | ccc | gac | acc | gga | ccg | ctg | ccg | ctg | ctc | tcg | gcc | cgc | acc | | 53654 |
| Pro | Ala | Pro | Asp | Thr | Gly | Pro | Leu | Pro | Leu | Leu | Ser | Ala | Arg | Thr | | |
| 445 | | | | | 450 | | | | | 455 | | | | | 460 | |
| ccg | cag | gca | ctc | gac | gca | cag | gta | cac | cgc | ctg | cgc | gcg | ttc | ctc | gac | 53702 |
| Pro | Gln | Ala | Leu | Asp | Ala | Gln | Val | His | Arg | Leu | Arg | Ala | Phe | Leu | Asp | |
| | | | | 465 | | | | | 470 | | | | | 475 | | |
| gac | aac | ccc | ggc | gcg | gac | cgg | gtc | gcc | gtc | gcg | cag | aca | ctc | gcc | cgg | 53750 |
| Asp | Asn | Pro | Gly | Ala | Asp | Arg | Val | Ala | Val | Ala | Gln | Thr | Leu | Ala | Arg | |
| | | | 480 | | | | | 485 | | | | | 490 | | | |
| cgc | acc | cag | ttc | gag | cac | cgc | gcc | gtg | ctg | ctc | ggc | gac | acg | ctc | atc | 53798 |
| Arg | Thr | Gln | Phe | Glu | His | Arg | Ala | Val | Leu | Leu | Gly | Asp | Thr | Leu | Ile | |
| | | 495 | | | | | 500 | | | | | 505 | | | | |
| acc | gtg | agc | ccg | aac | gcc | ggc | cgc | gga | ccg | gtg | gtc | ttc | gtc | tac | tcg | 53846 |
| Thr | Val | Ser | Pro | Asn | Ala | Gly | Arg | Gly | Pro | Val | Val | Phe | Val | Tyr | Ser | |
| | 510 | | | | | 515 | | | | | 520 | | | | | |
| ggg | caa | agc | acg | ctg | cac | ccg | cac | acc | ggg | cgg | caa | ctc | gcg | tcc | acc | 53894 |
| Gly | Gln | Ser | Thr | Leu | His | Pro | His | Thr | Gly | Arg | Gln | Leu | Ala | Ser | Thr | |
| 525 | | | | | 530 | | | | | 535 | | | | | 540 | |
| tac | ccc | gtg | ttc | gcc | gaa | gcg | tgg | cgc | gag | gcc | ctc | gac | cac | ctc | gac | 53942 |
| Tyr | Pro | Val | Phe | Ala | Glu | Ala | Trp | Arg | Glu | Ala | Leu | Asp | His | Leu | Asp | |
| | | | | 545 | | | | | 550 | | | | | 555 | | |
| ccc | acc | cag | ggc | ccg | gcc | acg | cac | ttc | gcc | cac | cag | acc | gcg | ctc | acc | 53990 |
| Pro | Thr | Gln | Gly | Pro | Ala | Thr | His | Phe | Ala | His | Gln | Thr | Ala | Leu | Thr | |
| | | | 560 | | | | | 565 | | | | | 570 | | | |
| gcg | ctc | ctg | cgg | tcc | tgg | ggc | atc | acc | ccg | cac | gcg | gtc | atc | ggc | cac | 54038 |
| Ala | Leu | Leu | Arg | Ser | Trp | Gly | Ile | Thr | Pro | His | Ala | Val | Ile | Gly | His | |
| | | 575 | | | | | 580 | | | | | 585 | | | | |
| tcc | ctc | ggt | gag | atc | acc | gcc | gcg | cac | gcc | gcc | ggt | gtc | ctg | tcc | ctg | 54086 |
| Ser | Leu | Gly | Glu | Ile | Thr | Ala | Ala | His | Ala | Ala | Gly | Val | Leu | Ser | Leu | |
| | 590 | | | | | 595 | | | | | 600 | | | | | |
| agg | gac | gcg | ggc | gcg | ctc | ctc | acc | acc | cgc | acc | cgc | ctg | atg | gac | caa | 54134 |
| Arg | Asp | Ala | Gly | Ala | Leu | Leu | Thr | Thr | Arg | Thr | Arg | Leu | Met | Asp | Gln | |
| 605 | | | | | 610 | | | | | 615 | | | | | 620 | |
| ctg | ccg | tcg | ggc | ggc | gcg | atg | gtc | acc | gtc | ctg | acc | agc | gag | gaa | aag | 54182 |
| Leu | Pro | Ser | Gly | Gly | Ala | Met | Val | Thr | Val | Leu | Thr | Ser | Glu | Glu | Lys | |
| | | | | 625 | | | | | 630 | | | | | 635 | | |
| gca | cgc | cag | gtg | ctg | cgg | ccg | ggc | gtg | gag | atc | gcc | gcc | gtc | aac | ggc | 54230 |
| Ala | Arg | Gln | Val | Leu | Arg | Pro | Gly | Val | Glu | Ile | Ala | Ala | Val | Asn | Gly | |
| | | | 640 | | | | | 645 | | | | | 650 | | | |
| ccc | cac | tcc | ctc | gtg | ctg | tcc | ggg | gac | gag | gaa | gcc | gta | ctc | gaa | gcc | 54278 |

| | | |
|---|---|---|
| Pro His Ser Leu Val Leu Ser Gly Asp Glu Ala Val Leu Glu Ala<br>655                  660                  665 | | |
| gcc cgg cag ctc ggc atc cac cac cgc ctg ccg acc cgc cac gcc ggc<br>Ala Arg Gln Leu Gly Ile His His Arg Leu Pro Thr Arg His Ala Gly<br>670                  675                  680 | 54326 |
| cac tcc gag cgc atg cag cca ctc gtc gcc ccc ctc ctc gac gtc gcc<br>His Ser Glu Arg Met Gln Pro Leu Val Ala Pro Leu Leu Asp Val Ala<br>685                  690                695                  700 | 54374 |
| cgg acc ctg acg tac cac cag ccc cac acc gcc atc ccc ggc gac ccc<br>Arg Thr Leu Thr Tyr His Gln Pro His Thr Ala Ile Pro Gly Asp Pro<br>                  705                  710                  715 | 54422 |
| acc acc gcc gaa tac tgg gcg cac cag gtc cgc gac caa gta cgt ttc<br>Thr Thr Ala Glu Tyr Trp Ala His Gln Val Arg Asp Gln Val Arg Phe<br>720                  725                  730 | 54470 |
| cag gcg cac acc gag cag tac ccg ggc gcg acg ttc ctc gag atc ggc<br>Gln Ala His Thr Glu Gln Tyr Pro Gly Ala Thr Phe Leu Glu Ile Gly<br>                  735                  740                  745 | 54518 |
| ccc aac cag gac ctc tcg ccg ctc gtc gac ggc gtt gcc gcc cag acc<br>Pro Asn Gln Asp Leu Ser Pro Leu Val Asp Gly Val Ala Ala Gln Thr<br>750                  755                  760 | 54566 |
| ggt acg ccc gac gag gtg cgg gcg ctg cac acc gcg ctc gcg cag ctc<br>Gly Thr Pro Asp Glu Val Arg Ala Leu His Thr Ala Leu Ala Gln Leu<br>765                  770                  775                  780 | 54614 |
| cac gtc cgc ggc gtc gcg atc gac tgg acg ctc gtc ctc ggc ggg gac<br>His Val Arg Gly Val Ala Ile Asp Trp Thr Leu Val Leu Gly Gly Asp<br>                  785                  790                  795 | 54662 |
| cgc gcg ccc gtc acg ctg ccc acg tat ccg ttc cag cac aag gac tac<br>Arg Ala Pro Val Thr Leu Pro Thr Tyr Pro Phe Gln His Lys Asp Tyr<br>                  800                  805                  810 | 54710 |
| tgg ctg cgg ccc acc tcc cgg gcc gat gtg acc ggc gcg ggg cag gag<br>Trp Leu Arg Pro Thr Ser Arg Ala Asp Val Thr Gly Ala Gly Gln Glu<br>                  815                  820                  825 | 54758 |
| cag gtg gcg cac ccg ctg ctc ggc gcc gcg gtc gcg ctg ccc ggc acg<br>Gln Val Ala His Pro Leu Leu Gly Ala Ala Val Ala Leu Pro Gly Thr<br>830                  835                  840 | 54806 |
| ggc gga gtc gtc ctg acc ggc cgc ctg tcg ctg gcc tcc cat ccg tgg<br>Gly Gly Val Val Leu Thr Gly Arg Leu Ser Leu Ala Ser His Pro Trp<br>845                  850                  855                  860 | 54854 |
| ctc ggc gag cac gcg gtc gac ggc acc gtg ctc ctg ccc ggc gcg gcc<br>Leu Gly Glu His Ala Val Asp Gly Thr Val Leu Leu Pro Gly Ala Ala<br>                  865                  870                  875 | 54902 |
| ttc ctc gaa ctc gcg gcg cgc gcc ggc gac gag gtc ggc tgc gac ctg<br>Phe Leu Glu Leu Ala Ala Arg Ala Gly Asp Glu Val Gly Cys Asp Leu<br>                  880                  885                  890 | 54950 |
| ctg cac gaa ctc gtc atc gag acg ccg ctc gtg ctg ccc gcg acc ggc<br>Leu His Glu Leu Val Ile Glu Thr Pro Leu Val Leu Pro Ala Thr Gly<br>                  895                  900                  905 | 54998 |
| ggt gtg gcg gtc tcc gtc gag atc gcc gaa ccc gac gac acg ggg cgg<br>Gly Val Ala Val Ser Val Glu Ile Ala Glu Pro Asp Asp Thr Gly Arg<br>910                  915                  920 | 55046 |
| cgg gcg gtc acc gtc cac gcg cgg gcc gac ggc tcg ggc ctg tgg acc<br>Arg Ala Val Thr Val His Ala Arg Ala Asp Gly Ser Gly Leu Trp Thr<br>925                  930                  935                  940 | 55094 |
| cga cac gcc ggc gga ttc ctc ggc acg gca ccg gca ccg gcg acg gcc<br>Arg His Ala Gly Gly Phe Leu Gly Thr Ala Pro Ala Pro Ala Thr Ala<br>                  945                  950                  955 | 55142 |
| acg gac ccg gca ccc tgg ccg ccc gcg gaa gcc gga ccg gtc gac gtc<br>Thr Asp Pro Ala Pro Trp Pro Pro Ala Glu Ala Gly Pro Val Asp Val<br>                  960                  965                  970 | 55190 |

```
gcc gac gtc tac gac cgg ttc gag gac atc ggg tac tcc tac gga ccg      55238
Ala Asp Val Tyr Asp Arg Phe Glu Asp Ile Gly Tyr Ser Tyr Gly Pro
            975                 980                 985 ggc ttc cgg ggg ctg cgg gcc gcc tgg cgc gcc ggc gac acc gtg tac      55286
Gly Phe Arg Gly Leu Arg Ala Ala Trp Arg Ala Gly Asp Thr Val Tyr
    990                 995                 1000 gcc gag gtc gcg ctc ccc gac gag cag agc gcc gac gcc gcc cgt ttc      55334
Ala Glu Val Ala Leu Pro Asp Glu Gln Ser Ala Asp Ala Ala Arg Phe
1005                1010                1015                1020 acg ctg cac ccc gcg ctg ctc gac gcc gcg ttc cag gcc ggc gcg ctg      55382
Thr Leu His Pro Ala Leu Leu Asp Ala Ala Phe Gln Ala Gly Ala Leu
            1025                1030                1035 gcc gcg ctc gac gca ccc ggg gcg gcc cga ctg ccg ttc tcg ttc          55430
Ala Ala Leu Asp Ala Pro Gly Gly Ala Ala Arg Leu Pro Phe Ser Phe
    1040                1045                1050 cag gac gtc cgc atc cac gcg gcc ggg gcg acg cgg ctg cgg gtc acg      55478
Gln Asp Val Arg Ile His Ala Ala Gly Ala Thr Arg Leu Arg Val Thr
1055                1060                1065 gtc ggc cgc gac ggc gag cgc agc acc gtc cgc atg acc ggc ccg gac      55526
Val Gly Arg Asp Gly Glu Arg Ser Thr Val Arg Met Thr Gly Pro Asp
            1070                1075                1080 ggg cag ctg gtg gcc gtg gtc ggt gcc gtg ctg tcg cgc ccg tac gcg      55574
Gly Gln Leu Val Ala Val Val Gly Ala Val Leu Ser Arg Pro Tyr Ala
    1085                1090                1095                1100 gaa ggc tcc ggt gac ggc ctg ctg cgc ccg gtc tgg acc gag ctg ccg      55622
Glu Gly Ser Gly Asp Gly Leu Leu Arg Pro Val Trp Thr Glu Leu Pro
1105                1110                1115 atg ccc gtc ccg tcc gcg gac gat ccg cgc gtg gag gtc ctc ggc gcc      55670
Met Pro Val Pro Ser Ala Asp Asp Pro Arg Val Glu Val Leu Gly Ala
            1120                1125                1130 gac ccg ggc gac ggc gac gtt ccg gcg gcc acc cgg gag ctg acc gcc      55718
Asp Pro Gly Asp Gly Asp Val Pro Ala Ala Thr Arg Glu Leu Thr Ala
    1135                1140                1145 cgc gtc ctc ggc gcg ctc cag cgc cac ctg tcc gcc gcc gag gac acc      55766
Arg Val Leu Gly Ala Leu Gln Arg His Leu Ser Ala Ala Glu Asp Thr
1150                1155                1160 acc ttg gtg gta cgg acc ggc acc ggc ccg gcc gct gcc gcc gcc gcg      55814
Thr Leu Val Val Arg Thr Gly Thr Gly Pro Ala Ala Ala Ala Ala Ala
            1165                1170                1175                1180 ggt ctg gtc cgc tcg gcg cag gcg gag aac ccc ggc cgc gtc gtg ctc      55862
Gly Leu Val Arg Ser Ala Gln Ala Glu Asn Pro Gly Arg Val Val Leu
    1185                1190                1195 gtc gag gcg tcc ccg gac acc tcg gtg gag ctg ctc gcc gcg tgc gcc      55910
Val Glu Ala Ser Pro Asp Thr Ser Val Glu Leu Leu Ala Ala Cys Ala
1200                1205                1210 gcg ctg gac gaa ccg cag ctg gcc gtc cgg gac ggc gtg ctc ttc gcg      55958
Ala Leu Asp Glu Pro Gln Leu Ala Val Arg Asp Gly Val Leu Phe Ala
            1215                1220                1225 ccg cgg ctg gtc cgg atg tcc gac ccc gcg cac ggc ccg ctg tcc ctg      56006
Pro Arg Leu Val Arg Met Ser Asp Pro Ala His Gly Pro Leu Ser Leu
    1230                1235                1240 ccg gac ggc gac tgg ctg ctc acc cgg tcc gcc tcc ggc acg ttg cac      56054
Pro Asp Gly Asp Trp Leu Leu Thr Arg Ser Ala Ser Gly Thr Leu His
1245                1250                1255                1260 gac gtc gcg ctc ata gcc gac gac acg ccc cgg cgg gcg ctc gaa gcc      56102
Asp Val Ala Leu Ile Ala Asp Asp Thr Pro Arg Arg Ala Leu Glu Ala
            1265                1270                1275 ggc gag gtc cgc atc gac gtc cgc gcg gcc gga ctg aac ttc cgc gat      56150
Gly Glu Val Arg Ile Asp Val Arg Ala Ala Gly Leu Asn Phe Arg Asp
    1280                1285                1290
```

```
                                                   -continued gtg ctg atc gcg ctc ggg acg tac acc ggg gcc acg gcc atg ggc ggc    56198
Val Leu Ile Ala Leu Gly Thr Tyr Thr Gly Ala Thr Ala Met Gly Gly
        1295                1300                1305 gag gcc gcg ggc gtc gtg gtg gag acc ggg ccc ggc gtg gac gac ctg    56246
Glu Ala Ala Gly Val Val Val Glu Thr Gly Pro Gly Val Asp Asp Leu
1310                1315                1320 tcc ccc ggc gac cgg gtg ttc ggc ctg acc cgg ggc ggc atc ggc ccg    56294
Ser Pro Gly Asp Arg Val Phe Gly Leu Thr Arg Gly Gly Ile Gly Pro
1325                1330                1335                1340 acg gcc gtc acc gac cgg cgc tgg ctg gcc cgg atc ccc gac ggc tgg    56342
Thr Ala Val Thr Asp Arg Arg Trp Leu Ala Arg Ile Pro Asp Gly Trp
                1345                1350                1355 agc ttc acc acg gcg gcg tcc gtc ccg atc gtg ttc gcg acc gcg tgg    56390
Ser Phe Thr Thr Ala Ala Ser Val Pro Ile Val Phe Ala Thr Ala Trp
        1360                1365                1370 tac ggc ctg gtc gac ctc ggc aca ctg cgc gcc ggc gag aag gtc ctc    56438
Tyr Gly Leu Val Asp Leu Gly Thr Leu Arg Ala Gly Glu Lys Val Leu
        1375                1380                1385 gtc cac gcg gcc acc ggc ggt gtc ggc atg gcc gcc gca cag atc gcc    56486
Val His Ala Ala Thr Gly Gly Val Gly Met Ala Ala Ala Gln Ile Ala
1390                1395                1400 cgc cac ctg ggc gcc gag ctc tac gcc acc gcc agt acc ggc aag cag    56534
Arg His Leu Gly Ala Glu Leu Tyr Ala Thr Ala Ser Thr Gly Lys Gln
1405                1410                1415                1420 cac gtc ctg cgc gcc gcc ggg ctg ccc gac acg cac atc gcc gac tct    56582
His Val Leu Arg Ala Ala Gly Leu Pro Asp Thr His Ile Ala Asp Ser
                1425                1430                1435 cgg acg acc gcg ttc cgg acc gct ttc ccg cgc atg gac gtc gtc ctg    56630
Arg Thr Thr Ala Phe Arg Thr Ala Phe Pro Arg Met Asp Val Val Leu
        1440                1445                1450 aac gcg ctg acc ggc gag ttc atc gac gcg tcg ctc gac ctg ctg gac    56678
Asn Ala Leu Thr Gly Glu Phe Ile Asp Ala Ser Leu Asp Leu Leu Asp
        1455                1460                1465 gcc gac ggc cgg ttc gtc gag atg ggc cgc acc gag ctg cgc gac ccg    56726
Ala Asp Gly Arg Phe Val Glu Met Gly Arg Thr Glu Leu Arg Asp Pro
1470                1475                1480 gcc gcg atc gtc ccc gcc tac ctg ccg ttc gac ctg ctg gac gcg ggc    56774
Ala Ala Ile Val Pro Ala Tyr Leu Pro Phe Asp Leu Leu Asp Ala Gly
1485                1490                1495                1500 gcc gac cgc atc ggc gag atc ctg ggc gaa ctg ctc cgg ctg ttc gac    56822
Ala Asp Arg Ile Gly Glu Ile Leu Gly Glu Leu Leu Arg Leu Phe Asp
                1505                1510                1515 gcg ggc gcg ctg gag ccg ctg ccg gtc cgt gcc tgg gac gtc cgg cag    56870
Ala Gly Ala Leu Glu Pro Leu Pro Val Arg Ala Trp Asp Val Arg Gln
        1520                1525                1530 gca cgc gac gcg ctc ggc tgg atg agc cgc gcc cgc cac atc ggc aag    56918
Ala Arg Asp Ala Leu Gly Trp Met Ser Arg Ala Arg His Ile Gly Lys
        1535                1540                1545 aac gtc ctg acg ctg ccc cgg ccg ctc gac ccg gag ggc gcc gtc gtc    56966
Asn Val Leu Thr Leu Pro Arg Pro Leu Asp Pro Glu Gly Ala Val Val
1550                1555                1560 ctc acc ggc ggc tcc ggc acg ctc gcc ggc atc ctc gcc cgc cac ctg    57014
Leu Thr Gly Gly Ser Gly Thr Leu Ala Gly Ile Leu Ala Arg His Leu
1565                1570                1575                1580 cgc gaa cgg cat gtc tac ctg ctg tcc cgg acg gca ccg ccc gag ggg    57062
Arg Glu Arg His Val Tyr Leu Leu Ser Arg Thr Ala Pro Pro Glu Gly
                1585                1590                1595 acg ccc ggc gtc cac ctg ccc tgc gac gtc ggt gac cgg gac cag ctg    57110
Thr Pro Gly Val His Leu Pro Cys Asp Val Gly Asp Arg Asp Gln Leu
```

-continued

```
              1600              1605              1610
gcg gcg gcc ctg gag cgg gtg gac cgg ccg atc acc gcc gtg gtg cac    57158
Ala Ala Ala Leu Glu Arg Val Asp Arg Pro Ile Thr Ala Val Val His
            1615              1620              1625 ctc gcc ggt gcg ctg gac gac ggc acc gtc gcg tcg ctc acc ccc gag    57206
Leu Ala Gly Ala Leu Asp Asp Gly Thr Val Ala Ser Leu Thr Pro Glu
        1630              1635              1640 cgt ttc gac acg gtg ctg cgc ccg aag gcc gac ggc gcc tgg tac ctg    57254
Arg Phe Asp Thr Val Leu Arg Pro Lys Ala Asp Gly Ala Trp Tyr Leu
1645              1650              1655              1660 cac gag ctg acg aag gag cag gac ctc gcc gcg ttc gtg ctc tac tcg    57302
His Glu Leu Thr Lys Glu Gln Asp Leu Ala Ala Phe Val Leu Tyr Ser
                1665              1670              1675 tcg gcc gcc ggc gtg ctc ggc aac gcc ggc cag ggc aac tac gtc gcc    57350
Ser Ala Ala Gly Val Leu Gly Asn Ala Gly Gln Gly Asn Tyr Val Ala
            1680              1685              1690 gcg aac gcg ttc ctc gac gcg ctc gcc gag ctg cgc cac ggt tcc ggg    57398
Ala Asn Ala Phe Leu Asp Ala Leu Ala Glu Leu Arg His Gly Ser Gly
        1695              1700              1705 ctg ccg gcc ctc tcc atc gcc tgg ggg ctc tgg gag gac gtg agc ggg    57446
Leu Pro Ala Leu Ser Ile Ala Trp Gly Leu Trp Glu Asp Val Ser Gly
    1710              1715              1720 ctc acc gcg gcg ctc ggc gaa gcc gac cgg gac cgg atg cgg cgc agc    57494
Leu Thr Ala Ala Leu Gly Glu Ala Asp Arg Asp Arg Met Arg Arg Ser
1725              1730              1735              1740 ggt ttc cgg gcc atc acc gcg caa cag ggc atg cac ctg tac gag gcg    57542
Gly Phe Arg Ala Ile Thr Ala Gln Gln Gly Met His Leu Tyr Glu Ala
                1745              1750              1755 gcc ggc cgc acc gga agt ccc gtg gtg gtc gcg gcg gcg ctc gac gac    57590
Ala Gly Arg Thr Gly Ser Pro Val Val Val Ala Ala Ala Leu Asp Asp
            1760              1765              1770 gcg ccg gac gtg ccg ctg ctg cgc ggc ctg cgg cgg acg acc gtc cgg    57638
Ala Pro Asp Val Pro Leu Leu Arg Gly Leu Arg Arg Thr Thr Val Arg
        1775              1780              1785 cgg gcc gcc gtc cgg gag tgt tcg tcc gcc gac cgg ctc gcc gcg ctg    57686
Arg Ala Ala Val Arg Glu Cys Ser Ser Ala Asp Arg Leu Ala Ala Leu
    1790              1795              1800 acc ggc gac gag ctc gcc gaa gcg ctg ctg acg ctc gtc cgg gag agc    57734
Thr Gly Asp Glu Leu Ala Glu Ala Leu Leu Thr Leu Val Arg Glu Ser
1805              1810              1815              1820 acc gcc gcc gtg ctc ggc cac gtg ggt ggc gag gac atc ccc gcg acg    57782
Thr Ala Ala Val Leu Gly His Val Gly Gly Glu Asp Ile Pro Ala Thr
                1825              1830              1835 gcg gcg ttc aag gac ctc ggc atc gac tcg ctc acc gcg gtc cag ctg    57830
Ala Ala Phe Lys Asp Leu Gly Ile Asp Ser Leu Thr Ala Val Gln Leu
            1840              1845              1850 cgc aac gcc ctc acc gag gcg acc ggt gtg cgg ctg aac gcc acg gcg    57878
Arg Asn Ala Leu Thr Glu Ala Thr Gly Val Arg Leu Asn Ala Thr Ala
        1855              1860              1865 gtc ttc gac ttc ccg acc ccg cac gtg ctc gcc ggg aag ctc ggc gac    57926
Val Phe Asp Phe Pro Thr Pro His Val Leu Ala Gly Lys Leu Gly Asp
    1870              1875              1880 gaa ctg acc ggc acc cgc gcg ccc gtc gtg ccc cgg acc gcg gcc acg    57974
Glu Leu Thr Gly Thr Arg Ala Pro Val Val Pro Arg Thr Ala Ala Thr
1885              1890              1895              1900 gcc ggt gcg cac gac gag ccg ctg gcg atc gtg gga atg gcc tgc cgg    58022
Ala Gly Ala His Asp Glu Pro Leu Ala Ile Val Gly Met Ala Cys Arg
                1905              1910              1915 ctg ccc ggc ggg gtc gcg tca ccc gag gag ctg tgg cac ctc gtg gca    58070
```

-continued

| | |
|---|---|
| Leu Pro Gly Gly Val Ala Ser Pro Glu Glu Leu Trp His Leu Val Ala<br>               1920                      1925                         1930 | |
| tcc ggc acc gac gcc atc acg gag ttc ccg acg gac cgc ggc tgg gac<br>Ser Gly Thr Asp Ala Ile Thr Glu Phe Pro Thr Asp Arg Gly Trp Asp<br>         1935                       1940                      1945 | 58118 |
| gtc gac gcg atc tac gac ccg gac ccc gac gcg atc ggc aag acc ttc<br>Val Asp Ala Ile Tyr Asp Pro Asp Pro Asp Ala Ile Gly Lys Thr Phe<br>1950                    1955                    1960 | 58166 |
| gtc cgg cac ggt ggc ttc ctc acc ggc gcg aca ggc ttc gac gcg gcg<br>Val Arg His Gly Gly Phe Leu Thr Gly Ala Thr Gly Phe Asp Ala Ala<br>1965                    1970                    1975                    1980 | 58214 |
| ttc ttc ggc atc agc ccg cgc gag gcc ctc gcg atg gac ccg cag cag<br>Phe Phe Gly Ile Ser Pro Arg Glu Ala Leu Ala Met Asp Pro Gln Gln<br>               1985                      1990                         1995 | 58262 |
| cgg gtg ctc ctg gag acg tcg tgg gag gcg ttc gaa agc gcc ggc atc<br>Arg Val Leu Leu Glu Thr Ser Trp Glu Ala Phe Glu Ser Ala Gly Ile<br>                    2000                      2005                    2010 | 58310 |
| acc ccg gac tcg acc cgc ggc agc gac acc ggc gtg ttc gtc ggc gcc<br>Thr Pro Asp Ser Thr Arg Gly Ser Asp Thr Gly Val Phe Val Gly Ala<br>               2015                      2020                    2025 | 58358 |
| ttc tcc tac ggt tac ggc acc ggt gcg gac acc gac ggc ttc ggc gcg<br>Phe Ser Tyr Gly Tyr Gly Thr Gly Ala Asp Thr Asp Gly Phe Gly Ala<br>         2030                       2035                      2040 | 58406 |
| acc ggc tcg cag acc agt gtg ctc tcc ggc cgg ctg tcg tac ttc tac<br>Thr Gly Ser Gln Thr Ser Val Leu Ser Gly Arg Leu Ser Tyr Phe Tyr<br>2045                    2050                    2055                    2060 | 58454 |
| ggt ctg gag ggt ccg gcg gtc acg gtc gac acg gcg tgt tcg tcg tcg<br>Gly Leu Glu Gly Pro Ala Val Thr Val Asp Thr Ala Cys Ser Ser Ser<br>                    2065                      2070                    2075 | 58502 |
| ctg gtg gcg ctg cac cag gcc ggg cag tcg ctg cgc tcc ggc gaa tgc<br>Leu Val Ala Leu His Gln Ala Gly Gln Ser Leu Arg Ser Gly Glu Cys<br>               2080                      2085                    2090 | 58550 |
| tcg ctc gcc ctg gtc ggc ggc gtc acg gtg atg gcg tct ccc ggc ggc<br>Ser Leu Ala Leu Val Gly Gly Val Thr Val Met Ala Ser Pro Gly Gly<br>             2095                      2100                    2105 | 58598 |
| ttc gtg gag ttc tcc cgg cag cgc ggc ctc gcg ccg gac ggc cgg gcg<br>Phe Val Glu Phe Ser Arg Gln Arg Gly Leu Ala Pro Asp Gly Arg Ala<br>         2110                       2115                      2120 | 58646 |
| aag gcg ttc ggc gcg ggt gcg gac ggc acg agc ttc gcc gag ggt gcc<br>Lys Ala Phe Gly Ala Gly Ala Asp Gly Thr Ser Phe Ala Glu Gly Ala<br>2125                    2130                    2135                    2140 | 58694 |
| ggt gtg ctg atc gtc gag agg ctc tcc gac gcc gaa cgc aac ggt cac<br>Gly Val Leu Ile Val Glu Arg Leu Ser Asp Ala Glu Arg Asn Gly His<br>               2145                      2150                    2155 | 58742 |
| acc gtc ctg gcg gtc gtc cgt ggt tcg gcg gtc aac cag gat ggt gcc<br>Thr Val Leu Ala Val Val Arg Gly Ser Ala Val Asn Gln Asp Gly Ala<br>             2160                      2165                    2170 | 58790 |
| tcc aac ggg ctg tcg gcg ccg aac ggg ccg tcg cag gag cgg gtg atc<br>Ser Asn Gly Leu Ser Ala Pro Asn Gly Pro Ser Gln Glu Arg Val Ile<br>         2175                       2180                    2185 | 58838 |
| cgg cag gcc ctg gcc aac gcc ggg ctc acc ccg gcg gac gtg gac gcc<br>Arg Gln Ala Leu Ala Asn Ala Gly Leu Thr Pro Ala Asp Val Asp Ala<br>2190                    2195                    2200 | 58886 |
| gtc gag gcc cac ggc acc ggc acc agg ctg ggc gac ccc atc gag gca<br>Val Glu Ala His Gly Thr Gly Thr Arg Leu Gly Asp Pro Ile Glu Ala<br>2205                    2210                    2215                    2220 | 58934 |
| cag gcg gta ctg gcc acc tac gga cag gag cgc gcc acc ccc ctg ctg<br>Gln Ala Val Leu Ala Thr Tyr Gly Gln Glu Arg Ala Thr Pro Leu Leu<br>               2225                      2230                    2235 | 58982 |

| | |
|---|---|
| ctg ggc tcg ctg aag tcc aac atc ggc cac gcc cag gcc gcg tcc ggc<br>Leu Gly Ser Leu Lys Ser Asn Ile Gly His Ala Gln Ala Ala Ser Gly<br>          2240                    2245                      2250 | 59030 |
| gtc gcc ggc atc atc aag atg gtg cag gcc ctc cgg cac ggg gag ctg<br>Val Ala Gly Ile Ile Lys Met Val Gln Ala Leu Arg His Gly Glu Leu<br>2255                    2260                    2265 | 59078 |
| ccg ccg acg ctg cac gcc gac gag ccg tcg ccg cac gtc gac tgg acg<br>Pro Pro Thr Leu His Ala Asp Glu Pro Ser Pro His Val Asp Trp Thr<br>2270                    2275                    2280 | 59126 |
| gcc ggc gcc gtc gaa ctg ctg acg tcg gcc cgg ccg tgg ccc gag acc<br>Ala Gly Ala Val Glu Leu Leu Thr Ser Ala Arg Pro Trp Pro Glu Thr<br>2285                    2290                    2295                    2300 | 59174 |
| gac cgg cca cgg cgt gcc gcc gtc tcc tcg ttc ggg gtg agc ggc acc<br>Asp Arg Pro Arg Arg Ala Ala Val Ser Ser Phe Gly Val Ser Gly Thr<br>                          2305                    2310                    2315 | 59222 |
| aac gcc cac gtc atc ctg gag gcc gga ccg gta acg gag acg ccc gcg<br>Asn Ala His Val Ile Leu Glu Ala Gly Pro Val Thr Glu Thr Pro Ala<br>          2320                    2325                    2330 | 59270 |
| gca tcg cct tcc ggt gac ctt ccc ctg ctg gtg tcg gca cgc tca ccg<br>Ala Ser Pro Ser Gly Asp Leu Pro Leu Leu Val Ser Ala Arg Ser Pro<br>2335                    2340                    2345 | 59318 |
| gaa gcg ctc gac gag cag atc cgc cga ctg cgc gcc tac ctg gac acc<br>Glu Ala Leu Asp Glu Gln Ile Arg Arg Leu Arg Ala Tyr Leu Asp Thr<br>2350                    2355                    2360 | 59366 |
| acc ccg gac gtc gac cgg gtg gcc gtg gca cag acg ctg gcc cgg cgc<br>Thr Pro Asp Val Asp Arg Val Ala Val Ala Gln Thr Leu Ala Arg Arg<br>2365                    2370                    2375                    2380 | 59414 |
| aca cac ttc gcc cac cgc gcc gtg ctg ctc ggt gac acc gtc atc acc<br>Thr His Phe Ala His Arg Ala Val Leu Leu Gly Asp Thr Val Ile Thr<br>                          2385                    2390                    2395 | 59462 |
| aca ccc ccc gcg gac cgg ccc gac gaa ctc gtc ttc gtc tac tcc ggc<br>Thr Pro Pro Ala Asp Arg Pro Asp Glu Leu Val Phe Val Tyr Ser Gly<br>2400                    2405                    2410 | 59510 |
| cag ggc acc cag cat ccc gcg atg ggc gag cag ctc gcc gcc gcc cat<br>Gln Gly Thr Gln His Pro Ala Met Gly Glu Gln Leu Ala Ala Ala His<br>                          2415                    2420                    2425 | 59558 |
| ccc gtg ttc gcc gac gcc tgg cat gaa gcg ctc cgc cgc ctt gac aac<br>Pro Val Phe Ala Asp Ala Trp His Glu Ala Leu Arg Arg Leu Asp Asn<br>2430                    2435                    2440 | 59606 |
| ccc gac ccc cac gac ccc acg cac agc cag cat gtg ctc ttc gcc cac<br>Pro Asp Pro His Asp Pro Thr His Ser Gln His Val Leu Phe Ala His<br>2445                    2450                    2455                    2460 | 59654 |
| cag gcg gcg ttc acc gcc ctc ctg cgg tcc tgg ggc atc acc ccg cac<br>Gln Ala Ala Phe Thr Ala Leu Leu Arg Ser Trp Gly Ile Thr Pro His<br>                          2465                    2470                    2475 | 59702 |
| gcg gtc atc ggc cac tcg ctg ggc gag atc acc gcg gcg cac gcc gcc<br>Ala Val Ile Gly His Ser Leu Gly Glu Ile Thr Ala Ala His Ala Ala<br>          2480                    2485                    2490 | 59750 |
| ggc atc ctg tcg ctg gac gac gcg tgc acc ctg atc acc acg cgc gcc<br>Gly Ile Leu Ser Leu Asp Asp Ala Cys Thr Leu Ile Thr Thr Arg Ala<br>2495                    2500                    2505 | 59798 |
| cgc ctc atg cac acg ctc ccg cca ccc ggt gcc atg gtc acc gta ctg<br>Arg Leu Met His Thr Leu Pro Pro Pro Gly Ala Met Val Thr Val Leu<br>          2510                    2515                    2520 | 59846 |
| acc agc gaa gag aag gca cgc cag gcg ttg cgg ccg ggc gtg gag atc<br>Thr Ser Glu Glu Lys Ala Arg Gln Ala Leu Arg Pro Gly Val Glu Ile<br>2525                    2530                    2535                    2540 | 59894 |
| gcc gcc gtc aac ggg ccc cac tcc atc gtg ctg tcc ggg gac gag gac<br>Ala Ala Val Asn Gly Pro His Ser Ile Val Leu Ser Gly Asp Glu Asp<br>                          2545                    2550                    2555 | 59942 |

-continued

| | |
|---|---|
| gcc gtg ctc acc gtc gcc ggg cag ctc ggc atc cac cac cgc ctg ccc<br>Ala Val Leu Thr Val Ala Gly Gln Leu Gly Ile His His Arg Leu Pro<br>          2560                2565                2570 | 59990 |
| gcc ccg cac gcc ggg cac tcc gcg cac atg gag ccc gtg gcc gcc gag<br>Ala Pro His Ala Gly His Ser Ala His Met Glu Pro Val Ala Ala Glu<br>2575                2580                2585 | 60038 |
| ctg ctc gcc acc acc cgc ggg ctc cgc tac cac cct ccc cac acc tcc<br>Leu Leu Ala Thr Thr Arg Gly Leu Arg Tyr His Pro Pro His Thr Ser<br>     2590                2595                2600 | 60086 |
| att ccg aac gac ccc acc acc gct gag tac tgg gcc gag cag gtc cgc<br>Ile Pro Asn Asp Pro Thr Thr Ala Glu Tyr Trp Ala Glu Gln Val Arg<br>2605                2610                2615                2620 | 60134 |
| aag ccc gtg ctg ttc cac gcc cac gcg cag cag tac ccg gac gcc gtg<br>Lys Pro Val Leu Phe His Ala His Ala Gln Gln Tyr Pro Asp Ala Val<br>          2625                2630                2635 | 60182 |
| ttc gtg gag atc ggc ccc gcc cag gac ctc tcc ccg ctc gtc gac ggg<br>Phe Val Glu Ile Gly Pro Ala Gln Asp Leu Ser Pro Leu Val Asp Gly<br>          2640                2645                2650 | 60230 |
| atc ccg ctg cag aac ggc acc gcg gac gag gtg cac gcg ctg cac acc<br>Ile Pro Leu Gln Asn Gly Thr Ala Asp Glu Val His Ala Leu His Thr<br>          2655                2660                2665 | 60278 |
| gcg ctc gcg cac ctc tac gcg cgc ggt gcc acg ctc gac tgg ccc cgc<br>Ala Leu Ala His Leu Tyr Ala Arg Gly Ala Thr Leu Asp Trp Pro Arg<br>          2670                2675                2680 | 60326 |
| atc ctc ggg gct ggg tca cgg cac gac gcg gat gtg ccc gcg tac gcg<br>Ile Leu Gly Ala Gly Ser Arg His Asp Ala Asp Val Pro Ala Tyr Ala<br>2685                2690                2695                2700 | 60374 |
| ttc caa cgg cgg cac tac tgg atc gag tcg gca cgc ccg gcc gca tcc<br>Phe Gln Arg Arg His Tyr Trp Ile Glu Ser Ala Arg Pro Ala Ala Ser<br>          2705                2710                2715 | 60422 |
| gac gcg ggc cac ccc gtg ctg ggc tcc ggt atc gcc ctc gcc ggg tcg<br>Asp Ala Gly His Pro Val Leu Gly Ser Gly Ile Ala Leu Ala Gly Ser<br>          2720                2725                2730 | 60470 |
| ccg ggc cgg gtg ttc acg ggt tcc gtg ccg acc ggt gcg gac cgc gcg<br>Pro Gly Arg Val Phe Thr Gly Ser Val Pro Thr Gly Ala Asp Arg Ala<br>          2735                2740                2745 | 60518 |
| gtg ttc gtc gcc gag ctg gcg ctg gcc gcc gcg gac gcg gtc gac tgc<br>Val Phe Val Ala Glu Leu Ala Leu Ala Ala Ala Asp Ala Val Asp Cys<br>          2750                2755                2760 | 60566 |
| gcc acg gtc gag cgg ctc gac atc gcc tcc gtg ccc ggc cgg ccg ggc<br>Ala Thr Val Glu Arg Leu Asp Ile Ala Ser Val Pro Gly Arg Pro Gly<br>2765                2770                2775                2780 | 60614 |
| cat ggc cgg acg acc gta cag acc tgg gtc gac gag ccg gcg gac gac<br>His Gly Arg Thr Thr Val Gln Thr Trp Val Asp Glu Pro Ala Asp Asp<br>          2785                2790                2795 | 60662 |
| ggc cgg cgc cgg ttc acc gtg cac acc cgc acc ggc gac gcc ccg tgg<br>Gly Arg Arg Arg Phe Thr Val His Thr Arg Thr Gly Asp Ala Pro Trp<br>          2800                2805                2810 | 60710 |
| acg ctg cac gcc gag ggg gtg ctg cgc ccc cat ggc acg gcc ctg ccc<br>Thr Leu His Ala Glu Gly Val Leu Arg Pro His Gly Thr Ala Leu Pro<br>          2815                2820                2825 | 60758 |
| gat gcg gcc gac gcc gag tgg ccc cca ccg ggc gcg gtg ccc gcg gac<br>Asp Ala Ala Asp Ala Glu Trp Pro Pro Pro Gly Ala Val Pro Ala Asp<br>          2830                2835                2840 | 60806 |
| ggg ctg ccg ggt gtg tgg cgc cgg ggg gac cag gtc ttc gcc gag gcc<br>Gly Leu Pro Gly Val Trp Arg Arg Gly Asp Gln Val Phe Ala Glu Ala<br>2845                2850                2855                2860 | 60854 |
| gag gtg gac gga ccg gac ggt ttc gtg gtg cac ccc gac ctg ctc gac<br>Glu Val Asp Gly Pro Asp Gly Phe Val Val His Pro Asp Leu Leu Asp | 60902 |

-continued

```
                    2865                2870                2875
gcg gtc ttc tcc gcg gtc ggc gac gga agc cgc cag ccg gcc gga tgg    60950
Ala Val Phe Ser Ala Val Gly Asp Gly Ser Arg Gln Pro Ala Gly Trp
        2880                2885                2890 cgc gac ctg acg gtg cac gcg tcg gac gcc acc gta ctg cgc gcc tgc    60998
Arg Asp Leu Thr Val His Ala Ser Asp Ala Thr Val Leu Arg Ala Cys
        2895                2900                2905 ctc acc cgg cgc acc gac gga gcc atg gga ttc gcc gcc ttc gac ggc    61046
Leu Thr Arg Arg Thr Asp Gly Ala Met Gly Phe Ala Ala Phe Asp Gly
        2910                2915                2920 gcc ggc ctg ccg gta ctc acc gcg gag gcg gtg acg ctg cgg gag gtg    61094
Ala Gly Leu Pro Val Leu Thr Ala Glu Ala Val Thr Leu Arg Glu Val
2925                2930                2935                2940 gcg tca ccg tcc ggc tcc gag gag tcg gac ggc ctg cac cgg ttg gag    61142
Ala Ser Pro Ser Gly Ser Glu Glu Ser Asp Gly Leu His Arg Leu Glu
                2945                2950                2955 tgg ctc gcg gtc gcc gag gcg gtc tac gac ggt gac ctg ccc gag gga    61190
Trp Leu Ala Val Ala Glu Ala Val Tyr Asp Gly Asp Leu Pro Glu Gly
                2960                2965                2970 cat gtc ctg atc acc gcc gcc cac ccc gac gac ccc gag gac ata ccc    61238
His Val Leu Ile Thr Ala Ala His Pro Asp Asp Pro Glu Asp Ile Pro
        2975                2980                2985 acc cgc gcc cac acc cgc gcc acc cgt gtc ctg acc gcc ctg caa cac    61286
Thr Arg Ala His Thr Arg Ala Thr Arg Val Leu Thr Ala Leu Gln His
        2990                2995                3000 cac ctc acc acc acc gac cac acc ctc atc gtc cac acc acc acc gac    61334
His Leu Thr Thr Thr Asp His Thr Leu Ile Val His Thr Thr Thr Asp
3005                3010                3015                3020 ccc gcc ggc gcc acc gtc acc ggc ctc acc cgc acc gcc cag aac gaa    61382
Pro Ala Gly Ala Thr Val Thr Gly Leu Thr Arg Thr Ala Gln Asn Glu
                3025                3030                3035 cac ccc cac cgc atc cgc ctc atc gaa acc gac cac ccc cac acc ccc    61430
His Pro His Arg Ile Arg Leu Ile Glu Thr Asp His Pro His Thr Pro
        3040                3045                3050 ctc ccc ctg gcc caa ctc gcc acc ctc gac cac ccc cac ctc cgc ctc    61478
Leu Pro Leu Ala Gln Leu Ala Thr Leu Asp His Pro His Leu Arg Leu
        3055                3060                3065 acc cac cac acc ctc cac cac ccc cac ctc acc ccc ctc cac acc acc    61526
Thr His His Thr Leu His His Pro His Leu Thr Pro Leu His Thr Thr
        3070                3075                3080 acc cca ccc acc acc acc ccc ctc aac ccc gaa cac gcc atc atc atc    61574
Thr Pro Pro Thr Thr Thr Pro Leu Asn Pro Glu His Ala Ile Ile Ile
3085                3090                3095                3100 acc ggc ggc tcc ggc acc ctc gcc ggc atc ctc gcc cgc cac ctg aac    61622
Thr Gly Gly Ser Gly Thr Leu Ala Gly Ile Leu Ala Arg His Leu Asn
                3105                3110                3115 cac ccc cac acc tac ctc ctc tcc cgc acc cca ccc ccc gac gcc acc    61670
His Pro His Thr Tyr Leu Leu Ser Arg Thr Pro Pro Pro Asp Ala Thr
        3120                3125                3130 ccc ggc acc cac ctc ccc tgc gac gtc ggc gac ccc cac caa ctc gcc    61718
Pro Gly Thr His Leu Pro Cys Asp Val Gly Asp Pro His Gln Leu Ala
        3135                3140                3145 acc acc ctc acc cac atc ccc caa ccc ctc acc gcc atc ttc cac acc    61766
Thr Thr Leu Thr His Ile Pro Gln Pro Leu Thr Ala Ile Phe His Thr
        3150                3155                3160 gcc gcc acc ctc gac gac ggc atc ctc cac gcc ctc acc ccc gac cgc    61814
Ala Ala Thr Leu Asp Asp Gly Ile Leu His Ala Leu Thr Pro Asp Arg
3165                3170                3175                3180 ctc acc acc gtc ctc cac ccc aaa gcc aac gcc gcc tgg cac ctg cac    61862
```

```
                                                    -continued

Leu Thr Thr Val Leu His Pro Lys Ala Asn Ala Ala Trp His Leu His
            3185                3190                3195 cac ctc acc caa aac caa ccc ctc acc cac ttc gtc ctc tac tcc agc     61910
His Leu Thr Gln Asn Gln Pro Leu Thr His Phe Val Leu Tyr Ser Ser
            3200                3205                3210 gcc gcc gcc gtc ctc ggc agc ccc gga caa gga aac tac gcc gcc gcc     61958
Ala Ala Ala Val Leu Gly Ser Pro Gly Gln Gly Asn Tyr Ala Ala Ala
            3215                3220                3225 aac gcc ttc ctc gac gcc ctc gcc acc cac cgc cac acc ctc ggc caa     62006
Asn Ala Phe Leu Asp Ala Leu Ala Thr His Arg His Thr Leu Gly Gln
            3230                3235                3240 ccc gcc acc tcc atc gcc tgg ggc atg tgg cac acc acc agc acc ctc     62054
Pro Ala Thr Ser Ile Ala Trp Gly Met Trp His Thr Thr Ser Thr Leu
3245            3250                3255                3260 acc gga caa ctc gac gac gcc gac cgg gac cgc atc cgc cgc ggc ggt     62102
Thr Gly Gln Leu Asp Asp Ala Asp Arg Asp Arg Ile Arg Arg Gly Gly
            3265                3270                3275 ttc ctc ccg atc acg gac gac gag ggc atg cgc ctc tac gag gcg gcc     62150
Phe Leu Pro Ile Thr Asp Asp Glu Gly Met Arg Leu Tyr Glu Ala Ala
            3280                3285                3290 gtc ggc tcc ggc gag gac ttc gtc atg gcc gcc gcg atg gac ccg gca     62198
Val Gly Ser Gly Glu Asp Phe Val Met Ala Ala Ala Met Asp Pro Ala
            3295                3300                3305 cag ccg atg acc ggc tcc gta ccg ccc atc ctg agc ggc ctg cgc agg     62246
Gln Pro Met Thr Gly Ser Val Pro Pro Ile Leu Ser Gly Leu Arg Arg
            3310                3315                3320 agc gcg cgg cgc gtc gcc cgt gcc ggg cag acg ttc gcc cag cgg ctc     62294
Ser Ala Arg Arg Val Ala Arg Ala Gly Gln Thr Phe Ala Gln Arg Leu
3325            3330                3335                3340 gcc gag ctg ccc gac gcc gac cgc ggc gcg gcg ctg acc acc ctc gtc     62342
Ala Glu Leu Pro Asp Ala Asp Arg Gly Ala Ala Leu Thr Thr Leu Val
            3345                3350                3355 tcg gac gcc acg gcc gcc gtg ctc ggc cac gcc gac gcc tcc gag atc     62390
Ser Asp Ala Thr Ala Ala Val Leu Gly His Ala Asp Ala Ser Glu Ile
            3360                3365                3370 gcg ccg acc acg acg ttc aag gac ctc ggc atc gac tcg ctc acc gcg     62438
Ala Pro Thr Thr Thr Phe Lys Asp Leu Gly Ile Asp Ser Leu Thr Ala
            3375                3380                3385 atc gag ctg cgc aac cgg ctc gcg gag gcg acc ggg ctg cgg ctg agt     62486
Ile Glu Leu Arg Asn Arg Leu Ala Glu Ala Thr Gly Leu Arg Leu Ser
            3390                3395                3400 gcc acg ctg gtg ttc gac cac ccg aca cct cgg gtc ctc gcc gcc aag     62534
Ala Thr Leu Val Phe Asp His Pro Thr Pro Arg Val Leu Ala Ala Lys
3405            3410                3415                3420 ctc cgc acc gat ctg ttc ggc acg gcc gtg ccc acg ccc gcg cgg acg     62582
Leu Arg Thr Asp Leu Phe Gly Thr Ala Val Pro Thr Pro Ala Arg Thr
            3425                3430                3435 gca cgg acc cac cac gac gag cca ctc gcg atc gtc ggc atg gcg tgc     62630
Ala Arg Thr His His Asp Glu Pro Leu Ala Ile Val Gly Met Ala Cys
            3440                3445                3450 cga ctg ccc ggc ggg gtc gcc tcg ccg gag gac ctg tgg cag ctc gtg     62678
Arg Leu Pro Gly Gly Val Ala Ser Pro Glu Asp Leu Trp Gln Leu Val
            3455                3460                3465 gcg tcc ggc acc gac gcg atc acc gag ttc ccc acc gac cgc ggc tgg     62726
Ala Ser Gly Thr Asp Ala Ile Thr Glu Phe Pro Thr Asp Arg Gly Trp
            3470                3475                3480 gac atc gac cgg ctg ttc gac ccg gac ccg gac gcc ccc ggc aag acc     62774
Asp Ile Asp Arg Leu Phe Asp Pro Asp Pro Asp Ala Pro Gly Lys Thr
3485            3490                3495                3500
```

```
tac gtc cgg cac ggc ggc ttc ctc gcc gag gcc gcc ggc ttc gat gcc        62822
Tyr Val Arg His Gly Gly Phe Leu Ala Glu Ala Ala Gly Phe Asp Ala
            3505                3510                3515 gcg ttc ttc ggc atc agc ccg cgc gag gca cgg gcc atg gac ccg cag        62870
Ala Phe Phe Gly Ile Ser Pro Arg Glu Ala Arg Ala Met Asp Pro Gln
        3520                3525                3530 cag cgc gtc atc ctc gaa acc tcc tgg gag gcg ttc gag aac gcg ggc        62918
Gln Arg Val Ile Leu Glu Thr Ser Trp Glu Ala Phe Glu Asn Ala Gly
    3535                3540                3545 atc gtg ccg gac acg ctg cgc ggc agc gac acc ggc gtg ttc atg ggc        62966
Ile Val Pro Asp Thr Leu Arg Gly Ser Asp Thr Gly Val Phe Met Gly
3550                3555                3560 gcg ttc tcc cat ggg tac ggc gcc ggc gtc gac ctg ggc ggg ttc ggc        63014
Ala Phe Ser His Gly Tyr Gly Ala Gly Val Asp Leu Gly Gly Phe Gly
3565                3570                3575                3580 gcc acc gcc acg cag aac agc gtg ctc tcc ggc cgg ttg tcg tac ttc        63062
Ala Thr Ala Thr Gln Asn Ser Val Leu Ser Gly Arg Leu Ser Tyr Phe
            3585                3590                3595 ttc ggc atg gag ggc ccg gcc gtc acc gtc gac acc gcc tgc tcg tcg        63110
Phe Gly Met Glu Gly Pro Ala Val Thr Val Asp Thr Ala Cys Ser Ser
        3600                3605                3610 tcg ctg gtc gcc ctg cac cag gcg gca cag gcg ctg cgg act gga gaa        63158
Ser Leu Val Ala Leu His Gln Ala Ala Gln Ala Leu Arg Thr Gly Glu
    3615                3620                3625 tgc tcg ctg gcg ctc gcc ggc ggt gtc acg gtg atg ccc acc ccg ctg        63206
Cys Ser Leu Ala Leu Ala Gly Gly Val Thr Val Met Pro Thr Pro Leu
3630                3635                3640 ggc tac gtc gag ttc tgc cgc cag cgg gga ctc gcc ccc gac ggc cgt        63254
Gly Tyr Val Glu Phe Cys Arg Gln Arg Gly Leu Ala Pro Asp Gly Arg
3645                3650                3655                3660 tgc cag gcc ttc gcg gaa ggc gcc gac ggc acg agc ttc tcg gag ggc        63302
Cys Gln Ala Phe Ala Glu Gly Ala Asp Gly Thr Ser Phe Ser Glu Gly
            3665                3670                3675 gcc ggc gtt ctt gtg ctg gag cgg ctc tcc gac gcc gag cgc aac gga        63350
Ala Gly Val Leu Val Leu Glu Arg Leu Ser Asp Ala Glu Arg Asn Gly
        3680                3685                3690 cac acc gtc ctc gcg gtc gtc cgc tcc tcc gcc gtc aac cag gac ggc        63398
His Thr Val Leu Ala Val Val Arg Ser Ser Ala Val Asn Gln Asp Gly
    3695                3700                3705 gcc tcc aac ggc atc tcc gca ccc aac ggc ccc tcc cag cag cgc gtc        63446
Ala Ser Asn Gly Ile Ser Ala Pro Asn Gly Pro Ser Gln Gln Arg Val
3710                3715                3720 atc cgc cag gcc ctc gac aag gcc ggg ctc gcc ccc gcc gac gtg gac        63494
Ile Arg Gln Ala Leu Asp Lys Ala Gly Leu Ala Pro Ala Asp Val Asp
3725                3730                3735                3740 gtg gtg gag gcc cac ggc acc gga acc ccg ctg ggc gac ccg atc gag        63542
Val Val Glu Ala His Gly Thr Gly Thr Pro Leu Gly Asp Pro Ile Glu
            3745                3750                3755 gca cag gcc atc atc gcg acc tac ggc cag gac cgc gac aca ccg ctc        63590
Ala Gln Ala Ile Ile Ala Thr Tyr Gly Gln Asp Arg Asp Thr Pro Leu
        3760                3765                3770 tac ctc ggt tcg gtc aag tcg aac atc gga cac acc cag acc acc gcc        63638
Tyr Leu Gly Ser Val Lys Ser Asn Ile Gly His Thr Gln Thr Thr Ala
    3775                3780                3785 ggt gtc gcc ggc gtc atc aag atg gtc atg gcg atg cgc cac ggc atc        63686
Gly Val Ala Gly Val Ile Lys Met Val Met Ala Met Arg His Gly Ile
3790                3795                3800 gcg ccg aag aca ctg cac gtg gac gag ccg tcg tcg cat gtg gac tgg        63734
Ala Pro Lys Thr Leu His Val Asp Glu Pro Ser Ser His Val Asp Trp
3805                3810                3815                3820
```

```
acc gag ggt gcg gtg gaa ctg ctc acc gag gcg agg ccg tgg ccc gac       63782
Thr Glu Gly Ala Val Glu Leu Leu Thr Glu Ala Arg Pro Trp Pro Asp
            3825                3830                3835 gcg gga cgc ccg cgc cgc gcg ggc gtg tcg tcg ctc ggt atc agc ggt       63830
Ala Gly Arg Pro Arg Arg Ala Gly Val Ser Ser Leu Gly Ile Ser Gly
3840                3845                3850 acg aac gcc cac gtg atc ctt gag ggt gtt ccc ggg ccg tcg cgt gtg       63878
Thr Asn Ala His Val Ile Leu Glu Gly Val Pro Gly Pro Ser Arg Val
        3855                3860                3865 gag ccg tct gtt gac ggg ttg gtg ccg ttg ccg gtg tcg gct cgg agt       63926
Glu Pro Ser Val Asp Gly Leu Val Pro Leu Pro Val Ser Ala Arg Ser
    3870                3875                3880 gag gcg agt ctg cgg ggg cag gtg gag cgg ctg gag ggg tat ctg cgc       63974
Glu Ala Ser Leu Arg Gly Gln Val Glu Arg Leu Glu Gly Tyr Leu Arg
3885                3890                3895                3900 ggg agt gtg gat gtg gcc gcg gtc gcg cag ggg ttg gtg cgt gag cgt       64022
Gly Ser Val Asp Val Ala Ala Val Ala Gln Gly Leu Val Arg Glu Arg
            3905                3910                3915 gct gtc ttc ggt cac cgt gcg gta ctg ctg ggt gat gcc cgg gtg atg       64070
Ala Val Phe Gly His Arg Ala Val Leu Leu Gly Asp Ala Arg Val Met
3920                3925                3930 ggt gtg gcg gtg gat cag ccg cgt acg gtg ttc gtc ttt ccc ggg cag       64118
Gly Val Ala Val Asp Gln Pro Arg Thr Val Phe Val Phe Pro Gly Gln
        3935                3940                3945 ggt gct cag tgg gtg ggc atg ggt gtg gag ttg atg gac cgt tct gcg       64166
Gly Ala Gln Trp Val Gly Met Gly Val Glu Leu Met Asp Arg Ser Ala
    3950                3955                3960 gtg ttc gcg gct cgt atg gag gag tgt gcg cgg gcg ttg ttg ccg cac       64214
Val Phe Ala Ala Arg Met Glu Glu Cys Ala Arg Ala Leu Leu Pro His
3965                3970                3975                3980 acg ggc tgg gat gtg cgg gag atg ttg gcg cgg ccg gat gtg gcg gag       64262
Thr Gly Trp Asp Val Arg Glu Met Leu Ala Arg Pro Asp Val Ala Glu
            3985                3990                3995 cgg gtg gag gtg gtc cag ccg gcc agc tgg gcg gtc gcg gtc agc ctg       64310
Arg Val Glu Val Val Gln Pro Ala Ser Trp Ala Val Ala Val Ser Leu
4000                4005                4010 gcc gca ctg tgg cag gcc cac ggg gtc gta ccc gac gcg gtg atc gga       64358
Ala Ala Leu Trp Gln Ala His Gly Val Val Pro Asp Ala Val Ile Gly
        4015                4020                4025 cac tcc cag ggc gag atc gcg gcg gcg tgc gtg gcc ggg gcc ctc agc       64406
His Ser Gln Gly Glu Ile Ala Ala Ala Cys Val Ala Gly Ala Leu Ser
    4030                4035                4040 ctt gag gac gcc gcc cgc gtg gtg gcc ttg cgc agc cag gtc atc gcg       64454
Leu Glu Asp Ala Ala Arg Val Val Ala Leu Arg Ser Gln Val Ile Ala
4045                4050                4055                4060 gcg cga ctg gcc ggg cgg gga gcg atg gct tcg gtg gca ttg ccg gcc       64502
Ala Arg Leu Ala Gly Arg Gly Ala Met Ala Ser Val Ala Leu Pro Ala
            4065                4070                4075 ggt gag gtc ggt ctg gtc gag ggc gtg tgg atc gcg gcg cgt aac ggc       64550
Gly Glu Val Gly Leu Val Glu Gly Val Trp Ile Ala Ala Arg Asn Gly
4080                4085                4090 ccc gcc tcg aca gtc gtg gcc ggc gag ccg tcg gcg gtg gag gac gtg       64598
Pro Ala Ser Thr Val Val Ala Gly Glu Pro Ser Ala Val Glu Asp Val
        4095                4100                4105 gtg acg cgg tat gag acc gaa ggc gtg cga gtg cgt cgt atc gcc gtc       64646
Val Thr Arg Tyr Glu Thr Glu Gly Val Arg Val Arg Arg Ile Ala Val
    4110                4115                4120 gac tac gcc tcc cac acg ccc cac gtg gaa gcc atc gag gac gaa ctc       64694
Asp Tyr Ala Ser His Thr Pro His Val Glu Ala Ile Glu Asp Glu Leu
```

```
                                                                      -continued
       4125                4130                4135                4140
gct gag gta ctg aag gga gtt gca ggg aag gcc gcg tcg gtg gcg tgg       64742
Ala Glu Val Leu Lys Gly Val Ala Gly Lys Ala Ala Ser Val Ala Trp
                    4145                4150                4155 tgg tcg acc gtg gac agc gcc tgg gtg acc gag ccg gtg gat gag agt       64790
Trp Ser Thr Val Asp Ser Ala Trp Val Thr Glu Pro Val Asp Glu Ser
                4160                4165                4170 tac tgg tac cgg aac ctg cgt cgc ccc gtc gcg ctg gac gcg gcg gtg       64838
Tyr Trp Tyr Arg Asn Leu Arg Arg Pro Val Ala Leu Asp Ala Ala Val
                4175                4180                4185 gcg gag ctg gac ggg tcc gtg ttc gtg gag tgc agc gcc cat ccg gtg       64886
Ala Glu Leu Asp Gly Ser Val Phe Val Glu Cys Ser Ala His Pro Val
                4190                4195                4200 ctg ctg ccg gcg atg gaa cag gcc cac acg gtg gcg tcg ttg cgc acc       64934
Leu Leu Pro Ala Met Glu Gln Ala His Thr Val Ala Ser Leu Arg Thr
4205                4210                4215                4220 ggt gac ggc ggc tgg gag cga tgg ctg acg gcg ttg gcg cag gcg tgg       64982
Gly Asp Gly Gly Trp Glu Arg Trp Leu Thr Ala Leu Ala Gln Ala Trp
                    4225                4230                4235 acc ctg ggc gcg gca gtg gac tgg gac acg gtg gtc gaa ccg gtg cca       65030
Thr Leu Gly Ala Ala Val Asp Trp Asp Thr Val Val Glu Pro Val Pro
                4240                4245                4250 ggg cgg ctg ctc gat ctg ccc acc tac gcg ttc gag cgc cgg cgc tac       65078
Gly Arg Leu Leu Asp Leu Pro Thr Tyr Ala Phe Glu Arg Arg Arg Tyr
                4255                4260                4265 tgg ctg gaa gcg gcc ggt gcc acc gac ctg tcc gcg gcc ggg ctg aca       65126
Trp Leu Glu Ala Ala Gly Ala Thr Asp Leu Ser Ala Ala Gly Leu Thr
                4270                4275                4280 ggg gca gca cat ccc atg ctg gcc gcc atc acg gca cta ccc gcc gac       65174
Gly Ala Ala His Pro Met Leu Ala Ala Ile Thr Ala Leu Pro Ala Asp
4285                4290                4295                4300 gac ggt ggt gtt gtt ctc acc ggc cgg atc tcg ttg cgc acg cat ccc       65222
Asp Gly Gly Val Val Leu Thr Gly Arg Ile Ser Leu Arg Thr His Pro
                4305                4310                4315 tgg ctg gct gat cac gcg gtg cgg ggc acg gtc ctg ctg ccg ggc acg       65270
Trp Leu Ala Asp His Ala Val Arg Gly Thr Val Leu Leu Pro Gly Thr
                4320                4325                4330 gcc ttt gtg gag ctg gtc atc cgg gcc ggt gac gag acc ggt tgc ggg       65318
Ala Phe Val Glu Leu Val Ile Arg Ala Gly Asp Glu Thr Gly Cys Gly
                4335                4340                4345 ata gtg gat gaa ctg gtc atc gaa tcc ccc ctc gtg gtg ccg gcg acc       65366
Ile Val Asp Glu Leu Val Ile Glu Ser Pro Leu Val Val Pro Ala Thr
                4350                4355                4360 gca gcc gtg gat ctg tcg gtg acc gtg gaa gga gct gac gag gcc gga       65414
Ala Ala Val Asp Leu Ser Val Thr Val Glu Gly Ala Asp Glu Ala Gly
4365                4370                4375                4380 cgg cgg cga gtg acc gtc cac gcc cgc acc gaa ggc acc ggc agc tgg       65462
Arg Arg Arg Val Thr Val His Ala Arg Thr Glu Gly Thr Gly Ser Trp
                4385                4390                4395 acc cgg cac gcc agc ggc acc ctg acc ccc gac acc ccc gac acc ccc       65510
Thr Arg His Ala Ser Gly Thr Leu Thr Pro Asp Thr Pro Asp Thr Pro
                4400                4405                4410 aac gct tcc ggt gtt gtc ggt gcg gag ccg ttc tcg cag tgg cca cct       65558
Asn Ala Ser Gly Val Val Gly Ala Glu Pro Phe Ser Gln Trp Pro Pro
                4415                4420                4425 gcc act gcc gcg gcc gtc gac acc tcg gag ttc tac ttg cgc ctg gac       65606
Ala Thr Ala Ala Ala Val Asp Thr Ser Glu Phe Tyr Leu Arg Leu Asp
                4430                4435                4440 gcg ctg ggc tac cgg ttc gga ccc atg ttc cgc gga atg cgg gct gcc       65654
```

```
Ala Leu Gly Tyr Arg Phe Gly Pro Met Phe Arg Gly Met Arg Ala Ala
     4445             4450             4455             4460 tgg cgt gat ggt gac acc gtg tac gcc gag gtc gcg ctc ccc gag gac       65702
Trp Arg Asp Gly Asp Thr Val Tyr Ala Glu Val Ala Leu Pro Glu Asp
             4465             4470             4475 cgt gcc gcc gac gcg gac ggt ttc ggc atg cac ccg gcg ctg ctc gac       65750
Arg Ala Ala Asp Ala Asp Gly Phe Gly Met His Pro Ala Leu Leu Asp
         4480             4485             4490 gcg gcc ttg cag agc ggc agc ctg ctc atg ctg gaa tcg gac ggc gag       65798
Ala Ala Leu Gln Ser Gly Ser Leu Leu Met Leu Glu Ser Asp Gly Glu
             4495             4500             4505 cag agc gtg caa ctg ccg ttc tcc tgg cac ggc gtc cgg ttc cac gcg       65846
Gln Ser Val Gln Leu Pro Phe Ser Trp His Gly Val Arg Phe His Ala
     4510             4515             4520 acg ggc gcg acc atg ctg cgg gtg gcg gtc gta ccg ggc ccg gac ggc       65894
Thr Gly Ala Thr Met Leu Arg Val Ala Val Val Pro Gly Pro Asp Gly
4525             4530             4535             4540 ctc cgg ctg cat gcc gcg gac agc ggg aac cgt ccc gtc gcg acg atc       65942
Leu Arg Leu His Ala Ala Asp Ser Gly Asn Arg Pro Val Ala Thr Ile
             4545             4550             4555 gac gcg ctc gtg acc cgg tcc ccg gaa gcg gac ctc gcg ccc gcc gat       65990
Asp Ala Leu Val Thr Arg Ser Pro Glu Ala Asp Leu Ala Pro Ala Asp
         4560             4565             4570 ccg atg ctg cgg gtc ggg tgg gcc ccg gtg ccc gta cct gcc ggg gcc       66038
Pro Met Leu Arg Val Gly Trp Ala Pro Val Pro Val Pro Ala Gly Ala
             4575             4580             4585 ggt ccg tcc gac gcg gac gtg ctg acg ctg cgc ggc gac gac gcc gac       66086
Gly Pro Ser Asp Ala Asp Val Leu Thr Leu Arg Gly Asp Asp Ala Asp
         4590             4595             4600 ccg ctc ggg gag acc cgg gac ctg acc acc cgt gtt ctc gac gcg ctg       66134
Pro Leu Gly Glu Thr Arg Asp Leu Thr Thr Arg Val Leu Asp Ala Leu
4605             4610             4615             4620 ctc cgg gcc gac cgg ccg gtg atc ttc cag gtg acc ggt ggc ctc gcc       66182
Leu Arg Ala Asp Arg Pro Val Ile Phe Gln Val Thr Gly Gly Leu Ala
             4625             4630             4635 gcc aag gcg gcc gca ggc ctg gtc cgc acc gct cag aac gag cag ccc       66230
Ala Lys Ala Ala Ala Gly Leu Val Arg Thr Ala Gln Asn Glu Gln Pro
         4640             4645             4650 ggc cgc ttc ttc ctc gtc gaa acg gac ccg gga gag gtc ctg gac ggc       66278
Gly Arg Phe Phe Leu Val Glu Thr Asp Pro Gly Glu Val Leu Asp Gly
             4655             4660             4665 gcg aag cgc gac gcg atc gcg gca ctc ggc gag ccc cat gtg cgg ctg       66326
Ala Lys Arg Asp Ala Ile Ala Ala Leu Gly Glu Pro His Val Arg Leu
         4670             4675             4680 cgc gac ggc ctc ttc gag gca gcc cgg ctg atg cgg gcc acg ccg tcc       66374
Arg Asp Gly Leu Phe Glu Ala Ala Arg Leu Met Arg Ala Thr Pro Ser
4685             4690             4695             4700 ctg acg ctc ccg gac acc ggg tcg tgg cag ctg cgg ccg tcc gcc acc       66422
Leu Thr Leu Pro Asp Thr Gly Ser Trp Gln Leu Arg Pro Ser Ala Thr
             4705             4710             4715 ggt tcc ctc gac gac ctt gcc gtc gtc ccc acc gac gcc ccg gac cgg       66470
Gly Ser Leu Asp Asp Leu Ala Val Val Pro Thr Asp Ala Pro Asp Arg
         4720             4725             4730 ccg ctc gcg gcc ggc gag gtg cgg atc gcg gta cgc gcg gcg ggc ctg       66518
Pro Leu Ala Ala Gly Glu Val Arg Ile Ala Val Arg Ala Ala Gly Leu
             4735             4740             4745 aac ttc cgg gat gtc acg gtc gcg ctc ggt gtg gtc gcc gat gcg cgt       66566
Asn Phe Arg Asp Val Thr Val Ala Leu Gly Val Val Ala Asp Ala Arg
         4750             4755             4760
```

```
ccg ctc ggc agc gag gcc gcg ggt gtc gtc ctg gag acc ggc ccc ggt     66614
Pro Leu Gly Ser Glu Ala Ala Gly Val Val Leu Glu Thr Gly Pro Gly
4765                4770                4775                4780 gtg cac gac ctg gcg ccc ggc gac cgg gtc ctg ggg atg ctc gcg ggc     66662
Val His Asp Leu Ala Pro Gly Asp Arg Val Leu Gly Met Leu Ala Gly
            4785                4790                4795 gcc ttc gga ccg gtc gcg atc acc gac cgg cgg ctc ctc ggc cgg atg     66710
Ala Phe Gly Pro Val Ala Ile Thr Asp Arg Arg Leu Leu Gly Arg Met
4800                4805                4810 ccg gac ggc tgg acg ttc ccg cag gcg gcg tcc gtg atg acc gcg ttc     66758
Pro Asp Gly Trp Thr Phe Pro Gln Ala Ala Ser Val Met Thr Ala Phe
            4815                4820                4825 gcg acc gcg tgg tac ggc ctg gtc gac ctg gcc ggg ctg cgc ccc ggc     66806
Ala Thr Ala Trp Tyr Gly Leu Val Asp Leu Ala Gly Leu Arg Pro Gly
4830                4835                4840 gag aag gtc ctg atc cac gcg gcg gcg acc ggt gtc ggc gcg gcg gcc     66854
Glu Lys Val Leu Ile His Ala Ala Ala Thr Gly Val Gly Ala Ala Ala
4845                4850                4855                4860 gtc cag atc gcg cgg cat ctg ggc gcg gag gtg tac gcg acc acc agc     66902
Val Gln Ile Ala Arg His Leu Gly Ala Glu Val Tyr Ala Thr Thr Ser
            4865                4870                4875 gcc gcg aag cgc cat ctg gtg gac ctg gac gga gcg cat ctg gcc gat     66950
Ala Ala Lys Arg His Leu Val Asp Leu Asp Gly Ala His Leu Ala Asp
4880                4885                4890 tcc cgc agc acc gcg ttc gcc gac gcg ttc ccg ccg gtc gat gtc gtg     66998
Ser Arg Ser Thr Ala Phe Ala Asp Ala Phe Pro Pro Val Asp Val Val
            4895                4900                4905 ctc aac tcg ctc acc ggt gaa ttc ctc gac gcg tcc gtc ggc ctg ctc     67046
Leu Asn Ser Leu Thr Gly Glu Phe Leu Asp Ala Ser Val Gly Leu Leu
4910                4915                4920 gcg gcg ggt ggc cgg ttc atc gag atg ggg aag acg gac atc cgg cac     67094
Ala Ala Gly Gly Arg Phe Ile Glu Met Gly Lys Thr Asp Ile Arg His
4925                4930                4935                4940 gcc gtc cag cag ccg ttc gac ctg atg gac gcc ggc ccc gac cgg atg     67142
Ala Val Gln Gln Pro Phe Asp Leu Met Asp Ala Gly Pro Asp Arg Met
            4945                4950                4955 cag cgg atc atc gtc gag ctg ctc ggc ctg ttc gcg cgc gac gtg ctg     67190
Gln Arg Ile Ile Val Glu Leu Leu Gly Leu Phe Ala Arg Asp Val Leu
4960                4965                4970 cac ccg ctg ccg gtc cac gcc tgg gac gtg cgg cag gcg cgg gag gcg     67238
His Pro Leu Pro Val His Ala Trp Asp Val Arg Gln Ala Arg Glu Ala
            4975                4980                4985 ttc ggc tgg atg agc agc ggg cgt cac acc ggc aag ctg gtg ctg acg     67286
Phe Gly Trp Met Ser Ser Gly Arg His Thr Gly Lys Leu Val Leu Thr
4990                4995                5000 gtc ccg cgg ccg ctg gat ccc gag ggg gcc gtc gtc atc acc ggc ggc     67334
Val Pro Arg Pro Leu Asp Pro Glu Gly Ala Val Val Ile Thr Gly Gly
5005                5010                5015                5020 tcc ggc acc ctc gcc ggc atc ctc gcc cgc cac ctg ggc cac ccc cac     67382
Ser Gly Thr Leu Ala Gly Ile Leu Ala Arg His Leu Gly His Pro His
            5025                5030                5035 acc tac ctg ctc tcc cgc acc cca ccc ccc gac acc acc ccc ggc acc     67430
Thr Tyr Leu Leu Ser Arg Thr Pro Pro Pro Asp Thr Thr Pro Gly Thr
5040                5045                5050 cac ctc ccc tgc gac gtc ggc gac ccc cac caa ctc gcc acc acc ctc     67478
His Leu Pro Cys Asp Val Gly Asp Pro His Gln Leu Ala Thr Thr Leu
            5055                5060                5065 gcc cgc atc ccc caa ccc ctc acc gcc gtc ttc cac acc gcc gga acc     67526
Ala Arg Ile Pro Gln Pro Leu Thr Ala Val Phe His Thr Ala Gly Thr
5070                5075                5080
```

```
                                                 -continued ctc gac gac gcc ctg ctc gac aac ctc acc ccc gac cgc gtc gac acc        67574
Leu Asp Asp Ala Leu Leu Asp Asn Leu Thr Pro Asp Arg Val Asp Thr
5085                5090                5095                5100 gtc ctc aaa ccc aag gcc gac gcc gcc tgg cac ctg cac cgg ctc acc        67622
Val Leu Lys Pro Lys Ala Asp Ala Ala Trp His Leu His Arg Leu Thr
        5105                5110                5115 cgc gac acc gac ctc gcc gcg ttc gtc gtc tac tcc gcg gtc gcc ggc        67670
Arg Asp Thr Asp Leu Ala Ala Phe Val Val Tyr Ser Ala Val Ala Gly
        5120                5125                5130 ctc atg ggc agc ccg ggg cag ggc aac tac gtc gcg gcg aac gcg ttc        67718
Leu Met Gly Ser Pro Gly Gln Gly Asn Tyr Val Ala Ala Asn Ala Phe
        5135                5140                5145 ctc gac gcg ctc gcc gaa cac cgc cgt gcg caa ggg ctg ccc gcg cag        67766
Leu Asp Ala Leu Ala Glu His Arg Arg Ala Gln Gly Leu Pro Ala Gln
        5150                5155                5160 tcc ctc gca tgg ggc atg tgg gcg gac gtc agc gcg ctc acc gcg aaa        67814
Ser Leu Ala Trp Gly Met Trp Ala Asp Val Ser Ala Leu Thr Ala Lys
5165                5170                5175                5180 ctc acc gac gcg gac cgc cag cgc atc cgg cgc agc gga ttc ccg ccg        67862
Leu Thr Asp Ala Asp Arg Gln Arg Ile Arg Arg Ser Gly Phe Pro Pro
        5185                5190                5195 ttg agc gcc gcg gac ggc atg cgg ctg ttc gac gcg gcg acg cgt acc        67910
Leu Ser Ala Ala Asp Gly Met Arg Leu Phe Asp Ala Ala Thr Arg Thr
        5200                5205                5210 ccg gaa ccg gtc gtc gtc gcg acg acc gtc gac ctc acc cag ctc gac        67958
Pro Glu Pro Val Val Val Ala Thr Thr Val Asp Leu Thr Gln Leu Asp
        5215                5220                5225 ggc gcc gtc gcg ccg ttg ctc cgc ggt ctg gcc gcg cac cgg gcc ggg        68006
Gly Ala Val Ala Pro Leu Leu Arg Gly Leu Ala Ala His Arg Ala Gly
        5230                5235                5240 ccg gcg cgc acg gtc gcc cgc aac gcc ggc gaa gag ccc ctg gcc gtg        68054
Pro Ala Arg Thr Val Ala Arg Asn Ala Gly Glu Glu Pro Leu Ala Val
5245                5250                5255                5260 cgt ctt gcc ggg cgt acc gcc gcc gag cag cgg cgc atc atg cag gag        68102
Arg Leu Ala Gly Arg Thr Ala Ala Glu Gln Arg Arg Ile Met Gln Glu
        5265                5270                5275 gtc gtg ctc cgc cac gcg gcc gcg gtc ctc gcg tac ggg ctg ggc gac        68150
Val Val Leu Arg His Ala Ala Ala Val Leu Ala Tyr Gly Leu Gly Asp
        5280                5285                5290 cgc gtg gcg gcg gac cgt ccg ttc cgc gag ctc ggt ttc gat tcg ctg        68198
Arg Val Ala Ala Asp Arg Pro Phe Arg Glu Leu Gly Phe Asp Ser Leu
        5295                5300                5305 acc gcg gtc gac ctg cgc aat cgg ctc gcg gcc gag acg ggg ctg cgg        68246
Thr Ala Val Asp Leu Arg Asn Arg Leu Ala Ala Glu Thr Gly Leu Arg
        5310                5315                5320 ctg ccg acg acg ctg gtg ttc agc cac ccg acg gcg gag gcg ctc acc        68294
Leu Pro Thr Thr Leu Val Phe Ser His Pro Thr Ala Glu Ala Leu Thr
5325                5330                5335                5340 gcc cac ctg ctc gac ctg atc gac gct ccc acc gcc cgg atc gcc ggg        68342
Ala His Leu Leu Asp Leu Ile Asp Ala Pro Thr Ala Arg Ile Ala Gly
        5345                5350                5355 gag tcc ctg ccc gcg gtg acg gcc gct ccc gtg gcg gcc gcg cgg gac        68390
Glu Ser Leu Pro Ala Val Thr Ala Ala Pro Val Ala Ala Ala Arg Asp
        5360                5365                5370 cag gac gag ccg atc gcc atc gtg gcg atg gcg tgc cgg ctg ccc ggt        68438
Gln Asp Glu Pro Ile Ala Ile Val Ala Met Ala Cys Arg Leu Pro Gly
        5375                5380                5385 ggt gtg acg tcg ccc gag gac ctg tgg cgg ctc gtc gag tcc ggc acc        68486
Gly Val Thr Ser Pro Glu Asp Leu Trp Arg Leu Val Glu Ser Gly Thr
```

```
      5390              5395              5400
gac gcg atc acc acg cct cct gac gac cgc ggc tgg gac gtc gac gcg    68534
Asp Ala Ile Thr Thr Pro Pro Asp Asp Arg Gly Trp Asp Val Asp Ala
5405              5410              5415              5420 ctg tac gac gcg gac ccg gac gcg gcc ggc aag gcg tac aac ctg cgg    68582
Leu Tyr Asp Ala Asp Pro Asp Ala Ala Gly Lys Ala Tyr Asn Leu Arg
              5425              5430              5435 ggc ggt tac ctg gcc ggg gcg gcg gag ttc gac gcg gcg ttc ttc gac    68630
Gly Gly Tyr Leu Ala Gly Ala Ala Glu Phe Asp Ala Ala Phe Phe Asp
              5440              5445              5450 atc agt ccg cgc gaa gcg ctc ggc atg gac ccg cag caa cgc ctg ctg    68678
Ile Ser Pro Arg Glu Ala Leu Gly Met Asp Pro Gln Gln Arg Leu Leu
              5455              5460              5465 ctc gaa acg gcg tgg gag gcg atc gag cgc ggc cgg atc agt ccg gcg    68726
Leu Glu Thr Ala Trp Glu Ala Ile Glu Arg Gly Arg Ile Ser Pro Ala
              5470              5475              5480 tcg ctc cgc ggc cgg gag gtc ggc gtc tat gtc ggt gcg gcc gcg cag    68774
Ser Leu Arg Gly Arg Glu Val Gly Val Tyr Val Gly Ala Ala Ala Gln
5485              5490              5495              5500 ggc tac ggg ctg ggc gcc gag gac acc gag ggc cac gcg atc acc ggt    68822
Gly Tyr Gly Leu Gly Ala Glu Asp Thr Glu Gly His Ala Ile Thr Gly
              5505              5510              5515 ggt tcc acg agc ctg ctg tcc gga cgg ctg gcg tac gtg ctc ggg ctg    68870
Gly Ser Thr Ser Leu Leu Ser Gly Arg Leu Ala Tyr Val Leu Gly Leu
              5520              5525              5530 gag ggc ccg gcg gtc acc gtg gac acg gcg tgc tcg tcg tct ctg gtc    68918
Glu Gly Pro Ala Val Thr Val Asp Thr Ala Cys Ser Ser Ser Leu Val
              5535              5540              5545 gcg ctg cat ctg gcg tgc cag ggg ctg cgc ctg ggc gag tgc gaa ctc    68966
Ala Leu His Leu Ala Cys Gln Gly Leu Arg Leu Gly Glu Cys Glu Leu
              5550              5555              5560 gct ctg gcc gga ggg gtc tcc gta ctg agt tcg ccg gcc gcg ttc gtg    69014
Ala Leu Ala Gly Gly Val Ser Val Leu Ser Ser Pro Ala Ala Phe Val
5565              5570              5575              5580 gag ttc tcc cgc cag cgc ggg ctc gcg gcc gac ggg cgc tgc aag tcg    69062
Glu Phe Ser Arg Gln Arg Gly Leu Ala Ala Asp Gly Arg Cys Lys Ser
              5585              5590              5595 ttc ggc gcg ggc gcg gac ggc acg acg tgg tcc gag ggc gtg ggc gtg    69110
Phe Gly Ala Gly Ala Asp Gly Thr Thr Trp Ser Glu Gly Val Gly Val
              5600              5605              5610 ctc gta ctg gaa cgg ctc tcc gac gcc gag cgg ctc ggg cac acc gtg    69158
Leu Val Leu Glu Arg Leu Ser Asp Ala Glu Arg Leu Gly His Thr Val
              5615              5620              5625 ctc gcc gtc gtc cgc ggc agc gcc gtc acg tcc gac ggc gcc tcc aac    69206
Leu Ala Val Val Arg Gly Ser Ala Val Thr Ser Asp Gly Ala Ser Asn
              5630              5635              5640 ggc ctc acc gcg ccg aac ggg ctc tcg cag cag cgg gtc atc cgg aag    69254
Gly Leu Thr Ala Pro Asn Gly Leu Ser Gln Gln Arg Val Ile Arg Lys
5645              5650              5655              5660 gcg ctc gcc gcg gcc ggg ctg acc ggc gcc gac gtg gac gtc gtc gag    69302
Ala Leu Ala Ala Ala Gly Leu Thr Gly Ala Asp Val Asp Val Val Glu
              5665              5670              5675 ggg cac ggc acc ggc acc cgg ctc ggc gac ccg gtc gag gcg gac gcg    69350
Gly His Gly Thr Gly Thr Arg Leu Gly Asp Pro Val Glu Ala Asp Ala
              5680              5685              5690 ctg ctc gcg acg tac ggg cag gac cgt ccg gca ccg gtc tgg ctg ggc    69398
Leu Leu Ala Thr Tyr Gly Gln Asp Arg Pro Ala Pro Val Trp Leu Gly
              5695              5700              5705 tcg ctg aag tcg aac atc gga cat gcc acg gcc gcg gcc ggt gtc gcg    69446
```

-continued

| | |
|---|---|
| Ser Leu Lys Ser Asn Ile Gly His Ala Thr Ala Ala Ala Gly Val Ala<br>    5710                5715                5720 | |
| ggc gtc atc aag atg gtg cag gcg atc ggc gcg ggc acg atg ccg cgg<br>Gly Val Ile Lys Met Val Gln Ala Ile Gly Ala Gly Thr Met Pro Arg<br>5725                5730                5735                5740 | 69494 |
| acg ctg cat gtg gag gag ccc tcg ccc gcc gtc gac tgg agc acc gga<br>Thr Leu His Val Glu Glu Pro Ser Pro Ala Val Asp Trp Ser Thr Gly<br>                5745                5750                5755 | 69542 |
| cag gtg tcc ctg ctc ggc tcc aac cgg ccc tgg ccg gac gac gag cgt<br>Gln Val Ser Leu Leu Gly Ser Asn Arg Pro Trp Pro Asp Asp Glu Arg<br>            5760                5765                5770 | 69590 |
| ccg cgc cgg gcg gcc gtc tcc gcg ttc ggg ctc agc ggg acg aac gcg<br>Pro Arg Arg Ala Ala Val Ser Ala Phe Gly Leu Ser Gly Thr Asn Ala<br>        5775                5780                5785 | 69638 |
| cac gtc atc ctg gaa cag cac cgt ccg gcg ccc gtg gcg tcc cag ccg<br>His Val Ile Leu Glu Gln His Arg Pro Ala Pro Val Ala Ser Gln Pro<br>    5790                5795                5800 | 69686 |
| ccc cgg ccg ccc cgt gag gag tcc cag ccg ctg ccg tgg gtg ctc tcc<br>Pro Arg Pro Pro Arg Glu Glu Ser Gln Pro Leu Pro Trp Val Leu Ser<br>5805                5810                5815                5820 | 69734 |
| gcg cgg act ccg gcc gcg ctg cgg gcc cag gcg gcc cgg ctg cgc gac<br>Ala Arg Thr Pro Ala Ala Leu Arg Ala Gln Ala Ala Arg Leu Arg Asp<br>                5825                5830                5835 | 69782 |
| cac ctc gcg gcg gca ccg gac gcg gat ccg ttg gac atc ggg tac gcg<br>His Leu Ala Ala Ala Pro Asp Ala Asp Pro Leu Asp Ile Gly Tyr Ala<br>            5840                5845                5850 | 69830 |
| ctg gcc acc agc cgc gcc cag ttc gcc cac cgt gcc gcg gtc gtc gcc<br>Leu Ala Thr Ser Arg Ala Gln Phe Ala His Arg Ala Ala Val Val Ala<br>        5855                5860                5865 | 69878 |
| acc acc ccg gac gga ttc cgt gcc gcg ctc gac ggc ctc gcg gac ggc<br>Thr Thr Pro Asp Gly Phe Arg Ala Ala Leu Asp Gly Leu Ala Asp Gly<br>    5870                5875                5880 | 69926 |
| gcg gag gcg ccc gga gtc gtc acc ggg acc gct cag gag cgg cgc gtc<br>Ala Glu Ala Pro Gly Val Val Thr Gly Thr Ala Gln Glu Arg Arg Val<br>5885                5890                5895                5900 | 69974 |
| gcc ttc ctc ttc gac ggc cag ggc gcc cag cgc gcc gga atg ggg cgc<br>Ala Phe Leu Phe Asp Gly Gln Gly Ala Gln Arg Ala Gly Met Gly Arg<br>                5905                5910                5915 | 70022 |
| gag ctc cac cgc cgg ttc ccc gtc ttc gcc gcc gcg tgg gac gag gtc<br>Glu Leu His Arg Arg Phe Pro Val Phe Ala Ala Ala Trp Asp Glu Val<br>            5920                5925                5930 | 70070 |
| tcc gac gcg ttc ggc aag cac ctc aag cac tcc ccc acg gac gtc tac<br>Ser Asp Ala Phe Gly Lys His Leu Lys His Ser Pro Thr Asp Val Tyr<br>        5935                5940                5945 | 70118 |
| cac ggc gaa cac ggc gct ctc gcc cat gac acc ctg tac gcc cag gcc<br>His Gly Glu His Gly Ala Leu Ala His Asp Thr Leu Tyr Ala Gln Ala<br>    5950                5955                5960 | 70166 |
| ggc ctg ttc acg ctc gaa gtg gcg ctg ctg cgg ctg ctg gag cac tgg<br>Gly Leu Phe Thr Leu Glu Val Ala Leu Leu Arg Leu Leu Glu His Trp<br>5965                5970                5975                5980 | 70214 |
| ggg gtg cgg ccg gac gtg ctc gtc ggg cac tcc gtc ggc gag gtg acc<br>Gly Val Arg Pro Asp Val Leu Val Gly His Ser Val Gly Glu Val Thr<br>                5985                5990                5995 | 70262 |
| gcg gcg tac gcg gcg ggg gtg ctc acc ctg gcg gac gcg acg gag ttg<br>Ala Ala Tyr Ala Ala Gly Val Leu Thr Leu Ala Asp Ala Thr Glu Leu<br>            6000                6005                6010 | 70310 |
| atc gtg gcc cgg ggg cgg gcg ctg cgg gcg ctg ccg ccc ggg gcg atg<br>Ile Val Ala Arg Gly Arg Ala Leu Arg Ala Leu Pro Pro Gly Ala Met<br>        6015                6020                6025 | 70358 |

```
ctc gcc gtc gac gga agc ccg gcg gag gtc ggc gcc cgc acg gat ctg      70406
Leu Ala Val Asp Gly Ser Pro Ala Glu Val Gly Ala Arg Thr Asp Leu
        6030            6035            6040 gac atc gcc gcg gtc aac ggc ccg tcc gcc gtg gtg ctc gcc ggt tcg      70454
Asp Ile Ala Ala Val Asn Gly Pro Ser Ala Val Val Leu Ala Gly Ser
6045            6050            6055            6060 ccg gac gat gtg gcg gcg ttc gaa cgg gag tgg tcg gcg gcc ggg cgg      70502
Pro Asp Asp Val Ala Ala Phe Glu Arg Glu Trp Ser Ala Ala Gly Arg
            6065            6070            6075 cgc acg aaa cgg ctc gac gtc ggg cac gcg ttc cac tcc cgg cac gtc      70550
Arg Thr Lys Arg Leu Asp Val Gly His Ala Phe His Ser Arg His Val
        6080            6085            6090 gac ggt gcg ctc gac ggc ttc cgt acg gtg ctg gag tcg ctc gcg ttc      70598
Asp Gly Ala Leu Asp Gly Phe Arg Thr Val Leu Glu Ser Leu Ala Phe
            6095            6100            6105 ggc gcg gcg cgg ctg ccg gtg gtg tcc acg acg ggc cgg gac gcc          70646
Gly Ala Ala Arg Leu Pro Val Val Ser Thr Thr Thr Gly Arg Asp Ala
6110            6115            6120 gcg gac gac ctc ata acg ccc gcg cac tgg ctg cgc cat gcg cgt cgg      70694
Ala Asp Asp Leu Ile Thr Pro Ala His Trp Leu Arg His Ala Arg Arg
6125            6130            6135            6140 ccg gtg ctg ttc tcg gat gcc gtc cgg gag ctg gcc gac cgc ggc gtc      70742
Pro Val Leu Phe Ser Asp Ala Val Arg Glu Leu Ala Asp Arg Gly Val
            6145            6150            6155 acc acg ttc gtg gcc gtc ggc ccc tcc ggc tcc ctg gcg tcg gcc gcg      70790
Thr Thr Phe Val Ala Val Gly Pro Ser Gly Ser Leu Ala Ser Ala Ala
            6160            6165            6170 gcg gag agc gcc ggg gag gac gcc ggg acc tac cac gcg gtg ctg cgc      70838
Ala Glu Ser Ala Gly Glu Asp Ala Gly Thr Tyr His Ala Val Leu Arg
            6175            6180            6185 gcc cgg acc ggt gag gag acc gcg gcg ctg acc gcc ctc gcc gag ctg      70886
Ala Arg Thr Gly Glu Glu Thr Ala Ala Leu Thr Ala Leu Ala Glu Leu
        6190            6195            6200 cac gcc cac ggc gtc ccg gtc gac ctg gcc gcg gta ctg gcc ggt ggc      70934
His Ala His Gly Val Pro Val Asp Leu Ala Ala Val Leu Ala Gly Gly
6205            6210            6215            6220 cgg cca gtg gac ctt ccc gtg tac gcg ttc cag cac cgt tcc tac tgg      70982
Arg Pro Val Asp Leu Pro Val Tyr Ala Phe Gln His Arg Ser Tyr Trp
            6225            6230            6235 ctg gcc ccg gcc gtg gcg ggg gcg ccg gcc acc gtg gcg gac acc ggg      71030
Leu Ala Pro Ala Val Ala Gly Ala Pro Ala Thr Val Ala Asp Thr Gly
            6240            6245            6250 ggt ccg gcg gag tcc gag ccg gag gac ctc acc gtc gcc gag atc gtc      71078
Gly Pro Ala Glu Ser Glu Pro Glu Asp Leu Thr Val Ala Glu Ile Val
        6255            6260            6265 cgt cgg cgc acc gcg gcg ctg ctc ggc gtc acg gac ccc gcc gac gtc      71126
Arg Arg Arg Thr Ala Ala Leu Leu Gly Val Thr Asp Pro Ala Asp Val
        6270            6275            6280 gat gcg gaa gcg acg ttc ttc gcg ctc ggt ttc gac tca ctg gcg gtg      71174
Asp Ala Glu Ala Thr Phe Phe Ala Leu Gly Phe Asp Ser Leu Ala Val
6285            6290            6295            6300 cag cgg ctg cgc aac cag ctc gcc tcg gca acc ggg ctg gac ctg ccg      71222
Gln Arg Leu Arg Asn Gln Leu Ala Ser Ala Thr Gly Leu Asp Leu Pro
            6305            6310            6315 gcg gcc gtc ctg ttc gac cac gac acc ccg gcc gcg ctc acc gcg ttc      71270
Ala Ala Val Leu Phe Asp His Asp Thr Pro Ala Ala Leu Thr Ala Phe
        6320            6325            6330 ctc cag gac cgg atc gag gcc ggc cag gac cgg atc gag gcc ggc gag      71318
Leu Gln Asp Arg Ile Glu Ala Gly Gln Asp Arg Ile Glu Ala Gly Glu
            6335            6340            6345
```

| | | |
|---|---|---|
| gac gac gac gcg ccc acc gtg ctc tcg ctc ctg gag gag atg gag tcg<br>Asp Asp Asp Ala Pro Thr Val Leu Ser Leu Leu Glu Glu Met Glu Ser<br>    6350                                   6355                          6360 | 71366 |
| ctc gac gcc gcg gac atc gcg gcg acg ccg gcc ccg gag cgt gcg gcc<br>Leu Asp Ala Ala Asp Ile Ala Ala Thr Pro Ala Pro Glu Arg Ala Ala<br>6365                        6370                          6375                          6380 | 71414 |
| atc gcc gat ctg ctc gac aag ctc gcc cat acc tgg aag gac tac cga<br>Ile Ala Asp Leu Leu Asp Lys Leu Ala His Thr Trp Lys Asp Tyr Arg<br>                  6385                          6390                          6395 | 71462 |
| tga gcaccgatac gcacgaggga acgccgcccg ccggccgctg cccattcgcg<br>* | 71515 |
| atccaggacg gtcaccgcgc atcctggag agcggcacgg tgggttcgtt cgacctgttc | 71575 |
| ggcgtcaagc actggctggt cgccgccgcc gaggacgtca agctggtcac caacgatccg | 71635 |
| cggttcagct cggccgcgcc gtccgagatg ctgcccgacc ggcggcccgg ctggttctcc | 71695 |
| gggatggact caccggagca caaccgctac ggcagaaga tcgcgggga cttcacactg | 71755 |
| cgcgcggcgc gcaagcggga ggacttcgtc gccgaggccg ccgacgcctg cctggacgac | 71815 |
| atcgaggccg cgggacccgg caccgacctc atccccgggt acgccaagcg gctgccctcc | 71875 |
| ctcgtcatca acgcgctgta cgggctcacc cctgaggagg gggccgtgct ggaggcacgg | 71935 |
| atgcgcgaca tcaccggctc ggccgatctg dacagcgtca agacgctgac cgacgacttc | 71995 |
| ttcgggcacg cgctgcggct ggtccgcgcg aagcgtgacg agcggggcga ggacctgctg | 72055 |
| caccggctgg cctcggccga cgacggcgag atctcgctca cgacgacga ggcgacgggc | 72115 |
| gtgttcgcga cgctgctgtt cgccggccac gactcggtgc agcagatggt cggctactgc | 72175 |
| ctctacgcac tgctcagcca ccccgagcag caggcggcgc tgcgcgcgcg cccggagctg | 72235 |
| gtcgacaacg cggtcgagga gatgctccgt ttcctgcccg tcaaccagat gggcgtaccg | 72295 |
| cgcgtctgtg tcgaggacgt cgatgtgcgg ggcgtgcgca tccgtgcggg cgacaacgtg | 72355 |
| atcccgctct actcgacggc caaccgcgac cccgaggtgt tcccgcagcc cgacaccttc | 72415 |
| gatgtgacgc gcccgctgga gggcaacttc gcgttcggcc acggcattca caagtgtccc | 72475 |
| ggccagcaca tcgcccgggt gctcatcaag gtcgcctgcc tgcggttgtt cgagcgtttc | 72535 |
| ccggacgtcc ggctggccgg cgacgtgccg atgaacgagg ggctcgggct gttcagcccg | 72595 |
| gccgagctgc gggtcacctg ggggcggca tgagtcaccc ggtggagacg ttgcggttgc | 72655 |
| cgaacgggac gacggtcgcg cacatcaacg cgggcgaggc gcagttcctc taccgggaga | 72715 |
| tcttcaccca gcgctgctac ctgcgccacg tgtcgacct cgcccggggg gacgtggtgt | 72775 |
| tcgacgtcgg cgcgaacatc ggcatgttca cgcttttcgc gcatctggag tgtcctggtg | 72835 |
| tgaccgtgca cgccttcgag cccgcgcccg tgccgttcgc ggcgctgcgg gcgaacgtga | 72895 |
| cgcggcacgg catcccgggc caggcggacc agtgcgcggt ctccgacagc tccggcaccc | 72955 |
| ggaagatgac cttctatccc gacgccacgc tgatgtccgg tttccacgcg gatgccgcgg | 73015 |
| cccggacgga gctgttgcgc acgctcggcc tcaacggcgg ctacaccgcc gaggacgtcg | 73075 |
| acaccatgct cgcgcaactg cccgacgtca gcgaggagat cgaaacccct gtggtccggc | 73135 |
| tctccgacgt catcgcggag cgcggtatcg aggccatcgg cctgctgaag gtcgacgtgg | 73195 |
| agaagagcga acggcaggtc ttcgccggcc tcgaggacac cgactggccc cgtatccgcc | 73255 |
| aggtcgtcgc ggaggtccac gacatcgacg gcgcgctcga ggagtcgtc acgctgctcc | 73315 |
| gcggccatgg cttcaccgtg gtcgccgagc aggaaccgct gttcgccggc acgggcatcc | 73375 |
| accaggtcgc cgcgcggcgg gtggccggct gagcgccgtc ggggccgcgg ccgtccgcac | 73435 |

-continued

```
cggcggccgc ggtgcggacg gcggctcagc cggcgtcgga cagttccttg ggcagttgct   73495
gacggcccct caccccccagc ttgcggaaca cgttggtgag gtgctgttcc accgtgctgg   73555
aggtgacgaa cagctggctg gcgatctcct tgttggtgcg cccgaccgcg gcgtgcgacg   73615
ccacccgccg ctccgcctcg gtcagcgatg tgatccgctg cgccggcgtc acgtcctggg   73675
tgccgtccgc gtccgaggac tccccaccga gccgccggag gagcggcacg gctccgcact   73735
gggtcgcgag gtgccgtgcg cggcggaaca gtccccgcgc acggctgtgc cgccggagca   73795
tgccgcacgc ttcgcccatg tcggcgagga gcgggccag ctcgtactgg tcgcggcaca   73855
tgatgagcag atcggcggcc tcgtcgagca gttcgatccg cttggccggc ggactgtagg   73915
ccgcctgcac ccgcagcgtc atcacccgcg cccgggaccc catcggccgg gacagctgct   73975
cggagatgag cctcagcccc tcgtcacggc gcggccgag cagcagaagc gcttcggcgg   74035
cgtcgacccg ccacagggcc aggcccggca cgtcgacgga ccagcgtcgc atccgctccc   74095
cgcagtcccg gaacgcgttg tacgccgccc ggtaccgccc ggccgcgaga tggtgttgcc   74155
cacgggccca gaccatgtgc agtccgaaga ggctgtcgga ggtctcctcc ggcaacggct   74215
cggcgagcca ccgctccgcc cggtccaggt cgcccagtcg gatcgcggcg ccacggtgc   74275 tgctcagcgg caatgcggcg gccatccccc aggagggcac gacccggggg gcgagcgcgg   74335
cctcgccgca ttcgacggcg gcggtcaggt cgccgcggcg cagcgcggcc tcggcgcgga   74395
accccgcgtg gaccgcctcg tcggccgggg tccgcatgtt gtcgtcaccg gccagcttgt   74455
cgacccagga ctggacggca tcggtgtcct cggcgtagag cagggccagc aacgccatca   74515
tggtcgtggt ccggtccgtc gtgacccggg agtgctggag cacgtactcg gctttggcct   74575
cggcctgttc ggaccagccg cgcagcgcgt tgctcagggc cttgtcggcg acggcgcggt   74635
gccggacggc tccggaaaac gaggcgacct cgtcctcggc cggcggatcg gccggacgcg   74695
gcggatcggc cgcgccggga tagatcagcg cgagggacag gtccgcgacg cgcaggtgcg   74755
cccggccctg ctcgctcggg gcggcggagc gctgggccgc caggacctcg gcggcctcgc   74815
ccggccgccc gtccatcgcc agccagcagg cgagcgacac ggcgtgctcg ctggagagga   74875
gccgttcccg cgacgcggtg agcagctcgg gcacatgccg gccggatctg gcgggatcgc   74935
agagccgctc gatggcggcg gtgtcgacgc gcagtgcggc gtggacggcg gggtcgtcgg   74995
aggcccggta ggcgaactcc aggtaggtga cggcctcgtc gagctcgccg cgcaggtggt   75055
gctcgcgcgc ggcgtcggtg aacagcccgg cgacctcggc gccgtgcacc cggccggtac   75115
ccatctggtg gcgggcgagc accttgctgg ccacgccgcg gtcccgcagc agttccagcg   75175
ccagctcgtg caggccacgc cgctcggcgg cggagaggtc gtcgagtacg acggagcggg   75235
ccgcggggtg cgggaaccgc ccttcccgca gcagccgccc ctcgaccagc tgttcgtggg   75295
cctgctcgac cgcctcggtg tcgaggccgg tcatccgctg gacagagggtg agttcgacac   75355 tctcgccgag cacggcggaa gctcgggcga cgctcagcgc ggccgggccg caacgataga   75415
gcgacccgag gtaggcgagc cggtacgccc gccccgcgac cacttccagg cacccctgagg   75475 tccgtgtccg tgcctcccgg atgtcgtcga tcaggccgtg gccgaggagc aggttgccgc   75535
cggtcgcccg gaacgcctgg gccaccacgt cgtcgtgcgc gtcctggccg aggtgccggc   75595
gcacgagttc ggtggtctgc gcctcggtga gcgggcgcag cgcgatctcc tggtagtggc   75655
gcagactcag cagtgccgcc cggaattggg agtgggcggg cgtcggccgg agcagctcgg   75715
tcagcacgat ggcgacacgg gcccggctga tgcggcgcgc gaggtggagc aggcagcgca   75775
```

-continued

```
gcgacggcgc gtcggcgtgg tgcacgtcgt cgatgccgat cagtacgggc cgctccgcgg    75835
cgagcgtcag caccgtgcgg gtgagttcgg tccccaggcg gttgtcgacg tcggccggca    75895
ggttttcgca cgatgccgtc agccggacca gctccggtgt ccgggcgcc agctcgggct    75955 ggtcgaggag ctggccgagc atgccgtacg gcagggcccg ctcctccatg gagcacaccg    76015
cgcgaagggt gacgaagccg gccttggccg cggcggcgtc gaggagttcg gtcttgccgc    76075
aggcgatcgg cccggtgacg gcggcgacga cgccccgccc gccccccgct cgggtgagcg    76135
cccggtggag ggaaccgaac tcgtcatcgc gggcgatcag gtctggggga gataagcgcg    76195
ctatcacgaa tggaactacc tcgcgaccgt cgtggaaacc cataggcatc acatggcttg    76255
ttgatctgta cggctgtgat tcagcctggc gggatgctgt gctacagatg gaagatgtg    76315 atctagggcc gtgccgttcc ctcaggagcc gaccgccccc ggcgccaccc gccgtacccc    76375
ctgggccacc agctcggcga cccgctcctg gtggtcgacg aggtagaagt gcccgccggg    76435
gaagacctcc accgtggtcg gcgcggtcgt gtgcccggcc caggcgtggg cctgctccac    76495
cgtcgtcttc ggatcgtcgt caccgatgca caccgtgatc ggcgtctcca cggcggcgc    76555 gggctcccac cggtacgtct ccgccgcgta gtagtccgcc cgcaacggcg ccaggatcag    76615
cgcgcgcatt tcgtcgtccg ccatcacatc ggcgctcgtc ccgccgaggc cgatgaccgc    76675
cgccagcagc tcgtcgtcgg acgcgaggtg gtcctggtcg gcgcgcggct gcgacgcgc    76735 ccgccggccc gagacgatca ggtgcgccac cgggagccgc tgggccagct cgaacgcgag    76795
tgtcgcgccc atgctgtggc cgaacagcac cagcggacgg tccagccccg gcttcaacgc    76855
ctcggccacg aggccggcga gaacacgcag gtcgcgcacc gcctcctcgt cgcggcggtc    76915
ctggcggccg gggtactgca cggcgtacac gtccgccacc ggggcgagcg cacgggccag    76975
cggaaggtag aacgtcgccg atccgccggc gtggggcagc agcaccaccc gtaccggggc    77035
ctcgggcgtg gggaagaact gccgcagcca gagttccgag ctcaccgcac ccctcggcc    77095 gcgacctggg gagcccggaa ccgggtgatc tcggccaagt gcttctcccg catctccggg    77155
tcggtcacgc cccatccctc ctccggcgcc agacagagga cgccgacttt gccgttgtgc    77215
acattgcgat gcacatcgcg caccgccgac ccgacgtcgt cgagcgggta ggtcaccgac    77275
agcgtcgggt gcaccatccc cttgcagatc aggcggttcg cctcccacgc ctcacgatag    77335
ttcgcgaagt gggtaccgat gatccgcttc acggacatcc acaggtaccg attgtcaaag    77395
gcgtgctcgt atcccgaggt tgacgcgcag gtgacgatcg tgccaccccg acgtgtcacg    77455
tagacactcg cgccgaacgt cgcgcgcccc gggtgctcga acacgatgtc gggatcgtca    77515
ccgccggtca gctcccggat c                                              77536
                                                                     77536
```

<210> SEQ ID NO 2
<211> LENGTH: 360
<212> TYPE: PRT
<213> ORGANISM: Streptomyces sp.

<400> SEQUENCE: 2

Met Thr Ile Val Lys Cys Leu Val Trp Asp Leu Asp Asn Thr Leu Trp
  1               5                  10                  15

Arg Gly Thr Val Leu Glu Asp Asp Glu Val Val Leu Thr Asp Glu Ile
             20                  25                  30

Arg Glu Val Ile Thr Thr Leu Asp Asp Arg Gly Ile Leu Gln Ala Val
         35                  40                  45

Ala Ser Lys Asn Asp His Asp Leu Ala Trp Glu Arg Leu Glu Arg Leu

-continued

```
            50                  55                  60
Gly Val Ala Glu Tyr Phe Val Leu Ala Arg Ile Gly Trp Gly Pro Lys
 65                  70                  75                  80
Ser Gln Ser Val Arg Glu Ile Ala Thr Glu Leu Asn Phe Ala Pro Thr
                 85                  90                  95
Thr Ile Ala Phe Ile Asp Asp Gln Pro Ala Glu Arg Ala Glu Val Ala
                100                 105                 110
Phe His Leu Pro Glu Val Arg Cys Tyr Pro Ala Glu Gln Ala Ala Thr
            115                 120                 125
Leu Leu Ser Leu Pro Glu Phe Ser Pro Pro Val Ser Thr Val Asp Ser
130                 135                 140
Arg Arg Arg Arg Leu Met Tyr Gln Ala Gly Phe Ala Arg Asp Gln Ala
145                 150                 155                 160
Arg Glu Ala Tyr Ser Gly Pro Asp Glu Asp Phe Leu Arg Ser Leu Asp
                165                 170                 175
Leu Ser Met Thr Ile Ala Pro Ala Gly Glu Glu Leu Ser Arg Val
                180                 185                 190
Glu Glu Leu Thr Leu Arg Thr Ser Gln Met Asn Ala Thr Gly Val His
            195                 200                 205
Tyr Ser Asp Ala Asp Leu Arg Ala Leu Leu Thr Asp Pro Ala His Glu
210                 215                 220
Val Leu Val Val Thr Met Gly Asp Arg Phe Gly Pro His Gly Ala Val
225                 230                 235                 240
Gly Ile Ile Leu Leu Glu Lys Lys Pro Ser Thr Trp His Leu Lys Leu
                245                 250                 255
Leu Ala Thr Ser Cys Arg Val Val Ser Phe Gly Ala Gly Ala Thr Ile
                260                 265                 270
Leu Asn Trp Leu Thr Asp Gln Gly Ala Arg Ala Gly Ala His Leu Val
            275                 280                 285
Ala Asp Phe Arg Arg Thr Asp Arg Asn Arg Met Met Glu Ile Ala Tyr
290                 295                 300
Arg Phe Ala Gly Phe Ala Asp Ser Asp Cys Pro Cys Val Ser Glu Val
305                 310                 315                 320
Ala Gly Ala Ser Ala Ala Gly Val Glu Arg Leu His Leu Glu Pro Ser
                325                 330                 335
Ala Arg Pro Ala Pro Thr Thr Leu Thr Leu Thr Ala Ala Asp Ile Ala
            340                 345                 350
Pro Val Thr Val Ser Ala Ala Gly
            355                 360
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Linker

<400> SEQUENCE: 3
ctagtgggca gatctggcag ct                                        22

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Linker -continued

```
<400> SEQUENCE: 4
gccagatctg ccca                                                14

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Linker

<400> SEQUENCE: 5
gggatgcatg gc                                                  12

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Linker

<400> SEQUENCE: 6
ttaagccatg catccccatg                                          20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
cgactcacta gtgggcagat ctgg                                     24

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 8
cacgcctagg ccggtcggtc tcgggccac                                29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 9
gcggctagct gctcgcccat cgcgggatgc                               30

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 10
gatgtacagc tcgagtcggc acgcccggcc gcatc                         35

<210> SEQ ID NO 11
<211> LENGTH: 23
```

```
<212> TYPE: DNA
<213> ORGANISM: Artificial Sequence
<220> FEATURE:
<223> OTHER INFORMATION: Description of Artificial Sequence: primer

<400> SEQUENCE: 11
cgactcactt aagccatgca tcc                                              23

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
atcctaggcg ggcrggygtg tcgtccttcg g                                     31

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 13
atgctagccg ccgcgttccc cgtcttcgcg cg                                    32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 14
atgctagcgg attcgtcggt ggtgttcgcc ga                                    32

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15
atctcgagcc agtascgctg gtgytggaag g                                     31

<210> SEQ ID NO 16
<211> LENGTH: 4478
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4466)

<400> SEQUENCE: 16 ag atc tgg cag ctc gcc gaa gcg ctg ctg acg ctc gtc cgg gag agc         47
   Ile Trp Gln Leu Ala Glu Ala Leu Leu Thr Leu Val Arg Glu Ser
   1               5                  10                  15 acc gcc gcc gtg ctc ggc cac gtg ggt ggc gag gac atc ccc gcg acg        95
Thr Ala Ala Val Leu Gly His Val Gly Gly Glu Asp Ile Pro Ala Thr
            20                  25                  30
```

-continued

| | | |
|---|---|---|
| gcg gcg ttc aag gac ctc ggc atc gac tcg ctc acc gcg gtc cag ctg<br>Ala Ala Phe Lys Asp Leu Gly Ile Asp Ser Leu Thr Ala Val Gln Leu<br>35                         40                       45 | 143 |
| cgc aac gcc ctc acc gag gcg acc ggt gtg cgg ctg aac gcc acg gcg<br>Arg Asn Ala Leu Thr Glu Ala Thr Gly Val Arg Leu Asn Ala Thr Ala<br>50                         55                       60 | 191 |
| gtc ttc gac ttc ccg acc ccg cac gtg ctc gcc ggg aag ctc ggc gac<br>Val Phe Asp Phe Pro Thr Pro His Val Leu Ala Gly Lys Leu Gly Asp<br>65                         70                       75 | 239 |
| gaa ctg acc ggc acc cgc gcg ccc gtc gtg ccc cgg acc gcg gcc acg<br>Glu Leu Thr Gly Thr Arg Ala Pro Val Val Pro Arg Thr Ala Ala Thr<br>80                         85                       90                       95 | 287 |
| gcc ggt gcg cac gac gag ccg ctg gcg atc gtg gga atg gcc tgc cgg<br>Ala Gly Ala His Asp Glu Pro Leu Ala Ile Val Gly Met Ala Cys Arg<br>                   100                       105                      110 | 335 |
| ctg ccc ggc ggg gtc gcg tca ccc gag gag ctg tgg cac ctc gtg gca<br>Leu Pro Gly Gly Val Ala Ser Pro Glu Glu Leu Trp His Leu Val Ala<br>                   115                      120                      125 | 383 |
| tcc ggc acc gac gcc atc acg gag ttc ccg acg gac cgc ggc tgg gac<br>Ser Gly Thr Asp Ala Ile Thr Glu Phe Pro Thr Asp Arg Gly Trp Asp<br>        130                      135                      140 | 431 |
| gtc gac gcg atc tac gac ccg gac ccc gac gcg atc ggc aag acc ttc<br>Val Asp Ala Ile Tyr Asp Pro Asp Pro Asp Ala Ile Gly Lys Thr Phe<br>145                       150                      155 | 479 |
| gtc cgg cac ggt ggc ttc ctc acc ggc gcg aca ggc ttc gac gcg gcg<br>Val Arg His Gly Gly Phe Leu Thr Gly Ala Thr Gly Phe Asp Ala Ala<br>160                       165                      170                      175 | 527 |
| ttc ttc ggc atc agc ccg cgc gag gcc ctc gcg atg gac ccg cag cag<br>Phe Phe Gly Ile Ser Pro Arg Glu Ala Leu Ala Met Asp Pro Gln Gln<br>                   180                      185                      190 | 575 |
| cgg gtg ctc ctg gag acg tcg tgg gag gcg ttc gaa agc gcc ggc atc<br>Arg Val Leu Leu Glu Thr Ser Trp Glu Ala Phe Glu Ser Ala Gly Ile<br>                   195                      200                      205 | 623 |
| acc ccg gac tcg acc cgc ggc agc gac acc ggc gtg ttc gtc ggc gcc<br>Thr Pro Asp Ser Thr Arg Gly Ser Asp Thr Gly Val Phe Val Gly Ala<br>        210                      215                      220 | 671 |
| ttc tcc tac ggt tac ggc acc ggt gcg gac acc gac ggc ttc ggc gcg<br>Phe Ser Tyr Gly Tyr Gly Thr Gly Ala Asp Thr Asp Gly Phe Gly Ala<br>225                       230                      235 | 719 |
| acc ggc tcg cag acc agt gtg ctc tcc ggc cgg ctg tcg tac ttc tac<br>Thr Gly Ser Gln Thr Ser Val Leu Ser Gly Arg Leu Ser Tyr Phe Tyr<br>240                       245                      250                      255 | 767 |
| ggt ctg gag ggt ccg gcg gtc acg gtc gac acg gcg tgt tcg tcg tcg<br>Gly Leu Glu Gly Pro Ala Val Thr Val Asp Thr Ala Cys Ser Ser Ser<br>                   260                      265                      270 | 815 |
| ctg gtg gcg ctg cac cag gcc ggg cag tcg ctg cgc tcc ggc gaa tgc<br>Leu Val Ala Leu His Gln Ala Gly Gln Ser Leu Arg Ser Gly Glu Cys<br>                   275                      280                      285 | 863 |
| tcg ctc gcc ctg gtc ggc ggc gtc acg gtg atg gcg tct ccc ggc ggc<br>Ser Leu Ala Leu Val Gly Gly Val Thr Val Met Ala Ser Pro Gly Gly<br>        290                      295                      300 | 911 |
| ttc gtg gag ttc tcc cgg cag cgc ggc ctc gcg ccg gac ggc cgg gcg<br>Phe Val Glu Phe Ser Arg Gln Arg Gly Leu Ala Pro Asp Gly Arg Ala<br>305                       310                      315 | 959 |
| aag gcg ttc ggc gcg ggt gcg gac ggc acg agc ttc gcc gag ggt gcc<br>Lys Ala Phe Gly Ala Gly Ala Asp Gly Thr Ser Phe Ala Glu Gly Ala<br>320                       325                      330                      335 | 1007 |
| ggt gtg ctg atc gtc gag agg ctc tcc gac gcc gaa cgc aac ggt cac<br>Gly Val Leu Ile Val Glu Arg Leu Ser Asp Ala Glu Arg Asn Gly His<br>                   340                      345                      350 | 1055 |

-continued

| | |
|---|---|
| acc gtc ctg gcg gtc gtc cgt ggt tcg gcg gtc aac cag gat ggt gcc<br>Thr Val Leu Ala Val Val Arg Gly Ser Ala Val Asn Gln Asp Gly Ala<br>                355                                  360                          365 | 1103 |
| tcc aac ggg ctg tcg gcg ccg aac ggg ccg tcg cag gag cgg gtg atc<br>Ser Asn Gly Leu Ser Ala Pro Asn Gly Pro Ser Gln Glu Arg Val Ile<br>                370                                  375                          380 | 1151 |
| cgg cag gcc ctg gcc aac gcc ggg ctc acc ccg gcg gac gtg gac gcc<br>Arg Gln Ala Leu Ala Asn Ala Gly Leu Thr Pro Ala Asp Val Asp Ala<br>385                                    390                                  395 | 1199 |
| gtc gag gcc cac ggc acc ggc acc agg ctg ggc gac ccc atc gag gca<br>Val Glu Ala His Gly Thr Gly Thr Arg Leu Gly Asp Pro Ile Glu Ala<br>400                                405                                410                      415 | 1247 |
| cag gcg gta ctg gcc acc tac gga cag gag cgc gcc acc ccc ctg ctg<br>Gln Ala Val Leu Ala Thr Tyr Gly Gln Glu Arg Ala Thr Pro Leu Leu<br>                    420                              425                              430 | 1295 |
| ctg ggc tcg ctg aag tcc aac atc ggc cac gcc cag gcc gcg tcc ggc<br>Leu Gly Ser Leu Lys Ser Asn Ile Gly His Ala Gln Ala Ala Ser Gly<br>                435                                  440                          445 | 1343 |
| gtc gcc ggc atc atc aag atg gtg cag gcc ctc cgg cac ggg gag ctg<br>Val Ala Gly Ile Ile Lys Met Val Gln Ala Leu Arg His Gly Glu Leu<br>450                                455                                460 | 1391 |
| ccg ccg acg ctg cac gcc gac gag ccg tcg ccg cac gtc gac tgg acg<br>Pro Pro Thr Leu His Ala Asp Glu Pro Ser Pro His Val Asp Trp Thr<br>465                                470                                475 | 1439 |
| gcc ggc gcc gtc gaa ctg ctg acg tcg gcc cgg ccg tgg ccc gag acc<br>Ala Gly Ala Val Glu Leu Leu Thr Ser Ala Arg Pro Trp Pro Glu Thr<br>480                                485                                490                      495 | 1487 |
| gac cgg cct agg cgg gca ggc gtg tcg tcc ttc ggg atc agt ggc acc<br>Asp Arg Pro Arg Arg Ala Gly Val Ser Ser Phe Gly Ile Ser Gly Thr<br>                    500                              505                              510 | 1535 |
| aac gcc cac gtc atc ctg gaa agc gca ccc ccc act cag cct gcg gac<br>Asn Ala His Val Ile Leu Glu Ser Ala Pro Pro Thr Gln Pro Ala Asp<br>                515                                  520                          525 | 1583 |
| aac gcg gtg atc gag cgg gca ccg gag tgg gtg ccg ttg gtg att tcg<br>Asn Ala Val Ile Glu Arg Ala Pro Glu Trp Val Pro Leu Val Ile Ser<br>530                                535                                540 | 1631 |
| gcc agg acc cag tcg gct ttg act gag cac gag ggc cgg ttg cgt gcg<br>Ala Arg Thr Gln Ser Ala Leu Thr Glu His Glu Gly Arg Leu Arg Ala<br>545                                550                                555 | 1679 |
| tat ctg gcg gcg tcg ccc ggg gtg gat atg cgg gct gtg gca tcg acg<br>Tyr Leu Ala Ala Ser Pro Gly Val Asp Met Arg Ala Val Ala Ser Thr<br>560                                565                                570                      575 | 1727 |
| ctg gcg atg aca cgg tcg gtg ttc gag cac cgt gcc gtg ctg ctg gga<br>Leu Ala Met Thr Arg Ser Val Phe Glu His Arg Ala Val Leu Leu Gly<br>                    580                              585                              590 | 1775 |
| gat gac acc gtc acc ggc acc gct gtg tct gac cct cgg gcg gtg ttc<br>Asp Asp Thr Val Thr Gly Thr Ala Val Ser Asp Pro Arg Ala Val Phe<br>                          595                                600                          605 | 1823 |
| gtc ttc ccg gga cag ggg tcg cag cgt gct ggc atg ggt gag gaa ctg<br>Val Phe Pro Gly Gln Gly Ser Gln Arg Ala Gly Met Gly Glu Glu Leu<br>610                                615 | 1871 |
| gcc gcc gcg ttc ccc gtc ttc gcg cgg atc cat cag cag gtg tgg gac<br>Ala Ala Ala Phe Pro Val Phe Ala Arg Ile His Gln Gln Val Trp Asp<br>625                                630                                635 | 1919 |
| ctg ctc gat gtg ccc gat ctg gag gtg aac gag acc ggt tac gcc cag<br>Leu Leu Asp Val Pro Asp Leu Glu Val Asn Glu Thr Gly Tyr Ala Gln<br>640                                645                                650                      655 | 1967 |
| ccg gcc ctg ttc gca atg cag gtg gct ctg ttc ggg ctg ctg gaa tcg<br>Pro Ala Leu Phe Ala Met Gln Val Ala Leu Phe Gly Leu Leu Glu Ser | 2015 |

-continued

|  |  |  |  |  |  |  | 660 |  |  |  |  |  | 665 |  |  |  |  |  | 670 |  |  |  |
|---|---|---|---|---|---|---|---|---|---|---|---|---|---|---|---|---|---|---|---|---|---|---|

```
tgg ggt gta cga ccg gac gcg gtg atc ggc cat tcg gtg ggt gag ctt       2063
Trp Gly Val Arg Pro Asp Ala Val Ile Gly His Ser Val Gly Glu Leu
            675                 680                 685 gcg gct gcg tat gtg tcc ggg gtg tgg tcg ttg gag gat gcc tgc act       2111
Ala Ala Ala Tyr Val Ser Gly Val Trp Ser Leu Glu Asp Ala Cys Thr
            690                 695                 700 ttg gtg tcg gcg cgg gct cgt ctg atg cag gct ctg ccc gcg ggt ggg       2159
Leu Val Ser Ala Arg Ala Arg Leu Met Gln Ala Leu Pro Ala Gly Gly
            705                 710                 715 gtg atg gtc gct gtc ccg gtc tcg gag gat gag gcc cgg gcc gtg ctg       2207
Val Met Val Ala Val Pro Val Ser Glu Asp Glu Ala Arg Ala Val Leu
720                 725                 730                 735 ggt gag ggt gtg gag atc gcc gcg gtc aac ggc ccg tcg tcg gtg gtt       2255
Gly Glu Gly Val Glu Ile Ala Ala Val Asn Gly Pro Ser Ser Val Val
                740                 745                 750 ctc tcc ggt gat gag gcc gcc gtg ctg cag gcc gcg gag ggg ctg ggg       2303
Leu Ser Gly Asp Glu Ala Ala Val Leu Gln Ala Ala Glu Gly Leu Gly
            755                 760                 765 aag tgg acg cgg ctg gcg acc agc cac gcg ttc cat tcc gcc cgt atg       2351
Lys Trp Thr Arg Leu Ala Thr Ser His Ala Phe His Ser Ala Arg Met
            770                 775                 780 gaa ccc atg ctg gag gag ttc cgg gcg gtc gcc gaa ggc ctg acc tac       2399
Glu Pro Met Leu Glu Glu Phe Arg Ala Val Ala Glu Gly Leu Thr Tyr
785                 790                 795 cgg acg ccg cag gtc tcc atg gcc gtt ggt gat cag gtg acc acc gct       2447
Arg Thr Pro Gln Val Ser Met Ala Val Gly Asp Gln Val Thr Thr Ala
800                 805                 810                 815 gag tac tgg gtg cgg cag gtc cgg gac acg gtc cgg ttc ggc gag cag       2495
Glu Tyr Trp Val Arg Gln Val Arg Asp Thr Val Arg Phe Gly Glu Gln
                820                 825                 830 gtg gcc tcg tac gag gac gcc gtg ttc gtc gag ctg ggt gcc gac cgg       2543
Val Ala Ser Tyr Glu Asp Ala Val Phe Val Glu Leu Gly Ala Asp Arg
            835                 840                 845 tca ctg gcc cgc ctg gtc gac ggt gtc gcg atg ctg cac ggc gac cac       2591
Ser Leu Ala Arg Leu Val Asp Gly Val Ala Met Leu His Gly Asp His
            850                 855                 860 gaa atc cag gcc gcg atc ggc gcc ctg gcc cac ctg tat gtc aac ggc       2639
Glu Ile Gln Ala Ala Ile Gly Ala Leu Ala His Leu Tyr Val Asn Gly
865                 870                 875 gtc acg gtc gac tgg ccc gcg ctc ctg ggc gat gct ccg gca aca cgg       2687
Val Thr Val Asp Trp Pro Ala Leu Leu Gly Asp Ala Pro Ala Thr Arg
880                 885                 890                 895 gtg ctg gac ctt ccg aca tac gcc ttc cag cac cag cgc tac tgg ctc       2735
Val Leu Asp Leu Pro Thr Tyr Ala Phe Gln His Gln Arg Tyr Trp Leu
                900                 905                 910 gag tcg gca cgc ccg gcc gca tcc gac gcg ggc cac ccc gtg ctg ggc       2783
Glu Ser Ala Arg Pro Ala Ala Ser Asp Ala Gly His Pro Val Leu Gly
            915                 920                 925 tcc ggt atc gcc ctc gcc ggg tcg ccg ggc cgg gtg ttc acg ggt tcc       2831
Ser Gly Ile Ala Leu Ala Gly Ser Pro Gly Arg Val Phe Thr Gly Ser
            930                 935                 940 gtg ccg acc ggt gcg gac cgc gcg gtg ttc gtc gcc gag ctg gcg ctg       2879
Val Pro Thr Gly Ala Asp Arg Ala Val Phe Val Ala Glu Leu Ala Leu
945                 950                 955 gcc gcc gcg gac gcg gtc gac tgc gcc acg gtc gag cgg ctc gac atc       2927
Ala Ala Ala Asp Ala Val Asp Cys Ala Thr Val Glu Arg Leu Asp Ile
960                 965                 970                 975 gcc tcc gtg ccc ggc cgg ccg ggc cat ggc cgg acg acc gta cag acc       2975
```

-continued

```
                Ala Ser Val Pro Gly Arg Pro His Gly Arg Thr Val Gln Thr
                            980                 985                 990 tgg gtc gac gag ccg gcg gac gac ggc cgg cgc cgg ttc acc gtg cac        3023
Trp Val Asp Glu Pro Ala Asp Asp Gly Arg Arg Arg Phe Thr Val His
            995                 1000                1005 acc cgc acc ggc gac gcc ccg tgg acg ctg cac gcg gag ggg gtg ctg        3071
Thr Arg Thr Gly Asp Ala Pro Trp Thr Leu His Ala Glu Gly Val Leu
        1010                1015                1020 cgc ccc cat ggc acg gcc ctg ccc gat gcg gcc gac gcc gag tgg ccc        3119
Arg Pro His Gly Thr Ala Leu Pro Asp Ala Ala Asp Ala Glu Trp Pro
    1025                1030                1035 cca ccg ggc gcg gtg ccc gcg gac ggg ctg ccg ggt gtg tgg cgc cgg        3167
Pro Pro Gly Ala Val Pro Ala Asp Gly Leu Pro Gly Val Trp Arg Arg
1040                1045                1050                1055 ggg gac cag gtc ttc gcc gag gcc gag gtg gac gga ccg gac ggt ttc        3215
Gly Asp Gln Val Phe Ala Glu Ala Glu Val Asp Gly Pro Asp Gly Phe
                1060                1065                1070 gtg gtg cac ccc gac ctg ctc gac gcg gtc ttc tcc gcg gtc ggc gac        3263
Val Val His Pro Asp Leu Leu Asp Ala Val Phe Ser Ala Val Gly Asp
            1075                1080                1085 gga agc cgc cag ccg gcc gga tgg cgc gac ctg acg gtg cac gcg tcg        3311
Gly Ser Arg Gln Pro Ala Gly Trp Arg Asp Leu Thr Val His Ala Ser
        1090                1095                1100 gac gcc acc gta ctg cgc gcc tgc ctc acc cgg cgc acc gac gga gcc        3359
Asp Ala Thr Val Leu Arg Ala Cys Leu Thr Arg Arg Thr Asp Gly Ala
    1105                1110                1115 atg gga ttc gcc gcc ttc gac ggc gcc ggc ctg ccg gta ctc acc gcg        3407
Met Gly Phe Ala Ala Phe Asp Gly Ala Gly Leu Pro Val Leu Thr Ala
1120                1125                1130                1135 gag gcg gtg acg ctg cgg gag gtg gcg tca ccg tcc ggc tcc gag gag        3455
Glu Ala Val Thr Leu Arg Glu Val Ala Ser Pro Ser Gly Ser Glu Glu
                1140                1145                1150 tcg gac ggc ctg cac cgg ttg gag tgg ctc gcg gtc gcc gag gcg gtc        3503
Ser Asp Gly Leu His Arg Leu Glu Trp Leu Ala Val Ala Glu Ala Val
            1155                1160                1165 tac gac ggt gac ctg ccc gag gga cat gtc ctg atc acc gcc gcc cac        3551
Tyr Asp Gly Asp Leu Pro Glu Gly His Val Leu Ile Thr Ala Ala His
        1170                1175                1180 ccc gac gac ccc gag gac ata ccc acc cgc gcc cac acc cgc gcc acc        3599
Pro Asp Asp Pro Glu Asp Ile Pro Thr Arg Ala His Thr Arg Ala Thr
    1185                1190                1195 cgc gtc ctg acc gcc ctg caa cac cac ctc acc acc acc gac cac acc        3647
Arg Val Leu Thr Ala Leu Gln His His Leu Thr Thr Thr Asp His Thr
1200                1205                1210                1215 ctc atc gtc cac acc acc acc gac ccc gcc ggc gcc acc gtc acc ggc        3695
Leu Ile Val His Thr Thr Thr Asp Pro Ala Gly Ala Thr Val Thr Gly
                1220                1225                1230 ctc acc cgc acc gcc cag aac gaa cac ccc cac cgc atc cgc ctc atc        3743
Leu Thr Arg Thr Ala Gln Asn Glu His Pro His Arg Ile Arg Leu Ile
            1235                1240                1245 gaa acc gac cac ccc cac acc ccc ctc ccc ctg gcc caa ctc gcc acc        3791
Glu Thr Asp His Pro His Thr Pro Leu Pro Leu Ala Gln Leu Ala Thr
        1250                1255                1260 ctc gac cac ccc cac ctc cgc ctc acc cac cac acc ctc cac cac ccc        3839
Leu Asp His Pro His Leu Arg Leu Thr His Thr Leu His His Pro
    1265                1270                1275 cac ctc acc ccc ctc cac acc acc acc cca ccc acc acc acc ccc ctc        3887
His Leu Thr Pro Leu His Thr Thr Thr Pro Thr Thr Thr Pro Leu
1280                1285                1290                1295
```

```
aac ccc gaa cac gcc atc atc atc acc ggc ggc tcc ggc acc ctc gcc        3935
Asn Pro Glu His Ala Ile Ile Ile Thr Gly Gly Ser Gly Thr Leu Ala
            1300                1305                1310 ggc atc ctc gcc cgc cac ctg aac cac ccc cac acc tac ctc ctc tcc        3983
Gly Ile Leu Ala Arg His Leu Asn His Pro His Thr Tyr Leu Leu Ser
        1315                1320                1325 cgc acc cca ccc ccc gac gcc acc ccc ggc acc cac ctc ccc tgc gac        4031
Arg Thr Pro Pro Pro Asp Ala Thr Pro Gly Thr His Leu Pro Cys Asp
    1330                1335                1340 gtc ggc gac ccc cac caa ctc gcc acc acc ctc acc cac atc ccc caa        4079
Val Gly Asp Pro His Gln Leu Ala Thr Thr Leu Thr His Ile Pro Gln
1345                1350                1355 ccc ctc acc gcc atc ttc cac acc gcc gcc acc ctc gac gac ggc atc        4127
Pro Leu Thr Ala Ile Phe His Thr Ala Ala Thr Leu Asp Asp Gly Ile
1360                1365                1370                1375 ctc cac gcc ctc acc ccc gac cgc ctc acc acc gtc ctc cac ccc aaa        4175
Leu His Ala Leu Thr Pro Asp Arg Leu Thr Thr Val Leu His Pro Lys
        1380                1385                1390 gcc aac gcc gcc tgg cac ctg cac cac ctc acc caa aac caa ccc ctc        4223
Ala Asn Ala Ala Trp His Leu His His Leu Thr Gln Asn Gln Pro Leu
            1395                1400                1405 acc cac ttc gtc ctc tac tcc agc gcc gcc gcc gtc ctc ggc agc ccc        4271
Thr His Phe Val Leu Tyr Ser Ser Ala Ala Ala Val Leu Gly Ser Pro
        1410                1415                1420 gga caa gga aac tac gcc gcc gcc aac gcc ttc ctc gac gcc ctc gcc        4319
Gly Gln Gly Asn Tyr Ala Ala Ala Asn Ala Phe Leu Asp Ala Leu Ala
    1425                1430                1435 acc cac cgc cac acc ctc ggc caa ccc gcc acc tcc atc gcc tgg ggc        4367
Thr His Arg His Thr Leu Gly Gln Pro Ala Thr Ser Ile Ala Trp Gly
1440                1445                1450                1455 atg tgg cac acc acc agc acc ctc acc gga caa ctc gac gac gcc gac        4415
Met Trp His Thr Thr Ser Thr Leu Thr Gly Gln Leu Asp Asp Ala Asp
            1460                1465                1470 cgg gac cgc atc cgc cgc ggt ttc ctc ccg atc acg gac gac gag           4463
Arg Asp Arg Ile Arg Arg Gly Phe Leu Pro Ile Thr Asp Asp Glu
        1475                1480                1485 ggc atggggatgc at                                                      4478
Gly

<210> SEQ ID NO 17
<211> LENGTH: 1488
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 17

Ile Trp Gln Leu Ala Glu Ala Leu Leu Thr Leu Val Arg Glu Ser Thr
 1               5                  10                  15

Ala Ala Val Leu Gly His Val Gly Gly Glu Asp Ile Pro Ala Thr Ala
                20                  25                  30

Ala Phe Lys Asp Leu Gly Ile Asp Ser Leu Thr Ala Val Gln Leu Arg
            35                  40                  45

Asn Ala Leu Thr Glu Ala Thr Gly Val Arg Leu Asn Ala Thr Ala Val
        50                  55                  60

Phe Asp Phe Pro Thr Pro His Val Leu Ala Gly Lys Leu Gly Asp Glu
    65                  70                  75                  80

Leu Thr Gly Thr Arg Ala Pro Val Val Pro Arg Thr Ala Ala Thr Ala
                85                  90                  95
```

```
Gly Ala His Asp Glu Pro Leu Ala Ile Val Gly Met Ala Cys Arg Leu
            100                 105                 110
Pro Gly Gly Val Ala Ser Pro Glu Glu Leu Trp His Leu Val Ala Ser
        115                 120                 125
Gly Thr Asp Ala Ile Thr Glu Phe Pro Thr Asp Arg Gly Trp Asp Val
    130                 135                 140
Asp Ala Ile Tyr Asp Pro Asp Pro Asp Ala Ile Gly Lys Thr Phe Val
145                 150                 155                 160
Arg His Gly Gly Phe Leu Thr Gly Ala Thr Gly Phe Asp Ala Ala Phe
                165                 170                 175
Phe Gly Ile Ser Pro Arg Glu Ala Leu Ala Met Asp Pro Gln Gln Arg
            180                 185                 190
Val Leu Leu Glu Thr Ser Trp Glu Ala Phe Glu Ser Ala Gly Ile Thr
        195                 200                 205
Pro Asp Ser Thr Arg Gly Ser Asp Thr Gly Val Phe Val Gly Ala Phe
    210                 215                 220
Ser Tyr Gly Tyr Gly Thr Gly Ala Asp Thr Asp Gly Phe Gly Ala Thr
225                 230                 235                 240
Gly Ser Gln Thr Ser Val Leu Ser Gly Arg Leu Ser Tyr Phe Tyr Gly
                245                 250                 255
Leu Glu Gly Pro Ala Val Thr Val Asp Thr Ala Cys Ser Ser Ser Leu
            260                 265                 270
Val Ala Leu His Gln Ala Gly Gln Ser Leu Arg Ser Gly Glu Cys Ser
        275                 280                 285
Leu Ala Leu Val Gly Gly Val Thr Val Met Ala Ser Pro Gly Gly Phe
    290                 295                 300
Val Glu Phe Ser Arg Gln Arg Gly Leu Ala Pro Asp Gly Arg Ala Lys
305                 310                 315                 320
Ala Phe Gly Ala Gly Ala Asp Gly Thr Ser Phe Ala Glu Gly Ala Gly
                325                 330                 335
Val Leu Ile Val Glu Arg Leu Ser Asp Ala Glu Arg Asn Gly His Thr
            340                 345                 350
Val Leu Ala Val Val Arg Gly Ser Ala Val Asn Gln Asp Gly Ala Ser
        355                 360                 365
Asn Gly Leu Ser Ala Pro Asn Gly Pro Ser Gln Glu Arg Val Ile Arg
    370                 375                 380
Gln Ala Leu Ala Asn Ala Gly Leu Thr Pro Ala Asp Val Asp Ala Val
385                 390                 395                 400
Glu Ala His Gly Thr Gly Thr Arg Leu Gly Asp Pro Ile Glu Ala Gln
                405                 410                 415
Ala Val Leu Ala Thr Tyr Gly Gln Glu Arg Ala Thr Pro Leu Leu Leu
            420                 425                 430
Gly Ser Leu Lys Ser Asn Ile Gly His Ala Gln Ala Ala Ser Gly Val
        435                 440                 445
Ala Gly Ile Ile Lys Met Val Gln Ala Leu Arg His Gly Glu Leu Pro
    450                 455                 460
Pro Thr Leu His Ala Asp Glu Pro Ser Pro His Val Asp Trp Thr Ala
465                 470                 475                 480
Gly Ala Val Glu Leu Leu Thr Ser Ala Arg Pro Trp Pro Glu Thr Asp
                485                 490                 495
Arg Pro Arg Arg Ala Gly Val Ser Ser Phe Gly Ile Ser Gly Thr Asn
            500                 505                 510
```

```
Ala His Val Ile Leu Glu Ser Ala Pro Pro Thr Gln Pro Ala Asp Asn
        515                 520                 525

Ala Val Ile Glu Arg Ala Pro Glu Trp Val Pro Leu Val Ile Ser Ala
        530                 535                 540

Arg Thr Gln Ser Ala Leu Thr Glu His Glu Gly Arg Leu Arg Ala Tyr
545                 550                 555                 560

Leu Ala Ala Ser Pro Gly Val Asp Met Arg Ala Val Ala Ser Thr Leu
                565                 570                 575

Ala Met Thr Arg Ser Val Phe Glu His Arg Ala Val Leu Leu Gly Asp
            580                 585                 590

Asp Thr Val Thr Gly Thr Ala Val Ser Asp Pro Arg Ala Val Phe Val
        595                 600                 605

Phe Pro Gly Gln Gly Ser Gln Arg Ala Gly Met Gly Glu Glu Leu Ala
    610                 615                 620

Ala Ala Phe Pro Val Phe Ala Arg Ile His Gln Gln Val Trp Asp Leu
625                 630                 635                 640

Leu Asp Val Pro Asp Leu Glu Val Asn Glu Thr Gly Tyr Ala Gln Pro
                645                 650                 655

Ala Leu Phe Ala Met Gln Val Ala Leu Phe Gly Leu Leu Glu Ser Trp
            660                 665                 670

Gly Val Arg Pro Asp Ala Val Ile Gly His Ser Val Gly Glu Leu Ala
        675                 680                 685

Ala Ala Tyr Val Ser Gly Val Trp Ser Leu Glu Asp Ala Cys Thr Leu
        690                 695                 700

Val Ser Ala Arg Ala Arg Leu Met Gln Ala Leu Pro Ala Gly Gly Val
705                 710                 715                 720

Met Val Ala Val Pro Val Ser Glu Asp Glu Ala Arg Ala Val Leu Gly
                725                 730                 735

Glu Gly Val Glu Ile Ala Ala Val Asn Gly Pro Ser Ser Val Val Leu
            740                 745                 750

Ser Gly Asp Glu Ala Ala Val Leu Gln Ala Ala Glu Gly Leu Gly Lys
        755                 760                 765

Trp Thr Arg Leu Ala Thr Ser His Ala Phe His Ser Ala Arg Met Glu
    770                 775                 780

Pro Met Leu Glu Glu Phe Arg Ala Val Ala Glu Gly Leu Thr Tyr Arg
785                 790                 795                 800

Thr Pro Gln Val Ser Met Ala Val Gly Asp Gln Val Thr Thr Ala Glu
                805                 810                 815

Tyr Trp Val Arg Gln Val Arg Asp Thr Val Arg Phe Gly Glu Gln Val
            820                 825                 830

Ala Ser Tyr Glu Asp Ala Val Phe Val Glu Leu Gly Ala Asp Arg Ser
        835                 840                 845

Leu Ala Arg Leu Val Asp Gly Val Ala Met Leu His Gly Asp His Glu
850                 855                 860

Ile Gln Ala Ala Ile Gly Ala Leu Ala His Leu Tyr Val Asn Gly Val
865                 870                 875                 880

Thr Val Asp Trp Pro Ala Leu Leu Gly Asp Ala Pro Ala Thr Arg Val
                885                 890                 895

Leu Asp Leu Pro Thr Tyr Ala Phe Gln His Gln Arg Tyr Trp Leu Glu
            900                 905                 910

Ser Ala Arg Pro Ala Ala Ser Asp Ala Gly His Pro Val Leu Gly Ser
        915                 920                 925

Gly Ile Ala Leu Ala Gly Ser Pro Gly Arg Val Phe Thr Gly Ser Val
```

-continued

```
            930                 935                 940
Pro Thr Gly Ala Asp Arg Ala Val Phe Val Ala Glu Leu Ala Leu Ala
945                 950                 955                 960

Ala Ala Asp Ala Val Asp Cys Ala Thr Val Glu Arg Leu Asp Ile Ala
                965                 970                 975

Ser Val Pro Gly Arg Pro Gly His Gly Arg Thr Thr Val Gln Thr Trp
            980                 985                 990

Val Asp Glu Pro Ala Asp Gly Arg Arg Phe Thr Val His Thr
            995                 1000                1005

Arg Thr Gly Asp Ala Pro Trp Thr Leu His Ala Glu Gly Val Leu Arg
            1010                1015                1020

Pro His Gly Thr Ala Leu Pro Asp Ala Ala Asp Ala Glu Trp Pro Pro
1025                1030                1035                1040

Pro Gly Ala Val Pro Ala Asp Gly Leu Pro Gly Val Trp Arg Arg Gly
                1045                1050                1055

Asp Gln Val Phe Ala Glu Ala Glu Val Asp Gly Pro Asp Gly Phe Val
                1060                1065                1070

Val His Pro Asp Leu Leu Asp Ala Val Phe Ser Ala Val Gly Asp Gly
            1075                1080                1085

Ser Arg Gln Pro Ala Gly Trp Arg Asp Leu Thr Val His Ala Ser Asp
            1090                1095                1100

Ala Thr Val Leu Arg Ala Cys Leu Thr Arg Arg Thr Asp Gly Ala Met
1105                1110                1115                1120

Gly Phe Ala Ala Phe Asp Gly Ala Gly Leu Pro Val Leu Thr Ala Glu
                1125                1130                1135

Ala Val Thr Leu Arg Glu Val Ala Ser Pro Ser Gly Ser Glu Glu Ser
                1140                1145                1150

Asp Gly Leu His Arg Leu Glu Trp Leu Ala Val Ala Glu Ala Val Tyr
            1155                1160                1165

Asp Gly Asp Leu Pro Glu Gly His Val Leu Ile Thr Ala Ala His Pro
            1170                1175                1180

Asp Asp Pro Glu Asp Ile Pro Thr Arg Ala His Thr Arg Ala Thr Arg
1185                1190                1195                1200

Val Leu Thr Ala Leu Gln His His Leu Thr Thr Thr Asp His Thr Leu
                1205                1210                1215

Ile Val His Thr Thr Asp Pro Ala Gly Ala Thr Val Thr Gly Leu
            1220                1225                1230

Thr Arg Thr Ala Gln Asn Glu His Pro His Arg Ile Arg Leu Ile Glu
            1235                1240                1245

Thr Asp His Pro His Thr Pro Leu Pro Leu Ala Gln Leu Ala Thr Leu
            1250                1255                1260

Asp His Pro His Leu Arg Leu Thr His Thr Leu His His Pro His
1265                1270                1275                1280

Leu Thr Pro Leu His Thr Thr Thr Pro Pro Thr Thr Pro Leu Asn
                1285                1290                1295

Pro Glu His Ala Ile Ile Ile Thr Gly Gly Ser Gly Thr Leu Ala Gly
            1300                1305                1310

Ile Leu Ala Arg His Leu Asn His Pro His Thr Tyr Leu Leu Ser Arg
            1315                1320                1325

Thr Pro Pro Pro Asp Ala Thr Pro Gly Thr His Leu Pro Cys Asp Val
            1330                1335                1340

Gly Asp Pro His Gln Leu Ala Thr Thr Leu Thr His Ile Pro Gln Pro
1345                1350                1355                1360
```

-continued

```
Leu Thr Ala Ile Phe His Thr Ala Ala Thr Leu Asp Asp Gly Ile Leu
                1365                1370                1375

His Ala Leu Thr Pro Asp Arg Leu Thr Thr Val Leu His Pro Lys Ala
            1380                1385                1390

Asn Ala Ala Trp His Leu His Leu Thr Gln Asn Gln Pro Leu Thr
        1395                1400                1405

His Phe Val Leu Tyr Ser Ser Ala Ala Val Leu Gly Ser Pro Gly
    1410                1415                1420

Gln Gly Asn Tyr Ala Ala Asn Ala Phe Leu Asp Ala Leu Ala Thr
1425                1430                1435                1440

His Arg His Thr Leu Gly Gln Pro Ala Thr Ser Ile Ala Trp Gly Met
                1445                1450                1455

Trp His Thr Thr Ser Thr Leu Thr Gly Gln Leu Asp Asp Ala Asp Arg
                1460                1465                1470

Asp Arg Ile Arg Arg Gly Gly Phe Leu Pro Ile Thr Asp Asp Glu Gly
            1475                1480                1485
```

<210> SEQ ID NO 18
<211> LENGTH: 4571
<212> TYPE: DNA
<213> ORGANISM: Artificial Sequence
<220> FEATURE:
<223> OTHER INFORMATION: Description of Artificial Sequence: DNA
    encoding synthetic PKS synthase fragment
<220> FEATURE:
<221> NAME/KEY: CDS
<222> LOCATION: (9)..(4559)

<400> SEQUENCE: 18

```
agatctgg cag ctc gcc gaa gcg ctg ctg acg ctc gtc cgg gag agc acc        50
         Gln Leu Ala Glu Ala Leu Leu Thr Leu Val Arg Glu Ser Thr
           1               5                  10 gcc gcc gtg ctc ggc cac gtg ggt ggc gag gac atc ccc gcg acg gcg         98
Ala Ala Val Leu Gly His Val Gly Gly Glu Asp Ile Pro Ala Thr Ala
 15                  20                  25                  30 gcg ttc aag gac ctc ggc atc gac tcg ctc acc gcg gtc cag ctg cgc        146
Ala Phe Lys Asp Leu Gly Ile Asp Ser Leu Thr Ala Val Gln Leu Arg
                 35                  40                  45 aac gcc ctc acc gag gcg acc ggt gtg cgg ctg aac gcc acg gcg gtc        194
Asn Ala Leu Thr Glu Ala Thr Gly Val Arg Leu Asn Ala Thr Ala Val
             50                  55                  60 ttc gac ttc ccg acc ccg cac gtg ctc gcc ggg aag ctc ggc gac gaa        242
Phe Asp Phe Pro Thr Pro His Val Leu Ala Gly Lys Leu Gly Asp Glu
 65                  70                  75 ctg acc ggc acc cgc gcg ccc gtc gtg ccc cgg acc gcg gcc acg gcc        290
Leu Thr Gly Thr Arg Ala Pro Val Val Pro Arg Thr Ala Ala Thr Ala
 80                  85                  90 ggt gcg cac gac gag ccg ctg gcg atc gtg gga atg gcc tgc cgg ctg        338
Gly Ala His Asp Glu Pro Leu Ala Ile Val Gly Met Ala Cys Arg Leu
 95                 100                 105                 110 ccc ggc ggg gtc gcg tca ccc gag gag ctg tgg cac ctc gtg gca tcc        386
Pro Gly Gly Val Ala Ser Pro Glu Glu Leu Trp His Leu Val Ala Ser
                115                 120                 125 ggc acc gac gcc atc acg gag ttc ccg acg gac cgc ggc tgg gac gtc        434
Gly Thr Asp Ala Ile Thr Glu Phe Pro Thr Asp Arg Gly Trp Asp Val
            130                 135                 140 gac gcg atc tac gac ccg gac ccc gac gcg atc ggc aag acc ttc gtc        482
Asp Ala Ile Tyr Asp Pro Asp Pro Asp Ala Ile Gly Lys Thr Phe Val
        145                 150                 155
```

-continued

| | |
|---|---|
| cgg cac ggt ggc ttc ctc acc ggc gcg aca ggc ttc gac gcg gcg ttc<br>Arg His Gly Gly Phe Leu Thr Gly Ala Thr Gly Phe Asp Ala Ala Phe<br>160                        165                    170 | 530 |
| ttc ggc atc agc ccg cgc gag gcc ctc gcg atg gac ccg cag cag cgg<br>Phe Gly Ile Ser Pro Arg Glu Ala Leu Ala Met Asp Pro Gln Gln Arg<br>175                   180                   185                   190 | 578 |
| gtg ctc ctg gag acg tcg tgg gag gcg ttc gaa agc gcc ggc atc acc<br>Val Leu Leu Glu Thr Ser Trp Glu Ala Phe Glu Ser Ala Gly Ile Thr<br>                   195                   200                   205 | 626 |
| ccg gac tcg acc cgc ggc agc gac acc ggc gtg ttc gtc ggc gcc ttc<br>Pro Asp Ser Thr Arg Gly Ser Asp Thr Gly Val Phe Val Gly Ala Phe<br>           210                   215                   220 | 674 |
| tcc tac ggt tac ggc acc ggt gcg gac acc gac ggc ttc ggc gcg acc<br>Ser Tyr Gly Tyr Gly Thr Gly Ala Asp Thr Asp Gly Phe Gly Ala Thr<br>225                       230                   235 | 722 |
| ggc tcg cag acc agt gtg ctc tcc ggc cgg ctg tcg tac ttc tac ggt<br>Gly Ser Gln Thr Ser Val Leu Ser Gly Arg Leu Ser Tyr Phe Tyr Gly<br>240                       245                   250 | 770 |
| ctg gag ggt ccg gcg gtc acg gtc gac acg gcg tgt tcg tcg tcg ctg<br>Leu Glu Gly Pro Ala Val Thr Val Asp Thr Ala Cys Ser Ser Ser Leu<br>255                       260                   265                   270 | 818 |
| gtg gcg ctg cac cag gcc ggg cag tcg ctg cgc tcc ggc gaa tgc tcg<br>Val Ala Leu His Gln Ala Gly Gln Ser Leu Arg Ser Gly Glu Cys Ser<br>                   275                   280                   285 | 866 |
| ctc gcc ctg gtc ggc ggc gtc acg gtg atg gcg tct ccc ggc ggc ttc<br>Leu Ala Leu Val Gly Gly Val Thr Val Met Ala Ser Pro Gly Gly Phe<br>           290                   295                   300 | 914 |
| gtg gag ttc tcc cgg cag cgc ggc ctc gcg ccg gac ggc cgg gcg aag<br>Val Glu Phe Ser Arg Gln Arg Gly Leu Ala Pro Asp Gly Arg Ala Lys<br>305                       310                   315 | 962 |
| gcg ttc ggc gcg ggt gcg gac ggc acg agc ttc gcc gag ggt gcc ggt<br>Ala Phe Gly Ala Gly Ala Asp Gly Thr Ser Phe Ala Glu Gly Ala Gly<br>320                       325                   330 | 1010 |
| gtg ctg atc gtc gag agg ctc tcc gac gcc gaa cgc aac ggt cac acc<br>Val Leu Ile Val Glu Arg Leu Ser Asp Ala Glu Arg Asn Gly His Thr<br>335                       340                   345                   350 | 1058 |
| gtc ctg gcg gtc gtc cgt ggt tcg gcg gtc aac cag gat ggt gcc tcc<br>Val Leu Ala Val Val Arg Gly Ser Ala Val Asn Gln Asp Gly Ala Ser<br>                   355                   360                   365 | 1106 |
| aac ggg ctg tcg gcg ccg aac ggg ccg tcg cag gag cgg gtg atc cgg<br>Asn Gly Leu Ser Ala Pro Asn Gly Pro Ser Gln Glu Arg Val Ile Arg<br>           370                   375                   380 | 1154 |
| cag gcc ctg gcc aac gcc ggg ctc acc ccg gcg gac gtg gac gcc gtc<br>Gln Ala Leu Ala Asn Ala Gly Leu Thr Pro Ala Asp Val Asp Ala Val<br>385                       390                   395 | 1202 |
| gag gcc cac ggc acc ggc acc agg ctg ggc gac ccc atc gag gca cag<br>Glu Ala His Gly Thr Gly Thr Arg Leu Gly Asp Pro Ile Glu Ala Gln<br>400                       405                   410 | 1250 |
| gcg gta ctg gcc acc tac gga cag gag cgc gcc acc ccc ctg ctg ctg<br>Ala Val Leu Ala Thr Tyr Gly Gln Glu Arg Ala Thr Pro Leu Leu Leu<br>415                       420                   425                   430 | 1298 |
| ggc tcg ctg aag tcc aac atc ggc cac gcc cag gcc gcg tcc ggc gtc<br>Gly Ser Leu Lys Ser Asn Ile Gly His Ala Gln Ala Ala Ser Gly Val<br>                   435                   440                   445 | 1346 |
| gcc ggc atc atc aag atg gtg cag gcc ctc cgg cac ggg gag ctg ccg<br>Ala Gly Ile Ile Lys Met Val Gln Ala Leu Arg His Gly Glu Leu Pro<br>           450                   455                   460 | 1394 |
| ccg acg ctg cac gcc gac gag ccg tcg ccg cac gtc gac tgg acg gcc<br>Pro Thr Leu His Ala Asp Glu Pro Ser Pro His Val Asp Trp Thr Ala<br>465                       470                   475 | 1442 |

-continued

| | |
|---|---|
| ggc gcc gtc gaa ctg ctg acg tcg gcc cgg ccg tgg ccc gag acc gac<br>Gly Ala Val Glu Leu Leu Thr Ser Ala Arg Pro Trp Pro Glu Thr Asp<br>480                        485                 490 | 1490 |
| cgg cct agg cgg gcg ggc gtg tcg tcc ttc gga gtc agc ggc acc aac<br>Arg Pro Arg Arg Ala Gly Val Ser Ser Phe Gly Val Ser Gly Thr Asn<br>495                   500                 505              510 | 1538 |
| gcc cac gtc atc ctg gag agc gca ccc ccc gct cag ccc gcg gag gag<br>Ala His Val Ile Leu Glu Ser Ala Pro Pro Ala Gln Pro Ala Glu Glu<br>                515                 520                  525 | 1586 |
| gcg cag cct gtt gag acg ccg gtg gtg gcc tcg gat gtg ctg ccg ctg<br>Ala Gln Pro Val Glu Thr Pro Val Val Ala Ser Asp Val Leu Pro Leu<br>530                        535                 540 | 1634 |
| gtg ata tcg gcc aag acc cag ccc gcc ctg acc gaa cac gaa gac cgg<br>Val Ile Ser Ala Lys Thr Gln Pro Ala Leu Thr Glu His Glu Asp Arg<br>545                        550                 555 | 1682 |
| ctg cgc gcc tac ctg gcg gcg tcg ccc ggg gcg gat ata cgg gct gtg<br>Leu Arg Ala Tyr Leu Ala Ala Ser Pro Gly Ala Asp Ile Arg Ala Val<br>          560                    565                 570 | 1730 |
| gca tcg acg ctg gcg gtg aca cgg tcg gtg ttc gag cac cgc gcc gta<br>Ala Ser Thr Leu Ala Val Thr Arg Ser Val Phe Glu His Arg Ala Val<br>575                        580                 585              590 | 1778 |
| ctc ctt gga gat gac acc gtc acc ggc acc gcg gtg acc gac ccc agg<br>Leu Leu Gly Asp Asp Thr Val Thr Gly Thr Ala Val Thr Asp Pro Arg<br>                595                 600                  605 | 1826 |
| atc gtg ttt gtc ttt ccc ggg cag ggg tgg cag tgg ctg ggg atg ggc<br>Ile Val Phe Val Phe Pro Gly Gln Gly Trp Gln Trp Leu Gly Met Gly<br>610                        615                 620 | 1874 |
| agt gca ctg cgc gat tcg tcg gtg gtg ttc gcc gag cgg atg gcc gag<br>Ser Ala Leu Arg Asp Ser Ser Val Val Phe Ala Glu Arg Met Ala Glu<br>625                        630                 635 | 1922 |
| tgt gcg gcg gcg ttg cgc gag ttc gtg gac tgg gat ctg ttc acg gtt<br>Cys Ala Ala Ala Leu Arg Glu Phe Val Asp Trp Asp Leu Phe Thr Val<br>640                        645                 650 | 1970 |
| ctg gat gat ccg gcg gtg gtg gac cgg gtt gat gtg gtc cag ccc gct<br>Leu Asp Asp Pro Ala Val Val Asp Arg Val Asp Val Val Gln Pro Ala<br>655                        660                 665              670 | 2018 |
| tcc tgg gcg atg atg gtt tcc ctg gcc gcg gtg tgg cag gcg gcc ggt<br>Ser Trp Ala Met Met Val Ser Leu Ala Ala Val Trp Gln Ala Ala Gly<br>                675                 680                  685 | 2066 |
| gtg cgg ccg gat gcg gtg atc ggc cat tcg cag ggt gag atc gcc gca<br>Val Arg Pro Asp Ala Val Ile Gly His Ser Gln Gly Glu Ile Ala Ala<br>690                        695                 700 | 2114 |
| gct tgt gtg gcg ggt gcg gtg tca cta cgc gat gcc gcc cgg atc gtg<br>Ala Cys Val Ala Gly Ala Val Ser Leu Arg Asp Ala Ala Arg Ile Val<br>705                        710                 715 | 2162 |
| acc ttg cgc agc cag gcg atc gcc cgg ggc ctg gcg ggc cgg ggc gcg<br>Thr Leu Arg Ser Gln Ala Ile Ala Arg Gly Leu Ala Gly Arg Gly Ala<br>720                        725                 730 | 2210 |
| atg gca tcc gtc gcc ctg ccc gcg cag gat gtc gag ctg gtc gac ggg<br>Met Ala Ser Val Ala Leu Pro Ala Gln Asp Val Glu Leu Val Asp Gly<br>735                        740                 745              750 | 2258 |
| gcc tgg atc gcc gcc cac aac ggg ccc gcc tcc acc gtg atc gcg ggc<br>Ala Trp Ile Ala Ala His Asn Gly Pro Ala Ser Thr Val Ile Ala Gly<br>                755                 760                  765 | 2306 |
| acc ccg gaa gcg gtc gac cat gtc ctc acc gct cat gag gca caa ggg<br>Thr Pro Glu Ala Val Asp His Val Leu Thr Ala His Glu Ala Gln Gly<br>770                        775                 780 | 2354 |
| gtg cgg gtg cgg cgg atc acc gtc gac tat gcc tcg cac acc ccg cac<br>Val Arg Val Arg Arg Ile Thr Val Asp Tyr Ala Ser His Thr Pro His | 2402 |

```
              785                 790                 795
gtc gag ctg atc cgc gac gaa cta ctc gac atc act agc gac agc agc    2450
Val Glu Leu Ile Arg Asp Glu Leu Leu Asp Ile Thr Ser Asp Ser Ser
    800                 805                 810 tcg cag acc ccg ctc gtg ccg tgg ctg tcg acc gtg gac ggc acc tgg    2498
Ser Gln Thr Pro Leu Val Pro Trp Leu Ser Thr Val Asp Gly Thr Trp
815                 820                 825                 830 gtc gac agc ccg ctg gac ggg gag tac tgg tac cgg aac ctg cgt gaa    2546
Val Asp Ser Pro Leu Asp Gly Glu Tyr Trp Tyr Arg Asn Leu Arg Glu
                835                 840                 845 ccg gtc ggt ttc cac ccc gcc gtc agc cag ttg cag gcc cag ggc gac    2594
Pro Val Gly Phe His Pro Ala Val Ser Gln Leu Gln Ala Gln Gly Asp
            850                 855                 860 acc gtg ttc gtc gag gtc agc gcc agc ccg gtg ttg ttg cag gcg atg    2642
Thr Val Phe Val Glu Val Ser Ala Ser Pro Val Leu Leu Gln Ala Met
            865                 870                 875 gac gac gat gtc gtc acg gtt gcc acg ctg cgt cgt gac gac ggc gac    2690
Asp Asp Asp Val Val Thr Val Ala Thr Leu Arg Arg Asp Asp Gly Asp
880                 885                 890 gcc acc cgg atg ctc acc gcc ctg gca cag gcc tat gtc cac ggc gtc    2738
Ala Thr Arg Met Leu Thr Ala Leu Ala Gln Ala Tyr Val His Gly Val
895                 900                 905                 910 acc gtc gac tgg ccc gcc atc ctc ggc acc acc aca ccg gta ctg        2786
Thr Val Asp Trp Pro Ala Ile Leu Gly Thr Thr Thr Arg Val Leu
                915                 920                 925 gac ctt ccg acc tac gcc ttc caa cac cag cgg tac tgg ctc gag tcg    2834
Asp Leu Pro Thr Tyr Ala Phe Gln His Gln Arg Tyr Trp Leu Glu Ser
            930                 935                 940 gca cgc ccg gcc gca tcc gac gcg ggc cac ccc gtg ctg ggc tcc ggt    2882
Ala Arg Pro Ala Ala Ser Asp Ala Gly His Pro Val Leu Gly Ser Gly
        945                 950                 955 atc gcc ctc gcc ggg tcg ccg ggc cgg gtg ttc acg ggt tcc gtg ccg    2930
Ile Ala Leu Ala Gly Ser Pro Gly Arg Val Phe Thr Gly Ser Val Pro
    960                 965                 970 acc ggt gcg gac cgc gcg gtg ttc gtc gcc gag ctg gcg ctg gcc gcc    2978
Thr Gly Ala Asp Arg Ala Val Phe Val Ala Glu Leu Ala Leu Ala Ala
975                 980                 985                 990 gcg gac gcg gtc gac tgc gcc acg gtc gag cgg ctc gac atc gcc tcc    3026
Ala Asp Ala Val Asp Cys Ala Thr Val Glu Arg Leu Asp Ile Ala Ser
                995                 1000                1005 gtg ccc ggc cgg ccg ggc cat ggc cgg acg acc gta cag acc tgg gtc    3074
Val Pro Gly Arg Pro Gly His Gly Arg Thr Thr Val Gln Thr Trp Val
            1010                1015                1020 gac gag ccg gcg gac gac ggc cgg cgc cgg ttc acc gtg cac acc cgc    3122
Asp Glu Pro Ala Asp Asp Gly Arg Arg Arg Phe Thr Val His Thr Arg
        1025                1030                1035 acc ggc gac gcc ccg tgg acg ctg cac gcc gag ggg gtg ctg cgc ccc    3170
Thr Gly Asp Ala Pro Trp Thr Leu His Ala Glu Gly Val Leu Arg Pro
    1040                1045                1050 cat ggc acg gcc ctg ccc gat gcg gcc gac gcc gag tgg ccc cca ccg    3218
His Gly Thr Ala Leu Pro Asp Ala Ala Asp Ala Glu Trp Pro Pro Pro
1055                1060                1065                1070 ggc gcg gtg ccc gcg gac ggg ctg ccg ggt gtg tgg cgc cgg ggg gac    3266
Gly Ala Val Pro Ala Asp Gly Leu Pro Gly Val Trp Arg Arg Gly Asp
                1075                1080                1085 cag gtc ttc gcc gag gcc gag gtg gac gga ccg gac ggt ttc gtg gtg    3314
Gln Val Phe Ala Glu Ala Glu Val Asp Gly Pro Asp Gly Phe Val Val
            1090                1095                1100 cac ccc gac ctg ctc gac gcg gtc ttc tcc gcg gtc ggc gac gga agc    3362
```

```
                                                                -continued

His Pro Asp Leu Leu Asp Ala Val Phe Ser Ala Val Gly Asp Gly Ser
    1105                1110                1115 cgc cag ccg gcc gga tgg cgc gac ctg acg gtg cac gcg tcg gac gcc         3410
Arg Gln Pro Ala Gly Trp Arg Asp Leu Thr Val His Ala Ser Asp Ala
    1120                1125                1130 acc gta ctg cgc gcc tgc ctc acc cgg cgc acc gac gga gcc atg gga         3458
Thr Val Leu Arg Ala Cys Leu Thr Arg Arg Thr Asp Gly Ala Met Gly
1135                1140                1145                1150 ttc gcc gcc ttc gac ggc gcc ggc ctg ccg gta ctc acc gcg gag gcg         3506
Phe Ala Ala Phe Asp Gly Ala Gly Leu Pro Val Leu Thr Ala Glu Ala
                1155                1160                1165 gtg acg ctg cgg gag gtg gcg tca ccg tcc ggc tcc gag gag tcg gac         3554
Val Thr Leu Arg Glu Val Ala Ser Pro Ser Gly Ser Glu Glu Ser Asp
            1170                1175                1180 ggc ctg cac cgg ttg gag tgg ctc gcg gtc gcc gag gcg gtc tac gac         3602
Gly Leu His Arg Leu Glu Trp Leu Ala Val Ala Glu Ala Val Tyr Asp
        1185                1190                1195 ggt gac ctg ccc gag gga cat gtc ctg atc acc gcc gcc cac ccc gac         3650
Gly Asp Leu Pro Glu Gly His Val Leu Ile Thr Ala Ala His Pro Asp
    1200                1205                1210 gac ccc gag gac ata ccc acc cgc gcc cac acc cgc gcc acc cgc gtc         3698
Asp Pro Glu Asp Ile Pro Thr Arg Ala His Thr Arg Ala Thr Arg Val
1215                1220                1225                1230 ctg acc gcc ctg caa cac cac ctc acc acc acc gac cac acc ctc atc         3746
Leu Thr Ala Leu Gln His His Leu Thr Thr Thr Asp His Thr Leu Ile
                1235                1240                1245 gtc cac acc acc acc gac ccc gcc ggc gcc acc gtc acc ggc ctc acc         3794
Val His Thr Thr Thr Asp Pro Ala Gly Ala Thr Val Thr Gly Leu Thr
            1250                1255                1260 cgc acc gcc cag aac gaa cac ccc cac cgc atc cgc ctc atc gaa acc         3842
Arg Thr Ala Gln Asn Glu His Pro His Arg Ile Arg Leu Ile Glu Thr
        1265                1270                1275 gac cac ccc cac acc ccc ctc ccc ctg gcc caa ctc gcc acc ctc gac         3890
Asp His Pro His Thr Pro Leu Pro Leu Ala Gln Leu Ala Thr Leu Asp
    1280                1285                1290 cac ccc cac ctc cgc ctc acc cac cac acc ctc cac cac ccc cac ctc         3938
His Pro His Leu Arg Leu Thr His His Thr Leu His His Pro His Leu
1295                1300                1305                1310 acc ccc ctc cac acc acc acc cca ccc acc acc acc ccc ctc aac ccc         3986
Thr Pro Leu His Thr Thr Thr Pro Pro Thr Thr Thr Pro Leu Asn Pro
                1315                1320                1325 gaa cac gcc atc atc atc acc ggc ggc tcc ggc acc ctc gcc ggc atc         4034
Glu His Ala Ile Ile Ile Thr Gly Gly Ser Gly Thr Leu Ala Gly Ile
            1330                1335                1340 ctc gcc cgc cac ctg aac cac ccc cac acc tac ctc ctc tcc cgc acc         4082
Leu Ala Arg His Leu Asn His Pro His Thr Tyr Leu Leu Ser Arg Thr
        1345                1350                1355 cca ccc ccc gac gcc acc ccc ggc acc cac ctc ccc tgc gac gtc ggc         4130
Pro Pro Pro Asp Ala Thr Pro Gly Thr His Leu Pro Cys Asp Val Gly
    1360                1365                1370 gac ccc cac caa ctc gcc acc acc ctc acc cac atc ccc caa ccc ctc         4178
Asp Pro His Gln Leu Ala Thr Thr Leu Thr His Ile Pro Gln Pro Leu
1375                1380                1385                1390 acc gcc atc ttc cac acc gcc gcc acc ctc gac gac ggc atc ctc cac         4226
Thr Ala Ile Phe His Thr Ala Ala Thr Leu Asp Asp Gly Ile Leu His
                1395                1400                1405 gcc ctc acc ccc gac cgc ctc acc acc gtc ctc cac ccc aaa gcc aac         4274
Ala Leu Thr Pro Asp Arg Leu Thr Thr Val Leu His Pro Lys Ala Asn
            1410                1415                1420
```

-continued

```
gcc gcc tgg cac ctg cac cac ctc acc caa aac caa ccc ctc acc cac    4322
Ala Ala Trp His Leu His His Leu Thr Gln Asn Gln Pro Leu Thr His
        1425                1430                1435 ttc gtc ctc tac tcc agc gcc gcc gtc ctc ggc agc ccc gga caa        4370
Phe Val Leu Tyr Ser Ser Ala Ala Val Leu Gly Ser Pro Gly Gln
1440                1445                1450 gga aac tac gcc gcc gcc aac gcc ttc ctc gac gcc ctc gcc acc cac    4418
Gly Asn Tyr Ala Ala Ala Asn Ala Phe Leu Asp Ala Leu Ala Thr His
1455                1460                1465                1470 cgc cac acc ctc ggc caa ccc gcc acc tcc atc gcc tgg ggc atg tgg    4466
Arg His Thr Leu Gly Gln Pro Ala Thr Ser Ile Ala Trp Gly Met Trp
        1475                1480                1485 cac acc acc agc acc ctc acc gga caa ctc gac gac gcc gac cgg gac    4514
His Thr Thr Ser Thr Leu Thr Gly Gln Leu Asp Asp Ala Asp Arg Asp
        1490                1495                1500 cgc atc cgc cgc ggc ggt ttc ctc ccg atc acg gac gac gag ggc        4559
Arg Ile Arg Arg Gly Gly Phe Leu Pro Ile Thr Asp Asp Glu Gly
        1505                1510                1515 atggggatgc at                                                       4571
```

<210> SEQ ID NO 19
<211> LENGTH: 1517
<212> TYPE: PRT
<213> ORGANISM: Artificial Sequence
<220> FEATURE:
<223> OTHER INFORMATION: Description of Artificial Sequence:
      Synthetic PKS synthase fragment

<400> SEQUENCE: 19

```
Gln Leu Ala Glu Ala Leu Leu Thr Leu Val Arg Glu Ser Thr Ala Ala
  1               5                  10                  15

Val Leu Gly His Val Gly Gly Glu Asp Ile Pro Ala Thr Ala Ala Phe
             20                  25                  30

Lys Asp Leu Gly Ile Asp Ser Leu Thr Ala Val Gln Leu Arg Asn Ala
         35                  40                  45

Leu Thr Glu Ala Thr Gly Val Arg Leu Asn Ala Thr Ala Val Phe Asp
     50                  55                  60

Phe Pro Thr Pro His Val Leu Ala Gly Lys Leu Gly Asp Glu Leu Thr
 65                  70                  75                  80

Gly Thr Arg Ala Pro Val Val Pro Arg Thr Ala Thr Ala Gly Ala
                 85                  90                  95

His Asp Glu Pro Leu Ala Ile Val Gly Met Ala Cys Arg Leu Pro Gly
            100                 105                 110

Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
        195                 200                 205

Ser Thr Arg Gly Ser Asp Thr Gly Val Phe Val Gly Ala Phe Ser Tyr
    210                 215                 220
```

-continued

```
Gly Tyr Gly Thr Gly Ala Asp Thr Asp Gly Phe Gly Ala Thr Gly Ser
225                 230                 235                 240

Gln Thr Ser Val Leu Ser Gly Arg Leu Ser Tyr Phe Tyr Gly Leu Glu
            245                 250                 255

Gly Pro Ala Val Thr Val Asp Thr Ala Cys Ser Ser Ser Leu Val Ala
            260                 265                 270

Leu His Gln Ala Gly Gln Ser Leu Arg Ser Gly Glu Cys Ser Leu Ala
            275                 280                 285

Leu Val Gly Gly Val Thr Val Met Ala Ser Pro Gly Gly Phe Val Glu
            290                 295                 300

Phe Ser Arg Gln Arg Gly Leu Ala Pro Asp Gly Arg Ala Lys Ala Phe
305                 310                 315                 320

Gly Ala Gly Ala Asp Gly Thr Ser Phe Ala Glu Gly Ala Gly Val Leu
                325                 330                 335

Ile Val Glu Arg Leu Ser Asp Ala Glu Arg Asn Gly His Thr Val Leu
            340                 345                 350

Ala Val Val Arg Gly Ser Ala Val Asn Gln Asp Gly Ala Ser Asn Gly
            355                 360                 365

Leu Ser Ala Pro Asn Gly Pro Ser Gln Glu Arg Val Ile Arg Gln Ala
370                 375                 380

Leu Ala Asn Ala Gly Leu Thr Pro Ala Asp Val Asp Ala Val Glu Ala
385                 390                 395                 400

His Gly Thr Gly Thr Arg Leu Gly Asp Pro Ile Glu Ala Gln Ala Val
                405                 410                 415

Leu Ala Thr Tyr Gly Gln Glu Arg Ala Thr Pro Leu Leu Leu Gly Ser
                420                 425                 430

Leu Lys Ser Asn Ile Gly His Ala Gln Ala Ala Ser Gly Val Ala Gly
            435                 440                 445

Ile Ile Lys Met Val Gln Ala Leu Arg His Gly Glu Leu Pro Pro Thr
            450                 455                 460

Leu His Ala Asp Glu Pro Ser Pro His Val Asp Trp Thr Ala Gly Ala
465                 470                 475                 480

Val Glu Leu Leu Thr Ser Ala Arg Pro Trp Pro Glu Thr Asp Arg Pro
                485                 490                 495

Arg Arg Ala Gly Val Ser Ser Phe Gly Val Ser Gly Thr Asn Ala His
                500                 505                 510

Val Ile Leu Glu Ser Ala Pro Pro Ala Gln Pro Ala Glu Glu Ala Gln
            515                 520                 525

Pro Val Glu Thr Pro Val Val Ala Ser Asp Val Leu Pro Leu Val Ile
            530                 535                 540

Ser Ala Lys Thr Gln Pro Ala Leu Thr Glu His Glu Asp Arg Leu Arg
545                 550                 555                 560

Ala Tyr Leu Ala Ala Ser Pro Gly Ala Asp Ile Arg Ala Val Ala Ser
                565                 570                 575

Thr Leu Ala Val Thr Arg Ser Val Phe Glu His Arg Ala Val Leu Leu
                580                 585                 590

Gly Asp Asp Thr Val Thr Gly Thr Ala Val Thr Asp Pro Arg Ile Val
            595                 600                 605

Phe Val Phe Pro Gly Gln Gly Trp Gln Trp Leu Gly Met Gly Ser Ala
            610                 615                 620

Leu Arg Asp Ser Ser Val Val Phe Ala Glu Arg Met Ala Glu Cys Ala
625                 630                 635                 640

Ala Ala Leu Arg Glu Phe Val Asp Trp Asp Leu Phe Thr Val Leu Asp
```

-continued

```
                645                 650                 655
Asp Pro Ala Val Val Asp Arg Val Asp Val Gln Pro Ala Ser Trp
            660                 665                 670
Ala Met Met Val Ser Leu Ala Ala Val Trp Gln Ala Ala Gly Val Arg
            675                 680                 685
Pro Asp Ala Val Ile Gly His Ser Gln Gly Glu Ile Ala Ala Ala Cys
            690                 695                 700
Val Ala Gly Ala Val Ser Leu Arg Asp Ala Ala Arg Ile Val Thr Leu
705                 710                 715                 720
Arg Ser Gln Ala Ile Ala Arg Gly Leu Ala Gly Arg Gly Ala Met Ala
                725                 730                 735
Ser Val Ala Leu Pro Ala Gln Asp Val Glu Leu Val Asp Gly Ala Trp
            740                 745                 750
Ile Ala Ala His Asn Gly Pro Ala Ser Thr Val Ile Ala Gly Thr Pro
            755                 760                 765
Glu Ala Val Asp His Val Leu Thr Ala His Glu Ala Gln Gly Val Arg
            770                 775                 780
Val Arg Arg Ile Thr Val Asp Tyr Ala Ser His Thr Pro His Val Glu
785                 790                 795                 800
Leu Ile Arg Asp Glu Leu Leu Asp Ile Thr Ser Asp Ser Ser Gln
            805                 810                 815
Thr Pro Leu Val Pro Trp Leu Ser Thr Val Asp Gly Thr Trp Val Asp
            820                 825                 830
Ser Pro Leu Asp Gly Glu Tyr Trp Tyr Arg Asn Leu Arg Glu Pro Val
            835                 840                 845
Gly Phe His Pro Ala Val Ser Gln Leu Gln Ala Gln Gly Asp Thr Val
            850                 855                 860
Phe Val Glu Val Ser Ala Ser Pro Val Leu Leu Gln Ala Met Asp Asp
865                 870                 875                 880
Asp Val Val Thr Val Ala Thr Leu Arg Arg Asp Gly Asp Ala Thr
                885                 890                 895
Arg Met Leu Thr Ala Leu Ala Gln Ala Tyr Val His Gly Val Thr Val
                900                 905                 910
Asp Trp Pro Ala Ile Leu Gly Thr Thr Thr Arg Val Leu Asp Leu
            915                 920                 925
Pro Thr Tyr Ala Phe Gln His Gln Arg Tyr Trp Leu Glu Ser Ala Arg
            930                 935                 940
Pro Ala Ala Ser Asp Ala Gly His Pro Val Leu Gly Ser Gly Ile Ala
945                 950                 955                 960
Leu Ala Gly Ser Pro Gly Arg Val Phe Thr Gly Ser Val Pro Thr Gly
                965                 970                 975
Ala Asp Arg Ala Val Phe Val Ala Glu Leu Ala Leu Ala Ala Ala Asp
            980                 985                 990
Ala Val Asp Cys Ala Thr Val Glu Arg Leu Asp Ile Ala Ser Val Pro
            995                 1000                1005
Gly Arg Pro Gly His Gly Arg Thr Thr Val Gln Thr Trp Val Asp Glu
            1010                1015                1020
Pro Ala Asp Asp Gly Arg Arg Arg Phe Thr Val His Thr Arg Thr Gly
1025                1030                1035                1040
Asp Ala Pro Trp Thr Leu His Ala Glu Gly Val Leu Arg Pro His Gly
                1045                1050                1055
Thr Ala Leu Pro Asp Ala Ala Asp Ala Glu Trp Pro Pro Gly Ala
            1060                1065                1070
```

-continued

Val Pro Ala Asp Gly Leu Pro Gly Val Trp Arg Arg Gly Asp Gln Val
        1075                1080                1085

Phe Ala Glu Ala Glu Val Asp Gly Pro Asp Gly Phe Val Val His Pro
    1090                1095                1100

Asp Leu Leu Asp Ala Val Phe Ser Ala Val Gly Asp Gly Ser Arg Gln
1105                1110                1115                1120

Pro Ala Gly Trp Arg Asp Leu Thr Val His Ala Ser Asp Ala Thr Val
            1125                1130                1135

Leu Arg Ala Cys Leu Thr Arg Arg Thr Asp Gly Ala Met Gly Phe Ala
                1140                1145                1150

Ala Phe Asp Gly Ala Gly Leu Pro Val Leu Thr Ala Glu Ala Val Thr
            1155                1160                1165

Leu Arg Glu Val Ala Ser Pro Ser Gly Ser Glu Glu Ser Asp Gly Leu
        1170                1175                1180

His Arg Leu Glu Trp Leu Ala Val Ala Glu Ala Val Tyr Asp Gly Asp
1185                1190                1195                1200

Leu Pro Glu Gly His Val Leu Ile Thr Ala Ala His Pro Asp Asp Pro
            1205                1210                1215

Glu Asp Ile Pro Thr Arg Ala His Thr Arg Ala Thr Arg Val Leu Thr
                1220                1225                1230

Ala Leu Gln His His Leu Thr Thr Thr Asp His Thr Leu Ile Val His
        1235                1240                1245

Thr Thr Thr Asp Pro Ala Gly Ala Thr Val Thr Gly Leu Thr Arg Thr
    1250                1255                1260

Ala Gln Asn Glu His Pro His Arg Ile Arg Leu Ile Glu Thr Asp His
1265                1270                1275                1280

Pro His Thr Pro Leu Pro Leu Ala Gln Leu Ala Thr Leu Asp His Pro
            1285                1290                1295

His Leu Arg Leu Thr His His Thr Leu His His Pro His Leu Thr Pro
                1300                1305                1310

Leu His Thr Thr Thr Pro Pro Thr Thr Thr Pro Leu Asn Pro Glu His
        1315                1320                1325

Ala Ile Ile Ile Thr Gly Gly Ser Gly Thr Leu Ala Gly Ile Leu Ala
    1330                1335                1340

Arg His Leu Asn His Pro His Thr Tyr Leu Leu Ser Arg Thr Pro Pro
1345                1350                1355                1360

Pro Asp Ala Thr Pro Gly Thr His Leu Pro Cys Asp Val Gly Asp Pro
            1365                1370                1375

His Gln Leu Ala Thr Thr Leu Thr His Ile Pro Gln Pro Leu Thr Ala
        1380                1385                1390

Ile Phe His Thr Ala Ala Thr Leu Asp Asp Gly Ile Leu His Ala Leu
    1395                1400                1405

Thr Pro Asp Arg Leu Thr Thr Val Leu His Pro Lys Ala Asn Ala Ala
    1410                1415                1420

Trp His Leu His His Leu Thr Gln Asn Gln Pro Leu Thr His Phe Val
1425                1430                1435                1440

Leu Tyr Ser Ser Ala Ala Ala Val Leu Gly Ser Pro Gly Gln Gly Asn
            1445                1450                1455

Tyr Ala Ala Ala Asn Ala Phe Leu Asp Ala Leu Ala Thr His Arg His
                1460                1465                1470

Thr Leu Gly Gln Pro Ala Thr Ser Ile Ala Trp Gly Met Trp His Thr
        1475                1480                1485

-continued

```
Thr Ser Thr Leu Thr Gly Gln Leu Asp Asp Ala Asp Arg Asp Arg Ile
    1490                1495                1500

Arg Arg Gly Gly Phe Leu Pro Ile Thr Asp Asp Glu Gly
1505                1510                1515

<210> SEQ ID NO 20
<211> LENGTH: 4466
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (9)..(4454)

<400> SEQUENCE: 20 agatctgg cag ctc gcc gaa gcg ctg ctg acg ctc gtc cgg gag agc acc        50
         Gln Leu Ala Glu Ala Leu Leu Thr Leu Val Arg Glu Ser Thr
          1               5                  10 gcc gcc gtg ctc ggc cac gtg ggt ggc gag gac atc ccc gcg acg gcg        98
Ala Ala Val Leu Gly His Val Gly Gly Glu Asp Ile Pro Ala Thr Ala
 15                  20                  25                  30 gcg ttc aag gac ctc ggc atc gac tcg ctc acc gcg gtc cag ctg cgc       146
Ala Phe Lys Asp Leu Gly Ile Asp Ser Leu Thr Ala Val Gln Leu Arg
                 35                  40                  45 aac gcc ctc acc gag gcg acc ggt gtg cgg ctg aac gcc acg gcg gtc       194
Asn Ala Leu Thr Glu Ala Thr Gly Val Arg Leu Asn Ala Thr Ala Val
             50                  55                  60 ttc gac ttc ccg acc ccg cac gtg ctc gcc ggg aag ctc ggc gac gaa       242
Phe Asp Phe Pro Thr Pro His Val Leu Ala Gly Lys Leu Gly Asp Glu
         65                  70                  75 ctg acc ggc acc cgc gcg ccc gtc gtg ccc cgg acc gcg gcc acg gcc       290
Leu Thr Gly Thr Arg Ala Pro Val Val Pro Arg Thr Ala Ala Thr Ala
     80                  85                  90 ggt gcg cac gac gag ccg ctg gcg atc gtg gga atg gcc tgc cgg ctg       338
Gly Ala His Asp Glu Pro Leu Ala Ile Val Gly Met Ala Cys Arg Leu
 95                 100                 105                 110 ccc ggc ggg gtc gcg tca ccc gag gag ctg tgg cac ctc gtg gca tcc       386
Pro Gly Gly Val Ala Ser Pro Glu Glu Leu Trp His Leu Val Ala Ser
                115                 120                 125 ggc acc gac gcc atc acg gag ttc ccg acg gac cgc ggc tgg gac gtc       434
Gly Thr Asp Ala Ile Thr Glu Phe Pro Thr Asp Arg Gly Trp Asp Val
            130                 135                 140 gac gcg atc tac gac ccg gac ccc gac gcg atc ggc aag acc ttc gtc       482
Asp Ala Ile Tyr Asp Pro Asp Pro Asp Ala Ile Gly Lys Thr Phe Val
        145                 150                 155 cgg cac ggt ggc ttc ctc acc ggc gcg aca ggc ttc gac gcg gcg ttc       530
Arg His Gly Gly Phe Leu Thr Gly Ala Thr Gly Phe Asp Ala Ala Phe
    160                 165                 170 ttc ggc atc agc ccg cgc gag gcc ctc gcg atg gac ccg cag cag cgg       578
Phe Gly Ile Ser Pro Arg Glu Ala Leu Ala Met Asp Pro Gln Gln Arg
175                 180                 185                 190 gtg ctc ctg gag acg tcg tgg gag gcg ttc gaa agc gcc ggc atc acc       626
Val Leu Leu Glu Thr Ser Trp Glu Ala Phe Glu Ser Ala Gly Ile Thr
                195                 200                 205 ccg gac tcg acc cgc ggc agc gac acc ggc gtg ttc gtc ggc gcc ttc       674
Pro Asp Ser Thr Arg Gly Ser Asp Thr Gly Val Phe Val Gly Ala Phe
            210                 215                 220 tcc tac ggt tac ggc acc ggt gcg gac acc gac ggc ttc ggc gcg acc       722
Ser Tyr Gly Tyr Gly Thr Gly Ala Asp Thr Asp Gly Phe Gly Ala Thr
        225                 230                 235
```

-continued

| | |
|---|---|
| ggc tcg cag acc agt gtg ctc tcc ggc cgg ctg tcg tac ttc tac ggt<br>Gly Ser Gln Thr Ser Val Leu Ser Gly Arg Leu Ser Tyr Phe Tyr Gly<br>240                      245                        250 | 770 |
| ctg gag ggt ccg gcg gtc acg gtc gac acg gcg tgt tcg tcg tcg ctg<br>Leu Glu Gly Pro Ala Val Thr Val Asp Thr Ala Cys Ser Ser Ser Leu<br>255                      260                        265                  270 | 818 |
| gtg gcg ctg cac cag gcc ggg cag tcg ctg cgc tcc ggc gaa tgc tcg<br>Val Ala Leu His Gln Ala Gly Gln Ser Leu Arg Ser Gly Glu Cys Ser<br>                     275                        280                        285 | 866 |
| ctc gcc ctg gtc ggc ggc gtc acg gtg atg gcg tct ccc ggc ggc ttc<br>Leu Ala Leu Val Gly Gly Val Thr Val Met Ala Ser Pro Gly Gly Phe<br>                290                        295                        300 | 914 |
| gtg gag ttc tcc cgg cag cgc ggc ctc gcg ccg gac ggc cgg gcg aag<br>Val Glu Phe Ser Arg Gln Arg Gly Leu Ala Pro Asp Gly Arg Ala Lys<br>305                      310                        315 | 962 |
| gcg ttc ggc gcg ggt gcg gac ggc acg agc ttc gcc gag ggt gcc ggt<br>Ala Phe Gly Ala Gly Ala Asp Gly Thr Ser Phe Ala Glu Gly Ala Gly<br>320                      325                        330 | 1010 |
| gtg ctg atc gtc gag agg ctc tcc gac gcc gaa cgc aac ggt cac acc<br>Val Leu Ile Val Glu Arg Leu Ser Asp Ala Glu Arg Asn Gly His Thr<br>335                      340                        345                  350 | 1058 |
| gtc ctg gcg gtc gtc cgt ggt tcg gcg gtc aac cag gat ggt gcc tcc<br>Val Leu Ala Val Val Arg Gly Ser Ala Val Asn Gln Asp Gly Ala Ser<br>                     355                        360                        365 | 1106 |
| aac ggg ctg tcg gcg ccg aac ggg ccg tcg cag gag cgg gtg atc cgg<br>Asn Gly Leu Ser Ala Pro Asn Gly Pro Ser Gln Glu Arg Val Ile Arg<br>                     370                        375                        380 | 1154 |
| cag gcc ctg gcc aac gcc ggg ctc acc ccg gcg gac gtg gac gcc gtc<br>Gln Ala Leu Ala Asn Ala Gly Leu Thr Pro Ala Asp Val Asp Ala Val<br>                   385                        390                        395 | 1202 |
| gag gcc cac ggc acc ggc acc agg ctg ggc gac ccc atc gag gca cag<br>Glu Ala His Gly Thr Gly Thr Arg Leu Gly Asp Pro Ile Glu Ala Gln<br>400                      405                        410 | 1250 |
| gcg gta ctg gcc acc tac gga cag gag cgc gcc acc ccc ctg ctg ctg<br>Ala Val Leu Ala Thr Tyr Gly Gln Glu Arg Ala Thr Pro Leu Leu Leu<br>415                      420                        425                  430 | 1298 |
| ggc tcg ctg aag tcc aac atc ggc cac gcc cag gcc gcg tcc ggc gtc<br>Gly Ser Leu Lys Ser Asn Ile Gly His Ala Gln Ala Ala Ser Gly Val<br>                     435                        440                        445 | 1346 |
| gcc ggc atc atc aag atg gtg cag gcc ctc cgg cac ggg gag ctg ccg<br>Ala Gly Ile Ile Lys Met Val Gln Ala Leu Arg His Gly Glu Leu Pro<br>                       450                        455                  460 | 1394 |
| ccg acg ctg cac gcc gac gag ccg tcg ccg cac gtc gac tgg acg gcc<br>Pro Thr Leu His Ala Asp Glu Pro Ser Pro His Val Asp Trp Thr Ala<br>                   465                        470                        475 | 1442 |
| ggc gcc gtc gaa ctg ctg acg tcg gcc cgg ccg tgg ccc gag acc gac<br>Gly Ala Val Glu Leu Leu Thr Ser Ala Arg Pro Trp Pro Glu Thr Asp<br>480                      485                        490 | 1490 |
| cgg cca cgg cgt gcc gcc gtc tcc tcg ttc ggg gtg agc ggc acc aac<br>Arg Pro Arg Arg Ala Ala Val Ser Ser Phe Gly Val Ser Gly Thr Asn<br>495                      500                        505                  510 | 1538 |
| gcc cac gtc atc ctg gag gcc gga ccg gta acg gag acg ccc gcg gca<br>Ala His Val Ile Leu Glu Ala Gly Pro Val Thr Glu Thr Pro Ala Ala<br>                     515                        520                        525 | 1586 |
| tcg cct tcc ggt gac ctt ccc ctg ctg gtg tcg gca cgc tca ccg gaa<br>Ser Pro Ser Gly Asp Leu Pro Leu Leu Val Ser Ala Arg Ser Pro Glu<br>                     530                        535                        540 | 1634 |
| gcg ctc gac gag cag atc cgc cga ctg cgc gcc tac ctg gac acc acc<br>Ala Leu Asp Glu Gln Ile Arg Arg Leu Arg Ala Tyr Leu Asp Thr Thr | 1682 |

-continued

```
                545                 550                 555
ccg gac gtc gac cgg gtg gcc gtg gca cag acg ctg gcc cgg cgc aca      1730
Pro Asp Val Asp Arg Val Ala Val Ala Gln Thr Leu Ala Arg Arg Thr
    560                 565                 570 cac ttc gcc cac cgc gcc gtg ctg ctc ggt gac acc gtc atc acc aca      1778
His Phe Ala His Arg Ala Val Leu Leu Gly Asp Thr Val Ile Thr Thr
575                 580                 585                 590 ccc ccc gcg gac cgg ccc gac gaa ctc gtc ttc gtc tac tcc ggc cag      1826
Pro Pro Ala Asp Arg Pro Asp Glu Leu Val Phe Val Tyr Ser Gly Gln
                595                 600                 605 ggc acc cag cat ccc gcg atg ggc gag cag cta gcc gcc gcg ttc ccc      1874
Gly Thr Gln His Pro Ala Met Gly Glu Gln Leu Ala Ala Ala Phe Pro
            610                 615                 620 gtc ttc gcg cgg atc cat cag cag gtg tgg gac ctg ctc gat gtg ccc      1922
Val Phe Ala Arg Ile His Gln Gln Val Trp Asp Leu Leu Asp Val Pro
        625                 630                 635 gat ctg gag gtg aac gag acc ggt tac gcc cag ccg gcc ctg ttc gca      1970
Asp Leu Glu Val Asn Glu Thr Gly Tyr Ala Gln Pro Ala Leu Phe Ala
    640                 645                 650 atg cag gtg gct ctg ttc ggg ctg ctg gaa tcg tgg ggt gta cga ccg      2018
Met Gln Val Ala Leu Phe Gly Leu Leu Glu Ser Trp Gly Val Arg Pro
655                 660                 665                 670 gac gcg gtg atc ggc cat tcg gtg ggt gag ctt gcg gct gcg tat gtg      2066
Asp Ala Val Ile Gly His Ser Val Gly Glu Leu Ala Ala Ala Tyr Val
                675                 680                 685 tcc ggg gtg tgg tcg ttg gag gat gcc tgc act ttg gtg tcg gcg cgg      2114
Ser Gly Val Trp Ser Leu Glu Asp Ala Cys Thr Leu Val Ser Ala Arg
            690                 695                 700 gct cgt ctg atg cag gct ctg ccc gcg ggt ggg gtg atg gtc gct gtc      2162
Ala Arg Leu Met Gln Ala Leu Pro Ala Gly Gly Val Met Val Ala Val
        705                 710                 715 ccg gtc tcg gag gat gag gcc cgg gcc gtg ctg ggt gag ggt gtg gag      2210
Pro Val Ser Glu Asp Glu Ala Arg Ala Val Leu Gly Glu Gly Val Glu
    720                 725                 730 atc gcc gcg gtc aac ggc ccg tcg tcg gtg gtt ctc tcc ggt gat gag      2258
Ile Ala Ala Val Asn Gly Pro Ser Ser Val Val Leu Ser Gly Asp Glu
735                 740                 745                 750 gcc gcc gtg ctg cag gcc gcg gag ggg ctg ggg aag tgg acg cgg ctg      2306
Ala Ala Val Leu Gln Ala Ala Glu Gly Leu Gly Lys Trp Thr Arg Leu
                755                 760                 765 gcg acc agc cac gcg ttc cat tcc gcc cgt atg gaa ccc atg ctg gag      2354
Ala Thr Ser His Ala Phe His Ser Ala Arg Met Glu Pro Met Leu Glu
            770                 775                 780 gag ttc cgg gcg gtc gcc gaa ggc ctg acc tac cgg acg ccg cag gtc      2402
Glu Phe Arg Ala Val Ala Glu Gly Leu Thr Tyr Arg Thr Pro Gln Val
        785                 790                 795 tcc atg gcc gtt ggt gat cag gtg acc acc gct gag tac tgg gtg cgg      2450
Ser Met Ala Val Gly Asp Gln Val Thr Thr Ala Glu Tyr Trp Val Arg
    800                 805                 810 cag gtc cgg gac acg gtc cgg ttc ggc gag cag gtg gcc tcg tac gag      2498
Gln Val Arg Asp Thr Val Arg Phe Gly Glu Gln Val Ala Ser Tyr Glu
815                 820                 825                 830 gac gcc gtg ttc gtc gag ctg ggt gcc gac cgg tca ctg gcc cgc ctg      2546
Asp Ala Val Phe Val Glu Leu Gly Ala Asp Arg Ser Leu Ala Arg Leu
                835                 840                 845 gtc gac ggt gtc gcg atg ctg cac ggc gac cac gaa atc cag gcc gcg      2594
Val Asp Gly Val Ala Met Leu His Gly Asp His Glu Ile Gln Ala Ala
            850                 855                 860 atc ggc gcc ctg gcc cac ctg tat gtc aac ggc gtc acg gtc gac tgg      2642
Ile Gly Ala Leu Ala His Leu Tyr Val Asn Gly Val Thr Val Asp Trp
```

-continued

| | |
|---|---|
| Ile Gly Ala Leu Ala His Leu Tyr Val Asn Gly Val Thr Val Asp Trp<br>    865                         870                          875 | |
| ccc gcg ctc ctg ggc gat gct ccg gca aca cgg gtg ctg gac ctt ccg<br>Pro Ala Leu Leu Gly Asp Ala Pro Ala Thr Arg Val Leu Asp Leu Pro<br>    880                       885                       890 | 2690 |
| aca tac gcc ttc cag cac cag cgc tac tgg ctc gag tcg gca cgc ccg<br>Thr Tyr Ala Phe Gln His Gln Arg Tyr Trp Leu Glu Ser Ala Arg Pro<br>895                     900                    905                910 | 2738 |
| gcc gca tcc gac gcg ggc cac ccc gtg ctg ggc tcc ggt atc gcc ctc<br>Ala Ala Ser Asp Ala Gly His Pro Val Leu Gly Ser Gly Ile Ala Leu<br>               915                    920                925 | 2786 |
| gcc ggg tcg ccg ggc cgg gtg ttc acg ggt tcc gtg ccg acc ggt gcg<br>Ala Gly Ser Pro Gly Arg Val Phe Thr Gly Ser Val Pro Thr Gly Ala<br>         930                       935                940 | 2834 |
| gac cgc gcg gtg ttc gtc gcc gag ctg gcg ctg gcc gcc gcg gac gcg<br>Asp Arg Ala Val Phe Val Ala Glu Leu Ala Leu Ala Ala Ala Asp Ala<br>         945                       950                955 | 2882 |
| gtc gac tgc gcc acg gtc gag cgg ctc gac atc gcc tcc gtg ccc ggc<br>Val Asp Cys Ala Thr Val Glu Arg Leu Asp Ile Ala Ser Val Pro Gly<br>    960                       965                    970 | 2930 |
| cgg ccg ggc cat ggc cgg acg acc gta cag acc tgg gtc gac gag ccg<br>Arg Pro Gly His Gly Arg Thr Thr Val Gln Thr Trp Val Asp Glu Pro<br>975                     980                    985                990 | 2978 |
| gcg gac gac ggc cgg cgc cgg ttc acc gtg cac acc cgc acc ggc gac<br>Ala Asp Asp Gly Arg Arg Arg Phe Thr Val His Thr Arg Thr Gly Asp<br>              995                    1000              1005 | 3026 |
| gcc ccg tgg acg ctg cac gcc gag ggg gtg ctg cgc ccc cat ggc acg<br>Ala Pro Trp Thr Leu His Ala Glu Gly Val Leu Arg Pro His Gly Thr<br>          1010                    1015              1020 | 3074 |
| gcc ctg ccc gat gcg gcc gac gcc gag tgg ccc cca ccg ggc gcg gtg<br>Ala Leu Pro Asp Ala Ala Asp Ala Glu Trp Pro Pro Pro Gly Ala Val<br>        1025                    1030              1035 | 3122 |
| ccc gcg gac ggg ctg ccg ggt gtg tgg cgc cgg ggg gac cag gtc ttc<br>Pro Ala Asp Gly Leu Pro Gly Val Trp Arg Arg Gly Asp Gln Val Phe<br>    1040                    1045                  1050 | 3170 |
| gcc gag gcc gag gtg gac gga ccg gac ggt ttc gtg gtg cac ccc gac<br>Ala Glu Ala Glu Val Asp Gly Pro Asp Gly Phe Val Val His Pro Asp<br>1055                 1060                  1065              1070 | 3218 |
| ctg ctc gac gcg gtc ttc tcc gcg gtc ggc gac gga agc cgc cag ccg<br>Leu Leu Asp Ala Val Phe Ser Ala Val Gly Asp Gly Ser Arg Gln Pro<br>          1075                  1080              1085 | 3266 |
| gcc gga tgg cgc gac ctg acg gtg cac gcg tcg gac gcc acc gta ctg<br>Ala Gly Trp Arg Asp Leu Thr Val His Ala Ser Asp Ala Thr Val Leu<br>       1090                  1095              1100 | 3314 |
| cgc gcc tgc ctc acc cgg cgc acc gac gga gcc atg gga ttc gcc gcc<br>Arg Ala Cys Leu Thr Arg Arg Thr Asp Gly Ala Met Gly Phe Ala Ala<br>   1105                 1110                1115 | 3362 |
| ttc gac ggc gcc ggc ctg ccg gta ctc acc gcg gag gcg gtg acg ctg<br>Phe Asp Gly Ala Gly Leu Pro Val Leu Thr Ala Glu Ala Val Thr Leu<br>1120                 1125                  1130 | 3410 |
| cgg gag gtg gcg tca ccg tcc ggc tcc gag gag tcg gac ggc ctg cac<br>Arg Glu Val Ala Ser Pro Ser Gly Ser Glu Glu Ser Asp Gly Leu His<br>1135                 1140                  1145              1150 | 3458 |
| cgg ttg gag tgg ctc gcg gtc gcc gag gcg gtc tac gac ggt gac ctg<br>Arg Leu Glu Trp Leu Ala Val Ala Glu Ala Val Tyr Asp Gly Asp Leu<br>          1155                  1160              1165 | 3506 |
| ccc gag gga cat gtc ctg atc acc gcc gcc cac ccc gac gac ccc gag<br>Pro Glu Gly His Val Leu Ile Thr Ala Ala His Pro Asp Asp Pro Glu<br>       1170                 1175              1180 | 3554 |

-continued

```
gac ata ccc acc cgc gcc cac acc cgc gcc acc cgc gtc ctg acc gcc    3602
Asp Ile Pro Thr Arg Ala His Thr Arg Ala Thr Arg Val Leu Thr Ala
        1185                1190                1195 ctg caa cac cac ctc acc acc acc gac cac acc ctc atc gtc cac acc    3650
Leu Gln His His Leu Thr Thr Thr Asp His Thr Leu Ile Val His Thr
1200                1205                1210 acc acc gac ccc gcc ggc gcc acc gtc acc ggc ctc acc cgc acc gcc    3698
Thr Thr Asp Pro Ala Gly Ala Thr Val Thr Gly Leu Thr Arg Thr Ala
1215                1220                1225                1230 cag aac gaa cac ccc cac cgc atc cgc ctc atc gaa acc gac cac ccc    3746
Gln Asn Glu His Pro His Arg Ile Arg Leu Ile Glu Thr Asp His Pro
            1235                1240                1245 cac acc ccc ctc ccc ctg gcc caa ctc gcc acc ctc gac cac ccc cac    3794
His Thr Pro Leu Pro Leu Ala Gln Leu Ala Thr Leu Asp His Pro His
        1250                1255                1260 ctc cgc ctc acc cac cac acc ctc cac cac ccc cac ctc acc ccc ctc    3842
Leu Arg Leu Thr His His Thr Leu His His Pro His Leu Thr Pro Leu
    1265                1270                1275 cac acc acc acc cca ccc acc acc acc ccc ctc aac ccc gaa cac gcc    3890
His Thr Thr Thr Pro Pro Thr Thr Thr Pro Leu Asn Pro Glu His Ala
1280                1285                1290 atc atc atc acc ggc ggc tcc ggc acc ctc gcc ggc atc ctc gcc cgc    3938
Ile Ile Ile Thr Gly Gly Ser Gly Thr Leu Ala Gly Ile Leu Ala Arg
1295                1300                1305                1310 cac ctg aac cac ccc cac acc tac ctc ctc tcc cgc acc cca ccc ccc    3986
His Leu Asn His Pro His Thr Tyr Leu Leu Ser Arg Thr Pro Pro Pro
            1315                1320                1325 gac gcc acc ccc ggc acc cac ctc ccc tgc gac gtc ggc gac ccc cac    4034
Asp Ala Thr Pro Gly Thr His Leu Pro Cys Asp Val Gly Asp Pro His
        1330                1335                1340 caa ctc gcc acc acc ctc acc cac atc ccc caa ccc ctc acc gcc atc    4082
Gln Leu Ala Thr Thr Leu Thr His Ile Pro Gln Pro Leu Thr Ala Ile
    1345                1350                1355 ttc cac acc gcc gcc acc ctc gac gac ggc atc ctc cac gcc ctc acc    4130
Phe His Thr Ala Ala Thr Leu Asp Asp Gly Ile Leu His Ala Leu Thr
1360                1365                1370 ccc gac cgc ctc acc acc gtc ctc cac ccc aaa gcc aac gcc gcc tgg    4178
Pro Asp Arg Leu Thr Thr Val Leu His Pro Lys Ala Asn Ala Ala Trp
1375                1380                1385                1390 cac ctg cac cac ctc acc caa aac caa ccc ctc acc cac ttc gtc ctc    4226
His Leu His His Leu Thr Gln Asn Gln Pro Leu Thr His Phe Val Leu
            1395                1400                1405 tac tcc agc gcc gcc gcc gtc ctc ggc agc ccc gga caa gga aac tac    4274
Tyr Ser Ser Ala Ala Ala Val Leu Gly Ser Pro Gly Gln Gly Asn Tyr
        1410                1415                1420 gcc gcc gcc aac gcc ttc ctc gac gcc ctc gcc acc cac cgc cac acc    4322
Ala Ala Ala Asn Ala Phe Leu Asp Ala Leu Ala Thr His Arg His Thr
    1425                1430                1435 ctc ggc caa ccc gcc acc tcc atc gcc tgg ggc atg tgg cac acc acc    4370
Leu Gly Gln Pro Ala Thr Ser Ile Ala Trp Gly Met Trp His Thr Thr
1440                1445                1450 agc acc ctc acc gga caa ctc gac gac gcc gac cgg gac cgc atc cgc    4418
Ser Thr Leu Thr Gly Gln Leu Asp Asp Ala Asp Arg Asp Arg Ile Arg
1455                1460                1465                1470 cgc ggc ggt ttc ctc ccg atc acg gac gac gag ggc atgggatgc at       4466
Arg Gly Gly Phe Leu Pro Ile Thr Asp Asp Glu Gly
            1475                1480
```

<210> SEQ ID NO 21
<211> LENGTH: 1482

```
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 21
```

| | | | | | | | | | | | | | | |
|---|---|---|---|---|---|---|---|---|---|---|---|---|---|---|
| Gln | Leu | Ala | Glu | Ala | Leu | Leu | Thr | Leu | Val | Arg | Glu | Ser | Thr | Ala | Ala |
| 1 | | | | 5 | | | | | 10 | | | | | 15 |
| Val | Leu | Gly | His | Val | Gly | Gly | Glu | Asp | Ile | Pro | Ala | Thr | Ala | Ala | Phe |
| | | | 20 | | | | | 25 | | | | | 30 | |
| Lys | Asp | Leu | Gly | Ile | Asp | Ser | Leu | Thr | Ala | Val | Gln | Leu | Arg | Asn | Ala |
| | | 35 | | | | | 40 | | | | | 45 | | |
| Leu | Thr | Glu | Ala | Thr | Gly | Val | Arg | Leu | Asn | Ala | Thr | Ala | Val | Phe | Asp |
| | 50 | | | | | 55 | | | | | 60 | | | | |
| Phe | Pro | Thr | Pro | His | Val | Leu | Ala | Gly | Lys | Leu | Gly | Asp | Glu | Leu | Thr |
| 65 | | | | | 70 | | | | 75 | | | | | | 80 |
| Gly | Thr | Arg | Ala | Pro | Val | Val | Pro | Arg | Thr | Ala | Ala | Thr | Ala | Gly | Ala |
| | | | | 85 | | | | | 90 | | | | | 95 | |
| His | Asp | Glu | Pro | Leu | Ala | Ile | Val | Gly | Met | Ala | Cys | Arg | Leu | Pro | Gly |
| | | | 100 | | | | | 105 | | | | 110 | | | |
| Gly | Val | Ala | Ser | Pro | Glu | Glu | Leu | Trp | His | Leu | Val | Ala | Ser | Gly | Thr |
| | | 115 | | | | | 120 | | | | | 125 | | | |
| Asp | Ala | Ile | Thr | Glu | Phe | Pro | Thr | Asp | Arg | Gly | Trp | Asp | Val | Asp | Ala |
| | 130 | | | | | 135 | | | | | 140 | | | | |
| Ile | Tyr | Asp | Pro | Asp | Pro | Asp | Ala | Ile | Gly | Lys | Thr | Phe | Val | Arg | His |
| 145 | | | | | 150 | | | | 155 | | | | | | 160 |
| Gly | Gly | Phe | Leu | Thr | Gly | Ala | Thr | Gly | Phe | Asp | Ala | Ala | Phe | Phe | Gly |
| | | | | 165 | | | | | 170 | | | | 175 | | |
| Ile | Ser | Pro | Arg | Glu | Ala | Leu | Ala | Met | Asp | Pro | Gln | Gln | Arg | Val | Leu |
| | | | 180 | | | | | 185 | | | | 190 | | | |
| Leu | Glu | Thr | Ser | Trp | Glu | Ala | Phe | Glu | Ser | Ala | Gly | Ile | Thr | Pro | Asp |
| | | | 195 | | | | | 200 | | | | | 205 | | |
| Ser | Thr | Arg | Gly | Ser | Asp | Thr | Gly | Val | Phe | Val | Gly | Ala | Phe | Ser | Tyr |
| | 210 | | | | | 215 | | | | | 220 | | | | |
| Gly | Tyr | Gly | Thr | Gly | Ala | Asp | Thr | Asp | Gly | Phe | Gly | Ala | Thr | Gly | Ser |
| 225 | | | | | 230 | | | | 235 | | | | | | 240 |
| Gln | Thr | Ser | Val | Leu | Ser | Gly | Arg | Leu | Ser | Tyr | Phe | Tyr | Gly | Leu | Glu |
| | | | | 245 | | | | | 250 | | | | | 255 | |
| Gly | Pro | Ala | Val | Thr | Val | Asp | Thr | Ala | Cys | Ser | Ser | Ser | Leu | Val | Ala |
| | | | 260 | | | | | 265 | | | | 270 | | | |
| Leu | His | Gln | Ala | Gly | Gln | Ser | Leu | Arg | Ser | Gly | Glu | Cys | Ser | Leu | Ala |
| | | 275 | | | | | 280 | | | | | 285 | | | |
| Leu | Val | Gly | Gly | Val | Thr | Val | Met | Ala | Ser | Pro | Gly | Gly | Phe | Val | Glu |
| | 290 | | | | | 295 | | | | | 300 | | | | |
| Phe | Ser | Arg | Gln | Arg | Gly | Leu | Ala | Pro | Asp | Gly | Arg | Ala | Lys | Ala | Phe |
| 305 | | | | | 310 | | | | 315 | | | | | | 320 |
| Gly | Ala | Gly | Ala | Asp | Gly | Thr | Ser | Phe | Ala | Glu | Gly | Ala | Gly | Val | Leu |
| | | | | 325 | | | | | 330 | | | | | 335 | |
| Ile | Val | Glu | Arg | Leu | Ser | Asp | Ala | Glu | Arg | Asn | Gly | His | Thr | Val | Leu |
| | | | 340 | | | | | 345 | | | | 350 | | | |
| Ala | Val | Val | Arg | Gly | Ser | Ala | Val | Asn | Gln | Asp | Gly | Ala | Ser | Asn | Gly |
| | | 355 | | | | | 360 | | | | | 365 | | | |
| Leu | Ser | Ala | Pro | Asn | Gly | Pro | Ser | Gln | Glu | Arg | Val | Ile | Arg | Gln | Ala |
| | 370 | | | | | 375 | | | | | 380 | | | | |

-continued

```
Leu Ala Asn Ala Gly Leu Thr Pro Ala Asp Val Asp Ala Val Glu Ala
385                 390                 395                 400

His Gly Thr Gly Thr Arg Leu Gly Asp Pro Ile Glu Ala Gln Ala Val
            405                 410                 415

Leu Ala Thr Tyr Gly Gln Glu Arg Ala Thr Pro Leu Leu Gly Ser
        420                 425                 430

Leu Lys Ser Asn Ile Gly His Ala Gln Ala Ser Gly Val Ala Gly
    435                 440                 445

Ile Ile Lys Met Val Gln Ala Leu Arg His Gly Glu Leu Pro Pro Thr
450                 455                 460

Leu His Ala Asp Glu Pro Ser Pro His Val Asp Trp Thr Ala Gly Ala
465                 470                 475                 480

Val Glu Leu Leu Thr Ser Ala Arg Pro Trp Pro Glu Thr Asp Arg Pro
                485                 490                 495

Arg Arg Ala Ala Val Ser Ser Phe Gly Val Ser Gly Thr Asn Ala His
            500                 505                 510

Val Ile Leu Glu Ala Gly Pro Val Thr Glu Thr Pro Ala Ala Ser Pro
    515                 520                 525

Ser Gly Asp Leu Pro Leu Leu Val Ser Ala Arg Ser Pro Glu Ala Leu
530                 535                 540

Asp Glu Gln Ile Arg Arg Leu Arg Ala Tyr Leu Asp Thr Thr Pro Asp
545                 550                 555                 560

Val Asp Arg Val Ala Val Ala Gln Thr Leu Ala Arg Arg Thr His Phe
                565                 570                 575

Ala His Arg Ala Val Leu Leu Gly Asp Thr Val Ile Thr Thr Pro Pro
            580                 585                 590

Ala Asp Arg Pro Asp Glu Leu Val Phe Val Tyr Ser Gly Gln Gly Thr
        595                 600                 605

Gln His Pro Ala Met Gly Glu Gln Leu Ala Ala Ala Phe Pro Val Phe
    610                 615                 620

Ala Arg Ile His Gln Gln Val Trp Asp Leu Leu Asp Val Pro Asp Leu
625                 630                 635                 640

Glu Val Asn Glu Thr Gly Tyr Ala Gln Pro Ala Leu Phe Ala Met Gln
                645                 650                 655

Val Ala Leu Phe Gly Leu Leu Glu Ser Trp Gly Val Arg Pro Asp Ala
            660                 665                 670

Val Ile Gly His Ser Val Gly Glu Leu Ala Ala Ala Tyr Val Ser Gly
        675                 680                 685

Val Trp Ser Leu Glu Asp Ala Cys Thr Leu Val Ser Ala Arg Ala Arg
    690                 695                 700

Leu Met Gln Ala Leu Pro Ala Gly Gly Val Met Val Ala Val Pro Val
705                 710                 715                 720

Ser Glu Asp Glu Ala Arg Ala Val Leu Gly Glu Gly Val Glu Ile Ala
                725                 730                 735

Ala Val Asn Gly Pro Ser Ser Val Leu Ser Gly Asp Glu Ala Ala
            740                 745                 750

Val Leu Gln Ala Ala Glu Gly Leu Gly Lys Trp Thr Arg Leu Ala Thr
        755                 760                 765

Ser His Ala Phe His Ser Ala Arg Met Glu Pro Met Leu Glu Glu Phe
    770                 775                 780

Arg Ala Val Ala Glu Gly Leu Thr Tyr Arg Thr Pro Gln Val Ser Met
785                 790                 795                 800
```

-continued

```
Ala Val Gly Asp Gln Val Thr Thr Ala Glu Tyr Trp Val Arg Gln Val
            805                 810                 815
Arg Asp Thr Val Arg Phe Gly Glu Gln Val Ala Ser Tyr Glu Asp Ala
            820                 825                 830
Val Phe Val Glu Leu Gly Ala Asp Arg Ser Leu Ala Arg Leu Val Asp
            835                 840                 845
Gly Val Ala Met Leu His Gly Asp His Glu Ile Gln Ala Ala Ile Gly
850                 855                 860
Ala Leu Ala His Leu Tyr Val Asn Gly Val Thr Val Asp Trp Pro Ala
865                 870                 875                 880
Leu Leu Gly Asp Ala Pro Ala Thr Arg Val Leu Asp Leu Pro Thr Tyr
            885                 890                 895
Ala Phe Gln His Gln Arg Tyr Trp Leu Glu Ser Ala Arg Pro Ala Ala
            900                 905                 910
Ser Asp Ala Gly His Pro Val Leu Gly Ser Gly Ile Ala Leu Ala Gly
            915                 920                 925
Ser Pro Gly Arg Val Phe Thr Gly Ser Val Pro Thr Gly Ala Asp Arg
            930                 935                 940
Ala Val Phe Val Ala Glu Leu Ala Leu Ala Ala Ala Asp Ala Val Asp
945                 950                 955                 960
Cys Ala Thr Val Glu Arg Leu Asp Ile Ala Ser Val Pro Gly Arg Pro
            965                 970                 975
Gly His Gly Arg Thr Thr Val Gln Thr Trp Val Asp Glu Pro Ala Asp
            980                 985                 990
Asp Gly Arg Arg Arg Phe Thr Val His Thr Arg Thr Gly Asp Ala Pro
            995                 1000                1005
Trp Thr Leu His Ala Glu Gly Val Leu Arg Pro His Gly Thr Ala Leu
            1010                1015                1020
Pro Asp Ala Ala Asp Ala Glu Trp Pro Pro Gly Ala Val Pro Ala
1025                1030                1035                1040
Asp Gly Leu Pro Gly Val Trp Arg Arg Gly Asp Gln Val Phe Ala Glu
            1045                1050                1055
Ala Glu Val Asp Gly Pro Asp Gly Phe Val Val His Pro Asp Leu Leu
            1060                1065                1070
Asp Ala Val Phe Ser Ala Val Gly Asp Gly Ser Arg Gln Pro Ala Gly
            1075                1080                1085
Trp Arg Asp Leu Thr Val His Ala Ser Asp Ala Thr Val Leu Arg Ala
            1090                1095                1100
Cys Leu Thr Arg Arg Thr Asp Gly Ala Met Gly Phe Ala Ala Phe Asp
1105                1110                1115                1120
Gly Ala Gly Leu Pro Val Leu Thr Ala Glu Ala Val Thr Leu Arg Glu
            1125                1130                1135
Val Ala Ser Pro Ser Gly Ser Glu Glu Ser Asp Gly Leu His Arg Leu
            1140                1145                1150
Glu Trp Leu Ala Val Ala Glu Ala Val Tyr Asp Gly Asp Leu Pro Glu
            1155                1160                1165
Gly His Val Leu Ile Thr Ala Ala His Pro Asp Asp Pro Glu Asp Ile
            1170                1175                1180
Pro Thr Arg Ala His Thr Arg Ala Thr Arg Val Leu Thr Ala Leu Gln
1185                1190                1195                1200
His His Leu Thr Thr Thr Asp His Thr Leu Ile Val His Thr Thr
            1205                1210                1215
Asp Pro Ala Gly Ala Thr Val Thr Gly Leu Thr Arg Thr Ala Gln Asn
```

```
                   1220                1225                1230
      Glu His Pro His Arg Ile Arg Leu Ile Glu Thr Asp His Pro His Thr
              1235                1240                1245

Pro Leu Pro Leu Ala Gln Leu Ala Thr Leu Asp His Pro His Leu Arg
              1250                1255                1260

Leu Thr His His Thr Leu His His Pro His Leu Thr Pro Leu His Thr
      1265                1270                1275                1280

Thr Thr Pro Pro Thr Thr Thr Pro Leu Asn Pro Glu His Ala Ile Ile
                      1285                1290                1295

Ile Thr Gly Gly Ser Gly Thr Leu Ala Gly Ile Leu Ala Arg His Leu
              1300                1305                1310

Asn His Pro His Thr Tyr Leu Leu Ser Arg Thr Pro Pro Asp Ala
              1315                1320                1325

Thr Pro Gly Thr His Leu Pro Cys Asp Val Gly Asp Pro His Gln Leu
              1330                1335                1340

Ala Thr Thr Leu Thr His Ile Pro Gln Pro Leu Thr Ala Ile Phe His
      1345                1350                1355                1360

Thr Ala Ala Thr Leu Asp Asp Gly Ile Leu His Ala Leu Thr Pro Asp
                      1365                1370                1375

Arg Leu Thr Thr Val Leu His Pro Lys Ala Asn Ala Ala Trp His Leu
              1380                1385                1390

His His Leu Thr Gln Asn Gln Pro Leu Thr His Phe Val Leu Tyr Ser
              1395                1400                1405

Ser Ala Ala Ala Val Leu Gly Ser Pro Gly Gln Gly Asn Tyr Ala Ala
              1410                1415                1420

Ala Asn Ala Phe Leu Asp Ala Leu Ala Thr His Arg His Thr Leu Gly
      1425                1430                1435                1440

Gln Pro Ala Thr Ser Ile Ala Trp Gly Met Trp His Thr Thr Ser Thr
                      1445                1450                1455

Leu Thr Gly Gln Leu Asp Asp Ala Asp Arg Asp Arg Ile Arg Arg Gly
              1460                1465                1470

Gly Phe Leu Pro Ile Thr Asp Asp Glu Gly
              1475                1480

<210> SEQ ID NO 22
<211> LENGTH: 4547
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (9)..(4535)

<400> SEQUENCE: 22 agatctgg cag ctc gcc gaa gcg ctg ctg acg ctc gtc cgg gag agc acc         50
         Gln Leu Ala Glu Ala Leu Leu Thr Leu Val Arg Glu Ser Thr
           1               5                  10 gcc gcc gtg ctc ggc cac gtg ggt ggc gag gac atc ccc gcg acg gcg         98
Ala Ala Val Leu Gly His Val Gly Gly Glu Asp Ile Pro Ala Thr Ala
 15                  20                  25                  30 gcg ttc aag gac ctc ggc atc gac tcg ctc acc gcg gtc cag ctg cgc        146
Ala Phe Lys Asp Leu Gly Ile Asp Ser Leu Thr Ala Val Gln Leu Arg
                 35                  40                  45 aac gcc ctc acc gag gcg acc ggt gtg cgg ctg aac gcc acg gcg gtc        194
Asn Ala Leu Thr Glu Ala Thr Gly Val Arg Leu Asn Ala Thr Ala Val
             50                  55                  60
```

| | | |
|---|---|---|
| ttc gac ttc ccg acc ccg cac gtg ctc gcc ggg aag ctc ggc gac gaa<br>Phe Asp Phe Pro Thr Pro His Val Leu Ala Gly Lys Leu Gly Asp Glu<br>                65                        70                    75 | 242 |
| ctg acc ggc acc cgc gcg ccc gtc gtg ccc cgg acc gcg gcc acg gcc<br>Leu Thr Gly Thr Arg Ala Pro Val Val Pro Arg Thr Ala Ala Thr Ala<br> 80                         85                       90 | 290 |
| ggt gcg cac gac gag ccg ctg gcg atc gtg gga atg gcc tgc cgg ctg<br>Gly Ala His Asp Glu Pro Leu Ala Ile Val Gly Met Ala Cys Arg Leu<br> 95                       100                  105             110 | 338 |
| ccc ggc ggg gtc gcg tca ccc gag gag ctg tgg cac ctc gtg gca tcc<br>Pro Gly Gly Val Ala Ser Pro Glu Glu Leu Trp His Leu Val Ala Ser<br>                115                       120                  125 | 386 |
| ggc acc gac gcc atc acg gag ttc ccg acg gac cgc ggc tgg gac gtc<br>Gly Thr Asp Ala Ile Thr Glu Phe Pro Thr Asp Arg Gly Trp Asp Val<br>                  130                       135                  140 | 434 |
| gac gcg atc tac gac ccg gac ccc gac gcg atc ggc aag acc ttc gtc<br>Asp Ala Ile Tyr Asp Pro Asp Pro Asp Ala Ile Gly Lys Thr Phe Val<br>                  145                       150                  155 | 482 |
| cgg cac ggt ggc ttc ctc acc ggc gcg aca ggc ttc gac gcg gcg ttc<br>Arg His Gly Gly Phe Leu Thr Gly Ala Thr Gly Phe Asp Ala Ala Phe<br>160                       165                       170 | 530 |
| ttc ggc atc agc ccg cgc gag gcc ctc gcg atg gac ccg cag cag cgg<br>Phe Gly Ile Ser Pro Arg Glu Ala Leu Ala Met Asp Pro Gln Gln Arg<br>175                       180                   185                  190 | 578 |
| gtg ctc ctg gag acg tcg tgg gag gcg ttc gaa agc gcc ggc atc acc<br>Val Leu Leu Glu Thr Ser Trp Glu Ala Phe Glu Ser Ala Gly Ile Thr<br>                  195                       200                  205 | 626 |
| ccg gac tcg acc cgc ggc agc gac acc ggc gtg ttc gtc ggc gcc ttc<br>Pro Asp Ser Thr Arg Gly Ser Asp Thr Gly Val Phe Val Gly Ala Phe<br>                  210                       215                  220 | 674 |
| tcc tac ggt tac ggc acc ggt gcg gac acc gac ggc ttc ggc gcg acc<br>Ser Tyr Gly Tyr Gly Thr Gly Ala Asp Thr Asp Gly Phe Gly Ala Thr<br>                  225                       230                  235 | 722 |
| ggc tcg cag acc agt gtg ctc tcc ggc cgg ctg tcg tac ttc tac ggt<br>Gly Ser Gln Thr Ser Val Leu Ser Gly Arg Leu Ser Tyr Phe Tyr Gly<br>240                       245                       250 | 770 |
| ctg gag ggt ccg gcg gtc acg gtc gac acg gcg tgt tcg tcg tcg ctg<br>Leu Glu Gly Pro Ala Val Thr Val Asp Thr Ala Cys Ser Ser Ser Leu<br>255                       260                   265             270 | 818 |
| gtg gcg ctg cac cag gcc ggg cag tcg ctg cgc tcc ggc gaa tgc tcg<br>Val Ala Leu His Gln Ala Gly Gln Ser Leu Arg Ser Gly Glu Cys Ser<br>                  275                       280                  285 | 866 |
| ctc gcc ctg gtc ggc ggc gtc acg gtg atg gcg tct ccc ggc ggc ttc<br>Leu Ala Leu Val Gly Gly Val Thr Val Met Ala Ser Pro Gly Gly Phe<br>                  290                       295                  300 | 914 |
| gtg gag ttc tcc cgg cag cgc ggc ctc gcg ccg gac ggc cgg gcg aag<br>Val Glu Phe Ser Arg Gln Arg Gly Leu Ala Pro Asp Gly Arg Ala Lys<br>                  305                       310                  315 | 962 |
| gcg ttc ggc gcg ggt gcg gac ggc acg agc ttc gcc gag ggt gcc ggt<br>Ala Phe Gly Ala Gly Ala Asp Gly Thr Ser Phe Ala Glu Gly Ala Gly<br>320                       325                   330 | 1010 |
| gtg ctg atc gtc gag agg ctc tcc gac gcc gaa cgc aac ggt cac acc<br>Val Leu Ile Val Glu Arg Leu Ser Asp Ala Glu Arg Asn Gly His Thr<br>335                       340                   345                  350 | 1058 |
| gtc ctg gcg gtc gtc cgt ggt tcg gcg gtc aac cag gat ggt gcc tcc<br>Val Leu Ala Val Val Arg Gly Ser Ala Val Asn Gln Asp Gly Ala Ser<br>                  355                       360                  365 | 1106 |
| aac ggg ctg tcg gcg ccg aac ggg ccg tcg cag gag cgg gtg atc cgg<br>Asn Gly Leu Ser Ala Pro Asn Gly Pro Ser Gln Glu Arg Val Ile Arg | 1154 |

-continued

|  |  |  |  |
|---|---|---|---|
| | 370 | 375 | 380 |
| cag gcc ctg gcc aac gcc ggg ctc acc ccg gcg gac gtg gac gcc gtc<br>Gln Ala Leu Ala Asn Ala Gly Leu Thr Pro Ala Asp Val Asp Ala Val<br>385 390 395 | | | 1202 |
| gag gcc cac ggc acc ggc acc agg ctg ggc gac ccc atc gag gca cag<br>Glu Ala His Gly Thr Gly Thr Arg Leu Gly Asp Pro Ile Glu Ala Gln<br>400 405 410 | | | 1250 |
| gcg gta ctg gcc acc tac gga cag gag cgc gcc acc ccc ctg ctg ctg<br>Ala Val Leu Ala Thr Tyr Gly Gln Glu Arg Ala Thr Pro Leu Leu Leu<br>415 420 425 430 | | | 1298 |
| ggc tcg ctg aag tcc aac atc ggc cac gcc cag gcc gcg tcc ggc gtc<br>Gly Ser Leu Lys Ser Asn Ile Gly His Ala Gln Ala Ala Ser Gly Val<br>435 440 445 | | | 1346 |
| gcc ggc atc atc aag atg gtg cag gcc ctc cgg cac ggg gag ctg ccg<br>Ala Gly Ile Ile Lys Met Val Gln Ala Leu Arg His Gly Glu Leu Pro<br>450 455 460 | | | 1394 |
| ccg acg ctg cac gcc gac gag ccg tcg ccg cac gtc gac tgg acg gcc<br>Pro Thr Leu His Ala Asp Glu Pro Ser Pro His Val Asp Trp Thr Ala<br>465 470 475 | | | 1442 |
| ggc gcc gtc gaa ctg ctg acg tcg gcc cgg ccg tgg ccc gag acc gac<br>Gly Ala Val Glu Leu Leu Thr Ser Ala Arg Pro Trp Pro Glu Thr Asp<br>480 485 490 | | | 1490 |
| cgg cca cgg cgt gcc gcc gtc tcc tcg ttc ggg gtg agc ggc acc aac<br>Arg Pro Arg Arg Ala Ala Val Ser Ser Phe Gly Val Ser Gly Thr Asn<br>495 500 505 510 | | | 1538 |
| gcc cac gtc atc ctg gag gcc gga ccg gta acg gag acg ccc gcg gca<br>Ala His Val Ile Leu Glu Ala Gly Pro Val Thr Glu Thr Pro Ala Ala<br>515 520 525 | | | 1586 |
| tcg cct tcc ggt gac ctt ccc ctg ctg gtg tcg gca cgc tca ccg gaa<br>Ser Pro Ser Gly Asp Leu Pro Leu Leu Val Ser Ala Arg Ser Pro Glu<br>530 535 540 | | | 1634 |
| gcg ctc gac gag cag atc cgc cga ctg cgc gcc tac ctg gac acc acc<br>Ala Leu Asp Glu Gln Ile Arg Arg Leu Arg Ala Tyr Leu Asp Thr Thr<br>545 550 555 | | | 1682 |
| ccg gac gtc gac cgg gtg gcc gtg gca cag acg ctg gcc cgg cgc aca<br>Pro Asp Val Asp Arg Val Ala Val Ala Gln Thr Leu Ala Arg Arg Thr<br>560 565 570 | | | 1730 |
| cac ttc gcc cac cgc gcc gtg ctg ctc ggt gac acc gtc atc acc aca<br>His Phe Ala His Arg Ala Val Leu Leu Gly Asp Thr Val Ile Thr Thr<br>575 580 585 590 | | | 1778 |
| ccc ccc gcg gac cgg ccc gac gaa ctc gtc ttc gtc tac tcc ggc cag<br>Pro Pro Ala Asp Arg Pro Asp Glu Leu Val Phe Val Tyr Ser Gly Gln<br>595 600 605 | | | 1826 |
| ggc acc cag cat ccc gcg atg ggc gag cag cta gcc gat tcg tcg gtg<br>Gly Thr Gln His Pro Ala Met Gly Glu Gln Leu Ala Asp Ser Ser Val<br>610 615 620 | | | 1874 |
| gtg ttc gcc gag cgg atg gcc gag tgt gcg gcg gcg ttg cgc gag ttc<br>Val Phe Ala Glu Arg Met Ala Glu Cys Ala Ala Ala Leu Arg Glu Phe<br>625 630 635 | | | 1922 |
| gtg gac tgg gat ctg ttc acg gtt ctg gat gat ccg gcg gtg gtg gac<br>Val Asp Trp Asp Leu Phe Thr Val Leu Asp Asp Pro Ala Val Val Asp<br>640 645 650 | | | 1970 |
| cgg gtt gat gtg gtc cag ccc gct tcc tgg gcg atg atg gtt tcc ctg<br>Arg Val Asp Val Val Gln Pro Ala Ser Trp Ala Met Met Val Ser Leu<br>655 660 665 670 | | | 2018 |
| gcc gcg gtg tgg cag gcg gcc ggt gtg cgg ccg gat gcg gtg atc ggc<br>Ala Ala Val Trp Gln Ala Ala Gly Val Arg Pro Asp Ala Val Ile Gly<br>675 680 685 | | | 2066 |
| cat tcg cag ggt gag atc gcc gca gct tgt gtg gcg ggt gcg gtg tca | | | 2114 |

-continued

```
His Ser Gln Gly Glu Ile Ala Ala Ala Cys Val Ala Gly Ala Val Ser
            690                 695                 700 cta cgc gat gcc gcc cgg atc gtg acc ttg cgc agc cag gcg atc gcc       2162
Leu Arg Asp Ala Ala Arg Ile Val Thr Leu Arg Ser Gln Ala Ile Ala
        705                 710                 715 cgg ggc ctg gcg ggc cgg ggc gcg atg gca tcc gtc gcc ctg ccc gcg       2210
Arg Gly Leu Ala Gly Arg Gly Ala Met Ala Ser Val Ala Leu Pro Ala
720                 725                 730 cag gat gtc gag ctg gtc gac ggg gcc tgg atc gcc gcc cac aac ggg       2258
Gln Asp Val Glu Leu Val Asp Gly Ala Trp Ile Ala Ala His Asn Gly
735                 740                 745                 750 ccc gcc tcc acc gtg atc gcg ggc acc ccg gaa gcg gtc gac cat gtc       2306
Pro Ala Ser Thr Val Ile Ala Gly Thr Pro Glu Ala Val Asp His Val
                755                 760                 765 ctc acc gct cat gag gca caa ggg gtg cgg gtg cgg cgg atc acc gtc       2354
Leu Thr Ala His Glu Ala Gln Gly Val Arg Val Arg Arg Ile Thr Val
            770                 775                 780 gac tat gcc tcg cac acc ccg cac gtc gag ctg atc cgc gac gaa cta       2402
Asp Tyr Ala Ser His Thr Pro His Val Glu Leu Ile Arg Asp Glu Leu
        785                 790                 795 ctc gac atc act agc gac agc agc tcg cag acc ccg ctc gtg ccg tgg       2450
Leu Asp Ile Thr Ser Asp Ser Ser Gln Thr Pro Leu Val Pro Trp
800                 805                 810 ctg tcg acc gtg gac ggc acc tgg gtc gac agc ccg ctg gac ggg gag       2498
Leu Ser Thr Val Asp Gly Thr Trp Val Asp Ser Pro Leu Asp Gly Glu
815                 820                 825                 830 tac tgg tac cgg aac ctg cgt gaa ccg gtc ggt ttc cac ccc gcc gtc       2546
Tyr Trp Tyr Arg Asn Leu Arg Glu Pro Val Gly Phe His Pro Ala Val
                835                 840                 845 agc cag ttg cag gcc cag ggc gac acc gtg ttc gtc gag gtc agc gcc       2594
Ser Gln Leu Gln Ala Gln Gly Asp Thr Val Phe Val Glu Val Ser Ala
            850                 855                 860 agc ccg gtg ttg ttg cag gcg atg gac gac gat gtc gtc acg gtt gcc       2642
Ser Pro Val Leu Leu Gln Ala Met Asp Asp Asp Val Val Thr Val Ala
        865                 870                 875 acg ctg cgt cgt gac gac ggc gac gcc acc cgg atg ctc acc gcc ctg       2690
Thr Leu Arg Arg Asp Asp Gly Asp Ala Thr Arg Met Leu Thr Ala Leu
880                 885                 890 gca cag gcc tat gtc cac ggc gtc acc gtc gac tgg ccc gcc atc ctc       2738
Ala Gln Ala Tyr Val His Gly Val Thr Val Asp Trp Pro Ala Ile Leu
895                 900                 905                 910 ggc acc acc aca acc cgg gta ctg gac ctt ccg acc tac gcc ttc caa       2786
Gly Thr Thr Thr Thr Arg Val Leu Asp Leu Pro Thr Tyr Ala Phe Gln
                915                 920                 925 cac cag cgg tac tgg ctc gag tcg gca cgc ccg gcc gca tcc gac gcg       2834
His Gln Arg Tyr Trp Leu Glu Ser Ala Arg Pro Ala Ala Ser Asp Ala
            930                 935                 940 ggc cac ccc gtg ctg ggc tcc ggt atc gcc ctc gcc ggg tcg ccg ggc       2882
Gly His Pro Val Leu Gly Ser Gly Ile Ala Leu Ala Gly Ser Pro Gly
        945                 950                 955 cgg gtg ttc acg ggt tcc gtg ccg acc ggt gcg gac cgc gcg gtg ttc       2930
Arg Val Phe Thr Gly Ser Val Pro Thr Gly Ala Asp Arg Ala Val Phe
960                 965                 970 gtc gcc gag ctg gcg ctg gcc gcc gcg gac gcg gtc gac tgc gcc acg       2978
Val Ala Glu Leu Ala Leu Ala Ala Ala Asp Ala Val Asp Cys Ala Thr
975                 980                 985                 990 gtc gag cgg ctc gac atc gcc tcc gtg ccc ggc cgg ccg ggc cat ggc       3026
Val Glu Arg Leu Asp Ile Ala Ser Val Pro Gly Arg Pro Gly His Gly
                995                 1000                1005
```

-continued

| | |
|---|---|
| cgg acg acc gta cag acc tgg gtc gac gag ccg gcg gac gac ggc cgg<br>Arg Thr Thr Val Gln Thr Trp Val Asp Glu Pro Ala Asp Asp Gly Arg<br>          1010                       1015                    1020 | 3074 |
| cgc cgg ttc acc gtg cac acc cgc acc ggc gac gcc ccg tgg acg ctg<br>Arg Arg Phe Thr Val His Thr Arg Thr Gly Asp Ala Pro Trp Thr Leu<br>          1025                       1030                    1035 | 3122 |
| cac gcc gag ggg gtg ctg cgc ccc cat ggc acg gcc ctg ccc gat gcg<br>His Ala Glu Gly Val Leu Arg Pro His Gly Thr Ala Leu Pro Asp Ala<br>   1040                       1045                    1050 | 3170 |
| gcc gac gcc gag tgg ccc cca ccg ggc gcg gtg ccc gcg gac ggg ctg<br>Ala Asp Ala Glu Trp Pro Pro Pro Gly Ala Val Pro Ala Asp Gly Leu<br>1055                      1060                    1065                 1070 | 3218 |
| ccg ggt gtg tgg cgc cgg ggg gac cag gtc ttc gcc gag gcc gag gtg<br>Pro Gly Val Trp Arg Arg Gly Asp Gln Val Phe Ala Glu Ala Glu Val<br>                 1075                    1080                    1085 | 3266 |
| gac gga ccg gac ggt ttc gtg gtg cac ccc gac ctg ctc gac gcg gtc<br>Asp Gly Pro Asp Gly Phe Val Val His Pro Asp Leu Leu Asp Ala Val<br>                    1090                    1095                    1100 | 3314 |
| ttc tcc gcg gtc ggc gac gga agc cgc cag ccg gcc gga tgg cgc gac<br>Phe Ser Ala Val Gly Asp Gly Ser Arg Gln Pro Ala Gly Trp Arg Asp<br>         1105                       1110                    1115 | 3362 |
| ctg acg gtg cac gcg tcg gac gcc acc gta ctg cgc gcc tgc ctc acc<br>Leu Thr Val His Ala Ser Asp Ala Thr Val Leu Arg Ala Cys Leu Thr<br>       1120                       1125                    1130 | 3410 |
| cgg cgc acc gac gga gcc atg gga ttc gcc gcc ttc gac ggc gcc ggc<br>Arg Arg Thr Asp Gly Ala Met Gly Phe Ala Ala Phe Asp Gly Ala Gly<br>1135                      1140                    1145                    1150 | 3458 |
| ctg ccg gta ctc acc gcg gag gcg gtg acg ctg cgg gag gtg gcg tca<br>Leu Pro Val Leu Thr Ala Glu Ala Val Thr Leu Arg Glu Val Ala Ser<br>                 1155                    1160                    1165 | 3506 |
| ccg tcc ggc tcc gag gag tcg gac ggc ctg cac cgg ttg gag tgg ctc<br>Pro Ser Gly Ser Glu Glu Ser Asp Gly Leu His Arg Leu Glu Trp Leu<br>            1170                       1175                    1180 | 3554 |
| gcg gtc gcc gag gcg gtc tac gac ggt gac ctg ccc gag gga cat gtc<br>Ala Val Ala Glu Ala Val Tyr Asp Gly Asp Leu Pro Glu Gly His Val<br>          1185                       1190                    1195 | 3602 |
| ctg atc acc gcc gcc cac ccc gac gac ccc gag gac ata ccc acc cgc<br>Leu Ile Thr Ala Ala His Pro Asp Asp Pro Glu Asp Ile Pro Thr Arg<br>       1200                       1205                    1210 | 3650 |
| gcc cac acc cgc gcc acc cgc gtc ctg acc gcc ctg caa cac cac ctc<br>Ala His Thr Arg Ala Thr Arg Val Leu Thr Ala Leu Gln His His Leu<br>1215                      1220                    1225                    1230 | 3698 |
| acc acc acc gac cac acc ctc atc gtc cac acc acc acc gac ccc gcc<br>Thr Thr Thr Asp His Thr Leu Ile Val His Thr Thr Thr Asp Pro Ala<br>               1235                    1240                    1245 | 3746 |
| ggc gcc acc gtc acc ggc ctc acc cgc acc gcc cag aac gaa cac ccc<br>Gly Ala Thr Val Thr Gly Leu Thr Arg Thr Ala Gln Asn Glu His Pro<br>         1250                       1255                    1260 | 3794 |
| cac cgc atc cgc ctc atc gaa acc gac cac ccc cac acc ccc ctc ccc<br>His Arg Ile Arg Leu Ile Glu Thr Asp His Pro His Thr Pro Leu Pro<br>      1265                       1270                    1275 | 3842 |
| ctg gcc caa ctc gcc acc ctc gac cac ccc cac ctc cgc ctc acc cac<br>Leu Ala Gln Leu Ala Thr Leu Asp His Pro His Leu Arg Leu Thr His<br>              1280                    1285                    1290 | 3890 |
| cac acc ctc cac cac ccc cac ctc acc ccc ctc cac acc acc acc cca<br>His Thr Leu His His Pro His Leu Thr Pro Leu His Thr Thr Thr Pro<br>1295                      1300                    1305                    1310 | 3938 |
| ccc acc acc acc ccc ctc aac ccc gaa cac gcc atc atc atc acc ggc<br>Pro Thr Thr Thr Pro Leu Asn Pro Glu His Ala Ile Ile Ile Thr Gly<br>                 1315                    1320                    1325 | 3986 |

```
ggc tcc ggc acc ctc gcc ggc atc ctc gcc cgc cac ctg aac cac ccc    4034
Gly Ser Gly Thr Leu Ala Gly Ile Leu Ala Arg His Leu Asn His Pro
            1330                1335                1340 cac acc tac ctc ctc tcc cgc acc cca ccc ccc gac gcc acc ccc ggc    4082
His Thr Tyr Leu Leu Ser Arg Thr Pro Pro Pro Asp Ala Thr Pro Gly
        1345                1350                1355 acc cac ctc ccc tgc gac gtc ggc gac ccc cac caa ctc gcc acc acc    4130
Thr His Leu Pro Cys Asp Val Gly Asp Pro His Gln Leu Ala Thr Thr
    1360                1365                1370 ctc acc cac atc ccc caa ccc ctc acc gcc atc ttc cac acc gcc gcc    4178
Leu Thr His Ile Pro Gln Pro Leu Thr Ala Ile Phe His Thr Ala Ala
1375                1380                1385                1390 acc ctc gac gac ggc atc ctc cac gcc ctc acc ccc gac cgc ctc acc    4226
Thr Leu Asp Asp Gly Ile Leu His Ala Leu Thr Pro Asp Arg Leu Thr
                1395                1400                1405 acc gtc ctc cac ccc aaa gcc aac gcc gcc tgg cac ctg cac cac ctc    4274
Thr Val Leu His Pro Lys Ala Asn Ala Ala Trp His Leu His His Leu
            1410                1415                1420 acc caa aac caa ccc ctc acc cac ttc gtc ctc tac tcc agc gcc gcc    4322
Thr Gln Asn Gln Pro Leu Thr His Phe Val Leu Tyr Ser Ser Ala Ala
        1425                1430                1435 gcc gtc ctc ggc agc ccc gga caa gga aac tac gcc gcc gcc aac gcc    4370
Ala Val Leu Gly Ser Pro Gly Gln Gly Asn Tyr Ala Ala Ala Asn Ala
    1440                1445                1450 ttc ctc gac gcc ctc gcc acc cac cgc cac acc ctc ggc caa ccc gcc    4418
Phe Leu Asp Ala Leu Ala Thr His Arg His Thr Leu Gly Gln Pro Ala
1455                1460                1465                1470 acc tcc atc gcc tgg ggc atg tgg cac acc acc agc acc ctc acc gga    4466
Thr Ser Ile Ala Trp Gly Met Trp His Thr Thr Ser Thr Leu Thr Gly
                1475                1480                1485 caa ctc gac gac gcc gac cgg gac cgc atc cgc cgc ggc ggt ttc ctc    4514
Gln Leu Asp Asp Ala Asp Arg Asp Arg Ile Arg Arg Gly Gly Phe Leu
            1490                1495                1500 ccg atc acg gac gac gag ggc atggggatgc at                          4547
Pro Ile Thr Asp Asp Glu Gly
        1505
```

<210> SEQ ID NO 23
<211> LENGTH: 1509
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 23

```
Gln Leu Ala Glu Ala Leu Leu Thr Leu Val Arg Glu Ser Thr Ala Ala
 1               5                  10                  15

Val Leu Gly His Val Gly Gly Glu Asp Ile Pro Ala Thr Ala Ala Phe
            20                  25                  30

Lys Asp Leu Gly Ile Asp Ser Leu Thr Ala Val Gln Leu Arg Asn Ala
        35                  40                  45

Leu Thr Glu Ala Thr Gly Val Arg Leu Asn Ala Thr Ala Val Phe Asp
    50                  55                  60

Phe Pro Thr Pro His Val Leu Ala Gly Lys Leu Gly Asp Glu Leu Thr
65                  70                  75                  80

Gly Thr Arg Ala Pro Val Val Pro Arg Thr Ala Ala Thr Ala Gly Ala
                85                  90                  95

His Asp Glu Pro Leu Ala Ile Val Gly Met Ala Cys Arg Leu Pro Gly
```

```
                    100                 105                 110
Gly Val Ala Ser Pro Glu Glu Leu Trp His Leu Val Ala Ser Gly Thr
            115                 120                 125

Asp Ala Ile Thr Glu Phe Pro Thr Asp Arg Gly Trp Asp Val Asp Ala
        130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
            195                 200                 205

Ser Thr Arg Gly Ser Asp Thr Gly Val Phe Val Gly Ala Phe Ser Tyr
        210                 215                 220

Gly Tyr Gly Thr Gly Ala Asp Thr Asp Gly Phe Gly Ala Thr Gly Ser
225                 230                 235                 240

Gln Thr Ser Val Leu Ser Gly Arg Leu Ser Tyr Phe Tyr Gly Leu Glu
                245                 250                 255

Gly Pro Ala Val Thr Val Asp Thr Ala Cys Ser Ser Leu Val Ala
            260                 265                 270

Leu His Gln Ala Gly Gln Ser Leu Arg Ser Gly Glu Cys Ser Leu Ala
        275                 280                 285

Leu Val Gly Gly Val Thr Val Met Ala Ser Pro Gly Gly Phe Val Glu
        290                 295                 300

Phe Ser Arg Gln Arg Gly Leu Ala Pro Asp Gly Arg Ala Lys Ala Phe
305                 310                 315                 320

Gly Ala Gly Ala Asp Gly Thr Ser Phe Ala Glu Gly Ala Gly Val Leu
                325                 330                 335

Ile Val Glu Arg Leu Ser Asp Ala Glu Arg Asn Gly His Thr Val Leu
            340                 345                 350

Ala Val Val Arg Gly Ser Ala Val Asn Gln Asp Gly Ala Ser Asn Gly
            355                 360                 365

Leu Ser Ala Pro Asn Gly Pro Ser Gln Glu Arg Val Ile Arg Gln Ala
370                 375                 380

Leu Ala Asn Ala Gly Leu Thr Pro Ala Asp Val Asp Ala Val Glu Ala
385                 390                 395                 400

His Gly Thr Gly Thr Arg Leu Gly Asp Pro Ile Glu Ala Gln Ala Val
                405                 410                 415

Leu Ala Thr Tyr Gly Gln Glu Arg Ala Thr Pro Leu Leu Gly Ser
            420                 425                 430

Leu Lys Ser Asn Ile Gly His Ala Gln Ala Ala Ser Gly Val Ala Gly
        435                 440                 445

Ile Ile Lys Met Val Gln Ala Leu Arg His Gly Glu Leu Pro Pro Thr
        450                 455                 460

Leu His Ala Asp Glu Pro Ser Pro His Val Asp Trp Thr Ala Gly Ala
465                 470                 475                 480

Val Glu Leu Leu Thr Ser Ala Arg Pro Trp Pro Glu Thr Asp Arg Pro
                485                 490                 495

Arg Arg Ala Ala Val Ser Ser Phe Gly Val Ser Gly Thr Asn Ala His
            500                 505                 510

Val Ile Leu Glu Ala Gly Pro Val Thr Glu Thr Pro Ala Ala Ser Pro
        515                 520                 525
```

-continued

```
Ser Gly Asp Leu Pro Leu Leu Val Ser Ala Arg Ser Pro Glu Ala Leu
    530                 535                 540
Asp Glu Gln Ile Arg Arg Leu Arg Ala Tyr Leu Asp Thr Thr Pro Asp
545                 550                 555                 560
Val Asp Arg Val Ala Val Ala Gln Thr Leu Ala Arg Arg Thr His Phe
                565                 570                 575
Ala His Arg Ala Val Leu Leu Gly Asp Thr Val Ile Thr Thr Pro Pro
                580                 585                 590
Ala Asp Arg Pro Asp Glu Leu Val Phe Val Tyr Ser Gly Gln Gly Thr
        595                 600                 605
Gln His Pro Ala Met Gly Glu Gln Leu Ala Asp Ser Ser Val Val Phe
        610                 615                 620
Ala Glu Arg Met Ala Glu Cys Ala Ala Ala Leu Arg Glu Phe Val Asp
625                 630                 635                 640
Trp Asp Leu Phe Thr Val Leu Asp Asp Pro Ala Val Val Asp Arg Val
                645                 650                 655
Asp Val Val Gln Pro Ala Ser Trp Ala Met Met Val Ser Leu Ala Ala
                660                 665                 670
Val Trp Gln Ala Ala Gly Val Arg Pro Asp Ala Val Ile Gly His Ser
        675                 680                 685
Gln Gly Glu Ile Ala Ala Cys Val Ala Gly Ala Val Ser Leu Arg
        690                 695                 700
Asp Ala Ala Arg Ile Val Thr Leu Arg Ser Gln Ala Ile Ala Arg Gly
705                 710                 715                 720
Leu Ala Gly Arg Gly Ala Met Ala Ser Val Ala Leu Pro Ala Gln Asp
                725                 730                 735
Val Glu Leu Val Asp Gly Ala Trp Ile Ala Ala His Asn Gly Pro Ala
                740                 745                 750
Ser Thr Val Ile Ala Gly Thr Pro Glu Ala Val Asp His Val Leu Thr
        755                 760                 765
Ala His Glu Ala Gln Gly Val Arg Val Arg Arg Ile Thr Val Asp Tyr
        770                 775                 780
Ala Ser His Thr Pro His Val Glu Leu Ile Arg Asp Glu Leu Leu Asp
785                 790                 795                 800
Ile Thr Ser Asp Ser Ser Gln Thr Pro Leu Val Pro Trp Leu Ser
                805                 810                 815
Thr Val Asp Gly Thr Trp Val Asp Ser Pro Leu Asp Gly Glu Tyr Trp
                820                 825                 830
Tyr Arg Asn Leu Arg Glu Pro Val Gly Phe His Pro Ala Val Ser Gln
        835                 840                 845
Leu Gln Ala Gln Gly Asp Thr Val Phe Val Glu Val Ser Ala Ser Pro
        850                 855                 860
Val Leu Leu Gln Ala Met Asp Asp Val Val Thr Val Ala Thr Leu
865                 870                 875                 880
Arg Arg Asp Asp Gly Asp Ala Thr Arg Met Leu Thr Ala Leu Ala Gln
                885                 890                 895
Ala Tyr Val His Gly Val Thr Val Asp Trp Pro Ala Ile Leu Gly Thr
                900                 905                 910
Thr Thr Thr Arg Val Leu Asp Leu Pro Thr Tyr Ala Phe Gln His Gln
        915                 920                 925
Arg Tyr Trp Leu Glu Ser Ala Arg Pro Ala Ala Ser Asp Ala Gly His
        930                 935                 940
```

-continued

```
Pro Val Leu Gly Ser Gly Ile Ala Leu Ala Gly Ser Pro Gly Arg Val
945                 950                 955                 960

Phe Thr Gly Ser Val Pro Thr Gly Ala Asp Arg Ala Val Phe Val Ala
                965                 970                 975

Glu Leu Ala Leu Ala Ala Asp Ala Val Asp Cys Ala Thr Val Glu
            980                 985                 990

Arg Leu Asp Ile Ala Ser Val Pro Gly Arg Pro Gly His Gly Arg Thr
            995                 1000                1005

Thr Val Gln Thr Trp Val Asp Glu Pro Ala Asp Gly Arg Arg Arg
        1010                1015                1020

Phe Thr Val His Thr Arg Thr Gly Asp Ala Pro Trp Thr Leu His Ala
1025                1030                1035                1040

Glu Gly Val Leu Arg Pro His Gly Thr Ala Leu Pro Asp Ala Ala Asp
                1045                1050                1055

Ala Glu Trp Pro Pro Pro Gly Ala Val Pro Ala Asp Gly Leu Pro Gly
                1060                1065                1070

Val Trp Arg Arg Gly Asp Gln Val Phe Ala Glu Ala Glu Val Asp Gly
        1075                1080                1085

Pro Asp Gly Phe Val Val His Pro Asp Leu Leu Asp Ala Val Phe Ser
    1090                1095                1100

Ala Val Gly Asp Gly Ser Arg Gln Pro Ala Gly Trp Arg Asp Leu Thr
1105                1110                1115                1120

Val His Ala Ser Asp Ala Thr Val Leu Arg Ala Cys Leu Thr Arg Arg
        1125                1130                1135

Thr Asp Gly Ala Met Gly Phe Ala Ala Phe Asp Gly Ala Gly Leu Pro
                1140                1145                1150

Val Leu Thr Ala Glu Ala Val Thr Leu Arg Glu Val Ala Ser Pro Ser
        1155                1160                1165

Gly Ser Glu Glu Ser Asp Gly Leu His Arg Leu Glu Trp Leu Ala Val
    1170                1175                1180

Ala Glu Ala Val Tyr Asp Gly Asp Leu Pro Glu Gly His Val Leu Ile
1185                1190                1195                1200

Thr Ala Ala His Pro Asp Asp Pro Glu Asp Ile Pro Thr Arg Ala His
                1205                1210                1215

Thr Arg Ala Thr Arg Val Leu Thr Ala Leu Gln His His Leu Thr Thr
                1220                1225                1230

Thr Asp His Thr Leu Ile Val His Thr Thr Asp Pro Ala Gly Ala
            1235                1240                1245

Thr Val Thr Gly Leu Thr Arg Thr Ala Gln Asn Glu His Pro His Arg
1250                1255                1260

Ile Arg Leu Ile Glu Thr Asp His Pro His Thr Pro Leu Pro Leu Ala
1265                1270                1275                1280

Gln Leu Ala Thr Leu Asp His Pro His Leu Arg Leu Thr His His Thr
            1285                1290                1295

Leu His His Pro His Leu Thr Pro Leu His Thr Thr Pro Pro Thr
            1300                1305                1310

Thr Thr Pro Leu Asn Pro Glu His Ala Ile Ile Ile Thr Gly Gly Ser
                1315                1320                1325

Gly Thr Leu Ala Gly Ile Leu Ala Arg His Leu Asn His Pro His Thr
            1330                1335                1340

Tyr Leu Leu Ser Arg Thr Pro Pro Asp Ala Thr Pro Gly Thr His
1345                1350                1355                1360

Leu Pro Cys Asp Val Gly Asp Pro His Gln Leu Ala Thr Thr Leu Thr
```

-continued

```
                1365                1370                1375
          His Ile Pro Gln Pro Leu Thr Ala Ile Phe His Thr Ala Ala Thr Leu
                      1380                1385                1390

Asp Asp Gly Ile Leu His Ala Leu Thr Pro Asp Arg Leu Thr Thr Val
                      1395                1400                1405

Leu His Pro Lys Ala Asn Ala Ala Trp His Leu His His Leu Thr Gln
                      1410                1415                1420

Asn Gln Pro Leu Thr His Phe Val Leu Tyr Ser Ser Ala Ala Ala Val
          1425                1430                1435                1440

Leu Gly Ser Pro Gly Gln Gly Asn Tyr Ala Ala Ala Asn Ala Phe Leu
                      1445                1450                1455

Asp Ala Leu Ala Thr His Arg His Thr Leu Gly Gln Pro Ala Thr Ser
                      1460                1465                1470

Ile Ala Trp Gly Met Trp His Thr Thr Ser Thr Leu Thr Gly Gln Leu
                      1475                1480                1485

Asp Asp Ala Asp Arg Asp Arg Ile Arg Arg Gly Gly Phe Leu Pro Ile
                      1490                1495                1500

Thr Asp Asp Glu Gly
          1505

<210> SEQ ID NO 24
<211> LENGTH: 4725
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4724)

<400> SEQUENCE: 24 gc atg cgg ctg tac gag gcg gca cgg cgc acc gga agt ccc gtg gtg        47
   Met Arg Leu Tyr Glu Ala Ala Arg Arg Thr Gly Ser Pro Val Val
   1               5                  10                  15 gtg gcg gcc gcg ctc gac gac gcg ccg gac gtg ccg ctg ctg cgc ggg       95
Val Ala Ala Ala Leu Asp Asp Ala Pro Asp Val Pro Leu Leu Arg Gly
            20                  25                  30 ctg cgg cgt acg acc gtc cgg cgt gcc gcc gtc cgg gaa cgc tct ctc      143
Leu Arg Arg Thr Thr Val Arg Arg Ala Ala Val Arg Glu Arg Ser Leu
        35                  40                  45 gcc gac cgc tcg ccg tgc tgc ccg acg acg agc gcg ccg acg cct ccc      191
Ala Asp Arg Ser Pro Cys Cys Pro Thr Thr Ser Ala Pro Thr Pro Pro
    50                  55                  60 tcg cgt tcg tcc tgg aac agc acc gcc acc gtg ctc ggc cac ctg ggc      239
Ser Arg Ser Ser Trp Asn Ser Thr Ala Thr Val Leu Gly His Leu Gly
65                  70                  75 gcc gaa gac atc ccg gcg acg acg acg ttc aag gaa ctc ggc atc gac      287
Ala Glu Asp Ile Pro Ala Thr Thr Thr Phe Lys Glu Leu Gly Ile Asp
80                  85                  90                  95 tcg ctc acc gcg gtc cag ctg cgc aac gcg ctg acc acg gcg acc ggc      335
Ser Leu Thr Ala Val Gln Leu Arg Asn Ala Leu Thr Thr Ala Thr Gly
                100                 105                 110 gta cgc ctc aac gcc aca gcg gtc ttc gac ttt ccg acg ccg cgc gcg      383
Val Arg Leu Asn Ala Thr Ala Val Phe Asp Phe Pro Thr Pro Arg Ala
            115                 120                 125 ctc gcc gcg aga ctc ggc gac gag ctg gcc ggt acc cgc gcc ccc gtc      431
Leu Ala Ala Arg Leu Gly Asp Glu Leu Ala Gly Thr Arg Ala Pro Val
        130                 135                 140
```

-continued

| | |
|---|---|
| gcg gcc cgg acc gcg gcc acc gcg gcc gcg cac gac gaa ccg ctg gcg<br>Ala Ala Arg Thr Ala Ala Thr Ala Ala Ala His Asp Glu Pro Leu Ala<br>145                   150                         155 | 479 |
| atc gtg ggc atg gcc tgc cgt ctg ccg ggc ggg gtc gcg tcg cca cag<br>Ile Val Gly Met Ala Cys Arg Leu Pro Gly Gly Val Ala Ser Pro Gln<br>160                   165                   170               175 | 527 |
| gag ctg tgg cgt ctc gtc gcg tcc ggc acc gac gcc atc acg gag ttc<br>Glu Leu Trp Arg Leu Val Ala Ser Gly Thr Asp Ala Ile Thr Glu Phe<br>                   180                   185                   190 | 575 |
| ccc gcg gac cgc ggc tgg gac gtg gac gcg ctc tac gac ccg gac ccc<br>Pro Ala Asp Arg Gly Trp Asp Val Asp Ala Leu Tyr Asp Pro Asp Pro<br>                   195                   200                   205 | 623 |
| gac gcg atc ggc aag acc ttc gtc cgg cac ggc ggc ttc ctc gac ggt<br>Asp Ala Ile Gly Lys Thr Phe Val Arg His Gly Gly Phe Leu Asp Gly<br>             210                   215                   220 | 671 |
| gcg acc ggc ttc gac gcg gcg ttc ttc ggg atc agc ccg cgc gag gcc<br>Ala Thr Gly Phe Asp Ala Ala Phe Phe Gly Ile Ser Pro Arg Glu Ala<br>225                   230                   235 | 719 |
| ctg gcc atg gac ccg cag caa cgg gtg ctc ctg gag acg tcc tgg gag<br>Leu Ala Met Asp Pro Gln Gln Arg Val Leu Leu Glu Thr Ser Trp Glu<br>240                   245                   250               255 | 767 |
| gcg ttc gaa agc gcg ggc atc acc ccg gac gcg gcg cgg ggc agc gac<br>Ala Phe Glu Ser Ala Gly Ile Thr Pro Asp Ala Ala Arg Gly Ser Asp<br>                   260                   265                   270 | 815 |
| acc ggc gtg ttc atc ggc gcg ttc tcc tac ggg tac ggc acg ggt gcg<br>Thr Gly Val Phe Ile Gly Ala Phe Ser Tyr Gly Tyr Gly Thr Gly Ala<br>             275                   280                   285 | 863 |
| gat acc aac ggc ttc ggc gcg aca ggg tcg cag acc agc gtg ctc tcc<br>Asp Thr Asn Gly Phe Gly Ala Thr Gly Ser Gln Thr Ser Val Leu Ser<br>             290                   295                   300 | 911 |
| ggc cgc ctc tcg tac ttc tac ggt ctg gag ggc cct tcg gtc acg gtc<br>Gly Arg Leu Ser Tyr Phe Tyr Gly Leu Glu Gly Pro Ser Val Thr Val<br>305                   310                   315 | 959 |
| gac acc gcc tgc tcg tcg tca ctg gtc gcc ctg cac cag gca ggg cag<br>Asp Thr Ala Cys Ser Ser Ser Leu Val Ala Leu His Gln Ala Gly Gln<br>320                   325                   330               335 | 1007 |
| tcc ctg cgc tcg ggc gaa tgc tcg ctc gcc ctg gtc ggc ggt gtc acg<br>Ser Leu Arg Ser Gly Glu Cys Ser Leu Ala Leu Val Gly Gly Val Thr<br>                   340                   345                   350 | 1055 |
| gtg atg gcg tcg ccc ggc gga ttc gtc gag ttc tcc cgg cag cgc ggg<br>Val Met Ala Ser Pro Gly Gly Phe Val Glu Phe Ser Arg Gln Arg Gly<br>                   355                   360                   365 | 1103 |
| ctc gcg ccg gac ggg cgg gcg aag gcg ttc ggc gcg ggc gcg gac ggt<br>Leu Ala Pro Asp Gly Arg Ala Lys Ala Phe Gly Ala Gly Ala Asp Gly<br>             370                   375                   380 | 1151 |
| acg agc ttc gcc gag ggc gcc ggt gcc ctg gtg gtc gag cgg ctc tcc<br>Thr Ser Phe Ala Glu Gly Ala Gly Ala Leu Val Val Glu Arg Leu Ser<br>385                   390                   395 | 1199 |
| gac gcg gag cgc cac ggc cac acc gtc ctc gcc ctc gta cgc ggc tcc<br>Asp Ala Glu Arg His Gly His Thr Val Leu Ala Leu Val Arg Gly Ser<br>400                   405                   410               415 | 1247 |
| gcg gct aac tcc gac ggc gcg tcg aac ggt ctg tcg gcg ccg aac ggc<br>Ala Ala Asn Ser Asp Gly Ala Ser Asn Gly Leu Ser Ala Pro Asn Gly<br>                   420                   425                   430 | 1295 |
| ccc tcc cag gaa cgc gtc atc cac cag gcc ctc gcg aac gcg aaa ctc<br>Pro Ser Gln Glu Arg Val Ile His Gln Ala Leu Ala Asn Ala Lys Leu<br>             435                   440                   445 | 1343 |
| acc ccc gcc gat gtc gac gcg gtc gag gcg cac ggc acc ggc acc cgc<br>Thr Pro Ala Asp Val Asp Ala Val Glu Ala His Gly Thr Gly Thr Arg<br>450                   455                   460 | 1391 |

-continued

| | |
|---|---|
| ctc ggc gac ccc atc gag gcg cag gcg ctg ctc gcg acg tac gga cag<br>Leu Gly Asp Pro Ile Glu Ala Gln Ala Leu Leu Ala Thr Tyr Gly Gln<br>465                    470                    475 | 1439 |
| gac cgg gcg acg ccc ctg ctg ctc ggc tcg ctg aag tcg aac atc ggg<br>Asp Arg Ala Thr Pro Leu Leu Leu Gly Ser Leu Lys Ser Asn Ile Gly<br>480                    485                    490                    495 | 1487 |
| cac gcc cag gcc gcg tca ggg gtc gcc ggg atc atc aag atg gtg cag<br>His Ala Gln Ala Ala Ser Gly Val Ala Gly Ile Ile Lys Met Val Gln<br>                  500                    505                    510 | 1535 |
| gcc atc cgg cac ggg gaa ctg ccg ccg aca ctg cac gcg gac gag ccg<br>Ala Ile Arg His Gly Glu Leu Pro Pro Thr Leu His Ala Asp Glu Pro<br>              515                    520                    525 | 1583 |
| tcg ccg cac gtc gac tgg acg gcc ggt gcc gtc gag ctc ctg acg tcg<br>Ser Pro His Val Asp Trp Thr Ala Gly Ala Val Glu Leu Leu Thr Ser<br>530                    535                    540 | 1631 |
| gcc cgg ccg tgg ccg ggg acc ggt cgc ccg cgc cgc gct gcc gtc tcg<br>Ala Arg Pro Trp Pro Gly Thr Gly Arg Pro Arg Arg Ala Ala Val Ser<br>545                    550                    555 | 1679 |
| tcg ttc ggc gtg agc ggc acg aac gcc cac atc atc ctt gag gca gga<br>Ser Phe Gly Val Ser Gly Thr Asn Ala His Ile Ile Leu Glu Ala Gly<br>560                    565                    570                    575 | 1727 |
| ccg gtc aaa acg gga ccg gtc gag gca gga gcg atc gag gca gga ccg<br>Pro Val Lys Thr Gly Pro Val Glu Ala Gly Ala Ile Glu Ala Gly Pro<br>                  580                    585                    590 | 1775 |
| gtc gaa gta gga ccg gtc gag gct gga ccg ctc ccc gcg gcg ccg ccg<br>Val Glu Val Gly Pro Val Glu Ala Gly Pro Leu Pro Ala Ala Pro Pro<br>              595                    600                    605 | 1823 |
| tca gca ccg ggc gaa gac ctt ccg ctg ctc gtg tcg gcg cgt tcc ccg<br>Ser Ala Pro Gly Glu Asp Leu Pro Leu Leu Val Ser Ala Arg Ser Pro<br>610                    615                    620 | 1871 |
| gag gca ctc gac gag cag atc ggg cgc ctg cgc gcc tat ctc gac acc<br>Glu Ala Leu Asp Glu Gln Ile Gly Arg Leu Arg Ala Tyr Leu Asp Thr<br>625                    630                    635 | 1919 |
| ggc ccg ggc gtc gac cgg gcg gcc gtg gcg cag aca ctg gcc cgg cgt<br>Gly Pro Gly Val Asp Arg Ala Ala Val Ala Gln Thr Leu Ala Arg Arg<br>640                    645                    650                    655 | 1967 |
| acg cac ttc acc cac cgg gcc gta ctg ctc ggg gac acc gtc atc ggc<br>Thr His Phe Thr His Arg Ala Val Leu Leu Gly Asp Thr Val Ile Gly<br>                  660                    665                    670 | 2015 |
| gct ccc ccc gcg gac cag gcc gac gaa ctc gtc ttc gtc tac tcc ggt<br>Ala Pro Pro Ala Asp Gln Ala Asp Glu Leu Val Phe Val Tyr Ser Gly<br>              675                    680                    685 | 2063 |
| cag ggc acc cag cat ccc gcg atg ggc gag caa ctc gcg gcc gcg ttc<br>Gln Gly Thr Gln His Pro Ala Met Gly Glu Gln Leu Ala Ala Ala Phe<br>              690                    695                    700 | 2111 |
| ccc gtg ttc gcc gat gcc tgg cac gac gcg ctc cga cgg ctc gac gac<br>Pro Val Phe Ala Asp Ala Trp His Asp Ala Leu Arg Arg Leu Asp Asp<br>705                    710                    715 | 2159 |
| ccc gac ccg cac gac ccc aca cgg agc cag cac acg ctc ttc gcc cac<br>Pro Asp Pro His Asp Pro Thr Arg Ser Gln His Thr Leu Phe Ala His<br>720                    725                    730                    735 | 2207 |
| cag gcg gcg ttc acc gcc ctc ctg agg tcc tgg gac atc acg ccg cac<br>Gln Ala Ala Phe Thr Ala Leu Leu Arg Ser Trp Asp Ile Thr Pro His<br>                  740                    745                    750 | 2255 |
| gcc gtc atc ggc cac tcg ctc ggc gag atc acc gcg gcg tac gcc gcc<br>Ala Val Ile Gly His Ser Leu Gly Glu Ile Thr Ala Ala Tyr Ala Ala<br>              755                    760                    765 | 2303 |
| ggg atc ctg tcg ctc gac gac gcc tgc acc ctg atc acc acg cgt gcc<br>Gly Ile Leu Ser Leu Asp Asp Ala Cys Thr Leu Ile Thr Thr Arg Ala | 2351 |

-continued

|  |  |
|---|---|
| cgc ctc atg cac acg ctt ccg ccg ccc ggc gcc atg gtc acc gtg ctg<br>Arg Leu Met His Thr Leu Pro Pro Pro Gly Ala Met Val Thr Val Leu<br>785                                 790                            795 | 2399 |
| acc agc gag gag gag gcc cgt cag gcg ctg cgg ccg ggc gtg gag atc<br>Thr Ser Glu Glu Glu Ala Arg Gln Ala Leu Arg Pro Gly Val Glu Ile<br>800                                 805                         810                        815 | 2447 |
| gcc gcg gtc ttc ggc ccg cac tcc gtg gtg ctc tcg ggc gac gag gac<br>Ala Ala Val Phe Gly Pro His Ser Val Val Leu Ser Gly Asp Glu Asp<br>                   820                         825                        830 | 2495 |
| gcc gtg ctc gac gtc gca cag cgg ctc ggc atc cac cac cgt ctg ccc<br>Ala Val Leu Asp Val Ala Gln Arg Leu Gly Ile His His Arg Leu Pro<br>                   835                         840                        845 | 2543 |
| gcg ccg cac gcg ggc cac tcc gcg cac atg gaa ccc gtg gcc gcc gag<br>Ala Pro His Ala Gly His Ser Ala His Met Glu Pro Val Ala Ala Glu<br>                   850                         855                        860 | 2591 |
| ctc ctc gcc acc act cgc gag ctc cgt tac gac cgg ccc cac acc gcc<br>Leu Leu Ala Thr Thr Arg Glu Leu Arg Tyr Asp Arg Pro His Thr Ala<br>                   865                         870                        875 | 2639 |
| atc ccg aac gac ccc acc acc gcc gag tac tgg gcc gag cag gtc cgc<br>Ile Pro Asn Asp Pro Thr Thr Ala Glu Tyr Trp Ala Glu Gln Val Arg<br>880                                 885                         890                        895 | 2687 |
| aac ccc gtg ctg ttc cac gcc cac acc cag cgg tac ccc gac gcc gtg<br>Asn Pro Val Leu Phe His Ala His Thr Gln Arg Tyr Pro Asp Ala Val<br>                   900                         905                        910 | 2735 |
| ttc gtc gag atc ggc ccc ggc cag gac ctc tca ccg ctg gtc gac ggc<br>Phe Val Glu Ile Gly Pro Gly Gln Asp Leu Ser Pro Leu Val Asp Gly<br>                   915                         920                        925 | 2783 |
| atc gcc ctg cag aac ggc acg gcg gac gag gtg cac gcg ctg cac acc<br>Ile Ala Leu Gln Asn Gly Thr Ala Asp Glu Val His Ala Leu His Thr<br>                   930                         935                        940 | 2831 |
| gcg ctc gcc cgc ctc ttc aca cgc ggc gcc acg ctc gac tgg tcc cgc<br>Ala Leu Ala Arg Leu Phe Thr Arg Gly Ala Thr Leu Asp Trp Ser Arg<br>945                                 950                         955 | 2879 |
| atc ctc ggc ggt gct tcg cgg cac gac cct gac gtc ccc tcg tac gcg<br>Ile Leu Gly Gly Ala Ser Arg His Asp Pro Asp Val Pro Ser Tyr Ala<br>960                                 965                         970                        975 | 2927 |
| ttc cag cgg cgt ccc tac tgg atc gag tcg gct ccc ccg gcc acg gcc<br>Phe Gln Arg Arg Pro Tyr Trp Ile Glu Ser Ala Pro Pro Ala Thr Ala<br>                   980                         985                        990 | 2975 |
| gac tcg ggc cac ccc gtc ctc ggc acc gga gtc gcc gtc gcc ggg tcg<br>Asp Ser Gly His Pro Val Leu Gly Thr Gly Val Ala Val Ala Gly Ser<br>                   995                         1000                      1005 | 3023 |
| ccg ggc cgg gtg ttc acg ggt ccc gtg ccc gcc ggt gcg gac cgc gcg<br>Pro Gly Arg Val Phe Thr Gly Pro Val Pro Ala Gly Ala Asp Arg Ala<br>                   1010                      1015                      1020 | 3071 |
| gtg ttc atc gcc gaa ctg gcg ctc gcc gcc gcc gac gcc acc gac tgc<br>Val Phe Ile Ala Glu Leu Ala Leu Ala Ala Ala Asp Ala Thr Asp Cys<br>1025                           1030                      1035 | 3119 |
| gcc acg gtc gaa cag ctc gac gtc acc tcc gtg ccc ggc gga tcc gcc<br>Ala Thr Val Glu Gln Leu Asp Val Thr Ser Val Pro Gly Gly Ser Ala<br>1040                           1045                      1050                      1055 | 3167 |
| cgc ggc agg gcc acc gcg cag acc tgg gtc gat gaa ccc gcc gcc gac<br>Arg Gly Arg Ala Thr Ala Gln Thr Trp Val Asp Glu Pro Ala Ala Asp<br>                   1060                      1065                      1070 | 3215 |
| ggg cgg cgc cgc ttc acc gtc cac acc cgc gtc ggc gac gcc ccg tgg<br>Gly Arg Arg Arg Phe Thr Val His Thr Arg Val Gly Asp Ala Pro Trp<br>                   1075                      1080                      1085 | 3263 |
| acg ctg cac gcc gag ggg gtt ctc cgc ccc ggc cgc gtg ccc cag ccc | 3311 |

```
                Thr Leu His Ala Glu Gly Val Leu Arg Pro Gly Arg Val Pro Gln Pro
                        1090                1095                1100 gaa gcc gtc gac acc gcc tgg ccc ccg ccg ggc gcg gtg ccc gcg gac          3359
Glu Ala Val Asp Thr Ala Trp Pro Pro Gly Ala Val Pro Ala Asp
    1105                1110                1115 ggg ctg ccc ggg gcg tgg cga cgc gcg gac cag gtc ttc gtc gaa gcc          3407
Gly Leu Pro Gly Ala Trp Arg Arg Ala Asp Gln Val Phe Val Glu Ala
1120                1125                1130                1135 gaa gtc gac agc cct gac ggc ttc gtg gca cac ccc gac ctg ctc gac          3455
Glu Val Asp Ser Pro Asp Gly Phe Val Ala His Pro Asp Leu Leu Asp
                1140                1145                1150 gcg gtc ttc tcc gcg gtc ggc gac ggg agc cgc cag ccg acc gga tgg          3503
Ala Val Phe Ser Ala Val Gly Asp Gly Ser Arg Gln Pro Thr Gly Trp
            1155                1160                1165 cgc gac ctc gcg gtg cac gcg tcg gac gcc acc gtg ctg cgc gcc tgc          3551
Arg Asp Leu Ala Val His Ala Ser Asp Ala Thr Val Leu Arg Ala Cys
        1170                1175                1180 ctc acc cgc cgc gac agt ggt gtc gtg gag ctc gcc gcc ttc gac ggt          3599
Leu Thr Arg Arg Asp Ser Gly Val Val Glu Leu Ala Ala Phe Asp Gly
    1185                1190                1195 gcc gga atg ccg gtg ctc acc gcg gag tcg gtg acg ctg ggc gag gtc          3647
Ala Gly Met Pro Val Leu Thr Ala Glu Ser Val Thr Leu Gly Glu Val
1200                1205                1210                1215 gcg tcg gca ggc gga tcc gac gag tcg gac ggt ctg ctt cgg ctt gag          3695
Ala Ser Ala Gly Gly Ser Asp Glu Ser Asp Gly Leu Leu Arg Leu Glu
                1220                1225                1230 tgg ttg ccg gtg gcg gag gcc cac tac gac ggt gcc gac gag ctg ccc          3743
Trp Leu Pro Val Ala Glu Ala His Tyr Asp Gly Ala Asp Glu Leu Pro
            1235                1240                1245 gag ggc tac acc ctc atc acc gcc aca cac ccc gac gac ccc gac gac          3791
Glu Gly Tyr Thr Leu Ile Thr Ala Thr His Pro Asp Asp Pro Asp Asp
        1250                1255                1260 ccc acc aac ccc cac aac aca ccc aca cgc acc cac aca caa acc aca          3839
Pro Thr Asn Pro His Asn Thr Pro Thr Arg Thr His Thr Gln Thr Thr
    1265                1270                1275 cgc gtc ctc acc gcc ctc caa cac cac ctc atc acc acc aac cac acc          3887
Arg Val Leu Thr Ala Leu Gln His His Leu Ile Thr Thr Asn His Thr
1280                1285                1290                1295 ctc atc gtc cac acc acc acc gac ccc cca ggc gcc gcc gtc acc ggc          3935
Leu Ile Val His Thr Thr Thr Asp Pro Pro Gly Ala Ala Val Thr Gly
                1300                1305                1310 ctc acc cgc acc gca caa aac gaa cac ccc ggc cgc atc cac ctc atc          3983
Leu Thr Arg Thr Ala Gln Asn Glu His Pro Gly Arg Ile His Leu Ile
            1315                1320                1325 gaa acc cac cac ccc cac acc cca ctc ccc ctc acc caa ctc acc acc          4031
Glu Thr His His Pro His Thr Pro Leu Pro Leu Thr Gln Leu Thr Thr
        1330                1335                1340 ctc cac caa ccc cac cta cgc ctc acc aac aac acc ctc cac acc ccc          4079
Leu His Gln Pro His Leu Arg Leu Thr Asn Asn Thr Leu His Thr Pro
    1345                1350                1355 cac ctc acc ccc atc acc acc cac cac aac acc acc aca acc acc ccc          4127
His Leu Thr Pro Ile Thr Thr His His Asn Thr Thr Thr Thr Thr Pro
1360                1365                1370                1375 aac acc cca ccc ctc aac ccc aac cac gcc atc ctc atc acc ggc ggc          4175
Asn Thr Pro Pro Leu Asn Pro Asn His Ala Ile Leu Ile Thr Gly Gly
                1380                1385                1390 tcc ggc acc ctc gcc ggc atc ctc gcc cgc cac ctc aac cac ccc cac          4223
Ser Gly Thr Leu Ala Gly Ile Leu Ala Arg His Leu Asn His Pro His
            1395                1400                1405
```

```
acc tac ctc ctc tcc cgc aca cca cca ccc ccc acc aca ccc ggc acc    4271
Thr Tyr Leu Leu Ser Arg Thr Pro Pro Pro Pro Thr Thr Pro Gly Thr
        1410                1415                1420 cac atc ccc tgc gac ctc acc gac ccc acc caa atc acc caa gcc ctc    4319
His Ile Pro Cys Asp Leu Thr Asp Pro Thr Gln Ile Thr Gln Ala Leu
1425                1430                1435 acc cac ata cca caa ccc ctc acc ggc atc ttc cac acc gcc gcc acc    4367
Thr His Ile Pro Gln Pro Leu Thr Gly Ile Phe His Thr Ala Ala Thr
1440                1445                1450                1455 ctc gac gac gcc acc ctc acc aac ctc acc ccc caa cac ctc acc acc    4415
Leu Asp Asp Ala Thr Leu Thr Asn Leu Thr Pro Gln His Leu Thr Thr
            1460                1465                1470 acc ctc caa ccc aaa gcc gac gcc gcc tgg cac ctc cac cac cac acc    4463
Thr Leu Gln Pro Lys Ala Asp Ala Ala Trp His Leu His His His Thr
        1475                1480                1485 caa aac caa ccc ctc acc cac ttc gtc ctc tac tcc agc gcc gcc gcc    4511
Gln Asn Gln Pro Leu Thr His Phe Val Leu Tyr Ser Ser Ala Ala Ala
        1490                1495                1500 acc ctc ggc agc ccc ggc caa gcc aac tac gcc gcc gcc aac gcc ttc    4559
Thr Leu Gly Ser Pro Gly Gln Ala Asn Tyr Ala Ala Ala Asn Ala Phe
1505                1510                1515 ctc gac gcc ctc gcc acc cac cgc cac acc caa gga caa ccc gcc acc    4607
Leu Asp Ala Leu Ala Thr His Arg His Thr Gln Gly Gln Pro Ala Thr
1520                1525                1530                1535 acc atc gcc tgg ggc atg tgg cac acc acc acc aca ctc acc agc caa    4655
Thr Ile Ala Trp Gly Met Trp His Thr Thr Thr Thr Leu Thr Ser Gln
            1540                1545                1550 ctc acc gac agc gac cgc gac cgc atc cgc cgc ggc ggc ttc ctg ccg    4703
Leu Thr Asp Ser Asp Arg Asp Arg Ile Arg Arg Gly Gly Phe Leu Pro
        1555                1560                1565 atc tcg gac gac gag ggc atg c                                      4725
Ile Ser Asp Asp Glu Gly Met
        1570
```

<210> SEQ ID NO 25
<211> LENGTH: 1574
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 25

```
Met Arg Leu Tyr Glu Ala Ala Arg Arg Thr Gly Ser Pro Val Val Val
 1               5                  10                  15

Ala Ala Ala Leu Asp Asp Ala Pro Asp Val Pro Leu Leu Arg Gly Leu
            20                  25                  30

Arg Arg Thr Thr Val Arg Arg Ala Ala Val Arg Glu Arg Ser Leu Ala
        35                  40                  45

Asp Arg Ser Pro Cys Cys Pro Thr Thr Ser Ala Pro Thr Pro Pro Ser
    50                  55                  60

Arg Ser Ser Trp Asn Ser Thr Ala Thr Val Leu Gly His Leu Gly Ala
65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125
```

```
Ala Ala Arg Leu Gly Asp Glu Leu Ala Gly Thr Arg Ala Pro Val Ala
    130                 135                 140

Ala Arg Thr Ala Ala Thr Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
                180                 185                 190

Ala Asp Arg Gly Trp Asp Val Asp Ala Leu Tyr Asp Pro Asp Pro Asp
                195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
                260                 265                 270

Gly Val Phe Ile Gly Ala Phe Ser Tyr Gly Tyr Gly Thr Gly Ala Asp
                275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
                340                 345                 350

Met Ala Ser Pro Gly Gly Phe Val Glu Phe Ser Arg Gln Arg Gly Leu
                355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
                420                 425                 430

Ser Gln Glu Arg Val Ile His Gln Ala Leu Ala Asn Ala Lys Leu Thr
    435                 440                 445

Pro Ala Asp Val Asp Ala Val Glu Ala His Gly Thr Gly Thr Arg Leu
450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
                500                 505                 510

Ile Arg His Gly Glu Leu Pro Pro Thr Leu His Ala Asp Glu Pro Ser
    515                 520                 525

Pro His Val Asp Trp Thr Ala Gly Ala Val Glu Leu Leu Thr Ser Ala
530                 535                 540

Arg Pro Trp Pro Gly Thr Gly Arg Pro Arg Arg Ala Ala Val Ser Ser
```

-continued

```
             545                 550                 555                 560
        Phe Gly Val Ser Gly Thr Asn Ala His Ile Ile Leu Glu Ala Gly Pro
                        565                 570                 575
        Val Lys Thr Gly Pro Val Glu Ala Gly Ala Ile Glu Ala Gly Pro Val
                        580                 585                 590
        Glu Val Gly Pro Val Glu Ala Gly Pro Leu Pro Ala Ala Pro Pro Ser
                    595                 600                 605
        Ala Pro Gly Glu Asp Leu Pro Leu Leu Val Ser Ala Arg Ser Pro Glu
                610                 615                 620
        Ala Leu Asp Glu Gln Ile Gly Arg Leu Arg Ala Tyr Leu Asp Thr Gly
        625                 630                 635                 640
        Pro Gly Val Asp Arg Ala Ala Val Ala Gln Thr Leu Ala Arg Arg Thr
                            645                 650                 655
        His Phe Thr His Arg Ala Val Leu Leu Gly Asp Thr Val Ile Gly Ala
                            660                 665                 670
        Pro Pro Ala Asp Gln Ala Asp Glu Leu Val Phe Val Tyr Ser Gly Gln
                        675                 680                 685
        Gly Thr Gln His Pro Ala Met Gly Glu Gln Leu Ala Ala Ala Phe Pro
                    690                 695                 700
        Val Phe Ala Asp Ala Trp His Asp Ala Leu Arg Arg Leu Asp Pro
        705                 710                 715                 720
        Asp Pro His Asp Pro Thr Arg Ser Gln His Thr Leu Phe Ala His Gln
                            725                 730                 735
        Ala Ala Phe Thr Ala Leu Leu Arg Ser Trp Asp Ile Thr Pro His Ala
                        740                 745                 750
        Val Ile Gly His Ser Leu Gly Glu Ile Thr Ala Ala Tyr Ala Ala Gly
                        755                 760                 765
        Ile Leu Ser Leu Asp Asp Ala Cys Thr Leu Ile Thr Thr Arg Ala Arg
                    770                 775                 780
        Leu Met His Thr Leu Pro Pro Gly Ala Met Val Thr Val Leu Thr
        785                 790                 795                 800
        Ser Glu Glu Glu Ala Arg Gln Ala Leu Arg Pro Gly Val Glu Ile Ala
                            805                 810                 815
        Ala Val Phe Gly Pro His Ser Val Val Leu Ser Gly Asp Glu Asp Ala
                        820                 825                 830
        Val Leu Asp Val Ala Gln Arg Leu Gly Ile His His Arg Leu Pro Ala
                    835                 840                 845
        Pro His Ala Gly His Ser Ala His Met Glu Pro Val Ala Ala Glu Leu
                850                 855                 860
        Leu Ala Thr Thr Arg Glu Leu Arg Tyr Asp Arg Pro His Thr Ala Ile
        865                 870                 875                 880
        Pro Asn Asp Pro Thr Thr Ala Glu Tyr Trp Ala Glu Gln Val Arg Asn
                            885                 890                 895
        Pro Val Leu Phe His Ala His Thr Gln Arg Tyr Pro Asp Ala Val Phe
                        900                 905                 910
        Val Glu Ile Gly Pro Gly Gln Asp Leu Ser Pro Leu Val Asp Gly Ile
                        915                 920                 925
        Ala Leu Gln Asn Gly Thr Ala Asp Glu Val His Ala Leu His Thr Ala
                    930                 935                 940
        Leu Ala Arg Leu Phe Thr Arg Gly Ala Thr Leu Asp Trp Ser Arg Ile
        945                 950                 955                 960
        Leu Gly Gly Ala Ser Arg His Asp Pro Asp Val Pro Ser Tyr Ala Phe
                            965                 970                 975
```

-continued

```
Gln Arg Arg Pro Tyr Trp Ile Glu Ser Ala Pro Pro Ala Thr Ala Asp
            980                 985                 990
Ser Gly His Pro Val Leu Gly Thr Gly Val Ala Val Ala Gly Ser Pro
        995                1000                1005
Gly Arg Val Phe Thr Gly Pro Val Pro Ala Gly Ala Asp Arg Ala Val
   1010                1015                1020
Phe Ile Ala Glu Leu Ala Leu Ala Ala Ala Asp Ala Thr Asp Cys Ala
1025                1030                1035                1040
Thr Val Glu Gln Leu Asp Val Thr Ser Val Pro Gly Gly Ser Ala Arg
                1045                1050                1055
Gly Arg Ala Thr Ala Gln Thr Trp Val Asp Glu Pro Ala Ala Asp Gly
            1060                1065                1070
Arg Arg Arg Phe Thr Val His Thr Arg Val Gly Asp Ala Pro Trp Thr
        1075                1080                1085
Leu His Ala Glu Gly Val Leu Arg Pro Gly Arg Val Pro Gln Pro Glu
    1090                1095                1100
Ala Val Asp Thr Ala Trp Pro Pro Gly Ala Val Pro Ala Asp Gly
1105                1110                1115                1120
Leu Pro Gly Ala Trp Arg Arg Ala Asp Gln Val Phe Val Glu Ala Glu
                1125                1130                1135
Val Asp Ser Pro Asp Gly Phe Val Ala His Pro Asp Leu Leu Asp Ala
            1140                1145                1150
Val Phe Ser Ala Val Gly Asp Gly Ser Arg Gln Pro Thr Gly Trp Arg
        1155                1160                1165
Asp Leu Ala Val His Ala Ser Asp Ala Thr Val Leu Arg Ala Cys Leu
    1170                1175                1180
Thr Arg Arg Asp Ser Gly Val Val Glu Leu Ala Ala Phe Asp Gly Ala
1185                1190                1195                1200
Gly Met Pro Val Leu Thr Ala Glu Ser Val Thr Leu Gly Glu Val Ala
                1205                1210                1215
Ser Ala Gly Gly Ser Asp Glu Ser Asp Gly Leu Leu Arg Leu Glu Trp
            1220                1225                1230
Leu Pro Val Ala Glu Ala His Tyr Asp Gly Ala Asp Glu Leu Pro Glu
        1235                1240                1245
Gly Tyr Thr Leu Ile Thr Ala Thr His Pro Asp Pro Asp Pro
    1250                1255                1260
Thr Asn Pro His Asn Thr Pro Thr Arg Thr His Thr Gln Thr Arg
1265                1270                1275                1280
Val Leu Thr Ala Leu Gln His His Leu Ile Thr Thr Asn His Thr Leu
                1285                1290                1295
Ile Val His Thr Thr Thr Asp Pro Pro Gly Ala Ala Val Thr Gly Leu
            1300                1305                1310
Thr Arg Thr Ala Gln Asn Glu His Pro Gly Arg Ile His Leu Ile Glu
        1315                1320                1325
Thr His His Pro His Thr Pro Leu Pro Leu Thr Gln Leu Thr Thr Leu
    1330                1335                1340
His Gln Pro His Leu Arg Leu Thr Asn Asn Thr Leu His Thr Pro His
1345                1350                1355                1360
Leu Thr Pro Ile Thr Thr His His Asn Thr Thr Thr Thr Pro Asn
                1365                1370                1375
Thr Pro Pro Leu Asn Pro Asn His Ala Ile Leu Ile Thr Gly Gly Ser
            1380                1385                1390
```

-continued

```
Gly Thr Leu Ala Gly Ile Leu Ala Arg His Leu Asn His Pro His Thr
        1395                1400                1405

Tyr Leu Leu Ser Arg Thr Pro Pro Pro Thr Thr Pro Gly Thr His
    1410                1415                1420

Ile Pro Cys Asp Leu Thr Asp Pro Thr Gln Ile Thr Gln Ala Leu Thr
1425                1430                1435                1440

His Ile Pro Gln Pro Leu Thr Gly Ile Phe His Thr Ala Ala Thr Leu
                1445                1450                1455

Asp Asp Ala Thr Leu Thr Asn Leu Thr Pro Gln His Leu Thr Thr Thr
            1460                1465                1470

Leu Gln Pro Lys Ala Asp Ala Ala Trp His Leu His His His Thr Gln
        1475                1480                1485

Asn Gln Pro Leu Thr His Phe Val Leu Tyr Ser Ser Ala Ala Ala Thr
    1490                1495                1500

Leu Gly Ser Pro Gly Gln Ala Asn Tyr Ala Ala Ala Asn Ala Phe Leu
1505                1510                1515                1520

Asp Ala Leu Ala Thr His Arg His Thr Gln Gly Gln Pro Ala Thr Thr
                1525                1530                1535

Ile Ala Trp Gly Met Trp His Thr Thr Thr Thr Leu Thr Ser Gln Leu
            1540                1545                1550

Thr Asp Ser Asp Arg Asp Arg Ile Arg Arg Gly Gly Phe Leu Pro Ile
        1555                1560                1565

Ser Asp Asp Glu Gly Met
    1570
```

<210> SEQ ID NO 26
<211> LENGTH: 4674
<212> TYPE: DNA
<213> ORGANISM: Artificial Sequence
<220> FEATURE:
<223> OTHER INFORMATION: Description of Artificial Sequence: DNA
    encoding synthetic PKS synthase fragment
<220> FEATURE:
<221> NAME/KEY: CDS
<222> LOCATION: (3)..(4673)

<400> SEQUENCE: 26

```
gc atg cgg ctg tac gag gcg gca cgg cgc acc gga agt ccc gtg gtg      47
   Met Arg Leu Tyr Glu Ala Ala Arg Arg Thr Gly Ser Pro Val Val
   1               5                   10                  15 gtg gcg gcc gcg ctc gac gac gcg ccg gac gtg ccg ctg ctg cgc ggg     95
Val Ala Ala Ala Leu Asp Asp Ala Pro Asp Val Pro Leu Leu Arg Gly
            20                  25                  30 ctg cgg cgt acg acc gtc cgg cgt gcc gcc gtc cgg gaa cgc tct ctc    143
Leu Arg Arg Thr Thr Val Arg Arg Ala Ala Val Arg Glu Arg Ser Leu
        35                  40                  45 gcc gac cgc tcg ccg tgc tgc ccg acg acg agc gcg ccg acg cct ccc    191
Ala Asp Arg Ser Pro Cys Cys Pro Thr Thr Ser Ala Pro Thr Pro Pro
    50                  55                  60 tcg cgt tcg tcc tgg aac agc acc gcc acc gtg ctc ggc cac ctg ggc    239
Ser Arg Ser Ser Trp Asn Ser Thr Ala Thr Val Leu Gly His Leu Gly
65                  70                  75 gcc gaa gac atc ccg gcg acg acg acg ttc aag gaa ctc ggc atc gac    287
Ala Glu Asp Ile Pro Ala Thr Thr Thr Phe Lys Glu Leu Gly Ile Asp
80                  85                  90                  95 tcg ctc acc gcg gtc cag ctg cgc aac gcg ctg acc acg gcg acc ggc    335
Ser Leu Thr Ala Val Gln Leu Arg Asn Ala Leu Thr Thr Ala Thr Gly
                100                 105                 110 gta cgc ctc aac gcc aca gcg gtc ttc gac ttt ccg acg ccg cgc gcg    383
```

```
Val Arg Leu Asn Ala Thr Ala Val Phe Asp Phe Pro Thr Pro Arg Ala
        115                 120                 125 ctc gcc gcg aga ctc ggc gac gag ctg gcc ggt acc cgc gcg ccc gtc     431
Leu Ala Ala Arg Leu Gly Asp Glu Leu Ala Gly Thr Arg Ala Pro Val
        130                 135                 140 gcg gcc cgg acc gcg gcc acc gcg gcc gcg cac gac gaa ccg ctg gcg     479
Ala Ala Arg Thr Ala Ala Thr Ala Ala Ala His Asp Glu Pro Leu Ala
        145                 150                 155 atc gtg ggc atg gcc tgc cgt ctg ccg ggc ggg gtc gcg tcg cca cag     527
Ile Val Gly Met Ala Cys Arg Leu Pro Gly Gly Val Ala Ser Pro Gln
160                 165                 170                 175 gag ctg tgg cgt ctc gtc gcg tcc ggc acc gac gcc atc acg gag ttc     575
Glu Leu Trp Arg Leu Val Ala Ser Gly Thr Asp Ala Ile Thr Glu Phe
                180                 185                 190 ccc gcg gac cgc ggc tgg gac gtg gac gcg ctc tac gac ccg gac ccc     623
Pro Ala Asp Arg Gly Trp Asp Val Asp Ala Leu Tyr Asp Pro Asp Pro
                195                 200                 205 gac gcg atc ggc aag acc ttc gtc cgg cac ggc ggc ttc ctc gac ggt     671
Asp Ala Ile Gly Lys Thr Phe Val Arg His Gly Gly Phe Leu Asp Gly
                210                 215                 220 gcg acc ggc ttc gac gcg gcg ttc ttc ggg atc agc ccg cgc gag gcc     719
Ala Thr Gly Phe Asp Ala Ala Phe Phe Gly Ile Ser Pro Arg Glu Ala
225                 230                 235 ctg gcc atg gac ccg cag caa cgg gtg ctc ctg gag acg tcc tgg gag     767
Leu Ala Met Asp Pro Gln Gln Arg Val Leu Leu Glu Thr Ser Trp Glu
240                 245                 250                 255 gcg ttc gaa agc gcg ggc atc acc ccg gac gcg gcg cgg ggc agc gac     815
Ala Phe Glu Ser Ala Gly Ile Thr Pro Asp Ala Ala Arg Gly Ser Asp
                260                 265                 270 acc ggc gtg ttc atc ggc gcg ttc tcc tac ggg tac ggc acg ggt gcg     863
Thr Gly Val Phe Ile Gly Ala Phe Ser Tyr Gly Tyr Gly Thr Gly Ala
                275                 280                 285 gat acc aac ggc ttc ggc gcg aca ggg tcg cag acc agc gtg ctc tcc     911
Asp Thr Asn Gly Phe Gly Ala Thr Gly Ser Gln Thr Ser Val Leu Ser
                290                 295                 300 ggc cgc ctc tcg tac ttc tac ggt ctg gag ggc cct tcg gtc acg gtc     959
Gly Arg Leu Ser Tyr Phe Tyr Gly Leu Glu Gly Pro Ser Val Thr Val
305                 310                 315 gac acc gcc tgc tcg tcg tca ctg gtc gcc ctg cac cag gca ggg cag    1007
Asp Thr Ala Cys Ser Ser Ser Leu Val Ala Leu His Gln Ala Gly Gln
320                 325                 330                 335 tcc ctg cgc tcg ggc gaa tgc tcg ctc gcc ctg gtc ggc ggt gtc acg    1055
Ser Leu Arg Ser Gly Glu Cys Ser Leu Ala Leu Val Gly Gly Val Thr
                340                 345                 350 gtg atg gcg tcg ccc ggc gga ttc gtc gag ttc tcc cgg cag cgc ggg    1103
Val Met Ala Ser Pro Gly Gly Phe Val Glu Phe Ser Arg Gln Arg Gly
                355                 360                 365 ctc gcg ccg gac ggg cgg gcg aag gcg ttc ggc gcg ggc gcg gac ggt    1151
Leu Ala Pro Asp Gly Arg Ala Lys Ala Phe Gly Ala Gly Ala Asp Gly
                370                 375                 380 acg agc ttc gcc gag ggc gcc ggt gcc ctg gtg gtc gag cgg ctc tcc    1199
Thr Ser Phe Ala Glu Gly Ala Gly Ala Leu Val Val Glu Arg Leu Ser
385                 390                 395 gac gcg gag cgc cac ggc cac acc gtc ctc gcc ctc gta cgc ggc tcc    1247
Asp Ala Glu Arg His Gly His Thr Val Leu Ala Leu Val Arg Gly Ser
400                 405                 410                 415 gcg gct aac tcc gac ggc gcg tcg aac ggt ctg tcg gcg ccg aac ggc    1295
Ala Ala Asn Ser Asp Gly Ala Ser Asn Gly Leu Ser Ala Pro Asn Gly
                420                 425                 430
```

-continued

| | |
|---|---|
| ccc tcc cag gaa cgc gtc atc cac cag gcc ctc gcg aac gcg aaa ctc<br>Pro Ser Gln Glu Arg Val Ile His Gln Ala Leu Ala Asn Ala Lys Leu<br>435 440 445 | 1343 |
| acc ccc gcc gat gtc gac gcg gtc gag gcg cac ggc acc ggc acc cgc<br>Thr Pro Ala Asp Val Asp Ala Val Glu Ala His Gly Thr Gly Thr Arg<br>450 455 460 | 1391 |
| ctc ggc gac ccc atc gag gcg cag gcg ctg ctc gcg acg tac gga cag<br>Leu Gly Asp Pro Ile Glu Ala Gln Ala Leu Leu Ala Thr Tyr Gly Gln<br>465 470 475 | 1439 |
| gac cgg gcg acg ccc ctg ctc ggc tcg ctg aag tcg aac atc ggg<br>Asp Arg Ala Thr Pro Leu Leu Leu Gly Ser Leu Lys Ser Asn Ile Gly<br>480 485 490 495 | 1487 |
| cac gcc cag gcc gcg tca ggg gtc gcc ggg atc atc aag atg gtg cag<br>His Ala Gln Ala Ala Ser Gly Val Ala Gly Ile Ile Lys Met Val Gln<br>500 505 510 | 1535 |
| gcc atc cgg cac ggg gaa ctg ccg ccg aca ctg cac gcg gac gag ccg<br>Ala Ile Arg His Gly Glu Leu Pro Pro Thr Leu His Ala Asp Glu Pro<br>515 520 525 | 1583 |
| tcg ccg cac gtc gac tgg acg gcc ggt gcc gtc gag ctc ctg acg tcg<br>Ser Pro His Val Asp Trp Thr Ala Gly Ala Val Glu Leu Leu Thr Ser<br>530 535 540 | 1631 |
| gcc cgg ccg tgg ccg ggg acc ggt cgc cct agg cgg gca ggc gtg tcg<br>Ala Arg Pro Trp Pro Gly Thr Gly Arg Pro Arg Arg Ala Gly Val Ser<br>545 550 555 | 1679 |
| tcc ttc ggg atc agt ggc acc aac gcc cac gtc atc ctg gaa agc gca<br>Ser Phe Gly Ile Ser Gly Thr Asn Ala His Val Ile Leu Glu Ser Ala<br>560 565 570 575 | 1727 |
| ccc ccc act cag cct gcg gac aac gcg gtg atc gag cgg gca ccg gag<br>Pro Pro Thr Gln Pro Ala Asp Asn Ala Val Ile Glu Arg Ala Pro Glu<br>580 585 590 | 1775 |
| tgg gtg ccg ttg gtg att tcg gcc agg acc cag tcg gct ttg act gag<br>Trp Val Pro Leu Val Ile Ser Ala Arg Thr Gln Ser Ala Leu Thr Glu<br>595 600 605 | 1823 |
| cac gag ggc cgg ttg cgt gcg tat ctg gcg gcg tcg ccc ggg gtg gat<br>His Glu Gly Arg Leu Arg Ala Tyr Leu Ala Ala Ser Pro Gly Val Asp<br>610 615 620 | 1871 |
| atg cgg gct gtg gca tcg acg ctg gcg atg aca cgg tcg gtg ttc gag<br>Met Arg Ala Val Ala Ser Thr Leu Ala Met Thr Arg Ser Val Phe Glu<br>625 630 635 | 1919 |
| cac cgt gcc gtg ctg ctg gga gat gac acc gtc acc ggc acc gct gtg<br>His Arg Ala Val Leu Leu Gly Asp Asp Thr Val Thr Gly Thr Ala Val<br>640 645 650 655 | 1967 |
| tct gac cct cgg gcg gtg ttc gtc ttc ccg gga cag ggg tcg cag cgt<br>Ser Asp Pro Arg Ala Val Phe Val Phe Pro Gly Gln Gly Ser Gln Arg<br>660 665 670 | 2015 |
| gct ggc atg ggt gag gaa ctg gcc gcc gcg ttc ccc gtc ttc gcg cgg<br>Ala Gly Met Gly Glu Glu Leu Ala Ala Ala Phe Pro Val Phe Ala Arg<br>675 680 685 | 2063 |
| atc cat cag cag gtg tgg gac ctg ctc gat gtg ccc gat ctg gag gtg<br>Ile His Gln Gln Val Trp Asp Leu Leu Asp Val Pro Asp Leu Glu Val<br>690 695 700 | 2111 |
| aac gag acc ggt tac gcc cag ccg gcc ctg ttc gca atg cag gtg gct<br>Asn Glu Thr Gly Tyr Ala Gln Pro Ala Leu Phe Ala Met Gln Val Ala<br>705 710 715 | 2159 |
| ctg ttc ggg ctg ctg gaa tcg tgg ggt gta cga ccg gac gcg gtg atc<br>Leu Phe Gly Leu Leu Glu Ser Trp Gly Val Arg Pro Asp Ala Val Ile<br>720 725 730 735 | 2207 |
| ggc cat tcg gtg ggt gag ctt gcg gct gcg tat gtg tcc ggg gtg tgg<br>Gly His Ser Val Gly Glu Leu Ala Ala Ala Tyr Val Ser Gly Val Trp<br>740 745 750 | 2255 |

-continued

| | |
|---|---|
| tcg ttg gag gat gcc tgc act ttg gtg tcg gcg cgg gct cgt ctg atg<br>Ser Leu Glu Asp Ala Cys Thr Leu Val Ser Ala Arg Ala Arg Leu Met<br>     755                     760                765 | 2303 |
| cag gct ctg ccc gcg ggt ggg gtg atg gtc gct gtc ccg gtc tcg gag<br>Gln Ala Leu Pro Ala Gly Gly Val Met Val Ala Val Pro Val Ser Glu<br>770                     775                    780 | 2351 |
| gat gag gcc cgg gcc gtg ctg ggt gag ggt gtg gag atc gcc gcg gtc<br>Asp Glu Ala Arg Ala Val Leu Gly Glu Gly Val Glu Ile Ala Ala Val<br>785                    790                   795 | 2399 |
| aac ggc ccg tcg tcg gtg gtt ctc tcc ggt gat gag gcc gcc gtg ctg<br>Asn Gly Pro Ser Ser Val Val Leu Ser Gly Asp Glu Ala Ala Val Leu<br>800                     805                 810           815 | 2447 |
| cag gcc gcg gag ggg ctg ggg aag tgg acg cgg ctg gcg acc agc cac<br>Gln Ala Ala Glu Gly Leu Gly Lys Trp Thr Arg Leu Ala Thr Ser His<br>     820                     825                 830 | 2495 |
| gcg ttc cat tcc gcc cgt atg gaa ccc atg ctg gag gag ttc cgg gcg<br>Ala Phe His Ser Ala Arg Met Glu Pro Met Leu Glu Glu Phe Arg Ala<br>           835                     840                845 | 2543 |
| gtc gcc gaa ggc ctg acc tac cgg acg ccg cag gtc tcc atg gcc gtt<br>Val Ala Glu Gly Leu Thr Tyr Arg Thr Pro Gln Val Ser Met Ala Val<br>850                     855                    860 | 2591 |
| ggt gat cag gtg acc acc gct gag tac tgg gtg cgg cag gtc cgg gac<br>Gly Asp Gln Val Thr Thr Ala Glu Tyr Trp Val Arg Gln Val Arg Asp<br>865                    870                   875 | 2639 |
| acg gtc cgg ttc ggc gag cag gtg gcc tcg tac gag gac gcc gtg ttc<br>Thr Val Arg Phe Gly Glu Gln Val Ala Ser Tyr Glu Asp Ala Val Phe<br>880                     885                   890           895 | 2687 |
| gtc gag ctg ggt gcc gac cgg tca ctg gcc cgc ctg gtc gac ggt gtc<br>Val Glu Leu Gly Ala Asp Arg Ser Leu Ala Arg Leu Val Asp Gly Val<br>     900                     905                 910 | 2735 |
| gcg atg ctg cac ggc gac cac gaa atc cag gcc gcg atc ggc gcc ctg<br>Ala Met Leu His Gly Asp His Glu Ile Gln Ala Ala Ile Gly Ala Leu<br>           915                     920                925 | 2783 |
| gcc cac ctg tat gtc aac ggc gtc acg gtc gac tgg ccc gcg ctc ctg<br>Ala His Leu Tyr Val Asn Gly Val Thr Val Asp Trp Pro Ala Leu Leu<br>930                     935                    940 | 2831 |
| ggc gat gct ccg gca aca cgg gtg ctg gac ctt ccg aca tac gcc ttc<br>Gly Asp Ala Pro Ala Thr Arg Val Leu Asp Leu Pro Thr Tyr Ala Phe<br>945                     950                    955 | 2879 |
| cag cac cag cgc tac tgg ctc gag tcg gct ccc ccg gcc acg gcc gac<br>Gln His Gln Arg Tyr Trp Leu Glu Ser Ala Pro Pro Ala Thr Ala Asp<br>960                     965                    970           975 | 2927 |
| tcg ggc cac ccc gtc ctc ggc acc gga gtc gcc gtc gcc ggg tcg ccg<br>Ser Gly His Pro Val Leu Gly Thr Gly Val Ala Val Ala Gly Ser Pro<br>           980                     985                990 | 2975 |
| ggc cgg gtg ttc acg ggt ccc gtg ccc gcc ggt gcg gac cgc gcg gtg<br>Gly Arg Val Phe Thr Gly Pro Val Pro Ala Gly Ala Asp Arg Ala Val<br>995                     1000                1005 | 3023 |
| ttc atc gcc gaa ctg gcg ctc gcc gcc gcc gac gcc acc gac tgc gcc<br>Phe Ile Ala Glu Leu Ala Leu Ala Ala Ala Asp Ala Thr Asp Cys Ala<br>          1010                    1015                1020 | 3071 |
| acg gtc gaa cag ctc gac gtc acc tcc gtg ccc ggc gga tcc gcc cgc<br>Thr Val Glu Gln Leu Asp Val Thr Ser Val Pro Gly Gly Ser Ala Arg<br>1025                 1030                  1035 | 3119 |
| ggc agg gcc acc gcg cag acc tgg gtc gat gaa ccc gcc gac ggg<br>Gly Arg Ala Thr Ala Gln Thr Trp Val Asp Glu Pro Ala Asp Gly<br>1040               1045                1050               1055 | 3167 |
| cgg cgc cgc ttc acc gtc cac acc cgc gtc ggc gac gcc ccg tgg acg<br>Arg Arg Arg Phe Thr Val His Thr Arg Val Gly Asp Ala Pro Trp Thr | 3215 |

```
                   1060              1065              1070
ctg cac gcc gag ggg gtt ctc cgc ccc ggc cgc gtg ccc cag ccc gaa       3263
Leu His Ala Glu Gly Val Leu Arg Pro Gly Arg Val Pro Gln Pro Glu
            1075              1080              1085 gcc gtc gac acc gcc tgg ccc ccg ccg ggc gcg gtg ccc gcg gac ggg       3311
Ala Val Asp Thr Ala Trp Pro Pro Gly Ala Val Pro Ala Asp Gly
        1090              1095              1100 ctg ccc ggg gcg tgg cga cgc gcg gac cag gtc ttc gtc gaa gcc gaa       3359
Leu Pro Gly Ala Trp Arg Arg Ala Asp Gln Val Phe Val Glu Ala Glu
    1105              1110              1115 gtc gac agc cct gac ggc ttc gtg gca cac ccc gac ctg ctc gac gcg       3407
Val Asp Ser Pro Asp Gly Phe Val Ala His Pro Asp Leu Leu Asp Ala
1120              1125              1130              1135 gtc ttc tcc gcg gtc ggc gac ggg agc cgc cag ccg acc gga tgg cgc       3455
Val Phe Ser Ala Val Gly Asp Gly Ser Arg Gln Pro Thr Gly Trp Arg
            1140              1145              1150 gac ctc gcg gtg cac gcg tcg gac gcc acc gtg ctg cgc gcc tgc ctc       3503
Asp Leu Ala Val His Ala Ser Asp Ala Thr Val Leu Arg Ala Cys Leu
        1155              1160              1165 acc cgc cgc gac agt ggt gtc gtg gag ctc gcc gcc ttc gac ggt gcc       3551
Thr Arg Arg Asp Ser Gly Val Val Glu Leu Ala Ala Phe Asp Gly Ala
    1170              1175              1180 gga atg ccg gtg ctc acc gcg gag tcg gtg acg ctg ggc gag gtc gcg       3599
Gly Met Pro Val Leu Thr Ala Glu Ser Val Thr Leu Gly Glu Val Ala
1185              1190              1195 tcg gca ggc gga tcc gac gag tcg gac ggt ctg ctt cgg ctt gag tgg       3647
Ser Ala Gly Gly Ser Asp Glu Ser Asp Gly Leu Leu Arg Leu Glu Trp
1200              1205              1210              1215 ttg ccg gtg gcg gag gcc cac tac gac ggt gcc gac gag ctg ccc gag       3695
Leu Pro Val Ala Glu Ala His Tyr Asp Gly Ala Asp Glu Leu Pro Glu
        1220              1225              1230 ggc tac acc ctc atc acc gcc aca cac ccc gac gac ccc gac gac ccc       3743
Gly Tyr Thr Leu Ile Thr Ala Thr His Pro Asp Asp Pro Asp Asp Pro
    1235              1240              1245 acc aac ccc cac aac aca ccc aca cgc acc cac aca caa acc aca cgc       3791
Thr Asn Pro His Asn Thr Pro Thr Arg Thr His Thr Gln Thr Thr Arg
1250              1255              1260 gtc ctc acc gcc ctc caa cac cac ctc atc acc acc aac cac acc ctc       3839
Val Leu Thr Ala Leu Gln His His Leu Ile Thr Thr Asn His Thr Leu
        1265              1270              1275 atc gtc cac acc acc acc gac ccc cca ggc gcc gcc gtc acc ggc ctc       3887
Ile Val His Thr Thr Thr Asp Pro Pro Gly Ala Ala Val Thr Gly Leu
1280              1285              1290              1295 acc cgc acc gca caa aac gaa cac ccc ggc cgc atc cac ctc atc gaa       3935
Thr Arg Thr Ala Gln Asn Glu His Pro Gly Arg Ile His Leu Ile Glu
        1300              1305              1310 acc cac cac ccc cac acc cca ctc ccc ctc acc caa ctc acc acc ctc       3983
Thr His His Pro His Thr Pro Leu Pro Leu Thr Gln Leu Thr Thr Leu
    1315              1320              1325 cac caa ccc cac cta cgc ctc acc aac aac acc ctc cac acc ccc cac       4031
His Gln Pro His Leu Arg Leu Thr Asn Asn Thr Leu His Thr Pro His
1330              1335              1340 ctc acc ccc atc acc acc cac cac aac acc acc aca acc acc ccc aac       4079
Leu Thr Pro Ile Thr Thr His His Asn Thr Thr Thr Thr Pro Asn
1345              1350              1355 acc cca ccc ctc aac ccc aac cac gcc atc ctc atc acc ggc ggc tcc       4127
Thr Pro Pro Leu Asn Pro Asn His Ala Ile Leu Ile Thr Gly Gly Ser
1360              1365              1370              1375 ggc acc ctc gcc ggc atc ctc gcc cgc cac ctc aac cac ccc cac acc       4175
```

-continued

```
Gly Thr Leu Ala Gly Ile Leu Ala Arg His Leu Asn His Pro His Thr
            1380                1385                1390 tac ctc ctc tcc cgc aca cca cca ccc ccc acc aca ccc ggc acc cac      4223
Tyr Leu Leu Ser Arg Thr Pro Pro Pro Pro Thr Thr Pro Gly Thr His
        1395                1400                1405 atc ccc tgc gac ctc acc gac ccc acc caa atc acc caa gcc ctc acc      4271
Ile Pro Cys Asp Leu Thr Asp Pro Thr Gln Ile Thr Gln Ala Leu Thr
        1410                1415                1420 cac ata cca caa ccc ctc acc ggc atc ttc cac acc gcc gcc acc ctc      4319
His Ile Pro Gln Pro Leu Thr Gly Ile Phe His Thr Ala Ala Thr Leu
        1425                1430                1435 gac gac gcc acc ctc acc aac ctc acc ccc caa cac ctc acc acc acc      4367
Asp Asp Ala Thr Leu Thr Asn Leu Thr Pro Gln His Leu Thr Thr Thr
1440                1445                1450                1455 ctc caa ccc aaa gcc gac gcc gcc tgg cac ctc cac cac cac acc caa      4415
Leu Gln Pro Lys Ala Asp Ala Ala Trp His Leu His His His Thr Gln
            1460                1465                1470 aac caa ccc ctc acc cac ttc gtc ctc tac tcc agc gcc gcc gcc acc      4463
Asn Gln Pro Leu Thr His Phe Val Leu Tyr Ser Ser Ala Ala Ala Thr
        1475                1480                1485 ctc ggc agc ccc ggc caa gcc aac tac gcc gcc gcc aac gcc ttc ctc      4511
Leu Gly Ser Pro Gly Gln Ala Asn Tyr Ala Ala Ala Asn Ala Phe Leu
        1490                1495                1500 gac gcc ctc gcc acc cac cgc cac acc caa gga caa ccc gcc acc acc      4559
Asp Ala Leu Ala Thr His Arg His Thr Gln Gly Gln Pro Ala Thr Thr
        1505                1510                1515 atc gcc tgg ggc atg tgg cac acc acc acc aca ctc acc agc caa ctc      4607
Ile Ala Trp Gly Met Trp His Thr Thr Thr Thr Leu Thr Ser Gln Leu
1520                1525                1530                1535 acc gac agc gac cgc gac cgc atc cgc cgc ggc ggc ttc ctg ccg atc      4655
Thr Asp Ser Asp Arg Asp Arg Ile Arg Arg Gly Gly Phe Leu Pro Ile
            1540                1545                1550 tcg gac gac gag ggc atg c                                            4674
Ser Asp Asp Glu Gly Met
        1555
```

<210> SEQ ID NO 27
<211> LENGTH: 1557
<212> TYPE: PRT
<213> ORGANISM: Artificial Sequence
<220> FEATURE:
<223> OTHER INFORMATION: Description of Artificial Sequence: Synthetic PKS synthase fragment

<400> SEQUENCE: 27

```
Met Arg Leu Tyr Glu Ala Ala Arg Arg Thr Gly Ser Pro Val Val Val
 1               5                  10                  15

Ala Ala Ala Leu Asp Asp Ala Pro Asp Val Pro Leu Leu Arg Gly Leu
                20                  25                  30

Arg Arg Thr Thr Val Arg Arg Ala Ala Val Arg Glu Arg Ser Leu Ala
            35                  40                  45

Asp Arg Ser Pro Cys Cys Pro Thr Thr Ser Ala Pro Thr Pro Pro Ser
        50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
            100                 105                 110
```

-continued

```
Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala His Asp Glu Pro Leu Ala Ile
145                 150                 155                 160

Val Gly Met Ala Cys Arg Leu Pro Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
```

```
                530                 535                 540
Arg Pro Trp Pro Gly Thr Gly Arg Pro Arg Ala Gly Val Ser Ser
545                 550                 555                 560

Phe Gly Ile Ser Gly Thr Asn Ala His Val Ile Leu Glu Ser Ala Pro
                565                 570                 575

Pro Thr Gln Pro Ala Asp Asn Ala Val Ile Glu Arg Ala Pro Glu Trp
                580                 585                 590

Val Pro Leu Val Ile Ser Ala Arg Thr Gln Ser Ala Leu Thr Glu His
                595                 600                 605

Glu Gly Arg Leu Arg Ala Tyr Leu Ala Ala Ser Pro Gly Val Asp Met
610                 615                 620

Arg Ala Val Ala Ser Thr Leu Ala Met Thr Arg Ser Val Phe Glu His
625                 630                 635                 640

Arg Ala Val Leu Leu Gly Asp Asp Thr Val Thr Gly Thr Ala Val Ser
                645                 650                 655

Asp Pro Arg Ala Val Phe Val Phe Pro Gly Gln Gly Ser Gln Arg Ala
                660                 665                 670

Gly Met Gly Glu Glu Leu Ala Ala Ala Phe Pro Val Phe Ala Arg Ile
                675                 680                 685

His Gln Gln Val Trp Asp Leu Leu Asp Val Pro Asp Leu Glu Val Asn
                690                 695                 700

Glu Thr Gly Tyr Ala Gln Pro Ala Leu Phe Ala Met Gln Val Ala Leu
705                 710                 715                 720

Phe Gly Leu Leu Glu Ser Trp Gly Val Arg Pro Asp Ala Val Ile Gly
                725                 730                 735

His Ser Val Gly Glu Leu Ala Ala Ala Tyr Val Ser Gly Val Trp Ser
                740                 745                 750

Leu Glu Asp Ala Cys Thr Leu Val Ser Ala Arg Ala Arg Leu Met Gln
                755                 760                 765

Ala Leu Pro Ala Gly Gly Val Met Val Ala Val Pro Val Ser Glu Asp
                770                 775                 780

Glu Ala Arg Ala Val Leu Gly Glu Gly Val Glu Ile Ala Ala Val Asn
785                 790                 795                 800

Gly Pro Ser Ser Val Val Leu Ser Gly Asp Glu Ala Ala Val Leu Gln
                805                 810                 815

Ala Ala Glu Gly Leu Gly Lys Trp Thr Arg Leu Ala Thr Ser His Ala
                820                 825                 830

Phe His Ser Ala Arg Met Glu Pro Met Leu Glu Glu Phe Arg Ala Val
                835                 840                 845

Ala Glu Gly Leu Thr Tyr Arg Thr Pro Gln Val Ser Met Ala Val Gly
850                 855                 860

Asp Gln Val Thr Thr Ala Glu Tyr Trp Val Arg Gln Val Arg Asp Thr
865                 870                 875                 880

Val Arg Phe Gly Glu Gln Val Ala Ser Tyr Glu Asp Ala Val Phe Val
                885                 890                 895

Glu Leu Gly Ala Asp Arg Ser Leu Ala Arg Leu Val Asp Gly Val Ala
                900                 905                 910

Met Leu His Gly Asp His Glu Ile Gln Ala Ile Gly Ala Leu Ala
                915                 920                 925

His Leu Tyr Val Asn Gly Val Thr Val Asp Trp Pro Ala Leu Leu Gly
                930                 935                 940

Asp Ala Pro Ala Thr Arg Val Leu Asp Leu Pro Thr Tyr Ala Phe Gln
945                 950                 955                 960
```

-continued

```
His Gln Arg Tyr Trp Leu Glu Ser Ala Pro Pro Ala Thr Ala Asp Ser
            965                 970                 975

Gly His Pro Val Leu Gly Thr Gly Val Ala Val Ala Gly Ser Pro Gly
            980                 985                 990

Arg Val Phe Thr Gly Pro Val Pro Ala Gly Ala Asp Arg Ala Val Phe
            995                1000                1005

Ile Ala Glu Leu Ala Leu Ala Ala Ala Asp Ala Thr Asp Cys Ala Thr
           1010                1015                1020

Val Glu Gln Leu Asp Val Thr Ser Val Pro Gly Gly Ser Ala Arg Gly
1025                1030                1035                1040

Arg Ala Thr Ala Gln Thr Trp Val Asp Glu Pro Ala Ala Asp Gly Arg
               1045                1050                1055

Arg Arg Phe Thr Val His Thr Arg Val Gly Asp Ala Pro Trp Thr Leu
               1060                1065                1070

His Ala Glu Gly Val Leu Arg Pro Gly Arg Val Pro Gln Pro Glu Ala
               1075                1080                1085

Val Asp Thr Ala Trp Pro Pro Gly Ala Val Pro Ala Asp Gly Leu
               1090                1095                1100

Pro Gly Ala Trp Arg Arg Ala Asp Gln Val Phe Val Glu Ala Glu Val
1105                1110                1115                1120

Asp Ser Pro Asp Gly Phe Val Ala His Pro Asp Leu Leu Asp Ala Val
               1125                1130                1135

Phe Ser Ala Val Gly Asp Gly Ser Arg Gln Pro Thr Gly Trp Arg Asp
               1140                1145                1150

Leu Ala Val His Ala Ser Asp Ala Thr Val Leu Arg Ala Cys Leu Thr
               1155                1160                1165

Arg Arg Asp Ser Gly Val Val Glu Leu Ala Ala Phe Asp Gly Ala Gly
               1170                1175                1180

Met Pro Val Leu Thr Ala Glu Ser Val Thr Leu Gly Glu Val Ala Ser
1185                1190                1195                1200

Ala Gly Gly Ser Asp Glu Ser Asp Gly Leu Leu Arg Leu Glu Trp Leu
               1205                1210                1215

Pro Val Ala Glu Ala His Tyr Asp Gly Ala Asp Glu Leu Pro Glu Gly
               1220                1225                1230

Tyr Thr Leu Ile Thr Ala Thr His Pro Asp Asp Pro Asp Pro Thr
               1235                1240                1245

Asn Pro His Asn Thr Pro Thr Arg Thr His Thr Gln Thr Thr Arg Val
               1250                1255                1260

Leu Thr Ala Leu Gln His His Leu Ile Thr Thr Asn His Thr Leu Ile
1265                1270                1275                1280

Val His Thr Thr Thr Asp Pro Pro Gly Ala Ala Val Thr Gly Leu Thr
               1285                1290                1295

Arg Thr Ala Gln Asn Glu His Pro Gly Arg Ile His Leu Ile Glu Thr
               1300                1305                1310

His His Pro His Thr Pro Leu Pro Leu Thr Gln Leu Thr Thr Leu His
               1315                1320                1325

Gln Pro His Leu Arg Leu Thr Asn Asn Thr Leu His Thr Pro His Leu
               1330                1335                1340

Thr Pro Ile Thr Thr His His Asn Thr Thr Thr Thr Pro Asn Thr
1345                1350                1355                1360

Pro Pro Leu Asn Pro Asn His Ala Ile Leu Ile Thr Gly Gly Ser Gly
               1365                1370                1375
```

```
Thr Leu Ala Gly Ile Leu Ala Arg His Leu Asn His Pro His Thr Tyr
        1380                1385                1390

Leu Leu Ser Arg Thr Pro Pro Pro Thr Thr Pro Gly Thr His Ile
        1395                1400                1405

Pro Cys Asp Leu Thr Asp Pro Thr Gln Ile Thr Gln Ala Leu Thr His
    1410                1415                1420

Ile Pro Gln Pro Leu Thr Gly Ile Phe His Thr Ala Thr Leu Asp
1425                1430                1435                1440

Asp Ala Thr Leu Thr Asn Leu Thr Pro Gln His Leu Thr Thr Thr Leu
                1445                1450                1455

Gln Pro Lys Ala Asp Ala Ala Trp His Leu His His Thr Gln Asn
        1460                1465                1470

Gln Pro Leu Thr His Phe Val Leu Tyr Ser Ser Ala Ala Thr Leu
        1475                1480                1485

Gly Ser Pro Gly Gln Ala Asn Tyr Ala Ala Ala Asn Ala Phe Leu Asp
        1490                1495                1500

Ala Leu Ala Thr His Arg His Thr Gln Gly Gln Pro Ala Thr Thr Ile
1505                1510                1515                1520

Ala Trp Gly Met Trp His Thr Thr Thr Leu Thr Ser Gln Leu Thr
                1525                1530                1535

Asp Ser Asp Arg Asp Arg Ile Arg Arg Gly Gly Phe Leu Pro Ile Ser
                1540                1545                1550

Asp Asp Glu Gly Met
        1555

<210> SEQ ID NO 28
<211> LENGTH: 4767
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4766)

<400> SEQUENCE: 28 gc atg cgg ctg tac gag gcg gca cgg cgc acc gga agt ccc gtg gtg       47
   Met Arg Leu Tyr Glu Ala Ala Arg Arg Thr Gly Ser Pro Val Val
   1               5                   10                  15 gtg gcg gcc gcg ctc gac gac gcg ccg gac gtg ccg ctg ctg cgc ggg      95
Val Ala Ala Ala Leu Asp Asp Ala Pro Asp Val Pro Leu Leu Arg Gly
                20                  25                  30 ctg cgg cgt acg acc gtc cgg cgt gcc gcc gtc cgg gaa cgc tct ctc     143
Leu Arg Arg Thr Thr Val Arg Arg Ala Ala Val Arg Glu Arg Ser Leu
            35                  40                  45 gcc gac cgc tcg ccg tgc tgc ccg acg acg agc gcg ccg acg cct ccc     191
Ala Asp Arg Ser Pro Cys Cys Pro Thr Thr Ser Ala Pro Thr Pro Pro
        50                  55                  60 tcg cgt tcg tcc tgg aac agc acc gcc acc gtg ctc ggc cac ctg ggc     239
Ser Arg Ser Ser Trp Asn Ser Thr Ala Thr Val Leu Gly His Leu Gly
    65                  70                  75 gcc gaa gac atc ccg gcg acg acg acg ttc aag gaa ctc ggc atc gac     287
Ala Glu Asp Ile Pro Ala Thr Thr Thr Phe Lys Glu Leu Gly Ile Asp
80                  85                  90                  95 tcg ctc acc gcg gtc cag ctg cgc aac gcg ctg acc acg gcg acc ggc     335
Ser Leu Thr Ala Val Gln Leu Arg Asn Ala Leu Thr Thr Ala Thr Gly
                100                 105                 110 gta cgc ctc aac gcc aca gcg gtc ttc gac ttt ccg acg ccg cgc gcg     383
```

-continued

```
Val Arg Leu Asn Ala Thr Ala Val Phe Asp Phe Pro Thr Pro Arg Ala
            115                 120                 125 ctc gcc gcg aga ctc ggc gac gag ctg gcc ggt acc cgc gcg ccc gtc        431
Leu Ala Ala Arg Leu Gly Asp Glu Leu Ala Gly Thr Arg Ala Pro Val
        130                 135                 140 gcg gcc cgg acc gcg gcc acc gcg gcc gcg cac gac gaa ccg ctg gcg        479
Ala Ala Arg Thr Ala Ala Thr Ala Ala Ala His Asp Glu Pro Leu Ala
    145                 150                 155 atc gtg ggc atg gcc tgc cgt ctg ccg ggc ggg gtc gcg tcg cca cag        527
Ile Val Gly Met Ala Cys Arg Leu Pro Gly Gly Val Ala Ser Pro Gln
160                 165                 170                 175 gag ctg tgg cgt ctc gtc gcg tcc ggc acc gac gcc atc acg gag ttc        575
Glu Leu Trp Arg Leu Val Ala Ser Gly Thr Asp Ala Ile Thr Glu Phe
            180                 185                 190 ccc gcg gac cgc ggc tgg gac gtg gac gcg ctc tac gac ccg gac ccc        623
Pro Ala Asp Arg Gly Trp Asp Val Asp Ala Leu Tyr Asp Pro Asp Pro
        195                 200                 205 gac gcg atc ggc aag acc ttc gtc cgg cac ggc ggc ttc ctc gac ggt        671
Asp Ala Ile Gly Lys Thr Phe Val Arg His Gly Gly Phe Leu Asp Gly
    210                 215                 220 gcg acc ggc ttc gac gcg gcg ttc ttc ggg atc agc ccg cgc gag gcc        719
Ala Thr Gly Phe Asp Ala Ala Phe Phe Gly Ile Ser Pro Arg Glu Ala
225                 230                 235 ctg gcc atg gac ccg cag caa cgg gtg ctc ctg gag acg tcc tgg gag        767
Leu Ala Met Asp Pro Gln Gln Arg Val Leu Leu Glu Thr Ser Trp Glu
240                 245                 250                 255 gcg ttc gaa agc gcg ggc atc acc ccg gac gcg gcg cgg ggc agc gac        815
Ala Phe Glu Ser Ala Gly Ile Thr Pro Asp Ala Ala Arg Gly Ser Asp
            260                 265                 270 acc ggc gtg ttc atc ggc gcg ttc tcc tac ggg tac ggc acg ggt gcg        863
Thr Gly Val Phe Ile Gly Ala Phe Ser Tyr Gly Tyr Gly Thr Gly Ala
        275                 280                 285 gat acc aac ggc ttc ggc gcg aca ggg tcg cag acc agc gtg ctc tcc        911
Asp Thr Asn Gly Phe Gly Ala Thr Gly Ser Gln Thr Ser Val Leu Ser
    290                 295                 300 ggc cgc ctc tcg tac ttc tac ggt ctg gag ggc cct tcg gtc acg gtc        959
Gly Arg Leu Ser Tyr Phe Tyr Gly Leu Glu Gly Pro Ser Val Thr Val
305                 310                 315 gac acc gcc tgc tcg tcg tca ctg gtc gcc ctg cac cag gca ggg cag       1007
Asp Thr Ala Cys Ser Ser Ser Leu Val Ala Leu His Gln Ala Gly Gln
320                 325                 330                 335 tcc ctg cgc tcg ggc gaa tgc tcg ctc gcc ctg gtc ggc ggt gtc acg       1055
Ser Leu Arg Ser Gly Glu Cys Ser Leu Ala Leu Val Gly Gly Val Thr
            340                 345                 350 gtg atg gcg tcg ccc ggc gga ttc gtc gag ttc tcc cgg cag cgc ggg       1103
Val Met Ala Ser Pro Gly Gly Phe Val Glu Phe Ser Arg Gln Arg Gly
        355                 360                 365 ctc gcg ccg gac ggg cgg gcg aag gcg ttc ggc gcg ggc gcg gac ggt       1151
Leu Ala Pro Asp Gly Arg Ala Lys Ala Phe Gly Ala Gly Ala Asp Gly
    370                 375                 380 acg agc ttc gcc gag ggc gcc ggt gcc ctg gtg gtc gag cgg ctc tcc       1199
Thr Ser Phe Ala Glu Gly Ala Gly Ala Leu Val Val Glu Arg Leu Ser
385                 390                 395 gac gcg gag cgc cac ggc cac acc gtc ctc gcc ctc gta cgc ggc tcc       1247
Asp Ala Glu Arg His Gly His Thr Val Leu Ala Leu Val Arg Gly Ser
400                 405                 410                 415 gcg gct aac tcc gac ggc gcg tcg aac ggt ctg tcg gcg ccg aac ggc       1295
Ala Ala Asn Ser Asp Gly Ala Ser Asn Gly Leu Ser Ala Pro Asn Gly
            420                 425                 430
```

-continued

| | |
|---|---|
| ccc tcc cag gaa cgc gtc atc cac cag gcc ctc gcg aac gcg aaa ctc<br>Pro Ser Gln Glu Arg Val Ile His Gln Ala Leu Ala Asn Ala Lys Leu<br>             435                               440                        445 | 1343 |
| acc ccc gcc gat gtc gac gcg gtc gag gcg cac ggc acc ggc acc cgc<br>Thr Pro Ala Asp Val Asp Ala Val Glu Ala His Gly Thr Gly Thr Arg<br>450                             455                             460 | 1391 |
| ctc ggc gac ccc atc gag gcg cag gcg ctc ctc gcg acg tac gga cag<br>Leu Gly Asp Pro Ile Glu Ala Gln Ala Leu Leu Ala Thr Tyr Gly Gln<br> 465                           470                           475 | 1439 |
| gac cgg gcg acg ccc ctg ctc ctc ggc tcg ctg aag tcg aac atc ggg<br>Asp Arg Ala Thr Pro Leu Leu Leu Gly Ser Leu Lys Ser Asn Ile Gly<br>480                         485                         490                        495 | 1487 |
| cac gcc cag gcc gcg tca ggg gtc gcc ggg atc atc aag atg gtg cag<br>His Ala Gln Ala Ala Ser Gly Val Ala Gly Ile Ile Lys Met Val Gln<br>                        500                           505                        510 | 1535 |
| gcc atc cgg cac ggg gaa ctg ccg ccg aca ctg cac gcg gac gag ccg<br>Ala Ile Arg His Gly Glu Leu Pro Pro Thr Leu His Ala Asp Glu Pro<br>            515                         520                         525 | 1583 |
| tcg ccg cac gtc gac tgg acg gcc ggt gcc gtc gag ctc ctg acg tcg<br>Ser Pro His Val Asp Trp Thr Ala Gly Ala Val Glu Leu Leu Thr Ser<br>                  530                         535                        540 | 1631 |
| gcc cgg ccg tgg ccg ggg acc ggt cgc cct agg cgg gcg ggc gtg tcg<br>Ala Arg Pro Trp Pro Gly Thr Gly Arg Pro Arg Arg Ala Gly Val Ser<br>545                             550                           555 | 1679 |
| tcc ttc gga gtc agc ggc acc aac gcc cac gtc atc ctg gag agc gca<br>Ser Phe Gly Val Ser Gly Thr Asn Ala His Val Ile Leu Glu Ser Ala<br>560                         565                         570                        575 | 1727 |
| ccc ccc gct cag ccc gcg gag gag gcg cag cct gtt gag acg ccg gtg<br>Pro Pro Ala Gln Pro Ala Glu Glu Ala Gln Pro Val Glu Thr Pro Val<br>                        580                           585                        590 | 1775 |
| gtg gcc tcg gat gtg ctg ccg ctg gtg ata tcg gcc aag acc cag ccc<br>Val Ala Ser Asp Val Leu Pro Leu Val Ile Ser Ala Lys Thr Gln Pro<br>                  595                         600                        605 | 1823 |
| gcc ctg acc gaa cac gaa gac cgg ctg cgc gcc tac ctg gcg gcg tcg<br>Ala Leu Thr Glu His Glu Asp Arg Leu Arg Ala Tyr Leu Ala Ala Ser<br>            610                         615                        620 | 1871 |
| ccc ggg gcg gat ata cgg gct gtg gca tcg acg ctg gcg gtg aca cgg<br>Pro Gly Ala Asp Ile Arg Ala Val Ala Ser Thr Leu Ala Val Thr Arg<br>625                             630                           635 | 1919 |
| tcg gtg ttc gag cac cgc gcc gta ctc ctt gga gat gac acc gtc acc<br>Ser Val Phe Glu His Arg Ala Val Leu Leu Gly Asp Asp Thr Val Thr<br>640                         645                         650                        655 | 1967 |
| ggc acc gcg gtg acc gac ccc agg atc gtg ttt gtc ttt ccc ggg cag<br>Gly Thr Ala Val Thr Asp Pro Arg Ile Val Phe Val Phe Pro Gly Gln<br>                        660                           665                        670 | 2015 |
| ggg tgg cag tgg ctg ggg atg ggc agt gca ctg cgc gat tcg tcg gtg<br>Gly Trp Gln Trp Leu Gly Met Gly Ser Ala Leu Arg Asp Ser Ser Val<br>                  675                         680                        685 | 2063 |
| gtg ttc gcc gag cgg atg gcc gag tgt gcg gcg gcg ttg cgc gag ttc<br>Val Phe Ala Glu Arg Met Ala Glu Cys Ala Ala Ala Leu Arg Glu Phe<br>                  690                         695                        700 | 2111 |
| gtg gac tgg gat ctg ttc acg gtt ctg gat gat ccg gcg gtg gtg gac<br>Val Asp Trp Asp Leu Phe Thr Val Leu Asp Asp Pro Ala Val Val Asp<br>705                             710                         715 | 2159 |
| cgg gtt gat gtg gtc cag ccc gct tcc tgg gcg atg atg gtt tcc ctg<br>Arg Val Asp Val Val Gln Pro Ala Ser Trp Ala Met Met Val Ser Leu<br>720                             725                         730                        735 | 2207 |
| gcc gcg gtg tgg cag gcg gcc ggt gtg cgg ccg gat gcg gtg atc ggc<br>Ala Ala Val Trp Gln Ala Ala Gly Val Arg Pro Asp Ala Val Ile Gly<br>                        740                           745                        750 | 2255 |

-continued

| | |
|---|---|
| cat tcg cag ggt gag atc gcc gca gct tgt gtg gcg ggt gcg gtg tca<br>His Ser Gln Gly Glu Ile Ala Ala Ala Cys Val Ala Gly Ala Val Ser<br>                            755                            760                        765 | 2303 |
| cta cgc gat gcc gcc cgg atc gtg acc ttg cgc agc cag gcg atc gcc<br>Leu Arg Asp Ala Ala Arg Ile Val Thr Leu Arg Ser Gln Ala Ile Ala<br>              770                        775                        780 | 2351 |
| cgg ggc ctg gcg ggc cgg ggc gcg atg gca tcc gtc gcc ctg ccc gcg<br>Arg Gly Leu Ala Gly Arg Gly Ala Met Ala Ser Val Ala Leu Pro Ala<br>785                           790                        795 | 2399 |
| cag gat gtc gag ctg gtc gac ggg gcc tgg atc gcc gcc cac aac ggg<br>Gln Asp Val Glu Leu Val Asp Gly Ala Trp Ile Ala Ala His Asn Gly<br>800                       805                       810                       815 | 2447 |
| ccc gcc tcc acc gtg atc gcg ggc acc ccg gaa gcg gtc gac cat gtc<br>Pro Ala Ser Thr Val Ile Ala Gly Thr Pro Glu Ala Val Asp His Val<br>                     820                        825                        830 | 2495 |
| ctc acc gct cat gag gca caa ggg gtg cgg gtg cgg cgg atc acc gtc<br>Leu Thr Ala His Glu Ala Gln Gly Val Arg Val Arg Arg Ile Thr Val<br>              835                        840                        845 | 2543 |
| gac tat gcc tcg cac acc ccg cac gtc gag ctg atc cgc gac gaa cta<br>Asp Tyr Ala Ser His Thr Pro His Val Glu Leu Ile Arg Asp Glu Leu<br>        850                        855                        860 | 2591 |
| ctc gac atc act agc gac agc agc tcg cag acc ccg ctc gtg ccg tgg<br>Leu Asp Ile Thr Ser Asp Ser Ser Ser Gln Thr Pro Leu Val Pro Trp<br>865                           870                        875 | 2639 |
| ctg tcg acc gtg gac ggc acc tgg gtc gac agc ccg ctg gac ggg gag<br>Leu Ser Thr Val Asp Gly Thr Trp Val Asp Ser Pro Leu Asp Gly Glu<br>880                       885                       890                     895 | 2687 |
| tac tgg tac cgg aac ctg cgt gaa ccg gtc ggt ttc cac ccc gcc gtc<br>Tyr Trp Tyr Arg Asn Leu Arg Glu Pro Val Gly Phe His Pro Ala Val<br>                    900                        905                        910 | 2735 |
| agc cag ttg cag gcc cag ggc gac acc gtg ttc gtc gag gtc agc gcc<br>Ser Gln Leu Gln Ala Gln Gly Asp Thr Val Phe Val Glu Val Ser Ala<br>              915                        920                        925 | 2783 |
| agc ccg gtg ttg ttg cag gcg atg gac gac gat gtc gtc acg gtt gcc<br>Ser Pro Val Leu Leu Gln Ala Met Asp Asp Asp Val Val Thr Val Ala<br>        930                        935                        940 | 2831 |
| acg ctg cgt cgt gac gac ggc gac gcc acc cgg atg ctc acc gcc ctg<br>Thr Leu Arg Arg Asp Asp Gly Asp Ala Thr Arg Met Leu Thr Ala Leu<br>945                           950                       955 | 2879 |
| gca cag gcc tat gtc cac ggc gtc acc gtc gac tgg ccc gcc atc ctc<br>Ala Gln Ala Tyr Val His Gly Val Thr Val Asp Trp Pro Ala Ile Leu<br>960                         965                       970                     975 | 2927 |
| ggc acc acc aca acc cgg gta ctg gac ctt ccg acc tac gcc ttc caa<br>Gly Thr Thr Thr Thr Arg Val Leu Asp Leu Pro Thr Tyr Ala Phe Gln<br>                    980                        985                        990 | 2975 |
| cac cag cgg tac tgg ctc gag tcg gct ccc ccg gcc acg gcc gac tcg<br>His Gln Arg Tyr Trp Leu Glu Ser Ala Pro Pro Ala Thr Ala Asp Ser<br>              995                        1000                      1005 | 3023 |
| ggc cac ccc gtc ctc ggc acc gga gtc gcc gtc gcc ggg tcg ccg ggc<br>Gly His Pro Val Leu Gly Thr Gly Val Ala Val Ala Gly Ser Pro Gly<br>        1010                        1015                      1020 | 3071 |
| cgg gtg ttc acg ggt ccc gtg ccc gcc ggt gcg gac cgc gcg gtg ttc<br>Arg Val Phe Thr Gly Pro Val Pro Ala Gly Ala Asp Arg Ala Val Phe<br>1025                        1030                      1035 | 3119 |
| atc gcc gaa ctg gcg ctc gcc gcc gcc gac gcc acc gac tgc gcc acg<br>Ile Ala Glu Leu Ala Leu Ala Ala Ala Asp Ala Thr Asp Cys Ala Thr<br>1040                        1045                      1050                      1055 | 3167 |
| gtc gaa cag ctc gac gtc acc tcc gtg ccc ggc gga tcc gcc cgc ggc<br>Val Glu Gln Leu Asp Val Thr Ser Val Pro Gly Gly Ser Ala Arg Gly | 3215 |

-continued

```
            1060                1065                1070
agg gcc acc gcg cag acc tgg gtc gat gaa ccc gcc gcc gac ggg cgg    3263
Arg Ala Thr Ala Gln Thr Trp Val Asp Glu Pro Ala Ala Asp Gly Arg
            1075                1080                1085 cgc cgc ttc acc gtc cac acc cgc gtc ggc gac gcc ccg tgg acg ctg    3311
Arg Arg Phe Thr Val His Thr Arg Val Gly Asp Ala Pro Trp Thr Leu
            1090                1095                1100 cac gcc gag ggg gtt ctc cgc ccc ggc cgc gtg ccc cag ccc gaa gcc    3359
His Ala Glu Gly Val Leu Arg Pro Gly Arg Val Pro Gln Pro Glu Ala
            1105                1110                1115 gtc gac acc gcc tgg ccc ccg ccg ggc gcg gtg ccc gcg gac ggg ctg    3407
Val Asp Thr Ala Trp Pro Pro Pro Gly Ala Val Pro Ala Asp Gly Leu
1120                1125                1130                1135 ccc ggg gcg tgg cga cgc gcg gac cag gtc ttc gtc gaa gcc gaa gtc    3455
Pro Gly Ala Trp Arg Arg Ala Asp Gln Val Phe Val Glu Ala Glu Val
                    1140                1145                1150 gac agc cct gac ggc ttc gtg gca cac ccc gac ctg ctc gac gcg gtc    3503
Asp Ser Pro Asp Gly Phe Val Ala His Pro Asp Leu Leu Asp Ala Val
            1155                1160                1165 ttc tcc gcg gtc ggc gac ggg agc cgc cag ccg acc gga tgg cgc gac    3551
Phe Ser Ala Val Gly Asp Gly Ser Arg Gln Pro Thr Gly Trp Arg Asp
            1170                1175                1180 ctc gcg gtg cac gcg tcg gac gcc acc gtg ctg cgc gcc tgc ctc acc    3599
Leu Ala Val His Ala Ser Asp Ala Thr Val Leu Arg Ala Cys Leu Thr
            1185                1190                1195 cgc cgc gac agt ggt gtc gtg gag ctc gcc gcc ttc gac ggt gcc gga    3647
Arg Arg Asp Ser Gly Val Val Glu Leu Ala Ala Phe Asp Gly Ala Gly
1200                1205                1210                1215 atg ccg gtg ctc acc gcg gag tcg gtg acg ctg ggc gag gtc gcg tcg    3695
Met Pro Val Leu Thr Ala Glu Ser Val Thr Leu Gly Glu Val Ala Ser
                    1220                1225                1230 gca ggc gga tcc gac gag tcg gac ggt ctg ctt cgg ctt gag tgg ttg    3743
Ala Gly Gly Ser Asp Glu Ser Asp Gly Leu Leu Arg Leu Glu Trp Leu
            1235                1240                1245 ccg gtg gcg gag gcc cac tac gac ggt gcc gac gag ctg ccc gag ggc    3791
Pro Val Ala Glu Ala His Tyr Asp Gly Ala Asp Glu Leu Pro Glu Gly
            1250                1255                1260 tac acc ctc atc acc gcc aca cac ccc gac gac ccc gac gac ccc acc    3839
Tyr Thr Leu Ile Thr Ala Thr His Pro Asp Asp Pro Asp Asp Pro Thr
            1265                1270                1275 aac ccc cac aac aca ccc aca cgc acc cac aca caa acc aca cgc gtc    3887
Asn Pro His Asn Thr Pro Thr Arg Thr His Thr Gln Thr Thr Arg Val
1280                1285                1290                1295 ctc acc gcc ctc caa cac cac ctc atc acc acc aac cac acc ctc atc    3935
Leu Thr Ala Leu Gln His His Leu Ile Thr Thr Asn His Thr Leu Ile
            1300                1305                1310 gtc cac acc acc acc gac ccc cca ggc gcc gcc gtc acc ggc ctc acc    3983
Val His Thr Thr Thr Asp Pro Pro Gly Ala Ala Val Thr Gly Leu Thr
            1315                1320                1325 cgc acc gca caa aac gaa cac ccc ggc cgc atc cac ctc atc gaa acc    4031
Arg Thr Ala Gln Asn Glu His Pro Gly Arg Ile His Leu Ile Glu Thr
            1330                1335                1340 cac cac ccc cac acc cca ctc ccc ctc acc caa ctc acc acc ctc cac    4079
His His Pro His Thr Pro Leu Pro Leu Thr Gln Leu Thr Thr Leu His
            1345                1350                1355 caa ccc cac cta cgc ctc acc aac aac acc ctc cac acc ccc cac ctc    4127
Gln Pro His Leu Arg Leu Thr Asn Asn Thr Leu His Thr Pro His Leu
1360                1365                1370                1375 acc ccc atc acc acc cac cac aac acc acc aca acc acc ccc aac acc    4175
```

-continued

```
Thr Pro Ile Thr Thr His His Asn Thr Thr Thr Thr Pro Asn Thr
            1380                1385                1390 cca ccc ctc aac ccc aac cac gcc atc ctc atc acc ggc ggc tcc ggc      4223
Pro Pro Leu Asn Pro Asn His Ala Ile Leu Ile Thr Gly Gly Ser Gly
            1395                1400                1405 acc ctc gcc ggc atc ctc gcc cgc cac ctc aac cac ccc cac acc tac      4271
Thr Leu Ala Gly Ile Leu Ala Arg His Leu Asn His Pro His Thr Tyr
            1410                1415                1420 ctc ctc tcc cgc aca cca cca ccc ccc acc aca ccc ggc acc cac atc      4319
Leu Leu Ser Arg Thr Pro Pro Pro Pro Thr Thr Pro Gly Thr His Ile
            1425                1430                1435 ccc tgc gac ctc acc gac ccc acc caa atc acc caa gcc ctc acc cac      4367
Pro Cys Asp Leu Thr Asp Pro Thr Gln Ile Thr Gln Ala Leu Thr His
1440                1445                1450                1455 ata cca caa ccc ctc acc ggc atc ttc cac acc gcc gcc acc ctc gac      4415
Ile Pro Gln Pro Leu Thr Gly Ile Phe His Thr Ala Ala Thr Leu Asp
            1460                1465                1470 gac gcc acc ctc acc aac ctc acc ccc caa cac ctc acc acc acc ctc      4463
Asp Ala Thr Leu Thr Asn Leu Thr Pro Gln His Leu Thr Thr Thr Leu
            1475                1480                1485 caa ccc aaa gcc gac gcc gcc tgg cac ctc cac cac cac acc caa aac      4511
Gln Pro Lys Ala Asp Ala Ala Trp His Leu His His His Thr Gln Asn
            1490                1495                1500 caa ccc ctc acc cac ttc gtc ctc tac tcc agc gcc gcc gcc acc ctc      4559
Gln Pro Leu Thr His Phe Val Leu Tyr Ser Ser Ala Ala Ala Thr Leu
            1505                1510                1515 ggc agc ccc ggc caa gcc aac tac gcc gcc gcc aac gcc ttc ctc gac      4607
Gly Ser Pro Gly Gln Ala Asn Tyr Ala Ala Ala Asn Ala Phe Leu Asp
1520                1525                1530                1535 gcc ctc gcc acc cac cgc cac acc caa gga caa ccc gcc acc acc atc      4655
Ala Leu Ala Thr His Arg His Thr Gln Gly Gln Pro Ala Thr Thr Ile
            1540                1545                1550 gcc tgg ggc atg tgg cac acc acc acc aca ctc acc agc caa ctc acc      4703
Ala Trp Gly Met Trp His Thr Thr Thr Thr Leu Thr Ser Gln Leu Thr
            1555                1560                1565 gac agc gac cgc gac cgc atc cgc cgc ggc ggc ttc ctg ccg atc tcg      4751
Asp Ser Asp Arg Asp Arg Ile Arg Arg Gly Gly Phe Leu Pro Ile Ser
            1570                1575                1580 gac gac gag ggc atg c                                                4767
Asp Asp Glu Gly Met
    1585

<210> SEQ ID NO 29
<211> LENGTH: 1588
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 29

Met Arg Leu Tyr Glu Ala Ala Arg Arg Thr Gly Ser Pro Val Val Val
  1               5                  10                  15

Ala Ala Ala Leu Asp Asp Ala Pro Asp Val Pro Leu Leu Arg Gly Leu
                20                  25                  30

Arg Arg Thr Thr Val Arg Arg Ala Ala Val Arg Glu Arg Ser Leu Ala
            35                  40                  45

Asp Arg Ser Pro Cys Cys Pro Thr Thr Ser Ala Pro Thr Pro Pro Ser
        50                  55                  60

Arg Ser Ser Trp Asn Ser Thr Ala Thr Val Leu Gly His Leu Gly Ala
```

-continued

```
                65                  70                  75                  80
        Glu Asp Ile Pro Ala Thr Thr Thr Phe Lys Glu Leu Gly Ile Asp Ser
                            85                  90                  95
        Leu Thr Ala Val Gln Leu Arg Asn Ala Leu Thr Thr Ala Thr Gly Val
                        100                 105                 110
        Arg Leu Asn Ala Thr Ala Val Phe Asp Phe Pro Thr Pro Arg Ala Leu
                        115                 120                 125
        Ala Ala Arg Leu Gly Asp Glu Leu Ala Gly Thr Arg Ala Pro Val Ala
                    130                 135                 140
        Ala Arg Thr Ala Ala Thr Ala Ala Ala His Asp Glu Pro Leu Ala Ile
        145                 150                 155                 160
        Val Gly Met Ala Cys Arg Leu Pro Gly Gly Val Ala Ser Pro Gln Glu
                        165                 170                 175
        Leu Trp Arg Leu Val Ala Ser Gly Thr Asp Ala Ile Thr Glu Phe Pro
                        180                 185                 190
        Ala Asp Arg Gly Trp Asp Val Asp Ala Leu Tyr Asp Pro Asp Pro Asp
                        195                 200                 205
        Ala Ile Gly Lys Thr Phe Val Arg His Gly Phe Leu Asp Gly Ala
                    210                 215                 220
        Thr Gly Phe Asp Ala Ala Phe Phe Gly Ile Ser Pro Arg Glu Ala Leu
        225                 230                 235                 240
        Ala Met Asp Pro Gln Gln Arg Val Leu Leu Glu Thr Ser Trp Glu Ala
                        245                 250                 255
        Phe Glu Ser Ala Gly Ile Thr Pro Asp Ala Ala Arg Gly Ser Asp Thr
                    260                 265                 270
        Gly Val Phe Ile Gly Ala Phe Ser Tyr Gly Tyr Gly Thr Gly Ala Asp
                    275                 280                 285
        Thr Asn Gly Phe Gly Ala Thr Gly Ser Gln Thr Ser Val Leu Ser Gly
                    290                 295                 300
        Arg Leu Ser Tyr Phe Tyr Gly Leu Glu Gly Pro Ser Val Thr Val Asp
        305                 310                 315                 320
        Thr Ala Cys Ser Ser Ser Leu Val Ala Leu His Gln Ala Gly Gln Ser
                        325                 330                 335
        Leu Arg Ser Gly Glu Cys Ser Leu Ala Leu Val Gly Gly Val Thr Val
                    340                 345                 350
        Met Ala Ser Pro Gly Gly Phe Val Glu Phe Ser Arg Gln Arg Gly Leu
                        355                 360                 365
        Ala Pro Asp Gly Arg Ala Lys Ala Phe Gly Ala Gly Ala Asp Gly Thr
                    370                 375                 380
        Ser Phe Ala Glu Gly Ala Gly Ala Leu Val Val Glu Arg Leu Ser Asp
        385                 390                 395                 400
        Ala Glu Arg His Gly His Thr Val Leu Ala Leu Val Arg Gly Ser Ala
                        405                 410                 415
        Ala Asn Ser Asp Gly Ala Ser Asn Gly Leu Ser Ala Pro Asn Gly Pro
                    420                 425                 430
        Ser Gln Glu Arg Val Ile His Gln Ala Leu Ala Asn Ala Lys Leu Thr
                    435                 440                 445
        Pro Ala Asp Val Asp Ala Val Glu Ala His Gly Thr Gly Thr Arg Leu
                    450                 455                 460
        Gly Asp Pro Ile Glu Ala Gln Ala Leu Leu Ala Thr Tyr Gly Gln Asp
        465                 470                 475                 480
        Arg Ala Thr Pro Leu Leu Leu Gly Ser Leu Lys Ser Asn Ile Gly His
                        485                 490                 495
```

-continued

```
Ala Gln Ala Ala Ser Gly Val Ala Gly Ile Ile Lys Met Val Gln Ala
            500                 505                 510
Ile Arg His Gly Glu Leu Pro Pro Thr Leu His Ala Asp Glu Pro Ser
        515                 520                 525
Pro His Val Asp Trp Thr Ala Gly Val Glu Leu Leu Thr Ser Ala
    530                 535                 540
Arg Pro Trp Pro Gly Thr Gly Arg Pro Arg Ala Gly Val Ser Ser
545                 550                 555                 560
Phe Gly Val Ser Gly Thr Asn Ala His Val Ile Leu Glu Ser Ala Pro
                565                 570                 575
Pro Ala Gln Pro Ala Glu Ala Gln Pro Val Glu Thr Pro Val Val
            580                 585                 590
Ala Ser Asp Val Leu Pro Leu Val Ile Ser Ala Lys Thr Gln Pro Ala
            595                 600                 605
Leu Thr Glu His Glu Asp Arg Leu Arg Ala Tyr Leu Ala Ala Ser Pro
        610                 615                 620
Gly Ala Asp Ile Arg Ala Val Ala Ser Thr Leu Ala Val Thr Arg Ser
625                 630                 635                 640
Val Phe Glu His Arg Ala Val Leu Leu Gly Asp Asp Thr Val Thr Gly
                645                 650                 655
Thr Ala Val Thr Asp Pro Arg Ile Val Phe Val Phe Pro Gly Gln Gly
                660                 665                 670
Trp Gln Trp Leu Gly Met Gly Ser Ala Leu Arg Asp Ser Ser Val Val
            675                 680                 685
Phe Ala Glu Arg Met Ala Glu Cys Ala Ala Ala Leu Arg Glu Phe Val
        690                 695                 700
Asp Trp Asp Leu Phe Thr Val Leu Asp Asp Pro Ala Val Val Asp Arg
705                 710                 715                 720
Val Asp Val Val Gln Pro Ala Ser Trp Ala Met Met Val Ser Leu Ala
                725                 730                 735
Ala Val Trp Gln Ala Ala Gly Val Arg Pro Asp Ala Val Ile Gly His
            740                 745                 750
Ser Gln Gly Glu Ile Ala Ala Cys Val Ala Gly Ala Val Ser Leu
        755                 760                 765
Arg Asp Ala Ala Arg Ile Val Thr Leu Arg Ser Gln Ala Ile Ala Arg
        770                 775                 780
Gly Leu Ala Gly Arg Gly Ala Met Ala Ser Val Ala Leu Pro Ala Gln
785                 790                 795                 800
Asp Val Glu Leu Val Asp Gly Ala Trp Ile Ala Ala His Asn Gly Pro
                805                 810                 815
Ala Ser Thr Val Ile Ala Gly Thr Pro Glu Ala Val Asp His Val Leu
                820                 825                 830
Thr Ala His Glu Ala Gln Gly Val Arg Val Arg Arg Ile Thr Val Asp
        835                 840                 845
Tyr Ala Ser His Thr Pro His Val Glu Leu Ile Arg Asp Glu Leu Leu
    850                 855                 860
Asp Ile Thr Ser Asp Ser Ser Gln Thr Pro Leu Val Pro Trp Leu
865                 870                 875                 880
Ser Thr Val Asp Gly Thr Trp Val Asp Ser Pro Leu Asp Gly Glu Tyr
                885                 890                 895
Trp Tyr Arg Asn Leu Arg Glu Pro Val Gly Phe His Pro Ala Val Ser
                900                 905                 910
```

-continued

```
Gln Leu Gln Ala Gln Gly Asp Thr Val Phe Val Glu Val Ser Ala Ser
        915                 920                 925

Pro Val Leu Leu Gln Ala Met Asp Asp Val Val Thr Val Ala Thr
    930                 935                 940

Leu Arg Arg Asp Asp Gly Asp Ala Thr Arg Met Leu Thr Ala Leu Ala
945                 950                 955                 960

Gln Ala Tyr Val His Gly Val Thr Val Asp Trp Pro Ala Ile Leu Gly
                965                 970                 975

Thr Thr Thr Thr Arg Val Leu Asp Leu Pro Thr Tyr Ala Phe Gln His
            980                 985                 990

Gln Arg Tyr Trp Leu Glu Ser Ala Pro Ala Thr Ala Asp Ser Gly
        995                 1000                1005

His Pro Val Leu Gly Thr Gly Val Ala Val Ala Gly Ser Pro Gly Arg
    1010                1015                1020

Val Phe Thr Gly Pro Val Pro Ala Gly Ala Asp Arg Ala Val Phe Ile
1025                1030                1035                1040

Ala Glu Leu Ala Leu Ala Ala Ala Asp Ala Thr Asp Cys Ala Thr Val
                1045                1050                1055

Glu Gln Leu Asp Val Thr Ser Val Pro Gly Gly Ser Ala Arg Gly Arg
            1060                1065                1070

Ala Thr Ala Gln Thr Trp Val Asp Glu Pro Ala Ala Asp Gly Arg Arg
        1075                1080                1085

Arg Phe Thr Val His Thr Arg Val Gly Asp Ala Pro Trp Thr Leu His
    1090                1095                1100

Ala Glu Gly Val Leu Arg Pro Gly Arg Val Pro Gln Pro Glu Ala Val
1105                1110                1115                1120

Asp Thr Ala Trp Pro Pro Pro Gly Ala Val Pro Ala Asp Gly Leu Pro
                1125                1130                1135

Gly Ala Trp Arg Arg Ala Asp Gln Val Phe Val Glu Ala Glu Val Asp
            1140                1145                1150

Ser Pro Asp Gly Phe Val Ala His Pro Asp Leu Leu Asp Ala Val Phe
        1155                1160                1165

Ser Ala Val Gly Asp Gly Ser Arg Gln Pro Thr Gly Trp Arg Asp Leu
    1170                1175                1180

Ala Val His Ala Ser Asp Ala Thr Val Leu Arg Ala Cys Leu Thr Arg
1185                1190                1195                1200

Arg Asp Ser Gly Val Val Glu Leu Ala Ala Phe Asp Gly Ala Gly Met
                1205                1210                1215

Pro Val Leu Thr Ala Glu Ser Val Thr Leu Gly Glu Val Ala Ser Ala
            1220                1225                1230

Gly Gly Ser Asp Glu Ser Asp Gly Leu Leu Arg Leu Glu Trp Leu Pro
        1235                1240                1245

Val Ala Glu Ala His Tyr Asp Gly Ala Asp Glu Leu Pro Glu Gly Tyr
    1250                1255                1260

Thr Leu Ile Thr Ala Thr His Pro Asp Asp Pro Asp Pro Thr Asn
1265                1270                1275                1280

Pro His Asn Thr Pro Thr Arg Thr His Thr Gln Thr Thr Arg Val Leu
                1285                1290                1295

Thr Ala Leu Gln His His Leu Ile Thr Thr Asn His Thr Leu Ile Val
            1300                1305                1310

His Thr Thr Thr Asp Pro Pro Gly Ala Ala Val Thr Gly Leu Thr Arg
        1315                1320                1325

Thr Ala Gln Asn Glu His Pro Gly Arg Ile His Leu Ile Glu Thr His
```

-continued

```
                     1330                1335                1340
His Pro His Thr Pro Leu Pro Leu Thr Gln Leu Thr Thr Leu His Gln
1345                1350                1355                1360

Pro His Leu Arg Leu Thr Asn Asn Thr Leu His Thr Pro His Leu Thr
                1365                1370                1375

Pro Ile Thr Thr His His Asn Thr Thr Thr Thr Thr Pro Asn Thr Pro
            1380                1385                1390

Pro Leu Asn Pro Asn His Ala Ile Leu Ile Thr Gly Gly Ser Gly Thr
        1395                1400                1405

Leu Ala Gly Ile Leu Ala Arg His Leu Asn His Pro His Thr Tyr Leu
    1410                1415                1420

Leu Ser Arg Thr Pro Pro Pro Thr Thr Pro Gly Thr His Ile Pro
1425                1430                1435                1440

Cys Asp Leu Thr Asp Pro Thr Gln Ile Thr Gln Ala Leu Thr His Ile
                1445                1450                1455

Pro Gln Pro Leu Thr Gly Ile Phe His Thr Ala Ala Thr Leu Asp Asp
            1460                1465                1470

Ala Thr Leu Thr Asn Leu Thr Pro Gln His Leu Thr Thr Thr Leu Gln
        1475                1480                1485

Pro Lys Ala Asp Ala Ala Trp His Leu His His Thr Gln Asn Gln
    1490                1495                1500

Pro Leu Thr His Phe Val Leu Tyr Ser Ser Ala Ala Ala Thr Leu Gly
1505                1510                1515                1520

Ser Pro Gly Gln Ala Asn Tyr Ala Ala Ala Asn Ala Phe Leu Asp Ala
                1525                1530                1535

Leu Ala Thr His Arg His Thr Gln Gly Gln Pro Ala Thr Thr Ile Ala
            1540                1545                1550

Trp Gly Met Trp His Thr Thr Thr Leu Thr Ser Gln Leu Thr Asp
        1555                1560                1565

Ser Asp Arg Asp Arg Ile Arg Arg Gly Gly Phe Leu Pro Ile Ser Asp
    1570                1575                1580

Asp Glu Gly Met
1585
```

<210> SEQ ID NO 30
<211> LENGTH: 4737
<212> TYPE: DNA
<213> ORGANISM: Artificial Sequence
<220> FEATURE:
<223> OTHER INFORMATION: Description of Artificial Sequence: DNA
    encoding synthetic PKS synthase fragment
<220> FEATURE:
<221> NAME/KEY: CDS
<222> LOCATION: (3)..(4736)

<400> SEQUENCE: 30

```
gc atg cgg ctg tac gag gcg gca cgg cgc acc gga agt ccc gtg gtg      47
   Met Arg Leu Tyr Glu Ala Ala Arg Arg Thr Gly Ser Pro Val Val
   1               5                  10                  15 gtg gcg gcc gcg ctc gac gac gcg ccg gac gtg ccg ctg ctg cgc ggg     95
Val Ala Ala Ala Leu Asp Asp Ala Pro Asp Val Pro Leu Leu Arg Gly
             20                  25                  30 ctg cgg cgt acg acc gtc cgg cgt gcc gcc gtc cgg gaa cgc tct ctc    143
Leu Arg Arg Thr Thr Val Arg Arg Ala Ala Val Arg Glu Arg Ser Leu
         35                  40                  45 gcc gac cgc tcg ccg tgc tgc ccg acg acg agc gcg ccg acg cct ccc    191
Ala Asp Arg Ser Pro Cys Cys Pro Thr Thr Ser Ala Pro Thr Pro Pro
     50                  55                  60
```

```
tcg cgt tcg tcc tgg aac agc acc gcc acc gtg ctc ggc cac ctg ggc     239
Ser Arg Ser Ser Trp Asn Ser Thr Ala Thr Val Leu Gly His Leu Gly
     65                  70                  75 gcc gaa gac atc ccg gcg acg acg ttc aag gaa ctc ggc atc gac         287
Ala Glu Asp Ile Pro Ala Thr Thr Thr Phe Lys Glu Leu Gly Ile Asp
 80                  85                  90                  95 tcg ctc acc gcg gtc cag ctg cgc aac gcg ctg acc acg gcg acc ggc     335
Ser Leu Thr Ala Val Gln Leu Arg Asn Ala Leu Thr Thr Ala Thr Gly
                100                 105                 110 gta cgc ctc aac gcc aca gcg gtc ttc gac ttt ccg acg ccg cgc gcg     383
Val Arg Leu Asn Ala Thr Ala Val Phe Asp Phe Pro Thr Pro Arg Ala
            115                 120                 125 ctc gcc gcg aga ctc ggc gac gag ctg gcc ggt acc cgc gcg ccc gtc     431
Leu Ala Ala Arg Leu Gly Asp Glu Leu Ala Gly Thr Arg Ala Pro Val
        130                 135                 140 gcg gcc cgg acc gcg gcc acc gcg gcc gcg cac gac gaa ccg ctg gcg     479
Ala Ala Arg Thr Ala Ala Thr Ala Ala Ala His Asp Glu Pro Leu Ala
    145                 150                 155 atc gtg ggc atg gcc tgc cgt ctg ccg ggc ggg gtc gcg tcg cca cag     527
Ile Val Gly Met Ala Cys Arg Leu Pro Gly Gly Val Ala Ser Pro Gln
160                 165                 170                 175 gag ctg tgg cgt ctc gtc gcg tcc ggc acc gac gcc atc acg gag ttc     575
Glu Leu Trp Arg Leu Val Ala Ser Gly Thr Asp Ala Ile Thr Glu Phe
                180                 185                 190 ccc gcg gac cgc ggc tgg gac gtg gac gcg ctc tac gac ccg gac ccc     623
Pro Ala Asp Arg Gly Trp Asp Val Asp Ala Leu Tyr Asp Pro Asp Pro
            195                 200                 205 gac gcg atc ggc aag acc ttc gtc cgg cac ggc ggc ttc ctc gac ggt     671
Asp Ala Ile Gly Lys Thr Phe Val Arg His Gly Gly Phe Leu Asp Gly
        210                 215                 220 gcg acc ggc ttc gac gcg gcg ttc ttc ggg atc agc ccg cgc gag gcc     719
Ala Thr Gly Phe Asp Ala Ala Phe Phe Gly Ile Ser Pro Arg Glu Ala
    225                 230                 235 ctg gcc atg gac ccg cag caa cgg gtg ctc ctg gag acg tcc tgg gag     767
Leu Ala Met Asp Pro Gln Gln Arg Val Leu Leu Glu Thr Ser Trp Glu
240                 245                 250                 255 gcg ttc gaa agc gcg ggc atc acc ccg gac gcg gcg cgg ggc agc gac     815
Ala Phe Glu Ser Ala Gly Ile Thr Pro Asp Ala Ala Arg Gly Ser Asp
                260                 265                 270 acc ggc gtg ttc atc ggc gcg ttc tcc tac ggg tac ggc acg ggt gcg     863
Thr Gly Val Phe Ile Gly Ala Phe Ser Tyr Gly Tyr Gly Thr Gly Ala
            275                 280                 285 gat acc aac ggc ttc ggc gcg aca ggg tcg cag acc agc gtg ctc tcc     911
Asp Thr Asn Gly Phe Gly Ala Thr Gly Ser Gln Thr Ser Val Leu Ser
        290                 295                 300 ggc cgc ctc tcg tac ttc tac ggt ctg gag ggc cct tcg gtc acg gtc     959
Gly Arg Leu Ser Tyr Phe Tyr Gly Leu Glu Gly Pro Ser Val Thr Val
    305                 310                 315 gac acc gcc tgc tcg tcg tca ctg gtc gcc ctg cac cag gca ggg cag     1007
Asp Thr Ala Cys Ser Ser Ser Leu Val Ala Leu His Gln Ala Gly Gln
320                 325                 330                 335 tcc ctg cgc tcg ggc gaa tgc tcg ctc gcc ctg gtc ggc ggt gtc acg     1055
Ser Leu Arg Ser Gly Glu Cys Ser Leu Ala Leu Val Gly Gly Val Thr
                340                 345                 350 gtg atg gcg tcg ccc gga gga ttc gtc gag ttc tcc cgg cag cgc ggg     1103
Val Met Ala Ser Pro Gly Gly Phe Val Glu Phe Ser Arg Gln Arg Gly
            355                 360                 365 ctc gcg ccg gac ggg cgg gcg aag gcg ttc ggc gcg ggc gcg gac ggt     1151
Leu Ala Pro Asp Gly Arg Ala Lys Ala Phe Gly Ala Gly Ala Asp Gly
```

-continued

```
                 370                 375                 380
acg agc ttc gcc gag ggc gcc ggt gcc ctg gtg gtc gag cgg ctc tcc    1199
Thr Ser Phe Ala Glu Gly Ala Gly Ala Leu Val Val Glu Arg Leu Ser
    385                 390                 395 gac gcg gag cgc cac ggc cac acc gtc ctc gcc ctc gta cgc ggc tcc    1247
Asp Ala Glu Arg His Gly His Thr Val Leu Ala Leu Val Arg Gly Ser
400                 405                 410                 415 gcg gct aac tcc gac ggc gcg tcg aac ggt ctg tcg gcg ccg aac ggc    1295
Ala Ala Asn Ser Asp Gly Ala Ser Asn Gly Leu Ser Ala Pro Asn Gly
                420                 425                 430 ccc tcc cag gaa cgc gtc atc cac cag gcc ctc gcg aac gcg aaa ctc    1343
Pro Ser Gln Glu Arg Val Ile His Gln Ala Leu Ala Asn Ala Lys Leu
                    435                 440                 445 acc ccc gcc gat gtc gac gcg gtc gag gcg cac ggc acc ggc acc cgc    1391
Thr Pro Ala Asp Val Asp Ala Val Glu Ala His Gly Thr Gly Thr Arg
            450                 455                 460 ctc ggc gac ccc atc gag gcg cag gcg ctg ctc gcg acg tac gga cag    1439
Leu Gly Asp Pro Ile Glu Ala Gln Ala Leu Leu Ala Thr Tyr Gly Gln
465                 470                 475 gac cgg gcg acg ccc ctg ctc ctc ggc tcg ctg aag tcg aac atc ggg    1487
Asp Arg Ala Thr Pro Leu Leu Leu Gly Ser Leu Lys Ser Asn Ile Gly
480                 485                 490                 495 cac gcc cag gcc gcg tca ggg gtc gcc ggg atc atc aag atg gtg cag    1535
His Ala Gln Ala Ala Ser Gly Val Ala Gly Ile Ile Lys Met Val Gln
                500                 505                 510 gcc atc cgg cac ggg gaa ctg ccg ccg aca ctg cac gcg gac gag ccg    1583
Ala Ile Arg His Gly Glu Leu Pro Pro Thr Leu His Ala Asp Glu Pro
            515                 520                 525 tcg ccg cac gtc gac tgg acg gcc ggt gcc gtc gag ctc ctg acg tcg    1631
Ser Pro His Val Asp Trp Thr Ala Gly Ala Val Glu Leu Leu Thr Ser
        530                 535                 540 gcc cgg ccg tgg ccg ggg acc ggt cgc ccg cgc gcg gct gcc gtc tcg    1679
Ala Arg Pro Trp Pro Gly Thr Gly Arg Pro Arg Ala Ala Val Ser
545                 550                 555 tcg ttc ggc gtg agc ggc acg aac gcc cac atc atc ctt gag gca gga    1727
Ser Phe Gly Val Ser Gly Thr Asn Ala His Ile Ile Leu Glu Ala Gly
560                 565                 570                 575 ccg gtc aaa acg gga ccg gtc gag gca gga gcg atc gag gca gga ccg    1775
Pro Val Lys Thr Gly Pro Val Glu Ala Gly Ala Ile Glu Ala Gly Pro
                580                 585                 590 gtc gaa gta gga ccg gtc gag gct gga ccg ctc ccc gcg gcg ccg ccg    1823
Val Glu Val Gly Pro Val Glu Ala Gly Pro Leu Pro Ala Ala Pro Pro
            595                 600                 605 tca gca ccg ggc gaa gac ctt ccg ctg ctc gtg tcg gcg cgt tcc ccg    1871
Ser Ala Pro Gly Glu Asp Leu Pro Leu Leu Val Ser Ala Arg Ser Pro
        610                 615                 620 gag gca ctc gac gag cag atc ggg cgc ctg cgc gcc tat ctc gac acc    1919
Glu Ala Leu Asp Glu Gln Ile Gly Arg Leu Arg Ala Tyr Leu Asp Thr
625                 630                 635 ggc ccg ggc gtc gac cgg gcg gcc gtg gcg cag aca ctg gcc cgg cgt    1967
Gly Pro Gly Val Asp Arg Ala Ala Val Ala Gln Thr Leu Ala Arg Arg
640                 645                 650                 655 acg cac ttc acc cac cgg gcc gta ctg ctc ggg gac acc gtc atc ggc    2015
Thr His Phe Thr His Arg Ala Val Leu Leu Gly Asp Thr Val Ile Gly
                660                 665                 670 gct ccc ccg gcg gac cag gcc gac gaa ctc gtc ttc gtc tac tcc ggt    2063
Ala Pro Pro Ala Asp Gln Ala Asp Glu Leu Val Phe Val Tyr Ser Gly
            675                 680                 685 cag ggc acc cag cat ccc gcg atg ggc gag cag cta gcc gcc gcg ttc    2111
```

-continued

```
Gln Gly Thr Gln His Pro Ala Met Gly Glu Gln Leu Ala Ala Ala Phe
            690                 695                 700 ccc gtc ttc gcg cgg atc cat cag cag gtg tgg gac ctg ctc gat gtg      2159
Pro Val Phe Ala Arg Ile His Gln Gln Val Trp Asp Leu Leu Asp Val
705                 710                 715 ccc gat ctg gag gtg aac gag acc ggt tac gcc cag ccg gcc ctg ttc      2207
Pro Asp Leu Glu Val Asn Glu Thr Gly Tyr Ala Gln Pro Ala Leu Phe
720                 725                 730                 735 gca atg cag gtg gct ctg ttc ggg ctg ctg gaa tcg tgg ggt gta cga      2255
Ala Met Gln Val Ala Leu Phe Gly Leu Leu Glu Ser Trp Gly Val Arg
            740                 745                 750 ccg gac gcg gtg atc ggc cat tcg gtg ggt gag ctt gcg gct gcg tat      2303
Pro Asp Ala Val Ile Gly His Ser Val Gly Glu Leu Ala Ala Ala Tyr
            755                 760                 765 gtg tcc ggg gtg tgg tcg ttg gag gat gcc tgc act ttg gtg tcg gcg      2351
Val Ser Gly Val Trp Ser Leu Glu Asp Ala Cys Thr Leu Val Ser Ala
            770                 775                 780 cgg gct cgt ctg atg cag gct ctg ccc gcg ggt ggg gtg atg gtc gct      2399
Arg Ala Arg Leu Met Gln Ala Leu Pro Ala Gly Gly Val Met Val Ala
785                 790                 795 gtc ccg gtc tcg gag gat gag gcc cgg gcc gtg ctg ggt gag ggt gtg      2447
Val Pro Val Ser Glu Asp Glu Ala Arg Ala Val Leu Gly Glu Gly Val
800                 805                 810                 815 gag atc gcc gcg gtc aac ggc ccg tcg tcg gtg gtt ctc tcc ggt gat      2495
Glu Ile Ala Ala Val Asn Gly Pro Ser Ser Val Val Leu Ser Gly Asp
                    820                 825                 830 gag gcc gcc gtg ctg cag gcc gcg gag ggg ctg ggg aag tgg acg cgg      2543
Glu Ala Ala Val Leu Gln Ala Ala Glu Gly Leu Gly Lys Trp Thr Arg
            835                 840                 845 ctg gcg acc agc cac gcg ttc cat tcc gcc cgt atg gaa ccc atg ctg      2591
Leu Ala Thr Ser His Ala Phe His Ser Ala Arg Met Glu Pro Met Leu
            850                 855                 860 gag gag ttc cgg gcg gtc gcc gaa ggc ctg acc tac cgg acg ccg cag      2639
Glu Glu Phe Arg Ala Val Ala Glu Gly Leu Thr Tyr Arg Thr Pro Gln
865                 870                 875 gtc tcc atg gcc gtt ggt gat cag gtg acc acc gct gag tac tgg gtg      2687
Val Ser Met Ala Val Gly Asp Gln Val Thr Thr Ala Glu Tyr Trp Val
880                 885                 890                 895 cgg cag gtc cgg gac acg gtc cgg ttc ggc gag cag gtg gcc tcg tac      2735
Arg Gln Val Arg Asp Thr Val Arg Phe Gly Glu Gln Val Ala Ser Tyr
                    900                 905                 910 gag gac gcc gtg ttc gtc gag ctg ggt gcc gac cgg tca ctg gcc cgc      2783
Glu Asp Ala Val Phe Val Glu Leu Gly Ala Asp Arg Ser Leu Ala Arg
            915                 920                 925 ctg gtc gac ggt gtc gcg atg ctg cac ggc gac cac gaa atc cag gcc      2831
Leu Val Asp Gly Val Ala Met Leu His Gly Asp His Glu Ile Gln Ala
            930                 935                 940 gcg atc ggc gcc ctg gcc cac ctg tat gtc aac ggc gtc acg gtc gac      2879
Ala Ile Gly Ala Leu Ala His Leu Tyr Val Asn Gly Val Thr Val Asp
            945                 950                 955 tgg ccc gcg ctc ctg ggc gat gct ccg gca aca cgg gtg ctg gac ctt      2927
Trp Pro Ala Leu Leu Gly Asp Ala Pro Ala Thr Arg Val Leu Asp Leu
960                 965                 970                 975 ccg aca tac gcc ttc cag cac cag cgc tac tgg ctc gag tcg gct ccc      2975
Pro Thr Tyr Ala Phe Gln His Gln Arg Tyr Trp Leu Glu Ser Ala Pro
                    980                 985                 990 ccg gcc acg gcc gac tcg ggc cac ccc gtc ctc ggc acc gga gtc gcc      3023
Pro Ala Thr Ala Asp Ser Gly His Pro Val Leu Gly Thr Gly Val Ala
            995                 1000                1005
```

-continued

| | |
|---|---|
| gtc gcc ggg tcg ccg ggc cgg gtg ttc acg ggt ccc gtg ccc gcc ggt<br>Val Ala Gly Ser Pro Gly Arg Val Phe Thr Gly Pro Val Pro Ala Gly<br>    1010                        1015                      1020 | 3071 |
| gcg gac cgc gcg gtg ttc atc gcc gaa ctg gcg ctc gcc gcc gcc gac<br>Ala Asp Arg Ala Val Phe Ile Ala Glu Leu Ala Leu Ala Ala Ala Asp<br>1025                      1030                      1035 | 3119 |
| gcc acc gac tgc gcc acg gtc gaa cag ctc gac gtc acc tcc gtg ccc<br>Ala Thr Asp Cys Ala Thr Val Glu Gln Leu Asp Val Thr Ser Val Pro<br>1040                      1045                      1050                      1055 | 3167 |
| ggc gga tcc gcc cgc ggc agg gcc acc gcg cag acc tgg gtc gat gaa<br>Gly Gly Ser Ala Arg Gly Arg Ala Thr Ala Gln Thr Trp Val Asp Glu<br>    1060                        1065                      1070 | 3215 |
| ccc gcc gcc gac ggg cgg cgc cgc ttc acc gtc cac acc cgc gtc ggc<br>Pro Ala Ala Asp Gly Arg Arg Arg Phe Thr Val His Thr Arg Val Gly<br>                1075                      1080                      1085 | 3263 |
| gac gcc ccg tgg acg ctg cac gcc gag ggg gtt ctc cgc ccc ggc cgc<br>Asp Ala Pro Trp Thr Leu His Ala Glu Gly Val Leu Arg Pro Gly Arg<br>                1090                      1095                      1100 | 3311 |
| gtg ccc cag ccc gaa gcc gtc gac acc gcc tgg ccc ccg ccg ggc gcg<br>Val Pro Gln Pro Glu Ala Val Asp Thr Ala Trp Pro Pro Pro Gly Ala<br>    1105                        1110                      1115 | 3359 |
| gtg ccc gcg gac ggg ctg ccc ggg gcg tgg cga cgc gcg gac cag gtc<br>Val Pro Ala Asp Gly Leu Pro Gly Ala Trp Arg Arg Ala Asp Gln Val<br>1120                      1125                      1130                      1135 | 3407 |
| ttc gtc gaa gcc gaa gtc gac agc cct gac ggc ttc gtg gca cac ccc<br>Phe Val Glu Ala Glu Val Asp Ser Pro Asp Gly Phe Val Ala His Pro<br>                1140                      1145                      1150 | 3455 |
| gac ctg ctc gac gcg gtc ttc tcc gcg gtc ggc gac ggg agc cgc cag<br>Asp Leu Leu Asp Ala Val Phe Ser Ala Val Gly Asp Gly Ser Arg Gln<br>                    1155                      1160                      1165 | 3503 |
| ccg acc gga tgg cgc gac ctc gcg gtg cac gcg tcg gac gcc acc gtg<br>Pro Thr Gly Trp Arg Asp Leu Ala Val His Ala Ser Asp Ala Thr Val<br>        1170                        1175                      1180 | 3551 |
| ctg cgc gcc tgc ctc acc cgc cgc gac agt ggt gtc gtg gag ctc gcc<br>Leu Arg Ala Cys Leu Thr Arg Arg Asp Ser Gly Val Val Glu Leu Ala<br>1185                      1190                      1195 | 3599 |
| gcc ttc gac ggt gcc gga atg ccg gtg ctc acc gcg gag tcg gtg acg<br>Ala Phe Asp Gly Ala Gly Met Pro Val Leu Thr Ala Glu Ser Val Thr<br>1200                      1205                      1210                      1215 | 3647 |
| ctg ggc gag gtc gcg tcg gca ggc gga tcc gac gag tcg gac ggt ctg<br>Leu Gly Glu Val Ala Ser Ala Gly Gly Ser Asp Glu Ser Asp Gly Leu<br>                1220                      1225                      1230 | 3695 |
| ctt cgg ctt gag tgg ttg ccg gtg gcg gag gcc cac tac gac ggt gcc<br>Leu Arg Leu Glu Trp Leu Pro Val Ala Glu Ala His Tyr Asp Gly Ala<br>    1235                        1240                      1245 | 3743 |
| gac gag ctg ccc gag ggc tac acc ctc atc acc gcc aca cac ccc gac<br>Asp Glu Leu Pro Glu Gly Tyr Thr Leu Ile Thr Ala Thr His Pro Asp<br>        1250                        1255                      1260 | 3791 |
| gac ccc gac gac ccc acc aac ccc cac aac aca ccc aca cgc acc cac<br>Asp Pro Asp Asp Pro Thr Asn Pro His Asn Thr Pro Thr Arg Thr His<br>1265                      1270                      1275 | 3839 |
| aca caa acc aca cgc gtc ctc acc gcc ctc caa cac cac ctc atc acc<br>Thr Gln Thr Thr Arg Val Leu Thr Ala Leu Gln His His Leu Ile Thr<br>1280                      1285                      1290                      1295 | 3887 |
| acc aac cac acc ctc atc gtc cac acc acc gac ccc cca ggc gcc<br>Thr Asn His Thr Leu Ile Val His Thr Thr Asp Pro Pro Gly Ala<br>                1300                      1305                      1310 | 3935 |
| gcc gtc acc ggc ctc acc cgc acc gca caa aac gaa cac ccc ggc cgc<br>Ala Val Thr Gly Leu Thr Arg Thr Ala Gln Asn Glu His Pro Gly Arg<br>                1315                      1320                      1325 | 3983 |

```
atc cac ctc atc gaa acc cac cac ccc cac acc cca ctc ccc ctc acc    4031
Ile His Leu Ile Glu Thr His His Pro His Thr Pro Leu Pro Leu Thr
        1330                1335                1340 caa ctc acc acc ctc cac caa ccc cac cta cgc ctc acc aac aac acc    4079
Gln Leu Thr Thr Leu His Gln Pro His Leu Arg Leu Thr Asn Asn Thr
    1345                1350                1355 ctc cac acc ccc cac ctc acc ccc atc acc acc cac cac aac acc acc    4127
Leu His Thr Pro His Leu Thr Pro Ile Thr Thr His His Asn Thr Thr
1360                1365                1370                1375 aca acc acc ccc aac acc cca ccc ctc aac ccc aac cac gcc atc ctc    4175
Thr Thr Thr Pro Asn Thr Pro Pro Leu Asn Pro Asn His Ala Ile Leu
                1380                1385                1390 atc acc ggc ggc tcc ggc acc ctc gcc ggc atc ctc gcc cgc cac ctc    4223
Ile Thr Gly Gly Ser Gly Thr Leu Ala Gly Ile Leu Ala Arg His Leu
            1395                1400                1405 aac cac ccc cac acc tac ctc ctc tcc cgc aca cca cca ccc ccc acc    4271
Asn His Pro His Thr Tyr Leu Leu Ser Arg Thr Pro Pro Pro Pro Thr
        1410                1415                1420 aca ccc ggc acc cac atc ccc tgc gac ctc acc gac ccc acc caa atc    4319
Thr Pro Gly Thr His Ile Pro Cys Asp Leu Thr Asp Pro Thr Gln Ile
    1425                1430                1435 acc caa gcc ctc acc cac ata cca caa ccc ctc acc ggc atc ttc cac    4367
Thr Gln Ala Leu Thr His Ile Pro Gln Pro Leu Thr Gly Ile Phe His
1440                1445                1450                1455 acc gcc gcc acc ctc gac gac gcc acc ctc acc aac ctc acc ccc caa    4415
Thr Ala Ala Thr Leu Asp Asp Ala Thr Leu Thr Asn Leu Thr Pro Gln
                1460                1465                1470 cac ctc acc acc acc ctc caa ccc aaa gcc gac gcc gcc tgg cac ctc    4463
His Leu Thr Thr Thr Leu Gln Pro Lys Ala Asp Ala Ala Trp His Leu
            1475                1480                1485 cac cac cac acc caa aac caa ccc ctc acc cac ttc gtc ctc tac tcc    4511
His His His Thr Gln Asn Gln Pro Leu Thr His Phe Val Leu Tyr Ser
        1490                1495                1500 agc gcc gcc gcc acc ctc ggc agc ccc ggc caa gcc aac tac gcc gcc    4559
Ser Ala Ala Ala Thr Leu Gly Ser Pro Gly Gln Ala Asn Tyr Ala Ala
    1505                1510                1515 gcc aac gcc ttc ctc gac gcc ctc gcc acc cac cgc cac acc caa gga    4607
Ala Asn Ala Phe Leu Asp Ala Leu Ala Thr His Arg His Thr Gln Gly
1520                1525                1530                1535 caa ccc gcc acc acc atc gcc tgg ggc atg tgg cac acc acc acc aca    4655
Gln Pro Ala Thr Thr Ile Ala Trp Gly Met Trp His Thr Thr Thr Thr
                1540                1545                1550 ctc acc agc caa ctc acc gac agc gac cgc gac cgc atc cgc cgc ggc    4703
Leu Thr Ser Gln Leu Thr Asp Ser Asp Arg Asp Arg Ile Arg Arg Gly
            1555                1560                1565 ggc ttc ctg ccg atc tcg gac gac gag ggc atg c                      4737
Gly Phe Leu Pro Ile Ser Asp Asp Glu Gly Met
        1570                1575

<210> SEQ ID NO 31
<211> LENGTH: 1578
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 31

Met Arg Leu Tyr Glu Ala Ala Arg Arg Thr Gly Ser Pro Val Val Val
  1               5                  10                  15
```

```
Ala Ala Ala Leu Asp Asp Ala Pro Asp Val Pro Leu Leu Arg Gly Leu
            20              25              30

Arg Arg Thr Thr Val Arg Arg Ala Val Arg Glu Arg Ser Leu Ala
        35              40              45

Asp Arg Ser Pro Cys Cys Pro Thr Thr Ser Ala Pro Thr Pro Pro Ser
    50              55              60

Arg Ser Ser Trp Asn Ser Thr Ala Thr Val Leu Gly His Leu Gly Ala
65              70              75              80

Glu Asp Ile Pro Ala Thr Thr Thr Phe Lys Glu Leu Gly Ile Asp Ser
                85              90              95

Leu Thr Ala Val Gln Leu Arg Asn Ala Leu Thr Thr Ala Thr Gly Val
            100             105             110

Arg Leu Asn Ala Thr Ala Val Phe Asp Phe Pro Thr Pro Arg Ala Leu
        115             120             125

Ala Ala Arg Leu Gly Asp Glu Leu Ala Gly Thr Arg Ala Pro Val Ala
    130             135             140

Ala Arg Thr Ala Ala Thr Ala Ala Ala His Asp Glu Pro Leu Ala Ile
145             150             155             160

Val Gly Met Ala Cys Arg Leu Pro Gly Gly Val Ala Ser Pro Gln Glu
                165             170             175

Leu Trp Arg Leu Val Ala Ser Gly Thr Asp Ala Ile Thr Glu Phe Pro
            180             185             190

Ala Asp Arg Gly Trp Asp Val Asp Ala Leu Tyr Asp Pro Asp Pro Asp
        195             200             205

Ala Ile Gly Lys Thr Phe Val Arg His Gly Gly Phe Leu Asp Gly Ala
    210             215             220

Thr Gly Phe Asp Ala Ala Phe Phe Gly Ile Ser Pro Arg Glu Ala Leu
225             230             235             240

Ala Met Asp Pro Gln Gln Arg Val Leu Leu Glu Thr Ser Trp Glu Ala
                245             250             255

Phe Glu Ser Ala Gly Ile Thr Pro Asp Ala Ala Arg Gly Ser Asp Thr
            260             265             270

Gly Val Phe Ile Gly Ala Phe Ser Tyr Gly Tyr Gly Thr Gly Ala Asp
        275             280             285

Thr Asn Gly Phe Gly Ala Thr Gly Ser Gln Thr Ser Val Leu Ser Gly
    290             295             300

Arg Leu Ser Tyr Phe Tyr Gly Leu Glu Gly Pro Ser Val Thr Val Asp
305             310             315             320

Thr Ala Cys Ser Ser Ser Leu Val Ala Leu His Gln Ala Gly Gln Ser
                325             330             335

Leu Arg Ser Gly Glu Cys Ser Leu Ala Leu Val Gly Gly Val Thr Val
            340             345             350

Met Ala Ser Pro Gly Gly Phe Val Glu Phe Ser Arg Gln Arg Gly Leu
        355             360             365

Ala Pro Asp Gly Arg Ala Lys Ala Phe Gly Ala Gly Ala Asp Gly Thr
    370             375             380

Ser Phe Ala Glu Gly Ala Gly Ala Leu Val Val Glu Arg Leu Ser Asp
385             390             395             400

Ala Glu Arg His Gly His Thr Val Leu Ala Leu Val Arg Gly Ser Ala
                405             410             415

Ala Asn Ser Asp Gly Ala Ser Asn Gly Leu Ser Ala Pro Asn Gly Pro
            420             425             430

Ser Gln Glu Arg Val Ile His Gln Ala Leu Ala Asn Ala Lys Leu Thr
```

-continued

```
                435                 440                 445
Pro Ala Asp Val Asp Ala Val Glu Ala His Gly Thr Gly Thr Arg Leu
450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
                500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
        530                 535                 540

Arg Pro Trp Pro Gly Thr Gly Arg Pro Arg Ala Ala Val Ser Ser
545                 550                 555                 560

Phe Gly Val Ser Gly Thr Asn Ala His Ile Ile Leu Glu Ala Gly Pro
                565                 570                 575

Val Lys Thr Gly Pro Val Glu Ala Gly Ala Ile Glu Ala Gly Pro Val
                580                 585                 590

Glu Val Gly Pro Val Glu Ala Gly Pro Leu Pro Ala Ala Pro Pro Ser
            595                 600                 605

Ala Pro Gly Glu Asp Leu Pro Leu Leu Val Ser Ala Arg Ser Pro Glu
610                 615                 620

Ala Leu Asp Glu Gln Ile Gly Arg Leu Arg Ala Tyr Leu Asp Thr Gly
625                 630                 635                 640

Pro Gly Val Asp Arg Ala Ala Val Ala Gln Thr Leu Ala Arg Arg Thr
                645                 650                 655

His Phe Thr His Arg Ala Val Leu Leu Gly Asp Thr Val Ile Gly Ala
                660                 665                 670

Pro Pro Ala Asp Gln Ala Asp Glu Leu Val Phe Val Tyr Ser Gly Gln
                675                 680                 685

Gly Thr Gln His Pro Ala Met Gly Glu Gln Leu Ala Ala Ala Phe Pro
        690                 695                 700

Val Phe Ala Arg Ile His Gln Gln Val Trp Asp Leu Leu Asp Val Pro
705                 710                 715                 720

Asp Leu Glu Val Asn Glu Thr Gly Tyr Ala Gln Pro Ala Leu Phe Ala
                725                 730                 735

Met Gln Val Ala Leu Phe Gly Leu Leu Glu Ser Trp Gly Val Arg Pro
        740                 745                 750

Asp Ala Val Ile Gly His Ser Val Gly Glu Leu Ala Ala Ala Tyr Val
                755                 760                 765

Ser Gly Val Trp Ser Leu Glu Asp Ala Cys Thr Leu Val Ser Ala Arg
        770                 775                 780

Ala Arg Leu Met Gln Ala Leu Pro Ala Gly Gly Val Met Val Ala Val
785                 790                 795                 800

Pro Val Ser Glu Asp Glu Ala Arg Ala Val Leu Gly Glu Gly Val Glu
                805                 810                 815

Ile Ala Ala Val Asn Gly Pro Ser Ser Val Val Leu Ser Gly Asp Glu
                820                 825                 830

Ala Ala Val Leu Gln Ala Ala Glu Gly Leu Gly Lys Trp Thr Arg Leu
                835                 840                 845

Ala Thr Ser His Ala Phe His Ser Ala Arg Met Glu Pro Met Leu Glu
        850                 855                 860
```

-continued

```
Glu Phe Arg Ala Val Ala Glu Gly Leu Thr Tyr Arg Thr Pro Gln Val
865                 870                 875                 880

Ser Met Ala Val Gly Asp Gln Val Thr Thr Ala Glu Tyr Trp Val Arg
                885                 890                 895

Gln Val Arg Asp Thr Val Arg Phe Gly Glu Gln Val Ala Ser Tyr Glu
                900                 905                 910

Asp Ala Val Phe Val Glu Leu Gly Ala Asp Arg Ser Leu Ala Arg Leu
                915                 920                 925

Val Asp Gly Val Ala Met Leu His Gly Asp His Glu Ile Gln Ala Ala
    930                 935                 940

Ile Gly Ala Leu Ala His Leu Tyr Val Asn Gly Val Thr Val Asp Trp
945                 950                 955                 960

Pro Ala Leu Leu Gly Asp Ala Pro Ala Thr Arg Val Leu Asp Leu Pro
                965                 970                 975

Thr Tyr Ala Phe Gln His Gln Arg Tyr Trp Leu Glu Ser Ala Pro Pro
                980                 985                 990

Ala Thr Ala Asp Ser Gly His Pro Val Leu Gly Thr Gly Val Ala Val
                995                 1000                1005

Ala Gly Ser Pro Gly Arg Val Phe Thr Gly Pro Val Pro Ala Gly Ala
    1010                1015                1020

Asp Arg Ala Val Phe Ile Ala Glu Leu Ala Leu Ala Ala Ala Asp Ala
1025                1030                1035                1040

Thr Asp Cys Ala Thr Val Glu Gln Leu Asp Val Thr Ser Val Pro Gly
                1045                1050                1055

Gly Ser Ala Arg Gly Arg Ala Thr Ala Gln Thr Trp Val Asp Glu Pro
                1060                1065                1070

Ala Ala Asp Gly Arg Arg Phe Thr Val His Thr Arg Val Gly Asp
                1075                1080                1085

Ala Pro Trp Thr Leu His Ala Glu Gly Val Leu Arg Pro Gly Arg Val
    1090                1095                1100

Pro Gln Pro Glu Ala Val Asp Thr Ala Trp Pro Pro Gly Ala Val
1105                1110                1115                1120

Pro Ala Asp Gly Leu Pro Gly Ala Trp Arg Arg Ala Asp Gln Val Phe
                1125                1130                1135

Val Glu Ala Glu Val Asp Ser Pro Asp Gly Phe Val Ala His Pro Asp
                1140                1145                1150

Leu Leu Asp Ala Val Phe Ser Ala Val Gly Asp Gly Ser Arg Gln Pro
                1155                1160                1165

Thr Gly Trp Arg Asp Leu Ala Val His Ala Ser Asp Ala Thr Val Leu
    1170                1175                1180

Arg Ala Cys Leu Thr Arg Arg Asp Ser Gly Val Val Glu Leu Ala Ala
1185                1190                1195                1200

Phe Asp Gly Ala Gly Met Pro Val Leu Thr Ala Glu Ser Val Thr Leu
                1205                1210                1215

Gly Glu Val Ala Ser Ala Gly Gly Ser Asp Glu Ser Asp Gly Leu Leu
                1220                1225                1230

Arg Leu Glu Trp Leu Pro Val Ala Glu Ala His Tyr Asp Gly Ala Asp
    1235                1240                1245

Glu Leu Pro Glu Gly Tyr Thr Leu Ile Thr Ala Thr His Pro Asp Asp
    1250                1255                1260

Pro Asp Asp Pro Thr Asn Pro His Asn Thr Pro Thr Arg Thr His Thr
1265                1270                1275                1280
```

```
Gln Thr Thr Arg Val Leu Thr Ala Leu Gln His His Leu Ile Thr Thr
            1285                1290                1295

Asn His Thr Leu Ile Val His Thr Thr Thr Asp Pro Pro Gly Ala Ala
        1300                1305                1310

Val Thr Gly Leu Thr Arg Thr Ala Gln Asn Glu His Pro Gly Arg Ile
        1315                1320                1325

His Leu Ile Glu Thr His His Pro His Thr Pro Leu Pro Leu Thr Gln
        1330                1335                1340

Leu Thr Thr Leu His Gln Pro His Leu Arg Leu Thr Asn Asn Thr Leu
1345                1350                1355                1360

His Thr Pro His Leu Thr Pro Ile Thr Thr His His Asn Thr Thr Thr
            1365                1370                1375

Thr Thr Pro Asn Thr Pro Pro Leu Asn Pro Asn His Ala Ile Leu Ile
            1380                1385                1390

Thr Gly Gly Ser Gly Thr Leu Ala Gly Ile Leu Ala Arg His Leu Asn
            1395                1400                1405

His Pro His Thr Tyr Leu Leu Ser Arg Thr Pro Pro Pro Thr Thr
        1410                1415                1420

Pro Gly Thr His Ile Pro Cys Asp Leu Thr Asp Pro Thr Gln Ile Thr
1425                1430                1435                1440

Gln Ala Leu Thr His Ile Pro Gln Pro Leu Thr Gly Ile Phe His Thr
            1445                1450                1455

Ala Ala Thr Leu Asp Asp Ala Thr Leu Thr Asn Leu Thr Pro Gln His
            1460                1465                1470

Leu Thr Thr Thr Leu Gln Pro Lys Ala Asp Ala Ala Trp His Leu His
        1475                1480                1485

His His Thr Gln Asn Gln Pro Leu Thr His Phe Val Leu Tyr Ser Ser
        1490                1495                1500

Ala Ala Ala Thr Leu Gly Ser Pro Gly Gln Ala Asn Tyr Ala Ala Ala
1505                1510                1515                1520

Asn Ala Phe Leu Asp Ala Leu Ala Thr His Arg His Thr Gln Gly Gln
            1525                1530                1535

Pro Ala Thr Thr Ile Ala Trp Gly Met Trp His Thr Thr Thr Thr Leu
            1540                1545                1550

Thr Ser Gln Leu Thr Asp Ser Asp Arg Asp Arg Ile Arg Arg Gly Gly
            1555                1560                1565

Phe Leu Pro Ile Ser Asp Asp Glu Gly Met
        1570                1575

<210> SEQ ID NO 32
<211> LENGTH: 4818
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4817)

<400> SEQUENCE: 32 gc atg cgg ctg tac gag gcg gca cgg cgc acc gga agt ccc gtg gtg         47
   Met Arg Leu Tyr Glu Ala Ala Arg Arg Thr Gly Ser Pro Val Val
   1               5                   10                  15 gtg gcg gcc gcg ctc gac gac gcg ccg gac gtg ccg ctg ctg cgc ggg        95
Val Ala Ala Ala Leu Asp Asp Ala Pro Asp Val Pro Leu Leu Arg Gly
            20                  25                  30
```

-continued

| | | |
|---|---|---|
| ctg cgg cgt acg acc gtc cgg cgt gcc gcc gtc cgg gaa cgc tct ctc<br>Leu Arg Arg Thr Thr Val Arg Arg Ala Ala Val Arg Glu Arg Ser Leu<br>35　　　　　　　　40　　　　　　　　45 | | 143 |
| gcc gac cgc tcg ccg tgc tgc ccg acg acg agc gcg ccg acg cct ccc<br>Ala Asp Arg Ser Pro Cys Cys Pro Thr Thr Ser Ala Pro Thr Pro Pro<br>　　50　　　　　　　　55　　　　　　　　60 | | 191 |
| tcg cgt tcg tcc tgg aac agc acc gcc acc gtg ctc ggc cac ctg ggc<br>Ser Arg Ser Ser Trp Asn Ser Thr Ala Thr Val Leu Gly His Leu Gly<br>65　　　　　　　　70　　　　　　　　75 | | 239 |
| gcc gaa gac atc ccg gcg acg acg acg ttc aag gaa ctc ggc atc gac<br>Ala Glu Asp Ile Pro Ala Thr Thr Thr Phe Lys Glu Leu Gly Ile Asp<br>80　　　　　　　　85　　　　　　　　90　　　　　　　　95 | | 287 |
| tcg ctc acc gcg gtc cag ctg cgc aac gcg ctg acc acg gcg acc ggc<br>Ser Leu Thr Ala Val Gln Leu Arg Asn Ala Leu Thr Thr Ala Thr Gly<br>　　　　100　　　　　　　　105　　　　　　　　110 | | 335 |
| gta cgc ctc aac gcc aca gcg gtc ttc gac ttt ccg acg ccg cgc gcg<br>Val Arg Leu Asn Ala Thr Ala Val Phe Asp Phe Pro Thr Pro Arg Ala<br>　　　　115　　　　　　　　120　　　　　　　　125 | | 383 |
| ctc gcc gcg aga ctc ggc gac gag ctg gcc ggt acc cgc gcg ccc gtc<br>Leu Ala Ala Arg Leu Gly Asp Glu Leu Ala Gly Thr Arg Ala Pro Val<br>　　　　130　　　　　　　　135　　　　　　　　140 | | 431 |
| gcg gcc cgg acc gcg gcc acc gcg gcc gcg cac gac gaa ccg ctg gcg<br>Ala Ala Arg Thr Ala Ala Thr Ala Ala Ala His Asp Glu Pro Leu Ala<br>145　　　　　　　　150　　　　　　　　155 | | 479 |
| atc gtg ggc atg gcc tgc cgt ctg ccg ggc ggg gtc gcg tcg cca cag<br>Ile Val Gly Met Ala Cys Arg Leu Pro Gly Gly Val Ala Ser Pro Gln<br>160　　　　　　　　165　　　　　　　　170　　　　　　　　175 | | 527 |
| gag ctg tgg cgt ctc gtc gcg tcc ggc acc gac gcc atc acg gag ttc<br>Glu Leu Trp Arg Leu Val Ala Ser Gly Thr Asp Ala Ile Thr Glu Phe<br>　　　　180　　　　　　　　185　　　　　　　　190 | | 575 |
| ccc gcg gac cgc ggc tgg gac gtg gac gcg ctc tac gac ccg gac ccc<br>Pro Ala Asp Arg Gly Trp Asp Val Asp Ala Leu Tyr Asp Pro Asp Pro<br>　　　　195　　　　　　　　200　　　　　　　　205 | | 623 |
| gac gcg atc ggc aag acc ttc gtc cgg cac ggc ggc ttc ctc gac ggt<br>Asp Ala Ile Gly Lys Thr Phe Val Arg His Gly Gly Phe Leu Asp Gly<br>210　　　　　　　　215　　　　　　　　220 | | 671 |
| gcg acc ggc ttc gac gcg gcg ttc ttc ggg atc agc ccg cgc gag gcc<br>Ala Thr Gly Phe Asp Ala Ala Phe Phe Gly Ile Ser Pro Arg Glu Ala<br>225　　　　　　　　230　　　　　　　　235 | | 719 |
| ctg gcc atg gac ccg cag caa cgg gtg ctc ctg gag acg tcc tgg gag<br>Leu Ala Met Asp Pro Gln Gln Arg Val Leu Leu Glu Thr Ser Trp Glu<br>240　　　　　　　　245　　　　　　　　250　　　　　　　　255 | | 767 |
| gcg ttc gaa agc gcg ggc atc acc ccg gac gcg gcg cgg ggc agc gac<br>Ala Phe Glu Ser Ala Gly Ile Thr Pro Asp Ala Ala Arg Gly Ser Asp<br>　　　　260　　　　　　　　265　　　　　　　　270 | | 815 |
| acc ggc gtg ttc atc ggc gcg ttc tcc tac ggg tac ggc acg ggt gcg<br>Thr Gly Val Phe Ile Gly Ala Phe Ser Tyr Gly Tyr Gly Thr Gly Ala<br>　　　　275　　　　　　　　280　　　　　　　　285 | | 863 |
| gat acc aac ggc ttc ggc gcg aca ggg tcg cag acc agc gtg ctc tcc<br>Asp Thr Asn Gly Phe Gly Ala Thr Gly Ser Gln Thr Ser Val Leu Ser<br>290　　　　　　　　295　　　　　　　　300 | | 911 |
| ggc cgc ctc tcg tac ttc tac ggt ctg gag ggc cct tcg gtc acg gtc<br>Gly Arg Leu Ser Tyr Phe Tyr Gly Leu Glu Gly Pro Ser Val Thr Val<br>305　　　　　　　　310　　　　　　　　315 | | 959 |
| gac acc gcc tgc tcg tcg tca ctg gtc gcc ctg cac cag gca ggg cag<br>Asp Thr Ala Cys Ser Ser Ser Leu Val Ala Leu His Gln Ala Gly Gln<br>320　　　　　　　　325　　　　　　　　330　　　　　　　　335 | | 1007 |
| tcc ctg cgc tcg ggc gaa tgc tcg ctc gcc ctg gtc ggc ggt gtc acg<br>Ser Leu Arg Ser Gly Glu Cys Ser Leu Ala Leu Val Gly Gly Val Thr<br>　　　　340　　　　　　　　345　　　　　　　　350 | | 1055 |

-continued

```
gtg atg gcg tcg ccc ggc gga ttc gtc gag ttc tcc cgg cag cgc ggg    1103
Val Met Ala Ser Pro Gly Gly Phe Val Glu Phe Ser Arg Gln Arg Gly
    355                 360                 365 ctc gcg ccg gac ggg cgg gcg aag gcg ttc ggc gcg ggc gcg gac ggt    1151
Leu Ala Pro Asp Gly Arg Ala Lys Ala Phe Gly Ala Gly Ala Asp Gly
                370                 375                 380 acg agc ttc gcc gag ggc gcc ggt gcc ctg gtg gtc gag cgg ctc tcc    1199
Thr Ser Phe Ala Glu Gly Ala Gly Ala Leu Val Val Glu Arg Leu Ser
385                 390                 395 gac gcg gag cgc cac ggc cac acc gtc ctc gcc ctc gta cgc ggc tcc    1247
Asp Ala Glu Arg His Gly His Thr Val Leu Ala Leu Val Arg Gly Ser
400                 405                 410                 415 gcg gct aac tcc gac ggc gcg tcg aac ggt ctg tcg gcg ccg aac ggc    1295
Ala Ala Asn Ser Asp Gly Ala Ser Asn Gly Leu Ser Ala Pro Asn Gly
                420                 425                 430 ccc tcc cag gaa cgc gtc atc cac cag gcc ctc gcg aac gcg aaa ctc    1343
Pro Ser Gln Glu Arg Val Ile His Gln Ala Leu Ala Asn Ala Lys Leu
                435                 440                 445 acc ccc gcc gat gtc gac gcg gtc gag gcg cac ggc acc ggc acc cgc    1391
Thr Pro Ala Asp Val Asp Ala Val Glu Ala His Gly Thr Gly Thr Arg
    450                 455                 460 ctc ggc gac ccc atc gag gcg cag gcg ctg ctc gcg acg tac gga cag    1439
Leu Gly Asp Pro Ile Glu Ala Gln Ala Leu Leu Ala Thr Tyr Gly Gln
465                 470                 475 gac cgg gcg acg ccc ctg ctc ctc ggc tcg ctg aag tcg aac atc ggg    1487
Asp Arg Ala Thr Pro Leu Leu Leu Gly Ser Leu Lys Ser Asn Ile Gly
480                 485                 490                 495 cac gcc cag gcc gcg tca ggg gtc gcc ggg atc atc aag atg gtg cag    1535
His Ala Gln Ala Ala Ser Gly Val Ala Gly Ile Ile Lys Met Val Gln
                500                 505                 510 gcc atc cgg cac ggg gaa ctg ccg ccg aca ctg cac gcg gac gag ccg    1583
Ala Ile Arg His Gly Glu Leu Pro Pro Thr Leu His Ala Asp Glu Pro
            515                 520                 525 tcg ccg cac gtc gac tgg acg gcc ggt gcc gtc gag ctc ctg acg tcg    1631
Ser Pro His Val Asp Trp Thr Ala Gly Ala Val Glu Leu Leu Thr Ser
    530                 535                 540 gcc cgg ccg tgg ccg ggg acc ggt cgc ccg cgc cgc gct gcc gtc tcg    1679
Ala Arg Pro Trp Pro Gly Thr Gly Arg Pro Arg Arg Ala Ala Val Ser
545                 550                 555 tcg ttc ggc gtg agc ggc acg aac gcc cac atc atc ctt gag gca gga    1727
Ser Phe Gly Val Ser Gly Thr Asn Ala His Ile Ile Leu Glu Ala Gly
560                 565                 570                 575 ccg gtc aaa acg gga ccg gtc gag gca gga gcg atc gag gca gga ccg    1775
Pro Val Lys Thr Gly Pro Val Glu Ala Gly Ala Ile Glu Ala Gly Pro
                580                 585                 590 gtc gaa gta gga ccg gtc gag gct gga ccg ctc ccc gcg gcg ccg ccg    1823
Val Glu Val Gly Pro Val Glu Ala Gly Pro Leu Pro Ala Ala Pro Pro
            595                 600                 605 tca gca ccg ggc gaa gac ctt ccg ctg ctc gtg tcg gcg cgt tcc ccg    1871
Ser Ala Pro Gly Glu Asp Leu Pro Leu Leu Val Ser Ala Arg Ser Pro
    610                 615                 620 gag gca ctc gac gag cag atc ggg cgc ctg cgc gcc tat ctc gac acc    1919
Glu Ala Leu Asp Glu Gln Ile Gly Arg Leu Arg Ala Tyr Leu Asp Thr
625                 630                 635 ggc ccg ggc gtc gac cgg gcg gcc gtg gcg cag aca ctg gcc cgg cgt    1967
Gly Pro Gly Val Asp Arg Ala Ala Val Ala Gln Thr Leu Ala Arg Arg
640                 645                 650                 655 acg cac ttc acc cac cgg gcc gta ctg ctc ggg gac acc gtc atc ggc    2015
Thr His Phe Thr His Arg Ala Val Leu Leu Gly Asp Thr Val Ile Gly
```

-continued

```
              660                 665                 670
gct ccc ccc gcg gac cag gcc gac gaa ctc gtc ttc gtc tac tcc ggt     2063
Ala Pro Pro Ala Asp Gln Ala Asp Glu Leu Val Phe Val Tyr Ser Gly
            675                 680                 685 cag ggc acc cag cat ccc gcg atg ggc gag cag cta gcc gat tcg tcg     2111
Gln Gly Thr Gln His Pro Ala Met Gly Glu Gln Leu Ala Asp Ser Ser
        690                 695                 700 gtg gtg ttc gcc gag cgg atg gcc gag tgt gcg gcg gcg ttg cgc gag     2159
Val Val Phe Ala Glu Arg Met Ala Glu Cys Ala Ala Ala Leu Arg Glu
    705                 710                 715 ttc gtg gac tgg gat ctg ttc acg gtt ctg gat gat ccg gcg gtg gtg     2207
Phe Val Asp Trp Asp Leu Phe Thr Val Leu Asp Asp Pro Ala Val Val
720                 725                 730                 735 gac cgg gtt gat gtg gtc cag ccc gct tcc tgg gcg atg atg gtt tcc     2255
Asp Arg Val Asp Val Val Gln Pro Ala Ser Trp Ala Met Met Val Ser
                740                 745                 750 ctg gcc gcg gtg tgg cag gcg gcc ggt gtg cgg ccg gat gcg gtg atc     2303
Leu Ala Ala Val Trp Gln Ala Ala Gly Val Arg Pro Asp Ala Val Ile
            755                 760                 765 ggc cat tcg cag ggt gag atc gcc gca gct tgt gtg gcg ggt gcg gtg     2351
Gly His Ser Gln Gly Glu Ile Ala Ala Ala Cys Val Ala Gly Ala Val
        770                 775                 780 tca cta cgc gat gcc gcc cgg atc gtg acc ttg cgc agc cag gcg atc     2399
Ser Leu Arg Asp Ala Ala Arg Ile Val Thr Leu Arg Ser Gln Ala Ile
    785                 790                 795 gcc cgg ggc ctg gcg ggc cgg ggc gcg atg gca tcc gtc gcc ctg ccc     2447
Ala Arg Gly Leu Ala Gly Arg Gly Ala Met Ala Ser Val Ala Leu Pro
800                 805                 810                 815 gcg cag gat gtc gag ctg gtc gac ggg gcc tgg atc gcc gcc cac aac     2495
Ala Gln Asp Val Glu Leu Val Asp Gly Ala Trp Ile Ala Ala His Asn
                820                 825                 830 ggg ccc gcc tcc acc gtg atc gcg ggc acc ccg gaa gcg gtc gac cat     2543
Gly Pro Ala Ser Thr Val Ile Ala Gly Thr Pro Glu Ala Val Asp His
            835                 840                 845 gtc ctc acc gct cat gag gca caa ggg gtg cgg gtg cgg cgg atc acc     2591
Val Leu Thr Ala His Glu Ala Gln Gly Val Arg Val Arg Arg Ile Thr
        850                 855                 860 gtc gac tat gcc tcg cac acc ccg cac gtc gag ctg atc cgc gac gaa     2639
Val Asp Tyr Ala Ser His Thr Pro His Val Glu Leu Ile Arg Asp Glu
    865                 870                 875 cta ctc gac atc act agc gac agc agc tcg cag acc ccg ctc gtg ccg     2687
Leu Leu Asp Ile Thr Ser Asp Ser Ser Ser Gln Thr Pro Leu Val Pro
880                 885                 890                 895 tgg ctg tcg acc gtg gac ggc acc tgg gtc gac agc ccg ctg gac ggg     2735
Trp Leu Ser Thr Val Asp Gly Thr Trp Val Asp Ser Pro Leu Asp Gly
                900                 905                 910 gag tac tgg tac cgg aac ctg cgt gaa ccg gtc ggt ttc cac ccc gcc     2783
Glu Tyr Trp Tyr Arg Asn Leu Arg Glu Pro Val Gly Phe His Pro Ala
            915                 920                 925 gtc agc cag ttg cag gcc cag ggc gac acc gtg ttc gtc gag gtc agc     2831
Val Ser Gln Leu Gln Ala Gln Gly Asp Thr Val Phe Val Glu Val Ser
        930                 935                 940 gcc agc ccg gtg ttg ttg cag gcg atg gac gac gat gtc gtc acg gtt     2879
Ala Ser Pro Val Leu Leu Gln Ala Met Asp Asp Asp Val Val Thr Val
    945                 950                 955 gcc acg ctg cgt cgt gac gac ggc gac gcc acc cgg atg ctc acc gcc     2927
Ala Thr Leu Arg Arg Asp Asp Gly Asp Ala Thr Arg Met Leu Thr Ala
960                 965                 970                 975 ctg gca cag gcc tat gtc cac ggc gtc acc gtc gac tgg ccc gcc atc     2975
```

```
                                                                           -continued Leu Ala Gln Ala Tyr Val His Gly Val Thr Val Asp Trp Pro Ala Ile
            980                 985                 990 ctc ggc acc acc aca acc cgg gta ctg gac ctt ccg acc tac gcc ttc      3023
Leu Gly Thr Thr Thr Thr Arg Val Leu Asp Leu Pro Thr Tyr Ala Phe
        995                1000                1005 caa cac cag cgg tac tgg ctc gag tcg gct ccc ccg gcc acg gcc gac      3071
Gln His Gln Arg Tyr Trp Leu Glu Ser Ala Pro Pro Ala Thr Ala Asp
        1010                1015                1020 tcg ggc cac ccc gtc ctc ggc acc gga gtc gcc gtc gcc ggg tcg ccg      3119
Ser Gly His Pro Val Leu Gly Thr Gly Val Ala Val Ala Gly Ser Pro
        1025                1030                1035 ggc cgg gtg ttc acg ggt ccc gtg ccc gcc ggt gcg gac cgc gcg gtg      3167
Gly Arg Val Phe Thr Gly Pro Val Pro Ala Gly Ala Asp Arg Ala Val
1040                1045                1050                1055 ttc atc gcc gaa ctg gcg ctc gcc gcc gcc gac gcc acc gac tgc gcc      3215
Phe Ile Ala Glu Leu Ala Leu Ala Ala Ala Asp Ala Thr Asp Cys Ala
            1060                1065                1070 acg gtc gaa cag ctc gac gtc acc tcc gtg ccc ggc gga tcc gcc cgc      3263
Thr Val Glu Gln Leu Asp Val Thr Ser Val Pro Gly Gly Ser Ala Arg
        1075                1080                1085 ggc agg gcc acc gcg cag acc tgg gtc gat gaa ccc gcc gcc gac ggg      3311
Gly Arg Ala Thr Ala Gln Thr Trp Val Asp Glu Pro Ala Ala Asp Gly
        1090                1095                1100 cgg cgc cgc ttc acc gtc cac acc cgt gtc ggc gac gcc ccg tgg acg      3359
Arg Arg Arg Phe Thr Val His Thr Arg Val Gly Asp Ala Pro Trp Thr
        1105                1110                1115 ctg cac gcc gag ggg gtt ctc cgc ccc ggc cgc gtg ccc cag ccc gaa      3407
Leu His Ala Glu Gly Val Leu Arg Pro Gly Arg Val Pro Gln Pro Glu
1120                1125                1130                1135 gcc gtc gac acc gcc tgg ccc ccg ccg ggc gcg gtg ccc gcg gac ggg      3455
Ala Val Asp Thr Ala Trp Pro Pro Pro Gly Ala Val Pro Ala Asp Gly
                1140                1145                1150 ctg ccc ggg gcg tgg cga cgc gcg gac cag gtc ttc gtc gaa gcc gaa      3503
Leu Pro Gly Ala Trp Arg Arg Ala Asp Gln Val Phe Val Glu Ala Glu
            1155                1160                1165 gtc gac agc cct gac ggc ttc gtg gca cac ccc gac ctg ctc gac gcg      3551
Val Asp Ser Pro Asp Gly Phe Val Ala His Pro Asp Leu Leu Asp Ala
        1170                1175                1180 gtc ttc tcc gcg gtc ggc gac ggg agc cgc cag ccg acc gga tgg cgc      3599
Val Phe Ser Ala Val Gly Asp Gly Ser Arg Gln Pro Thr Gly Trp Arg
        1185                1190                1195 gac ctc gcg gtg cac gcg tcg gac gcc acc gtg ctg cgc gcc tgc ctc      3647
Asp Leu Ala Val His Ala Ser Asp Ala Thr Val Leu Arg Ala Cys Leu
1200                1205                1210                1215 acc cgc cgc gac agt ggt gtc gtg gag ctc gcc gcc ttc gac ggt gcc      3695
Thr Arg Arg Asp Ser Gly Val Val Glu Leu Ala Ala Phe Asp Gly Ala
                1220                1225                1230 gga atg ccg gtg ctc acc gcg gag tcg gtg acg ctg ggc gag gtc gcg      3743
Gly Met Pro Val Leu Thr Ala Glu Ser Val Thr Leu Gly Glu Val Ala
            1235                1240                1245 tcg gca ggc gga tcc gac gag tcg gac ggt ctg ctt cgg ctt gag tgg      3791
Ser Ala Gly Gly Ser Asp Glu Ser Asp Gly Leu Leu Arg Leu Glu Trp
        1250                1255                1260 ttg ccg gtg gcg gag gcc cac tac gac ggt gcc gac gag ctg ccc gag      3839
Leu Pro Val Ala Glu Ala His Tyr Asp Gly Ala Asp Glu Leu Pro Glu
        1265                1270                1275 ggc tac acc ctc atc acc gcc aca cac ccc gac gac ccc gac gac ccc      3887
Gly Tyr Thr Leu Ile Thr Ala Thr His Pro Asp Asp Pro Asp Asp Pro
1280                1285                1290                1295
```

| | |
|---|---|
| acc aac ccc cac aac aca ccc aca cgc acc cac aca caa acc aca cgc<br>Thr Asn Pro His Asn Thr Pro Thr Arg Thr His Thr Gln Thr Thr Arg<br>　　　　　　　　1300　　　　　　　　　1305　　　　　　　　1310 | 3935 |
| gtc ctc acc gcc ctc caa cac cac ctc atc acc acc aac cac acc ctc<br>Val Leu Thr Ala Leu Gln His His Leu Ile Thr Thr Asn His Thr Leu<br>1315　　　　　　　　　1320　　　　　　　　1325 | 3983 |
| atc gtc cac acc acc acc gac ccc cca ggc gcc gtc acc ggc ctc<br>Ile Val His Thr Thr Thr Asp Pro Pro Gly Ala Ala Val Thr Gly Leu<br>　　　　1330　　　　　　　　1335　　　　　　　　　1340 | 4031 |
| acc cgc acc gca caa aac gaa cac ccc ggc cgc atc cac ctc atc gaa<br>Thr Arg Thr Ala Gln Asn Glu His Pro Gly Arg Ile His Leu Ile Glu<br>1345　　　　　　　　　1350　　　　　　　　1355 | 4079 |
| acc cac cac ccc cac acc cca ctc ccc ctc acc caa ctc acc acc ctc<br>Thr His His Pro His Thr Pro Leu Pro Leu Thr Gln Leu Thr Thr Leu<br>1360　　　　　　　　1365　　　　　　　　　1370　　　　　　　　1375 | 4127 |
| cac caa ccc cac cta cgc ctc acc aac aac acc ctc cac acc ccc cac<br>His Gln Pro His Leu Arg Leu Thr Asn Asn Thr Leu His Thr Pro His<br>　　　　　　　　　1380　　　　　　　　1385　　　　　　　　　1390 | 4175 |
| ctc acc ccc atc acc acc cac cac aac acc acc aca acc acc ccc aac<br>Leu Thr Pro Ile Thr Thr His His Asn Thr Thr Thr Thr Thr Pro Asn<br>　　　　1395　　　　　　　　1400　　　　　　　　　1405 | 4223 |
| acc cca ccc ctc aac ccc aac cac gcc atc ctc atc acc ggc ggc tcc<br>Thr Pro Pro Leu Asn Pro Asn His Ala Ile Leu Ile Thr Gly Gly Ser<br>　　　　　　　1410　　　　　　　　　1415　　　　　　　　1420 | 4271 |
| ggc acc ctc gcc ggc atc ctc gcc cgc cac ctc aac cac ccc cac acc<br>Gly Thr Leu Ala Gly Ile Leu Ala Arg His Leu Asn His Pro His Thr<br>1425　　　　　　　　　1430　　　　　　　　1435 | 4319 |
| tac ctc ctc tcc cgc aca cca cca ccc ccc acc aca ccc ggc acc cac<br>Tyr Leu Leu Ser Arg Thr Pro Pro Pro Pro Thr Thr Pro Gly Thr His<br>1440　　　　　　　　1445　　　　　　　　　1450　　　　　　　　1455 | 4367 |
| atc ccc tgc gac ctc acc gac ccc acc caa atc acc caa gcc ctc acc<br>Ile Pro Cys Asp Leu Thr Asp Pro Thr Gln Ile Thr Gln Ala Leu Thr<br>　　　　　　　　　1460　　　　　　　　1465　　　　　　　　　1470 | 4415 |
| cac ata cca caa ccc ctc acc ggc atc ttc cac acc gcc gcc acc ctc<br>His Ile Pro Gln Pro Leu Thr Gly Ile Phe His Thr Ala Ala Thr Leu<br>　　　　1475　　　　　　　　1480　　　　　　　　　1485 | 4463 |
| gac gac gcc acc ctc acc aac ctc acc ccc caa cac ctc acc acc acc<br>Asp Asp Ala Thr Leu Thr Asn Leu Thr Pro Gln His Leu Thr Thr Thr<br>　　　　　　　1490　　　　　　　　　1495　　　　　　　　1500 | 4511 |
| ctc caa ccc aaa gcc gac gcc gcc tgg cac ctc cac cac cac acc caa<br>Leu Gln Pro Lys Ala Asp Ala Ala Trp His Leu His His His Thr Gln<br>1505　　　　　　　　　1510　　　　　　　　1515 | 4559 |
| aac caa ccc ctc acc cac ttc gtc ctc tac tcc agc gcc gcc gcc acc<br>Asn Gln Pro Leu Thr His Phe Val Leu Tyr Ser Ser Ala Ala Ala Thr<br>1520　　　　　　　　1525　　　　　　　　　1530　　　　　　　　1535 | 4607 |
| ctc ggc agc ccc ggc caa gcc aac tac gcc gcc gcc aac gcc ttc ctc<br>Leu Gly Ser Pro Gly Gln Ala Asn Tyr Ala Ala Ala Asn Ala Phe Leu<br>　　　　　　　　　1540　　　　　　　　1545　　　　　　　　　1550 | 4655 |
| gac gcc ctc gcc acc cac cgc cac acc caa gga caa ccc gcc acc acc<br>Asp Ala Leu Ala Thr His Arg His Thr Gln Gly Gln Pro Ala Thr Thr<br>　　　　1555　　　　　　　　1560　　　　　　　　　1565 | 4703 |
| atc gcc tgg ggc atg tgg cac acc acc aca ctc acc agc caa ctc<br>Ile Ala Trp Gly Met Trp His Thr Thr Thr Leu Thr Ser Gln Leu<br>　　　　　　　1570　　　　　　　　　1575　　　　　　　　1580 | 4751 |
| acc gac agc gac cgc gac cgc atc cgc cgc ggc ggc ttc ctg ccg atc<br>Thr Asp Ser Asp Arg Asp Arg Ile Arg Arg Gly Gly Phe Leu Pro Ile<br>1585　　　　　　　　　1590　　　　　　　　1595 | 4799 |
| tcg gac gac gag ggc atg c<br>Ser Asp Asp Glu Gly Met<br>1600　　　　　　　　1605 | 4818 |

<210> SEQ ID NO 33
<211> LENGTH: 1605
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 33

```
Met Arg Leu Tyr Glu Ala Ala Arg Thr Gly Ser Pro Val Val
 1               5                  10                  15

Ala Ala Ala Leu Asp Asp Ala Pro Val Pro Leu Leu Arg Gly Leu
            20                  25                  30

Arg Arg Thr Thr Val Arg Arg Ala Ala Val Arg Glu Arg Ser Leu Ala
                35                  40                  45

Asp Arg Ser Pro Cys Cys Pro Thr Thr Ser Ala Pro Thr Pro Pro Ser
         50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
```

```
                    355                 360                 365
Ala Pro Asp Gly Arg Ala Lys Ala Phe Gly Ala Gly Ala Asp Gly Thr
            370                 375                 380
Ser Phe Ala Glu Gly Ala Gly Ala Leu Val Val Glu Arg Leu Ser Asp
385                 390                 395                 400
Ala Glu Arg His Gly His Thr Val Leu Ala Leu Val Arg Gly Ser Ala
            405                 410                 415
Ala Asn Ser Asp Gly Ala Ser Asn Gly Leu Ser Ala Pro Asn Gly Pro
            420                 425                 430
Ser Gln Glu Arg Val Ile His Gln Ala Leu Ala Asn Ala Lys Leu Thr
            435                 440                 445
Pro Ala Asp Val Asp Ala Val Glu Ala His Gly Thr Gly Thr Arg Leu
            450                 455                 460
Gly Asp Pro Ile Glu Ala Gln Ala Leu Leu Ala Thr Tyr Gly Gln Asp
465                 470                 475                 480
Arg Ala Thr Pro Leu Leu Leu Gly Ser Leu Lys Ser Asn Ile Gly His
            485                 490                 495
Ala Gln Ala Ala Ser Gly Val Ala Gly Ile Ile Lys Met Val Gln Ala
            500                 505                 510
Ile Arg His Gly Glu Leu Pro Pro Thr Leu His Ala Asp Glu Pro Ser
            515                 520                 525
Pro His Val Asp Trp Thr Ala Gly Ala Val Glu Leu Leu Thr Ser Ala
            530                 535                 540
Arg Pro Trp Pro Gly Thr Gly Arg Pro Arg Ala Ala Val Ser Ser
545                 550                 555                 560
Phe Gly Val Ser Gly Thr Asn Ala His Ile Ile Leu Glu Ala Gly Pro
            565                 570                 575
Val Lys Thr Gly Pro Val Glu Ala Gly Ala Ile Glu Ala Gly Pro Val
            580                 585                 590
Glu Val Gly Pro Val Glu Ala Gly Pro Leu Pro Ala Ala Pro Pro Ser
            595                 600                 605
Ala Pro Gly Glu Asp Leu Pro Leu Leu Val Ser Ala Arg Ser Pro Glu
            610                 615                 620
Ala Leu Asp Glu Gln Ile Gly Arg Leu Arg Ala Tyr Leu Asp Thr Gly
625                 630                 635                 640
Pro Gly Val Asp Arg Ala Ala Val Ala Gln Thr Leu Ala Arg Arg Thr
            645                 650                 655
His Phe Thr His Arg Ala Val Leu Leu Gly Asp Thr Val Ile Gly Ala
            660                 665                 670
Pro Pro Ala Asp Gln Ala Asp Glu Leu Val Phe Val Tyr Ser Gly Gln
            675                 680                 685
Gly Thr Gln His Pro Ala Met Gly Glu Gln Leu Ala Asp Ser Ser Val
            690                 695                 700
Val Phe Ala Glu Arg Met Ala Glu Cys Ala Ala Leu Arg Glu Phe
705                 710                 715                 720
Val Asp Trp Asp Leu Phe Thr Val Leu Asp Asp Pro Ala Val Val Asp
            725                 730                 735
Arg Val Asp Val Val Gln Pro Ala Ser Trp Ala Met Met Val Ser Leu
            740                 745                 750
Ala Ala Val Trp Gln Ala Ala Gly Val Arg Pro Asp Ala Val Ile Gly
            755                 760                 765
His Ser Gln Gly Glu Ile Ala Ala Cys Val Ala Gly Ala Val Ser
770                 775                 780
```

-continued

```
Leu Arg Asp Ala Ala Arg Ile Val Thr Leu Arg Ser Gln Ala Ile Ala
785                 790                 795                 800

Arg Gly Leu Ala Gly Arg Gly Ala Met Ala Ser Val Ala Leu Pro Ala
            805                 810                 815

Gln Asp Val Glu Leu Val Asp Gly Ala Trp Ile Ala Ala His Asn Gly
            820                 825                 830

Pro Ala Ser Thr Val Ile Ala Gly Thr Pro Glu Ala Val Asp His Val
            835                 840                 845

Leu Thr Ala His Glu Ala Gln Gly Val Arg Val Arg Arg Ile Thr Val
            850                 855                 860

Asp Tyr Ala Ser His Thr Pro His Val Glu Leu Ile Arg Asp Glu Leu
865                 870                 875                 880

Leu Asp Ile Thr Ser Asp Ser Ser Gln Thr Pro Leu Val Pro Trp
                885                 890                 895

Leu Ser Thr Val Asp Gly Thr Trp Val Asp Ser Pro Leu Asp Gly Glu
                900                 905                 910

Tyr Trp Tyr Arg Asn Leu Arg Glu Pro Val Gly Phe His Pro Ala Val
            915                 920                 925

Ser Gln Leu Gln Ala Gln Gly Asp Thr Val Phe Val Glu Val Ser Ala
            930                 935                 940

Ser Pro Val Leu Leu Gln Ala Met Asp Asp Val Val Thr Val Ala
945                 950                 955                 960

Thr Leu Arg Arg Asp Asp Gly Asp Ala Thr Arg Met Leu Thr Ala Leu
                965                 970                 975

Ala Gln Ala Tyr Val His Gly Val Thr Val Asp Trp Pro Ala Ile Leu
            980                 985                 990

Gly Thr Thr Thr Thr Arg Val Leu Asp Leu Pro Thr Tyr Ala Phe Gln
                995                 1000                1005

His Gln Arg Tyr Trp Leu Glu Ser Ala Pro Pro Ala Thr Ala Asp Ser
        1010                1015                1020

Gly His Pro Val Leu Gly Thr Gly Val Ala Val Ala Gly Ser Pro Gly
1025                1030                1035                1040

Arg Val Phe Thr Gly Pro Val Pro Ala Gly Ala Asp Arg Ala Val Phe
                1045                1050                1055

Ile Ala Glu Leu Ala Leu Ala Ala Ala Asp Ala Thr Asp Cys Ala Thr
            1060                1065                1070

Val Glu Gln Leu Asp Val Thr Ser Val Pro Gly Gly Ser Ala Arg Gly
        1075                1080                1085

Arg Ala Thr Ala Gln Thr Trp Val Asp Glu Pro Ala Ala Asp Gly Arg
        1090                1095                1100

Arg Arg Phe Thr Val His Thr Arg Val Gly Asp Ala Pro Trp Thr Leu
1105                1110                1115                1120

His Ala Glu Gly Val Leu Arg Pro Gly Arg Val Pro Gln Pro Glu Ala
                1125                1130                1135

Val Asp Thr Ala Trp Pro Pro Gly Ala Val Pro Ala Asp Gly Leu
            1140                1145                1150

Pro Gly Ala Trp Arg Arg Ala Asp Gln Val Phe Val Glu Ala Glu Val
        1155                1160                1165

Asp Ser Pro Asp Gly Phe Val Ala His Pro Asp Leu Leu Asp Ala Val
        1170                1175                1180

Phe Ser Ala Val Gly Asp Gly Ser Arg Gln Pro Thr Gly Trp Arg Asp
1185                1190                1195                1200
```

-continued

Leu Ala Val His Ala Ser Asp Ala Thr Val Leu Arg Ala Cys Leu Thr
            1205                1210                1215

Arg Arg Asp Ser Gly Val Val Glu Leu Ala Ala Phe Asp Gly Ala Gly
            1220                1225                1230

Met Pro Val Leu Thr Ala Glu Ser Val Thr Leu Gly Glu Val Ala Ser
            1235                1240                1245

Ala Gly Gly Ser Asp Glu Ser Asp Gly Leu Leu Arg Leu Glu Trp Leu
            1250                1255                1260

Pro Val Ala Glu Ala His Tyr Asp Gly Ala Asp Glu Leu Pro Glu Gly
1265                1270                1275                1280

Tyr Thr Leu Ile Thr Ala Thr His Pro Asp Pro Asp Pro Thr
            1285                1290                1295

Asn Pro His Asn Thr Pro Thr Arg Thr His Thr Gln Thr Thr Arg Val
            1300                1305                1310

Leu Thr Ala Leu Gln His His Leu Ile Thr Thr Asn His Thr Leu Ile
            1315                1320                1325

Val His Thr Thr Thr Asp Pro Pro Gly Ala Ala Val Thr Gly Leu Thr
            1330                1335                1340

Arg Thr Ala Gln Asn Glu His Pro Gly Arg Ile His Leu Ile Glu Thr
1345                1350                1355                1360

His His Pro His Thr Pro Leu Pro Leu Thr Gln Leu Thr Thr Leu His
            1365                1370                1375

Gln Pro His Leu Arg Leu Thr Asn Asn Thr Leu His Thr Pro His Leu
            1380                1385                1390

Thr Pro Ile Thr Thr His His Asn Thr Thr Thr Thr Pro Asn Thr
            1395                1400                1405

Pro Pro Leu Asn Pro Asn His Ala Ile Leu Ile Thr Gly Gly Ser Gly
            1410                1415                1420

Thr Leu Ala Gly Ile Leu Ala Arg His Leu Asn His Pro His Thr Tyr
1425                1430                1435                1440

Leu Leu Ser Arg Thr Pro Pro Pro Thr Thr Pro Gly Thr His Ile
            1445                1450                1455

Pro Cys Asp Leu Thr Asp Pro Thr Gln Ile Thr Gln Ala Leu Thr His
            1460                1465                1470

Ile Pro Gln Pro Leu Thr Gly Ile Phe His Thr Ala Ala Thr Leu Asp
            1475                1480                1485

Asp Ala Thr Leu Thr Asn Leu Thr Pro Gln His Leu Thr Thr Thr Leu
1490                1495                1500

Gln Pro Lys Ala Asp Ala Ala Trp His Leu His His His Thr Gln Asn
1505                1510                1515                1520

Gln Pro Leu Thr His Phe Val Leu Tyr Ser Ser Ala Ala Ala Thr Leu
            1525                1530                1535

Gly Ser Pro Gly Gln Ala Asn Tyr Ala Ala Ala Asn Ala Phe Leu Asp
            1540                1545                1550

Ala Leu Ala Thr His Arg His Thr Gln Gly Gln Pro Ala Thr Thr Ile
            1555                1560                1565

Ala Trp Gly Met Trp His Thr Thr Thr Leu Thr Ser Gln Leu Thr
            1570                1575                1580

Asp Ser Asp Arg Asp Arg Ile Arg Arg Gly Gly Phe Leu Pro Ile Ser
1585                1590                1595                1600

Asp Asp Glu Gly Met
            1605

```
<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 34 ggc cgt ccg cgc cgt gcg gcg gtc tcg tcg ttc                         33
Gly Arg Pro Arg Arg Ala Ala Val Ser Ser Phe
  1               5                  10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 35

Gly Arg Pro Arg Arg Ala Ala Val Ser Ser Phe
  1               5                  10

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 36 acc cag cat ccc gcg atg ggt gag cgg ctc gcc                         33
Thr Gln His Pro Ala Met Gly Glu Arg Leu Ala
  1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 37

Thr Gln His Pro Ala Met Gly Glu Arg Leu Ala
  1               5                  10

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 38 tac gcc ttc cag cgg cgg ccc tac tgg atc gag                         33
Tyr Ala Phe Gln Arg Arg Pro Tyr Trp Ile Glu
```

```
<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 39

Tyr Ala Phe Gln Arg Arg Pro Tyr Trp Ile Glu
 1               5                  10

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 40 gac cgg ccc cgt cgg gcg ggc gtg tcg tcc ttc                           33
Asp Arg Pro Arg Arg Ala Gly Val Ser Ser Phe
 1               5                  10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 41

Asp Arg Pro Arg Arg Ala Gly Val Ser Ser Phe
 1               5                  10

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 42 tgg cag tgg ctg ggg atg ggc agt gcc ctg cgg                           33
Trp Gln Trp Leu Gly Met Gly Ser Ala Leu Arg
 1               5                  10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 43

Trp Gln Trp Leu Gly Met Gly Ser Ala Leu Arg
 1               5                  10
```

```
<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 44 tac gcc ttc caa cac cag cgg tac tgg gtc gag                      33
Tyr Ala Phe Gln His Gln Arg Tyr Trp Val Glu
  1               5                  10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 45

Tyr Ala Phe Gln His Gln Arg Tyr Trp Val Glu
  1               5                  10

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 46 ggc cga gcg cgc cgg gca ggc gtg tcg tcc ttc                      33
Gly Arg Ala Arg Arg Ala Gly Val Ser Ser Phe
  1               5                  10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 47

Gly Arg Ala Arg Arg Ala Gly Val Ser Ser Phe
  1               5                  10

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 48
```

```
tcg cag cgt gct ggc atg ggt gag gaa ctg gcc                    33
Ser Gln Arg Ala Gly Met Gly Glu Glu Leu Ala
 1               5                  10
```

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 49

```
Ser Gln Arg Ala Gly Met Gly Glu Glu Leu Ala
 1               5                  10
```

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 50

```
tac gcc ttc cag cac cag cgc tac tgg ctc gag                    33
Tyr Ala Phe Gln His Gln Arg Tyr Trp Leu Glu
 1               5                  10
```

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 51

```
Tyr Ala Phe Gln His Gln Arg Tyr Trp Leu Glu
 1               5                  10
```

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 52

```
gcg cga ccg cgc cgg gcg ggg gtc tcg tcg ttc                    33
Ala Arg Pro Arg Arg Ala Gly Val Ser Ser Phe
 1               5                  10
```

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 53

```
Ala Arg Pro Arg Arg Ala Gly Val Ser Ser Phe
 1               5                  10
```

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 54

```
tgg cag tgg gcg ggc atg gcc gtc gac ctg ctc                    33
Trp Gln Trp Ala Gly Met Ala Val Asp Leu Leu
 1               5                  10
```

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 55

```
Trp Gln Trp Ala Gly Met Ala Val Asp Leu Leu
 1               5                  10
```

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 56

```
tac ccg ttc cag cgc gag cgc gtc tgg ctc gaa                    33
Tyr Pro Phe Gln Arg Glu Arg Val Trp Leu Glu
 1               5                  10
```

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 57

```
Tyr Pro Phe Gln Arg Glu Arg Val Trp Leu Glu
 1               5                  10
```

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

-continued

```
<400> SEQUENCE: 58 gac ggg gtg cgc cgg gca ggt gtg tcg gcg ttc                              33
Asp Gly Val Arg Arg Ala Gly Val Ser Ala Phe
 1               5                  10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 59

Asp Gly Val Arg Arg Ala Gly Val Ser Ala Phe
 1               5                  10

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 60 gcc cag tgg gaa ggc atg gcg cgg gag ttg ttg                              33
Ala Gln Trp Glu Gly Met Ala Arg Glu Leu Leu
 1               5                  10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 61

Ala Gln Trp Glu Gly Met Ala Arg Glu Leu Leu
 1               5                  10

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 62 tat cct ttc cag ggc aag cgg ttc tgg ctg ctg                              33
Tyr Pro Phe Gln Gly Lys Arg Phe Trp Leu Leu
 1               5                  10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment
```

<400> SEQUENCE: 63

Tyr Pro Phe Gln Gly Lys Arg Phe Trp Leu Leu
 1               5                  10

<210> SEQ ID NO 64
<211> LENGTH: 480
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(479)

<400> SEQUENCE: 64

```
cc ggc gcc gtc gaa ctg ctg acg tcg gcc cgg ccg tgg ccc gag acc       47
   Gly Ala Val Glu Leu Leu Thr Ser Ala Arg Pro Trp Pro Glu Thr
    1               5                  10                  15 gac cgg cca cgg cgt gcc gcc gtc tcc tcg ttc ggg gtg agc ggc acc      95
Asp Arg Pro Arg Arg Ala Ala Val Ser Ser Phe Gly Val Ser Gly Thr
             20                  25                  30 aac gcc cac gtc atc ctg gag gcc gga ccg gta acg gag acg ccc gcg     143
Asn Ala His Val Ile Leu Glu Ala Gly Pro Val Thr Glu Thr Pro Ala
         35                  40                  45 gca tcg cct tcc ggt gac ctt ccc ctg ctg gtg tcg gca cgc tca ccg     191
Ala Ser Pro Ser Gly Asp Leu Pro Leu Leu Val Ser Ala Arg Ser Pro
     50                  55                  60 gaa gcg ctc gac gag cag atc cgc cga ctg cgc gcc tac ctg gac acc     239
Glu Ala Leu Asp Glu Gln Ile Arg Arg Leu Arg Ala Tyr Leu Asp Thr
 65                  70                  75 acc ccg gac gtc gac cgg gtg gcc gtg gca cag acg ctg gcc cgg cgc     287
Thr Pro Asp Val Asp Arg Val Ala Val Ala Gln Thr Leu Ala Arg Arg
 80                  85                  90                  95 aca cac ttc gcc cac cgc gcc gtg ctg ctc ggt gac acc gtc atc acc     335
Thr His Phe Ala His Arg Ala Val Leu Leu Gly Asp Thr Val Ile Thr
                100                 105                 110 aca ccc ccc gcg gac cgg ccc gac gaa ctc gtc ttc gtc tac tcc ggc     383
Thr Pro Pro Ala Asp Arg Pro Asp Glu Leu Val Phe Val Tyr Ser Gly
            115                 120                 125 cag ggc acc cag cat ccc gcg atg ggc gag cag ctc gcc gcc gcc cat     431
Gln Gly Thr Gln His Pro Ala Met Gly Glu Gln Leu Ala Ala Ala His
        130                 135                 140 ccc gtg ttc gcc gac gcc tgg cat gaa gcg ctc cgc cgc ctt gac aac c  480
Pro Val Phe Ala Asp Ala Trp His Glu Ala Leu Arg Arg Leu Asp Asn
    145                 150                 155
```

<210> SEQ ID NO 65
<211> LENGTH: 159
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 65

Gly Ala Val Glu Leu Leu Thr Ser Ala Arg Pro Trp Pro Glu Thr Asp
 1               5                  10                  15

Arg Pro Arg Arg Ala Ala Val Ser Ser Phe Gly Val Ser Gly Thr Asn
             20                  25                  30

Ala His Val Ile Leu Glu Ala Gly Pro Val Thr Glu Thr Pro Ala Ala
         35                  40                  45

```
Ser Pro Ser Gly Asp Leu Pro Leu Leu Val Ser Ala Arg Ser Pro Glu
 50                  55                  60

Ala Leu Asp Glu Gln Ile Arg Arg Leu Arg Ala Tyr Leu Asp Thr Thr
 65                  70                  75                  80

Pro Asp Val Asp Arg Val Ala Val Ala Gln Thr Leu Ala Arg Arg Thr
                 85                  90                  95

His Phe Ala His Arg Ala Val Leu Leu Gly Asp Thr Val Ile Thr Thr
            100                 105                 110

Pro Pro Ala Asp Arg Pro Asp Glu Leu Val Phe Val Tyr Ser Gly Gln
        115                 120                 125

Gly Thr Gln His Pro Ala Met Gly Glu Gln Leu Ala Ala His Pro
130                 135                 140

Val Phe Ala Asp Ala Trp His Glu Ala Leu Arg Arg Leu Asp Asn
145                 150                 155

<210> SEQ ID NO 66
<211> LENGTH: 120
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(119)

<400> SEQUENCE: 66 tc ctc ggg gct ggg tca cgg cac gac gcg gat gtg ccc gcg tac gcg      47
   Leu Gly Ala Gly Ser Arg His Asp Ala Asp Val Pro Ala Tyr Ala
     1               5                  10                  15 ttc caa cgg cgg cac tac tgg atc gag tcg gca cgc ccg gcc gca tcc     95
Phe Gln Arg Arg His Tyr Trp Ile Glu Ser Ala Arg Pro Ala Ala Ser
                 20                  25                  30 gac gcg ggc cac ccc gtg ctg ggc t                                  120
Asp Ala Gly His Pro Val Leu Gly
            35

<210> SEQ ID NO 67
<211> LENGTH: 39
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 67

Leu Gly Ala Gly Ser Arg His Asp Ala Asp Val Pro Ala Tyr Ala Phe
  1               5                  10                  15

Gln Arg Arg His Tyr Trp Ile Glu Ser Ala Arg Pro Ala Ala Ser Asp
             20                  25                  30

Ala Gly His Pro Val Leu Gly
         35

<210> SEQ ID NO 68
<211> LENGTH: 480
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(480)
```

<400> SEQUENCE: 68

```
tcg gcc agg ccg tgg ccg cgg acc ggc cgt ccg cgc cgt gcg gcg gtc      48
Ser Ala Arg Pro Trp Pro Arg Thr Gly Arg Pro Arg Arg Ala Ala Val
 1               5                  10                  15 tcg tcg ttc ggg gtg agc ggc acc aac gcc cac atc atc ctg gag gcc      96
Ser Ser Phe Gly Val Ser Gly Thr Asn Ala His Ile Ile Leu Glu Ala
             20                  25                  30 gga ccc gac cag gag gag ccg tcg gca gaa ccg gcc ggt gac ctc ccg     144
Gly Pro Asp Gln Glu Glu Pro Ser Ala Glu Pro Ala Gly Asp Leu Pro
         35                  40                  45 ctg ctc gtg tcg gca cgg tcc ccg gag gca ctg gac gag cag atc ggg     192
Leu Leu Val Ser Ala Arg Ser Pro Glu Ala Leu Asp Glu Gln Ile Gly
     50                  55                  60 cgc ctg cgc gac tat ctc gac gcc gcc ccc ggc gtg gac ctg gcg gcc     240
Arg Leu Arg Asp Tyr Leu Asp Ala Ala Pro Gly Val Asp Leu Ala Ala
 65                  70                  75                  80 gtg gcg cgg aca ctg gcc acg cgt acg cac ttc tcc cac cgc gcc gta     288
Val Ala Arg Thr Leu Ala Thr Arg Thr His Phe Ser His Arg Ala Val
                 85                  90                  95 ctg ctc ggt gac acc gtc atc acc gct ccc ccc gtg gaa cag ccg ggc     336
Leu Leu Gly Asp Thr Val Ile Thr Ala Pro Pro Val Glu Gln Pro Gly
            100                 105                 110 gag ctc gtc ttc gtc tac tcg gga cag ggc acc cag cat ccc gcg atg     384
Glu Leu Val Phe Val Tyr Ser Gly Gln Gly Thr Gln His Pro Ala Met
        115                 120                 125 ggt gag cgg ctc gcc gca gcc ttc ccc gtg ttc gcc gac ccg gac gta     432
Gly Glu Arg Leu Ala Ala Ala Phe Pro Val Phe Ala Asp Pro Asp Val
    130                 135                 140 ccc gcc tac gcc ttc cag cgg cgg ccc tac tgg atc gag tcc gcg ccg     480
Pro Ala Tyr Ala Phe Gln Arg Arg Pro Tyr Trp Ile Glu Ser Ala Pro
145                 150                 155                 160
```

<210> SEQ ID NO 69
<211> LENGTH: 160
<212> TYPE: PRT
<213> ORGANISM: Artificial Sequence
<220> FEATURE:
<223> OTHER INFORMATION: Description of Artificial Sequence: Synthetic PKS synthase fragment

<400> SEQUENCE: 69

```
Ser Ala Arg Pro Trp Pro Arg Thr Gly Arg Pro Arg Arg Ala Ala Val
 1               5                  10                  15

Ser Ser Phe Gly Val Ser Gly Thr Asn Ala His Ile Ile Leu Glu Ala
             20                  25                  30

Gly Pro Asp Gln Glu Glu Pro Ser Ala Glu Pro Ala Gly Asp Leu Pro
         35                  40                  45

Leu Leu Val Ser Ala Arg Ser Pro Glu Ala Leu Asp Glu Gln Ile Gly
     50                  55                  60

Arg Leu Arg Asp Tyr Leu Asp Ala Ala Pro Gly Val Asp Leu Ala Ala
 65                  70                  75                  80

Val Ala Arg Thr Leu Ala Thr Arg Thr His Phe Ser His Arg Ala Val
                 85                  90                  95

Leu Leu Gly Asp Thr Val Ile Thr Ala Pro Pro Val Glu Gln Pro Gly
            100                 105                 110

Glu Leu Val Phe Val Tyr Ser Gly Gln Gly Thr Gln His Pro Ala Met
        115                 120                 125

Gly Glu Arg Leu Ala Ala Ala Phe Pro Val Phe Ala Asp Pro Asp Val
    130                 135                 140
```

-continued

```
Pro Ala Tyr Ala Phe Gln Arg Arg Pro Tyr Trp Ile Glu Ser Ala Pro
145                 150                 155                 160
```

<210> SEQ ID NO 70
<211> LENGTH: 60
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(60)

<400> SEQUENCE: 70

```
gac ccg gac gta ccc gcc tac gcc ttc cag cgg cgg ccc tac tgg atc        48
Asp Pro Asp Val Pro Ala Tyr Ala Phe Gln Arg Arg Pro Tyr Trp Ile
  1               5                  10                  15 gag tcc gcg ccg                                                        60
Glu Ser Ala Pro
            20
```

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 71

```
Asp Pro Asp Val Pro Ala Tyr Ala Phe Gln Arg Arg Pro Tyr Trp Ile
  1               5                  10                  15

Glu Ser Ala Pro
            20
```

<210> SEQ ID NO 72
<211> LENGTH: 6396
<212> TYPE: PRT
<213> ORGANISM: Streptomyces hygroscopicus

<400> SEQUENCE: 72

```
Met Pro Glu Gln Asp Lys Thr Val Glu Tyr Leu Arg Trp Ala Thr Ala
  1               5                  10                  15

Glu Leu Gln Lys Thr Arg Ala Glu Leu Ala Ala His Ser Glu Pro Leu
                 20                  25                  30

Ala Ile Val Gly Met Ala Cys Arg Leu Pro Gly Gly Val Ala Ser Pro
             35                  40                  45

Glu Asp Leu Trp Gln Leu Leu Glu Ser Gly Gly Asp Gly Ile Thr Ala
         50                  55                  60

Phe Pro Thr Asp Arg Gly Trp Glu Thr Ala Asp Gly Arg Gly Gly
 65                  70                  75                  80

Phe Leu Thr Gly Ala Ala Gly Phe Asp Ala Ala Phe Gly Ile Ser
                 85                  90                  95

Pro Arg Glu Ala Leu Ala Met Asp Pro Gln Arg Leu Ala Leu Glu
                100                 105                 110

Thr Ser Trp Glu Ala Phe Glu His Ala Gly Ile Asp Pro Gln Thr Leu
            115                 120                 125

Arg Gly Ser Asp Thr Gly Val Phe Leu Gly Ala Phe Phe Gln Gly Tyr
        130                 135                 140

Gly Ile Gly Ala Asp Phe Asp Gly Tyr Gly Thr Thr Ser Ile His Thr
```

-continued

```
            145                 150                 155                 160
Ser Val Leu Ser Gly Arg Leu Ala Tyr Phe Tyr Gly Leu Glu Gly Pro
                    165                 170                 175
Ala Val Thr Val Asp Thr Ala Cys Ser Ser Leu Val Ala Leu His
                180                 185                 190
Gln Ala Gly Gln Ser Leu Arg Ser Gly Glu Cys Ser Leu Ala Leu Val
                195                 200                 205
Gly Gly Val Thr Val Met Ala Ser Pro Ala Gly Phe Ala Asp Phe Ser
        210                 215                 220
Glu Gln Gly Gly Leu Ala Pro Asp Ala Arg Cys Lys Ala Phe Ala Glu
225                 230                 235                 240
Ala Ala Asp Gly Thr Gly Phe Ala Glu Gly Ser Gly Val Leu Ile Val
                245                 250                 255
Glu Lys Leu Ser Asp Ala Glu Arg Asn Gly His Arg Val Leu Ala Val
                260                 265                 270
Val Arg Gly Ser Ala Val Asn Gln Asp Gly Ala Ser Asn Gly Leu Ser
                275                 280                 285
Ala Pro Asn Gly Pro Ser Gln Glu Arg Val Ile Arg Gln Ala Leu Ala
        290                 295                 300
Asn Ala Gly Leu Thr Pro Ala Asp Val Asp Ala Val Glu Ala His Gly
305                 310                 315                 320
Thr Gly Thr Arg Leu Gly Asp Pro Ile Glu Ala Gln Ala Val Leu Ala
                325                 330                 335
Thr Tyr Gly Gln Gly Arg Asp Thr Pro Val Leu Leu Gly Ser Leu Lys
                340                 345                 350
Ser Asn Ile Gly His Thr Gln Ala Ala Gly Val Ala Gly Val Ile
                355                 360                 365
Lys Met Val Leu Ala Met Arg His Gly Thr Leu Pro Arg Thr Leu His
        370                 375                 380
Val Asp Thr Pro Ser Ser His Val Asp Trp Thr Ala Gly Ala Val Glu
385                 390                 395                 400
Leu Leu Thr Asp Ala Arg Pro Trp Pro Glu Thr Asp Arg Pro Arg Arg
                405                 410                 415
Ala Gly Val Ser Ser Phe Gly Val Ser Gly Thr Asn Ala His Ile Ile
                420                 425                 430
Leu Glu Ser His Pro Arg Pro Ala Pro Glu Pro Ala Pro Ala Pro Asp
                435                 440                 445
Thr Gly Pro Leu Pro Leu Leu Leu Ser Ala Arg Thr Pro Gln Ala Leu
        450                 455                 460
Asp Ala Gln Val His Arg Leu Arg Ala Phe Leu Asp Asp Asn Pro Gly
465                 470                 475                 480
Ala Asp Arg Val Ala Val Ala Gln Thr Leu Ala Arg Arg Thr Gln Phe
                485                 490                 495
Glu His Arg Ala Val Leu Leu Gly Asp Thr Leu Ile Thr Val Ser Pro
                500                 505                 510
Asn Ala Gly Arg Gly Pro Val Val Phe Val Tyr Ser Gly Gln Ser Thr
                515                 520                 525
Leu His Pro His Thr Gly Arg Gln Leu Ala Ser Thr Tyr Pro Val Phe
        530                 535                 540
Ala Glu Ala Trp Arg Glu Ala Leu Asp His Leu Asp Pro Thr Gln Gly
545                 550                 555                 560
Pro Ala Thr His Phe Ala His Gln Thr Ala Leu Thr Ala Leu Leu Arg
                565                 570                 575
```

-continued

```
Ser Trp Gly Ile Thr Pro His Ala Val Ile Gly His Ser Leu Gly Glu
            580                 585                 590

Ile Thr Ala Ala His Ala Ala Gly Val Leu Ser Leu Arg Asp Ala Gly
        595                 600                 605

Ala Leu Leu Thr Thr Arg Thr Arg Leu Met Asp Gln Leu Pro Ser Gly
    610                 615                 620

Gly Ala Met Val Thr Val Leu Thr Ser Glu Glu Lys Ala Arg Gln Val
625                 630                 635                 640

Leu Arg Pro Gly Val Glu Ile Ala Ala Val Asn Gly Pro His Ser Leu
                645                 650                 655

Val Leu Ser Gly Asp Glu Ala Val Leu Glu Ala Ala Arg Gln Leu
            660                 665                 670

Gly Ile His His Arg Leu Pro Thr Arg His Ala Gly His Ser Glu Arg
        675                 680                 685

Met Gln Pro Leu Val Ala Pro Leu Leu Asp Val Ala Arg Thr Leu Thr
    690                 695                 700

Tyr His Gln Pro His Thr Ala Ile Pro Gly Asp Pro Thr Thr Ala Glu
705                 710                 715                 720

Tyr Trp Ala His Gln Val Arg Asp Gln Val Arg Phe Gln Ala His Thr
                725                 730                 735

Glu Gln Tyr Pro Gly Ala Thr Phe Leu Glu Ile Gly Pro Asn Gln Asp
            740                 745                 750

Leu Ser Pro Leu Val Asp Gly Val Ala Ala Gln Thr Gly Thr Pro Asp
        755                 760                 765

Glu Val Arg Ala Leu His Thr Ala Leu Ala Gln Leu His Val Arg Gly
    770                 775                 780

Val Ala Ile Asp Trp Thr Leu Val Leu Gly Asp Arg Ala Pro Val
785                 790                 795                 800

Thr Leu Pro Thr Tyr Pro Phe Gln His Lys Asp Tyr Trp Leu Arg Pro
                805                 810                 815

Thr Ser Arg Ala Asp Val Thr Gly Ala Gly Gln Glu Gln Val Ala His
            820                 825                 830

Pro Leu Leu Gly Ala Ala Val Ala Leu Pro Gly Thr Gly Val Val
        835                 840                 845

Leu Thr Gly Arg Leu Ser Leu Ala Ser His Pro Trp Leu Gly Glu His
    850                 855                 860

Ala Val Asp Gly Thr Val Leu Leu Pro Gly Ala Ala Phe Leu Glu Leu
865                 870                 875                 880

Ala Ala Arg Ala Gly Asp Glu Val Gly Cys Asp Leu Leu His Glu Leu
                885                 890                 895

Val Ile Glu Thr Pro Leu Val Leu Pro Ala Thr Gly Val Ala Val
            900                 905                 910

Ser Val Glu Ile Ala Glu Pro Asp Asp Thr Gly Arg Arg Ala Val Thr
        915                 920                 925

Val His Ala Arg Ala Asp Gly Ser Gly Leu Trp Thr Arg His Ala Gly
    930                 935                 940

Gly Phe Leu Gly Thr Ala Pro Ala Pro Ala Thr Ala Thr Asp Pro Ala
945                 950                 955                 960

Pro Trp Pro Pro Ala Glu Ala Gly Pro Val Asp Val Ala Asp Val Tyr
                965                 970                 975

Asp Arg Phe Glu Asp Ile Gly Tyr Ser Tyr Gly Pro Gly Phe Arg Gly
            980                 985                 990
```

-continued

Leu Arg Ala Ala Trp Arg Ala Gly Asp Thr Val Tyr Ala Glu Val Ala
            995                 1000                1005

Leu Pro Asp Glu Gln Ser Ala Asp Ala Ala Arg Phe Thr Leu His Pro
    1010                1015                1020

Ala Leu Leu Asp Ala Ala Phe Gln Ala Gly Ala Leu Ala Ala Leu Asp
1025                1030                1035                1040

Ala Pro Gly Gly Ala Ala Arg Leu Pro Phe Ser Phe Gln Asp Val Arg
                1045                1050                1055

Ile His Ala Ala Gly Ala Thr Arg Leu Arg Val Thr Val Gly Arg Asp
                1060                1065                1070

Gly Glu Arg Ser Thr Val Arg Met Thr Gly Pro Asp Gly Gln Leu Val
            1075                1080                1085

Ala Val Val Gly Ala Val Leu Ser Arg Pro Tyr Ala Glu Gly Ser Gly
            1090                1095                1100

Asp Gly Leu Leu Arg Pro Val Trp Thr Glu Leu Pro Met Pro Val Pro
1105                1110                1115                1120

Ser Ala Asp Asp Pro Arg Val Glu Val Leu Gly Ala Asp Pro Gly Asp
                1125                1130                1135

Gly Asp Val Pro Ala Ala Thr Arg Glu Leu Thr Ala Arg Val Leu Gly
            1140                1145                1150

Ala Leu Gln Arg His Leu Ser Ala Ala Glu Asp Thr Thr Leu Val Val
            1155                1160                1165

Arg Thr Gly Thr Gly Pro Ala Ala Ala Ala Ala Gly Leu Val Arg
            1170                1175                1180

Ser Ala Gln Ala Glu Asn Pro Gly Arg Val Val Leu Val Glu Ala Ser
1185                1190                1195                1200

Pro Asp Thr Ser Val Glu Leu Leu Ala Ala Cys Ala Ala Leu Asp Glu
                1205                1210                1215

Pro Gln Leu Ala Val Arg Asp Gly Val Leu Phe Ala Pro Arg Leu Val
            1220                1225                1230

Arg Met Ser Asp Pro Ala His Gly Pro Leu Ser Leu Pro Asp Gly Asp
            1235                1240                1245

Trp Leu Leu Thr Arg Ser Ala Ser Gly Thr Leu His Asp Val Ala Leu
            1250                1255                1260

Ile Ala Asp Asp Thr Pro Arg Arg Ala Leu Glu Ala Gly Glu Val Arg
1265                1270                1275                1280

Ile Asp Val Arg Ala Ala Gly Leu Asn Phe Arg Asp Val Leu Ile Ala
                1285                1290                1295

Leu Gly Thr Tyr Thr Gly Ala Thr Ala Met Gly Gly Glu Ala Ala Gly
            1300                1305                1310

Val Val Val Glu Thr Gly Pro Gly Val Asp Asp Leu Ser Pro Gly Asp
            1315                1320                1325

Arg Val Phe Gly Leu Thr Arg Gly Ile Gly Pro Thr Ala Val Thr
            1330                1335                1340

Asp Arg Arg Trp Leu Ala Arg Ile Pro Asp Gly Trp Ser Phe Thr Thr
1345                1350                1355                1360

Ala Ala Ser Val Pro Ile Val Phe Ala Thr Ala Trp Tyr Gly Leu Val
                1365                1370                1375

Asp Leu Gly Thr Leu Arg Ala Gly Glu Lys Val Leu Val His Ala Ala
            1380                1385                1390

Thr Gly Gly Val Gly Met Ala Ala Ala Gln Ile Ala Arg His Leu Gly
            1395                1400                1405

Ala Glu Leu Tyr Ala Thr Ala Ser Thr Gly Lys Gln His Val Leu Arg

-continued

```
            1410                1415                1420
Ala Ala Gly Leu Pro Asp Thr His Ile Ala Asp Ser Arg Thr Thr Ala
1425                1430                1435                1440

Phe Arg Thr Ala Phe Pro Arg Met Asp Val Val Leu Asn Ala Leu Thr
                1445                1450                1455

Gly Glu Phe Ile Asp Ala Ser Leu Asp Leu Leu Asp Ala Asp Gly Arg
                    1460                1465                1470

Phe Val Glu Met Gly Arg Thr Glu Leu Arg Asp Pro Ala Ala Ile Val
                1475                1480                1485

Pro Ala Tyr Leu Pro Phe Asp Leu Leu Asp Ala Gly Ala Asp Arg Ile
            1490                1495                1500

Gly Glu Ile Leu Gly Glu Leu Leu Arg Leu Phe Asp Ala Gly Ala Leu
1505                1510                1515                1520

Glu Pro Leu Pro Val Arg Ala Trp Asp Val Arg Gln Ala Arg Asp Ala
                1525                1530                1535

Leu Gly Trp Met Ser Arg Ala Arg His Ile Gly Lys Asn Val Leu Thr
                1540                1545                1550

Leu Pro Arg Pro Leu Asp Pro Glu Gly Ala Val Val Leu Thr Gly Gly
                1555                1560                1565

Ser Gly Thr Leu Ala Gly Ile Leu Ala Arg His Leu Arg Glu Arg His
        1570                1575                1580

Val Tyr Leu Leu Ser Arg Thr Ala Pro Pro Glu Gly Thr Pro Gly Val
1585                1590                1595                1600

His Leu Pro Cys Asp Val Gly Asp Arg Asp Gln Leu Ala Ala Ala Leu
                    1605                1610                1615

Glu Arg Val Asp Arg Pro Ile Thr Ala Val Val His Leu Ala Gly Ala
                1620                1625                1630

Leu Asp Asp Gly Thr Val Ala Ser Leu Thr Pro Glu Arg Phe Asp Thr
            1635                1640                1645

Val Leu Arg Pro Lys Ala Asp Gly Ala Trp Tyr Leu His Glu Leu Thr
            1650                1655                1660

Lys Glu Gln Asp Leu Ala Ala Phe Val Leu Tyr Ser Ser Ala Ala Gly
1665                1670                1675                1680

Val Leu Gly Asn Ala Gly Gln Gly Asn Tyr Val Ala Ala Asn Ala Phe
                    1685                1690                1695

Leu Asp Ala Leu Ala Glu Leu Arg His Gly Ser Gly Leu Pro Ala Leu
                1700                1705                1710

Ser Ile Ala Trp Gly Leu Trp Glu Asp Val Ser Gly Leu Thr Ala Ala
            1715                1720                1725

Leu Gly Glu Ala Asp Arg Asp Arg Met Arg Arg Ser Gly Phe Arg Ala
    1730                1735                1740

Ile Thr Ala Gln Gln Gly Met His Leu Tyr Glu Ala Ala Gly Arg Thr
1745                1750                1755                1760

Gly Ser Pro Val Val Ala Ala Leu Asp Asp Ala Pro Asp Val
                1765                1770                1775

Pro Leu Leu Arg Gly Leu Arg Arg Thr Thr Val Arg Arg Ala Ala Val
            1780                1785                1790

Arg Glu Cys Ser Ser Ala Asp Arg Leu Ala Ala Leu Thr Gly Asp Glu
        1795                1800                1805

Leu Ala Glu Ala Leu Leu Thr Leu Val Arg Glu Ser Thr Ala Ala Val
    1810                1815                1820

Leu Gly His Val Gly Gly Glu Asp Ile Pro Ala Thr Ala Ala Phe Lys
1825                1830                1835                1840
```

-continued

```
Asp Leu Gly Ile Asp Ser Leu Thr Ala Val Gln Leu Arg Asn Ala Leu
            1845                1850                1855

Thr Glu Ala Thr Gly Val Arg Leu Asn Ala Thr Ala Val Phe Asp Phe
        1860                1865                1870

Pro Thr Pro His Val Leu Ala Gly Lys Leu Gly Asp Glu Leu Thr Gly
        1875                1880            1885

Thr Arg Ala Pro Val Val Pro Arg Thr Ala Ala Thr Ala Gly Ala His
        1890                1895                1900

Asp Glu Pro Leu Ala Ile Val Gly Met Ala Cys Arg Leu Pro Gly Gly
1905                1910                1915                1920

Val Ala Ser Pro Glu Glu Leu Trp His Leu Val Ala Ser Gly Thr Asp
            1925                1930                1935

Ala Ile Thr Glu Phe Pro Thr Asp Arg Gly Trp Asp Val Asp Ala Ile
            1940                1945                1950

Tyr Asp Pro Asp Pro Asp Ala Ile Gly Lys Thr Phe Val Arg His Gly
            1955                1960                1965

Gly Phe Leu Thr Gly Ala Thr Gly Phe Asp Ala Ala Phe Phe Gly Ile
        1970                1975                1980

Ser Pro Arg Glu Ala Leu Ala Met Asp Pro Gln Gln Arg Val Leu Leu
1985                1990                1995                2000

Glu Thr Ser Trp Glu Ala Phe Glu Ser Ala Gly Ile Thr Pro Asp Ser
            2005                2010                2015

Thr Arg Gly Ser Asp Thr Gly Val Phe Val Gly Ala Phe Ser Tyr Gly
            2020                2025                2030

Tyr Gly Thr Gly Ala Asp Thr Asp Gly Phe Gly Ala Thr Gly Ser Gln
            2035                2040                2045

Thr Ser Val Leu Ser Gly Arg Leu Ser Tyr Phe Tyr Gly Leu Glu Gly
        2050                2055                2060

Pro Ala Val Thr Val Asp Thr Ala Cys Ser Ser Ser Leu Val Ala Leu
2065                2070                2075                2080

His Gln Ala Gly Gln Ser Leu Arg Ser Gly Glu Cys Ser Leu Ala Leu
            2085                2090                2095

Val Gly Gly Val Thr Val Met Ala Ser Pro Gly Gly Phe Val Glu Phe
            2100                2105                2110

Ser Arg Gln Arg Gly Leu Ala Pro Asp Gly Arg Ala Lys Ala Phe Gly
        2115                2120                2125

Ala Gly Ala Asp Gly Thr Ser Phe Ala Glu Gly Ala Gly Val Leu Ile
        2130                2135                2140

Val Glu Arg Leu Ser Asp Ala Glu Arg Asn Gly His Thr Val Leu Ala
2145                2150                2155                2160

Val Val Arg Gly Ser Ala Val Asn Gln Asp Gly Ala Ser Asn Gly Leu
            2165                2170                2175

Ser Ala Pro Asn Gly Pro Ser Gln Glu Arg Val Ile Arg Gln Ala Leu
            2180                2185                2190

Ala Asn Ala Gly Leu Thr Pro Ala Asp Val Asp Ala Val Glu Ala His
        2195                2200                2205

Gly Thr Gly Thr Arg Leu Gly Asp Pro Ile Glu Ala Gln Ala Val Leu
    2210                2215                2220

Ala Thr Tyr Gly Gln Glu Arg Ala Thr Pro Leu Leu Leu Gly Ser Leu
2225                2230                2235                2240

Lys Ser Asn Ile Gly His Ala Gln Ala Ala Ser Gly Val Ala Gly Ile
            2245                2250                2255
```

-continued

```
Ile Lys Met Val Gln Ala Leu Arg His Gly Glu Leu Pro Pro Thr Leu
        2260                2265                2270

His Ala Asp Glu Pro Ser Pro His Val Asp Trp Thr Ala Gly Ala Val
        2275                2280            2285

Glu Leu Leu Thr Ser Ala Arg Pro Trp Pro Glu Thr Asp Arg Pro Arg
        2290                2295                2300

Arg Ala Ala Val Ser Ser Phe Gly Val Ser Gly Thr Asn Ala His Val
2305                2310                2315                2320

Ile Leu Glu Ala Gly Pro Val Thr Glu Thr Pro Ala Ala Ser Pro Ser
            2325                2330                2335

Gly Asp Leu Pro Leu Val Ser Ala Arg Ser Pro Glu Ala Leu Asp
            2340                2345                2350

Glu Gln Ile Arg Arg Leu Arg Ala Tyr Leu Asp Thr Thr Pro Asp Val
            2355                2360                2365

Asp Arg Val Ala Val Ala Gln Thr Leu Ala Arg Arg Thr His Phe Ala
2370                2375                2380

His Arg Ala Val Leu Leu Gly Asp Thr Val Ile Thr Thr Pro Pro Ala
2385                2390                2395                2400

Asp Arg Pro Asp Glu Leu Val Phe Val Tyr Ser Gly Gln Gly Thr Gln
            2405                2410                2415

His Pro Ala Met Gly Glu Gln Leu Ala Ala His Pro Val Phe Ala
            2420                2425                2430

Asp Ala Trp His Glu Ala Leu Arg Arg Leu Asp Asn Pro Asp Pro His
            2435                2440                2445

Asp Pro Thr His Ser Gln His Val Leu Phe Ala His Gln Ala Ala Phe
            2450                2455                2460

Thr Ala Leu Leu Arg Ser Trp Gly Ile Thr Pro His Ala Val Ile Gly
2465                2470                2475                2480

His Ser Leu Gly Glu Ile Thr Ala Ala His Ala Ala Gly Ile Leu Ser
            2485                2490                2495

Leu Asp Asp Ala Cys Thr Leu Ile Thr Thr Arg Ala Arg Leu Met His
            2500                2505                2510

Thr Leu Pro Pro Pro Gly Ala Met Val Thr Val Leu Thr Ser Glu Glu
            2515                2520                2525

Lys Ala Arg Gln Ala Leu Arg Pro Gly Val Glu Ile Ala Ala Val Asn
            2530                2535                2540

Gly Pro His Ser Ile Val Leu Ser Gly Asp Glu Asp Ala Val Leu Thr
2545                2550                2555                2560

Val Ala Gly Gln Leu Gly Ile His His Arg Leu Pro Ala Pro His Ala
            2565                2570                2575

Gly His Ser Ala His Met Glu Pro Val Ala Ala Glu Leu Leu Ala Thr
            2580                2585                2590

Thr Arg Gly Leu Arg Tyr His Pro Pro His Thr Ser Ile Pro Asn Asp
            2595                2600                2605

Pro Thr Thr Ala Glu Tyr Trp Ala Glu Gln Val Arg Lys Pro Val Leu
            2610                2615                2620

Phe His Ala His Ala Gln Gln Tyr Pro Asp Ala Val Phe Val Glu Ile
2625                2630                2635                2640

Gly Pro Ala Gln Asp Leu Ser Pro Leu Val Asp Gly Ile Pro Leu Gln
            2645                2650                2655

Asn Gly Thr Ala Asp Glu Val His Ala Leu His Thr Ala Leu Ala His
            2660                2665                2670

Leu Tyr Ala Arg Gly Ala Thr Leu Asp Trp Pro Arg Ile Leu Gly Ala
```

-continued

```
              2675                2680                2685
Gly Ser Arg His Asp Ala Asp Val Pro Ala Tyr Ala Phe Gln Arg Arg
    2690                2695                2700
His Tyr Trp Ile Glu Ser Ala Arg Pro Ala Ala Ser Asp Ala Gly His
2705                2710                2715                2720
Pro Val Leu Gly Ser Gly Ile Ala Leu Ala Gly Ser Pro Gly Arg Val
            2725                2730                2735
Phe Thr Gly Ser Val Pro Thr Gly Ala Asp Arg Ala Val Phe Val Ala
            2740                2745                2750
Glu Leu Ala Leu Ala Ala Asp Ala Val Asp Cys Ala Thr Val Glu
            2755                2760                2765
Arg Leu Asp Ile Ala Ser Val Pro Gly Arg Pro Gly His Gly Arg Thr
    2770                2775                2780
Thr Val Gln Thr Trp Val Asp Glu Pro Ala Asp Asp Gly Arg Arg
2785                2790                2795                2800
Phe Thr Val His Thr Arg Thr Gly Asp Ala Pro Trp Thr Leu His Ala
            2805                2810                2815
Glu Gly Val Leu Arg Pro His Gly Thr Ala Leu Pro Asp Ala Asp
            2820                2825                2830
Ala Glu Trp Pro Pro Gly Ala Val Pro Ala Asp Gly Leu Pro Gly
            2835                2840                2845
Val Trp Arg Arg Gly Asp Gln Val Phe Ala Glu Ala Glu Val Asp Gly
    2850                2855                2860
Pro Asp Gly Phe Val Val His Pro Asp Leu Leu Asp Ala Val Phe Ser
2865                2870                2875                2880
Ala Val Gly Asp Gly Ser Arg Gln Pro Ala Gly Trp Arg Asp Leu Thr
            2885                2890                2895
Val His Ala Ser Asp Ala Thr Val Leu Arg Ala Cys Leu Thr Arg Arg
            2900                2905                2910
Thr Asp Gly Ala Met Gly Phe Ala Ala Phe Asp Gly Ala Gly Leu Pro
            2915                2920                2925
Val Leu Thr Ala Glu Ala Val Thr Leu Arg Glu Val Ala Ser Pro Ser
            2930                2935                2940
Gly Ser Glu Glu Ser Asp Gly Leu His Arg Leu Glu Trp Leu Ala Val
2945                2950                2955                2960
Ala Glu Ala Val Tyr Asp Gly Asp Leu Pro Glu Gly His Val Leu Ile
            2965                2970                2975
Thr Ala Ala His Pro Asp Asp Pro Glu Asp Ile Pro Thr Arg Ala His
            2980                2985                2990
Thr Arg Ala Thr Arg Val Leu Thr Ala Leu Gln His His Leu Thr Thr
            2995                3000                3005
Thr Asp His Thr Leu Ile Val His Thr Thr Asp Pro Ala Gly Ala
    3010                3015                3020
Thr Val Thr Gly Leu Thr Arg Thr Ala Gln Asn Glu His Pro His Arg
3025                3030                3035                3040
Ile Arg Leu Ile Glu Thr Asp His Pro His Thr Pro Leu Pro Leu Ala
            3045                3050                3055
Gln Leu Ala Thr Leu Asp His Pro His Leu Arg Leu Thr His His Thr
            3060                3065                3070
Leu His His Pro His Leu Thr Pro Leu His Thr Thr Pro Pro Thr
            3075                3080                3085
Thr Thr Pro Leu Asn Pro Glu His Ala Ile Ile Ile Thr Gly Gly Ser
        3090                3095                3100
```

```
Gly Thr Leu Ala Gly Ile Leu Ala Arg His Leu Asn His Pro His Thr
3105                3110                3115                3120

Tyr Leu Leu Ser Arg Thr Pro Pro Asp Ala Thr Pro Gly Thr His
            3125                3130                3135

Leu Pro Cys Asp Val Gly Asp Pro His Gln Leu Ala Thr Thr Leu Thr
                3140                3145                3150

His Ile Pro Gln Pro Leu Thr Ala Ile Phe His Thr Ala Ala Thr Leu
            3155                3160                3165

Asp Asp Gly Ile Leu His Ala Leu Thr Pro Asp Arg Leu Thr Thr Val
3170                3175                3180

Leu His Pro Lys Ala Asn Ala Ala Trp His Leu His Leu Thr Gln
3185                3190                3195                3200

Asn Gln Pro Leu Thr His Phe Val Leu Tyr Ser Ser Ala Ala Val
                3205                3210                3215

Leu Gly Ser Pro Gly Gln Gly Asn Tyr Ala Ala Ala Asn Ala Phe Leu
                3220                3225                3230

Asp Ala Leu Ala Thr His Arg His Thr Leu Gly Gln Pro Ala Thr Ser
            3235                3240                3245

Ile Ala Trp Gly Met Trp His Thr Thr Ser Thr Leu Thr Gly Gln Leu
3250                3255                3260

Asp Asp Ala Asp Arg Asp Arg Ile Arg Arg Gly Gly Phe Leu Pro Ile
3265                3270                3275                3280

Thr Asp Asp Glu Gly Met Arg Leu Tyr Glu Ala Ala Val Gly Ser Gly
            3285                3290                3295

Glu Asp Phe Val Met Ala Ala Met Asp Pro Ala Gln Pro Met Thr
                3300                3305                3310

Gly Ser Val Pro Pro Ile Leu Ser Gly Leu Arg Arg Ser Ala Arg Arg
            3315                3320                3325

Val Ala Arg Ala Gly Gln Thr Phe Ala Gln Arg Leu Ala Glu Leu Pro
3330                3335                3340

Asp Ala Asp Arg Gly Ala Ala Leu Thr Thr Leu Val Ser Asp Ala Thr
3345                3350                3355                3360

Ala Ala Val Leu Gly His Ala Asp Ala Ser Glu Ile Ala Pro Thr Thr
                3365                3370                3375

Thr Phe Lys Asp Leu Gly Ile Asp Ser Leu Thr Ala Ile Glu Leu Arg
            3380                3385                3390

Asn Arg Leu Ala Glu Ala Thr Gly Leu Arg Leu Ser Ala Thr Leu Val
            3395                3400                3405

Phe Asp His Pro Thr Pro Arg Val Leu Ala Ala Lys Leu Arg Thr Asp
3410                3415                3420

Leu Phe Gly Thr Ala Val Pro Thr Pro Ala Arg Thr Ala Arg Thr His
3425                3430                3435                3440

His Asp Glu Pro Leu Ala Ile Val Gly Met Ala Cys Arg Leu Pro Gly
            3445                3450                3455

Gly Val Ala Ser Pro Glu Asp Leu Trp Gln Leu Val Ala Ser Gly Thr
                3460                3465                3470

Asp Ala Ile Thr Glu Phe Pro Thr Asp Arg Gly Trp Asp Ile Asp Arg
            3475                3480                3485

Leu Phe Asp Pro Asp Pro Asp Ala Pro Gly Lys Thr Tyr Val Arg His
            3490                3495                3500

Gly Gly Phe Leu Ala Glu Ala Ala Gly Phe Asp Ala Ala Phe Phe Gly
3505                3510                3515                3520
```

-continued

```
Ile Ser Pro Arg Glu Ala Arg Ala Met Asp Pro Gln Gln Arg Val Ile
            3525                3530                3535

Leu Glu Thr Ser Trp Glu Ala Phe Glu Asn Ala Gly Ile Val Pro Asp
            3540                3545                3550

Thr Leu Arg Gly Ser Asp Thr Gly Val Phe Met Gly Ala Phe Ser His
            3555                3560                3565

Gly Tyr Gly Ala Gly Val Asp Leu Gly Gly Phe Gly Ala Thr Ala Thr
            3570                3575                3580

Gln Asn Ser Val Leu Ser Gly Arg Leu Ser Tyr Phe Phe Gly Met Glu
3585                3590                3595                3600

Gly Pro Ala Val Thr Val Asp Thr Ala Cys Ser Ser Leu Val Ala
            3605                3610                3615

Leu His Gln Ala Ala Gln Ala Leu Arg Thr Gly Glu Cys Ser Leu Ala
            3620                3625                3630

Leu Ala Gly Gly Val Thr Val Met Pro Thr Pro Leu Gly Tyr Val Glu
            3635                3640                3645

Phe Cys Arg Gln Arg Gly Leu Ala Pro Asp Gly Arg Cys Gln Ala Phe
            3650                3655                3660

Ala Glu Gly Ala Asp Gly Thr Ser Phe Ser Glu Gly Ala Gly Val Leu
3665                3670                3675                3680

Val Leu Glu Arg Leu Ser Asp Ala Glu Arg Asn Gly His Thr Val Leu
            3685                3690                3695

Ala Val Val Arg Ser Ser Ala Val Asn Gln Asp Gly Ala Ser Asn Gly
            3700                3705                3710

Ile Ser Ala Pro Asn Gly Pro Ser Gln Gln Arg Val Ile Arg Gln Ala
            3715                3720                3725

Leu Asp Lys Ala Gly Leu Ala Pro Ala Asp Val Asp Val Val Glu Ala
            3730                3735                3740

His Gly Thr Gly Thr Pro Leu Gly Asp Pro Ile Glu Ala Gln Ala Ile
3745                3750                3755                3760

Ile Ala Thr Tyr Gly Gln Asp Arg Asp Thr Pro Leu Tyr Leu Gly Ser
            3765                3770                3775

Val Lys Ser Asn Ile Gly His Thr Gln Thr Thr Ala Gly Val Ala Gly
            3780                3785                3790

Val Ile Lys Met Val Met Ala Met Arg His Gly Ile Ala Pro Lys Thr
            3795                3800                3805

Leu His Val Asp Glu Pro Ser Ser His Val Asp Trp Thr Glu Gly Ala
            3810                3815                3820

Val Glu Leu Leu Thr Glu Ala Arg Pro Trp Pro Asp Ala Gly Arg Pro
3825                3830                3835                3840

Arg Arg Ala Gly Val Ser Ser Leu Gly Ile Ser Gly Thr Asn Ala His
            3845                3850                3855

Val Ile Leu Glu Gly Val Pro Gly Pro Ser Arg Val Glu Pro Ser Val
            3860                3865                3870

Asp Gly Leu Val Pro Leu Pro Val Ser Ala Arg Ser Glu Ala Ser Leu
            3875                3880                3885

Arg Gly Gln Val Glu Arg Leu Glu Gly Tyr Leu Arg Gly Ser Val Asp
            3890                3895                3900

Val Ala Ala Val Ala Gln Gly Leu Val Arg Glu Arg Ala Val Phe Gly
3905                3910                3915                3920

His Arg Ala Val Leu Leu Gly Asp Ala Arg Val Met Gly Val Ala Val
            3925                3930                3935

Asp Gln Pro Arg Thr Val Phe Val Phe Pro Gly Gln Gly Ala Gln Trp
```

-continued

```
              3940            3945            3950
Val Gly Met Gly Val Glu Leu Met Asp Arg Ser Ala Val Phe Ala Ala
        3955            3960            3965
Arg Met Glu Glu Cys Ala Arg Ala Leu Leu Pro His Thr Gly Trp Asp
        3970            3975            3980
Val Arg Glu Met Leu Ala Arg Pro Asp Val Ala Glu Arg Val Glu Val
3985            3990            3995            4000
Val Gln Pro Ala Ser Trp Ala Val Ala Val Ser Leu Ala Ala Leu Trp
                4005            4010            4015
Gln Ala His Gly Val Val Pro Asp Ala Val Ile Gly His Ser Gln Gly
        4020            4025            4030
Glu Ile Ala Ala Ala Cys Val Ala Gly Ala Leu Ser Leu Glu Asp Ala
        4035            4040            4045
Ala Arg Val Val Ala Leu Arg Ser Gln Val Ile Ala Ala Arg Leu Ala
4050            4055            4060
Gly Arg Gly Ala Met Ala Ser Val Ala Leu Pro Ala Gly Glu Val Gly
4065            4070            4075            4080
Leu Val Glu Gly Val Trp Ile Ala Ala Arg Asn Gly Pro Ala Ser Thr
                4085            4090            4095
Val Val Ala Gly Glu Pro Ser Ala Val Glu Asp Val Val Thr Arg Tyr
        4100            4105            4110
Glu Thr Glu Gly Val Arg Val Arg Arg Ile Ala Val Asp Tyr Ala Ser
        4115            4120            4125
His Thr Pro His Val Glu Ala Ile Glu Asp Glu Leu Ala Glu Val Leu
        4130            4135            4140
Lys Gly Val Ala Gly Lys Ala Ala Ser Val Ala Trp Trp Ser Thr Val
4145            4150            4155            4160
Asp Ser Ala Trp Val Thr Glu Pro Val Asp Glu Ser Tyr Trp Tyr Arg
                4165            4170            4175
Asn Leu Arg Arg Pro Val Ala Leu Asp Ala Ala Val Ala Glu Leu Asp
                4180            4185            4190
Gly Ser Val Phe Val Glu Cys Ser Ala His Pro Val Leu Leu Pro Ala
                4195            4200            4205
Met Glu Gln Ala His Thr Val Ala Ser Leu Arg Thr Gly Asp Gly Gly
        4210            4215            4220
Trp Glu Arg Trp Leu Thr Ala Leu Ala Gln Ala Trp Thr Leu Gly Ala
4225            4230            4235            4240
Ala Val Asp Trp Asp Thr Val Val Glu Pro Val Pro Gly Arg Leu Leu
                4245            4250            4255
Asp Leu Pro Thr Tyr Ala Phe Glu Arg Arg Arg Tyr Trp Leu Glu Ala
        4260            4265            4270
Ala Gly Ala Thr Asp Leu Ser Ala Ala Gly Leu Thr Gly Ala Ala His
        4275            4280            4285
Pro Met Leu Ala Ala Ile Thr Ala Leu Pro Ala Asp Asp Gly Gly Val
        4290            4295            4300
Val Leu Thr Gly Arg Ile Ser Leu Arg Thr His Pro Trp Leu Ala Asp
4305            4310            4315            4320
His Ala Val Arg Gly Thr Val Leu Leu Pro Gly Thr Ala Phe Val Glu
                4325            4330            4335
Leu Val Ile Arg Ala Gly Asp Glu Thr Gly Cys Gly Ile Val Asp Glu
                4340            4345            4350
Leu Val Ile Glu Ser Pro Leu Val Val Pro Ala Thr Ala Ala Val Asp
                4355            4360            4365
```

-continued

Leu Ser Val Thr Val Glu Gly Ala Asp Glu Ala Gly Arg Arg Val
    4370            4375            4380

Thr Val His Ala Arg Thr Glu Gly Thr Gly Ser Trp Thr Arg His Ala
4385            4390            4395            4400

Ser Gly Thr Leu Thr Pro Asp Thr Pro Asp Thr Pro Asn Ala Ser Gly
        4405            4410            4415

Val Val Gly Ala Glu Pro Phe Ser Gln Trp Pro Pro Ala Thr Ala Ala
            4420            4425            4430

Ala Val Asp Thr Ser Glu Phe Tyr Leu Arg Leu Asp Ala Leu Gly Tyr
        4435            4440            4445

Arg Phe Gly Pro Met Phe Arg Gly Met Arg Ala Trp Arg Asp Gly
        4450            4455            4460

Asp Thr Val Tyr Ala Glu Val Ala Leu Pro Glu Asp Arg Ala Ala Asp
4465            4470            4475            4480

Ala Asp Gly Phe Gly Met His Pro Ala Leu Leu Asp Ala Ala Leu Gln
            4485            4490            4495

Ser Gly Ser Leu Leu Met Leu Glu Ser Asp Gly Glu Gln Ser Val Gln
        4500            4505            4510

Leu Pro Phe Ser Trp His Gly Val Arg Phe His Ala Thr Gly Ala Thr
        4515            4520            4525

Met Leu Arg Val Ala Val Val Pro Gly Pro Asp Gly Leu Arg Leu His
        4530            4535            4540

Ala Ala Asp Ser Gly Asn Arg Pro Val Ala Thr Ile Asp Ala Leu Val
4545            4550            4555            4560

Thr Arg Ser Pro Glu Ala Asp Leu Ala Pro Ala Asp Pro Met Leu Arg
            4565            4570            4575

Val Gly Trp Ala Pro Val Pro Val Pro Ala Gly Ala Gly Pro Ser Asp
            4580            4585            4590

Ala Asp Val Leu Thr Leu Arg Gly Asp Asp Ala Asp Pro Leu Gly Glu
        4595            4600            4605

Thr Arg Asp Leu Thr Thr Arg Val Leu Asp Ala Leu Leu Arg Ala Asp
        4610            4615            4620

Arg Pro Val Ile Phe Gln Val Thr Gly Gly Leu Ala Ala Lys Ala Ala
4625            4630            4635            4640

Ala Gly Leu Val Arg Thr Ala Gln Asn Glu Gln Pro Gly Arg Phe Phe
            4645            4650            4655

Leu Val Glu Thr Asp Pro Gly Val Leu Asp Gly Ala Lys Arg Asp
            4660            4665            4670

Ala Ile Ala Ala Leu Gly Glu Pro His Val Arg Leu Arg Asp Gly Leu
        4675            4680            4685

Phe Glu Ala Ala Arg Leu Met Arg Ala Thr Pro Ser Leu Thr Leu Pro
4690            4695            4700

Asp Thr Gly Ser Trp Gln Leu Arg Pro Ser Ala Thr Gly Ser Leu Asp
4705            4710            4715            4720

Asp Leu Ala Val Val Pro Thr Asp Ala Pro Asp Arg Pro Leu Ala Ala
            4725            4730            4735

Gly Glu Val Arg Ile Ala Val Arg Ala Ala Gly Leu Asn Phe Arg Asp
            4740            4745            4750

Val Thr Val Ala Leu Gly Val Val Ala Asp Ala Arg Pro Leu Gly Ser
        4755            4760            4765

Glu Ala Ala Gly Val Val Leu Glu Thr Gly Pro Gly Val His Asp Leu
    4770            4775            4780

-continued

```
Ala Pro Gly Asp Arg Val Leu Gly Met Leu Ala Gly Phe Gly Pro
4785                4790                4795                4800

Val Ala Ile Thr Asp Arg Arg Leu Leu Gly Arg Met Pro Asp Gly Trp
                4805                4810                4815

Thr Phe Pro Gln Ala Ala Ser Val Met Thr Ala Phe Ala Thr Ala Trp
            4820                4825                4830

Tyr Gly Leu Val Asp Leu Ala Gly Leu Arg Pro Gly Glu Lys Val Leu
        4835                4840                4845

Ile His Ala Ala Ala Thr Gly Val Gly Ala Ala Val Gln Ile Ala
4850                4855                4860

Arg His Leu Gly Ala Glu Val Tyr Ala Thr Thr Ser Ala Ala Lys Arg
4865                4870                4875                4880

His Leu Val Asp Leu Asp Gly Ala His Leu Ala Asp Ser Arg Ser Thr
            4885                4890                4895

Ala Phe Ala Asp Ala Phe Pro Val Asp Val Leu Asn Ser Leu
                4900                4905                4910

Thr Gly Glu Phe Leu Asp Ala Ser Val Gly Leu Leu Ala Ala Gly Gly
            4915                4920                4925

Arg Phe Ile Glu Met Gly Lys Thr Asp Ile Arg His Ala Val Gln Gln
        4930                4935                4940

Pro Phe Asp Leu Met Asp Ala Gly Pro Asp Arg Met Gln Arg Ile Ile
4945                4950                4955                4960

Val Glu Leu Leu Gly Leu Phe Ala Arg Asp Val Leu His Pro Leu Pro
                4965                4970                4975

Val His Ala Trp Asp Val Arg Gln Ala Arg Glu Ala Phe Gly Trp Met
            4980                4985                4990

Ser Ser Gly Arg His Thr Gly Lys Leu Val Leu Thr Val Pro Arg Pro
        4995                5000                5005

Leu Asp Pro Glu Gly Ala Val Val Ile Thr Gly Gly Ser Gly Thr Leu
    5010                5015                5020

Ala Gly Ile Leu Ala Arg His Leu Gly His Pro His Thr Tyr Leu Leu
5025                5030                5035                5040

Ser Arg Thr Pro Pro Asp Thr Thr Pro Gly Thr His Leu Pro Cys
            5045                5050                5055

Asp Val Gly Asp Pro His Gln Leu Ala Thr Thr Leu Ala Arg Ile Pro
            5060                5065                5070

Gln Pro Leu Thr Ala Val Phe His Thr Ala Gly Thr Leu Asp Asp Ala
        5075                5080                5085

Leu Leu Asp Asn Leu Thr Pro Asp Arg Val Asp Thr Val Leu Lys Pro
    5090                5095                5100

Lys Ala Asp Ala Ala Trp His Leu His Arg Leu Thr Arg Asp Thr Asp
5105                5110                5115                5120

Leu Ala Ala Phe Val Val Tyr Ser Ala Val Ala Gly Leu Met Gly Ser
            5125                5130                5135

Pro Gly Gln Gly Asn Tyr Val Ala Ala Asn Ala Phe Leu Asp Ala Leu
        5140                5145                5150

Ala Glu His Arg Arg Ala Gln Gly Leu Pro Ala Gln Ser Leu Ala Trp
    5155                5160                5165

Gly Met Trp Ala Asp Val Ser Ala Leu Thr Ala Lys Leu Thr Asp Ala
    5170                5175                5180

Asp Arg Gln Arg Ile Arg Arg Ser Gly Phe Pro Pro Leu Ser Ala Ala
5185                5190                5195                5200

Asp Gly Met Arg Leu Phe Asp Ala Ala Thr Arg Thr Pro Glu Pro Val
```

-continued

```
                  5205                5210                5215
Val Val Ala Thr Thr Val Asp Leu Thr Gln Leu Asp Gly Ala Val Ala
            5220                5225                5230

Pro Leu Leu Arg Gly Leu Ala Ala His Arg Ala Gly Pro Ala Arg Thr
            5235                5240                5245

Val Ala Arg Asn Ala Gly Glu Glu Pro Leu Ala Val Arg Leu Ala Gly
            5250                5255                5260

Arg Thr Ala Ala Glu Gln Arg Arg Ile Met Gln Glu Val Val Leu Arg
5265                5270                5275                5280

His Ala Ala Ala Val Leu Ala Tyr Gly Leu Gly Asp Arg Val Ala Ala
            5285                5290                5295

Asp Arg Pro Phe Arg Glu Leu Gly Phe Asp Ser Leu Thr Ala Val Asp
            5300                5305                5310

Leu Arg Asn Arg Leu Ala Ala Glu Thr Gly Leu Arg Leu Pro Thr Thr
            5315                5320                5325

Leu Val Phe Ser His Pro Thr Ala Glu Ala Leu Thr Ala His Leu Leu
            5330                5335                5340

Asp Leu Ile Asp Ala Pro Thr Ala Arg Ile Ala Gly Glu Ser Leu Pro
5345                5350                5355                5360

Ala Val Thr Ala Ala Pro Val Ala Ala Arg Asp Gln Asp Glu Pro
            5365                5370                5375

Ile Ala Ile Val Ala Met Ala Cys Arg Leu Pro Gly Gly Val Thr Ser
            5380                5385                5390

Pro Glu Asp Leu Trp Arg Leu Val Glu Ser Gly Thr Asp Ala Ile Thr
            5395                5400                5405

Thr Pro Pro Asp Asp Arg Gly Trp Asp Val Asp Ala Leu Tyr Asp Ala
            5410                5415                5420

Asp Pro Asp Ala Ala Gly Lys Ala Tyr Asn Leu Arg Gly Gly Tyr Leu
5425                5430                5435                5440

Ala Gly Ala Ala Glu Phe Asp Ala Ala Phe Phe Asp Ile Ser Pro Arg
            5445                5450                5455

Glu Ala Leu Gly Met Asp Pro Gln Gln Arg Leu Leu Leu Glu Thr Ala
            5460                5465                5470

Trp Glu Ala Ile Glu Arg Gly Arg Ile Ser Pro Ala Ser Leu Arg Gly
            5475                5480                5485

Arg Glu Val Gly Val Tyr Val Gly Ala Ala Gln Gly Tyr Gly Leu
            5490                5495                5500

Gly Ala Glu Asp Thr Glu Gly His Ala Ile Thr Gly Gly Ser Thr Ser
5505                5510                5515                5520

Leu Leu Ser Gly Arg Leu Ala Tyr Val Leu Gly Leu Glu Gly Pro Ala
            5525                5530                5535

Val Thr Val Asp Thr Ala Cys Ser Ser Ser Leu Val Ala Leu His Leu
            5540                5545                5550

Ala Cys Gln Gly Leu Arg Leu Gly Glu Cys Glu Leu Ala Leu Ala Gly
            5555                5560                5565

Gly Val Ser Val Leu Ser Ser Pro Ala Ala Phe Val Glu Phe Ser Arg
            5570                5575                5580

Gln Arg Gly Leu Ala Ala Asp Gly Arg Cys Lys Ser Phe Gly Ala Gly
5585                5590                5595                5600
```

-continued

```
Ala Asp Gly Thr Thr Trp Ser Glu Gly Val Gly Val Leu Val Leu Glu
            5605                5610                5615

Arg Leu Ser Asp Ala Glu Arg Leu Gly His Thr Val Leu Ala Val Val
            5620                5625                5630

Arg Gly Ser Ala Val Thr Ser Asp Gly Ala Ser Asn Gly Leu Thr Ala
            5635                5640                5645

Pro Asn Gly Leu Ser Gln Gln Arg Val Ile Arg Lys Ala Leu Ala Ala
        5650                5655                5660

Ala Gly Leu Thr Gly Ala Asp Val Asp Val Val Glu Gly His Gly Thr
5665                5670                5675                5680

Gly Thr Arg Leu Gly Asp Pro Val Glu Ala Asp Ala Leu Leu Ala Thr
            5685                5690                5695

Tyr Gly Gln Asp Arg Pro Ala Pro Val Trp Leu Gly Ser Leu Lys Ser
            5700                5705                5710

Asn Ile Gly His Ala Thr Ala Ala Gly Val Ala Gly Val Ile Lys
            5715                5720                5725

Met Val Gln Ala Ile Gly Ala Gly Thr Met Pro Arg Thr Leu His Val
            5730                5735                5740

Glu Glu Pro Ser Pro Ala Val Asp Trp Ser Thr Gly Gln Val Ser Leu
5745                5750                5755                5760

Leu Gly Ser Asn Arg Pro Trp Pro Asp Asp Glu Arg Pro Arg Arg Ala
            5765                5770                5775

Ala Val Ser Ala Phe Gly Leu Ser Gly Thr Asn Ala His Val Ile Leu
            5780                5785                5790

Glu Gln His Arg Pro Ala Pro Val Ala Ser Gln Pro Pro Arg Pro Pro
            5795                5800                5805

Arg Glu Glu Ser Gln Pro Leu Pro Trp Val Leu Ser Ala Arg Thr Pro
            5810                5815                5820

Ala Ala Leu Arg Ala Gln Ala Ala Arg Leu Arg Asp His Leu Ala Ala
5825                5830                5835                5840

Ala Pro Asp Ala Asp Pro Leu Asp Ile Gly Tyr Ala Leu Ala Thr Ser
            5845                5850                5855

Arg Ala Gln Phe Ala His Arg Ala Val Val Ala Thr Thr Pro Asp
            5860                5865                5870

Gly Phe Arg Ala Ala Leu Asp Gly Leu Ala Asp Gly Ala Glu Ala Pro
            5875                5880                5885

Gly Val Val Thr Gly Thr Ala Gln Glu Arg Arg Val Ala Phe Leu Phe
            5890                5895                5900

Asp Gly Gln Gly Ala Gln Arg Ala Gly Met Gly Arg Glu Leu His Arg
5905                5910                5915                5920

Arg Phe Pro Val Phe Ala Ala Ala Trp Asp Glu Val Ser Asp Ala Phe
            5925                5930                5935

Gly Lys His Leu Lys His Ser Pro Thr Asp Val Tyr His Gly Glu His
            5940                5945                5950

Gly Ala Leu Ala His Asp Thr Leu Tyr Ala Gln Ala Gly Leu Phe Thr
            5955                5960                5965

Leu Glu Val Ala Leu Leu Arg Leu Leu Glu His Trp Gly Val Arg Pro
            5970                5975                5980
```

-continued

```
Asp Val Leu Val Gly His Ser Val Gly Glu Val Thr Ala Ala Tyr Ala
5985                5990                5995                6000

Ala Gly Val Leu Thr Leu Ala Asp Ala Thr Glu Leu Ile Val Ala Arg
           6005                6010                6015

Gly Arg Ala Leu Arg Ala Leu Pro Pro Gly Ala Met Leu Ala Val Asp
           6020                6025                6030

Gly Ser Pro Ala Glu Val Gly Ala Arg Thr Asp Leu Asp Ile Ala Ala
           6035                6040                6045

Val Asn Gly Pro Ser Ala Val Val Leu Ala Gly Ser Pro Asp Asp Val
6050                6055                6060

Ala Ala Phe Glu Arg Glu Trp Ser Ala Ala Gly Arg Arg Thr Lys Arg
6065                6070                6075                6080

Leu Asp Val Gly His Ala Phe His Ser Arg His Val Asp Gly Ala Leu
                6085                6090                6095

Asp Gly Phe Arg Thr Val Leu Glu Ser Leu Ala Phe Gly Ala Ala Arg
           6100                6105                6110

Leu Pro Val Val Ser Thr Thr Thr Gly Arg Asp Ala Ala Asp Asp Leu
           6115                6120                6125

Ile Thr Pro Ala His Trp Leu Arg His Ala Arg Arg Pro Val Leu Phe
     6130                6135                6140

Ser Asp Ala Val Arg Glu Leu Ala Asp Arg Gly Val Thr Thr Phe Val
6145                6150                6155                6160

Ala Val Gly Pro Ser Gly Ser Leu Ala Ser Ala Ala Ala Glu Ser Ala
                6165                6170                6175

Gly Glu Asp Ala Gly Thr Tyr His Ala Val Leu Arg Ala Arg Thr Gly
           6180                6185                6190

Glu Glu Thr Ala Ala Leu Thr Ala Leu Ala Glu Leu His Ala His Gly
           6195                6200                6205

Val Pro Val Asp Leu Ala Ala Val Leu Ala Gly Gly Arg Pro Val Asp
     6210                6215                6220

Leu Pro Val Tyr Ala Phe Gln His Arg Ser Tyr Trp Leu Ala Pro Ala
6225                6230                6235                6240

Val Ala Gly Ala Pro Ala Thr Val Ala Asp Thr Gly Pro Ala Glu
           6245                6250                6255

Ser Glu Pro Glu Asp Leu Thr Val Ala Glu Ile Val Arg Arg Arg Thr
           6260                6265                6270

Ala Ala Leu Leu Gly Val Thr Asp Pro Ala Asp Val Asp Ala Glu Ala
           6275                6280                6285

Thr Phe Phe Ala Leu Gly Phe Asp Ser Leu Ala Val Gln Arg Leu Arg
     6290                6295                6300

Asn Gln Leu Ala Ser Ala Thr Gly Leu Asp Leu Pro Ala Ala Val Leu
6305                6310                6315                6320

Phe Asp His Asp Thr Pro Ala Ala Leu Thr Ala Phe Leu Gln Asp Arg
                6325                6330                6335

Ile Glu Ala Gly Gln Asp Arg Ile Glu Ala Gly Glu Asp Asp Ala
           6340                6345                6350

Pro Thr Val Leu Ser Leu Leu Glu Glu Met Glu Ser Leu Asp Ala Ala
           6355                6360                6365

Asp Ile Ala Ala Thr Pro Ala Pro Glu Arg Ala Ala Ile Ala Asp Leu
     6370                6375                6380

Leu Asp Lys Leu Ala His Thr Trp Lys Asp Tyr Arg
6385                6390                6395
```

POLYNUCLEOTIDES ENCODING THE FKBA GENE OF THE FK-520 POLYKETIDE SYNTHASE GENE CLUSTER

CROSS-REFERENCE TO RELATED APPLICATIONS

The present application claims priority to related U.S. patent application Serial No. 60/102,748, filed Oct. 2, 1998; No. 60/139,650, filed Jun. 17, 1999; and No. 60/123,810, filed Mar. 11, 1999, each of which is incorporated herein by reference.

SUBMISSION ON COMPACT DISC

The contents of the following submission on compact discs are incorporated herein by reference in their entirety: a compact disc copy of the substitute Sequence Listing (COPY 1) (file name: 3006220026.txt, date recorded: Feb. 19, 2002, size: 521 KB); a duplicate compact disc copy of the substitute Sequence Listing (COPY 2) (file name: 3006220026.txt, date recorded: Feb. 19, 2002, size: 521 KB); and a computer readable form copy of the substitute Sequence Listing (CRF COPY) (file name: 3006220026.txt, date recorded: Feb. 19, 2002, size: 521 KB).

FIELD OF THE INVENTION

The present invention relates to polyketides and the polyketide synthase (PKS) enzymes that produce them. The invention also relates generally to genes encoding PKS enzymes and to recombinant host cells containing such genes and in which expression of such genes leads to the production of polyketides. The present invention also relates to compounds useful as medicaments having immunosuppressive and/or neurotrophic activity. Thus, the invention relates to the fields of chemistry, molecular biology, and agricultural, medical, and veterinary technology.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothilone, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672, 491; 5,712,146; 5,830,750; and 5,843,718; and Fu et al., 1994, Biochemistry 33: 9321–9326; McDaniel et al., 1993, Science 262: 1546–1550; and Rohr, 1995, Angew. Chem. Int. Ed. Engl. 34(8): 881–888, each of which is incorporated herein by reference.

Polyketides are synthesized in nature by PKS enzymes. These enzymes, which are complexes of multiple large proteins, are similar to the synthases that catalyze condensation of 2-carbon units in the biosynthesis of fatty acids. PKSs catalyze the biosynthesis of polyketides through repeated, decarboxylative Claisen condensations between acylthioester building blocks. The building blocks used to form complex polyketides are typically acylthioesters, such as acetyl, butyryl, propionyl, malonyl, hydroxymalonyl, methylmalonyl, and ethylmalonyl CoA. Other building blocks include amino acid like acylthioesters. PKS enzymes that incorporate such building blocks include an activity that functions as an amino acid ligase (an AMP ligase) or as a non-ribosomal peptide synthetase (NRPS). Two major types of PKS enzymes are known; these differ in their composition and mode of synthesis of the polyketide synthesized. These two major types of PKS enzymes are commonly referred to as Type I or "modular" and Type II "iterative" PKS enzymes.

In the Type I or modular PKS enzyme group, a set of separate catalytic active sites (each active site is termed a "domain", and a set thereof is termed a "module") exists for each cycle of carbon chain elongation and modification in the polyketide synthesis pathway. The typical modular PKS is composed of several large polypeptides, which can be segregated from amino to carboxy termini into a loading module, multiple extender modules, and a releasing (or thioesterase) domain. The PKS enzyme known as 6-deoxyerythronolide B synthase (DEBS) is a Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See Caffrey et al., 1992, FEBS Letters 304: 205, and U.S. Pat. No. 5,824,513, each of which is incorporated herein by reference.

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated ketosynthase (KS) domain and AT and ACP domains. This inactivated KS is in some instances called KSQ, where the superscript letter is the abbreviation for the amino acid, glutamine, that is present instead of the active site cysteine required for ketosynthase activity. In other PKS enzymes, including the FK-506 PKS, the loading module incorporates an unusual starter unit and is composed of a CoA ligase like activity domain. In any event, the loading module recognizes a particular acyl-CoA (usually acetyl or propionyl but sometimes butyryl or other acyl-CoA) and transfers it as a thiol ester to the ACP of the loading module.

The AT on each of the extender modules recognizes a particular extender-CoA (malonyl or alpha-substituted malonyl, i.e., methylmalonyl, ethylmalonyl, and 2-hydroxymalonyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module.

Each extender module of a modular PKS contains a KS, AT, ACP, and zero, one, two, or three domains that modify the beta-carbon of the growing polyketide chain. A typical (non-loading) minimal Type I PKS extender module is exemplified by extender module three of DEBS, which contains a KS domain, an AT domain, and an ACP domain. These three domains are sufficient to activate a 2-carbon extender unit and attach it to the growing polyketide molecule. The next extender module, in turn, is responsible for attaching the next building block and transferring the growing compound to the next extender module until synthesis is complete.

Once the PKS is primed with acyl- and malonyl-ACPs, the acyl group of the loading module is transferred to form a thiol ester (trans-esterification) at the KS of the first extender module; at this stage, extender module one possesses an acyl-KS and a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading building block (elongation or extension).

The polyketide chain, growing by two carbons each extender module, is sequentially passed as covalently bound thiol esters from extender module to extender module, in an assembly line-like process. The carbon chain produced by this process alone would possess a ketone at every other carbon atom, producing a polyketone, from which the name polyketide arises. Most commonly, however, additional enzymatic activities modify the beta keto group of each two carbon unit just after it has been added to the growing polyketide chain but before it is transferred to the next module.

Thus, in addition to the minimal module containing KS, AT, and ACP domains necessary to form the carbon-carbon bond, and as noted above, other domains that modify the beta-carbonyl moiety can be present. Thus, modules may contain a ketoreductase (KR) domain that reduces the keto group to an alcohol. Modules may also contain a KR domain plus a dehydratase (DH) domain that dehydrates the alcohol to a double bond. Modules may also contain a KR domain, a DH domain, and an enoylreductase (ER) domain that converts the double bond product to a saturated single bond using the beta carbon as a methylene function. An extender module can also contain other enzymatic activities, such as, for example, a methylase or dimethylase activity.

After traversing the final extender module, the polyketide encounters a releasing domain that cleaves the polyketide from the PKS and typically cyclizes the polyketide. For example, final synthesis of 6-dEB is regulated by a TE domain located at the end of extender module six. In the synthesis of 6-dEB, the TE domain catalyzes cyclization of the macrolide ring by formation of an ester linkage. In FK-506, FK-520, rapamycin, and similar polyketides, the TE activity is replaced by a RapP (for rapamycin) or RapP like activity that makes a linkage incorporating a pipecolate acid residue. The enzymatic activity that catalyzes this incorporation for the rapamycin enzyme is known as RapP, encoded by the rap? gene. The polyketide can be modified further by tailoring enzymes; these enzymes add carbohydrate groups or methyl groups, or make other modifications, i.e., oxidation or reduction, on the polyketide core molecule. For example, 6-dEB is hydroxylated at C-6 and C-12 and glycosylated at C-3 and C-5 in the synthesis of erythromycin A.

In Type I PKS polypeptides, the order of catalytic domains is conserved. When all beta-keto processing domains are present in a module, the order of domains in that module from N-to-C-terminus is always KS, AT, DH, ER, KR, and ACP. Some or all of the beta-keto processing domains may be missing in particular modules, but the order of the domains present in a module remains the same. The order of domains within modules is believed to be important for proper folding of the PKS polypetides into an active complex. Importantly, there is considerable flexibility in PKS enzymes, which allows for the genetic engineering of novel catalytic complexes. The engineering of these enzymes is achieved by modifying, adding, or deleting domains, or replacing them with those taken from other Type I PKS enzymes. It is also achieved by deleting, replacing, or adding entire modules with those taken from other sources. A genetically engineered PKS complex should of course have the ability to catalyze the synthesis of the product predicted from the genetic alterations made.

Alignments of the many available amino acid sequences for Type I PKS enzymes has approximately defined the boundaries of the various catalytic domains. Sequence alignments also have revealed linker regions between the catalytic domains and at the N- and C-termini of individual polypeptides. The sequences of these linker regions are less well conserved than are those for the catalytic domains, which is in part how linker regions are identified. Linker regions can be important for proper association between domains and between the individual polypeptides that comprise the PKS complex. One can thus view the linkers and domains together as creating a scaffold on which the domains and modules are positioned in the correct orientation to be active. This organization and positioning, if retained, permits PKS domains of different or identical substrate specificities to be substituted (usually at the DNA level) between PKS enzymes by various available methodologies. In selecting the boundaries of, for example, an AT replacement, one can thus make the replacement so as to retain the linkers of the recipient PKS or to replace them with the linkers of the donor PKS AT domain, or, preferably, make both constructs to ensure that the correct linker regions between the KS and AT domains have been included in at least one of the engineered enzymes. Thus, there is considerable flexibility in the design of new PKS enzymes with the result that known polyketides can be produced more effectively, and novel polyketides useful as pharmaceuticals or for other purposes can be made.

By appropriate application of recombinant DNA technology, a wide variety of polyketides can be prepared in a variety of different host cells provided one has access to nucleic acid compounds that encode PKS proteins and polyketide modification enzymes. The present invention helps meet the need for such nucleic acid compounds by providing recombinant vectors that encode the FK-520 PKS enzyme and various FK-520 modification enzymes. Moreover, while the FK-506 and FK-520 polyketides have many useful activities, there remains a need for compounds with similar useful activities but with better pharmacokinetic profile and metabolism and fewer side-effects. The present invention helps meet the need for such compounds as well.

SUMMARY OF THE INVENTION

In one embodiment, the present invention provides recombinant DNA vectors that encode all or part of the FK-520 PKS enzyme. Illustrative vectors of the invention include cosmid pKOS034-120, pKOS034-124, pKOS065-C31, pKOS065-C3, pKOS065-M27, and pKOS065-M21. The invention also provides nucleic acid compounds that encode the various domains of the FK-520 PKS, i.e., the KS, AT, ACP, KR, DH, and ER domains. These compounds can be readily used, alone or in combination with nucleic acids encoding other FK-520 or non-FK-520 PKS domains, as intermediates in the construction of recombinant vectors that encode all or part of PKS enzymes that make novel polyketides.

The invention also provides isolated nucleic acids that encode all or part of one or more modules of the FK-520 PKS, each module comprising a ketosynthase activity, an acyl transferase activity, and an acyl carrier protein activity. The invention provides an isolated nucleic acid that encodes one or more open reading frames of FK-520 PKS genes, said open reading frames comprising coding sequences for a CoA ligase activity, an NRPS activity, or two or more extender modules. The invention also provides recombinant expression vectors containing these nucleic acids.

In another embodiment, the invention provides isolated nucleic acids that encode all or a part of a PKS that contains at least one module in which at least one of the domains in the module is a domain from a non-FK-520 PKS and at least one domain is from the FK-520 PKS. The non-FK-520 PKS domain or module originates from the rapamycin PKS, the FK-506 PKS, DEBS, or another PKS. The invention also provides recombinant expression vectors containing these nucleic acids.

In another embodiment, the invention provides a method of preparing a polyketide, said method comprising transforming a host cell with a recombinant DNA vector that encodes at least one module of a PKS, said module comprising at least one FK-520 PKS domain, and culturing said host cell under conditions such that said PKS is produced and catalyzes synthesis of said polyketide. In one aspect, the method is practiced with a Streptomyces host cell. In another aspect, the polyketide produced is FK-520. In another aspect, the polyketide produced is a polyketide related in structure to FK-520. In another aspect, the polyketide produced is a polyketide related in structure to FK-506 or rapamycin.

In another embodiment, the invention provides a set of genes in recombinant form sufficient for the synthesis of ethylmalonyl CoA in a heterologous host cell. These genes and the methods of the invention enable one to create recombinant host cells with the ability to produce polyketides or other compounds that require ethylmalonyl CoA for biosynthesis. The invention also provides recombinant nucleic acids that encode AT domains specific for ethylmalonyl CoA. Thus, the compounds of the invention can be used to produce polyketides requiring ethylmalonyl CoA in host cells that otherwise are unable to produce such polyketides.

In another embodiment, the invention provides a set of genes in recombinant form sufficient for the synthesis of 2-hydroxymalonyl CoA and 2-methoxymalonyl CoA in a heterologous host cell. These genes and the methods of the invention enable one to create recombinant host cells with the ability to produce polyketides or other compounds that require 2-hydroxymalonyl CoA for biosynthesis. The invention also provides recombinant nucleic acids that encode AT domains specific for 2-hydroxymalonyl CoA and 2-methoxymalonyl CoA. Thus, the compounds of the invention can be used to produce polyketides requiring 2-hydroxymalonyl CoA or 2-methoxymalonyl CoA in host cells that are otherwise unable to produce such polyketides.

In another embodiment, the invention provides a compound related in structure to FK-520 or FK-506 that is useful in the treatment of a medical condition. These compounds include compounds in which the C-13 methoxy group is replaced by a moiety selected from the group consisting of hydrogen, methyl, and ethyl moieties. Such compounds are less susceptible to the main in vivo pathway of degradation for FK-520 and FK-506 and related compounds and thus exhibit an improved pharmacokinetic profile. The compounds of the invention also include compounds in which the C-15 methoxy group is replaced by a moiety selected from the group consisting of hydrogen, methyl, and ethyl moieties. The compounds of the invention also include the above compounds further modified by chemical methodology to produce derivatives such as, but not limited to, the C-18 hydroxyl derivatives, which have potent neurotrophin but not immunosuppresion activities.

Thus, the invention provides polyketides having the structure:

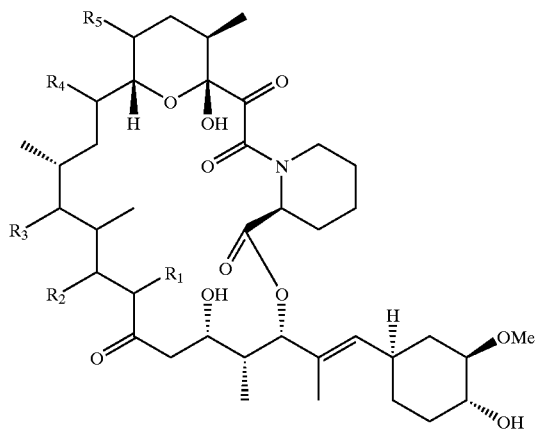

wherein, $R_1$ is hydrogen, methyl, ethyl, or allyl; $R_2$ is hydrogen or hydroxyl, provided that when $R_2$ is hydrogen, there is a double bond between C-20 and C-19; $R_3$ is hydrogen or hydroxyl; $R_4$ is methoxyl, hydrogen, methyl, or ethyl; and $R_5$ is methoxyl, hydrogen, methyl, or ethyl; but not including FK-506, FK-520, 18-hydroxy-FK-520, and 18-hydroxy-FK-506. The invention provides these compounds in purified form and in pharmaceutical compositions.

In another embodiment, the invention provides a method for treating a medical condition by administering a pharmaceutically efficacious dose of a compound of the invention. The compounds of the invention may be administered to achieve immunosuppression or to stimulate nerve growth and regeneration.

These and other embodiments and aspects of the invention will be more fully understood after consideration of the attached Drawings and their brief description below, together with the detailed description, examples, and claims that follow.

DETAILED DESCRIPTION OF THE INVENTION

Figure 1:
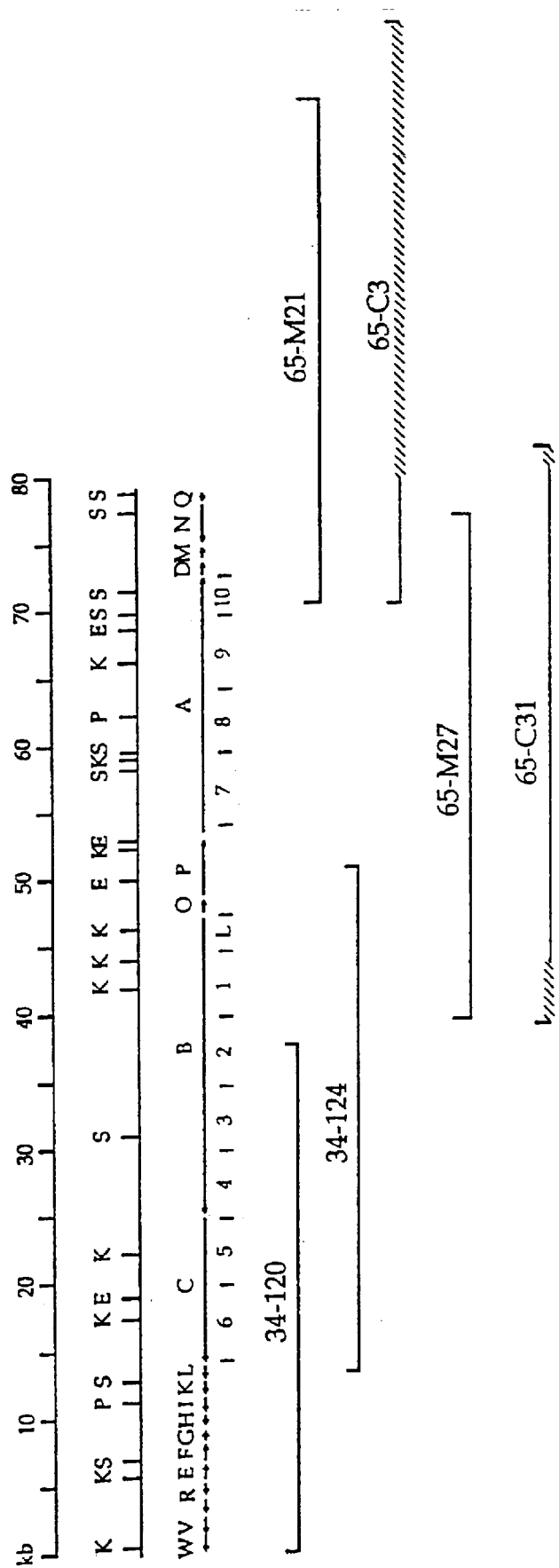
FIG. 1 shows a diagram of the FK-520 biosynthetic gene cluster. The top line provides a scale in kilobase pairs (kb). The second line shows a restriction map with selected restriction enzyme recognition sequences indicated. K is KpnI; X is XhoI, S is SacI; P is PstI; and E is EcoRI. The third line indicates the position of FK-520 PKS and related genes. Genes are abbreviated with a one letter designation, i.e., C fkbC. Immediately under the third line are numbered segments showing where the loading module (L) and ten different extender modules (numbered 1–10) are encoded on the various genes shown. At the bottom of the Figure, the DNA inserts of various cosmids of the invention (i.e., 34-124 is cosmid pKOS034-124) are shown in alignment with the FK-520 biosynthetic gene cluster.

Given the valuable pharmaceutical properties of polyketides, there is a need for methods and reagents for producing large quantities of polyketides, as well as for producing related compounds not found in nature. The present invention provides such methods and reagents, with particular application to methods and reagents for producing the polyketides known as FK-520, also known as ascomycin or L-683,590 (see Holt et al., 1993, *JACS* 115:9925), and FK-506, also known as tacrolimus. Tacrolimus is a macrolide immunosuppressant used to prevent or treat rejection of transplanted heart, kidney, liver, lung, pancreas, and small bowel allografts. The drug is also useful for the prevention and treatment of graft-versus-host disease in patients receiving bone marrow transplants, and for the treatment of severe, refractory uveitis. There have been additional reports of the unapproved use of tacrolimus for other conditions, including alopecia universalis, autoimmune chronic active hepatitis, inflammatory bowel disease, multiple sclerosis, primary biliary cirrhosis, and scleroderma. The invention provides methods and reagents for making novel polyketides related in structure to FK-520 and FK-506. and structurally related polyketides such as rapamycin.

The FK-506 and rapamycin polyketides are potent immunosuppressants, with chemical structures shown below.

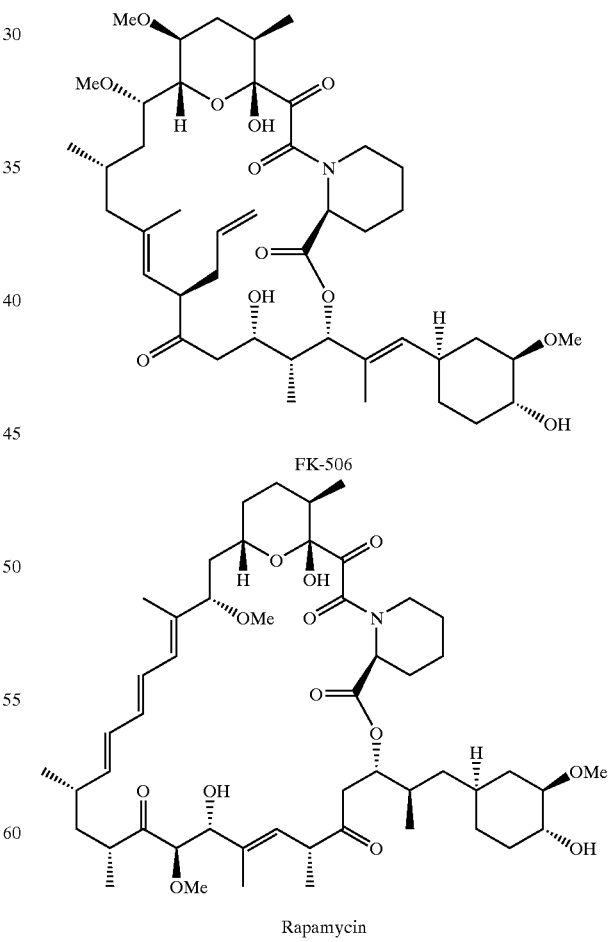

FK-520 differs from FK-506 in that it lacks the allyl group at C-21 of FK-506, having instead an ethyl group at that position, and has similar activity to FK-506, albeit reduced immunosuppressive activity.

These compounds act through initial formation of an intermediate complex with protein "immunophilins" known as FKBPs (FK-506 binding proteins), including FKBP-12. Immunophilins are a class of cytosolic proteins that form complexes with molecules such as FK-506, FK-520, and rapamycin that in turn serve as ligands for other cellular targets involved in signal transduction. Binding of FK-506, FK-520, and rapamycin to FKBP occurs through the structurally similar segments of the polyketide molecules, known as the "FKBP-binding domain" (as generally but not precisely indicated by the stippled regions in the structures above). The FK-506-FKBP complex then binds calcineurin, while the rapamycin-FKBP complex binds to a protein known as RAFT-1. Binding of the FKBP-polyketide complex to these second proteins occurs through the dissimilar regions of the drugs known as the "effector" domains.

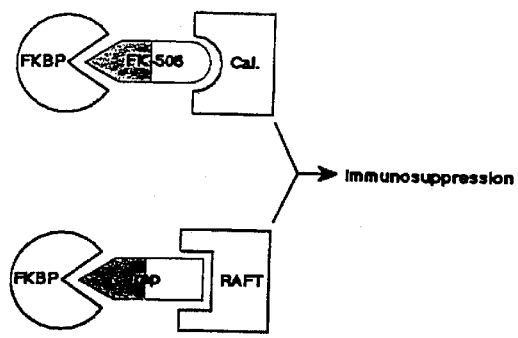

The three component FKBP-polyketide-effector complex is required for signal transduction and subsequent immunosuppressive activity of FK-506, FK-520, and rapamycin. Modifications in the effector domains of FK-506, FK-520, and rapamycin that destroy binding to the effector proteins (calcineurin or RAFT) lead to loss of immunosuppressive activity, even though FKBP binding is unaffected. Further, such analogs antagonize the immunosuppressive effects of the parent polyketides, because they compete for FKBP. Such non-immunosuppressive analogs also show reduced toxicity (see Dumont et al., 1992, *Journal of Experimental Medicine* 176, 751–760), indicating that much of the toxicity of these drugs is not linked to FKBP binding.

In addition to immunosuppressive activity, FK-520, FK-506, and rapamycin have neurotrophic activity. In the central nervous system and in peripheral nerves, immunophilins are referred to as "neuroimmunophilins". The neuroimmunophilin FKBP is markedly enriched in the central nervous system and in peripheral nerves. Molecules that bind to the neuroimmunophilin FKBP, such as FK-506 and FK-520, have the remarkable effect of stimulating nerve growth. In vitro, they act as neurotrophins, i.e., they promote neurite outgrowth in NGF-treated PC 12 cells and in sensory neuronal cultures, and in intact animals, they promote regrowth of damaged facial and sciatic nerves, and repair lesioned serotonin and dopamine neurons in the brain. See Gold et al., June 1999, *J. Pharm. Exp. Ther.* 289(3): 1202–1210; Lyons et al., 1994, *Proc. National Academy of Science* 91: 3191–3195; Gold et al., 1995, *Journal of Neuroscience* 15: 7509–7516; and Steiner et al., 1997, *Proc. National Academy of Science* 94: 2019–2024. Further, the restored central and peripheral neurons appear to be functional.

Compared to protein neurotrophic molecules (BNDF, NGF, etc.), the small-molecule neurotrophins such as FK-506, FK-520, and rapamycin have different, and often advantageous, properties. First, whereas protein neurotrophins are difficult to deliver to their intended site of action and may require intra-cranial injection, the small-molecule neurotrophins display excellent bioavailability; they are active when administered subcutaneously and orally. Second, whereas protein neurotrophins show quite specific effects, the small-molecule neurotrophins show rather broad effects. Finally, whereas protein neurotrophins often show effects on normal sensory nerves, the small-molecule neurotrophins do not induce aberrant sprouting of normal neuronal processes and seem to affect damaged nerves specifically. Neuroimmunophilin ligands have potential therapeutic utility in a variety of disorders involving nerve degeneration (e.g. multiple sclerosis, Parkinson's disease, Alzheimer's disease, stroke, traumatic spinal cord and brain injury, peripheral neuropathies).

Recent studies have shown that the immunosuppressive and neurite outgrowth activity of FK-506, FK-520, and rapamycin can be separated; the neuroregenerative activity in the absence of immunosuppressive activity is retained by agents which bind to FKBP but not to the effector proteins calcineurin or RAFT. See Steiner et al., 1997, *Nature Medicine* 3: 421–428.

Available structure-activity data show that the important features for neurotrophic activity of rapamycin, FK-520, and FK-506 lie within the common, contiguous segments of the macrolide ring that bind to FKBP. This portion of the molecule is termed the "FKBP binding domain" (see VanDuyne et al., 1993, *Journal of Molecular Biology* 229: 105–124.). Nevertheless, the effector domains of the parent macrolides contribute to conformational rigidity of the binding domain and thus indirectly contribute to FKBP binding.

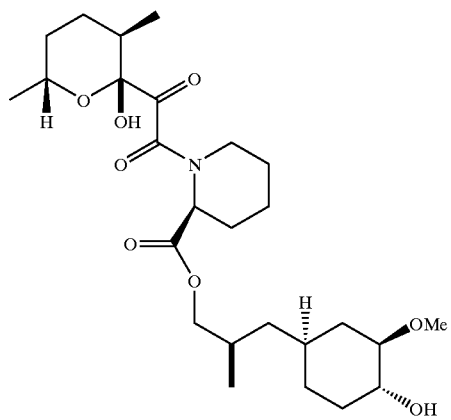

"FKBP binding domain"

There are a number of other reported analogs of FK-506, FK-520, and rapamycin that 110 bind to FKBP but not the effector protein calcineurin or RAFT. These analogs show effects on nerve regeneration without immunosuppressive effects.

Naturally occurring FK-520 and FK-506 analogs include the antascomycins, which are FK-506-like macrolides that lack the functional groups of FK-506 that bind to calcineurin (see Fehr et al., 1996, *The Journal of Antibiotics* 49: 230–233). These molecules bind FKBP as effectively as does FK-506; they antagonize the effects of both FK-506 and rapamycin, yet lack immunosuppressive activity.

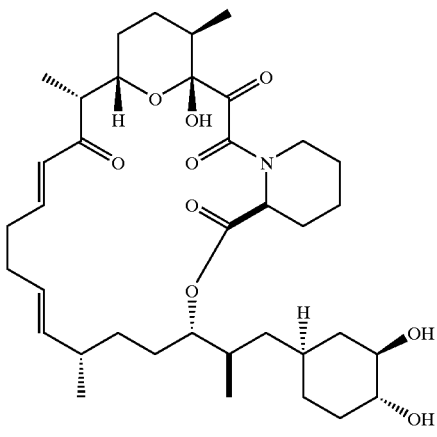

Antascomycin A

Other analogs can be produced by chemically modifying FK-506, FK-520, or rapamycin. One approach to obtaining neuroimmunophilin ligands is to destroy the effector binding region of FK-506, FK-520, or rapamycin by chemical modification. While the chemical modifications permitted on the parent compounds are quite limited, some useful chemically modified analogs exist. The FK-520 analog L-685,818 ($ED_{50}$=0.7 nM for FKBP binding; see Dumont et al., 1992), and the rapamycin analog WAY-124,466 ($IC_{50}$ 12.5 nM; see Ocain et al., 1993, *Biochemistry Biophysical Research Communications* 192: 1340–134693) are about as effective as FK-506, FK-520, and rapamycin at promoting neurite outgrowth in sensory neurons (see Steiner et al., 1997).

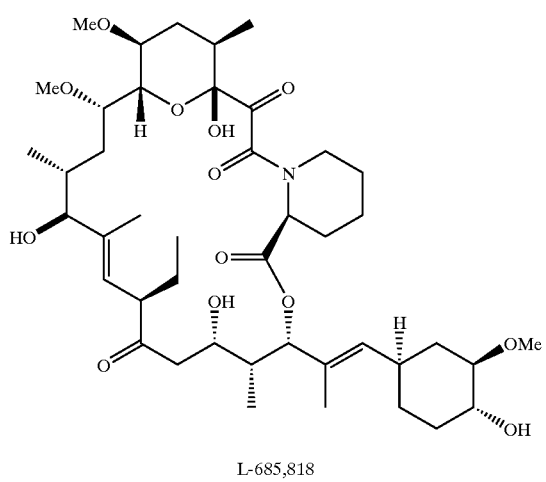

L-685,818

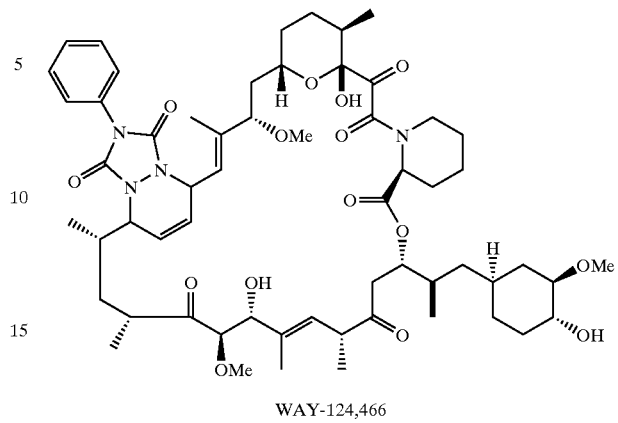

WAY-124,466

One of the few positions of rapamycin that is readily amenable to chemical modification is the allylic 16-methoxy group; this reactive group is readily exchanged by acid-catalyzed nucleophilic substitution. Replacement of the 16-methoxy group of rapamycin with a variety of bulky groups has produced analogs showing selective loss of immunosuppressive activity while retaining FKBP-binding (see Luengo et al., 1995, *Chemistry & Biology* 2: 471–481). One of the best compounds, 1, below, shows complete loss of activity in the splenocyte proliferation assay with only a 10-fold reduction in binding to FKBP.

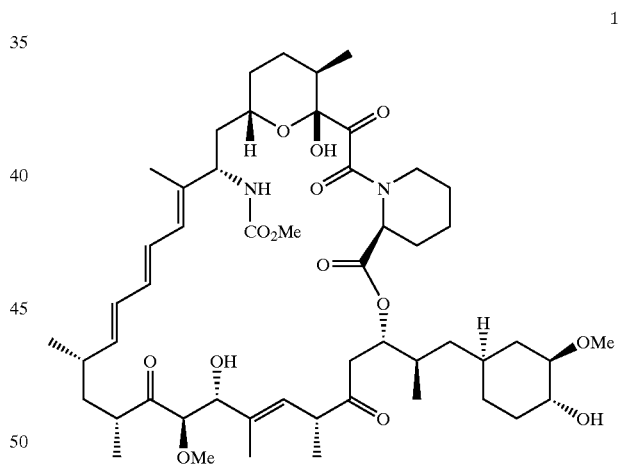

1

There are also synthetic analogs of FKBP binding domains. These compounds reflect an approach to obtaining neuroimmunophilin ligands based on "rationally designed" molecules that retain the FKBP-binding region in an appropriate conformation for binding to FKBP, but do not possess the effector binding regions. In one example, the ends of the FKBP binding domain were tethered by hydrocarbon chains (see Holt et al., 1993, *Journal of the American Chemical Society* 115: 9925–9938); the best analog, 2, below, binds to FKBP about as well as FK-506. In a similar approach, the ends of the FKBP binding domain were tethered by a tripeptide to give analog 3, below, which binds to FKBP about 20-fold poorer than FK-506. These compounds are anticipated to have neuroimmunophilin binding activity.

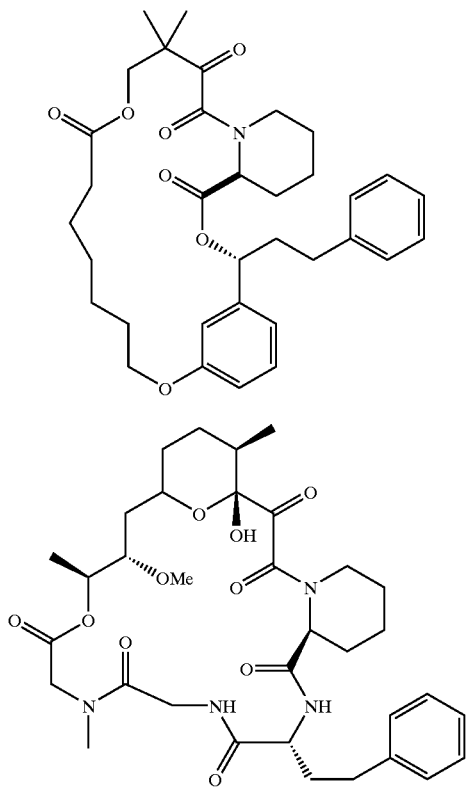

In a primate MPTP model of Parkinson's disease, administration of FKBP ligand GPI-1046 caused brain cells to regenerate and behavioral measures to improve. MPTP is a neurotoxin, which, when administered to animals, selectively damages nigral-striatal dopamine neurons in the brain, mimicking the damage caused by Parkinson's disease. Whereas, before treatment, animals were unable to use affected limbs, the FKBP ligand restored the ability of animals to feed themselves and gave improvements in measures of locomotor activity, neurological outcome, and fine motor control. There were also corresponding increases in regrowth of damaged nerve terminals. These results demonstrate the utility of FKBP ligands for treatment of diseases of the CNS.

From the above description, two general approaches towards the design of non-immunosuppressant, neuroimmunophilin ligands can be seen. The first involves the construction of constrained cyclic analogs of FK-506 in which the FKBP binding domain is fixed in a conformation optimal for binding to FKBP. The advantages of this approach are that the conformation of the analogs can be accurately modeled and predicted by computational methods, and the analogs closely resemble parent molecules that have proven pharmacological properties. A disadvantage is that the difficult chemistry limits the numbers and types of compounds that can be prepared. The second approach involves the trial and error construction of acyclic analogs of the FKBP binding domain by conventional medicinal chemistry. The advantages to this approach are that the chemistry is suitable for production of the numerous compounds needed for such interactive chemistry-bioassay approaches. The disadvantages are that the molecular types of compounds that have emerged have no known history of appropriate pharmacological properties, have rather labile ester functional groups, and are too conformationally mobile to allow accurate prediction of conformational properties.

The present invention provides useful methods and reagents related to the first approach, but with significant advantages. The invention provides recombinant PKS genes that produce a wide variety of polyketides that cannot otherwise be readily synthesized by chemical methodology alone. Moreover, the present invention provides polyketides that have either or both of the desired immunosuppressive and neurotrophic activities, some of which are produced only by fermentation and others of which are produced by fermentation and chemical modification. Thus, in one aspect, the invention provides compounds that optimally bind to FKBP but do not bind to the effector proteins. The methods and reagents of the invention can be used to prepare numerous constrained cyclic analogs of FK-520 in which the FKBP binding domain is fixed in a conformation optimal for binding to FKBP. Such compounds will show neuroimmunophilin binding (neurotrophic) but not immunosuppressive effects. The invention also allows direct manipulation of FK-520 and related chemical structures via genetic engineering of the enzymes involved in the biosynthesis of FK-520 (as well as related compounds, such as FK-506 and rapamycin); similar chemical modifications are simply not possible because of the complexity of the structures. The invention can also be used to introduce "chemical handles" into normally inert positions that permit subsequent chemical modifications.

Several general approaches to achieve the development of novel neuroimmunophilin ligands are facilitated by the methods and reagents of the present invention. One approach is to make "point mutations" of the functional groups of the parent FK-520 structure that bind to the effector molecules to eliminate their binding potential. These types of structural modifications are difficult to perform by chemical modification, but can be readily accomplished with the methods and reagents of the invention.

A second, more extensive approach facilitated by the present invention is to utilize molecular modeling to predict optimal structures ab initio that bind to FKBP but not effector molecules. Using the available X-ray crystal structure of FK-520 (or FK-506) bound to FKBP, molecular modeling can be used to predict polyketides that should optimally bind to FKBP but not calcineurin. Various macrolide structures can be generated by linking the ends of the FKBP-binding domain with "all possible" polyketide chains of variable length and substitution patterns that can be prepared by genetic manipulation of the FK-520 or FK-506 PKS gene cluster in accordance with the methods of the invention. The ground state conformations of the virtual library can be determined, and compounds that possess binding domains most likely to bind well to FKBP can be prepared and tested.

Once a compound is identified in accordance with the above approaches, the invention can be used to generate a focused library of analogs around the lead candidate, to "fine tune" the compound for optimal properties. Finally, the genetic engineering methods of the invention can be directed towards producing "chemical handles" that enable medicinal chemists to modify positions of the molecule previously inert to chemical modification. This opens the path to previously prohibited chemical optimization of lead compounds by time-proven approaches.

Moreover, the present invention provides polyketide compounds and the recombinant genes for the PKS enzymes that produce the compounds that have significant advantages over FK-506 and FK-520 and their analogs. The metabolism and pharmacokinetics of tacrolimus has been exstensively studied, and FK-520 is believed to be similar in these respects. Absorption of tacrolimus is rapid, variable, and incomplete from the gastrointestinal tract (Harrison's Principles of Internal Medicine, 14th edition, 1998, McGraw Hill, 14, 20, 21, 64–67). The mean bioavailability of the oral dosage form is 27%, (range 5 to 65%). The volume of distribution (VoID) based on plasma is 5 to 65 L per kg of body weight (L/kg), and is much higher than the VoID based on whole blood concentrations, the difference reflecting the binding of tacrolimus to red blood cells. Whole blood concentrations may be 12 to 67 times the plasma concentrations. Protein binding is high (75 to 99%), primarily to albumin and alpha1-acid glycoprotein. The half-life for distribution is 0.9 hour; elimination is biphasic and variable: terminal-11.3 hr (range, 3.5 to 40.5 hours). The time to peak concentration is 0.5 to 4 hours after oral administration.

Tacrolimus is metabolized primarily by cytochrome P4503A enzymes in the liver and small intestine. The drug is extensively metabolized with less than 1% excreted unchanged in urine. Because hepatic dysfunction decreases clearance of tacrolimus, doses have to be reduced substantially in primary graft non-function, especially in children. In addition, drugs that induce the cytochrome P4503A enzymes reduce tacrolimus levels, while drugs that inhibit these P450s increase tacrolimus levels. Tacrolimus bioavailability doubles with co-administration of ketoconazole, a drug that inhibits P4503A. See, Vincent et al., 1992, In vitro metabolism of FK-506 in rat, rabbit, and human liver microsomes: Identification of a major metabolite and of cytochrome P4503A as the major enzymes responsible for its metabolism, *Arch. Biochem. Biophys.* 294: 454–460; Iwasaki et al., 1993, Isolation, identification, and biological activities of oxidative metabolites of FK-506, a potent immunosuppressive macrolide lactone, *Drug Metabolism & Disposition* 21: 971–977; Shiraga et al., 1994, Metabolism of FK-506, a potent immunosuppressive agent, by cytochrome P4503A enzymes in rat, dog, and human liver microsomes, *Biochem. Pharmacol* 47: 727–735; and Iwasaki et al., 1995, Further metabolism of FK-506 (Tacrolimus); Identification and biological activities of the metabolites oxidized at multiple sites of FK-506, *Drug Metabolism & Disposition* 23: 28–34. The cytochrome P4503A subfamily of isozymes has been implicated as important in this degradative process.

Figure 6:
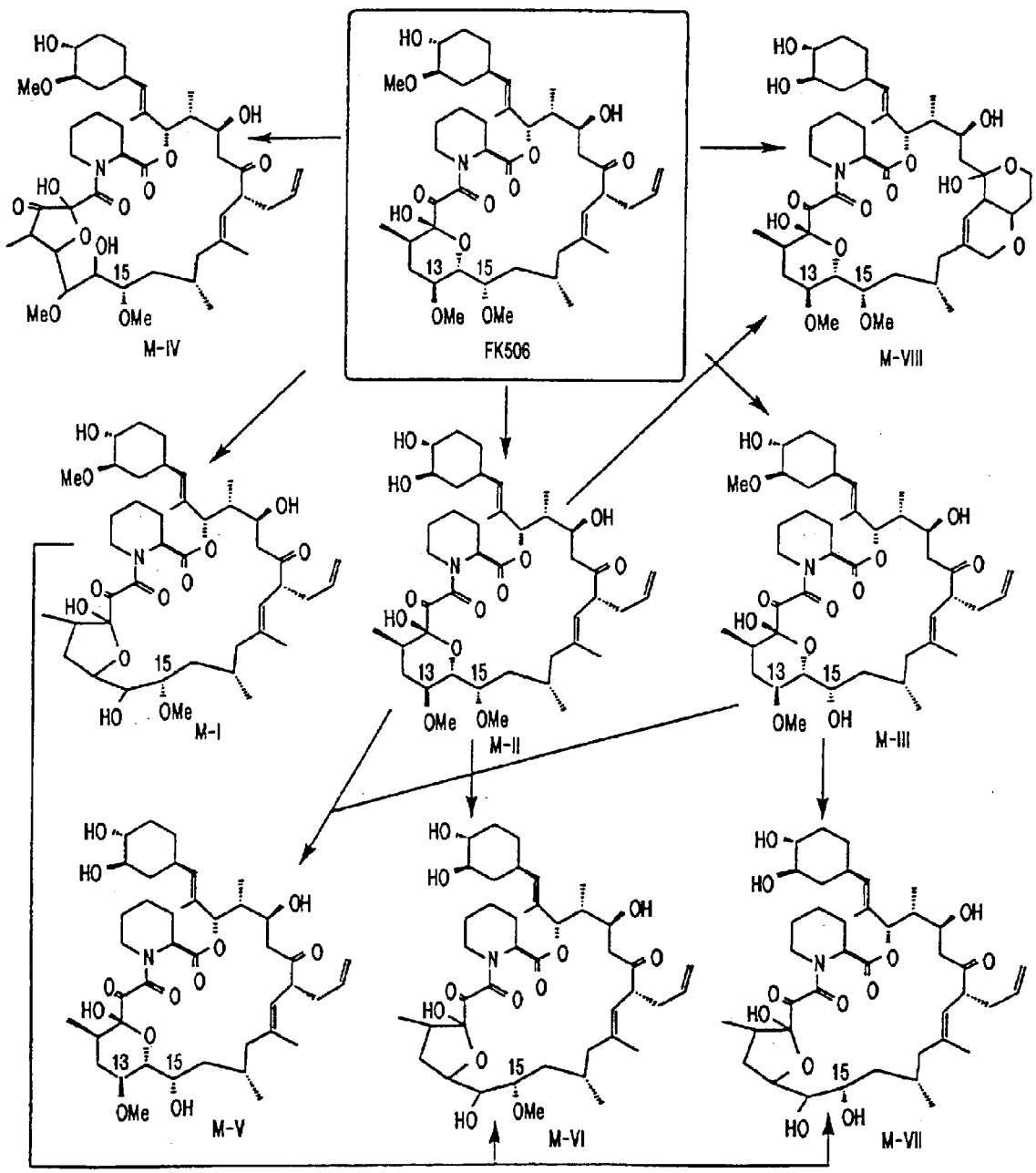
FIG. 6 shows the proposed degradative pathway for tacrolimus (FK-506) metabolism.
Figure 7A:
FIG. 7 shows a schematic process for the construction of recombinant PKS genes of the invention that encode PKS enzymes that produce 13-desmethoxy FK-506 and FK-520 polyketides of the invention, as described in Example 4, below.
Figure 7B:
Figure 7C:
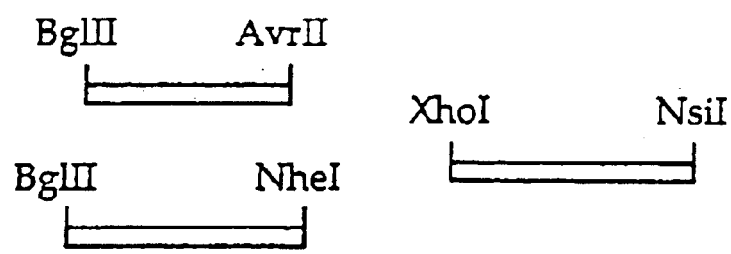
Figure 7D:
Figure 7E:
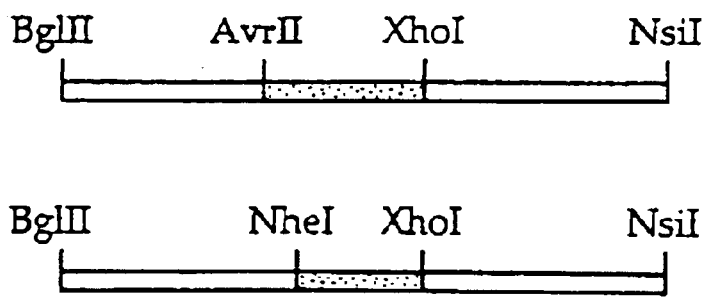

Structures of the eight isolated metabolites formed by liver microsomes are shown in FIG. 6. Four metabolites of FK-506 involve demethylation of the oxygens on carbons 13, 15, and 31, and hydroxylation of carbon 12. The 13-demethylated (hydroxy) compounds undergo cyclizations of the 13-hydroxy at C-10 to give MI, MVI and MVII, and the 12-hydroxy metabolite at C-10 to give I. Another four metabolites formed by oxidation of the four metabolites mentioned above were isolated by liver microsomes from dexamethasone treated rats. Three of these are metabolites doubly demethylated at the methoxy groups on carbons 15 and 31 (M-V), 13 and 31 (M-VI), and 13 and 15 (M-VII). The fourth, M-VIII, was the metabolite produced after demethylation of the 31-methoxy group, followed by formation of a fused ring system by further oxidation. Among the eight metabolites, M-II has immunosuppressive activity comparable to that of FK-506, whereas the other metabolites exhibit weak or negligible activities. Importantly, the major metabolite of human, dog, and rat liver microsomes is the 13-demethylated and cyclized FK-506 (M-I).

Thus, the major metabolism of FK-506 proceeds via 13-demethylation followed by cyclization to the inactive M-I, this representing about 90% of the metabolic products after a 10 minute incubation with liver microsomes. Analogs of tacrolimus that do not possess a C-13 methoxy group would not be susceptible to the first and most important biotransformation in the destructive metabolism of tacrolimus (i.e. cyclization of 13-hydroxy to C-10). Thus, a 13-desmethoxy analog of FK-506 should have a longer half-life in the body than does FK-506. The C-13 methoxy group is believed not to be required for binding to FKBP or calcineurin. The C-13 methoxy is not present on the identical position of rapamycin, which binds to FKBP with equipotent affinity as tacrolimus. Also, analysis of the 3-dimensional structure of the FKBP-tacrolimus-calcineurin complex shows that the C-13 methoxy has no interaction with FKBP and only aminor interaction with calcineurin. The present invention provides C-13-desmethoxy analogs of FK-506 and FK-520, as well as the recombinant genes that encode the PKS enzymes that catalyze their synthesis and host cells that produce the compounds.

These compounds exhibit, relative to their naturally occurring counterparts, prolonged immunosuppressive action in vivo, thereby allowing a lower dosage and/or reduced frequency of administration. Dosing is more predictable, because the variability in FK-506 dosage is largely due to variation of metabolism rate. FK-506 levels in blood can vary widely depending on interactions with drugs that induce or inhibit cytochrome P4503A (summarized in USP Drug Information for the Health Care Professional). Of particular importance are the numerous drugs that inhibit or compete for CYP 3A, because they increase FK-506 blood levels and lead to toxicity (Prograf package insert, Fujisawa□US, Rev April 1997, Rec June. 1997). Also important are the drugs that induce P4503A (e.g. Dexamethasone), because they decrease FK-506 blood levels and reduce efficacy. Because the major site of CYP 3A action on FK-506 is removed in the analogs provided by the present invention, those analogs are not as susceptible to drug interactions as the naturally occurring compounds.

Hyperglycemia, nephrotoxicity, and neurotoxicity are the most significant adverse effects resulting from the use of FK-506 and are believed to be similar for FK-520. Because these effects appear to occur primarily by the same mechanism as the immunosuppressive action (i.e. FKBP-calcineurin interaction), the intrinsic toxicity of the desmethoxy analogs may be similar to FK-506. However, toxicity of FK-506 is dose related and correlates with high blood levels of the drug (Prograf package insert, Fujisawa□US, Rev April 1997, Rec June 1997). Because the levels of the compounds provided by the present invention should be more controllable, the incidence of toxicity should be significantly decreased with the 13-desmethoxy analogs. Some reports show that certain FK-506 metabolites are more toxic than FK-506 itself, and this provides an additional reason to expect that a CYP 3A resistant analog can have lower toxicity and a higher therapeutic index.

Thus, the present invention provides novel compounds related in structure to FK-506 and FK-520 but with improved properties. The invention also provides methods for making these compounds by fermentation of recombinant host cells, as well as the recombinant host cells, the recombinant vectors in those host cells, and the recombinant proteins encoded by those vectors. The present invention also provides other valuable materials useful in the construction of these recombinant vectors that have many other important applications as well. In particular, the present invention provides the FK-520 PKS genes, as well as certain genes involved in the biosynthesis of FK-520 in recombinant form.

FK-520 is produced at relatively low levels in the naturally occurring cells, *Streptomyces hygroscopicus* var.

*ascomyceticus*, in which it was first identified. Thus, another benefit provided by the recombinant FK-520 PKS and related genes of the present invention is the ability to produce FK-520 in greater quantities in the recombinant host cells provided by the invention. The invention also provides methods for making novel FK-520 analogs, in addition to the desmethoxy analogs described above, and derivatives in recombinant host cells of any origin.

The biosynthesis of FK-520 involves the action of several enzymes. The FK-520 PKS enzyme, which is composed of the fkbA, fkbB, fkbC, and fkbP gene products, synthesizes the core structure of the molecule. There is also a hydroxylation at C-9 mediated by the P450 hydroxylase that is the fkbD gene product and that is oxidized by the fkbO gene product to result in the formation of a keto group at C-9. There is also a methylation at C-31 that is mediated by an O-methyltransferase that is the fkbM gene product. There are also methylations at the C-13 and C-15 positions by a methyltransferase believed to be encoded by the fkbG gene; this methyltransferase may act on the hydroxymalonyl CoA substrates prior to binding of the substrate to the AT domains of the PKS during polyketide synthesis. The present invention provides the genes encoding these enzymes in recombinant form. The invention also provides the genes encoding the enzymes involved in ethylmalonyl CoA and 2-hydroxymalonyl CoA biosynthesis in recombinant form. Moreover, the invention provides *Streptomyces hygroscopicus* var. *ascomyceticus* recombinant host cells lacking one or more of these genes that are useful in the production of useful compounds.

The cells are useful in production in a variety of ways. First, certain cells make a useful FK-520-related compound merely as a result of inactivation of one or more of the FK-520 biosynthesis genes. Thus, by inactivating the C-310-methyltransferase gene in *Streptomyces hygroscopicus* var. *ascomyceticus*, one creates a host cell that makes a desmethyl (at C-31) derivative of FK-520. Second, other cells of the invention are unable to make FK-520 or FK-520 related compounds due to an inactivation of one or more of the PKS genes. These cells are useful in the production of other polyketides produced by PKS enzymes that are encoded on recombinant expression vectors and introduced into the host cell.

Moreover, if only one PKS gene is inactivated, the ability to produce FK-520 or an FK-520 derivative compound is restored by introduction of a recombinant expression vector that contains the functional gene in a modified or unmodified form. The introduced gene produces a gene product that, together with the other endogenous and functional gene products, produces the desired compound. This methodology enables one to produce FK-520 derivative compounds without requiring that all of the genes for the PKS enzyme be present on one or more expression vectors. Additional applications and benefits of such cells and methodology will be readily apparent to those of skill in the art after consideration of how the recombinant genes were isolated and employed in the construction of the compounds of the invention.

The FK-520 biosynthetic genes were isolated by the following procedure. Genomic DNA was isolated from *Streptomyces hygroscopicus* var. *ascomyceticus* (ATCC 14891) using the lysozyme/proteinase K protocol described in Genetic Manipulation of *Streptomyces*—A Laboratory Manual (Hopwood et al., 1986). The average size of the DNA was estimated to be between 80–120 kb by electrophoresis on 0.3% agarose gels. A library was constructed in the SuperCos™ vector according to the manufacturer's instructions and with the reagents provided in the commercially available kit (Stratagene). Briefly, 100 μg of genomic DNA was partially digested with 4 units of Sau3A I for 20 min. in a reaction volume of 1 mL, and the fragments were dephosphorylated and ligated to SuperCos vector arms. The ligated DNA was packaged and used to infect log-stage XL1-BlueMR cells. A library of about 10,000 independent cosmid clones was obtained.

Based on recently published sequence from the FK-506 cluster (Motamedi and Shafiee, 1998, *Eur. J. Biochem.* 256: 528), a probe for the fkbO gene was isolated from ATCC 14891 using PCR with degenerate primers. With this probe, a cosmid designated pKOS034-124 was isolated from the library. With probes made from the ends of cosmid pKOS034-124, an additional cosmid designated pKOS034-120 was isolated. These cosmids (pKOS034-124 and pKOS034-120) were shown to contain DNA inserts that overlap with one another. Initial sequence data from these two cosmids generated sequences similar to sequences from the FK-506 and rapamycin clusters, indicating that the inserts were from the FK-520 PKS gene cluster. Two EcoRI fragments were subcloned from cosmids pKOS034-124 and pKOS034-120. These subclones were used to prepare shotgun libraries by partial digestion with Sau3AI, gel purification of fragments between 1.5 kb and 3 kb in size, and ligation into the pLitmus28 vector (New England Biolabs). These libraries were sequenced using dye terminators on a Beckmann CEQ2000 capillary electrophoresis sequencer, according to the manufacturer's protocols.

To obtain cosmids containing sequence on the left and right sides of the sequenced region described above, a new cosmid library of ATCC 14891 DNA was prepared essentially as described above. This new library was screened with a new fkbM probe isolated using DNA from ATCC 14891. A probe representing the fkbP gene at the end of cosmid pKOS034-124 was also used. Several additional cosmids to the right of the previously sequenced region were identified. Cosmids pKOS065-C31 and pKOS065-C3 were identified and then mapped with restriction enzymes. Initial sequences from these cosmids were consistent with the expected organization of the cluster in this region. More extensive sequencing showed that both cosmids contained in addition to the desired sequences, other sequences not contiguous to the desired sequences on the host cell chromosomal DNA. Probing of additional cosmid libraries identified two additional cosmids, pKOS065-M27 and pKOS065-M21, that contained the desired sequences in a contiguous segment of chromosomal DNA. Cosmids pKOS034-124, pKOS034-120, pKOS065-M27, and pKOS065-M21 have been deposited with the American Type Culture Collection, Manassas, Va., USA. The complete nucleotide sequence of the coding sequences of the genes that encode the proteins of the FK-520 PKS are shown below but can also be determined from the cosmids of the invention deposited with the ATCC using standard methodology.

Figure 3:
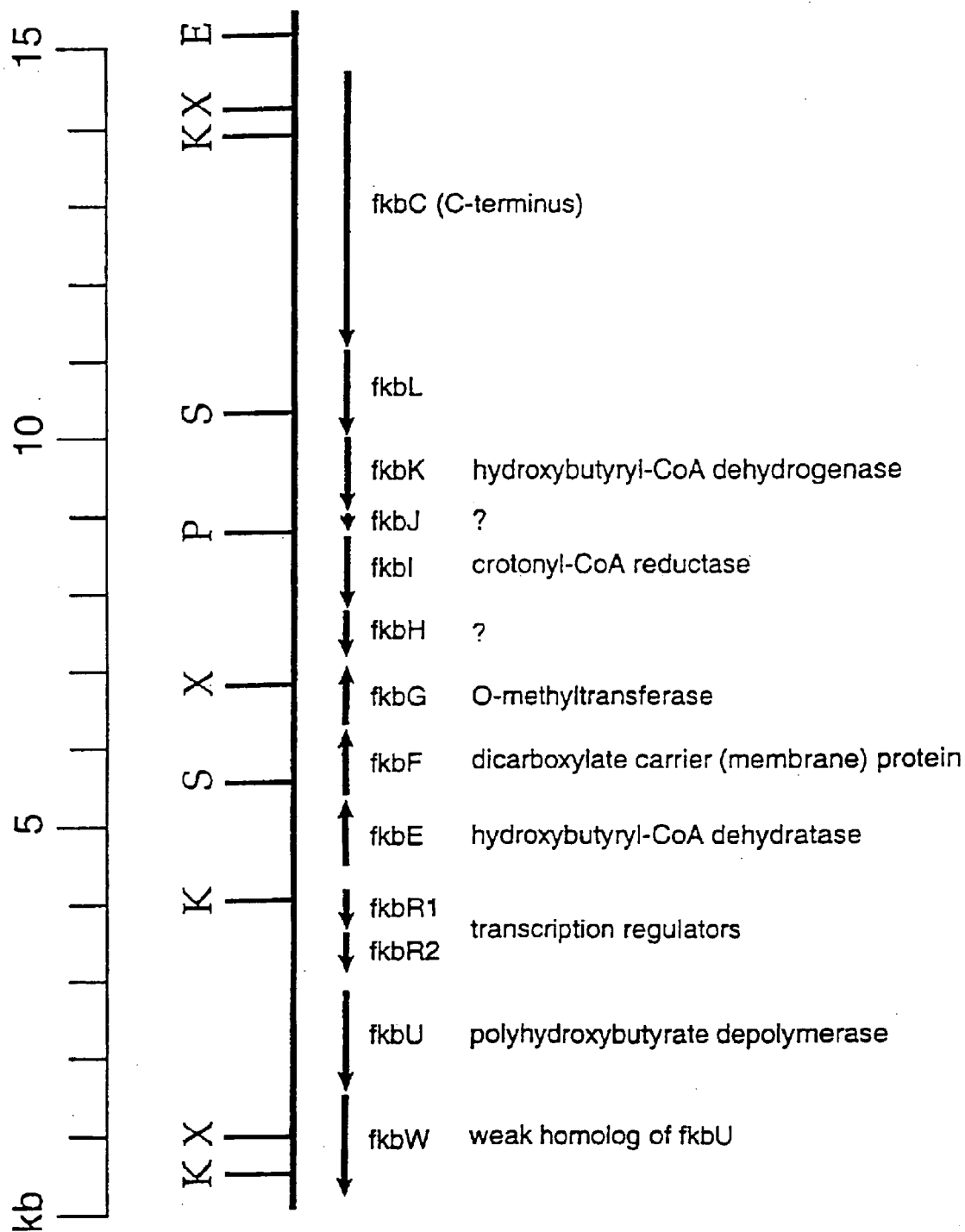
FIG. 3 shows a close-up view of the left end of the FK-520 gene cluster, which contains at least ten additional genes. The ethyl side chain on carbon 21 of FK-520 (FIG. 2) is derived from an ethylmalonyl CoA extender unit that is incorporated by an ethylmalonyl specific AT domain in extender module 4 of the PKS. At least four of the genes in this region code for enzymes involved in ethylmalonyl biosynthesis. The polyhydroxybutyrate depolymerase is involved in maintaining hydroxybutyryl-CoA pools during FK-520 production. Polyhydroxybutyrate accumulates during vegetative growth and disappears during stationary phase in other Streptomyces (Ranade and Vining, 1993, *Can. J Microbiol.* 39:377). Open reading frames with unknown function are indicated with a question mark.

Referring to FIGS. 1 and 3, the FK-520 PKS gene cluster is composed of four open reading frames designated fkbB, fkbC, fkbA, and fkbP. The fkbB open reading frame encodes the loading module and the first four extender modules of the PKS. The fkbC open reading frame encodes extender modules five and six of the PKS. The fkbA open reading frame encodes extender modules seven, eight, nine, and ten of the PKS. The fkbP open reading frame encodes the NRPS of the PKS. Each of these genes can be isolated from the cosmids of the invention described above. The DNA sequences of these genes are provided below (SEQ ID NO:1) preceded by the following table identifying the start and stop codons of the open reading frames of each gene and the modules and domains contained therein.

| Nucleotides | Gene or Domain |
| --- | --- |
| complement (412–1836) | fkbW |
| complement (2020–3579) | fkbV |
| complement (3969–4496) | fkbR2 |
| complement (4595–5488) | fkbR1 |
| 5601–6818 | fkbE |
| 6808–8052 | fkbF |
| 8156–8824 | fkbG |
| complement (9122–9883) | fkbH |
| complement (9894–10994) | fkbI |
| complement (10987–11247) | fkbJ |
| complement (11244–12092) | fkbK |
| complement (12113–13150) | fkbL |
| complement (13212–23988) | fkbC |
| complement (23992–46573) | fkbB |
| 46754–47788 | fkbO |
| 47785–52272 | fkbP |
| 52275–71465 | fkbA (SEQ ID NO:72) |
| 71462–72628 | fkbD |
| 72625–73407 | fkbM |
| complement (73460–76202) | fkbN |
| complement (76336–77080) | fkbQ |
| complement (77076–77535) | fkbS |
| complement (44974–46573) | CoA ligase of loading domain |
| complement (43777–44629) | ER of loading domain |
| complement (43144–43660) | ACP of loading domain |
| complement (41842–43093) | KS of extender module 1 (KS1) |
| complement (40609–41842) | AT1 |
| complement (39442–40609) | DH1 |
| complement (38677–39307) | KR1 |
| complement (38371–38581) | ACP1 |
| complement (37145–38296) | KS2 |
| complement (35749–37144) | AT2 |
| complement (34606–35749) | DH2 (inactive) |
| complement (33823–34480) | KR2 |
| complement (33505–33715) | ACP2 |
| complement (32185–33439) | KS3 |
| complement (31018–32185) | AT3 |
| complement (29869–31018) | DH3 (inactive) |
| complement (29092–29740) | KR3 |

-continued

| Nucleotides | Gene or Domain |
| --- | --- |
| complement (28750–28960) | ACP3 |
| complement (27430–28684) | KS4 |
| complement (26146–27430) | AT4 |
| complement (24997–26146) | DH4 (inactive) |
| complement (24163–24373) | ACP4 |
| complement (22653–23892) | KS5 |
| complement (21420–22653) | AT5 |
| complement (20241–21420) | DH5 |
| complement (19464–20097) | KR5 |
| complement (19116–19326) | ACP5 |
| complement (17820–19053) | KS6 |
| complement (16587–17820) | AT6 |
| complement (15438–16587) | DH6 |
| complement (14517–15294) | ER6 |
| complement (13761–14394) | KR6 |
| complement (13452–13662) | ACP6 |
| 52362–53576 | KS7 |
| 53577–54716 | AT7 |
| 54717–55871 | DH7 |
| 56019–56819 | ER7 |
| 56943–57575 | KR7 |
| 57711–57920 | ACP7 |
| 57990–59243 | KS8 |
| 59244–60398 | AT8 |
| 60399–61412 | DH8 (inactive) |
| 61548–62180 | KR8 |
| 62328–62537 | ACP8 |
| 62598–63854 | KS9 |
| 63855–65084 | AT9 |
| 65085–66254 | DH9 |
| 66399–67175 | ER9 |
| 67299–67931 | KR9 |
| 68094–68303 | ACP9 |
| 68397–69653 | KS10 |
| 69654–70985 | AT10 |
| 71064–71273 | ACP10 |

```
  1  GATCTCAGGC ATGAAGTCCT CCAGGCGAGG CGCCGAGGTG GTGAACACCT CGCCGCTGCT

61  TGTACGGACC ACTTCAGTCA GCGGCGATTG CGGAACCAAG TCATCCGGAA TAAAGGGCGG

121  TTACAAGATC CTCACATTGC CCGACCGCCA GCATACGCTG AGTTGCCTCA GAGGCAAACC

181  GAAAGGCGC GGGCGGTCCG CACCAGGGCG GAGTACGCGA CGAGAGTGGC GCACCCGCGC

241  ACCGTCACCT CTCTCCCCCG CCGGCGGGAT GCCCGGCGTG ACACGGTTGG GCTCTCCTCG

301  ACGCTGAACA CCCGCGCGGT GTGGCGTCGG GCACACCGCC TGGCATCGGC CGGGTGACGG

361  TACGGGGAGG GCGTACGGCG GCCGTGGCTC GTGCTCACGG CCGCCGGGCG GTCATCCGTC

421  GAGACGGCAC TCGGCGAGCA GGGACGCCTG GTCGGCACCT GCGGGCCGGA CGACCGTGTG

481  GTTCGCGGGC GGGCGGTGGC CGGTGGTGAG CCAGCTCTCC AGGGCGGTGA AGGCTGAGCG

541  GTCACACGGC AGCAAAGGCC GGAGTCGGTC GGGGAAGGTG TCGACGAGGG CGTCGGTGTG

601  CGTGCCGTCC TCGATGCGGT AGTAGCGGTA CCGGCCGCCA GGCCGCTGCC GGACATACGC

661  GCGTACACGT CGGAGCCCGG GCGGCAGGCA GCAGCACGTC GAGAGTGCCT GGATGGTGAT

721  CAGCGGCTTG CCGATACGAC CGGTCAACGC GATGCGTTCC ACGGCCGCGT GGACGCCGGA

781  GGAGCGGGTG GCGTAGTCGT AGTCGGCATC GCAGCCCGGG ACCGTCCCCG GGGCGCAATA

841  CGGTGTGCCG GCTTCCTTCT CCCCATCGAA GCCGGGGTCG AACTCCTCGC GGTAGACGCG
```

```
 901 CTGCGTCAGA TCCCACTAGA CCTCGTGGTG GTACGGCCAC AAGAACTCCC AGTCGCCCGG
 961 GAACCCGGCC CGGAGCAGCG CCTCGCGCGC CTGGCCGGCT GCGGGGCCGC CTGCCGCGTA
1021 GGTCGGGTAC TCGCGCAGGG CGGCCGGCAG GAAGGTGAAG AGGTTGGGAC CCTCCGCGCG
1081 CCACAGGGTG CCTTCCCAGT CGACTCCTCC GTCGTACAGC TCCGGATGGT TCTCCAGCTG
1141 CCAGCGCACG AGGTAGCCGC CGTTGGACAT CCCGGTGACC AGGGTGCGCT CGAGCGGCCG
1201 GTGGTAGCGC TGGGCGACCG ACGCGCGGGC GGCCCGCGTC AGCTGGCTGA GGCGGGTGTT
1261 CCACTCGGCG ACGGCGTCGC CCGGCCGGGA GCCATCACGG TAGAACGCGG GGCCGGTGTT
1321 GCCCTTGTCG GTGGCGGCGT AGGCGTAACC GCGGGCGAGC ACCCAGTCGG CGATGGCCCG
1381 GTCGTTGGCG TACTGCTCGC GGTTACCGGG GGTGCCGGCC ACGACCAGGC CACCGTTCCA
1441 GCGGTCGGGC AGCCGGATGA CGAACTGGGC GTCGTGGTTC CACCCGTGGT TGGTGTTGGT
1501 GGTGGACGTG TCGGGAAGT AGCCGTCGAT CTGGATCCCG GCACTCCGG TGGGAGTGGG
1561 CAGGTTCTTG GGCGTCAGCC CTGCCCAGTC CGCCGGGTCG GTGTGGCCGG TGGCCGCCGT
1621 TCCCGCCGTG GTCAGCTCGT CCAGGCAGTC GGCCTGCTGA CGTGCCGCCG CCGGGACACG
1681 CAGCTGGGAC AGACGGGCGC AGTGACCGTC CGGGGCATCG GGAGCAGGCC GGGCCGTGGC
1741 CGGTGAGGGG AGCAGGACGG CGACTGCGGC CAGGGTGAGA GCGCCGAGGC CGGTGCGTCT
1801 TCTCGGCGCC CGTCCGACAC CGAGGGGCAG AACCATGGAG AGCCTCCAGA CGTGCGGATG
1861 GATGACGGAC TGGAGGCTAG GTCGCGCACG GTGGAGACGA ACATGGGTGC GCCCGCCATG
1921 ACTGAGGCCC CTCAGAGGTG GGCCGCCGCC ATGACGGGCG CGGGACCGCG GGCGCTCCGG
1981 GGCGGTGCCC GCGGCCGCCA CCGGTTCCGG GTCCCCGGGT CAGGGACAGG TGTCGTTCGC
2041 GACGGTGAAG TAGCCGGTCG GCGACTCTTT CAAGGTGGTC GTGACGAAGG TGTTGTACAG
2101 GCCCATGTTC TGGCCGGAGC CCTTGGCGTA GGTGTAACCG GCGCTCGTCG TGGCGCGGCC
2161 CGCCTGGACG TGAGCGTAGT TGCCGGCGGT CCAGCAGACG GCCGTGGCAC CGGTCGTCTG
2221 CGCGGTGACC GCGCCCGAGA GCGGTCCGGC CTTGCCGTCC GCGTCCCGGG CGGCGACCGC
2281 GTAGGTGTGC GATGTGCCCG CCCTCAGGCC GGTGTCCGTG TACGACGTCG TGGCGGACGT
2341 GGTGATCTGG GCACCGTCGC GGTGGACGGC GTAGTCGGTG GCGCCGTCGA CGGGTTTCCA
2401 GGTCAGGCTG ATGGTGGTGT CGGTGGCGCC GGTGGCGGCC AGGCCGGACG GAGCGGGCAG
2461 CGAACCGGGG TCGGAGGCGG ATCCGCTCAG GCCGAAGAAC TGCGTGATCC AGTAGCTGGA
2521 ACAGATCGAG TCCAGGAAGT AGGCGGCGCC GGTGCTGCCG CACTGCTGTG CTCCGGTGCC
2581 GGGATCGACC GGGGTGCCGT GCCCGATGCC CGGCACCCGG TTCACCTCCA CGGCCACCGA
2641 TCCGTCCGCG GCCAGGTACT CCTCGTGCCG GGTGGAGTTC GGGCCGATCA CCGAGGTACG
2701 GTCCGGCGTC TGGGACACGC CGTGCACAGC GGTCCACTGG TCGCGCAACT CGTCGGCGTT
2761 GCGCGGCGCG ACGGTGGTGT CCTTGTCGCC GTGCCAGATG GCCACGCGCG GCCACGGGCC
2821 CGACCACGAG GGGTAGCCCT CACGGACCCG CCGCGCCCAC TGGTCCGCGG TCAGGTCGGT
2881 CCCGGGGTTC ATGCACAGGT ACGCGCTGCT GACGTCGGTG GCACAGCCGA AGGGCAGGCC
2941 GGCGACGACC GCGCCGGCCT GGAAGACGTC CGGATAGGTG GCGAGCATCA CCGACGTCAT
3001 GGCACCGCCG GCGGACAGCC CGGTGATGTA GGTGCGCTGG GGGTCCGCGC CGTAGGCGGA
3061 GACGGTGTGA GCGGCCATCT GCCGCATCGA CGCGGCTTCG CCCTGGCCCC TGCGGTTGTC
3121 GCTGCTCTGG AACCAGTTGA AGCACCTGTT CGCGTTGTTC GACGACGTGG TCTCGGCGAA
3181 CACGAGCAGG AAGCCATAGC GGTCCCCGAA TGAGAGCAGG CCGGAGTTGT CGCCGTAGCC
3241 CTGGGCGTCC TGGGTGCAAC CGTGCAGGGC GAACACCACC GCCGGCTCCG CGGGCAGGGA
```

-continued

```
3301  CGCGGGCCGG TAGACGTACA TGTTCAGCCG GCCCGGGTTC GTGCCGAAGT CCGCGACCTC
3361  GGTCAGGTCC GCCTTGGTCA GACCGGGCTT GGCCAGGCCC GCCGCGGCGT GGGCCGTCGG
3421  CGCCGGGCCG AGCAGGGCCG CTCCGAGTAC GAGGGCCACG ACGGCCACGA GACGGGTGAG
3481  CACCCCCCGC CGTCCCGGAC GCGACAACGA CCCGACCGGC GGCGAGGAGG AGAGGGGGAA
3541  CAGCGGGGTG AGGATTCCCC GGAACGGCGG CGGCTGCATG GCGGCTCCCT CGATGTCGTG
3601  GGGGCGACAC GGAGGGCTCC CTGACGTCGA TCAGTGGGAG CGCCCCGGTG CCCGGCACCG
3661  TAGGGGTGGT TCAACCCGCA ACGGTATGGC CCGGAGCACC ACACCCCGCA CCGCGCGATG
3721  TGCGCCCGGA CGGATTGTGT CGCCTTGCGG AATCTGATAC CCGGACGCGA CGAACGCCCC
3781  ACCCGACACC GCTAGGGCGT CATGGTGTCC GACTCGGCCG GTCGGCCTTG CCTGCCCTGG
3841  ACGGACCGGG CGTCGGCGGA CCGGGCGTCG GCGGGCTGGG CGGTATGGCG GCCGAGGACG
3901  CCAGCCGCGT GGGGCGGCCG CGCCCAAGTG CAGTACGCCG ACCGTGGCCG GCGGGAGGGC
3961  CGGACCGGTC AGTGCAGTCC CGCGGCCCTG CGGGACCGCT CGTCCCAGAC GGGTTCCACC
4021  GCGGCGAACC GGGGTCCGTG TCCGCGGCGG TAGACCATCA GTGTCCGCTC GAAGGTGATG
4081  ACGATGACAC CGTCCTGGTT GTAGCCGATG GTGCGCACGC TGATGATGCC TACGTCAGGT
4141  CGGCTGGCGG ACTCCCGGGT GTTCAGGACC TCGGACTGCG AGTAGATGGT GTCGCCCTCG
4201  AAGACCGGGT TCGGCAGCCT GACCCGGTCC CAGCCGAGGT TGGCCATCAC ATGCTGGGAG
4261  ATGTCGGTGA CGCTCTGCCC GGTGACCAGG GCGAGGGTGA AGGTGGAGTC CACCAGCGGC
4321  TTGCCCCAGG TCGTGCCCGC CGAGTAGTGG CGGTCGAAGT GCAGCGGCGC GGTGTTCTGC
4381  GTCAGGAGCG TGAGCCAGGA GTTGTCGGTC TCCAGGACCG TGCGGCCCAG GGGGTGGCGG
4441  TACACGTCGC CGGTGGTGAA GTCCTCGAAG TAGCGGCCCT GCCAGCCCTC GACCACAGCG
4501  GTGCGGGTGG CGTCCTGGTC CGGGTTCTCA GTCGTCATGG CGCTCATTCT GGGAAGTCCC
4561  CGGTCCGCTG TGAAATGCCG AACCTTCACC GGGCTCATAC GTGCGGCGCA TGAGCCCTGG
4621  ACCGTACGTA GTCGTAGAAC CTCGCCACCA CTGGCGCGCG TGGTCCTCCG GCGAGTGTGA
4681  CCACGCCGAC CGTGCGCCGC GCCTGCGGGT CGTCGAGCGG CACGGCGACG GCGTGGTCAC
4741  CCGGCCCGGA CGGGCTGCCG GTGAGGGGGG CGACGGCCAC ACCGAGGCCG GCGGCGACCA
4801  GGGCCCGCAG CGTGCTCAGC TCGGTGCTCT CCAGGACGAC CCGCGGCACG AATCCGGCCG
4861  CGGCGCACAG CCGGTCGGTG ATCTGGCGCA GTCCGAAGAC CGGCTCCAGT GCCACGAACG
4921  CCTCATCGGC CAGCTCCCCG GTCCGCACCC CGCGGCGTCT GGCCAGCCGG TCTCCGGGTG
4981  GGACGAGCAG GCACAGTGCC TCGTCCCGCA GTGGTGTCCA CTCCACATCG TCCCCGGCGG
5041  GTCGTGGGCT GGTCAGCCCC AGGTCCAGCC TGCTGTTGCG GACGTCGTCG ACCACGGCGT
5101  CGGCGGCGTC GCCGCGCAGT TCGAAGGTGG TGCCGGGAGC CAGCCGGCGG TACCCGGCGA
5161  GGAGCTCGGG CACCAGCCAG GTGCCGTAGG AGTGCAGGAA ACCCACTGCC ACGGTGCCGG
5221  TGTCGGGGTC GATCAGGGCG GTGATGCGCT GCTCGGCGCC GGAGACCTCA CTGATCGCGC
5281  GCAGGGCGTG GGCGCGGAAG ACCTCGCCGT ACTTGTTGAG CCGGAGCCGG TTCTGGTGCC
5341  GGTCGAACAG CGGCACGCCC ACTCGTCGCT CCAGCCGCCG GATGGCCCTG ACAGGGTCG
5401  GCTGGGAGAT GTTGAGCGGT TCCGCGGTGA TCGTCACGTG CTCGTGCTCG GCCAAGGCCG
5461  TGAACCACTG CAACTCCCGT ATCTCCATGC AGGGACTATA CGTACCGGGC ATGGTCCTGG
5521  CGAGGTTTCG TCATTTCACA GCGGCCGGGC GGCGGCCCAC AGTGAGTCCT CACCAACCAG
5581  GACCCCATGG GAGGGACCCC ATGTCCGAGC CGCATCCTCG CCCTGAACAG GAACGCCCCG
5641  CCGGGCCCCT GTCCGGTCTG CTCGTGGTTT CTTTGGAGCA GGCCGTCGCC GCTCCGTTCG
```

-continued

```
5701  CCACCCGCCA CCTGGCGGAC CTGGGCGCCC GTGTCATCAA GATCGAACGC CCCGGCAGCG
5761  GCGACCTCGC CCGCGGCTAC GACCGCACGG TGCGTGGCAT GTCCAGCCAC TTCGTCTGGC
5821  TGAACCGGGG GAAGGAGAGC GTCCACCTCG ATGTGCGCTC GCCGGACCGC AACCGGCACC
5881  TGCACGCCTT GGTGGACCGG GCCGATGTCC TGGTGCAGAA TCTGGCACCC GGCGCCGCGG
5941  GCCGCCTGGC ATCGGCCACC AGGTCCTCGC GCGGAGCCAC CGAGGCTGAT CACCTGCGGA
6001  CATATCCGGC TACGGCAGTA CCGGCTGCTA CCGCGGACCG CAAGGCGTAC GACCTCCTGG
6061  TCCAGTGCGA AGCGGGGCTG GTCTCCATCA CCGGCACCCC CGAGACCCCG TCCAAGGTGG
6121  GCCTGTCCAT CGCGGACATC TGTGCGGGGA TGTACGCGTA CTCCGGCATC CTCACGGCCC
6181  TGCTGAAGCG GGCCCGCACC GGCCGGGGCT CGCAGTTGGA GGTCTCGATG CTCGAAGCCC
6241  TCGGTGAATG GATGGGATAC GCCGAGTACT ACACGCGCTA CGGCGGCACC GCTCCGGCCC
6301  GCGCCGGCCC CAGCCACGCG ACGATCGCCC CCTACGGCCC GTTCACCACG CGCGACGGGC
6361  AGACGATCAA TCTCGGGCTC CAGAACGAGC GGGAGTGGGC TTCCTTCTGC GGTGTCGTGC
6421  TACAACGCCC CGGTCTCTGC GACGACCCGC GCTTTTCCGG CAACGCCGAC CGGGTGGCGC
6481  ACCGCACCGA GCTCGACGCC CTGGTGAGCG AGGTGACGGG CACGCTCACC GGCGAGGAAC
6541  TGGTGGCGCG GCTGGAGGAG GCGTCGATCG CCTACGCACG CCAGCGCACC GTGCGCGAGT
6601  TCAGCGAACA CCCCCAACTG CGTGACCGTG GACGCTGGGC TCCGTTCGAC AGCCCGGTCG
6661  GTGCGCTGGA GGGCCTGATC CCCCCGGTCA CCTTCCACGG CGAGCACCCG CGGCGGCTGG
6721  GCCGGGTCCC GGAGCTGGGC GAGCATACCG AGTCCGTCCT GGCGTGGCTG GCCGCGCCCC
6781  ACAGCGCCGA CCGCGAAGAG GCCGGCCATG CCGAATGAAC TCACCGGAGT CCTGATCCTG
6841  GCCGCCGTGT TCCTGCTCGC CGGCGTACGG GGGCTGAACA TGGGCCTGCT CGCGCTGGTC
6901  GCCACCTTTC TGCTCGGGGT GGTCGCACTC GACCGAACGC CGGACGAGGT GCTGGCGGGT
6961  TTCCCCGCGA GCATGTTCCT GGTGCTGGTC GCCGTCACGT TCCTCTTCGG GATCGCCCGC
7021  GTCAACGGCA CGGTGGACTG GCTGGTACGT GTCGCGGTGC GGGCGGTGGG GGCCCGGGTG
7081  GGAGCCGTCC CCTGGGTGCT CTTCGGCCTG GCGGCACTGC TCTGCGCGAC AGGCGCGGCC
7141  TCGCCCGCGG CGGTGGCGAT CGTGGCGCCG ATCAGCGTCG CGTTCGCCGT CAGGCACCGC
7201  ATCGATCCGC TGTACGCCGG ACTGATGGCG GTGAACGGGG CCGCAGCCGG CAGTTTCGCC
7261  CCCTCCGGGA TCCTGGGCGG CATCGTCCAC TCGGCGCTGG AGAAGAACCA TCTGCCCGTC
7321  AGCGGCGGGC TGCTCTTCGC ACGCACCTTC GCCTTCAACC TGGCGGTCGC CGCGGTGTCA
7381  TGGCTCGTCC TCGGGCGCAG GCGCCTCGAA CCACATCACC TGGACGAGGA CACCGATCCC
7441  ACGCAAGGGG ACCCGGCTTC CCGCCCCGGC GCGGAACACG TGATGACGCT GACCGCGATG
7501  GCCGCGCTGG TGCTGGGAAC CACGGTCCTC TCCCTGGACA CCGGCTTCCT GGCCCTCACC
7561  TTGGCGGCGT TGCTGGCGCT GCTCTTCCCG CGCACCTCCC AGCAGGCCAC CAAGGAGATC
7621  GCCTGGCCCG TGGTGCTGCT GGTATGCGGG ATCGTGACCT ACGTCGCCCT GCTCCAGGAG
7681  CTGGGCATCG TGGACTCCCT GGGGAAGATG ATCGCGCCGA TCGGCACCCC GCTGCTGGCC
7741  GCCCTGGTGA TCTGCTACGT GGGCGGTGTC GTCTCGGCCT TCGCCTCGAC CACCGGGATC
7801  CTCGGTGCCC TGATGCCGCT GTCCGAGCCG TTCCTGAAGT CCGGTGCCAT CGGGACGACC
7861  GGCATGGTGA TGGCCCTGGC GGCCGCGGCG ACCGTGGTGG ACCCGAGTCC CTTCTCCACC
7921  AATGGTGCTC TGGTGGTGGC CAACGCTCCC GAGCGGCTGC GGCCCGGCGT GTACCAGGGG
7981  TTGCTGTGGT GGGGCGCCGG GGTGTGCGCA CTGGCTCCCG CGGCCGCCTG GGCGGCCTTC
8041  GTGGTGGCGT GAGCGCAGCG GAGCGGCAAT CCCCTGGACC CCGTTTCCCG TGCTGTGTCG
```

-continued

```
8101  CTGACGTAGC GTCAAGTCCA CGTGCCGGGC GGGCAGTACG CCTAGCATGT CGGGCATGGC
8161  TAATCAGATA ACCCTGTCCG ACACGCTGCT CGCTTACGTA CGGAAGGTGT CCCTGCGCGA
8221  TGACGAGGTG CTGAGCCGGC TGCGCGCGCA GACGGCCGAG CTGCCGGGCG GTGGCGTACT
8281  GCCGGTGCAG GCCGAGGAGG GACAGTTCCT CGAGTTCCTG GTGCGGTTGA CCGGCGCGCG
8341  TCAGGTGCTG GAGATCGGGA CGTACACCGG CTACAGCACG CTCTGCCTGG CCCGCGGATT
8401  GGCGCCCGGG GGCCGTGTGG TGACGTGCGA TGTCATGCCG AAGTGGCCCG AGGTGGGCGA
8461  GCGGTACTGG GAGGAGGCCG GGGTTGCCGA CCGGATCGAC GTCCGGATCG GCGACGCCCG
8521  GACCGTCCTC ACCGGGCTGC TCGACGAGGC GGGCGCGGGG CCGGAGTCGT TCGACATGGT
8581  GTTCATCGAC GCCGACAAGG CCGGCTACCC CGCCTACTAC GAGGCGGCGC TGCCGCTGGT
8641  ACGCCGCGGC GGGCTGATCG TCGTCGACAA CACGCTGTTC TTCGGCCGGG TGGCCGACGA
8701  AGCGGTGCAG GACCCGGACA CGGTCGCGGT ACGCGAACTC AACGCGGCAC TGCGCGACGA
8761  CGACCGGGTG GACCTGGCGA TGCTGACGAC GCCCGACGGC CTCACCCTCC TCCGGAAACG
8821  GTGACCGGGG CGATGTCGGC GGCGGTCAGC GTCAGCGTCG TCGGCGCGGG CCTCGCGGAG
8881  GGCTCCAGAT GCAGGCGTTC GACGCCGGCG GCGGAAGCGC CCGCCACCTC GGACACGCAG
8941  GGGCAGTCGG AGTCCGCGAA GCCCGCGAAC CGGTAGGCGA TCTCCATCAT GCGGTTGCGG
9001  TCCGTACGCC GGAAGTCCGC CACCAGGTGC GCCCCGCGC GGGCGCCCTG GTCCGTGAGC
9061  CAGTTCAGGA TCGTCGCACC GGCACCGAAC GACACGACCC GGCAGGACGT GGCGAGCAGT
9121  TTCAGGTGCC ACGTCGACGG CTTCTTCTCC AGCAGGATGA TGCCGACGGC GCCGTGCGGG
9181  CCGAAGCGGT CGCCCATGCT GACGACGAGG ACCTCATGGG CGGGATCGGT GAGCACGCGC
9241  GCAGGTCGGC GTCGGAGTAG TGCACGCCGG TCGCGTTCAT CTGGCTGGTC CGCAGCGTCA
9301  GTTCCTCGAC GCGGCTGAGT TCCTCCTCCC CCGCGGGTGC GATCGTCATG GAGAGGTCGA
9361  GCGAGCGCAG GAAGTCCTCG TCGGGACCGG AGTACGCCTC CCGGGCCTGG TCGCGCGCGA
9421  AACCCGCCTG GTACATCAGG CGGCGCCGAC GCGAGTCGAC CGTGGACACC GGCGGGCTGA
9481  ACTCCGGCAG CGACAGGAGC GTGGCCGCCT GCTCGGCCGG GTAGCACCGC ACCTCGGGCA
9541  GGTGGAACGC CACCTCGGCA CGCTCGGCGG GCTGGTCGTC GATGAACGCG ATCGTGGTCG
9601  GTGCGAAGTT CAGCTCCGTG GCGATCTCGC GGACGGACTG CGACTTCGGC CCCCATCCGA
9661  TGCGGGCCAG CACGAAGTAC TCCGCCACAC CGAGGCGTTC CAGACGCTCC CACGCGAGGT
9721  CGTGGTCGTT CTTGCTCGCC ACCGCCTGGA GGATGCCGCG GTCGTCGAGC GTGGTGATCA
9781  CCTCGCGGAT CTCGTCGGTG AGGACCACCT CGTCGTCCTC CAGCACGGTG CCCCGCCACA
9841  AGGTGTTGTC CAGGTCCCAG ACCAGACACT TGACAATGGT CATGGCTGTC CTCTCAAGCC
9901  GGGAGCGCCA GCGCGTGCTG GGCCAGCATC ACCCGGCACA TCTCGCTGCT GCCCTCGATG
9961  ATCTCCATGA GCTTGGCGTC GCGGTACGCC CGTTCGACGA CGTGTCCCTC TCTCGCGCCT
10021 GCCGACGCGA GCACCTGTGC GGCGGTCGCG GCCCCGGCGG CGGCTCGTTC GGCGGCGACG
10081 TGCTTGGCCA GGATCCTCCC GGCCACCATC TCGGCCCAGC CCTCCTCCCA GTGCTCGCTG
10141 GCGTACTCGC ACACGCGGGC CGCGATCTGC TCCGCGCTCC ACAGGTCGGC GATCTGCCCC
10201 GCGACGAGTT GGTGGTCGCC GAGCGGCCGG CCGAACTGCT CCCGGGTCCG GGCGTGGGCC
10261 ACCGCGGCGG TGCGGCAGGC CCGCAGGATC CCGACGCAGC CCCAGGCGAC CGACTTGCGC
10321 CCGTAGGCGA GTGACGCCCC GACCAGCATC GGCAGTGACG CGCCGGAGCC GGCCAGGACC
10381 GCGCCGGCCG GCACACGCAC CTGGTCCAGG TGCAGATCGC CGTGGCCGGC GGCGCGGCAG
10441 CCGGACGGCT TCGGGACGCG CTCGACGCGT ACGCCCGGGG TGTCGCCGGG CACGACCACC
```

```
10501 ACCGCACCGG AACCATCCTC CTGGAGACCG AAGACGACCA GCTGGTCCGC GTAGGCGGCG
10561 GCAGTCGTCC AGACCTTGTC GCCCTCCACC ACACCGGTGT CCCCGTCGAG CCGAACCCGC
10621 GTCCGCATCG CCGACAGATC GCTGCCCGCC TGCCGCTCAC TGAAGCCGAC GGCCGCGAGT
10681 TTCCCGCTGG TCAGCTCCTT CAGGAAGGTC GCCCGCTGAC CGGCGTCGCC GAGCCGCTGC
10741 ACGGTCCACG CGGCCATGCC CTGCGACGTC ATGACACTGC GCAGCGAACT GCACAGGCTG
10801 CCGACGTGTG CGGTGAACTC GCCGTTCTCC CGGCTGCCGA GTCCCAGACC GCCGTGCTCG
10861 GCCGCCACTT CCGCGCAGAG CAGGCCGTCG GCGCCGAGCC GGACGAGCAG GTCGCGCGGC
10921 AGTTCGCCGG ACGTGTCCCA CTCGGCGGCC CGCTCACCGA CAAGGTCGGT CAGCAGCGCG
10981 TCACGCTCAG GCATCGACGG CCCGCAGCCG GTGGACGAGT GCGACCATGG ACTCGACGGT
11041 ACGGAAGTTC GCGAGCTGGA GGTCCGGGCC GGCGATCGTG ACGTCGAACG TCTTCTCCAG
11101 GTACACGACC AGTTCCATCG CGAACAGCGA CGTGAGGCCG CCCTCCGCGA ACAGGTCGCG
11161 GTCCACGGGC CACTCCGACC TGGTCTTCGT CTTGAGGAAC GCGACCAACG CGTGCGCGAC
11221 GGGGTCGTCC TTGACGGGTG CGGTCATGAG AACACCTTCT CGTATTCGTA GAAGCCCCGG
11281 CCGGTCTTCC GGCCGTGGTG TCCCTCGCGG ACCTTGCCCA GCAGCAGGTC ACAGGGCCGG
11341 CTGCGCTCGT CGCCGGTGCG TTTGTGCAGC ACCCACAGCG CGTCGACGAG GTTGTCGATG
11401 CCGATCAGGT CCGCGGTGCG CAGCGGCCCG GTCGGATGGC CGAGGCACCC CGTCATGAGC
11461 GCGTCGACGT CCTCGACGGA CGCGGTGCCC TCCTGCACCA TCCGCGCCGC GTCGTTGATC
11521 ATCGGGTGCA GCAGCCGGCT CGTGACGAAG CCGGGCGCGT CCCGGACGAC GATCGGCTTG
11581 CGCCGCAGCG CCGCGAGCAG GTCCCCGGCG GCGGCCATGG CCTTCTCACC GGTCCGGGGT
11641 CCGCGGATCA CCTCGACCGT CGGGATCAGG TACGACGGGT TCATGAAGTG CGTGCCGAGC
11701 AGGTCCTCGG GCCGGGCCAC GGAGTCGGCC AGTTCGTCAA CCGGGATCGA CGACGTGTTC
11761 GTGATGACCG GGATACCGGG CGCCGCTGCC GAGACCGTGG CGAGTACCTC CGCCTTGACC
11821 TCGGCGTCCT CGACGACGGC CTCGATCACC GCGGTGGCCG TACCGATCGC GGGCAGCGCG
11881 GACGTGGCCG TCCGCAGCAC ACCGGGGTCG GCCTCGGCGG GCCCGGCCAC GAGTTGTGCC
11941 GTCCGCAGTT CGGTGGCGAT CCGCGCCCGC GCCGCCGTAA GGATCTCCTC GGACCTGTCG
12001 ACGAGTGTCA CCGGGACGCC GTGGCGCAGC GCGAGCGTGG TGATGCCGGT GCCCATCACT
12061 CCCGCGCCGA GCACGATCAG CTGGTGGTCC ACGCTGTTTC CTCCCTCCGG GGTCACCATG
12121 GCAGCGAGTA CGGGTCGAGG ACGTCTTCCG GGGTCGACCC GATCGCGTCC TTGCGGCCGA
12181 GGCCGAGTTC GTCGGCGAAG CCGAGCAGCA CGTCGAACGC GATGTGGTCG GCGAACGCGC
12241 TGCCCGTCGA GTCGAGGACG CTCAGGCTGT CCCGGTGGTC CGCCGCGGTG TCCGGTGCCG
12301 CGCACAGCGC CGCCAGCGAC GGGCCGAGCT CGCGGTCCGG CAGTTGCTGG TACTCGCCCT
12361 CGGCGCGGGC CTGCCCCGGA TGGTCGACGC AGATGAACGC GTCGTCGAGC AGGGTCTTCG
12421 GCAGTTCGGT CTTGCCCGGC TCGTCGGCGC CGATGGCGTT CACATGCAGG TGCGGCAGCC
12481 GCGGCTCGGC GGGCAGCACC GGCCCTTTGC CGAGGGCAC CGAGGTGACG GTGGACAGGA
12541 CATCCGCGGC GGCGGCGGCC TCCGCCGGAT CGGTCACCTT GACCGGCAGT CCGAGGAACG
12601 CGATGCGGTC CGCGAACGAC GCCGCGTGGC CGGGGTCGGT GTCGCTGACC AGCATCCGCT
12661 CGATGGGCAG GACCCTGCTG AGCGCGTGCG CCTGGGTCAC CGCCTGTGCG CCCGCGGCGA
12721 TCAGCGTGAG CGTGGCGCTG TCGGACCGGG CCAGCAGCCG GCTCGCGACG GCGGCGACCG
12781 CGCCGGTCCG CATCGCGGTG ATCACGCCTG CGTCGGCGAG GGCGGTCAGA CTGCCGCTGT
12841 CGTCGTCGAG GCGCGACATC GTGCCGACGA TCGTCGGCAG CCGGAAGCGC GGATAGTTGT
```

```
12901  CCGGACTGTA CGAAACCGTC TTCATGGTCA CGCCGACACC GGGGACCCGG TACGGCATGA

12961  ACTCGATGAC GCCGGGAATG TCGCCGCCGC GGACGAATCC GGTACCCGGC GGCGCCTCGG

13021  CGAACTCGCC GCGGCCGACC GCGGCGAACC CGTCGTGCAG CTCGCTGATC AGCCGGTCCA

13081  TCATCACGTC GCGGCCGATC ACGGAGAGAA TCCGCTTGAT GTCACGTTGG CGCAGGACCC

13141  TGGTCTGCAT GTGTCACCTC CCTTTCGTGG CCGGAGCTGT CTTGGTGGTG CCGCTCGGGG

13201  CGGCTTCCGT TCTCATCGCA GCTCCCTGTC GATGAGGTCG AAAATCTCGT CCGCGGTCGC

13261  GTCCGCGGAC AGCACGCCGG CCGGCGTGGT CGGGCGGGTC TCCCGCCGCC AGCGGTTCAG

13321  CAGGGCGTCC ACCCGGGTTC CGATCGCGTC CGCCTGGCGG GCGCCCGGGT CGACACCGGC

13381  AACGAGTGCT TCCAGCCGGT CGAGCTGCGC GAGCACCACG GTCACCGGGT CGTCCGGGGA

13441  CAGCAGTTCA CCGATGCGGT CGGCGAGTGC GCGCGGCGAC GGGTAGTCGA AGACGAGCGT

13501  GGCGGACAGT CGCAGACCGG TCGCCTCGTT GAGGCCGTTG CGCAGCTGCA CCGCGATGAG

13561  CGAGTCCACA CCGAGTTCCC GGAACGCCGC GTCCTCCGGG ATGTCCTCCG GGTCGGCGTG

13621  GCCCAGGACG GCCGCTGCCT TCTGCCGGAC GAGGGCGAGC AGGTCGGTCG GGCGTTCCTG

13681  CTCGTTGCGG GCGCTCCGGC GGGCCGACGG CTTCGGCCGG CCACGCAGCA GCGGGAGGTC

13741  CGGCGGCAGG TCGCCCGCCA CGGCGACGAC ACTGCCCGTT CCGGTGTGGA CGGCGGCGTC

13801  GTACATGCGC ATGCCCTGTT CGGCGGTGAG CGCGCTCGCC CCACCCTTGC GCATACGGCG

13861  CCGGTCGGCG TCGGTCAGGT CCGCGGTCAC GCCACTCGCC TGGTCCCACA GCCCCCACGC

13921  GATCGACAGC CCTGGCACCC CTTGTGCACG CCGGTGTTCG GCGAGCGCGT CGAGGAACGC

13981  GTTCGCCGCC GCGTAGTTGC CCTGACCGGG GGTGCCCAGC ACACCGGCCG CCGACGAGTA

14041  GACGACGAAT GCGGCGAGGT CGGTGTCGCG GGTGAGCCGG TGCAGGTGCC AGGCGGCGTC

14101  GGCCTTGGGT TTGAGGACGG TGTCGATGCG GTCGGGGGTG AGGTTGTCGA GCAGGGCGTC

14161  GTCGAGGGTT CCGGCGGTGT GGAAGACGGC GGTGAGGGGT TGAGGGATGT GGGCGAGGGT

14221  GGTGGCGAGT TGGTGGGGGT CGCCGACGTC GCAGGGGAGG TGGGTGCCGG GGGTGGTGTC

14281  GGCGGGTGGG GTGCGGGAGA GGAGCTACGT GTGGGGGTGG TTCAGGTGGC GGCCGAGGAT

14341  GCCGGCGAGG GTGCCGGAGC CGCCGGTGAT GACGACGGCC CCCTCGGGGT CCAGCGGCCG

14401  CGGGACCGTG AGGACGATCT TGCCGGTGTG CTCGCCGCGG CTCATGGTCG CCAGCGCCTC

14461  GCGGACCTGC CGCATGTCGT GCACCGTCAC CGGCAGCGGG TGCAGCACAC CGCGCGCGAA

14521  CAGGCCCAGC AGCTCCGCGA TGATCTCCTT GAGCCGGTCG GGCCCCGCGT CCATCAGGTC

14581  GAACGGTCGC TGGACGGCGT GCCGGATGTC CGTCTTCCCC ATCTCGATGA ACCGGCCACC

14641  CGGCGCGAGC AGGCCGACGG ACGCGTCGAG GAGTTCACCG GTGAGCGAGT TGAGCACGAC

14701  GTCGACCGGC GGGAACGCGT CGGCGAACGC GGTGCTGCGG GAATCGGCCA GATGCGCTCC

14761  GTCCAGGTCC ACCAGATGGC GCTTCGCGGC GCTGGTGGTC GCGTACACCT CCGCGCCCAG

14821  GTGCCGCGCG ATCTGCCGGG CGGCGGAACC GACACCGCCG GTGGCCGCGT GGATCAGGAC

14881  CTTCTCGCCG GGGCGCAGCC CGGCGAGGTC GACCAGGCCG TACCACGCGG TCGCGAACGC

14941  GGTCATCACG GACGCCGCCT GCGGGAACGT CCAGCCGTCC GGCATCCGGC CGAGCATCCG

15001  GTGGTCGGCG ATGACCGTGG GGCCGAAGCC GGTGCCGACG AGGCCGAAGA CGCGGTCGCC

15061  CGGTGCCAGA CCGGAGACGT CGGCGCCGGT CTCCAGGACG ATGCCCGCGG CCTCGCCGCC

15121  GAGCACGCCC TGACCGGGGT ACGTGCCGAG CGCGATCAGC ACATCGCGGA AGTTGAGGCC

15181  CGCCGCACGC ACACCGATCC GGACCTCGGC CGGGGCGAGG GGGCGCCGGG GCTCCGCCGA

15241  GTCGGCCGCG GTGAGGCCGT CGAGGGTGCC CGTCCGCGCC GGCCGGATCA GCCACGTGTC
```

```
15301 GCTGTCCGGC ACGGTGAGCG GCTCCGGCAC GCGGGTGAGG CGGGCCGCCT CGAACCGGCC
15361 GCCGCGCAGC CGCAGACGCG GCTCGCCGAG TGCGACGGCG ATGCGCTGCT GCTCGGGGGC
15421 GAGCGTGACG CCGGACTCGG TCTCGACGTG GACGAACCGG CCGGGCTGCT CGGCCTGGGC
15481 GGCGCGCAGC AGTCCGGCCG CCGCGCCGGT GGCGAGGCCC GCGGTGGTGT GCACGAGCAG
15541 ATCCCCGCCG GAGCCGGTCA GGGCGGTCAG CAGCCGGGTG GTGAGCGCAC GCGTCTCGGC
15601 CACCGGGTCG TCGCCATCAG CGGCAGGCAA CGTGATGACG TCCACGTCGG TCGCGGGGAC
15661 ATCCGTGGGT GCGGCGACCT CGATCCAGGT GAGACGCATC AGGCCGGTGC CGACGGGTGG
15721 GGACAGCGGG CGGGTGCGGA CCGTCCGGAT CTCGGCGACG AGTTGGCCGG CGGAGTCGGC
15781 GACGCGCAGA CTCAGCTCGT CGCCGTCACG AGTGATCACG GCTCGGAGCA TGGCCGAGCC
15841 CGTGGCGACG AACCGGGCCC CCTTCCAGGC GAACGGCAGA CCCGCAGCGC TGTCGTCCGG
15901 CGTGGTGAGG GCGACGGCGT GCAGGGCCGC GTCGAGCAGC GCCGGATGCA CACCGAAACC
15961 GTCCGCCTCG GCGGCCTGCT CGTCGGGCAG CGCCACCTCG GCATACACGG TGTCACCATC
16021 ACGCCAGGCA GCCCGCAACC CCTGGAACGC CGACCCGTAC TCATAACCGG CATCCCGCAG
16081 TTCGTCATAG AACCCCGAGA CGTCGACGGC CACGGCCGTG ACCGGCGGCC ACTGCGAGAA
16141 CGGCTCCACA CCGACAACAC CGGGGGTGTC GGGGGTGTCG GGGGTCAGGG TGCCGCTGGC
16201 GTGCCGGGTC CAGCTGCCCG TGCCCTCGGT ACGCGCGTGG ACGGTCACCG GCCGCCGTCC
16261 GGCCTCATCA GCCCCTTCCA CGGTCACCGA CACATCCACC GCTGCGGTCA CCGGCACCAC
16321 AAGGGGGGAT TCGATGACCA GCTCGTCCAC TATCCCGCAA CCGGTCTCGT CACCGGCCCG
26381 GATGACCAGC TCCACAAACG CCGTACCCGG CAGCAGGACC GTGCCCCGCA CCGCGTGATC
26441 AGCCAGCCAG GGGTGAGTGC GCAATGAGAT CCGGCCAGTG AGAACAACAC CACCATCGTC
26501 GGCGGGCAGC GCTGTGACAG CGGCCAGCAT CGGATGCGCC GCACCCGTCA ACCCCGCCGC
26561 CCACAGATCG GTGGCACCGG CCGCCTCCAG CCAGTACCGC CTGTGCTCGA ACGCGTACGT
16621 GGGCAGATCC AGCAGCCGTC CCGGCACCGG TTCGACCACC GTGTCCCAGT CCACTGCCGT
16681 GCCCAGGGTC CACGCCTGCG CCAACGCCGT CAGCCACCGC TCCCAGCCGC CGTCACCGGT
16741 CCGCAACGAC GCCACCGTGT GAGCCTGCTC CATCGCCGGC AGCAGCACCG GATGGGCACT
16801 GCACTCCACG AACACCGACC CATCCAGCTC CGCCACCGCC GCGTCCAACG CCACCGGACG
26861 ACGCAGATTC CGGTACCAGT ACCCCTCATC CACCGGCTCC GTCACCCAGG CGCTGTCCAC
16921 GGTCGACCAC CACGCCACCG ACGCGGCCTT CCCTGCCACC CCCTCCAGTA CCTTGGCCAG
16981 TTCATCCTCG ATGGCTTCCA CGTGGGCGT GTGGGAGGCG TAGTCGACCG CGATACGACG
17041 CACCCGCACG CCTTCGGCCT CATACCGCGC CACCACCTCC TCCACCGCCG ACGGGTCCCC
17101 CGCCACCACC GTCGAAGCCG GGCCGTTACG CGCCGCGATC CACACACCCT CGACCAGACC
17161 CACCTCACCC GCCGGCAACG CCACCGAAGC CATCGCTCCC CCCCGGCCA GTCGCGCCGC
17221 GATGACCTGA CTGCGCAATG CCACCACGCG GGCGGCGTCC TCGAGGCTGA GGCCTCCGGC
17281 CACGCACGCC GCCGCCATCT CGCCCTGGGA GTGTCCGATC ACCGCGTCCG GCACGACCCC
17341 ATGCGCCTGC CACAGCGCGG CCAGGCTCAC CGCGACCGCC CAGCTGGCCG GCTGGACCAC
17401 CTCCACCCGC TCCGCCACAT CCGGCCGCGC CAACATCTCC CGCACATCCC AGCCCGTGTC
17461 CGGCAGCAAC CCCTGAGCCC ACTCCTCCAT ACGCGCGGCG AACACCGCGG AGTGGGCCAT
17521 GAGTTCCACG CCCATGCCGA CCCACTGGGC GCCCTGGCCG GGGAAGACGA ACACCGTACG
17581 CGGCTGGTCC ACCGCCACAC CCGTCACCCG GGCATCGCCC AGCAGCACCG CACGCTGACC
17641 GAAGACAGCA CGCTCCCGCA CCAACCCCTG CGCGACCGCG GCCACATCCA CACCACCCCC
```

-continued

```
17701 GCGCAGATAC CCCTCCAGCC GCTCCACCTG CCCCCGCAGA CTCACCTCAC CACGAGCCGA
17761 CACCGGCAAC GGCACCAACC CGTCAACAAC CGACTCCCCA CGCGACGGCC CAGGAACACC
17821 CTCAAGGATC ACGTGCGCGT TCGTACCGCT CACCCCGAAC GACGACACAC CCGCATGCGG
17881 TGCCCGATCC GACTCGGGCC ACGGCCTCGC CTCGGTGAGC AGCTCCACCG CACCGGCCGA
17941 CCAGTCCACA TGCGACGACG GCTCGTCCAC ATGCAGCGTC TTCGGCGCGA TCCCGTACCG
18001 CATCGCCATG ACCATCTTGA TCACACCGGC GACACCCGCC GCCGCCTGCG CATGACCGAT
18061 GTTCGACTTC AACGAACCCA GCAGCAGCGG AACCTCACGC TCCTGCCCGT ACGTCGCCAG
18121 AATGGCCTGC GCCTCGATGG GATCGCCCAG CGTCGTCCCC GTCCCGTGCG CCTCCACCAC
18181 GTCCACATCG GCGGCGCGCA GTCCGGCGTT CACCAACGCC TGCTGGATGA CACGCTGCTG
18241 GGACGGGCCG TTGGGGCGG ACAGCCCGTT GGAGGCACCG TCCTGGTTCA CCGCCGACCC
18301 GCGGACGACC GCGAGAACGG TGTGTCCGTT GCGCTCGGCG TCGGAGAGCC GCTCCAGCAC
18361 AAGAACGCCG GCGCCCTCCG CCCAGCCGGT GCCGTTGGCG GCGTCCGCGA ACGCGCGGCA
18421 GCGGCCGTCG GGGGAGAGTC CGCCCTGCTG CTGGAATTCC ACGAACCCGG TCGGGTCGC
18481 CATGACGGTG ACACCGCCGA CCAGCGCCAG CGAGCACTCC CCGTGGCGCA GTGCGTGCCC
18541 GGCCTGGTGC AGCGCGACCA GCGACGACGA GCACGCCGTG TCCACCGTGA ACGCCGGTCC
18601 CTGGAGCCCA TAGAAGTACG AGATCCGGCC GGTGAGCACG CTGGGCTGCA TGCCGATCGA
18661 GCCGAACCCG TCCAGGTCCG CGCCGACGCC GTACCCGTAC GAGAAGGCGC CCATGAACAC
18721 GCCGGTGTCG CTGCCGCGCA GTGTGCCCGG CACGATGCCC GCGCTCTCGA ACGCCTCCCA
18781 TGTCGTTTCC AGCAGGATCC GCTGCTGGGG GTCCATGGCC CGTGCCTCAC GGGGGCTGAT
18841 GCCGAAGAAC GCGGCATCGA AGCCGGCGGC GTCGGAGAGG AAGCCGCCGC GGTCCGTGTC
18901 CGATCCCCCG GTGAGGCCGG ACGGGTCCCA GCCACGGTCG GCCGGGAAGC CGGTGACCGC
18961 GTCGCCGCCA CTGTCCACCA TGCGCCACAG GTCGTCGGGC GAGGTGACGC CGCCCGGCAG
19021 TCGGCAGGCC ATGCCCACGA TGGCCAGCGG TTCGTCACGG GTCGCGGCGG CTGTGGGAAC
19081 AGCGACCGGT GCGGCACCAC CGACCAGAGC CTCGTCCAAC CGCGACGCGA TGGCCCGCGG
19141 CGTCGGGTAG TCGAAGACAA GCGTGGCGGG CAGTCGGACA CCGGTCGCCG CGGCGAGTCG
19201 GTTCCGCAGT TCGACGGCGG TCAGCGAGTC GATACCCAGT TCCTTGAAGG CCGCGTCCGC
19261 GGACACGTCC GCGGCGTCCG CGTGGCCGAG CACCGCCGCC GCCTTGTCGC GGACCAGTGC
19321 CAGCAGCGCC GTGTCCCGCT CAGCGCCGGA CATGCTGCCG AGCCGGTCGG CGAGCGGAAC
19381 GGCGGTGGCC GCCGCCGGGC GCGATACGGC GCGGCGCAGA TCGGCGAAAA GCGGCGATGT
19441 GTGCGCGCTG AGGTCCATCG TGGCCGCCAC GGCGAACGCG GTGCCGGTTC CGGCCGCGGC
19501 TTCCAGCAGG CGCATGCCCA CACCGGCCGA CATGGGGCGG AAACCGCCGC GGCGGACACG
19561 GGTGCGGTTG GTGCCGCTCA TGCTGCCGGT GAGTCCGCTG TCATCGGCCC AGAGGCCCCA
19621 GGCCAGCGAC AGCGCGGGCA GTCCTTCGGC ATGGCGCAGC GTCGCGAGTC CGTCGAGGAA
19681 CCCGTTCGCC GCCGAGTAGT TGCCCTGGCC GCGGCCGCCC ATGATGCCCG CGACGGACGA
19741 GTACAGGACG AACGAGCGCA GGTCCGCGTC CCGGGTCAGC TCGTGCAGGT GCCAGGCGCC
19801 GTCGGCTTTG GGGCGCAGTG TGGTGGCGAG CCGCTCCGGG GTGAGTGCCG TGGTCACGCC
19861 GTCGTCGAGC ACGGCTGCCG TGTGGAAGAC CGCCGTGAGC GGCCTGCCGG CGGCGGCGAG
19921 CGCGGCGGCG AGCTGGTCCC GGTCGGCGAC GTCACAGCGG ATGTGGACAC CGGGAGTGTC
19981 CGCCGGCGGT TCGCTGCGCG ACAGCAACAG GAGGTGGCGG GCGCCATGCT CGGCGACGAG
20041 ATGCCGGGCG AGGAGACCTG CCAGCACACC CGAGCCGCCG GTGATGACCA CCGTGCCGTC
```

-continued

```
20101 CGGGTCGAGC AGCGGTTCGG GCGTTTCCGC GGCGGCCGTG CGGGTGAACC GCGGCGCTTC
20161 GTACCGGCCG TCGGTGACGC GGACGTACGG CTCGGCCAGT GTCGTGGCGG CGGCCAGCGC
20221 CTCGATGGGG GTGTCGGTGC CGGTCTCCAC CAGCACGAAC CGGCCCGGGT GCTCGGCCTG
20281 GGCGGACCGG ACGAGGCCGG CGACCGCTCC TCCGACCGGT CCCGCGTCGA TCCGGACGAC
20341 GAGGGTGGTC TCCGCAGGGC CGTCCTCGGC GATCACCCGG TGCAGCTCGC CGAGCACGAA
20401 CTCGGTGAGC CGGTACGTCT CGTCGAGGAC ATCCGCGCCC GGTTCCGGGA GCGCGGAGAC
20461 GATGTGGACC GCGTCCGCAG GACCGGGCCC GGGAGTGGGC AGCTCGGTCC AGGAGAGGCC
20521 GTACAAGGAG TTCCGTACGA CGGCGGCGTC GCCGTCGACG TTCACCGGTC GCGCGGTCAG
20581 CGCGGCGACG GTCACCACCG GTTGGCCGAC CGGGTCCGTC GCATGCACGG CAGCGCCGTC
20641 CGGGCCCTGA GTGATCGTGA CGCGCAGCGT GGTGGCCCCG GTCGTGTGGA ACCGCACGCC
20701 GCTCCACGAG AACGGCAGCC GCACCTCCGC TTCCTGTTCC GCGAGCAGCG GCAGGCAGGT
20761 GACGTGCAAG GCCGCGTCGA ACAGCGCCGG GTGGACGCCA TAGTGCGGCG TGTCGTCCGC
20821 CTGTTCCCCG GCGATCTCCA CCTGGGCGTA CAGGGTTTCG CCCTCGCGCC AGCCGGTGCC
20881 CAGTCCCTGG AACGCTGGGC CGTAGCTGTA GCCGGTCTCG GCCAGCCGCT CGTAGAACGC
20941 GCTCACGTCG ACGCGTCGCG CGCCCGGCGG CGGCCACGCG GGCGGCGGGA CCGCCGCGAC
21001 GCTTCCGGCC CGGCCGAGGG TGCCGCTGGC GTGCCGGGTC CAGCTGTCCG TGCCCTCGGT
21061 ACGCGCGTGG ACGGTCACTC GCCGCCGTCC GGCCTCATCG GCCCCTTCGA CGGTCACCGA
21121 CACATCCACC GCGCCGGTCA CCGGCACCAC GAGCGGGGTC TCGATGACCA GTTCATCCAC
21181 CACCCCGCAA CCGGTCTCGT CACCGGCCCG GATGACCAGC TCCACAAACG CCGTACCCGG
21241 CAGCAGAACC GTGCCCCGCA CCGCGTGATC AGCCAGCCAG GGATGCGTAC GCAACGAGAT
21301 CCGGCCAGTG AGAACAACAC CACCACCGTC GTCGGCGGGC AGTGCTGTGA CGGCGGCCAG
21361 CATCGGATGC GCCGGCCCGG TCAGCCCGGC CGCGGACAGA TCGGTGGCAC CGGCCGCCTC
21421 CAGCCAGTAC CGCCTGTGCT CGAACGCGTA GGTGGGCAGA TCGAGCAGCC GTCCCGGCAC
21481 CGGTTCGACC ACCGTGTCCC AGTCCACTGC CGTGCCCAGG GTCCACGCCT GCGCCAACGC
21541 CGTCAGCCAC CGCTCCCAGC CGCCGTCACC GGTCCGCAAC GACGCCACCG TGTGAGCCTG
21601 TTCCATCGCC GGCAGCAGCA CCGGATGGGC GCTGCACTCC ACCAACACGG ACCCGTCCAG
21661 CTCCGCCACC GCCGCGTCCA GCGCGACGGG GCGACGCAGG TTCCGGTACC AGTAGCCCTC
21721 ATCCACCGGC TCGGTCACCC AGGCGCTGTC CACCGTGGAC CACCAGGCCA CCGACCCGGT
21781 CCCGCCGGAA ATCCCCTCCA GTACCTCGGC CAACTCGTCC TCGATGGCTT CCACGTGGGG
21841 CGTGTGGGAG GCGTAGTCGA CCGCCATACG GCGCACTCGC ACGCCTTCGG CCTCCTACCG
21901 CGTCACCACT TCTTCCACCG CGGACGGGTC CCCCGCCACC ACAGTCGAAG ACGGGCCGTT
21961 ACGCGCCGCG ATCCACACGC CCTCGACCAG GTCCACCTCA CCGGCCGGCA ACGCCACCGA
22021 AGCCATCGCC CCCCGCCCGC CCAGCCGCCC GGCGATCACC TGGCTGCGCA AGGCCACCAC
22081 GCGGGCGGCG TCCTCAAGGC TGAGGGCTCC GGCCACACAC GCCGCCGCGA TCTCGCCCTG
22141 GGAGTGTCCG ACCACCGCGT CCGGCACGAC CCCATGCGCC TGCCACAGCG CGGCCAGGCT
22201 CACCGCGACC GCCCAGCTGG CCGGCTGGAC CACCTCCACC CGCTCCGCGA CATCCGGCCG
22261 CGCCAACATC TCCCGCACAT CCCAGCCCGT GTGCGGCAAC AACGCCCGCG CACACTCCTC
22321 CATACGAGCC GCGAACACCG CAGAACACGC CATCAACTCC ACACCCATGC CCACCCACTG
22381 AGCACCCTGC CCGGGAAAGA CGAACACCGT ACGCGGCTGA TCCACCGCCA CACCCATCAC
22441 CCGGGCATCG CCCAACAACA CCGCACGGTG ACCGAAGACA GCACGCTCAC GCACCAACCC
```

-continued

```
22501 CTGCGCGACC GCGGCCACAT CCACACCACC CCCGCGCAGA TACCCCTCCA GCCGCTCCAC
22561 CTGCCCCCGC AGACTCACCT CACTCCGAGC CGACACCGGC AACGGCACCA ACCCATCGAC
22621 AGCCGACTCC CCACGCGACG GCCCGGGAAC ACCCTCAAGG ATCACGTGCG CGTTCGTACC
22681 GCTCACCCCG AAAGCGGAGA CACCGGCCCG GCGCGGACGT CCCGCGTCGG GCCACGCCCG
22741 CGCCTCGGTG AGCAGTTCCA CCCGCGCCCTC GGTCCAGTCC ACATGCGACG ACCGCTCGTC
22801 CACATGCAGC GTCTTCGGCG CGATGCCATA CCGCATCGCC ATGACCATCT TGATGACACC
22861 GGCGACACCC GCAGCCGCCT GCGCATGACC GATGTTCGAC TTCAACGAAC CCAGCAGCAG
22921 CGGAACCTCA CGCTCCTGCC CGTACGTCGC CAGAATCGCG TGCGCCTCGA TGGGATCGCC
22981 CAGCGTCGTC CCCGTCCCGT GCGCCTCCAC CACGTCCACG TCCGCGGGGG CGAGCCCCGC
23041 CTTGTGGAGG GCCTGGCGGA TGACGCGCTG CTGGGAGGGG CCGTTGGGTG CGGAGATGCC
23101 GTTGGAGGCG CCGTCCTGGT TGACGGCGGA GGAGCGGACG ACCGCGAGGA CGGTGTGTCC
23161 GTTGCGCTCG GCGTCGGAGA GCTTTTCGAC GACGAGGACG CCGGCCCCCT CGGCGAAACC
23221 GGTGCCGTCC GCCGCGTCAG CGAACGCCTT GCACCGTCCG TCCGGCGCGA CGCCGCCCTG
23281 CCGGGAGAAC TCCACGAAGG TCTGTGGTGA TGCCATCACT GTGACACCAC CGACCAGCGC
23341 CAGCGAGCAC TCCCCGGTCC GCAGCGCCTG CCCGGCCTGG TGCAGCGCGA CCAGCGACGA
23401 CGAACACGCC GTGTCGACCG TGACCGCCGG ACCCTCCATG CCGAAGAAGT ACGACAGCCG
23461 TCCGGCGAGC ACCGCGGGCT GTGTGCTGTA GGCGCCGAAT CCGCCCAGGT CCGCGCCCGT
23521 GCCGTAGCCG TAGTAGAAGC CGCCGACGAA GACGCCGGTG TCGCTGCCGC GCAGGGTGTC
23581 CGGCACGATG CCCGCGTGTT CGAGCGCCTC CCAGGCGATT TCGAGGAGGA TCCGCTGCTG
23641 CGGGTCGAGT GCGGTGGCCT CGCGCGGACT GATGCCGAAG AACGCGGCAT CGAAGTCGGC
23701 GGCGCCCGCG AGTGCGCCGC CCCGCCCGGT GGCGGACTCG GCGGCGGCGT GCAGCGCGGC
23761 CACGTCCCAG CCGCGGTCGG TGGGGAAGTC GCCGATCGCG TCGCGGCCGT CCGCGACGAG
23821 CTGCCACAGC TCTTCCGGTG AGGTGACGCC GCCCGGCAGT CGGCAGGCCA TGCCGACGAC
23881 GGCGAGCGGC TCGTTCGCCG CGGCGCGCAG CGCGGTGTTC TCCCGGCGGA GCTGCGCGTT
23941 GTCCTTGACC GACGTCCGCA GCGCCTCGAT CAGGTCGTTC TCGGCCATCG CCTCATCCCT
24001 TCAGCACGTG CGCGATGAGC GCGTCTGGGT CCATGTCGTC GAACAGTTCG TCGTCCGGCT
24061 CCGCGGTCGT GGTGCTCGCG GGTGCCTGTG CCGGTGGTTC ACCGCCGTCC GGGGTCCCGT
24121 TGTCGTCCGG GGTCCCGTTG ACGTCCGGCG CCAGGAGGGT CAGCAGATGA CGGGTGAGCG
24181 CGCCGGCGGC GGGATAGTCG AAGACGAGCG TGGCCGGCAG CGGAATGCCG AGGGCCTCGG
24241 AGAGCCGGTT GCGCAGGCCG AGCGCGGTGA GCGAGTCGAC CCCGAGGTCC TTGAACGCCG
24301 TGGTGGCCGT GACCGCCGCC GCGTCGGTGT GGCCCAGCAG GGTGGCGGCC GTGTCGCGGA
24361 CGACGCCCAG CAGCACCTGT TCCCGTTCCT TGTGGGGCAG GTCCGGCAGG CGTTCCAGCA
24421 GGGAGCCGCC GTCGGTCGCG GAGCGCCGGG TGGGGCGCTG GATCGGTCGC CACAGCGGTG
24481 ACGGCTCGCC GCGCCCGGGT GCGGCGGTCG CCACGACCAC GGCTTCCCCG GTGGCGCACG
24541 CGGCGTCGAG GAGGTCGGTC AGCGGGTCCG CCGCGGCGGT GAACGCCACG GCCGGCAGGC
24601 CTTGTGCCCG GCGCAGGTCG GCCAGGGCCT GGAGCGGTCC GGCCGCCTCG CCGGACGGAA
24661 CGGCGAGAAC CAACGCGGTC AGGTCGAGGT CGCGGGTCAG GCGGTGCAGT TCCCAGGCCG
24721 ACTCGGCGGT GCCGTCCGCG TGGACGACCG CGGTCACCGG GGTTTCCGGC ACTGTGCCCG
24781 GCTCGTACCG GATCACTTCG GCGCCGTGTC CGCCGAGGTG TCCGGCGAGT TCCTCCGAAC
24841 CGCCCGCGAG GAGGACGGTG TCGCCGTACG AGGCCGCGGC CGTGGTGGGC GCGGCGGGGA
```

-continued

```
24901 CGAGGCGGGG CGCTTCGAGG CGCCCGTCGG CCAGGCGCAG GTGCGGTTCG TCGAGGCGGG
24961 AGAGGGCGGC GGCGCGGCGG GGGGTGACCG TGTCGGTGGT CTCCACGAGC ACGAGCCGCC
25021 CCGGTTCCGC GGTGTCGAGC AGTGCGGCGA CGGCACCGGC GACGGGCCCG CCCTCGGCGG
25081 ACACCACCAG CGTGCCGCCG GCGGTCCTCG GGTCGTCCAG TGCGGTACGG ACCTCGTCGG
25141 GACCGGATAC CGGGACGACG ATGACGTCGG GCGTGGCGTC GTCGCCGAGG TCGGTGTACC
25201 GGCGGGCCGT GGTGCCGGGT GCCGCCGGGG CCCGGACGCC GGTCCAGGTG CGCCGGAACA
25261 GCCGCACGTC CCCGTCCGGG CCCGTCGTGG CGGGGGGCCG GGTGATGAGC GAGCCGATCT
25321 GAGCCACCGG CCGTCCCAGT TCGTCGGCGA GGTGCACCCG GCGCCGCCC TCGCCCTCGC
25381 CGTGGACGAA GGTGACGCGC AGTTTCGTGG CGCCGCTGGT GTGGACACGG ACGCCGGTGA
25441 ACGCGAACGG CAACCGTACC CCCGCGTTCT CGGCGGCCGC GCCGATGCTG CCCGCTTGCA
25501 GCGCGGTGAC GAGCAGCGCC GGGTGCAGTG TGTAGCGGGC GGCGTCCCTG GCGAGGGCGC
25561 CGTCGAGGGC GACTTCGGCG CAGACGGTGT CTCCGTGGCT CCACGCGGCG GACATGCCGC
25621 GGAACTCGGG GCCGAACTCG TATCCCGCGT CGTCGAGTCG CTGGTAGAAG GCCGCGACGT
25681 CGACCGGTTC CGCGTGCTCG GGCGGCCAGG GCCCCGGCGT GGTGGCCGGT TCGGTGGTGG
25741 CGATGCCGGC GAAGCCGGAG GCGTGGCGGG TCCATGTCCG GTCGCCGTCC GTCCGGGCGT
25801 GGACGCGCAC GGCACGGCGT CCGGTGTCGT CGGGCGCGGC GACGGTCACG CCCACCTGGA
25861 CGGCGCCGGT GGCGGGCAGG ACCAGCGGTG TCTCGACGAC CAGTTCGTCG AGCAGGTCGC
25921 AGCCTGCCTC GTCGGCGCCG CGTCCGGCCA ATTCCAGGAA GGCGGGTCCG GGCAGCAGTA
25981 CGGCGCCGTC GACGGACTGA CCGGCCAGCC ATGGCTGGCT GGCCAGCGAG AACCGGCCGG
26041 TGAGCAGCAC CTCGTCGGAG TCGGGGAGCG CCACCGACGC GGCGAGCAGC GGGTGGTCGA
26101 CGGCGTCGAG TCCGAGGCCG GAAGCGTCCG TGCCGGCCGC GCTCTCGATC CAGTAGCGCT
26161 CATGGTGGAA GGCGTATGTG GGCAGGTCGT GTGCCGTCGC CGTCGCGGGG ACGACCGCCG
26221 CCCAGTCGAC GGGCACGCCG GTTGTGTGCG CCTCGGCCAG CGCGGTGAGC AGCCGGTGGA
26281 CTCCCCCGCC GCGGCGGAGC GTGGCGACGG TCGCGCCGTC GATCGCGGGC AGCAGCACGG
26341 GGTGCGCGCT GACCTCGACG AACACGGTGT CACCCGGCTC GCGGGCAGCG GTCACGGCCG
26401 TGGCGAAGCC TACGGGGTGG CGCATGTTGC GGAACCAGTA CTCGTCGTCG AGCGGCGCGT
26461 CGATCCAGCG TTCGTCGGCG GTGGAGAACC ACGGGATCTC GGGCGTCCGC GAGGTGGTGT
26521 CCGCGACGAT CCGCTGGAGT TCGTCGTACA GCGGGTCGAC GAACGGGGTG TGGGTCGGGC
26581 AGTCCACGGC GATGCGGCGC ACCCAGACGC CGCGGGCCTC GTAGTCGGCG ATCAGCGTTT
26641 CGACGGCGTC CGGGCGCCCG GCGACGGTCG TGGTGGTGGC GCCGTTGCGG CCCGCGACCC
26701 AGACGCCCTC GATCCGGGCG GCATCCGCCT CGACGTCGGC GGCCGGGAGC GCGACCGAGC
26761 CCATCGCGCC GCGTCCGGCG AGTTCGCGCA GGAGCAGGAG AACGCTGCGC AGCGCGACGA
26821 GGCGGGCACC GTCCTCCAGG GTGAGCGCTC CGGCGACACA GGCCGCGGCG ATCTCGCCCT
26881 GGGAGTGTCC GATGACGGCG TCCGGGCGTA CGCCCGCGGC CTCCCACACG GCGGCCAGCG
26941 ACACCATGAC GGCCCAGCAG ACGGGGTGCA CGACGTCGAC GCGGCGGGTC ACCTCCGGGT
27001 CGTCGAGCAT GGCGATGGGG TCCCAGCCCG TGTGCGGGAT CAGCGCGTCG GCGCATTGGC
27061 CCATCCTGCC GCCGAACACC GGGGACGCCG CCATCAGTTC GACGCCCATG CCGCGCCACT
27121 GCGGTCCTTG TCCGGGGAAG ACGAAGACGG TGCGCGGCTC GGTGACCGCC GTGCCGGTGA
27181 CGACGTCGTC GTCGAGCAGC ACGGCGCGGT GCGGGAACGT CGTACGCCTG GCGAGCAGGC
27241 CCGCGGCGAT GGCGCGCGGG TCGTGGCCGG GACGGGCGGC GAGGTGCTCG CGGAGTCGGC
```

-continued

```
27301 GGACCTGGCC GTCGAGGGCC GTGGCGGTCC GCGCCGAGAC GGGCAGTGGT GTGAGCGGCG
27361 TGGCGATCAG CGGCTCACCG GGCTTCGAGG CCGACGGCTC CTCGGCCGGC GGCTCCCCGG
27421 CCGGGTGGGC TTCCAGCAGG ACGTGGGCGT TGGTGCCGCT GACGCCGAAG GAGGACACAC
27481 CGCCGCGCCG CCGGCGGTCG GTCTCGGGCC AGGGCCGGGC ATCGGTGAGG AGTTCGACGG
27541 CGCCGGCCGT CCAGTCGACG TGCGAGGACG GCGTGTCCAC GTGCAGGGTG CGCGGCAGGG
27601 TGCCGTGCCG CATGGCGAGG ACCATCTTGA TGACACCGGC GACACCCGCG GCGGCCTGAG
27661 TGTGGCCGAT GTTGGACTTC AGCGAGCCCA GCAGCACCGG GGTGTCGCGC CCCTGCCCGT
27721 AGGTGGCCAG CACCGCCTGT GCCTCGATGG GATCGCCCAG CCTGGTGCCG GTGCCCTGCG
27781 CCTCCACGGC GTCCACGTCC GCCGGGGTGA GCCCGGCGTT GGCCAGGGCC TGCCGGATCA
27841 CCCGCTCCTG CGAGGGCCCG TTCGCCGCCG ACAACCCGTT GGAAGCACCG TCCTGGTTGA
27901 CCGCCGAACC CCGGACAACC GCCAGCACAC GGTGGCCGTT GCGCTCGGCA TCGGAGAGCC
27961 TCTCGACGAT CAGCACACCG GACCCCTCGG CGAAACCGGT GCCCTCAGCC GCATCCGCGA
28021 ACGCCTTGCA GCGCGCGTCG GGCGCGAGAC CCCGCTGCTG GGAGAACTCG ACGAAGCCGG
28081 ACGGCGAGGC CATCACCGTG ACGCCGCCGA CCAGGGCGAG CGAGCATTCG CCGGAGCGCA
28141 GTGACTGCCC GGCCTGGTGC AGCGCCACCA GCGACGACGA ACACGCCGTG TCGACCGTGA
28201 CCGCCGGACC CTCCAGACCG TAGAAGTACG ACAGCCGACC GGACAGCACA CTGGTCTGGG
28261 TGCCGGTCGC GCCGAAACCG CCCAGGTCGG TGCCGAGTCC GTACCCGTCG GAGAAGGCGC
28321 CCATGAACAC GCCGGTGTCG CTTCCGCGCA GCGACTCCGG GAGGATCCCG GCGTGTTCCA
28381 GCGCCTCCCA CGAGGTCTCC AGGACCAGAC GCTGCTGCGG GTCCATCGCC AGCGCCTCAC
28441 GCGGACTGAT CCCGAAGAAC GCCGCGTCGA AGTCCGCCAC CCCGGCGAGG AAGCCACCAT
28501 GACGCACGGT CGACGTGCCC GGATGATCCG GATCGGGATC GTACAGCCCG TCCACGTCCC
28561 AACCACGGTC CGTCGGAAAC GCCGTGATCC CGTCACCACC CGACTCCAGC AGCCGCCACA
28621 AGTCCTCCGG CGACGCGACC CCACCCGGCA GCCGGCAGGC CATCCCCACG ATCGCCAACG
28681 GCTCGTCCTG CCGGACGGCC GCGGTCGTGG TGCGGGTCGG CGATGCCGTC CGGCCGGACA
28741 GCGCCGCGGT GAGCTTCGCC GCGACGGCGC GCGGCGTCGG GAAGTCGAAG ACCGCGGTGG
28801 CGGGCAGCCG TACGCCCGTC GCCTCGGTGA AGGCGTTGCG CAGCCGGATC GCCATGAGCG
28861 AGTCGACGCC GAGTTCCTTG AACGTGGCGG TCGCCTCGAC CCGTGCGGCA CCGTCGTGGC
28921 CGAGTACGGC CGCGGTGCAC TGCCGGACGA CGGCGAGCAC GTCCTTTTCG CCCTCCGCGG
28981 CGGAGAGCCG CGCGATCCGG TCGCCGAGGG TGGTGGCGCC GGCCGCCCGG CGCCGCGGCT
29041 CCCGGCGCGG TGCGCGCAGC AGGGGCGAGC TGCCGAGGCC GGCCGGGTCG GCGGCGACCA
29101 GCGCCGGGTC CGAGGACCGC AACGCCGCGT CGAACAGCGT CAGTCCGCCT TCGGCGGTCA
29161 GCGCCGTCAC GCCGTCGCGG CGCATGCGGG CGCCGGTGCC GACCGTCAGC CCGCTCTCCG
29221 GTTCCCACAG GCCCCAGGCC ACGGACAACG CGGGCAGTCC GGCTGCCCGG CGCTGTTCGG
29281 CCAGCGCGTC GAGGAACGCG TTCGCGGCCG CGTAGTTGCC CTGTCCGGGG CTGCCGAGCA
29341 CACCGGCGGC CGACGAGTAG AGGACGAACG CGGCCAGTTC CGTGTCCTGG GTGAGTTCGT
29401 GCAGGTGCCA CGCGGCGTCC ACCTTCGGGC GCAGCACCGT CTCGAGCCGG TCGGGGGTGA
29461 GCGCGCTGAG GACGCCGTCG TCGAGGACCG CCGCGGTGTG CACGACGGCC GTGAGCGGGT
29521 GCGCCGGGTC GATCCCCGCC AGTACGGAGG CGAGTTCGTC CCGGTCGGCG ACGTCGCAGG
29581 CGATCGCCGT GACCTCGGCG CCGGGCACGT CGCTCGCCGT GCCGCTGCGC GACAGCATCA
29641 GCAGCCGGCG CACGCCGTGG CGTTCGACGA GGTGGCGGCT GATGATGCCG GCCAGCGTCC
```

```
-continued
29701 CGGAGCCACC GGTGACGAGC ACGGTGCCGT CCGGGTCGAG CGCCGGAGCG TCACCCGCCG
29761 GGACCGCCGG GGCCAGACGG CGGGCGTACA CCTGGCCGTC ACGCAGCACC ACCTGGGGCT
29821 CATCGAGCGC GGTGGCCGCT GCGAGCAGCG GCTCGGCGGT GTCCGGGGCG GCGTCGACGA
29881 GGACGATCCG GCCCGGCTGT TCGGCCTGCG CGGTCCGCAC CAGTCCGGCG GCCGCGGCCG
29941 ACGCGAGACC GGGCCCGGTG TGGACGGCCA GGACCGCGTC GGCGTACCGG TCGTCGGTGA
30001 GGAAGCGCTG CACGGCGGTC AGGACGCCGG CGCCCAGTTC GCGGGTGTCG TCGAGCGGGG
30061 CACCGCCGCC GCCGTGCGCG GGGAGGATCA CCACGTCCGG GACCGTCGGG TCGTCGAGGC
30121 GGCCGGTCGT CGCGGTCGTG GGCGGCAGCT CCGGGAGCTC GGCCAGCACC GGGCGCAGCA
30181 GGCCCGGAAC GGCTCCCGTG ATCGTCAGGG GGCGCCTGCG CACGGCGCCG ATGGTGGCGA
30241 CGGGCCCGCC GGTCTCGTCC CCGAGGTGTA CGCCGTCAGC GGTGACGGCG ACGCGTACCG
30301 CCGTGGCGCC GGTGGCGTGG ACGCGGACGT CGTCGAACGC GTACGGAAGG TGGTCCCCTT
30361 CCGCGGCGAG GCGGAGTGCG GCGCCGAGCA GCGCCGGGTG CAGGCCGTAC CGTCCGGCGT
30421 CGGCGAGCTG TCCGTCGGCG AGGGCCACTT CCGCCCAGAC GGCGTCGTCG TCGGCCCAGA
30481 CGGCGCGCGG GCGGGGCAGC GCGGGCCCGT CCGTGTACCC GGCTCGGGCC AGACGGTCGG
30541 CGATGTCGTC GGGGTCCACC GGCCGGGCCG TGGCGGGCGG CCACGTCGAC GGCATCTCCC
30601 GCACGGCCGG GGCCGTCCGC GGGTCGGGGG CGAGGATTCC GTGCGCGTGC TCGGTCCACT
30661 CCCCCGCCGC GTGCCGCGTG TGCACGGTGA CCGCGCGGCG GCCGTCCGCC CCGGGCGCGC
30721 TCACCGTGAC GGAGAGCGCC AGCGCACCGG ACCGCGGCAG CGTGAGGGGG GTGTCCACGG
30781 TGAACGTGTC GAGGGCGCCG CAGCCGGCTT CGTCGCCCGC CCGGATCGCC AGATCCAGGA
30841 GGGCCGCGGC GGGCAGCACC GCGAGGCCGT GCAGGGAGTG CGCCAGCGGA TCGGCGGCGT
30901 CGACCCGGCC GGTGAGCACC AGGTCGCCGG TGCCGGGCAG GGTGACCGCC GCGGTCAGCG
30961 CCGGGTGCGC GACCGGCGTC TGTCCGGCCG GGGCCGCGTC GCCCGCGGTC TGGGTGCCGA
31021 GCCAGTAGCG GACCCGCTCG AACGGGTACG TCGGCGGGTG CGAGGCGCGT GCCGGCGCGG
31081 GGTCGATGAC CTTCGGCCAG TCGACCGTGA CGCCGTCGGT GTGCAGCCGG GCGAGCGCGG
31141 TCAGGGCCGA TCGCGGTTCG TCGTCGGCCT GCAGCATCGG GATGCCGTCG ACGAGTCGGG
31201 TCAGGCTCCG GTCCGGGCCA ATCTCCAGGA GCACCGCCCC GTCGTGCGCG GCGACCTGTT
31261 CCCCGAACCG GACGGTGTCG CGGACCTGTC GTACCCAGTA CTCCGGCGTG GTGCAGGCGG
31321 CGCCCGCGGC CATCGGGATC CTCGGCTCGT GGTACGTCAG GCTCTCCGCG ACCTTGCGGA
31381 ACTCCTCGAG CATCGGCTCC ATCCGCGCCG AGTGGAACGC GTGGCTGGTC CGCAGGCGGG
31441 TGAAGCGGCC GAGCCGGGCC GCGACGTCGA GCACCGCCTC CTCGTCACCG GAGAGCACGA
31501 TCGACGCGGG CCCGTTGACC GCGGCGATCT CCACGCCGTC CGCAGCAGC GGCAGCGCGT
31561 CCCGTTCCGA CGCGATCACG GCGGCCATCG CCCCGCGGGA CGGCAGCGCC TGCATCAGGC
31621 GGGCCCGTGC GGACACCAGC CTGCACGCGT CCTCCAGGGA CCAGACGCCG GCGACGTACG
31681 CGGCGGCCAG CTCGCCGATC GAATGGCCCA CGAAGGCCTC CGGGCGTACG CCCCACGCCT
31741 CGAGCTGTGC GCCGAGTGCG ACCTGGAGCG CGAACACCGC GGGCTGGGCG TACCCGGTGT
31801 CGTGGAGGTC GAGCCCGGCG GGCACGTCGA GGGCGTCCAG CACCTCGCGG CGAGTGCGGG
31861 CGAAGACGTC GTAGGCGGCG GCCAGTCCGT CGCCCATGCC GGGACCTTGT GAGCCCTGTC
31921 CGGAGAAGAG CCACACGAGG CGGCGGTCCG GTTCTGCGGC GCCGGTGACC GTGTCGGTGC
31981 CGATCAGCGC GGCCCGGTGC GGGAAGGCCG TGCGGGCGAG CAGGGCCGCG GCCACCGCGC
32041 GCTCGTCCTC CTCGCCGGTG GCGAGGTGGG CGCGCAGGCG GTGTACCTGT GCGTCGAGTG
```

-continued

```
32101 CCTGCGGGGT GCGTGCCGAG AGCAGCAGGG GCAGCGGTCC GGTGTCGGGT GCCGGGGCGG
32161 GTTCGGGGGC CGGTCGGCGG TGGCTTTCGA GGATGATGTG AGCGTTGGTG CCGCTAACGC
32221 CGAAGGAGGA CACCCCGGCG CGCCGTGGGC GGTCGGTTTC GGGCCAGGGG CGGGCGTCGG
32281 TGAGGAGTTC GACGGCGCCG GCCGTCCAGT CGACGTGCGA GGACGGCGTG TCCACGTGCA
32341 GGGTGCGCGG CAGGGTGCCG TGCCGCATGG CGAGGACCAT CTTGATGACA CCGGCGACGC
32401 CCGCGGCGGC CTGAGTGTGG CCGATGTTGG ACTTCAGCGA GCCCAGCAGC ACCGGGGTGT
32461 CGCGATGCTG CCCGTAGGTG GCCAGTACCG CCTGCGCCTC GATGGGGTCG CCCAGCCTGG
32521 TCCCGGTGCC ATGCGCCTCG ACAGCGTCCA CATCCGCCGG GGTGAGCCCG GCGTTGGCCA
32581 GCGCCTGCCG GATCACCCGC TCCTGCGACG GCCCGTTCGG CGCCGACAAC CCGTTGGAAG
32641 CACCGTCCTG GTTGACCGCC GAACCACGCA CGACCGCCAG GACATTGTGG CCGTGCCGCT
32701 CGGCGTCGGA GAGCCTCTCG ACGATCAGCA CACCGGATCC CTCGGCGAAA CCGGTGCCAT
32761 CAGCCGCATC CGCGAACGCC TTGCAGCGGC CGTCCGGGGA GAGGCCCCGC TGCTGGGAGA
32821 AGTCCACGAA GCCGGACGGC GAGGCCATCA CCGTGACGCC GCCGACCACG CCGAGCGAGC
32881 ACTCCCCCGA GCGCAGCGAC TGCCCGGCCT GGTGCAGCGC CACCAGCGAC GACGAACACG
32941 CCGTGTCCAC CGTGACCGCC GGACCCTCCA AACCGTAGAA GTACGACAGC CGACCGGACA
33001 GCACACTGGT CTGGGTGCTG GTGGCACCGA AACCGCCGCG GTCGGCTCCA GTGCCGTACC
33061 CGTAGAAGTA GCCGCCCATG AACACGCCGG TGTCGCTTCC GCGCAGCGAC TCCGGGAGGA
33121 TCCCGGCGTG TTCCAGCGCC TCCCACGAGG TCTCCAGGAC CAGACGCTGC TGCGGGTCCA
33181 TCGCCAGCGC CTCACGCGGA CTGATCCCGA AGAACGCCGC GTCGAAGTCC GCCACCCCGG
33241 CGAGGAAGCC ACCATGACGC ACGGTCGACG TGCCCGGATG ATCCGGATCG GGATCGTACA
33301 GCCCGTCCAC GTCCCAACCA CGGTCCGTCG GAAACGCCGT GATCCCGTCA CCACCCGACT
33361 CCAGCAGCCG CCACAAGTCC TCCGGCGACG CGACCCCACC CGGCAGCCGG CAGGCCATCC
33421 CCACGATCGC CAACGGCTCG TCCTGCCGGA CGGCCGCGGT CGGGGTACGC CGCCGGGTGG
33481 TGGCCCGCGC GCCGGCCAGT TCGTCCAGGT GGGCGGCGAG CGCCTGCGCC GTGGGGTGGT
33541 CGAAGACGAG CGTAGCGGGC AGCGTCAGGC CCGTCGCGTC GGCCAGCCGG TTGCGCAGTT
33601 CGACGCCGGT CAGCGAGTCG AAGCCCACTT CCCTGAACGC GCGCGCGGGT GCGATGGCGT
33661 GGGCGTCGCG GTGGCCGAGC ACCGCGGCAG CGCTGGTACG GACGAGGTCG AGCATGTCGC
33721 GCGCGGCCGG AGGTGCGGAC GTGCGCCGGA CGGCCGGCAC GAGGGTGCGT AGGACCGGCG
33781 GGACCCGGTC GGACGCGGCG ACCGCGGCGA GGTCGAGCCG GATCGGCACG AGCGCGGCCC
33841 GGTCGGTGTG CAGGGCCGCG TCGAACAGGG CGAGCCCCTG TGCGGCCGTC ATCGGGGTCA
33901 TGCCGTTGCG GGCGATGCGG GCCAGGTCGG TGGCGGTCAG CCGCCCGCCC ATCCCGTCCG
33961 CCGCGTCCCA CAGTCCCCAG GCGAGCGAGA CGGCGGGCAG CCCCTGGTGG TGCCGGTGGC
34021 GGGCGAGCGC GTCGAGGAAC GCGTTGCCGG TCGCGTAGTT GGCCTGACCC GCGCCGCCGA
34081 ACGTGGCGGA TATGGACGAG TACAGGACGA ACGCGGCCAG GTCGAGATCG CGCGTCAGCT
34141 CGTGCAGGTG CCAGGCGACG TCCGCCTTGA CCCGCAGCAC GGCGTCCCAC TGCTCCGGCC
34201 GCATGGTCGT CACGGCCGCG TCGTCGACGA TCCCGGCCAT GTGCACGACG GCGCGCAGCC
34261 GCTGGGCGAC GTCGGCGACG ACTGCGGCCA GCTCGTCGCG GTCGACGACG TCGGCGGCCA
34321 CGTACCGCAC GCGGTCGTCC TCCGGCGTGT CGCCGGGCCG GCCGTTGCGG GACACCACGA
34381 CGACCTCGGC GGCCTCGTGC ACGGTGAGCA GGTGGTCCAC GAGGAGGCGG CCGAGCCCGC
34441 CGGTGCCGCC GGTGACGAGG ACGGTCCCGC CGGTCAGCGG GGAGGTTCCG GTGGCCGCGG
```

-continued

```
34501 CGACACGGCG CAGACGGGCC GCACGCGCTG TGCCGTCGGC GACCCGGACG TGCGGCTCGT
34561 CGCCGGCGGC GACCCCGGCC GCTATGGCGG CGGGCGTGAT CTCCTCCGCT TCGATCAGGG
34621 CGACGCGGCC GGGATGCTCC GTCTCCGCCG TCCGGACCAG GCCGCCGAGC GCTTCCTGCG
34681 CGGGATCGCC GGTACGGGTG GCCACGATGA GCCGGGATCG CGCCCAGCGC GGCTCGGCGA
34741 GCCAGGTCTG CACGGTGGTG AGCAGGTCGC GGCCCACCTC CCGGGTCCGG GCGCCCGGCG
34801 AGGTGCCCGG GTCGCCGGGT TCCACGGCCA GGACCACGAC CGGGGGGTGC TCGCCGTCGG
34861 GCACGTCGGC GAGGTACGTC CAGTCGGGGA CGGGTGACGG GGGCACGGGC ACCCAGGCGA
34921 TCTCGAACAG CGCCTCGGCA TCGGGGTCGG CGGCCCGCAC GGTCAGGCTG TCGACGTCAA
34981 GGACCGGTCA GCCGTGCTCG TCCGTGGCGA CGATGCGGAC CATGTCGGGG CCGACGCGTT
35041 CCAGCAGCAC GCGCAGCGCG GTCGCGGCGC GCGCGTGGAT CCTCACGCCG GACCAGGAGA
35101 ACGCCAGCCG GCGCCGCTCC GGGTCCGTGA AGACCGTCCC GAGGGCGTGC AGGGCCGCGT
35161 CCAGCAGCAC GGGCTGCAGC CCGTACCGGG CGTCGCTGAG CTGTTCGGCG AGGCGGACCG
35221 ACGCGTAGCC GCGGCCCTCC CCCGTCCACA TCGCGGTCAT GGCCCGGAAC GCGGGCCCGT
35281 ACGAGAGCGG CAGCGCGTCG TAGAAGCCGG TCAGGTCGGC CGGCTCGGCG TCGGCGCGCG
35341 GCCAGTCCAC GGGCTCCGCC GGACCGCCAG TGTCCACGCT CAGCGCTCCG GTCGCACTGA
35401 GCGCCCAGGG GCCCGTGCCG GTACGGCTGT GCAGACTCAC CGACCGCCGT CCGGACACCT
35461 CGGTTCCGAC GGTGGCCTGG ATCTCCGTGT CGCCGTCGCC GTCGACCACC ACCGCCGCGA
35521 CGATGGTCAG CTCCGCCATC TCCGGCGTGC CGAGCCGGGC TCCCGCTTCG GCGAGCAGTT
35581 CCACGAGCGC CGAGCCGGGC ACGATGACCC GGCCGTCCAC CTCGTGGTCG GCGAGCCAGG
35641 GCTGACGGCG TACCGAGACA CCGCGGTGGC CAGCGCGCCC TCGCCGTCGG GCGAGGTCGA
35701 CCCACGAGCC GAGCAGCGGG TGGCCGGACG TTCCCCCCGG TTCCGCGTCG ATCCAGTACC
35761 GGTCACGGCG GAACGGGTAC GTGGGCAGCG GCACCACCCG ACGCGTCGCG AACGACCAGG
35821 TGACGGGCAC GCCCCGGACC CAGAGCGCGG CGAGCGACCG AGTGAAGCGG TCCAGGCCGC
35881 CCTCGCCTCG CCGCAGTGTG CCGGTGACGA CCGTATGCGC ATGCCCGGCG AGCGTGTCCT
35941 CCAGTGCGGT GCTGACCACG GGATGCCCGC TGACCTCCAC CAACGCGCGG TATCCGCGGT
36001 CCGCCAGGTG GCCGGTCGCG GCGGCGAACC GAACGGTGCG GCGCAGGTTG TCGTACCAGT
36061 AGGCGGCGTC CGCGGGCCGG TCCAGCCACG CCTCGTCCAC GGTGGAGAAG AACGGGACGT
36121 CCGGCGTGCG CGCAGTGATG CCGGCGAGAG CGTCGAGCAG CGCGCCGCGG ATCGTTTCGA
36181 CATGCGCGGT GTGCGACGCG TAGTCGACGG CGATCCGGCG GGCGCGGGGG GTGGCGGCCA
36241 GCAGCTCCTC CACGGCGTCG GCCGCACCGG CGACAACGAT CGACGCGGGT CCGTTGACCG
36301 CGGCGACCTC CAGGCGCCCG GCCCACACGG CGGCGTCGAA GTCGGCGGGC GGCACCGAGA
36361 CCATGCCGCC CTGCCCGGCC AGTTCGGTGG CGACGAGTCG GCTGCGCACC GCGACGACCT
36421 TCGCGGCGTC GTCCAGGGTG AGCACCCCGG CGACGCAGGC GCGGCGACT TCGCCCTGGG
36481 AGTGGCCGAC GACCGCGGCC GGGGCGACCC CGTGCGCACG CCACAGCTCC GCCAGCGCCA
36541 CCATCACCGC GAACGACGCG GGCTGCACGA CATCGACCCG GTCGAACGCG GGCGCTCCGG
36601 GCCGCTGGGC GATGACGTCC AGCAGGTCCC ATCCGGTGTG CGGGGCGAGC GCCGTGGCGC
36661 ACTCGCGGAG CCGCCGGGCG AACACGGGCT CGGTGGCGAG CAGTTCGGCA CCCATGCCGG
36721 CCCACTGGGA GCCCTGCCCG GGGAACGCGA ACACGACACG TGTGTCGGTG ACGTCGGCGG
36781 TTCCCGTCAC GGCCCCCGGC ACTTCGGCAC CACGGGCGAA CGCCTCCGCC TCTCGGGCCG
36841 GCACGACCGC CCGGTGGCGC ATGGCCGTCC GGGTGGTGGC GAGCGAGTGG CCGACCGCGG
```

```
36901 CCGCGGCGCC AGTGAGCGGG GCCAGCTGTC CCGCGACGTC CCGCAGTCCC TCCGGGGTCC
36961 GGGCCGACAT CGGCCAGACC ACGTCCTCGG GCACCGGCTC GGCTTCGGGT GCGGACACGG
37021 GTGCGGGCGC GGCGGGGGGC CCGGCCTCCA GGACGACATG GGCGTTGGTG CCGCTGATGC
37081 CGAACGACGA GACACCCGCA CGCCGGGCGC GCCCGGTGAC CGGCCACGGC TCACTGCGGT
37141 GCAGCAGCCG GATCTCGCCG TCCCAGTCGA CGTGCCGGGA CGGCTCGTCG ACGTGCAGCG
37201 TGCGCGGCAG GACGCCGTGC CGCATCGCCA TGACCATCTT GATGACGCCG GCGACGCCGG
37261 CCGCGGCCTG GGTGTGGCCG ATGTTCGACT TGAGCGAGCC GATCAGCAGC GGATGCACGC
37321 GTTCGCGCCC GTAGGCCACT TGCAGGGCCT GGGCCTCGAC GGGGTCGCCG AGACGGGTGC
37381 CGGTGCCGTG TGCCTCCACG GCGTCGACGT CACCCGGCGC CAGGCCGGCG TCGGCGAGCG
37441 CACGCTGGAT GACGCGCTGC TGCGCAGGCC CGTTCGGGGC GGACAGCCCG TTCGACGCGC
37501 CGTCGGAGTT GACCGCGGAG CCGCGCACCA GCGCCAGCAC GGGGTGGCCG TGGCGGGTGG
37561 CGTCGGAGAG CCGCTCCAGC ACCAGGACAC CGGCGCCCTC GGCGAAGCTC GTGCCGTCCG
37621 CGGTGTCCGC GAAGGCCTTG GCACGGCCGT CGGGGGCGAG CCCGCGCTGC CGGGAGAACT
37681 CGACGAACCC GGTCGTCCTC GCCATCACCG TGACACCGCC GACCAGGGCG AGCGAGCACT
37741 CCCCCGAGCG CAGCGACCGC GCGGCCTGGT GCAGCGCCAC CAGCGACGAC GAACACGCCG
37801 TGTCGACGGT GACCGACGGG CCCTCCAGAC CGAAGTAGTA CGAGAGCCGC CCGGAGAGAA
37861 CGCTGGTCGC CGTGCCGCTC GCCCCGAAAC CGCCCAGGTC CACGCCCGCG CCGTAGCCCT
37921 GGGTGAACGC GCCCATGAAT ACGCCGGTGT CGCTGCCGCG GACGCTTTCG GGCAGGATGC
37981 CCGCTCGTTC GAACGCCTCC CACGACGCTT CGAGGACCAG ACGCTGCTGC GGGTCCATCG
38041 CCAGCGCCTC ACGCGGGCTG ATCCCGAAGA ACGCGGCGTC GAAGTCGGCG GCGCCGGTGA
38101 GGAAGCCGCC GTGACGCACG GAAACCTTGC CGACCGCGTC GGGGTTCGGG TCGTAGAGCG
38161 CCGCGACCTC CCAGCCCCGG TCCGCGGGGA ACTCGGTGAT CGCGTCCCCG CCGGAGTCGA
38221 CCAGCCGCCA CAGGTCCTCC GGTGACCGCA CGCCACCGGG CATCCGGCAC GCCATGGCCA
38281 CGATCGCCAG CGGCTCGTTC CCCGCCACCG TCGGTGCGGG CACTGTCGCC GCCGGAGCGG
38341 CAGGGCCCGG CTCACCCCGC CGTTCCTCAT CCAGGCGGGC GGCGAGCGCG GCCGGTGTCG
38401 GGTGGTCGAA GACGGCCGTC GCGGAGAGCC GTACCCCCGT CGTCTCGGCG AGGCTGTTGC
38461 CCAACCGGAC ACCGCTGAGC GAGTCGATGC CGAGGTCCTT CAACGCCGTC GTGGGCGTGA
38521 TCTCGGAGGC GTCGGCGTGG CCGAGCACGG CGGCCGTGGC CGCACACACG ATGGCCAGCA
38581 GGTCACGATC GCGGTCGCGG TCGCGGTCGC GGTTCTCCTC CGCACCGGCC GCGATGCGGC
38641 GCTCGGTCCG CTGCCGGACC GGCTCGGTGG GAATCGCCGC GACCATGAAC GGCACGTCCG
38701 CGGCGAGGCT CGCGTCGATG AAGTGGGTGC CCTCGGCCTC GGTGAGCGGC CGGAACCCGT
38761 CGCGCACCCG CTGCCGGTCG GCGTCGTCAA GTTGTCCGGT GAGGGTGCTG CTGGTGTGCC
38821 ACATGCCCCA GGCGATGGAC GTGGCGCCTT GCCCGAGGGT GTGCCCGTCG GTGCCGACGG
38881 CGTCGAGGAA GGCGTTGGCG GCGGCGTAGT TTCCTTGTCC GGGGCTGCCG AGGACGGCGG
38941 CGGCGCTGGA GTAGAGGACG AAGTGGGTGA GGGGTTGGTT TTGGGTGAGG TGGTGCAGGT
39001 GCCAGGCGGC GTTGGCTTTG GGGTGGAGGA CGGTGGTGAC GCGGTCGGGC GTGAGGGCGT
39061 CGAGGATGCC GTCGTCGAGG GTGGCGGCGG TGTGGAAGAC GGCGGTGAGG GGTTGGGGGA
39121 TGTGGGCGAG GGTGGTGGCG AGTTGGTGGG GGTCGCCGAC GTCGCAGGGG AGGTGGGTGC
39181 CGCGGGTGGT GTCGGGGGGT GGGGTGCGGG ACAGGAGGTA GCTCTGCGGG TGGTTCAGGT
39241 GGCGGGCGAG GATGCCGGCG AGGGTGCCGG AGCCGCCGGT GATGATGATG GCGTGTTCGG
```

-continued

```
39301 GCTTGAGGGG GGTGGTGGTC GGTGGGGTGG TGGTGTGGAG GGGGGTGAGG TGGGGTCGGT
39361 GGAGGGTGTG GTGGGTGAGG CGGAGGTGGG GGTGGTCGAG GGTGGCGAGT TGGGCCAGGG
39421 GCAGGCGAGT CTCGGGGTGG TCGGTTTCGA TGACGCGGAT GCGGTGGGGG TGTTCGTTCT
39481 GGGCGCTGCG GGTGAGGCCG GTGACGGTGG CGCCGGCGGG GTCGGTGGTG GTGTGGACGA
39541 TGAGGGTGTG GTCGGTGGTG GTGAGGTGGT GTTGCAGGCC GGTCAGGACG CGGGTGGCGC
39601 GGGTGTGCGC GCGGCTGGCT ATGTCCTCGG GGTCGTCGGG GTGGGCGGCG GTGATCAGGA
39661 CGTGTCCCTC GGGCAGGTCA CCGTCGTAGA CCGCCTCGGC GACCGCGAGC CACTCCAACC
39721 GGAGCGGGTT CGGCCCCGAC GGGGTGTCGG CCCGCTCCCT CAGCACCAGC GAGTCCACCG
39781 ACACGACAGG ACGGCCATCC GGGTCGGCCA CGCGCACGGC GACGCCGGCC TCCCCCCGGG
39841 TGAGGGCGAC GCGCACCGCG GCGGCCCCGG TGGCGTTCAG GCGCACGCCC GTCCAGGAGA
39901 ACGGCAGCTC GATCCCGCCG CCCGCGTCGA GGCGCCCGGC GTGCAGGGCC GCGTCGAGCA
39961 GTGCCGGATG CACACCGAAA CCCTCCGCCT CCGCCGCCTC CTCGTCGGGC AGCGCCACCT
40021 CGGCATACAC GGTGTCACCA TCACGCCAGG CAGCCCGCAA CCCCTGGAAC GCCGACCCGT
40081 ACTCATAACC GGCATCCCGC AGTTCGTCAT AGAACCCCGA CGTCGACG GCCGCGGCCG
40141 TGGCCGGCGG CCACTGCGAG AACGGCTCAC CGGAAGCGTT GGAGGTATCC GGGGTGTCGG
40201 GGGTCAGGGT GCCGCTGGCG TGCCGGGTCC AGCTGCCCGT GCCCTCGGTA CGCGCGTGGA
40261 CGGTCACCGG CCGCCGTCCG GCCTCATCGG CCCCTTCCAC GGTCACCGAC ACATCCACCG
40321 CTGCGGTCAC CGGCACCACG AGCGGGGATT CGATGACCAG TTCATCCACC ACCCCGCAAC
40381 CGGTCTCGTC ACCGGCCCGG ATGACCAGCT CCACAAACGC CGTACCCGGC AGCAGAACCG
40441 TGCCCCGCAC CGCGTGATCA GCCAGCCAGG GATGCGTACG CAATGAGATC CGGCCGGTGA
40501 GAACAACACC ACCACCGTCG TCGGCGGGCA GTGCTGTGAC GGCGGCCAGC ATCGGATGCG
40561 CCGCCCCGGT CAGCCCGGCC GCGGACAGGT CGGTGGCACC GGCCGCCTCC AGCCAGTACC
40621 GCCTGTGCTC GAACGCGTAG GTGGGCAGAT CCAGCAGCCG CCCCGGCACC GGTTCGACCA
40681 CCGTGCCCCA GTCCACCCCC GCACCCAGAG TCCACGCCTG CGCCAACGCC CCCAGCCACC
40741 GCTCCCAGCC ACCGTCACCA GTCCGCAACG ACGCCACCGT GCGGGCCTGT TCCATCGCCG
40801 GCAGCAGCAC CGGATGGGCA CTGCACTCCA CGAACACCGA CCCGTCCAGC TCCGCCACCG
40861 CCGCATCCAG CGCGACAGGG CGACGCAGGT TCCGGTACCA GTACCCCTCA TCCACCGGCT
40921 CGGTCACCCA GGCGCTGTCC ACGGTCGACC ACCACGCCAC CGACCCGGTC CCGCCGGAAA
40981 TTCCCTTCAG TACCTCAGCG AGTTCGTCCT CGATGGCCTC CACGTGAGGC GTGTGGGAGG
41041 CGTAGTCGAC CGCGATACGA CGCACCCGCA CCCCATCAGC CTCATACCGC GCCACCACCT
41101 CCTCCACCGC CGACGGGTCC CCCGCCACCA CCGTCGAAGC CGGACCATTA CGCGCCGCGA
41161 TCCACACACC CTCGACCAGA CCCACCTCAC CGGCCGGCAA CGCCACCGAA GCCATCGCCC
41221 CCCGGCCGGC CAGCCGCGCC GCGATCACCC GACTGCGCAA CGCCACCACG CGGGCGGCGT
41281 CCTCCAGGCT GAGGGCTCCG GCCACACACG CCGCCGCGAT CTCCCCCTGC GAGTGTCCGA
41341 CCACAGCGTC CGGCACGACC CCATGCGCCT GCCACACCGC GGCCAGGCTC ACCGCGACCC
41401 CCCAGCTGGC CGGCTGGACC ACCTCCACCC GCTCCGCCAC ATCCGACCGC GACAACATCT
41461 CCCGCACATC CCAGCCCGTG TGCGGCAACA ACGCCCGCGC ACACTCCTCC ATACGAGCCG
41521 CGAACACCGC GGAACGGTCC ATGAGTTCCA CGCCCATGCC CACCCACTGG GCACCCTGCC
41581 CGGGGAAGAC GAACACCGTA CGCGGCTGAT CCACCGCCAC ACCCATCACC CGGGCATCAC
41641 CCAGCAGCAC CGCACGGTGA CCGAAGACAG CACGCTCACG CACCAACCCC TGCGCGACCG
```

-continued

```
41701 CGGCCACATC CACCCCACCC CCGCGCAGAT ACCCCTCCAG CCGCTCCACC TGCCCCCGCA
41761 GACTCACCTC ACCACGAGCC GACACCGGCA ACGGCACCAA CCCATCACCA CCCGACTCCA
41821 CACGCGACGG CCCAGGAACA CCCTCCAGGA TCACGTGCGC GTTCGTACCG CTCACCCCGA
41881 ACGACGACAC ACCCGCATGC GGTGCCCGAT CCGACTCGGG CCACGGCCTC GCCTCGGTGA
41941 GCAGCTCCAC CGCACCGGCC CACCAGTCCA CATGCGACGA CGGCTCGTCC ACGTGCAGCG
42001 TCTTCGGCGC GATCCCATGC CGCATCGCCA TGACCATCTT GATGACACCG GCGACACCCG
42061 CAGCCGCCTG CGCATGACCG ATGTTCGACT TGACCGAACC GAGGTAGAGC GGCGTGTCGC
42121 GGTCCTGCCC GTAGGCCGCG AGGACGGCCT GCGCCTCGAT CGGGTCGCCC AGCCGCGTGC
42181 CGGTGCCGTG CGCCTCCACC ACGTCCACAT CGGCGGCGCG CAGTCCGGCG TTGACCAACG
42241 CCTGCCGGAT CACGCGCTGC TGGGCGACGC CGTTGGGGGC GGACAGTCCG TTGGAGGCAC
42301 CGTCCTGGTT CACCGCCGAG CCGCGGACGA CCGCGAGAAC GGTGTGCCCG TTGCGCTCGG
42361 CGTCGGAGAG CCGCTCCAGC ACGAGAACGC CGACGCCCTC GGCGAAGCCG GTCCCGTCCG
42421 CCGCGTCGGC GAACGCCTTG CACCGTCCGT CCGGGGAGAG TCCGCGCTGC CGGGAGAACT
42481 CCACGAGCTC TGCGGTGTTC GCCATGACGG TGACACCGCC GACCAGCGCC AGGGAGCACT
42541 CCCCGGCCCG CAGTGCCTGT GCCGCCTGGT GCAGGGCGAC CAGCGACGAC GAGCACGCCG
42601 TGTCGACCCT GACCGCCGGG CCCTGAAGTC CGTACACGTA CGAGAGGCGC CCGGACAGGA
42661 CGCTCGTCTG CGTCGCCGTG ACACCGAGCC CGCCCAGGTC CCGGCCGACG CCGTAGCCCT
42721 GGTTGAACGC GCCCATGAAC ACGCCGGTGT CGCTCTCCCG GAGCCTGTCC GGCACGATGC
42781 CGGCGTTCTC GAACGCCTCC CAGGAGGTCT CCAGGATCAG GCGCTGCTGG GGGTCCATCG
42841 CCAGCGCCTC GTTCGGACTG ATGCCGAAGA ACGCGGCGTC GAACCCGGCG CCGGCCAGGA
42901 ATCCGCCGTG GCGTGTCGTG GAGCGGCCGG CCGCGTCCGG GTCCCGGTCG TACAGCGCGT
42961 CGACGTCCCA GCCCCGGTCG GTGGCGAACT CGGTGATCGC CTCGGTACCG GCGGCGACGA
43021 GCCGCCACAG GTCCTCCGGC GAGGCGACCC CGCCGGGCAG TCGGCACGCC ATGCCGACGA
43081 TCGCGACGGG GTCGCCGGAG CCGAGGGTCT GGGCGGTCGC GGGTGCCGCT GTCGCGGAGC
43141 CGGCGAGGTG GGCGGCGAAC GCACGCGGAG TGGGGTGGTC GAACGCGGTT GACGCGGGCA
43201 CCCGCAGACC CGTCCGCGCG GCGACGGTGT TGGTGAACTC GACGGTGGTG AGCGAGTCGA
43261 GGCCGTTCTC GCGGAACGTG CGGTCCGGGG AGCAGTGTCC GGCGCCCGGC AGGCCCAGGA
43321 CGGTGGCGAC GCTGTCGCGG ACCAGGTCGA GCAGTACGTC CTCCCGGCCC GCACGGGCCG
43381 CGGCGAGGCG GTTCGCCCAC TCCTGTTCCG TGGCGTCGGG CTCGGCCGGT CCGGTCAGTG
43441 CGGTGAGGAT CGGCGGCGTG GCGCCCGCCA TCGTCGCGGC CCGCGCCCCG GCGGAACCGG
43501 TCCGGGCCAC GATGTACGAG CCGCCGCCCG CGATGGCCTT CTCGATCAGC TCGCCGGTGA
43561 GCGCCGGCCG TTCGATGCCG GGCAGCGCGC GGACGGTGAC GGTGGGGAGT CCCTCCGCGG
43621 CCCGTGGCCG GGTGTGGGCG TCGGCGCCGG CCGGGCCGTC GAGCAGGACG TGCACGAGCG
43681 CGCCGGGGTT CGCGGCTTCC TCGGCTGCGG TGGTCACGTG GGTGAGGCCG GTCTCGTCGC
43741 GCAGCAGGCC GGCGACGGTG TCGGCGTCCT CCCCGGTGAC CAGGACCCGC GCGTCCGGGC
43801 CGATCGGAGG CGGCACGGTG AGGACCATCT TGCCGGTGTG CCGGGCGTGG CTCATCCACG
43861 CGAACGCGTC CCGCGCACGG CGGATGTCCC ACGGCTGCAC CGGCAGCGGG CACAGCTCAC
43921 CGCGGTCGAA CAGGTCGAGG AGCAGTTCGA GGATCTCCCG CAGGCGCGCG GGATCCACGT
43981 CGGCCAGGTC GAACGGCTGC TGGGCGGCGT GGCGGATGTC GGTCTTGCCC ATCTCGACGA
44041 ACCGGCCGCC CGGTGCGAGC AGGCCGATGG ACGCGTCGAG GAGTTCACCG GTGAGCGAGT
```

-continued

```
44101 TGAGCACGAC GTCGACCGGC GGGAAGGTGT CGGCGAACGC GGCGCTGCGG GAGTTCGCCA
44161 CATGGTCGGT GTCGAAGCCG TCGGCGTGCA GCAGGTGTTG TTTGGCGGGA CTGGCGGTGG
44221 CGTACACCTC GGCGCCGAGG TGGCGGGCGA TCCGGGTCGC CGCCATGCCG ACACCGCCCG
44281 TCGCGGCGTG GACCAGGACC TTCTGGCCGG GTCGCAGCTC GCCCGCGTCG ACGAGGCCGT
44341 ACCAGGCGGT GGCGAACACG ATGGGCACGG ACGCGGCGAT GGGGAACGAC CATCCCCGTG
44401 GGATCCGTGC GACCAGCCGC CGGTCCGCGA CCACGCTGCG CCGGAACGCG TCCTGCACGA
44461 GACCGAACAC GCGGTCGCCG GGGGCCAGGT CGTCGACGCC GGGTCCGACT TCGGTCACGA
44521 TGCCCGCGGC CTCCCCGCCC ATCTCGCCCT CGCCCGGGTA GGTGCCGAGC GCGATCAGCA
44581 CGTCGCGGAA GTTCAGCCCC GCGGCGCGGA CGTCGATGCG GACCTCGCCG GCGGCCAGGG
44641 GCGCGGCGGG ACGTCGAGCG GGGCGACGAC GAGGTCGCGG AGCGTTCCGG AGGCGGGCGG
44701 GCGCAGCGCC CACTGGCGCG GTCGGCAGGG GGGTGGTGTC CGCGCGTACC AGCCGGGGCA
44761 CGTAGGCCAC GCCGGCCCGC AGCGCGATCT GGGGTTCGCC GAGCGAGGCC GCGGCGGGGA
44821 CGAGCTCGTC ATCGCCGTCC GTGTCCACCA GCACGAACGA TCCGGGTTCG GCGGCCTGGC
44881 GGCGCAGCGC CTCGTCCCAG AGCCGGGCCT GGTCCGCGTC CGGGATCTCG GCCGGGCCGA
44941 CGCCCACCGC GCGGCGGGTG ACGACCGTCC GGCGGGGTGA CGGGGTGCCG GGCAGGTCGC
45001 GCCGCTCCCA GACCAGTTCG CACAGCGTCG CCTCGCCACT GCCGCTGGCG ACCAGATGGG
45061 CCGGCAGCCC CGCGAGCCGC GCGCGCTGGA CCTTGCCCGA CGCGGTGCGG GGGATCGTGG
45121 TGACGTGCCA GATCTCGTCG GGCACCTTGA AGTAGGCGAG CCGGCGGCGG CACTCGGCGA
45181 GGATCGCCTC GGCGGGGACG CGGGGGCCGT CGGAAACGAC GTAGAGCACG GGTATGTCGC
45241 CGAGGACGGG GTGCGGGCGG CCCGCCGCGG CGGCGTCCCG GACACCGGCC ACCTCCTGGG
45301 CGACGGTCTC GATCTCCCGG GGGTGGATGT TCTCCCCGCC GCGGATGATC AGCTCCTTGA
45361 CCCGGCCGGT GATCGTCACG TGTCCGGTCT CGGCCTGACG TGCGAGGTCC CCGCTGCGGT
45421 ACCAGCCGTC CACGAGCACC TGCGCGGTCG CCTCCGGCTG GCCGTGGTAG CCGAGCATGA
45481 GGCTCGGCCC GCTCGCCCAC AGCTCGCCCT CCTCGCCGGG TGCCACGTCG GCGCCGGACA
45541 CCGGGTCGAC GAACCGCAGC GACAGGCCCG GCACGGGCAG CCCGCACGAG CCGGGAACCC
45601 GCGCATCCTC CAGGGTGTTG GCGGTGAGCG AGCCGGTCGT CTCGGTGCAG CCGTACGTGT
45661 CGAGCAGGGG CACGCCGAAC GTCGCCTCGA AATCCCTGGT GAGCGACGCC GGCGAGGTGG
45721 ATCCGGCGAC CAGCGCCACG CCCAGCGCGC GAGCCCGCGG CTCGCCGGAC ACGGCGCCGA
45781 GGAGGTAGCG GTACATCGTC GGCACGCCGA CGAGCACGGT GCTGGAGTGT TCGGCCAGGG
45841 CGTCGAGGAC GTCACGCGCG ACGAAGCCGC CCAGGATACG GGCGGACGCG CCGACCGTGA
45901 GGACGGCGAG CAGGCAGAGG TGGTGGCCGA GGCTGTGCAA CAGCGGGGCG GGCCAGAGCA
45961 GTTCGTCGTC CTCGGTCAGC CGCCAGGACG GCACGTCGCA GTGCATCGCG GACCACAGGC
46021 CGCTGCGCTG TGCGGAAACC ACGCCCTTGG GACGGCCGGT GGTGCCGGAG GTGTAGAGCA
46081 TCCAGGCGGG TTCGTCCAGG CCGAGGTCGT CGCGGGGCGG GCACGGCGGC TCGGTCCCGG
46141 CGAGGTCCTC GTAGGAGACG CAGTCCGGTG CCCGGCGCCC GACCAGCACG ACGGTGGCGT
46201 CGGTGCCGGT GCGGCGCACC TGGTCGAGGT GGGTTTCGTC GGTGACCAGC ACGGTCCCGC
46261 CGGAGTCCGT CAGGAAGTGG GCGAGTTCGG CGTCGGCGGC GTCCGGGTTG AGCGGGACGG
46321 CGACGGCGGC GGCGCGGGCG GCGGCGAGGT AGACCTCGAT GGTCTCGATC CGGTTGCCGA
46381 GCAGCATCGC GACCCGGTCG CCGCGGTCGA CGCCGGACGC GGCGACGTGT CCGGCGAGCC
46441 GCCCGGCCCG GAGCCGGAGT TGCGTGTACG TCACGGCGCG TTGGGAATCC GTGTAGGCGA
```

-continued

```
46501 TCCGGTCGCC GCGTCGCTCG GCATGGATGC GGAGCAATTC GTGCAACGGC CGGATTGGTT
46561 CCACACGCGC CATGGAAACA CCTTTCTCTC GACCAACCGC ACAACAGCAC GGAACCGGCC
46621 ACGAGTAGAC GCCGGCGACG CTAGCAGCGT TTTCCGGACC GCCACCCCCT GAAGATCCCC
46681 CTACCGTGGC CGGCCTCCCC GGACGCTCAT CTAGGGGGTT GCACGCATAC CGCCGTGCGT
46741 AATTGCCTTC CTGATGACCG ATGCCGGACG CCAGGGAAGG GTGGAGGCGT TGTCCATATC
46801 TGTCACGGCG CCGTATTGCC GCTTCGAGAA GACCGGATCA CCGGACCTCG AGGGTGACGA
46861 GACGGTGCTC GGCCTGATCG AGCACGGCAC CGGCCACACC GACGTGTCGC TGGTGGACGG
46921 TGCTCCCCGG ACCGCCGTGC ACACCACGAC CCGTGACGAC GAGGCGTTCA CCGAGGTCTG
46981 GCACGCACAG CGCCCTGTCG AGTCCGGCAT GGACAACGGC ATCGCCTGGG CCCGCACCGA
47041 CGCGTACCTG TTCGGTGTCG TGCGCACCGG CGAGAGCGGC AGGTACGCCG ATGCCACCGC
47101 GGCCCTCTAC ACGAACGTCT TCCAGCTCAC CCGGTCGCTG GGGTATCCCC TGCTCGCCCG
47161 GACCTGGAAC TACGTCAGCG GTATCAACAC GACGAACGCG GACGGGCTGG AGGTGTACCG
47221 GGACTTCTCC GTGGGCCGCG CCCAGGCGCT CGACGAGGGC GGGATCGACC CGGCCACCAT
47281 GCCCGCGGCC ACCGGTATCG GCGCCCACGG GGGCGGCATC ACCTGCGTGT TCCTCGCCGC
47341 CCGGGGCGGA GTGCGGATCA ACATCGAGAA CCCCGCCGTC CTCACGGCCC ACCACTACCC
47401 GACGACGTAC GGTCCGCGGC CCCCGGTCTT CGCACGGGCC ACCTGGCTGG GCCCGCCGGA
47461 GGGGGGCCGG CTGTTCATCT CCGCGACGGC CGGCATCCTC GGACACCGAA CGGTGCACCA
47521 CGGTGATGTG ACCGGCCAGT GCGAGGTCGC CCTCGACAAC ATGGCCCGGG TCATCGGCGC
47581 GGAGAACCTG CGGCGCCACG GCGTCCAGCG GGGGCACGTC CTCGCCGACG TGGACCACCT
47641 CAAGGTCTAC GTCCGCCGCC GCGAGGATCT CGATACGGTC CGCCGGGTCT GCGCCGCACG
47701 CCTGTCGAGC ACCGCGGCCG TCGCCCTTTT GCACACCGAC ATAGCCCGCG AGGATCTGCT
47761 CGTCGAAATC GAAGGCATGG TGGCGTGACA ATACCCGGTA AAAGGCCCGC GACGCTGCGC
47821 CTCGGCGGAT CCGCGAAGAG AAAGAAGAGC GTCACCGCAC AGCGCGGCAG CCCGGTCCTT
47881 TCGTCCTTCC CACAGCGGCG GATCTGGTTT CTCCAGCAAT TGGACCCGGA GAGCAACGCC
47941 TATAATCTCC CGCTCGTGCA ACGCCTGCGC GGTCTATTGG ACGCGCCGGC CCTGGAGCGT
48001 GCGCTGGCGC TCGTCGTCGC GCGCCACGAG GCGTTGCGGA CGGTGTTCGA CACCGCCGAC
48061 GGCGAGCCCC TCCAGCGGGT GCTTCCCGCC CCGGAACACC TCCTGCGCCA CGCGCGGGCG
48121 GGCAGCGAGG AGGACGCCGC CCGGCTCGTC CGCGACGAGA TCGCCGCGCC GTTCGACCTC
48181 GCCACCGGGC CGTTGATCAG GGCCCTGCTG ATCCGCCTCG GTGACGACGA CCACGTTCTC
48241 GCGGTGACCG TGCACCATGT CGCCGGCGAC GGCTGGTCGT TCGGGCTCCT CCAACATGAA
48301 CTCGCAGCCC ACTACACGGC GCTGCGCGAC ACTGCCCGCC CTGCCGAACT GCCGCCGTTG
48361 CCGGTGCAGT ACGCCGACTT CGCCGCCTGG GAGCGGCGCG AACTCACCGG CGCCGGACTG
48421 GACAGGCGTC TGGCCTACTG GCGCGAGCAA CTCCGGGGCG CCCCGGCGCG GCTCGCCCTC
48481 CCCACCGACC GTCCCCGCCC GCCGGTCGCC GACGCGGACG CGGGCATGGC CGAGTGGCGG
48541 CCGCCGGCCG CGCTGGCCAC CGCGGTCCTC ACGCTCGCGC GCGACTCCGG TGCGTCCGTG
48601 TTCATGACCC TGCTGGCGGC CTTCCAAGCG GTCCTCGCCC GGCAGGCGGG CACGCGGGAC
48661 GTGCTGGTCG GCACGCCCGT GGCGAACCGT ACGCGGGCGG CGTACGAGGG CCTGATCGGC
48721 ATGTTCGTCA ACACGCTCGC GCTGCGCGGC GACCTCTCGG GCGATCCGTC GTTCCGGGAA
48781 CTCCTCGACC GCTGCCGGGC CACGACCACG GACGCGTTCG CCCACGCCGA CCTGCCGTTC
48841 GAGAACGTCA TCGAACTCGT CGCACCGGAA CGCGACCTGT CGGTCAACCC GGTCGTCCAG
```

-continued

```
48901 GTGCTGTTGC AGGTGCTGCG GCGCGACGCG GCGACGGCCG CGCTGCCCGG CATCGCGGCC
48961 GAACCGTTCC GCACCGGACG CTGGTTCACC CGCTTCGACC TCGAATTCCA TGTGTACGAG
49021 GAGCCGGGTG GCGCGCTGAC CGGCGAACTG CTCTACAGCC GTGCGCTGTT CGACGAGCCA
49081 CGGATCACGG GGTTGCTGGA GGAGTTCACG GCGGTGCTTC AGGCGGTCAC CGCCGACCCG
49141 GACGTACGGC TGTCGCGGCT GCCGGCCGGC GACGCGACGG CGGCAGCGCC CGTGGTGCCC
49201 TCGAACGACA CGGCGCGGGA CCTGCCCGTC GACACGCTGC CGGGCCTGCT GGCCCGGTAC
49261 GCCGCACGCA CCCCCGGCGC CGTGGCCGTC ACCGACCCGC ACATCTCCCT CACCTACGCG
49321 CAGCTGGACC GGCGGGCGAA CCGCCTCGCG CACCTGCTCC GCGCGCGCGG CACCGCCACC
49381 GGCGACCTGG TCGGGATCTG CGCCGATCGC GGCGCCGACC TGATCGTCGG CATCGTGGGG
49441 ATCCTCAAGG CGGGCGCCGC TTATGTGCCG CTGGACCCCG AACATCCTCC GGAGCGCACG
49501 GCGTTCGTGC TGGCCGACGC GCAGCTGACC ACGGTGGTGG CGCACGAGGT CTACCGTTCC
49561 CGGTTCCCCG ATGTGCCGCA CGTGGTGGCG TTGGACGACC CGGAGCTGGA CCGGCAGCCG
49621 GACGACACCG CGCCGGACGT CGAGCTGGAC CGGGACAGCC TCCCCTACGC GATCTACACG
49681 TCCGGGTCGA CCGGCAGGCC GAAGGCCGTG CTCATGCCGG GTGTCAGCGC CGTCAACCTG
49741 CTGCTCTGGC AGGAGCGCAC GATGGGCCGC GAGCCGGCCA GCCGCACCGT CCAGTTCGTG
49801 ACGCCCACGT TCGACTACTC GCTCCAGGAG ATCTTTTCCG CGCTGCTGGG CGGCACGCTC
49861 GTCATCCCGC CGGACGAGGT GCGGTTCGAC CCGCCGGGAC TCGCCCGGTG GATGGACGAA
49921 CAGGCGATTA CCCCGGATCTA CGCGCCGACG GCCGTACTGC GCGCGCTGAT CGAGCACGTC
49981 GATCCGCACA GCGACCAGCT CGCCGCCCTG CGGCACCTGT GCCAGGGCGG CGAGGCGCTG
50041 ATCCTCGACG CGCGGTTGCG CGAGGTGTGC CGGCACCGGC CCCACCTGCG CGTGCACAAT
50101 CACTACGGTC CGGCCGAAAG CCAGCTCATC ACCGGGTACA CGCTGCCCGC CGACCCCGAC
50161 GCGTGGCCCG CCACCGCACC GATCGGCCCG CCGATCGACA CACCCGCAT CCATCTGCTC
50221 GACGAGGCGA TGCGGCCGGT TCCGGACGGT ATGCCGGGGC AGCTCTGCGT CGCCGGCGTC
50281 GGCCTCGCCC GTGGGTACCT GGCCCGTCCC GAGCTGACCG CCGAGCGCTG GGTGCCGGGA
50341 GATGCGGTCG GCGAGGAGCG CATGTACCTC ACCGGCGACC TGGCCCGCCG CGCGCCCGAC
50401 GCCGACCTGG AATTCCTCGG CCGGATCGAC GACCAGGTCA AGATCCGCGG CATCCGCGTC
50461 GAACCGGGTG AGATCGAGAG CCTGCTCGCC GAGGACGCCC GCGTCACGCA GGCGGCGGTG
50521 TCCGTGCGCG AGGACCGGCG GGGCGAGAAG TTCCTGGCCG CGTACGTCGT ACCGGTGGCC
50581 GGCCGGCACG GCGACGACTT CGCCGCGTCG CTGCGCGCGG GACTGGCCGC CCGGCTGCCC
50641 GCCGCGCTCG TGCCCTCCGC CGTCGTCCTG GTGGAGCGAC TGCCGAGGAC CACGAGCGGC
50701 AAGGTGGACC GGCGCGCGCT GCCCGACCCG GAGCCGGGCC CGGCGTCGAC CGGGGCCGTT
50761 ACGCCCCGCA CCGATGCCGA GCGGACGGTG TGCCGGATCT TCCAGGAGGT GCTCGACGTC
50821 CCGCGGGTCG GTGCCGACGA CGACTTCTTC ACGCTCGGCG GGCACTCCCT GCTCGCCACC
50881 CGGGTCGTCT CCCGCATCCG CGCCGAGCTG GGTGCCGATG TCCCGCTGCG TACGCTCTTC
50941 GACGGCGGA CGCCCGCCGC GCTCGCCCGT GCGGCGGACG AGGCCGGCCC GGCCGCCCTG
51001 CCCCCGATCG CGCCCTCCGC GGAGAACGGG CCGGCCCCCC TCACCGCGGC ACAGGAACAG
51061 ATGCTGCACT CGCACGGCTC GCTGCTCGCC GCGCCCTCCT ACACGGTCGC CCCGTACGGG
51121 TTCCGGCTGC GCGGGCCACT CGACCGCGAA GCGCTCGACG CGGCACTGAC CCGGATCGCC
51181 GCGCGCCACG ACCCGCTGCG CACCGGGTTC CGCGATCGGG AACAGGTCGT CCGGCCGCCC
51241 GCTCCGGTGC GCGCCGAGGT GGTTCCGGTG CCGGTCGGCG ACGTCGACGC CGCGGTCCGG
```

-continued

```
51301 GTCGCCCACC GGGAGCTGAC CCGGCCGTTC GACCTCGTGA ACGGGTCGTT GCTGCGTGCC
51361 GTGCTGCTGC CGCTGGGCGC CGAGGATCAC GTGCTGCTGC TGATGCTGCA CCACCTCGCC
51421 GGTGACGGAT GGTCCTTCGA CCTCCTGGTC CGGGAGTTGT CGGGGACGCA ACCGGACCTT
51481 CCGGTGTCCT ACACGGACGT GGCCCGGTGG GAACGGAGTC CGGCCGTGAT CGCGGCCAGG
51541 GAGAACGACC GGGCCTACTG GCGCCGGCGG CTGGGGGGCC CCACCGCGCC GGAGCTGCCC
51601 GCGGTCCGGC CCGGCGGGGC ACCGACCGGG CGGGCGTTCC TGTGGACGCT CAAGGACACC
51661 GCCGTCCTGG CGGCACGCCG GGTCGCGGAC GCCCACGACG CGACGTTGCA CGAAACCGTG
51721 CTCGGCGCCT TCGCCCTGGT CGTGGCGGAG ACCGCCGACA CCGACGACGT GCTCGTCGCG
51781 ACGCCGTTCG CGGACCGGGG GTACGCCGGG ACCGACCACC TCATCGGCTT CTTCGCGAAG
51841 GTCCTCGCGC TGCGCCTCGA CCTCGGCGGC ACGCCGTCGT TCCCCGAGGT GCTGCGCCGG
51901 GTGCACACCG CGATGGTGGG CGCGCACGCC CACCAGGCGG TGCCCTACTC CGCGCTGCGC
51961 GCCGAGGACC CCGCGCTGCC GCCGGCCCCC GTGTCGTTCC AGCTCATCAG CGCGCTCAGC
52021 GCGGAACTGC GGCTGCCCGG CATGCACACC GAGCCGTTCC CCGTCGTCGC CGAGACCGTC
52081 GACGAGATGA CCGGCGAACT GTCGATCAAC CTCTTCGACG ACGGTCGCAC CGTCTCCGGC
52141 GCGGTGGTCC ACGATGCCGC GCTGCTCGAC CGTGCCACCG TCGACGATTT GCTCACCCGG
52201 GTGGAGGCGA CGCTGCGTGC CGCCGCGGGC GACCTCACCG TACGCGTCAC CGGTTACGTG
52261 GAAAGCGAGT AGCCATGCCC GAGCAGGACA AGACAGTCGA GTACCTTCGC TGGGCGACCG
52321 CGGAACTCCA GAAGACCCGT GCGGAACTCG CCGCGCACAG CGAGCCGTTG GCGATCGTGG
52381 GGATGGCCTG CCGGCTGCCC GGCGGGGTCG CGTCGCCGGA GGACCTGTGC CAGTTGCTGG
52441 AGTCCGGTGG CGACGGCATC ACCGCGTTCC CCACGGACCG GGGCTGGGAG ACCACCGCCG
52501 ACGGTCGCGG CGGCTTCCTC ACCGGGGCGG CCGGCTTCGA CGCGGCGTTC TTCGGCATCA
52561 GCCCGCGCGA GGCGCTGGCG ATGGACCCGC AGCAGCGCCT GGCCCTGGAG ACCTCGTGGG
52621 AGGCGTTCGA GCACGCGGGC ATCGATCCGC AGACGCTGCG GGGCAGTGAC ACGGGGGTGT
52681 TCCTCGGCGC GTTCTTCCAG GGGTACGGCA TCGGCGCCGA CTTCGACGGT TACGGCACCA
52741 CGAGCATTCA CACGAGCGTG CTCTCCGGCC GCCTCGCGTA CTTCTACGGT CTGGAGGGTC
52801 CGGCGGTCAC GGTCGACACG GCGTGTTCGT CGTCGCTGGT GGCGCTGCAC CAGGCCGCGC
52861 AGTCGCTGCG CTCCGGCGAA TGCTCGCTCG CCCTGGTCGG CGGCGTCACG GTGATGGCCT
52921 CGCCGGCGGG GTTCGCGGAC TTCTCCGACC AGGGCGGCCT GGCCCCCCAC GCGCGCTGCA
52981 AGGCCTTCGC GGAAGCGGCT GACGGCACCG GTTTCGCCCA GGGGTCCGGC GTCCTGATCG
53041 TCGAGAAGCT CTCCGACGCC GAGCGCAACG GCCACCGCGT GCTGGCGGTC GTCCGGGGTT
53101 CCGCCGTCAA CCAGGACGGT GCCTCCAACG GGCTGTCCGC GCCGAACGGG CCGTCGCAGG
53161 AGCGGGTGAT CCGGCAGGCC CTGGCCAACG CCGGACTCAC CCCGGCGGAC GTGGACGCCG
53221 TCGAGGCCCA CGGCACCGGC ACCAGGCTGG GCGACCCCAT CGAGGCACAG GCCGTGCTGG
53281 CCACCTACGG GCAGGGGCGC GACACCCCTG TGCTGCTGGG CTCGCTGAAG TCCAACATCG
53341 GCCACACCCA GGCCGCCGCG GGCGTCGCCG GTGTCATCAA GATGGTCCTC GCCATGCGGC
53401 ACGCCACCCT GCCCCGCACC CTGCACGTGG ACACGCCGTC CTCGCACGTC GACTGGACGG
53461 CCGGCGCCGT CGAACTCCTC ACCGACGCCC GGCCCTGGCC CGAAACCGAC CGCCCACGGC
53521 GCGCCGGTGT CTCCTCCTTC GGCGTCAGCG GCACCAACGC CCACATCATC CTCGAAAGCC
53581 ACCCCGACCC GGCCCCCGAA CCCGCCCCGG CACCCGACAC CGGACCGCTG CCGCTGCTGC
53641 TCTCGGCCCG CACCCCGCAG GCACTCGACG CACAGGTACA CCGCCTGCGC GCGTTCCTCG
```

-continued

```
53701 ACGACAACCC CGCCGCGGAC CGGGTCGCCG TCGCGCAGAC ACTCGCCCGG CGCACCCAGT
53761 TCGAGCACCG CGCCGTGCTG CTCGGCGACA CGCTCATCAC CGTGAGCCCG AACGCCGGCC
53821 GCGGACCGGT GGTCTTCGTC TACTCGGGGC AAAGCACGCT GCACCCGCAC ACCGGGCGGC
53881 AACTCGCGTC CACCTACCCC GTGTTCGCCC AAGCGTGGCG CGAGGCCCTC GACCACCTCG
53941 ACCCCACCCA GGGCCCGGCC ACGCACTTCG CCCACCAGAC CGCGCTCACC GCGCTCCTGC
54001 GGTCCTGGGG CATCACCCCG CACGCCGTCA TCGGCCACTC CCTCGGTGAG ATCACCGCCC
54061 CGCACGCCGC CGGTGTCCTG TCCCTGAGGG ACGCGGGCGC GCTCCTCACC ACCCGCACCC
54121 GCCTGATGGA CCAACTGCCG TCGGGCGGCG CGATGGTCAC CGTCCTGACC AGCGAGGAAA
54181 AGGCACGCCA GGTGCTGCGG CCGGGCGTGG AGATCGCCGC CGTCAACCGC CCCCACTCCC
54241 TCGTGCTGTC CGGGGACGAG GAAGCCGTAC TCGAAGCCGC CCGGCAGCTC GGCATCCACC
54301 ACCGCCTGCC GACCCGCCAC GCCGGCCACT CCGAGCGCAT GCAGCCACTC GTCGCCCCCC
54361 TCCTCGACGT CGCCCGGACC CTGACGTACC ACCAGCCCCA CACCGCCATC CCCGGCGACC
54421 CCACCACCGC CGAATACTGG GCGCACCAGG TCCGCGACCA AGTACGTTTC CAGGCGCACA
54481 CCGAGCAGTA CCCGGGCGCG ACGTTCCTCG AGATCGGCCC CAACCAGGAC CTCTCGCCGC
54541 TCGTCGACGG CGTTGCCGCC CAGACCGGTA CGCCCGACGA GGTGCGGGCG CTGCACACCG
54601 CGCTCGCGCA GCTCCACGTC CGCGGCGTCG CGATCCACTG GACGCTCGTC CTCGGCCGGG
54661 ACCGCGCGCC CGTCACGCTG CCCACGTATC CGTTCCAGCA CAAGGACTAC TGGCTCCGGC
54721 CCACCTCCCG GGCCGATGTG ACCGGCGCGG GGCAGGAGCA GGTGGCGCAC CCGCTGCTCG
54781 GCGCCGCGGT CGCGCTGCCC GGCACGGGCG GAGTCGTCCT GACCGGCCGC CTGTCGCTGG
54841 CCTCCCATCC GTGGCTCGGC GAGCACGCGG TCGACGGCAC CGTGCTCCTG CCCGGCGCGG
54901 CCTTCCTCGA ACTCGCGGCG CGCGCCGGCG ACGAGGTCGG CTGCGACCTG CTGCACGAAC
54961 TCGTCATCGA GACGCCGCTC GTGCTGCCCG CGACCGGCGG TGTGGCGGTC TCCGTCGAGA
55021 TCCCCGAACC CGACGACACG GCGCGGCGGG CGGTCACCGT CCACGCGCGG GCCGACGGCT
55081 CGCGCCTGTG GACCCGACAC GCCGGCGGAT TCCTCGGCAC GGCACCGGCA CCGGCCACGG
55141 CCACGGACCC GGCACCCTGG CCGCCCGCGG AAGCCGGACC GGTCGACGTC GCCGACGTCT
55201 ACGACCGCTT CGAGGACATC GGGTACTCCT ACGGACCGGG CTTCCGGGGG CTGCGGGCCG
55261 CCTGGCGCGC CGGCGACACC GTGTACGCCG AGGTCGCGCT CCCCGACGAG CAGAGCGCCG
55321 ACGCCGCCCG TTTCACGCTG CACCCCGCGC TGCTCGACGC CGCGTTCCAG GCCGGCGCGC
55381 TGGCCGCGCT CGACGCACCC CGCGGGGCGG CCCGACTGCC GTTCTCGTTC CAGGACCTCC
55441 GCATCCACGC GGCCGGGGCG ACCCGGCTGC GGGTCACGGT CGGCCGCGAC GGCGAGCGCA
55501 GCACCGTCCG CATGACCGGC CCGGACGGGC AGCTGGTGGC CGTGGTCGGT GCCGTGCTGT
55561 CGCGCCCGTA CGCGGAAGGC TCCGCTGACG GCCTGCTGCG CCCGGTCTGG ACCGAGCTGC
55621 CGATGCCCGT CCCGTCCCCG GACGATCCGC GCGTGGAGGT CCTCGGCGCC GACCCGGGCG
55681 ACGGCGACGT TCCGGCGGCC ACCCGGGAGC TGACCGCCCG CGTCCTCGGC GCGCTCCAGC
55741 GCCACCTGTC CCCCGCCGAG CACACCACCT TGGTGCTACG ACCGGCACC GGCCCGGCCG
55801 CTGCCCCCGC CGCGGGTCTG GTCCGCTCGG CGCAGGCGGA GAACCCCGGC CGCGTCGTGC
55861 TCGTCGAGGC GTCCCCGCAC ACCTCGGTGG AGCTGCTCGC CGCGTGCGCC GCGCTGGACG
55921 AACCGCAGCT GGCCGTCCGG GACGGCGTGC TCTTCGCGCC GCGGCTGGTC CGGATGTCCG
55981 ACCCCGCGCA CGGCCCGCTG TCCCTGCCGC ACGGCGACTG GCTGCTCACC CGGTCCGCCT
56041 CCGGCACGTT GCACGACGTC GCGCTCATAG CCGACGACAC GCCCCGGCGG GCGCTCGAAG
```

-continued

```
56101 CCGGCGAGGT CCGCATCGAC GTCCGCGCGG CCCGACTCAA CTTCCGCGAT GTGCTGATCG
56161 CGCTCGGGAC GTACACCGGG GCCACGGCCA TGGGCCCCGA CGCCGCGGGC GTCGTGGTGG
56221 AGACCGGGCC CGGCGTGGAC GACCTGTCCC CCGGCGACCG GGTGTTCGGC CTGACCCGGG
56281 GCGGCATCGG CCCGACGGCC GTCACCGACC GGCGCTGGCT GGCCCGGATC CCCGACGGCT
56341 GGAGCTTCAC CACGGCGGCG TCCGTCCCGA TCGTGTTCGC GACCGCGTGG TACGGCCTGG
56401 TCGACCTCGG CACACTGCGC CCCGGCGAGA AGGTCCTCGT CCACGCGGCC ACCGGCGGTG
56461 TCGGCATGGC CGCCGCACAG ATCGCCCGCC ACCTGGGCGC CGAGCTCTAC GCCACCGCCA
56521 GTACCGGCAA GCAGCACGTC CTGCGCGCCG CCGGGCTGCC CGACACGCAC ATCGCGGACT
56581 CTCGGACGAC CGCGTTCCGG ACCGCTTTCC CGCGCATGGA CGTCGTCCTG AACGCGCTGA
56641 CCGGCGAGTT CATCGACGCG TCGCTCGACC TGCTGGACGC CGACGGCCGG TTCGTCGAGA
56701 TGGGCCGCAC CGAGCTGCGC GACCCGGCCG CGATCGTCCC CGCCTACCTG CCGTTCGACC
56761 TGCTGGACGC GGGCGCCGAC CGCATCGGCG AGATCCTGGG CGAACTGCTC CGGCTGTTCG
56821 ACGCGGGCGC GCTGGAGCCG CTGCCGGTCC GTGCCTGGGA CGTCCGGCAG GCACGCGACG
56881 CGCTCGGCTG GATGAGCCGC GCCCGCCACA TCGGCAAGAA CGTCCTGACG CTGCCCCGGC
56941 CGCTCGACCC GGAGGGCGCC GTCGTCCTCA CCGGCGGCTC CGGCACCCTC GCCGGCATCC
57001 TCGCCCGCCA CCTGCGCGAA CGGCATGTCT ACCTGCTGTC CCGGACGGCA CCGCCCGAGG
57061 GCACGCCCGG CGTCCACCTG CCCTGCGACG TCGGTGACCG GGACCAGCTG GCGGCGGCCC
57121 TGGAGCGGGT GGACCGGCCG ATCACCGCCG TGGTGCACCT CGCCGGTGCG CTGGACGACG
57181 GCACCGTCGC GTCGCTCACC CCCGAGCGTT TCGACACGGT GCTGCGCCCG AAGGCCGACG
57241 GCGCCTGGTA CCTGCACGAG CTGACGAAGG AGCAGGACCT CGCCGCGTTC GTGCTCTACT
57301 CGTCGGCCGC CGGCGTGCTC GGCAACGCCG GCCAGGGCAA CTACGTCGCC GCGAACGCCT
57361 TCCTCGACGC GCTCGCCGAG CTGCGCCACG GTTCCGGGCT GCCGGCCCTC TCCATCGCCT
57421 GGGGGCTCTG GGAGGACGTG AGCGGGCTCA CCGCGGCGCT CGGCGAAGCC GACCGGGACC
57481 GGATGCGGCG CAGCGGTTTC CGGGCCATCA CCGCGCAACA GGGCATGCAC CTGTACGAGG
57541 CGGCCGGCCG CACCGGAAGT CCCGTGGTGG TCGCGGCGGC GCTCGACGAC GCGCCGGACG
57601 TGCCGCTGCT GCGCGGCCTG CGGCGGACGA CCGTCCGGCG GGCCGCCGTC CGGGAGTGTT
57661 CGTCCGCCGA CCGGCTCGCC GCGCTGACCG GCGACGAGCT CGCCGAACCG CTGCTGACGC
57721 TCGTCCGGGA GAGCACCGCC GCCGTGCTCG GCCACGTGGG TGGCGAGGAC ATCCCCGCGA
57781 CGGCGGCGTT CAAGGACCTC GGCATCGACT CGCTCACCGC GGTCCAGCTG CGCAACGCCC
57841 TCACCGAGGC GACCGGTGTG CGGCTGAACG CCACGGCGGT CTTCGACTTC CCGACCCCGC
57901 ACGTGCTCGC CGGGAAGCTC GGCGACGAAC TGACCGGCAC CCGCGCGCCC GTCGTGCCCC
57961 GGACCGCGGC CACGGCCGGT GCGCACGACG AGCCGCTGGC GATCGTGGGA ATGGCCTGCC
58021 GGCTGCCCGG CGGGGTCGCG TCACCCGAGG AGCTGTGGCA CCTCGTGGCA TCCGGCACCG
58081 ACGCCATCAC GGAGTTCCCG ACGGACCGCG GCTGGGACGT CGACGCGATC TACGACCCGG
58141 ACCCCGACGC GATCGCCAAG ACCTTCGTCC GGCACGGTCG CTTCCTCACC GGCGCGACAG
58201 GCTTCGACGC GGCGTTCTTC GGCATCAGCC CGCGCGAGGC CCTCGCGATG GACCCGCAGC
58261 AGCGGGTGCT CCTGGAGACG TCGTGGGAGG CGTTCGAAAG CGCCGGCATC ACCCCGGACT
58321 CGACCCGCCG CAGCGACACC GGCGTGTTCG TCGGCGCCTT CTCCTACGGT TACGGCACCG
58381 GTGCGGACAC CGACGGCTTC GGCGCGACCG GCTCGCAGAC CAGTGTGCTC TCCGGCCGGC
58441 TGTCGTACTT CTACGGTCTG GAGGGTCCGG CGGTCACGGT CGACACGGCG TGTTCGTCGT
```

```
58501 CGCTGGTGGC GCTGCACCAG GCCGGGCAGT CGCTGCGCTC CGGCGAATGC TCGCTCGCCC
58561 TGGTCGGCGG CGTCACGGTG ATGGCGTCTC CCGGCGGCTT CGTGGAGTTC TCCCGGCAGC
58621 GCGGCCTCGC GCCGGACGGC CGGGCGAAGG CGTTCGGCGC GGGTGCGGAC GGCACGAGCT
58681 TCGCCGAGGG TGCCGGTGTG CTGATCGTCG AGAGGCTCTC CGACGCCGAA CGCAACGGTC
58741 ACACCGTCCT GGCGGTCGTC CGTGGTTCGG CGGTCAACCA GGATGGTGCC TCCAACGGGC
58801 TGTCGGCGCC GAACGGGCCG TCGCAGGAGC GGGTGATCCG GCAGGCCCTG GCCAACGCCG
58861 GGCTCACCCC GGCGGACGTG GACGCCGTCG AGGCCCACGG CACCGGCACC AGGCTGGGCG
58921 ACCCCATCGA GGCACAGGCG GTACTGGCCA CCTACGCACA GGAGCGCGCC ACCCCCCTGC
58981 TGCTGGGCTC GCTGAAGTCC AACATCGGCC ACGCCCAGGC CGCGTCCGGC GTCGCCGGCA
59041 TCATCAAGAT GGTGCAGGCC CTCCGGCACG GGAGCTGCC GCCGACGCTG CACGCCGACG
59101 AGCCGTCGCC GCACGTCGAC TGGACGGCCG GCGCCGTCGA ACTGCTGACG TCGGCCCGGC
59161 CGTGGCCCGA GACCGACCGG CCACGGCGTG CCGCCGTCTC CTCGTTCGGG GTGAGCGGCA
59221 CCAACGCCCA CGTCATCCTG GAGGCCGGAC CGGTAACGGA GACGCCCGCG GCATCGCCTT
59281 CCGGTGACCT TCCCCTGCTG GTGTCGGCAC GCTCACCGGA AGCGCTCGAC GAGCAGATCC
59341 GCCGACTGCG CGCCTACCTG GACACCACCC CGGACGTCGA CCGGGTGGCC GTGGCACAGA
59401 CGCTGGCCCG GCGCACACAC TTCGCCCACC GCGCCGTGCT GCTCGGTGAC ACCGTCATCA
59461 CCACACCCCC CGCGGACCGG CCCCACGAAC TCGTCTTCGT CTACTCCGGC CAGGGCACCC
59521 AGCATCCCGC GATGGGCGAG CAGCTCGCCG CCGCCCATCC CGTGTTCGCC GACGCCTGGC
59581 ATGAAGCGCT CCGCCGCCTT GACAACCCCG ACCCCCACGA CCCCACGCAC AGCCAGCATG
59641 TGCTCTTCGC CCACCAGGCG GCGTTCACCG CCCTCCTGCG GTCCTGGGGC ATCACCCCGC
59701 ACGCGGTCAT CGGCCACTCG CTGGGCGAGA TCACCGCGGC GCACGCCGCC GGCATCCTGT
59761 CGCTGGACGA CGCGTGCACC CTGATCACCA CGCGCGCCCG CCTCATGCAC ACGCTCCCGC
59821 CACCCGGTGC CATGGTCACC GTACTGACCA GCGAAGAGAA GGCACGCCAG GCGTTGCGGC
59881 CGGGCGTGGA GATCGCCGCC GTCAACGGGC CCCACTCCAT CGTGCTGTCC GGGGACGAGG
59941 ACGCCGTGCT CACCGTCGCC GGGCAGCTCG GCATCCACCA CCGCCTGCCC GCCCCGCACG
60001 CCGGGCACTC CGCGCACATG GAGCCCGTGG CCGCCGAGCT GCTCGCCACC ACCCGCGGGC
60061 TCCGCTACCA CCCTCCCCAC ACCTCCATTC CGAACGACCC CACCACCCCT GAGTACTGGG
60121 CCGAGCAGGT CCGCAAGCCC GTGCTGTTCC ACGCCCACGC GCAGCAGTAC CCGGACGCCG
60181 TGTTCGTGGA GATCGGCCCC GCCCAGGACC TCTCCCCGCT CGTCGACGGG ATCCCGCTGC
60241 AGAACGGCAC CGCGGACGAG GTGCACGCGC TGCACACCGC GCTCGCGCAC CTCTACGCGC
60301 GCGGTGCCAC GCTCGACTGG CCCCGCATCC TCGGGCCTGG GTCACGGCAC GACGCGGATG
60361 TGCCCGCGTA CGCGTTCCAA CGGCGGCACT ACTGGATCGA GTCGGCACGC CCGGCCGCAT
60421 CCGACGCGGG CCACCCCGTG CTGGGCTCCG GTATCGCCCT CGCCGGGTCG CCGGGCCGGG
60481 TGTTCACGGG TTCCGTGCCG ACCGGTGCGG ACCGCGCGGT GTTCGTCGCC GAGCTGGCGC
60541 TGGCCGCCGC GGACGCGGTC GACTGCGCCA CGGTCGAGCG GCTCGACATC GCCTCCGTGC
60601 CCGGCCGGCC GGGCCATGGC CGGACGACCG TACAGACCTG GGTCGACGAG CCGGCGGACG
60661 ACGGCCGGCG CCGGTTCACC GTGCACACCC GCACCGGCGA CGCCCCGTGG ACGCTGCACG
60721 CCGAGGGGGT GCTGCGCCCC CATGGCACGG CCCTGCCCGA TGCGGCCGAC GCCGAGTGGC
60781 CCCCACCGGG CGCGGTGCCC GCGGACGGGC TGCCGGGTGT GTGGCGCCGG GGGGACCACG
60841 TCTTCGCCGA GGCCGAGGTG GACGGACCGG ACGGTTTCGT GGTGCACCCC GACCTGCTCG
```

-continued

```
60901 ACGCGGTCTT CTCCGCGCTC GGCGACGGAA GCCGCCAGCC GGCCGGATGG CGCGACCTGA
60961 CGGTGCACGC GTCGGACGCC ACCGTACTGC GCGCCTGCCT CACCCGGCGC ACCGACGGAG
61021 CCATGGGATT CGCCGCCTTC GACGGCGCCG GCCTGCCGGT ACTCACCGCG GAGGCGGTGA
61081 CGCTGCGGGA GGTGGCGTCA CCGTCCGGCT CCGAGGAGTC GGACGGCCTG CACCGGTTGG
61141 AGTGGCTCGC GGTCGCCGAG GCGGTCTACG ACGGTGACCT GCCCGAGGGA CATGTCCTGA
61201 TCACCGCCGC CCACCCCGAC GACCCCGAGG ACATACCCAC CCGCGCCCAC ACCCGCGCCA
61261 CCCGCGTCCT GACCGCCCTG CAACACCACC TCACCACCAC CCACCACACC CTCATCGTCC
61321 ACACCACCAC CGACCCCGCC GGCGCCACCG TCACCGGCCT CACCCGCACC GCCCAGAACG
61381 AACACCCCCA CCCCATCCGC CTCATCGAAA CCGACCACCC CCACACCCCC CTCCCCCTGG
61441 CCCAACTCGC CACCCTCGAC CACCCCCACC TCCGCCTCAC CCACCACACC CTCCACCACC
61501 CCCACCTCAC CCCCCTCCAC ACCACCACCC CACCCACCAC CACCCCCCTC AACCCCGAAC
61561 ACGCCATCAT CATCACCGCC GGCTCCCGCA CCCTCGCCGC CATCCTCCCC CCCCACCTGA
61621 ACCACCCCCA CACCTACCTC CTCTCCCGCA CCCCACCCCC CGACGCCACC CCCGGCACCC
61681 ACCTCCCCTG CGACGTCGGC GACCCCCACC AACTCGCCAC CACCCTCACC CACATCCCCC
61741 AACCCCTCAC CGCCATCTTC CACACCGCCG CCACCCTCGA CCACGGCATC CTCCACGCCC
61801 TCACCCCCCA CCCCCTCACC ACCGTCCTCC ACCCCAAAGC CAACGCCGCC TGGCACCTGC
61861 ACCACCTCAC CCAAAACCAA CCCCTCACCC ACTTCGTCCT CTACTCCAGC GCCGCCGCCG
61921 TCCTCGGCAG CCCCGGACAA GGAAACTACG CCCCCGCCAA CCCCTTCCTC GACGCCCTCG
61981 CCACCCACCG CCACACCCTC GGCCAACCCG CCACCTCCAT CGCCTGGGGC ATGTGGCACA
62041 CCACCAGCAC CCTCACCGGA CAACTCGACG ACGCCGACCG GGACCGCATC CGCCCCGGCG
62101 GTTTCCTCCC GATCACGGAC GACGAGGGCA TGCGCCTCTA CGAGGCGGCC GTCGGCTCCG
62161 GCGAGGACTT CGTCATGGCC GCCGCGATGG ACCCGGCACA GCCGATGACC GGCTCCGTAC
62221 CGCCCATCCT GAGCGGCCTG CGCACGAGCG CGCGGCGCGT CGCCCGTGCC GGGCAGACGT
62281 TCGCCCAGCG GCTCGCCGAG CTGCCCGACG CCGACCGCGC CGCGCCGCTC ACCACCCTCG
62341 TCTCGGACGC CACGGCCGCC GTGCTCGGCC ACCCCGACGC CTCCGAGATC GCGCCGACCA
62401 CGACGTTCAA GCACCTCGGC ATCGACTCCC TCACCGCGAT CGAGCTGCGC AACCGGCTCG
62461 CGGAGGCGAC CGGGCTGCGG CTGAGTGCCA CGCTGGTGTT CGACCACCCG ACACCTCGGG
62521 TCCTCCCCGC CAAGCTCCGC ACCGATCTGT TCGGCACGGC CGTGCCCACG CCCGCGCGGA
62581 CGGCACGGAC CCACCACGAC GAGCCACTCG CGATCGTCGG CATGGCGTGC CGACTGCCCG
62641 GCGGGGTCGC CTCGCCGGAG GACCTGTGGC AGCTCCTGGC GTCCGGCACC CACCCCATCA
62701 CCGACTTCCC CACCGACCGC CGCTCGGACA TCGACCGCCT GTTCGACCCC GACCCGGACG
62761 CCCCCGGCAA GACCTACGTC CGCCACGGCG GCTTCCTCGC CGAGGCCGCC GGCTTCCATG
62821 CCGCGTTCTT CGGCATCAGC CCGCGCGAGG CACGGGCCAT GGACCCGCAG CAGCGCGTCA
62881 TCCTCGAAAC CTCCTGGGAG GCGTTCGAGA ACGCGGGCAT CGTGCCGGAC ACGCTGCGCG
62941 GCAGCGACAC CGGCGTGTTC ATGGGCGCGT TCTCCCATGG GTACCGCGCC GGCGTCGACC
63001 TGGGCGGGTT CGCCGCCACC GCCACGCAGA ACAGCGTGCT CTCCGGCCGG TTGTCGTACT
63061 TCTTCGGCAT GGAGGGCCCG GCCGTCACCG TCGACACCGC CTGCTCGTCG TCGCTGGTCG
63121 CCCTGCACCA GGCGGCACAG GCGCTGCGGA CTGGAGAATG CTCGCTGGCG CTCGCCGGCG
63181 GTGTCACGGT GATGCCCACC CCGCTGGGCT ACGTCGAGTT CTGCCGCCAG CGGGGACTCG
63241 CCCCCGACGG CCGTTGCCAG GCCTTCGCGG AAGGCGCCGA CGGCACGAGC TTCTCGGAGG
```

```
-continued
63301 GCGCCGGCGT TCTTGTGCTG GAGCCGCTCT CCGACGCCGA GCGCAACGGA CACACCGTCC
63361 TCGCGGTCGT CCGCTCCTCC GCCGTCAACC AGGACGGCGC CTCCAACGGC ATCTCCGCAC
63421 CCAACGGCCC CTCCCAGCAG CGCGTCATCC GCCAGGCCCT CGACAAGGCC GGGCTCGCCC
63481 CCGCCGACGT GGACGTGGTG GAGGCCCACG GCACCGGAAC CCCGCTGGGC GACCCGATCG
63541 AGGCACAGGC CATCATCGCG ACCTACGGCC AGGACCGCGA CACACCGCTC TACCTCGGTT
63601 CGGTCAAGTC GAACATCGGA CACACCCAGA CCACCGCCGG TGTCGCCGGC GTCATCAAGA
63661 TGGTCATGGC GATGCGCCAC GGCATCGCGC CGAAGACACT GCACGTGGAC GAGCCGTCGT
63721 CGCATGTGGA CTGGACCGAG GGTGCGGTGG AACTGCTCAC CGAGGCGAGG CCGTGGCCCG
63781 ACCCGGGACG CCCGCGCCGC GCGGGCGTGT CGTCGCTCGG TATCAGCGGT ACGAACGCCC
63841 ACGTGATCCT TGAGGGTGTT CCCGGGCCGT CGCGTGTGGA GCCGTCTGTT GACGGGTTGG
63901 TGCCGTTGCC GGTGTCGGCT CGGAGTGAGG CGAGTCTGCG GGGGCAGGTG GAGCGGCTGG
63961 AGGGGTATCT GCGCGGGAGT GTGGATGTGG CCGCGGTCGC GCAGGGGTTG GTGCGTGAGC
64021 GTGCTGTCTT CGGTCACCGT GCGGTACTGC TGGGTGATGC CCGGGTGATG GGTGTGGCGG
64081 TGGATCAGCC GCGTACGGTG TTCGTCTTTC CCGGGCAG3G TGCTCACTGG GTGGGCATGG
64141 GTGTGGAGTT GATGGACCCT TCTGCGGTGT TCGCGGCTCG TATGGAGGAG TGTGCGCGGG
64201 CGTTGTTGCC GCACACGGGC TGGGATGTGC GGGAGATGTT GGCGCGGCCG GATGTGGCGG
64261 AGCGGGTGGA GGTGGTCCAG CCGGCCAGCT GGGCGGTCGC CGTCAGCCTG GCCGCACTGT
64321 GGCAGGCCCA CGGGGTCGTA CCCGACGCGG TGATCGGACA CTCCCAGGGC GAGATCGCGG
64381 CGGCGTGCGT GGCCGGGGCC CTCAGCCTTG AGGACGCCGC CCGCGTGGTG GCCTTGCGCA
64441 GCCAGGTCAT CGCGGCGCGA CTGGCCGGGC GGGGAGCGAT GGCTTCGGTG GCATTGCCGG
64501 CCGGTGAGGT CGGTCTGGTC GAGGGCGTGT GGATCGCGGC GCGTAACGGC CCCGCCTCGA
64561 CAGTCGTGGC CGGCGAGCCG TCGGCGGTGG AGGACGTGGT GACGCGGTAT GAGACCGAAG
64621 GCGTGCGAGT GCGTCGTATC GCCGTCGACT ACGCCTCCCA CACGCCCCAC GTGGAAGCCA
64681 TCGAGGACGA ACTCGCTGAG GTACTGAAGG GAGTTGCAGG GAAGGCCGCG TCGGTGGCGT
64741 GGTGGTCGAC CGTGGACAGC GCCTGGGTGA CCGAGCCGGT GGATGAGAGT TACTGGTACC
64801 GGAACCTGCG TCGCCCCGTC GCGCTGGACG CGGCGGTGGC GGAGCTGGAC GGGTCCGTGT
64861 TCGTGGAGTG CAGCGCCCAT CCGGTGCTGC TGCCGGCGAT GGAACAGGCC CACACGGTGG
64921 CGTCGTTGCG CACCGGTGAC GGCGGCTGGG AGCGATGGCT GACGGCGTTG GCGCAGGCGT
64981 GGACCCTGGG CGCGGCAGTG GACTGGGACA CGGTGGTCGA ACCGGTGCCA GGGCGGCTGC
65041 TCGATCTGCC CACCTACGCG TTCGAGCGCC GGCGCTACTG GCTGGAAGCG GCCGGTGCCA
65101 CCGACCTCTC CGCGGCCGGG CTGACAGGGG CAGCACATCC CATGCTGGCC GCCATCACGG
65161 CACTACCCGC CGACGACGGT GGTGTTGTTC TCACCGGCCG GATCTCGTTG CGCACGCATC
65221 CCTGGCTGGC TGATCACGCG GTGCGGGGCA CGGTCCTGCT GCCGGGCACG GCCTTTGTGG
65281 AGCTGGTCAT CCGGGCCGGT GACGAGACCG GTTGCGGGAT AGTGGATGAA CTGGTCATCG
65341 AATCCCCCCT CGTGGTGCCG GCGACCGCAG CCGTGGATCT GTCGGTGACC GTGGAAGGAG
65401 CTGACGAGGC CGGACGGCGG CGAGTGACCG TCCACGCCCG CACCGAAGGC ACCGGCAGCT
65461 GGACCCGGCA CGCCAGCGGC ACCCTGACCC CCGACACCCC CGACACCCCC AACGCTTCCG
65521 GTGTTGTCGG TGCGGAGCCG TTCTCGCAGT GGCCACCTGC CACTGCCGCG GCCGTCGACA
65581 CCTCGGAGTT CTACTTGCGC CTGGACGCGC TGGGCTACCG GTTCGGACCC ATGTTCCGCG
65641 GAATGCGGGC TGCCTGGCGT GATGGTGACA CCGTGTACGC CGAGGTCGCG CTCCCCGAGG
```

-continued

```
65701 ACCGTGCCGC CGACGCGGAC GGTTTCGGCA TGCACCCGGC GCTGCTCGAC GCGGCCTTGC
65761 AGAGCGGCAG CCTGCTCATG CTGGAATCGG ACGGCGAGCA GAGCGTGCAA CTGCCGTTCT
65821 CCTGGCACGG CGTCCGGTTC CACGCGACGG GCGCGACCAT GCTGCGGGTG GCGGTCGTAC
65881 CGGGCCCGGA CGGCCTCCGG CTGCATGCCG CGGACAGCGG GAACCGTCGC GTCGCGACGA
65941 TCGACGCGCT CGTGACCCGG TCCCCGGAAG CGGACCTCGC GCCCGCCGAT CCGATGCTGC
66001 GGGTCGGGTG GGCCCCGGTG CCCGTACCTG CCGGGGCCGG TCCGTCCGAC GCGGACGTGC
66061 TGACGCTGCG CGGCGACGAC GCCGACCCGC TCGGGGAGAC CCGGGACCTG ACCACCCGTG
66121 TTCTCGACGC GCTGCTCCGG GCCGACCGGC CGGTGATCTT CCAGGTGACC GGTGGCCTCG
66181 CCGCCAAGGC GGCCGCAGGC CTGGTGCGCA CCGCTCAGAA CGAGCAGCCC GGCCGCTTCT
66241 TCCTCGTCCA AACGGACCCG GGAGAGGTCC TGGACGGCGC GAAGCGCGAC GCGATCGCGG
66301 CACTCGGCCA GCCCCATGTG CGGCTGCGCG ACGGCCTCTT CGAGGCAGCC CGGCTGATGC
66361 GGGCCACGCC GTCCCTGACG CTCCCGGACA CCGGGTCGTG GCAGCTGCCG CCGTCCGCCA
66421 CCGGTTCCCT CGACGACCTT GCCGTCGTCC CCACCGACGC CCCGGACCGG CCGCTCGCGG
66481 CCGGCGAGGT GCGGATCGCG GTACGCGCGG CGGGCCTGAA CTTCCGGGAT GTCACGGTCG
66541 CGCTCGGTGT GGTCGCCGAT GCGCGTCCGC TCGGCAGCGA GGCCGCGGGT CTCGTCCTGG
66601 AGACCGGCCC CGGTGTGCAC GACCTGGCGC CCGGCGACCG GGTCCTGGGG ATGCTCGCGG
66661 GCGCCTTCGG ACCGGTCGCG ATCACCGACC GGCGGCTGCT CGGCCGGATG CCGGACGGCT
66721 GGACGTTCCC GCAGGCGGCG TCCGTGATGA CCGCGTTCGC GACCGCGTGG TACGGCCTGG
66781 TCGACCTGGC CGGGCTGCGC CCCGGCGAGA AGGTCCTGAT CCACGCGGCG GCGACCGGTG
66841 TCGGCGCGGC GGCCGTCCAG ATCGCGCGGC ATCTGGGCGC GGAGGTGTAC GCGACCACCA
66901 GCGCCGCGAA GCGCCATCTG GTGGACCTGG ACGGAGCGCA TCTGGCCGAT TCCCGCAGCA
66961 CCGCGTTCGC CGACGCGTTC CCGCCGGTCG ATGTCGTGCT CAACTCGCTC ACCGGTGAAT
67021 TCCTCGACGC GTCCGTCGGC CTGCTCGCGG CGGGTGGCCG GTTCATCGAG ATGGGGAAGA
67081 CGGACATCCG GCACGCCGTC CAGCAGCCGT TCGACCTGAT GGACGCCGGC CCCGACCGGA
67141 TGCAGCGGAT CATCGTCGAG CTGCTCGGCC TGTTCGCGCG CGACGTGCTG CACCCGCTGC
67201 CCGTCCACGC CTGGGACGTG CGGCAGGCGC GGGAGGCGTT CGGCTGGATG AGCAGCGGGC
67261 GTCACACCGG CAAGCTGGTG CTGACGGTCC CGCGGCCGCT GGATCCCGAG GGGGCCGTCG
67321 TCATCACCGG CGGCTCCGGC ACCCTCGCCG GCATCCTCGC CCGCCACCTG GGCCACCCCC
67381 ACACCTACCT GCTCTCCCGC ACCCCACCCC CCGACACCAC CCCCGGCACC CACCTCCCCT
67441 GCGACGTCGG CGACCCCCAC CAACTCGCCA CCACCCTCGC CCGCATCCCC CAACCCCTCA
67501 CCGCCGTCTT CCACACCGCC GGAACCCTCG ACGACGCCCT GCTCGACAAC CTCACCCCCG
67561 ACCGCGTCGA CACCGTCCTC AAACCCAAGG CCGACGCCGC CTGGCACCTG CACCGGCTCA
67621 CCCGCGACAC CGACCTCGCC GCGTTCGTCG TCTACTCCGC GGTCGCCGGC CTCATGGGCA
67681 GCCCGGGGCA GGGCAACTAC GTCGCGGCGA ACGCGTTCCT CGACGCGCTC GCCGAACACC
67741 GCCGTGCGCA AGGGCTGCCC GCGCAGTCCC TCGCATGGGG CATGTGGGCG GACGTCAGCG
67801 CGCTCACCGC GAAACTCACC GACGCGGACC GCCAGCGCAT CCGGCGCAGC GGATTCCCGC
67861 CGTTGAGCGC CCCGACGGC ATGCGGCTGT TCGACGCGGC GACGCCTACC CCGGAACCGG
67921 TCGTCGTCGC GACGACCGTC GACCTCACCC AGCTCGACGG CGCCGTCGCG CCGTTGCTCC
67981 GCGGTCTGGC CGCGCACCGG GCCGGGCCGG CGCGCACGGT CGCCCGCAAC GCCGGCGAAG
68041 AGCCCCTGGC CGTGCGTCTT GCCGGGCGTA CCGCCGCCGA CCACCGGCGC ATCATGCAGG
```

-continued

```
68101  AGGTCGTGCT CCGCCACGCG GCCGCGGTCC TCGCGTACGG GCTGGGCGAC CGCGTGGCGG
68161  CGGACCGTCC GTTCCGCGAG CTCGGTTTCG ATTCGCTGAC CGCGGTCGAC CTGCGCAATC
68221  GGCTCGCGGC CGAGACGGGG CTGCGGCTGC CGACGACGCT GGTGTTCAGC CACCCGACGG
68281  CGGAGGCGCT CACCGCCCAC CTGCTCGACC TGATCGACGC TCCCACCGCC CGGATCGCCG
68341  GGGAGTCCCT GCCCGCGGTG ACGCCCGCTC CCGTGGCGGC CGCGCGGGAC CAGGACGAGC
68401  CGATCGCCAT CGTGGCGATG GCGTGCCGGC TGCCCGGTGG TGTGACGTCG CCCGAGGACC
68461  TGTGGCGGCT CGTCGAGTCC GGCACCGACG CGATCACCAC GCCTCCTGAC GACCGCGGCT
68521  GGGACGTCGA CGCGCTGTAC GACGCGGACC CGGACGCGGC CGGCAAGGCG TACAACCTGC
68581  GGGGCGGTTA CCTGGCCGGG GCGGCGGAGT TCGACGCGGC GTTCTTCGAC ATCAGTCCGC
68641  GCGAAGCGCT CGGCATGGAC CCGCAGCAAC GCCTGCTGCT CGAAACGGCG TGGGAGGCGA
68701  TCGAGCGCGG CCGGATCAGT CCGGCGTCGC TCCGCGGCCG GGAGCTCGGC CTCTATGTCG
68761  GTGCGGCCGC GCAGGGCTAC GGGCTGGGCG CCGAGGACAC CGAGGGCCAC GCGATCACCG
68821  GTGGTTCCAC GAGCCTGCTG TCCGGACGGC TGGCGTACGT GCTCGGGCTG GAGGGCCCGG
68881  CGGTCACCGT CGACACGGCG TGCTCGTCGT CTCTGGTCGC GCTGCATCTG GCCTGCCAGG
68941  GGCTGCGCCT GGGCGAGTGC GAACTCGCTC TGGCCGGAGG GGTCTCCGTA CTGAGTTCGC
69001  CGGCCGCGTT CGTGGAGTTC TCCCGCCAGC GCGGGCTCGC GGCCGACGGG CGCTGCAAGT
69061  CGTTCGGCCC GGGCGCGGAC GGCACGACGT GGTCCGAGGG CGTGGGCGTG CTCGTACTGC
69121  AACGGCTCTC CGACGCCGAG CGGCTCGGGC ACACCGTGCT CGCCGTCGTC CGCGGCAGCG
69181  CCGTCACGTC CGACGGCGCC TCCAACGGCC TCACCGCGCC GAACGGGCTC TCGCAGCAGC
69241  GGGTCATCCG GAAGGCGCTC GCCGCGGCCC GGCTGACCGG CGCCGACGTC GACGTCGTCG
69301  AGGGGCACGG CACCGGCACC CGGCTCGGCG ACCCGGTCGA GGCGGACGCG CTGCTCGCGA
69361  CGTACGGGCA GGACCCTCCG GCACCGGTCT GGCTGGGCTC GCTGAAGTCG AACATCGGAC
69421  ATGCCACGGC CGCGGCCGGT GTCGCGGGCG TCATCAAGAT GGTGCAGGCG ATCGGCGCGG
69481  GCACGATGCC GCGGACGCTG CATGTGGAGG AGCCCTCGCC CGCCGTCGAC TGGAGCACCG
69541  GACAGGTGTC GCTGCTCGGC TCCAACCGGC CCTGGCCGGA CGACGAGCGT CCGCGCCGGG
69601  CGGCCGTCTC CGCGTTCGGG CTCAGCGGGA CGAACCCGCA CGTCATCCTG GAACAGCACC
69661  GTCCGGCGCC CGTGGCGTCC CAGCCGCCCC GGCCGCCCCG TGAGGAGTCC CAGCCGCTGC
69721  CGTGGGTGCT CTCCGCGCGG ACTCCGGCCG CGCTGCGGCC CCAGGCGGCC CGGCTGCGCG
69781  ACCACCTCGC GGCGGCACCG GACGCGGATC CGTTGGACAT CGGGTACGCG CTGGCCACCA
69841  GCCGCGCCCA GTTCGCCCAC CGTGCCGCGG TCGTCGCCAC CACCCCGGAC GGATTCCGTG
69901  CCGCGCTCGA CGGCCTCGCG GACGGCGCGG AGGCGCCCGG AGTCGTCACC GGGACCGCTC
69961  AGGAGCGGCG CGTCGCCTTC CTCTTCGACG GCCAGGGCGC CCAGCGCGCC GGAATGGGGC
70021  GCGAGCTCCA CCGCCGGTTC CCCGTCTTCG CCGCCGCGTG GGACGAGGTC TCCGACGCGT
70081  TCGGCAAGCA CCTCAAGCAC TCCCCCACGG ACGTCTACCA CGGCGAACAC GGCGCTCTCG
70141  CCCATGACAC CCTGTACGCC CAGGCCGGCC TGTTCACGCT CGAAGTGGCG CTGCTGCGGC
70201  TGCTGGAGCA CTGGGGGCTG CGGCCGGACG TGCTCGTCGG GCACTCCGTC GGCGAGGTGA
70261  CCGCGGCGTA CGCGGCGGGG GTGCTCACCC TGGCGGACGC GACGGAGTTG ATCGTGGCCC
70321  GGGGGCGGCC GCTGCGGGCG CTGCCGCCCG GGCGATGCT CGCCGTCGAC GGAAGCCCGG
70381  CGGAGGTCGG CGCCCGCACG GATCTGGACA TCGCCGCCGT CAACGGCCCG TCCGCCGTGG
70441  TGCTCGCCGG TTCGCCGGAC GATGTGCCGG CGTTCGAACG GGAGTGGTCG GCGGCCGGGC
```

-continued

```
70501 GGCGCACGAA ACGGCTCGAC GTCGGGCACG CGTTCCACTC CCGGCACGTC GACGGTGCGC
70561 TCGACGGCTT CCGTACGGTG CTGGAGTCGC TCGCGTTCGG CGCGGCGCGG CTGCCGGTGG
70621 TGTCCACGAC GACGGGCCGG GACGCCGCGG ACGACCTCAT AACGCCCGCG CACTGGCTGC
70681 GCCATGCGCG TCGGCCGGTG CTGTTCTCGG ATGCCGTCCG GGAGCTGGCC GACCGCGGCG
70741 TCACCACGTT CGTGGCCGTC GGCCCCTCCG GCTCCCTGGC GTCGGCCGCG GCGGAGAGCG
70801 CCGGGGAGGA CGCCGGGACC TACCACGCGG TGCTGCGCGC CCGGACCGGT GAGGAGACCG
70861 CGGCGCTGAC CGCCCTCGCC GAGCTGCACG CCCACGGCGT CCCGGTCGAC CTGGCCGCGG
70921 TACTGGCCGG TGGCCGGCCA GTGGACCTTC CCGTGTACGC GTTCCAGCAC CGTTCCTACT
70981 GGCTGGCCCC GGCCGTGGCG GGGGCGCCGG CCACCGTGGC GGACACCGGG GGTCCGGCGG
71041 AGTCCGAGCC GGAGGACCTC ACCGTCGCCG AGATCGTCCG TCGGCGCACC GCGGCGCTGC
71101 TCGGCGTCAC GGACCCCGCC GACGTCGATG CGGAAGCGAC GTTCTTCGCG CTCGGTTTCG
71161 ACTCACTGGC GGTGCAGCGG CTGCGCAACC AGCTCGCCTC GGCAACCGGG CTGGACCTGC
71221 CGGCGGCCGT CCTGTTCGAC CACGACACCC CGGCCGCGCT CACCGCGTTC CTCCAGGACC
71281 GGATCGAGGC CGGCCAGGAC CGGATCGAGG CCGGCGAGGA CGACGACGCG CCCACCGTGC
71341 TCTCGCTCCT GGAGGAGATG GAGTCGCTCG ACGCCGCGGA CATCGCGGCG ACGCCGGCCC
71401 CGGAGCGTGC GGCCATCGCC GATCTGCTCG ACAAGCTCGC CCATACCTGG AAGGACTACC
71461 GATGAGCACC GATACGCACG AGGGAACGCC GCCCGCCGGC CGCTGCCCAT TCGCGATCCA
71521 GGACGGTCAC CGCGCCATCC TGGAGAGCGG CACGGTGGGT TCGTTCGACC TGTTCGGCGT
71581 CAAGCACTGG CTGGTCGCCG CCGCCGAGGA CGTCAAGCTG GTCACCAACG ATCCGCGGTT
71641 CAGCTCGGCC GCGCCGTCCG AGATGCTGCC CGACCGGCGG CCCGGCTGGT TCTCCGGGAT
71701 GGACTCACCG GAGCACAACC GCTACCGGCA GAAGATCGCG GGGGACTTCA CACTGCGCGC
71761 GGCGCGCAAG CGGGAGGACT TCGTCGCCGA GGCCGCCGAC GCCTGCCTGG ACGACATCGA
71821 GGCCGCGGGA CCCGGCACCG ACCTCATCCC CGGGTACGCC AAGCGGCTGC CCTCCCTCGT
71881 CATCAACGCG CTGTACGGGC TCACCCCTGA GGAGGGGGCC GTGCTGGAGG CACGGATGCG
71941 CGACATCACC GGCTCGGCCG ATCTGGACAG CGTCAAGACG CTGACCGACG ACTTCTTCGG
72001 CCACGCGCTG CGGCTGGTCC GCGCGAAGCG TGACGAGCGG GGCGAGGACC TGCTGCACCG
72061 GCTGGCCTCG GCCGACGACG GCGAGATCTC GCTCAGCGAC GACGAGGCGA CGGGCGTGTT
72121 CGCGACGCTG CTGTTCGCCG GCCACGACTC GGTGCAGCAG ATGGTCGGCT ACTGCCTCTA
72181 CGCACTGCTC AGCCACCCCG AGCAGCAGGC GGCGCTGCGC GCGCGCCCGG AGCTGGTCGA
72241 CAACGCGGTC GAGGAGATGC TCCGTTTCCT GCCCGTCAAC CAGATGGGCG TACCGCGCGT
72301 CTGTGTCGAG GACGTCGATG TGCGGGGCGT GCGCATCCGT GCGGGCGACA ACGTGATCCC
72361 GCTCTACTCG ACGGCCAACC GCGACCCCGA GGTGTTCCCG CAGCCCGACA CCTTCGATGT
72421 GACGCGCCCG CTGGAGGGCA ACTTCGCGTT CGGCCACGGC ATTCACAAGT GTCCCGGCCA
72481 GCACATCGCC CCGGTGCTCA TCAAGGTCGC CTGCCTGCGG TTGTTCGAGC GTTTCCCGGA
72541 CGTCCGGCTG GCCGGCGACG TGCCGATGAA CGAGGGGCTC GGGCTGTTCA GCCCGGCCGA
72601 GCTGCGGGTC ACCTGGGGGG CGGCATGAGT CACCCGGTGG AGACGTTGCG GTTGCCGAAC
72661 GGGACGACGG TCGCGCACAT CAACGCGGGC GAGGCGCAGT TCCTCTACCG GGAGATCTTC
72721 ACCCAGCGCT GCTACCTGCG CCACGGTGTC GACCTGCGCC CGGGGGACGT GGTGTTCGAC
72781 GTCGGCGCGA ACATCGGCAT GTTCACGCTT TTCGCGCATC TGGAGTGTCC TGGTGTGACC
72841 GTGCACGCCT TCGAGCCCGC GCCCGTGCCG TTCGCGGCGC TGCGGGCGAA CGTGACGCGG
```

-continued

```
72901 CACGGCATCC CGGGCCAGGC GGACCAGTGC GCGGTCTCCG ACAGCTCCGG CACCCGGAAG
72961 ATGACCTTCT ATCCCGACGC CACGCTGATG TCCGGTTTCC ACGCGGATGC CGCGGCCCGG
73021 ACGGAGCTGT TGCGCACGCT CGGCCTCAAC GGCGGCTACA CCGCCGAGGA CGTCGACACC
73081 ATGCTCGCGC AACTGCCCGA CGTCAGCGAG GAGATCGAAA CCCCTGTGGT CCGGCTCTCC
73141 GACGTCATCG CGGAGCGCGG TATCGAGGCC ATCGGCCTGC TGAAGGTCGA CGTGGAGAAG
73201 AGCGAACGGC AGGTCTTCGC CGGCCTCGAG GACACCGACT GGCCCCGTAT CCGCCAGGTC
73261 GTCGCGGAGG TCCACGACAT CGACGGCGCG CTCGAGGAGG TCGTCACGCT GCTCCGCGGC
73321 CATGGCTTCA CCGTGGTCGC CGAGCAGGAA CCGCTGTTCG CCGGCACGGG CATCCACCAG
73381 GTCGCCGCGC GGCGGGTGGC CGGCTGAGCG CCGTCGGCGC CGCGGCCCTC CCCACCCCCC
73441 GCCGCGCTGC GCACGGCGGC TCAGCCGGCG TCGGACAGTT CCTTGGGCAG TTGCTCACGG
73501 CCCTTCACCC CCAGCTTGCG CAACACGTTG GTGAGGTGCT GTTCCACCGT GCTGGAGGTG
73561 ACGAACAGCT GGCTGGCGAT CTCCTTGTTG GTGCGCCCGA CCGCGGCGTG CGACGCCACC
73621 CGCCGCTCCG CCTCGGTCAG CGATGTGATC CGCTGCGCCG GCGTCACGTC CTGGGTGCCG
73681 TCCGCGTCCG AGGACTCCCC ACCGAGCCGC CGGAGGAGCG GCACGGCTCC GCACTGGGTC
73741 GCGAGGTGCC GTGCGCGGCG GAACAGTCCC CGCGCACGGC TGTGCCGCCG GAGCATCCCG
73801 CACGCTTCGC CCATGTCGGC GAGGACGCGG GCCAGCTCGT ACTGGTCGCG GCACATGATG
73861 AGCACATCGG CGGCCTCGTC GAGCAGTTCG ATCCGCTTGG CCGGCGGACT GTAGGCCGCC
73921 TGCACCCGCA GCGTCATCAC CCGCGCCCGG GACCCCATCG GCCGGGACAG CTGCTCGGAG
73981 ATGAGCCTCA GCCCCTCGTC ACGGCCGCGG CCGAGCAGCA GAAGCGCTTC GGCGGCGTCG
74041 ACCCGCCACA GGGCCAGGCC CGGCACGTCG ACGGACCAGC GTCGCATCCG CTCCCCGCAG
74101 TCCCGGAACG CGTTGTACGC CGCCCGGTAC CGCCCGGCCG CGAGATGGTG TTGCCCACGG
74161 GCCCAGACCA TGTGCAGTCC GAAGAGGCTG TCGGAGGTCT CCTCCGGCAA CGGCTCGGCG
74221 ACCCACCGCT CCGCCCGGTC CAGGTCGCCC AGTCGGATCG CGGCGGCCAC GGTGCTGCTC
74281 AGCGGCAATG CGGCGGCCAT CCCCCAGGAG GGCACGACCC GGGGGGCGAG CGCGGCCTCG
74341 CCGCATTCGA CGGCGGCGGT CAGGTCGCCG CGGCGCAGCG CGGCCTCGGC GCGGAACCCC
74401 GCGTGGACCC CCTCGTCGGC CCGGGTCCGC ATGTTGTCGT CACCGGCCAG CTTGTCGACC
74461 CAGGACTGGA CGGCATCGGT GTCCTCGGCG TAGAGCAGGG CCAGCAACGC CATCATGGTC
74521 GTGGTCCGGT CCGTCGTGAC CCGGGAGTGC TGGAGCACGT ACTCGGCTTT GGCCTCGGCC
74581 TGTTCGGACC AGCCGCCCAG CGCGTTGCTC AGGGCCTTGT CGGCGACGGC GCGGTGCCGG
74641 ACGGCTCCGG AAAACGAGGC GACCTCGTCC TCGGCCGGCG GATCGGCCGG ACGCGGCGGA
74701 TCGGCCGCGC CGGGATAGAT CAGCGCGAGG GACAGGTCCG CGACGCGCAG GTGCGCCCGG
74761 CCCTGCTCGC TCGGGGCGGC GGAGCGCTGG GCCGCCAGGA CCTCGGCGGC CTCGCCCGGC
74821 CGCCCGTCCA TCGCCAGCCA GCAGGCGAGC GACACGGCGT GCTCGCTGGA GAGGAGCCGT
74881 TCCCGCGACG CGGTGAGCAG CTCGGGCACA TGCCGGCCGC ATCTGGCGGG ATCGCAGACC
74941 CGCTCGATGG CGCCGGTGTC GACGCGCAGT GCGGCGTGGA CGGCGGGGTC GTCGGAGGCC
75001 CGGTAGGCGA ACTCCAGGTA GGTGACGGCC TCGTCGAGCT CGCCGCGCAG GTGGTGCTCG
75061 CGCGCGGCGT CGGTGAACAG CCCGGCGACC TCGGCGCCGT GCACCCGGCC GGTACCCATC
75121 TGGTGGCGGG CGAGCACCTT GCTGGCCACG CCGCGGTCCC GCAGCAGTTC CAGCGCCAGC
75181 TCGTGCAGGC CACGCCGCTC GGCGGCGGAG AGGTCGTCGA GTACGACGGA GCCGGCCCCG
75241 GGGTGCGGGA ACCGCCCTTC CCGCAGCAGC CGCCCCTCGA CCAGCTGTTC CTGGGCCTGC
```

-continued

```
75301 TCGACCGCCT CGGTGTCGAG GCCGCTCATC CGCTGGACGA GGGTGAGTTC GACACTCTCG
75361 CCGAGCACGG CGGAAGCTCC GGCGACGCTC AGCGCGGCCG GGCCGCAACG ATAGAGCGAC
75421 CCGAGGTAGG CGAGCCGGTA CGCCCGCCCC GCGACCACTT CCAGGCACCC TGAGGTCCGT
75481 GTCCGTGCCT CCCGGATGTC GTCGATCAGG CCGTGGCCGA GGAGCAGGTT GCCGCCGGTC
75541 GCCCGGAACG CCTGGGCCAC CACGTCGTCG TGCGCGTCCT GGCCGAGGTG CCGGCGCACG
75601 AGTTCGGTGG TCTGCGCCTC GGTGAGCGGG CGCAGCGCGA TCTCCTGGTA GTGGCGCAGA
75661 CTCAGCAGTG CCGCCCGGAA TTGGGAGTGG GCGGGCGTCG GCCGGAGCAG CTCGGTCAGC
75721 ACGATGGCGA CACGGGCCCG GCTGATGCGG CGCGCGAGGT GGAGCAGGCA GCGCAGCGAC
75781 GGCGCGTCGG CGTGGTGCAC GTCGTCGATG CCGATCAGTA CGGGCCGCTC CGCGGCGAGC
75841 GTCAGCACCG TGCGGGTGAG TTCGGTCCCC AGGCGGTTGT CGACGTCGGC CCGCAGCTTT
75901 TCGCACGATG CCGTCACCCG GACCAGCTCC GGTGTCCGGG CGGCCAGCTC GGGCTGGTCG
75961 AGGAGCTGGC CGAGCATGCC GTACGGCAGG GCCCGCTCCT CCATGGAGCA CACCGCGCGA
76021 AGGGTGACGA AGCCGGCCTT GGCCGCGGCG GCGTCGAGGA CTTCGGTCTT GCCCCAGGCG
76081 ATCGGCCCGG TGACCGCCGC GACGACGCCC CGCCCGCCCC CCGCTCGGGT GAGCGCCCGG
76141 TGGAGGGAAC CGAACTCGTC ATCGCGGGCG ATCAGGTCTG GGGGAGATAA GCGCGCTATC
76201 ACGAATGGAA CTACCTCGCG ACCGTCGTGG AAACCCATAG GCATCACATG GCTTGTTGAT
76261 CTGTACGGCT GTGATTCAGC CTGGCGGGAT GCTGTGCTAC AGATGGGAAG ATGTGATCTA
76321 GGGCCGTGCC GTTCCCTCAG GAGCCGACCG CCCCCGGCGC CACCCGCCGT ACCCCCTGGG
76381 CCACCAGCTC GGCGACCCGC TCCTGGTGGT CGACGAGGTA GAAGTGCCCG CCGGGGAAGA
76441 CCTCCACCGT GGTCGGCGCG GTCGTGTGCC CGGCCCAGGC GTGGGCCTGC TCGACCGTCG
76501 TCTTCGGATC GTCGTCACCC ATGCACACCG TGATCGGCGT CTCCAGCGGC GGCGCGGGCT
76561 CCCACCGGTA CGTCTCCGCC GCGTAGTAGT CCGCCCGCAA CGGCGCCAGG ATCAGCGCGC
76621 GCATTTCGTC GTCCGCCATC ACATCGGCGC TCGTCCCGCC GAGGCCGATG ACCGCCGCCA
76681 GCAGCTCGTC GTCGGACGCG AGGTGGTCCT GGTCGGCGCG CGGCTGCGAC GGCGCCCGCC
76741 GGCCCGAGAC GATCAGGTGC GCCACCGGGA GCCGCTGGGC CAGCTCGAAC GCGAGTGTCG
76801 CGCCCATGCT GTGGCCGAAC AGCACCAGCG GACGGTCCAG CCCCGGCTTC AACGCCTCGG
76861 CCACGAGGCC GGCGACAACA CGCAGGTCGC GCACCGCCTC CTCGTCGCGG CGGTCCTGGC
76921 GGCCGGGGTA CTGCACGGCG TACACGTCCG CCACCGGGGC GAGCGCACGG GCCAGCGGAA
76981 GGTAGAACGT CGCCGATCCG CCGGCGTGGG GCACCAGCAC CACCCCTACC GGGGCCTCGG
77041 GCGTGGGGAA GAACTGCCGC AGCCAGAGTT CCGAGCTCAC CGCACCCCCT CGGCCGCGAC
77101 CTGGGGAGCC CGGAACCGGG TGATCTCGGC CAAGTGCTTC TCCCGCATCT CCGGGTCGGT
77161 CACGCCCCAT CCCTCCTCCG GCGCCAGACA GAGGACGCCG ACTTTGCCGT TGTGCACATT
77221 GCGATGCACA TCGCGCACCG CCGACCCGAC GTCGTCGAGC GGGTAGGTCA CCGACAGCGT
77281 CGGGTGCACC ATCCCCTTGC AGATCAGGCG GTTCGCCTCC CACGCCTCAC GATAGTTCGC
77341 GAAGTGGGTA CCGATGATCC GCTTCACGGA CATCCACAGG TACCGATTGT CAAAGGCGTG
77401 CTCGTATCCC GAGGTTGACG CGCAGGTGAC GATCGTGCCA CCCCGACGTG TCACGTAGAC
77461 ACTCGCGCCG AACGTCGCGC GCCCCGGGTG CTCGAACACG ATGTCGGGAT CGTCACCGCC
77521 GGTCAGCTCC CGGATC
```

Those of skill in the art will recognize that, due to the degenerate nature of the genetic code, a variety of DNA compounds differing in their nucleotide sequences can be used to encode a given amino acid sequence of the invention. The native DNA sequence encoding the FK-520 PKS of Streptomyces hygroscopicus is shown herein merely to illustrate a preferred embodiment of the invention, and the present invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences shown merely illustrate preferred embodiments of the invention.

The recombinant nucleic acids, proteins, and peptides of the invention are many and diverse. To facilitate an understanding of the invention and the diverse compounds and methods provided thereby, the following general description of the FK-520 PKS genes and modules of the PKS proteins encoded thereby is provided. This general description is followed by a more detailed description of the various domains and modules of the FK-520 PKS contained in and encoded by the compounds of the invention. In this description, reference to a heterologous PKS refers to any PKS other than the FK-520 PKS. Unless otherwise indicated, reference to a PKS includes reference to a portion of a PKS. Moreover, reference to a domain, module, or PKS includes reference to the nucleic acids encoding the same and vice-versa, because the methods and reagents of the invention provide or enable one to prepare proteins and the nucleic acids that encode them.

The FK-520 PKS is composed of three proteins encoded by three genes designated fkbA, fkbB, and fkbC. The fkbA ORF encodes extender modules 7–10 of the PKS. The fkbB ORF encodes the loading module (the CoA ligase) and extender modules 1–4 of the PKS. The fkbC ORF encodes extender modules 5–6 of the PKS. The fkbP ORF encodes the NRPS that attaches the pipecolic acid and cyclizes the FK-520 polyketide.

The loading module of the FK-520 PKS includes a CoA ligase, an ER domain, and an ACP domain. The starter building block or unit for FK-520 is believed to be a dihydroxycyclohexene carboxylic acid, which is derived from shikimate. The recombinant DNA compounds of the invention that encode the loading module of the FK-520 PKS and the corresponding polypeptides encoded thereby are useful for a variety of methods and in a variety of compounds. In one embodiment, a DNA compound comprising a sequence that encodes the FK-520 loading module is inserted into a DNA compound that comprises the coding sequence for a heterologous PKS. The resulting construct, in which the coding sequence for the loading module of the heterologous PKS is replaced by the coding sequence for the FK-520 loading module, provides a novel PKS coding sequence. Examples of heterologous PKS coding sequences include the rapamycin, FK-506, rifamycin, and avermectin PKS coding sequences. In another embodiment, a DNA compound comprising a sequence that encodes the FK-520 loading module is inserted into a DNA compound that comprises the coding sequence for the FK-520 PKS or a recombinant FK-520 PKS that produces an FK-520 derivative.

In another embodiment, a portion of the loading module coding sequence is utilized in conjunction with a heterologous coding sequence. In this embodiment, the invention provides, for example, either replacing the CoA ligase with a different CoA ligase, deleting the ER, or replacing the ER with a different ER. In addition, or alternatively, the ACP can be replaced by another ACP. In similar fashion, the corresponding domains in another loading or extender module can be replaced by one or more domains of the FK-520 PKS. The resulting heterologous loading module coding sequence can be utilized in conjunction with a coding sequence for a PKS that synthesizes FK-520, an FK-520 derivative, or another polyketide.

The first extender module of the FK-520 PKS includes a KS domain, an AT domain specific for methylmalonyl CoA, a DH domain, a KR domain, and an ACP domain. The recombinant DNA compounds of the invention that encode the first extender module of the FK-520 PKS and the corresponding polypeptides encoded thereby are useful for a variety of applications. In one embodiment, a DNA compound comprising a sequence that encodes the FK-520 first extender module is inserted into a DNA compound that comprises the coding sequence for a heterologous PKS. The resulting construct, in which the coding sequence for a module of the heterologous PKS is either replaced by that for the first extender module of the FK-520 PKS or the latter is merely added to coding sequences for modules of the heterologous PKS, provides a novel PKS coding sequence. In another embodiment, a DNA compound comprising a sequence that encodes the first extender module of the FK-520 PKS is inserted into a DNA compound that comprises the remainder of the coding sequence for the FK-520 PKS or a recombinant FK-520 PKS that produces an FK-520 derivative.

In another embodiment, all or only a portion of the first extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with another DH or KR; and/or inserting an ER. In replacing or inserting KR, DH, and ER domains, it is often beneficial to replace the existing KR, DH, and ER domains with the complete set of domains desired from another module. Thus, if one desires to insert an ER domain, one may simply replace the existing KR and DH domains with a KR, DH, and ER set of domains from a module containing such domains. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a gene for a PKS that produces a polyketide other than FK-520, or from chemical synthesis. The resulting heterologous first extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the first extender module of the FK-520 PKS.

In an illustrative embodiment of this aspect of the invention, the invention provides recombinant PKSs and recombinant DNA compounds and vectors that encode such PKSs in which the KS domain of the first extender module has been inactivated. Such constructs are especially useful when placed in translational reading frame with the remaining modules and domains of an FK-520 or FK-520 derivative PKS. The utility of these constructs is that host cells expressing, or cell free extracts containing, the PKS encoded thereby can be fed or supplied with N-acylcysteamine thioesters of novel precursor molecules to prepare FK-520 derivatives. See U.S. patent application Ser. No. 60/117,384, filed Jan. 27, 1999, and PCT patent publication Nos. US97/02358 and US99/03986, each of which is incorporated herein by reference.

The second extender module of the FK-520 PKS includes a KS, an AT specific for methylmalonyl CoA, a KR, an inactive DH, and an ACP. The recombinant DNA compounds of the invention that encode the second extender module of the FK-520 PKS and the corresponding polypeptides encoded thereby are useful for a variety of applications. In one embodiment, a DNA compound comprising a sequence that encodes the FK-520 second extender module is inserted into a DNA compound that comprises the coding sequence for a heterologous PKS. The resulting construct, in which the coding sequence for a module of the heterologous PKS is either replaced by that for the second extender module of the FK-520 PKS or the latter is merely added to coding sequences for the modules of the heterologous PKS, provides a novel PKS coding sequence. In another embodiment, a DNA compound comprising a sequence that encodes the second extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the second extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous second extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the second extender module of the FK-520 PKS.

The third extender module of the FK-520 PKS includes a KS, an AT specific for malonyl CoA, a KR, an inactive DH, and an ACP. The recombinant DNA compounds of the invention that encode the third extender module of the FK-520 PKS and the corresponding polypeptides encoded thereby are useful for a variety of applications. In one embodiment, a DNA compound comprising a sequence that encodes the FK-520 third extender module is inserted into a DNA compound that comprises the coding sequence for a heterologous PKS. The resulting construct, in which the coding sequence for a module of the heterologous PKS is either replaced by that for the third extender module of the FK-520 PKS or the latter is merely added to coding sequences for the modules of the heterologous PKS, provides a novel PKS coding sequence. In another embodiment, a DNA compound comprising a sequence that encodes the third extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the third extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous third extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the third extender module of the FK-520 PKS.

The fourth extender module of the FK-520 PKS includes a KS, an AT that binds ethylmalonyl CoA, an inactive DH, and an ACP. The recombinant DNA compounds of the invention that encode the fourth extender module of the FK-520 PKS and the corresponding polypeptides encoded thereby are useful for a variety of applications. In one embodiment, a DNA compound comprising a sequence that encodes the FK-520 fourth extender module is inserted into a DNA compound that comprises the coding sequence for a heterologous PKS. The resulting construct, in which the coding sequence for a module of the heterologous PKS is either replaced by that for the fourth extender module of the FK-520 PKS or the latter is merely added to coding sequences for the modules of the heterologous PKS, provides a novel PKS coding sequence. In another embodiment, a DNA compound comprising a sequence that encodes the fourth extender module of the FK-520 PKS is inserted into a DNA compound that comprises the remainder of the coding sequence for the FK-520 PKS or a recombinant FK-520 PKS that produces an FK-520 derivative.

In another embodiment, a portion of the fourth extender module coding sequence is utilized in conjunction with other PKS coding sequences to create a hybrid module. In this embodiment, the invention provides, for example, either replacing the ethylmalonyl CoA specific AT with a malonyl CoA, methylmalonyl CoA, or 2-hydroxymalonyl CoA specific AT; and/or deleting the inactive DH, inserting a KR, a KR and an active DH, or a KR, an active DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, a PKS for a polyketide other than FK-520, or from chemical synthesis. The resulting heterologous fourth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fourth extender module of the FK-520 PKS.

As illustrative examples, the present invention provides recombinant genes, vectors, and host cells that result from the conversion of the FK-506 PKS to an FK-520 PKS and vice-versa. In one embodiment, the invention provides a recombinant set of FK-506 PKS genes but in which the coding sequences for the fourth extender module or at least those for the AT domain in the fourth extender module have been replaced by those for the AT domain of the fourth extender module of the FK-520 PKS. This recombinant PKS can be used to produce FK-520 in recombinant host cells. In another embodiment, the invention provides a recombinant set of FK-520 PKS genes but in which the coding sequences for the fourth extender module or at least those for the AT domain in the fourth extender module have been replaced by those for the AT domain of the fourth extender module of the FK-506 PKS. This recombinant PKS can be used to produce FK-506 in recombinant host cells.

Other examples of hybrid PKS enzymes of the invention include those in which the AT domain of module 4 has been replaced with a malonyl specific AT domain to provide a PKS that produces 21-desethyl-FK520 or with a methylmalonyl specific AT domain to provide a PKS that produces 21-desethyl-21-methyl-FK520. Another hybrid PKS of the invention is prepared by replacing the AT and inactive KR domain of FK-520 extender module 4 with a methylmalonyl specific AT and an active KR domain, such as, for example, from module 2 of the DEBS or oleandolide PKS enzymes, to produce 21-desethyl-21-methyl-22-desoxo-22-hydroxy-FK520. The compounds produced by these hybrid PKS enzymes are neurotrophins.

The fifth extender module of the FK-520 PKS includes a KS, an AT that binds methylmalonyl CoA, a DH, a KR, and an ACP. The recombinant DNA compounds of the invention that encode the fifth extender module of the FK-520 PKS and the corresponding polypeptides encoded thereby are useful for a variety of applications. In one embodiment, a DNA compound comprising a sequence that encodes the FK-520 fifth extender module is inserted into a DNA compound that comprises the coding sequence for a heterologous PKS. The resulting construct, in which the coding sequence for a module of the heterologous PKS is either replaced by that for the fifth extender module of the FK-520 PKS or the latter is merely added to coding sequences for the modules of the heterologous PKS, provides a novel PKS. In another embodiment, a DNA compound comprising a sequence that encodes the fifth extender module of the FK-520 PKS is inserted into a DNA compound that comprises the coding sequence for the FK-520 PKS or a recombinant FK-520 PKS that produces an FK-520 derivative.

In another embodiment, a portion of the fifth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one or both of the DH and KR; replacing any one or both of the DH and KR with either a KR and/or DH; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous fifth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fifth extender module of the FK-520 PKS.

In an illustrative embodiment, the present invention provides a set of recombinant FK-520 PKS genes in which the coding sequences for the DH domain of the fifth extender module have been deleted or mutated to render the DH non-functional. In one such mutated gene, the KR and DH coding sequences are replaced with those encoding only a KR domain from another PKS gene. The resulting PKS genes code for the expression of an FK-520 PKS that produces an FK-520 analog that lacks the C-19 to C-20 double bond of FK-520 and has a C-20 hydroxyl group. Such analogs are preferred neurotrophins, because they have little or no immunosuppressant activity. This recombinant fifth extender module coding sequence can be combined with other coding sequences to make additional compounds of the invention. In an illustrative embodiment, the present invention provides a recombinant FK-520 PKS that contains both this fifth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (lacking the C-19 to C-20 double bond of FK-506 and having a C-20 hydroxyl group) FK-506 derivative. In another embodiment, the present invention provides a recombinant FK-506 PKS in which the DH domain of module 5 has been deleted or otherwise rendered inactive and thus produces this novel polyketide.

The sixth extender module of the FK-520 PKS includes a KS, an AT specific for methylmalonyl CoA, a KR, a DH, an ER, and an ACP. The recombinant DNA compounds of the invention that encode the sixth extender module of the FK-520 PKS and the corresponding polypeptides encoded thereby are useful for a variety of applications. In one embodiment, a DNA compound comprising a sequence that encodes the FK-520 sixth extender module is inserted into a DNA compound that comprises the coding sequence for a heterologous PKS. The resulting construct, in which the coding sequence for a module of the heterologous PKS is either replaced by that for the sixth extender module of the FK-520 PKS or the latter is merely added to coding sequences for the modules of the heterologous PKS, provides a novel PKS coding sequence. In another embodiment, a DNA compound comprising a sequence that encodes the sixth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the sixth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous sixth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the sixth extender module of the FK-520 PKS.

In an illustrative embodiment, the present invention provides a set of recombinant FK-520 PKS genes in which the coding sequences for the DH and ER domains of the sixth extender module have been deleted or mutated to render them non-functional. In one such mutated gene, the KR, ER, and DH coding sequences are replaced with those encoding only a KR domain from another PKS gene. This can also be accomplished by simply replacing the coding sequences for extender module six with those for an extender module having a methylmalonyl specific AT and only a KR domain from a heterologous PKS gene, such as, for example, the coding sequences for extender module two encoded by the eryAI gene. The resulting PKS genes code for the expression of an FK-520 PKS that produces an FK-520 analog that has a C-18 hydroxyl group. Such analogs are preferred neurotrophins, because they have little or no immunosuppressant activity. This recombinant sixth extender module coding sequence can be combined with other coding sequences to make additional compounds of the invention. In an illustrative embodiment, the present invention provides a recombinant FK-520 PKS that contains both this sixth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (having a C-18 hydroxyl group) FK-506 derivative. In another embodiment, the present invention provides a recombinant FK-506 PKS in which the DH and ER domains of module 6 have been deleted or otherwise rendered inactive and thus produces this novel polyketide.

The seventh extender module of the FK-520 PKS includes a KS, an AT specific for 2-hydroxymalonyl CoA, a KR, a DH, an ER, and an ACP. The recombinant DNA compounds of the invention that encode the seventh extender module of the FK-520 PKS and the corresponding polypeptides encoded thereby are useful for a variety of applications. In one embodiment, a DNA compound comprising a sequence that encodes the FK-520 seventh extender module is inserted into a DNA compound that comprises the coding sequence for a heterologous PKS. The resulting construct, in which the coding sequence for a module of the heterologous PKS is either replaced by that for the seventh extender module of the FK-520 PKS or the latter is merely added to coding sequences for the modules of the heterologous PKS, provides a novel PKS coding sequence. In another embodiment, a DNA compound comprising a sequence that encodes the seventh extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the seventh extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting the KR, the DH, and/or the ER; and/or replacing the KR, DH, and/or ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous seventh extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the seventh extender module of the FK-520 PKS.

In an illustrative embodiment, the present invention provides a set of recombinant FK-520 PKS genes in which the coding sequences for the AT domain of the seventh extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-15 methoxy group, having instead a hydrogen, methyl, or ethyl group at that position, respectively. Such analogs are preferred, because they are more slowly metabolized than FK-520. This recombinant seventh extender module coding sequence can be combined with other coding sequences to make additional compounds of the invention. In an illustrative embodiment, the present invention provides a recombinant FK-520 PKS that contains both this seventh extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-15-desmethoxy) FK-506 derivative. In another embodiment, the present invention provides a recombinant FK-506 PKS in which the AT domain of module 7 has been replaced and thus produces this novel polyketide.

In another illustrative embodiment, the present invention provides a hybrid PKS in which the AT and KR domains of module 7 of the FK-520 PKS are replaced by a methylmalonyl specific AT domain and an inactive KR domain, such as, for example, the AT and KR domains of extender module 6 of the rapamycin PKS. The resulting hybrid PKS produces 15-desmethoxy-15-methyl-16-oxo-FK-520, a neurotrophin compound.

The eighth extender module of the FK-520 PKS includes a KS, an AT specific for 2-hydroxymalonyl CoA, a KR, and an ACP. The recombinant DNA compounds of the invention that encode the eighth extender module of the FK-520 PKS and the corresponding polypeptides encoded thereby are useful for a variety of applications. In one embodiment, a DNA compound comprising a sequence that encodes the FK-520 eighth extender module is inserted into a DNA compound that comprises the coding sequence for a heterologous PKS. The resulting construct, in which the coding sequence for a module of the heterologous PKS is either replaced by that for the eighth extender module of the FK-520 PKS or the latter is merely added to coding sequences for the modules of the heterologous PKS, provides a novel PKS coding sequence. In another embodiment, a DNA compound comprising a sequence that encodes the eighth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the eighth extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting or replacing the KR; and/or inserting a DH or a DH and an ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous eighth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the eighth extender module of the FK-520 PKS.

In an illustrative embodiment, the present invention provides a set of recombinant FK-520 PKS genes in which the coding sequences for the AT domain of the eighth extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-13 methoxy group, having instead a hydrogen, methyl, or ethyl group at that position, respectively. Such analogs are preferred, because they are more slowly metabolized than FK-520. This recombinant eighth extender module coding sequence can be combined with other coding sequences to make additional compounds of the invention. In an illustrative embodiment, the present invention provides a recombinant FK-520 PKS that contains both this eighth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-13-desmethoxy) FK-506 derivative. In another embodiment, the present invention provides a recombinant FK-506 PKS in which the AT domain of module 8 has been replaced and thus produces this novel polyketide.

The ninth extender module of the FK-520 PKS includes a KS, an AT specific for methylmalonyl CoA, a KR, a DH, an ER, and an ACP. The recombinant DNA compounds of the invention that encode the ninth extender module of the FK-520 PKS and the corresponding polypeptides encoded thereby are useful for a variety of applications. In one embodiment, a DNA compound comprising a sequence that encodes the FK-520 ninth extender module is inserted into a DNA compound that comprises the coding sequence for a heterologous PKS. The resulting construct, in which the coding sequence for a module of the heterologous PKS is either replaced by that for the ninth extender module of the FK-520 PKS or the latter is merely added to coding sequences for the modules of the heterologous PKS, provides a novel PKS coding sequence. In another embodiment, a DNA compound comprising a sequence that encodes the ninth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the ninth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and/or ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous ninth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the ninth extender module of the FK-520 PKS.

The tenth extender module of the FK-520 PKS includes a KS, an AT specific for malonyl CoA, and an ACP. The recombinant DNA compounds of the invention that encode the tenth extender module of the FK-520 PKS and the corresponding polypeptides encoded thereby are useful for a variety of applications. In one embodiment, a DNA compound comprising a sequence that encodes the FK-520 tenth extender module is inserted into a DNA compound that comprises the coding sequence for a heterologous PKS. The resulting construct, in which the coding sequence for a module of the heterologous PKS is either replaced by that for the tenth extender module of the FK-520 PKS or the latter is merely added to coding sequences for the modules of the heterologous PKS, provides a novel PKS coding sequence. In another embodiment, a DNA compound comprising a sequence that encodes the tenth extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the tenth extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; and/or inserting a KR, a KR and DH, or a KR, DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous tenth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the tenth extender module of the FK-520 PKS.

The FK-520 polyketide precursor produced by the action of the tenth extender module of the PKS is then attached to pipecolic acid and cyclized to form FK-520. The enzyme FkbP is the NRPS like enzyme that catalyzes these reactions. FkbP also includes a thioesterase activity that cleaves the nascent FK-520 polyketide from the NRPS. The present invention provides recombinant DNA compounds that encode the fkbP gene and so provides recombinant methods for expressing the fkbP gene product in recombinant host cells. The recombinant fkbP genes of the invention include those in which the coding sequence for the adenylation domain has been mutated or replaced with coding sequences from other NRPS like enzymes so that the resulting recombinant FkbP incorporates a moiety other than pipecolic acid. For the construction of host cells that do not naturally produce pipecolic acid, the present invention provides recombinant DNA compounds that express the enzymes that catalyze at least some of the biosynthesis of pipecolic acid (see Nielsen et al., 1991, *Biochem.* 30: 5789–96). The fkbL gene encodes a homolog of RapL, a lysine cyclodeaminase responsible in part for producing the pipecolate unit added to the end of the polyketide chain. The fkbB and fkbL recombinant genes of the invention can be used in heterologous hosts to produce compounds such as FK-520 or, in conjunction with other PKS or NRPS genes, to produce known or novel polyketides and non-ribosmal peptides.

Figure 2:
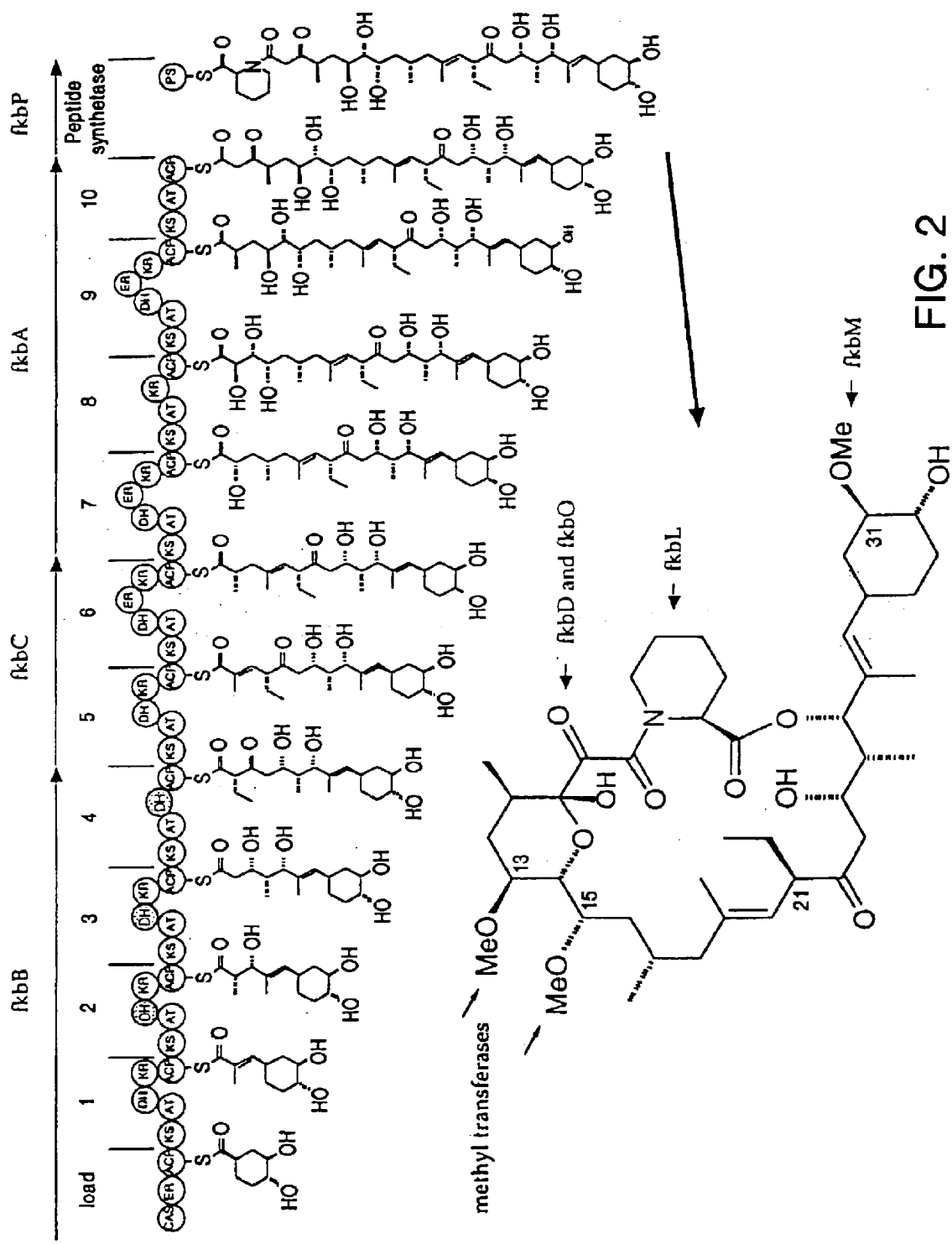
FIG. 2 shows the loading module (load), the ten extender modules, and the peptide synthetase domain of the FK-520 PKS, together with, on the top line, the genes that encode the various domains and modules. Also shown are the various intermediates in FK-520 biosynthesis, as well as the structure of FK-520, with carbons 13, 15, 21, and 31 numbered. The various domains of each module and subdomains of the loading module are also shown. The darkened circles showing the DH domains in modules 2, 3, and 4 indicate that the dehydratase domain is not functional as a dehydratase; this domain may affect the stereochemistry at the corresponding position in the polyketide. The substituents on the FK-520 structure that result from the action of non-PKS enzymes are also indicated by arrows, together with the types of enzymes or the genes that code for the enzymes that mediate the action. Although the methyltransferase is shown acting at the C-13 and C-15 hydroxyl groups after release of the polyketide from the PKS, the methyltransferase may act on the 2-hydroxymalonyl substrate prior to or contemporaneously with its incorporation during polyketide synthesis.

The present invention also provides recombinant DNA compounds that encode the P450 oxidase and methyltransferase genes involved in the biosynthesis of FK-520. FIG. 2 shows the various sites on the FK-520 polyketide core structure at which these enzymes act. By providing these genes in recombinant form, the present invention provides recombinant host cells that can produce FK-520. This is accomplished by introducing the recombinant PKS, P450 oxidase, and methyltransferase genes into a heterologous host cell. In a preferred embodiment, the heterologous host cell is *Streptomyces coelicolor* CH999 or *Streptomyces lividans* K4-114, as described in U.S. Pat. No. 5,830,750 and U.S. patent application Ser. No. 08/828,898, filed Mar. 31, 1997, and Ser. No. 09/181,833, filed Oct. 28, 1998, each of which is incorporated herein by reference. In addition, by providing recombinant host cells that express only a subset of these genes, the present invention provides methods for making FK-520 precursor compounds not readily obtainable by other means.

In a related aspect, the present invention provides recombinant DNA compounds and vectors that are useful in generating, by homologous recombination, recombinant host cells that produce FK-520 precursor compounds. In this aspect of the invention, a native host cell that produces FK-520 is transformed with a vector (such as an SCP2* derived vector for Streptomyces host cells) that encodes one or more disrupted genes (i.e., a hydroxylase, a methyltransferase, or both) or merely flanking regions from those genes. When the vector integrates by homologous recombination, the native, functional gene is deleted or replaced by the non-functional recombinant gene, and the resulting host cell thus produces an FK-520 precursor. Such host cells can also be complemented by introduction of a modified form of the deleted or mutated non-functional gene to produce a novel compound.

In one important embodiment, the present invention provides a hybrid PKS and the corresponding recombinant DNA compounds that encode those hybrid PKS enzymes. For purposes of the present invention a hybrid PKS is a recombinant PKS that comprises all or part of one or more modules and thioesterase/cyclase domain of a first PKS and all or part of one or more modules, loading module, and thioesterase/cyclase domain of a second PKS. In one preferred embodiment, the first PKS is all or part of the FK-520 PKS, and the second PKS is only a portion or all of a non-FK-520 PKS.

One example of the preferred embodiment is an FK-520 PKS in which the AT domain of module 8, which specifies a hydroxymalonyl CoA and from which the C-13 methoxy group of FK-520 is derived, is replaced by an AT domain that specifies a malonyl, methylmalonyl, or ethylmalonyl CoA. Examples of such replacement AT domains include the AT domains from modules 3, 12, and 13 of the rapaymycin PKS and from modules 1 and 2 of the erythromycin PKS. Such replacements, conducted at the level of the gene for the PKS, are illustrated in the examples below. Another illustrative example of such a hybrid PKS includes an FK-520 PKS in which the natural loading module has been replaced with a loading module of another PKS. Another example of such a hybrid PKS is an FK-520 PKS in which the AT domain of module three is replaced with an AT domain that binds methylmalonyl CoA.

In another preferred embodiment, the first PKS is most but not all of a non-FK-520 PKS, and the second PKS is only a portion or all of the FK-520 PKS. An illustrative example of such a hybrid PKS includes an erythromycin PKS in which an AT specific for methylmalonyl CoA is replaced with an AT from the FK-520 PKS spectfic for malonyl CoA.

Those of skill in the art will recognize that all or part of either the first or second PKS in a hybrid PKS of the invention need not be isolated from a naturally occurring source. For example, only a small portion of an AT domain determines its specificity. See U.S. provisional patent application Serial No. 60/091,526, incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

Thus, the hybrid modules of the invention are incorporated into a PKS to provide a hybrid PKS of the invention. A hybrid PKS of the invention can result not only:

(i) from fusions of heterologous domain (where heterologous means the domains in that module are from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more FK-520 PKS genes with one or more non-FK-520 PKS genes, including both naturally occurring and recombinant non-FK-520 PKS genes, and (iv) from combinations of the foregoing.

Various hybrid PKSs of the invention illustrating these various alternatives are described herein.

Examples of the production of a hybrid PKS by co-expression of PKS genes from the FK-520 PKS and another non-FK-520 PKS include hybrid PKS enzymes produced by coexpression of FK-520 and rapamycin PKS genes. Preferably, such hybrid PKS enzymes are produced in recombinant Streptomyces host cells that produce FK-520 or FK-506 but have been mutated to inactivate the gene whose function is to be replaced by the rapamycin PKS gene introduced to produce the hybrid PKS. Particular examples include (i) replacement of the fkbC gene with the rapB gene; and (ii) replacement of the fkbA gene with the rapC gene. The latter hybrid PKS produces 13,15-didesmethoxy-FK-520, if the host cell is an FK-520 producing host cell, and 13,15-didesmethoxy-FK-506, if the host cell is an FK-506 producing host cell. The compounds produced by these hybrid PKS enzymes are immunosuppressants and neurotrophins but can be readily modified to act only as neurotrophins, as described in Example 6, below.

Other illustrative hybrid PKS enzymes of the invention are prepared by replacing the fkbA gene of an FK-520 or FK-506 producing host cell with a hybrid fkbA gene in which: (a) the extender module 8 through 10, inclusive, coding sequences have been replaced by the coding sequnces for extender modules 12 to 14, inclusive, of the rapamycin PKS; and (b) the module 8 coding sequences have been replaced by the module 8 coding sequence of the rifamycin PKS. When expressed with the other, naturally occurring FK-520 or FK-506 PKS genes and the genes of the modification enzymes, the resulting hybrid PKS enzymes produce, respectively, (a) 13-desmethoxy-FK-520 or 13-desmethoxy-FK-506; and (b) 13-desmethoxy-13-methyl-FK-520 or 13-desmethoxy-13-methyl-FK-506. In a preferred embodiment, these recombinant PKS genes of the invention are introduced into the producing host cell by a vector such as pHU204, which is a plamsid pRM5 derivative that has the well-characterized SCP2* replicon, the colE1 replicon, the tsr and bla resistance genes, and a cos site. This vector can be used to introduce the recombinant fkbA replacement gene in an FK-520 or FK-506 producing host cell (or a host cell derived therefrom in which the endogenous fkbA gene has either been rendered inactive by mutation, deletion or homologous recombination with the gene that replaces it) to produce the desired hybrid PKS.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units," *Biochemistry* 38(5):1643–1651, incorporated herein by reference. Stereochemistry can also be changed by changing the KR domain. Also, one can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, "Dissecting and Exploiting Intermodular Communication in Polyketide Synthases," *Science* 284: 482–485, incorporated herein by reference.

The following Table lists references describing illustrative PKS genes and corresponding enzymes that can be utilized in the construction of the recombinant PKSs and the corresponding DNA compounds that encode them of the invention. Also presented are various references describing tailoring enzymes and corresponding genes that can be employed in accordance with the methods of the present invention.

Avermectin
 U.S. Pat. No. 5,252,474 to Merck.
 MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
 MacNeil et al., 1992, *Gene* 115: 119–125, Complex Organization of the *Streptomyces avermitilis* genes encoding the avermectin polyketide synthase.
 Ikeda et al., August 1999, Organization of the biosynthetic gene cluster for the polyketide anthelmintic macrolide avermectin in *Streptomyces avermitilis*, *Proc. Natl. Acad. Sci. USA* 96: 9509–9514.

Candicidin (FR008)
 Hu et al., 1994, *Mol. Microbiol.* 14: 163–172.

Epothilone
 U.S. Pat. App. Ser. No. 60/130,560, filed Apr. 22, 1999.

Erythromycin
 PCT Pub. No. 93/13663 to Abbott.
 U.S. Pat. No. 5,824,513 to Abbott.
 Donadio et al., 1991, *Science* 252:675–9.
 Cortes et al., Nov. 8, 1990, *Nature* 348:176–8, An unusually large multifunctional polypeptide in the erythromycin producing polyketide synthase of *Saccharopolyspora erythraea*.

Glycosylation Enzymes
 PCT Pat. App. Pub. No. 97/23630 to Abbott. FK-506
 Motamedi et al., 1998, The biosynthetic gene cluster for the macrolactone ring of the immunosuppressant FK-506, *Eur. J. biochem.* 256: 528–534.
 Motamedi et al., 1997, Structural organization of a multifunctional polyketide synthase involved in the biosynthesis of the macrolide immunosuppressant FK-506, *Eur. J. Biochem.* 244: 74–80.

Methyltransferase
 U.S. Pat. No. 5,264,355, issued Nov. 23, 1993, Methylating enzyme from Streptomyces MA6858. 31-O-desmethyl-FK-506 methyltransferase.
 Motamedi et al., 1996, Characterization of methyltransferase and hydroxylase genes involved in the biosynthesis of the immunosuppressants FK-506 and FK-520, *J. Bacteriol.* 178: 5243–5248.

*Streptomyces hygroscopicus*
 U.S. patent application Ser. No. 09/154,083, filed Sep. 16, 1998.

Lovastatin
 U.S. Pat. No. 5,744,350 to Merck.

Narbomycin
 U.S. patent application Ser. No. 60/107,093, filed Nov. 5, 1998, and Serial No. 60/120,254, filed Feb. 16, 1999.

Nemadectin
 MacNeil et al., 1993, supra.

Niddamycin
 Kakavas et al., 1997, Identification and characterization of the niddamycin polyketide synthase genes from *Streptomyces caelestis*, *J. Bacteriol.* 179: 7515–7522.

Oleandomycin
 Swan et al., 1994, Characterisation of a *Streptomyces antibioticus* gene encoding a type I polyketide synthase which has an unusual coding sequence, *Mol. Gen. Genet.* 242: 358–362.
 U.S. patent application Ser. No. 60/120,254, filed Feb. 16, 1999.
 Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.

Picromycin
 PCT patent application US99/15047, filed Jul. 2, 1999.
 Xue et al., 1998, Hydroxylation of macrolactones YC-17 and narbomycin is mediated by the pikC-encoded cytochrome P450 in *Streptomyces venezuelae*, *Chemistry & Biology* 5(11): 661–667.

Xue et al., October 1998, A gene cluster for macrolide antibiotic biosynthesis in *Streptomyces venezuelae*: Architecture of metabolic diversity, *Proc. Natl. Acad. Sci. USA* 95: 12111 12116.
Platenolide
   EP Pat. App. Pub. No. 791,656 to Lilly.
Rapamycin
   Schwecke et al., August 1995, The biosynthetic gene cluster for the polyketide rapamycin, *Proc. Natl. Acad. Sci. USA* 92:7839–7843.
   Aparicio et al., 1996, Organization of the biosynthetic gene cluster for rapamycin in *Streptomyces hygroscopicus*: analysis of the enzymatic domains in the modular polyketide synthase, *Gene* 169: 9–16.
Rifamycin
   August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.
Sorangium PKS
   U.S. patent application Ser. No. 09/144,085, filed Aug. 31, 1998.
Soraphen
   U.S. Pat. No. 5,716,849 to Novartis.
   Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.
Spiramycin
   U.S. Pat. No. 5,098,837 to Lilly.
   Activator Gene
   U.S. Pat. No. 5,514,544 to Lilly.
Tylosin
   EP Pub. No. 791,655 to Lilly.
   U.S. Pat. No. 5,876,991 to Lilly.
   Kuhstoss et al., 1996, *Gene* 183:231–6., Production of a novel polyketide through the construction of a hybrid polyketide synthase.
   Tailoring Enzymes
   Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there are a wide variety of polyketide synthase genes that serve as readily available sources of DNA and sequence information for use in constructing the hybrid PKS-encoding DNA compounds of the invention. Methods for constructing hybrid PKS-encoding DNA compounds are described without reference to the FK-520 PKS in PCT patent publication No. 98/51695; U.S. Pat. Nos. 5,672,491 and 5,712,146 and U.S. patent application Ser. No. 09/073,538, filed May 6, 1998, and Ser. No. 09/141,908, filed Aug. 28, 1998, each of which is incorporated herein by reference.

The hybrid PKS-encoding DNA compounds of the invention can be and often are hybrids of more than two PKS genes. Moreover, there are often two or more modules in the hybrid PKS in which all or part of the module is derived from a second (or third) PKS. Thus, as one illustrative example, the present invention provides a hybrid FK-520 PKS that contains the naturally occurring loading module and FkbP as well as modules one, two, four, six, seven, and eight, nine, and ten of the FK-520 PKS and further contains hybrid or heterologous modules three and five. Hybrid or heterologous module three contains an AT domain that is specific of methylmalonyl CoA and can be derived for example, from the erythromycin or rapamycin PKS genes. Hybrid or heterologous module five contains an AT domain that is specific for malonyl CoA and can be derived for example, from the picromycin or rapamycin PKS genes.

While an important embodiment of the present invention relates to hybrid PKS enzymes and corresponding genes, the present invention also provides recombinant FK-520 PKS genes in which there is no second PKS gene sequence present but which differ from the FK-520 PKS gene by one or more deletions. The deletions can encompass one or more modules and/or can be limited to a partial deletion within one or more modules. When a deletion encompasses an entire module, the resulting FK-520 derivative is at least two carbons shorter than the gene from which it was derived. When a deletion is within a module, the deletion typically encompasses a KR, DH, or ER domain, or both DH and ER domains, or both KR and DH domains, or all three KR, DH, and ER domains.

To construct a hybrid PKS or FK-520 derivative PKS gene of the invention, one can employ a technique, described in PCT Pub. No. 98/27203 and U.S. patent application Ser. No. 08/989,332, filed Dec. 11, 1997, now U.S. Pat. No. 6,033,883, each of which is incorporated herein by reference, in which the large PKS gene is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

Thus, in one important embodiment, the recombinant DNA compounds of the invention are expression vectors. As used herein, the term expression vector refers to any nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA that is translated into a polypeptide in the cell or cell extract. Furthermore, expression vectors typically contain additional functional elements, such as resistance-conferring genes to act as selectable markers.

The various components of an expression vector can vary widely, depending on the intended use of the vector. In particular, the components depend on the host cell(s) in which the vector will be used or is intended to function. Vector components for expression and maintenance of vectors in *E. coli* are widely known and commercially available, as are vector components for other commonly used organisms, such as yeast cells and Streptomyces cells.

In a preferred embodiment, the expression vectors of the invention are used to construct recombinant Streptomyces host cells that express a recombinant PKS of the invention. Preferred Streptomyces host cell/vector combinations of the invention include *S. coelicolor* CH999 and *S. lividans* K4-114 host cells, which do not produce actinorhodin, and expression vectors derived from the pRM1 and pRM5 vectors, as described in U.S. Pat. No. 5,830,750 and U.S. patent application Ser. No. 08/828,898, filed Mar. 31, 1997, and Ser. No. 09/181,833, filed Oct. 28, 1998, each of which is incorporated herein by reference.

The present invention provides a wide variety of expression vectors for use in Streptomyces. For replicating vectors, the origin of replication can be, for example and without limitation, a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP1.2 (Thompson et al., 1982, *Gene* 20: 51–62, incorporated herein by reference), and SG5(ts) (Muth et al., 1989, *Mol. Gen. Genet.* 219: 341–348, and Bierman et al., 1992, *Gene* 116: 43–49, each of which is incorporated herein by reference), or a high copy number vector, such as pIJI01 and pJV1 (see Katz et al., 1983, *J. Gen. Microbiol.* 129: 2703–2714; Vara et al., 1989, *J. Bacteriol.* 171: 5782–5781; and Servin-Gonzalez, 1993, *Plasmid* 30: 131–140, each of which is incorporated herein by reference). Generally, however, high copy number vectors are not preferred for expression of genes contained on large segments of DNA. For non-replicating and integrating vectors, it is useful to include at least an *E. coli* origin of replication, such as from pUC, p1P, p1I, and pBR. For phage based vectors, the phages phiC31 and KC515 can be employed (see Hopwood et al., supra).

Typically, the expression vector will comprise one or more marker genes by which host cells containing the vector can be identified and/or selected. Useful antibiotic resistance conferring genes for use in Streptomyces host cells include the ermE (confers resistance to erythromycin and other macrolides and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

The recombinant PKS gene on the vector will be under the control of a promoter, typically with an attendant ribosome binding site sequence. The present invention provides the endogenous promoters of the FK-520 PKS and related biosynthetic genes in recombinant form, and these promoters are preferred for use in the native hosts and in heterologous hosts in which the promoters function. A preferred promoter of the invention is the fkbO gene promoter, comprised in a sequence of about 270 bp between the start of the open reading frames of the fkbO and fkbB genes. The fkbO promoter is believed to be bi-directional in that it promotes transcription of the genes fkbO, fkbP, and fkbA in one direction and fkbB, fkbC, and fkbL in the other. Thus, in one aspect, the present invention provides a recombinant expression vector comprising the promoter of the fkbO gene of an FK-520 producing organism positioned to transcribe a gene other than fkbO. In a preferred embodiment the transcribed gene is an FK-520 PKS gene. In another preferred embodiment, the transcribed gene is a gene that encodes a protein comprised in a hybrid PKS.

Heterologous promoters can also be employed and are preferred for use in host cells in which the endogenous FK-520 PKS gene promoters do not function or function poorly. A preferred heterologous promoter is the actI promoter and its attendant activator gene actII1-ORF4, which is provided in the pRM1 and pRM5 expression vectors, supra. This promoter is activated in the stationary phase of growth when secondary metabolites are normally synthesized. Other useful Streptomyces promoters include without limitation those from the ermE gene and the melC1 gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the acti-ORF4 gene discussed above include dnrI, redD, and ptpA genes (see U.S. patent application Ser. No. 09/181,833, supra) to activate promoters under their control.

Figure 4:
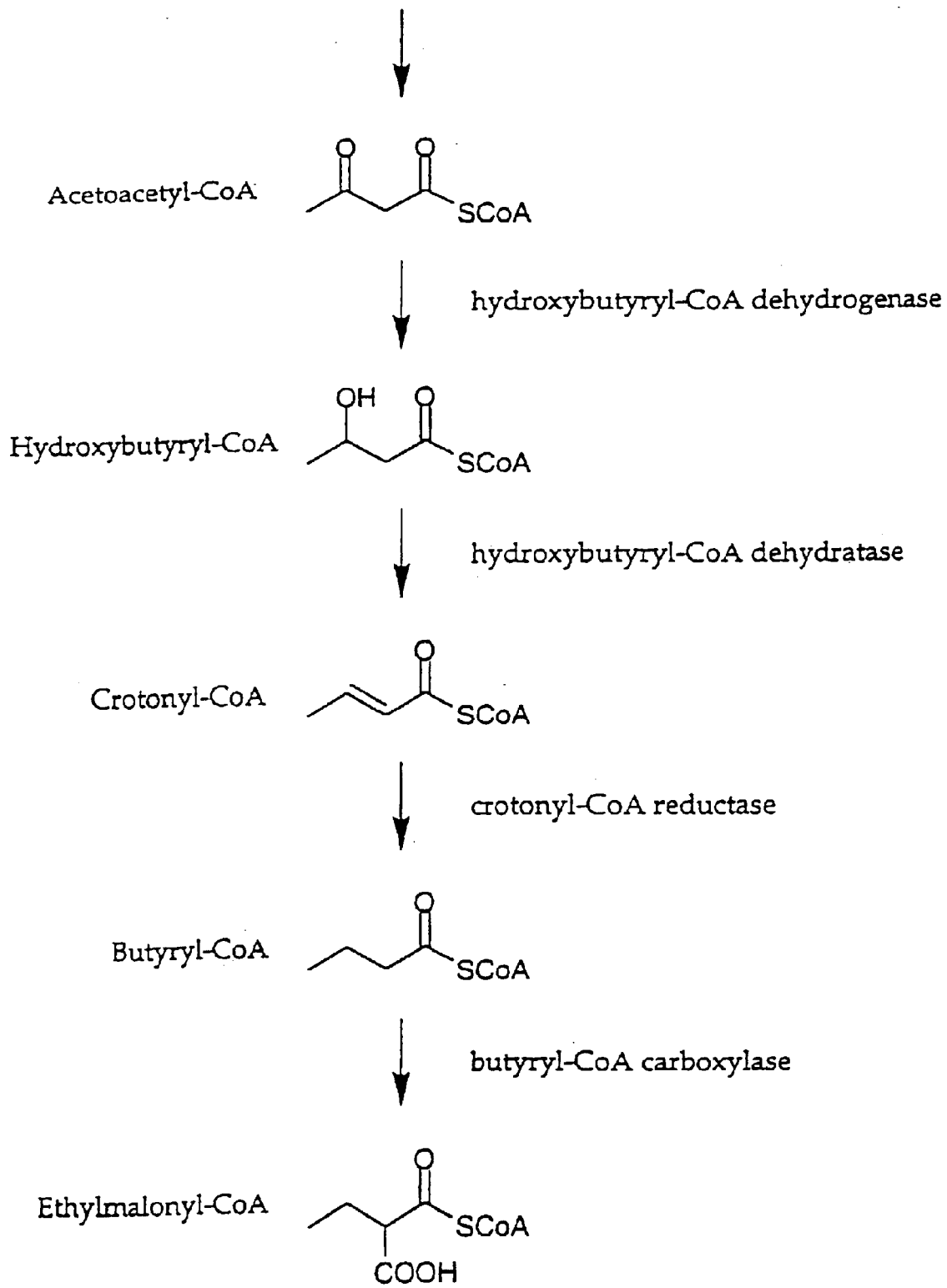
FIG. 4 shows a biosynthetic pathway for the biosynthesis of ethylmalonyl CoA from acetoacetyl CoA consistent with the function assigned to four of the genes in the FK-520 gene cluster shown in FIG. 3.
Figure 5:
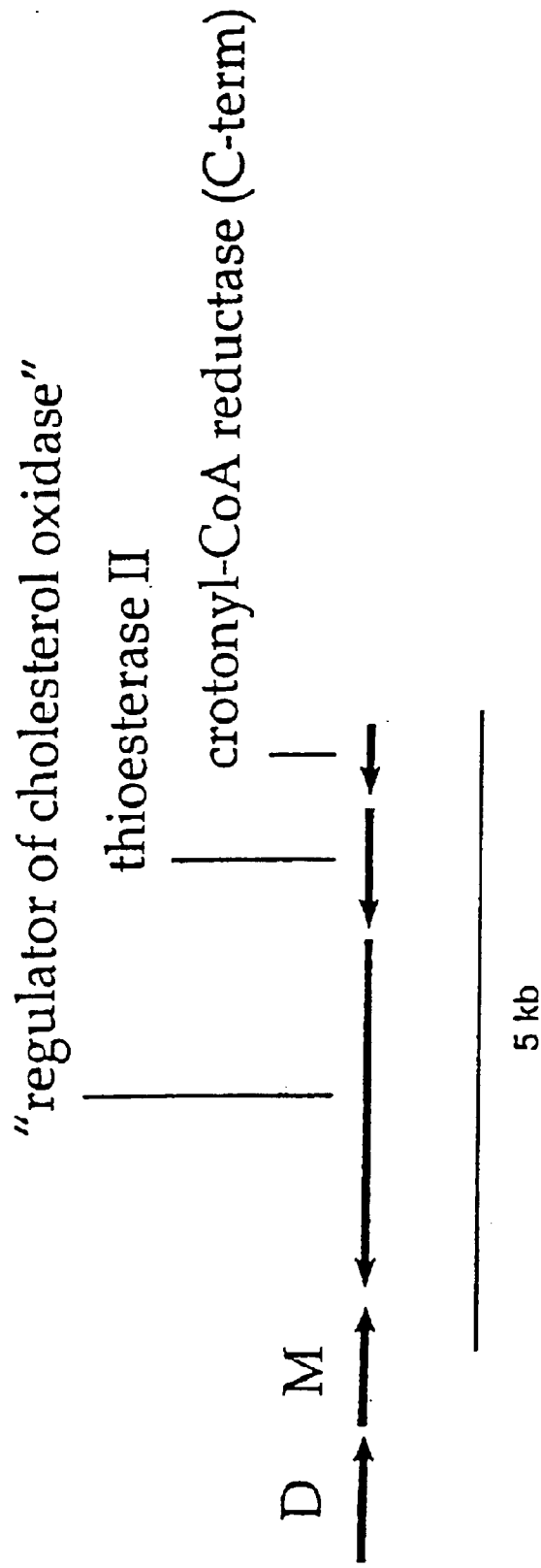
FIG. 5 shows a close-up view of the right-end of the FK-520 PKS gene cluster (and of the sequences on cosmid pKOS065-C31). The genes shown include fkbD, fkbM (a methyl transferase that methylates the hydroxyl group on C-31 of FK-520), fkbN (a homolog of a gene described as a regulator of cholesterol oxidase and that is believed to be a transcriptional activator), fkbQ (a type II thioesterase, which can increase polyketide production levels), and fkbS (a crotonyl-CoA reductase involved in the biosynthesis of ethylmalonyl CoA).

In addition to providing recombinant DNA compounds that encode the FK-520 PKS, the present invention also provides DNA compounds that encode the ethylmalonyl CoA and 2-hydroxymalonyl CoA utilized in the synthesis of FK-520. Thus, the present invention also provides recombinant host cells that express the genes required for the biosynthesis of ethylmalonyl CoA and 2-hydroxymalonyl CoA. FIGS. 3 and 4 show the location of these genes on the cosmids of the invention and the biosynthetic pathway that produces ethylmalonyl CoA.

For 2-hydroxymalonyl CoA biosynthesis, the fkbH, fkbI, fkbJ, and fkbK genes are sufficient to confer this ability on Streptomcyces host cells. For conversion of 2-hydroxymalonyl to 2-methoxymalonyl, the fkbG gene is also employed. While the complete coding sequence for fkbH is provided on the cosmids of the invention, the sequence for this gene provided herein may be missing a T residue, based on a comparison made with a similar gene cloned from the ansamitocin gene cluster by Dr. H. Floss. Where the sequence herein shows one T, there may be two, resulting in an extension of the fkbH reading frame to encode the amino acid sequence (SEQ ID NO:2):

For ethylmalonyl CoA biosynthesis, one requires only a crotonyl CoA reductase, which can be supplied by the host cell but can also be supplied by recombinant expression of the frbS gene of the present invention. To increase yield of ethylmalonyl CoA, one can also express the fkbE and fkbU genes as well. While such production can be achieved using only the recombinant genes above, one can also achieve such production by placing into the recombinant host cell a large segment of the DNA provided by the cosmids of the invention. Thus, for 2-hydroxymalonyl and 2-methoxymalonyl CoA biosynthesis, one can simply provide the cells with the segment of DNA located on the left side of the FK-520 PKS genes shown in FIG. 1. For ethylmalonyl CoA biosynthesis, one can simply provide the cells with the segment of DNA located on the right side of the FK-520 PKS genes shown in FIG. 1 or, alternatively, both the right and left segments of DNA.

The recombinant DNA expression vectors that encode these genes can be used to construct recombinant host cells that can make these important polyketide building blocks from cells that otherwise are unable to produce them. For example, *Streptomyces coelicolor* and *Streptomyces lividans* do not synthesisze ethylmalonyl CoA or 2-hydroxymalonyl CoA. The invention provides methods and vectors for constructing recombinant *Streptomyces coelicolor* and *Streptomyces lividans* that are able to synthesize either or both ethylmalonyl CoA and 2-hydroxymalonyl CoA. These host cells are thus able to make polyketides, those requiring these substrates, that cannot otherwise be made in such cells.

In a preferred embodiment, the present invention provides recombinant Streptomyces host cells, such as *S. coelicolor* and *S. lividans*, that have been transformed with a recombinant vector of the invention that codes for the expression of the ethylmalonyl CoA biosynthetic genes. The resulting host cells produce ethylmalonyl CoA and so are preferred host cells for the production of polyketides produced by PKS enzymes that comprise one or more AT domains specific for ethylmalonyl CoA. Illustrative PKS enzymes of this type include the FK-520 PKS and a recombinant PKS in which one or more AT domains is specific for ethylmalonyl CoA.

In a related embodiment, the present invention provides Streptomyces host cells in which one or more of the ethylmalonyl or 2-hydroxymalonyl biosynthetic genes have been deleted by homologous recombination or rendered inactive by mutation. For example, deletion or inactivation of the fkbG gene can prevent formation of the methoxyl groups at C-13 and C-15 of FK-520 (or, in the corresponding FK-506 producing cell, FK-506), leading to the production of 13,15-didesmethoxy-13,15-dihydroxy-FK-520 (or, in the corresponding FK-506 producing cell, 13,15-didesmethoxy-13,15-dihydroxy-FK-506). If the fkbG gene product acts on 2-hydroxymalonyl and the resulting 2-methoxymalonyl substrate is required for incorporation by the PKS, the AT domains of modules 7 and 8 may bind malonyl CoA and methylmalonyl CoA. Such incorporation results in the production of a mixture of polyketides in which the methoxy groups at C-13 and C-15 of FK-520 (or FK-506) are replaced by either hydrogen or methyl.

This possibility of non-specific binding results from the construction of a hybrid PKS of the invention in which the AT domain of module 8 of the FK-520 PKS replaced the AT domain of module 6 of DEBS. The resulting PKS produced, in *Streptomyces lividans,* 6-dEB and 2-desmethyl-6-dEB, indicating that the AT domain of module 8 of the FK-520 PKS could bind malonyl CoA and methylmalonyl CoA substrates. Thus, one could possibly also prepare the 13,15-didesmethoxy-FK-520 and corresponding FK-506 compounds of the invention by deleting or otherwise inactivating one or more or all of the genes required for 2-hydroxymalonyl CoA biosynthesis, i.e., the fkbH, fkbI, fkbJ, and fkbK genes. In any event, the deletion or inactivation of one or more biosynthetic genes required for ethylmalonyl and/or 2-hydroxymalonyl production prevents the formation of polyketides requiring ethylmalonyl and/or 2-hydroxymalonyl for biosynthesis, and the resulting host cells are thus preferred for production of polyketides that do not require the same.

The host cells of the invention can be grown and fermented under conditions known in the art for other purposes to produce the compounds of the invention. See, e.g., U.S. Pat. Nos. 5,194,378; 5,116,756; and 5,494,820, incorporated herein by reference, for suitable fermentation processes. The compounds of the invention can be isolated from the fermentation broths of these cultured cells and purified by standard procedures. Preferred compounds of the invention include the following compounds: 13-desmethoxy-FK-506; 13-desmethoxy-FK-520; 13,15-didesmethoxy-FK-506; 13,15-didesmethoxy-FK-520; 13-desmethoxy-18-hydroxy-FK-506; 13-desmethoxy-18-hydroxy-FK-520; 13,15-didesmethoxy-18-hydroxy-FK-506; and 13,15-didesmethoxy-18-hydroxy-FK-520. These compounds can be further modified as described for tacrolimus and FK-520 in U.S. Pat. Nos. 5,225,403; 5,189,042; 5,164,495; 5,068,323; 4,980,466; and 4,920,218, incorporated herein by reference.

Figure 8A:
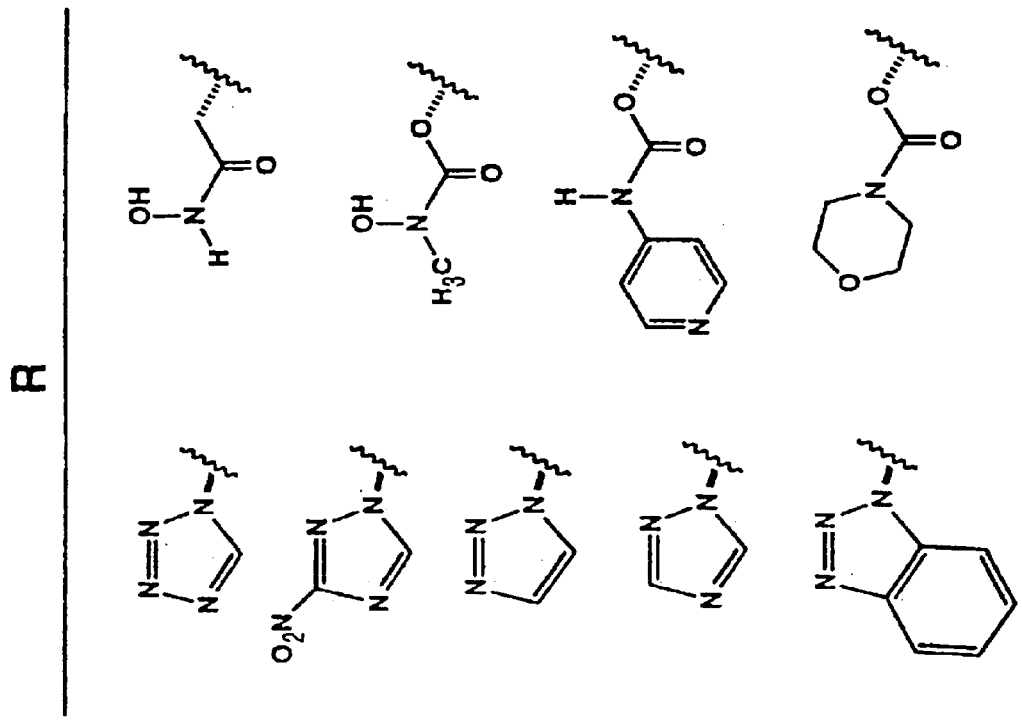
FIG. 8, in Parts A and B, shows certain compounds of the invention preferred for dermal application in Part A and a synthetic route for making those compounds in Part B.
Figure 8A:
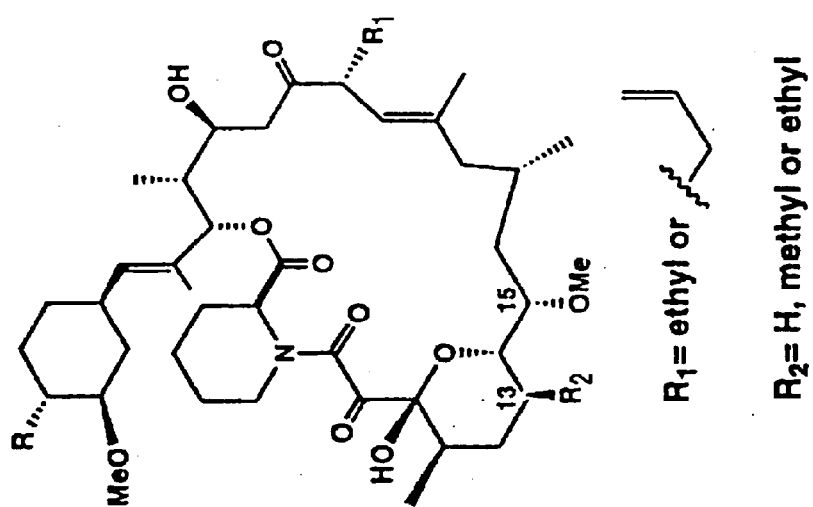
Figure 8B:
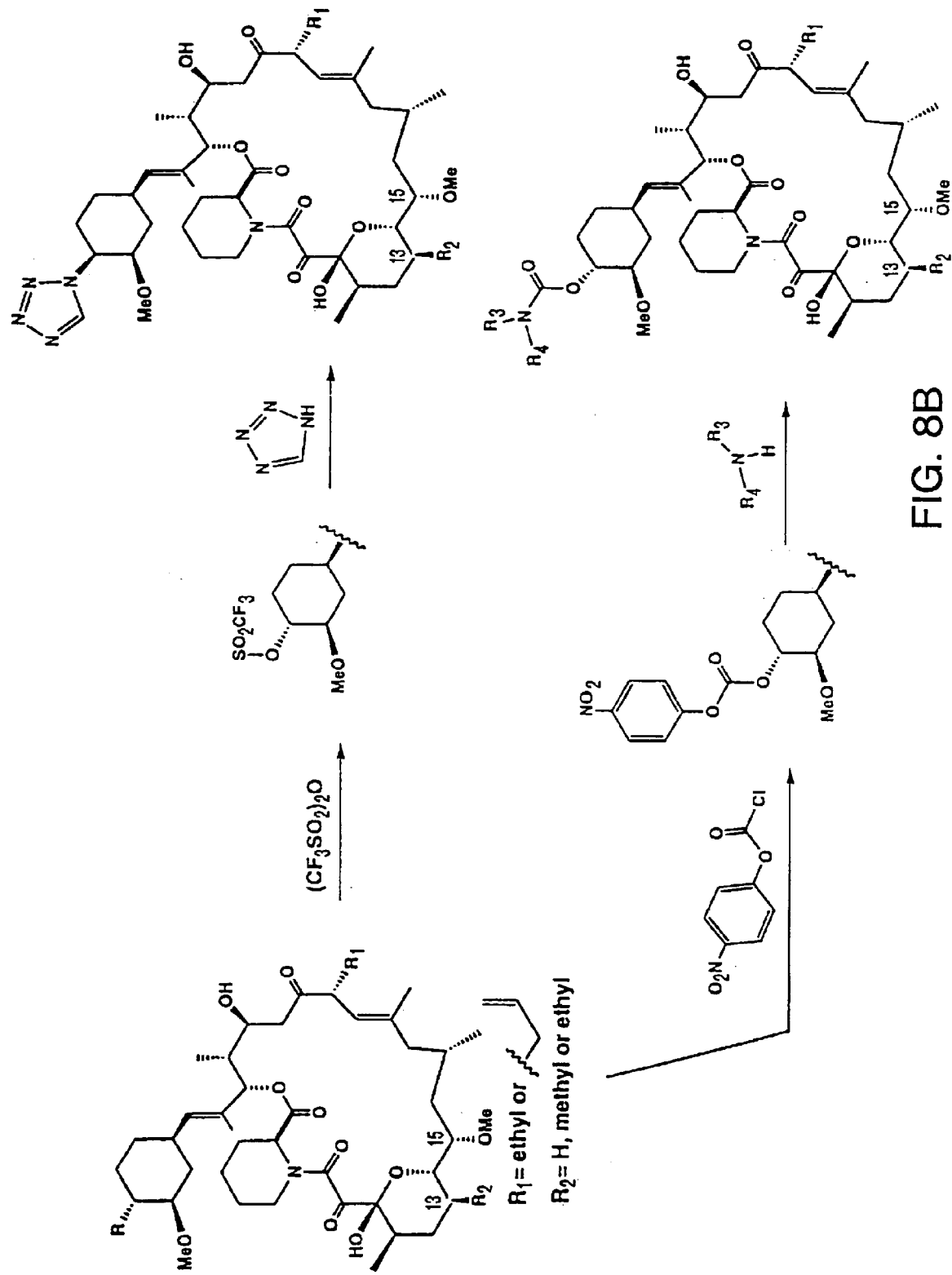

Other compounds of the invention are shown in FIG. 8, Parts A and B. In FIG. 8, Part A, illustrative C-32-substituted compounds of the invention are shown in two columns under the heading R. The substituted compounds are preferred for topical administration and are applied to the dermis for treatment of conditions such as psoriasis. In FIG. 8, Part B, illustrative reaction schemes for making the compounds shown in FIG. 8, Part A, are provided. In the upper scheme in FIG. 8, Part B, the C-32 substitution is a tetrazole moiety, illustrative of the groups shown in the left column under R in FIG. 8, Part A. In the lower scheme in FIG. 8, Part B, the C-32 substitution is a disubstituted amino group, where $R_3$ and $R_4$ can be any group similar to the illustrative groups shown attached to the amine in the right column under R in FIG. 8, Part A. While FIG. 8 shows the C-32-substituted compounds in which the C-15-methoxy is present, the invention includes these C-32-substituted compounds in which C-15 is ethyl, methyl, or hydrogen. Also, while C-21 is shown as substituted with ethyl or allyl, the compounds of the invention includes the C-32-substituted compounds in which C-21 is substituted with hydrogen or methyl.

To make these C-32-substituted compounds, FIG. 8, Part B, provides illustrative reaction schemes. Thus, a selective reaction of the starting compound (see FIG. 8, Part B, for an illustrative starting compound) with trifluoromethanesulfonic anhydride in the presence of a base yields the C-32 O-triflate derivative, as shown in the upper scheme of FIG. 8, Part B. Displacement of the triflate with 1H-tetrazole or triazole derivatives provides the C-32 tetrazole or teiazole derivative. As shown in the lower scheme of FIG. 8, Part B, reacting the starting compound with p-nitrophenylchloroformate yields the corresponding carbonate, which, upon displacement with an amino compound, provides the corresponding carbamate derivative.

The compounds can be readily formulated to provide the pharmaceutical compositions of the invention. The pharmaceutical compositions of the invention can be used in the form of a pharmaceutical preparation, for example, in solid, semisolid, or liquid form. This preparation contains one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use. Suitable formulation processes and compositions for the compounds of the present invention are described with respect to tacrolimus in U.S. Pat. Nos. 5,939,427; 5,922,729; 5,385,907; 5,338,684; and 5,260,301, incorporated herein by reference. Many of the compounds of the invention contain one or more chiral centers, and all of the stereoisomers are included within the scope of the invention, as pure compounds as well as mixtures of stereoisomers. Thus the compounds of the invention may be supplied as a mixture of stereoisomers in any proportion.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX,* Supp. 6: 17–22, incorporated herein by reference. Dosage forms for external application may be prepared essentially as described in EPO patent publication No.

423,714, incorporated herein by reference. The active compound is included in the pharmaceutical composition in an amount sufficient to produce the desired effect upon the disease process or condition.

For the treatment of conditions and diseases relating to immunosuppression or neuronal damage, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the present invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 g of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention can be formulated within the range of, for example, 0.00001% to 60% by weight, preferably from 0.001% to 10% by weight, and most preferably from about 0.005% to 0.8% by weight. The compounds and compositions of the invention are useful in treating disease conditions using doses and administration schedules as described for tacrolimus in U.S. Pat. Nos. 5,542,436; 5,365,948; 5,348,966; and 5,196,437, incorporated herein by reference. The compounds of the invention can be used as single therapeutic agents or in combination with other therapeutic agents. Drugs that can be usefully combined with compounds of the invention include one or more immunosuppressant agents such as rapamycin, cyclosporin A, FK-506, or one or more neurotrophic agents.

It will be understood, however, that the specific dosage level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the present invention and shall not be construed as being a limitation on the scope of the invention or claims.

Example 1

Replacement of Methoxyl with Hydrogen or Methyl at C-13 of FK-520

The C-13 methoxyl group is introduced into FK-520 via an AT domain in extender module 8 of the PKS that is specific for hydroxymalonyl and by methylation of the hydroxyl group by an S-adenosyl methionine (SAM) dependent methyltransferase. Metabolism of FK-506 and FK-520 primarily involves oxidation at the C-13 position into an inactive derivative that is further degraded by host P450 and other enzymes. The present invention provides compounds related in structure to FK-506 and FK-520 that do not contain the C-13 methoxy group and exhibit greater stability and a longer half-life in vivo. These compounds are useful medicaments due to their immunosuppressive and neurotrophic activities, and the invention provides the compounds in purified form and as pharmaceutical compositions.

The present invention also provides the novel PKS enzymes that produce these novel compounds as well as the expression vectors and host cells that produce the novel PKS enzymes. The novel PKS enzymes include, among others, those that contain an AT domain specific for either malonyl CoA or methylmalonyl CoA in module 8 of the FK-506 and FK-520 PKS. This example describes the construction of recombinant DNA compounds that encode the novel FK-520 PKS enzymes and the transformation of host cells with those recombinant DNA compounds to produce the novel PKS enzymes and the polyketides produced thereby.

To construct an expression cassette for performing module 8 AT domain replacements in the FK-520 PKS, a 4.6 kb SphI fragment from the FK-520 gene cluster was cloned into plasmid pLitmus 38 (a cloning vector available from New England Biolabs). The 4.6 kb SphI fragment, which encodes the ACP domain of module 7 followed by module 8 through the KR domain, was isolated from an agarose gel after digesting the cosmid pKOS65-C31 with Sph I. The clone having the insert oriented so the single SacI site was nearest to the SpeI end of the polylinker was identified and designated as plasmid pKOS60-21-67. To generate appropriate cloning sites, two linkers were ligated sequentially as follows. First, a linker was ligated between the SpeI and SacI sites to introduce a BglII site at the 5' end of the cassette, to eliminate interfering polylinker sites, and to reduce the total insert size to 4.5 kb (the limit of the phage KC515). The ligation reactions contained 5 picomolar unphosphorylated linker DNA and 0.1 picomolar vector DNA, i.e., a 50-fold molar excess of linker to vector. The linker had the following sequence (SEQ ID NOS:3–4):

```
5'-CTAGTGGGCAGATCTGGCAGCT-3'

3'-ACCCGTCTAGACCG-5'
```

The resulting plasmid was designated pKOS60-27-1.

Next, a linker of the following sequence was ligated between the unique SphI and AflII sites of plasmid pKOS60-27-1 to introduce an NsiI site at the 3' end of the module 8 cassette. The linker employed was (SEQ ID NOS:5–6):

```
5'-GGGATGCATGGC-3'

3'-GTACCCCTACGTACCGAATT-5'
```

The resulting plasmid was designated pKOS60-29-55.

To allow in-frame insertions of alternative AT domains, sites were engineered at the 5' end (Avr II or Nhe I) and 3' end (Xho I) of the AT domain using the polymerase chain reaction (PCR) as follows. Plasmid pKOS60-29-55 was used as a template for the PCR and sequence 5' to the AT domain was amplified with the primers SpeBgl-fwd and either Avr-rev or Nhe-rev: (SEQ ID NOS:7–9)

```
SpeBgl-fwd    5'-CGACTCACTAGTGGGCAGATCTGG-3'

Avr-rev       5'-CACGCCTAGGCCGGTCGGTCTCGGGCCAC-3'

Nhe-rev       5'-GCGGCTAGCTGCTCGCCCATCGCGGGATGC-3'
```

The PCR included, in a 50 µl reaction, 5 µl of 10×Pfi polymerase buffer (Stratagene), 5 µl 10×z-dNTP mixture (2 mM dATP, 2 mM dCTP, 2 mM dTTP, 1 mM dGTP, 1 mM 7-deaza-GTP), 5 µl DMSO, 2 µl of each primer (10 EM), 1 µl of template DNA (0.1 µg/µl), and 1 µl of cloned Pfu polymerase (Stratagene). The PCR conditions were 95° C. for 2 min., 25 cycles at 95° C. for 30 sec., 60° C. for 30 sec., and 72° C. for 4 min., followed by 4 min. at 72° C. and a hold at 0° C. The amplified DNA products and the Litmus vectors were cut with the appropriate restriction enzymes (BglII and AvrII or SpeI and NheI), and cloned into either pLitmus 28 or pLitmus38 (New England Biolabs), respectively, to generate the constructs designated pKOS60-37-4 and pKOS60-37-2, respectively.

Plasmid pKOS60-29-55 was again used as a template for PCR to amplify sequence 3' to the AT domain using the primers BsrXho-fwd and NsiAfl-rev (SEQ ID NOS:10–11):

```
BsrXho-fwd
5'-GATGTACAGCTCGAGTCGGCACGCCCGGCCGCATC-3'

NsiAfl-rev
5'-CGACTCACTTAAGCCATGCATCC-3'
```

PCR conditions were as described above. The PCR fragment was cut with BsrGI and AflII, gel isolated, and ligated into pKOS60-37-4 cut with Asp718 and AflII and inserted into pKOS60-37-2 cut with BsrGI and AflII, to give the plasmids pKOS60-39-1 and pKOS60-39-13, respectively. These two plasmids can be digested with AvrII and XhoI or NheI and XhoI, respectively, to insert heterologous AT domains specific for malonyl, methylmalonyl, ethylmalonyl, or other extender units.

Malonyl and methylmalonyl-specific AT domains were cloned from the rapamycin cluster using PCR amplification with a pair of primers that introduce an AvrII or NheI site at the 5' end and an XhoI site at the 3' end. The PCR conditions were as given above and the primer sequences were as follows (SEQ ID NOS:12–15):

```
RATN1    5'-ATCCTAGGCGGGCRGGYGTGTCGTCCTTCGG-3'
(3' end of Rap KS sequence and universal for
malonyl and methylmalonyl CoA), RATMN2   5'-ATGCTAGCCGCCGCGTTCCCCGTCTTCGCGCG-3'
(Rap AT shorter version 5'-sequence and specific
for malonyl CoA), RATMMN2  5'-ATGCTAGCGGATTCGTCGGTGGTGTTCGCCGA-3'
(Rap AT shorter version 5'-sequence and specific
for methylmalonyl CoA), and RATC     5'-ATCTCGAGCCAGTASCGCTGGTGYTGGAAGG-3'
(Rap DH 5'-sequence and universal for malonyl
and methylmalonyl CoA).
```

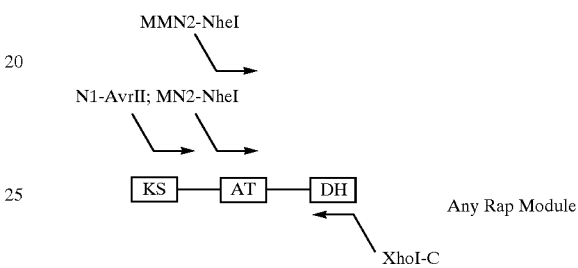

Because of the high sequence similarity in each module of the rapamycin cluster, each primer was expected to prime any of the AT domains. PCR products representing ATs specific for malonyl or methylmalonyl extenders were identified by sequencing individual cloned PCR products. Sequencing also confirmed that the chosen clones contained no cloning artifacts. Examples of hybrid modules with the rapamycin AT12 and AT13 domains are shown in a separate figure.

The AvrII-XhoI restriction fragment that encodes module 8 of the FK-520 PKS with the endogenous AT domain replaced by the AT domain of module 12 of the rapamycin PKS has the DNA sequence and encodes the amino acid sequence shown below. The AT of rap module 12 is specific for incorporation of malonyl units (SEQ ID NOS:16–17).

```
AGATCTGGCAGCTCGCCGAAGCGCTGCTGACGCTCGTCCGGGAGAGCACC    50
   I  W  Q  L  A  E  A  L  L  T  L  V  R  E  S  T

GCCGCCGTGCTCGGCCACGTGGGTGGCGAGGACATCCCCGCGACGGCGGC    100
  A  A  V  L  G  H  V  G  G  E  D  I  P  A  T  A  A

GTTCAAGGACCTCGGCATCGACTCGCTCACCGCGGTCCAGCTGCGCAACG    150
   F  K  D  L  G  I  D  S  L  T  A  V  Q  L  R  N

CCCTCACCGAGGCGACCGGTGTGCGGCTGAACGCCACGGCGGTCTTCGAC    200
   A  L  T  E  A  T  G  V  R  L  N  A  T  A  V  F  D

TTCCCGACCCCGCACGTGCTCGCCGGGAAGCTCGGCGACGAACTGACCGG    250
   F  P  T  P  H  V  L  A  G  K  L  G  D  E  L  T  G

CACCCGCGCGCCCGTCGTGCCCCGGACCGCGGCCACGGCCGGTGCGCACG    300
   T  R  A  P  V  V  P  R  T  A  A  T  A  G  A  H

ACGAGCCGCTGGCGATCGTGGGAATGGCCTGCCGGCTGCCCGGCGGGGTC    350
   D  E  P  L  A  I  V  G  M  A  C  R  L  P  G  G  V

GCGTCACCCGAGGAGCTGTGGCACCTCGTGGCATCCGGCACCGACGCCAT    400
   A  S  P  E  E  L  W  H  L  V  A  S  G  T  D  A  I
```

-continued

```
CACGGAGTTCCCGACGGACCGCGGCTGGGACGTCGACGCGATCTACGACC     450
  T  E  F  P  T  D  R  G  W  D  V  D  A  I  Y  D

CGGACCCCGACGCGATCGGCAAGACCTTCGTCCGGCACGGTGGCTTCCTC     500
 P  D  P  D  A  I  G  K  T  F  V  R  H  G  G  F  L

ACCGGCGCGACAGGCTTCGACGCGGCGTTCTTCGGCATCAGCCCGCGCGA     550
  T  G  A  T  G  F  D  A  A  F  F  G  I  S  P  R  E

GGCCCTCGCGATGGACCCGCAGCAGCGGGTGCTCCTGGAGACGTCGTGGG     600
  A  L  A  M  D  P  Q  Q  R  V  L  L  E  T  S  W

AGGCGTTCGAAAGCGCCGGCATCACCCCGGACTCGACCCGCGGCAGCGAC     650
 E  A  F  E  S  A  G  I  T  P  D  S  T  R  G  S  D

ACCGGCGTGTTCGTCGGCGCCTTCTCCTACGGTTACGGCACCGGTGCGGA     700
  T  G  V  F  V  G  A  F  S  Y  G  Y  G  T  G  A  D

CACCGACGGCTTCGGCGCGACCGGCTCGCAGACCAGTGTGCTCTCCGGCC     750
  T  D  G  F  G  A  T  G  S  Q  T  S  V  L  S  G

GGCTGTCGTACTTCTACGGTCTGGAGGGTCCGGCGGTCACGGTCGACACG     800
 R  L  S  Y  F  Y  G  L  E  G  P  A  V  T  V  D  T

GCGTGTTCGTCGTCGCTGGTGGCGCTGCACCAGGCCGGGCAGTCGCTGCG     850
  A  C  S  S  S  L  V  A  L  H  Q  A  G  Q  S  L  R

CTCCGGCGAATGCTCGCTCGCCCTGGTCGGCGGCGTGACGGTGATGGCGT     900
  S  G  E  C  S  L  A  L  V  G  G  V  T  V  M  A

CTCCCGGCGGCTTCGTGGAGTTCTCCCGGCAGCGCGGCCTCGCGCCGGAC     950
 S  P  G  G  F  V  E  F  S  R  Q  R  G  L  A  P  D

GGCCGGGCGAAGGCGTTCGGCGCGGGTGCGGACGGCACGAGCTTCGCCGA    1000
  G  R  A  K  A  F  G  A  G  A  D  G  T  S  F  A  E

GGGTGCCGGTGTGCTGATCGTCGAGAGGCTCTCCGACGCCGAACGCAACG    1050
  G  A  G  V  L  I  V  E  R  L  S  D  A  E  R  N

GTCACACCGTCCTGGCGGTCGTCCGTGGTTCGGCGGTCAACCAGGATGGT    1100
 G  H  T  V  L  A  V  V  R  G  S  A  V  N  Q  D  G

GCCTCCAACGGGCTGTCGGCGCCGAACGGGCCGTCGCAGGAGCGGGTGAT    1150
  A  S  N  G  L  S  A  P  N  G  P  S  Q  E  R  V  I

CCGGCAGGCCCTGGCCAACGCCGGGCTCACCCCGGCGGACGTGGACGCCG    1200
  R  Q  A  L  A  N  A  G  L  T  P  A  D  V  D  A

TCGAGGCCCACGGCACCGGCACCAGGCTGGGCGACCCCATCGAGGCACAG    1250
  V  E  A  H  G  T  G  T  R  L  G  D  P  I  E  A  Q

GCGGTACTGGCCACCTACGGACAGGAGCGCGCCACCCCCCTGCTGCTGGG    1300
 A  V  L  A  T  Y  G  Q  E  R  A  T  P  L  L  L  G

CTCGCTGAAGTCCAACATCGGCCACGCCCAGGCCGCGTCCGGCGTCGCCG    1350
  S  L  K  S  N  I  G  H  A  Q  A  A  S  G  V  A

GCATCATCAAGATGGTGCAGGCCCTCCGGCACGGGGAGCTGCCGCCGACG    1400
  G  I  I  K  M  V  Q  A  L  R  H  G  E  L  P  P  T

CTGCACGCCGACGAGCCGTCGCCGCACGTCGACTGGACGGCCGGCGCCGT    1450
  L  H  A  D  E  P  S  P  H  V  D  W  T  A  G  A  V

CGAACTGCTGACGTCGGCCCGGCCGTGGCCCGAGACCGACCGGCCTAGGC    1500
 E  L  L  T  S  A  R  P  W  P  E  T  D  R  P  R

GGGCAGGCGTGTCGTCCTTCGGGATCAGTGGCACCAACGCCCACGTCATC    1550
  R  A  G  V  S  S  F  G  I  S  G  T  N  A  H  V  I

CTGGAAAGCGCACCCCCCACTCAGCCTGCGGACAACGCGGTGATCGAGCG    1600
  L  E  S  A  P  P  T  Q  P  A  D  N  A  V  I  E  R

GGCACCGGAGTGGGTGCCGTTGGTGATTTCGGCCAGGACCCAGTCGGCTT    1650
  A  P  E  W  V  P  L  V  I  S  A  R  T  Q  S  A

TGACTGAGCACGAGGGCCGGTTGCGTGCGTATCTGGCGGCGTCGCCCGGG    1700
 L  T  E  H  E  G  R  L  R  A  Y  L  A  A  S  P  G

GTGGATATGCGGGCTGTGGCATCGACGCTGGCGATGACACGGTCGGTGTT    1750
  V  D  M  R  A  V  A  S  T  L  A  M  T  R  S  V  F
```

```
CGAGCACCGTGCCGTGCTGCTGGGAGATGACACCGTCACCGGCACCGCTG    1800
 E  H  R  A  V  L  L  G  D  D  T  V  T  G  T  A

TGTCTGACCCTCGGGCGGTGTTCGTCTTCCCGGGACAGGGGTCGCAGCGT    1850
 V  S  D  P  R  A  V  F  V  F  P  G  Q  G  S  Q  R

GCTGGCATGGGTGAGGAACTGGCCGCCGCGTTCCCCGTCTTCGCGCGGAT    1900
 A  G  M  G  E  E  L  A  A  A  F  P  V  F  A  R  I

CCATCAGCAGGTGTGGGACCTGCTCGATGTGCCCGATCTGGAGGTGAACG    1950
 H  Q  Q  V  W  D  L  L  D  V  P  D  L  E  V  N

AGACCGGTTACGCCCAGCCGGCCCTGTTCGCAATGCAGGTGGCTCTGTTC    2000
 E  T  G  Y  A  Q  P  A  L  F  A  M  Q  V  A  L  F

GGGCTGCTGGAATCGTGGGGTGTACGACCGGACGCGGTGATCGGCCATTC    2050
 G  L  L  E  S  W  G  V  R  P  D  A  V  I  G  H  S

GGTGGGTGAGCTTGCGGCTGCGTATGTGTCCGGGGTGTGGTCGTTGGAGG    2100
 V  G  E  L  A  A  A  Y  V  S  G  V  W  S  L  E

ATGCCTGCACTTTGGTGTCGGCGCGGGCTCGTCTGATGCAGGCTCTGCCC    2150
 D  A  C  T  L  V  S  A  R  A  R  L  M  Q  A  L  P

GCGGGTGGGGTGATGGTCGCTGTCCCGGTCTCGGAGGATGAGGCCCGGGC    2200
 A  G  G  V  M  V  A  V  P  V  S  E  D  E  A  R  A

CGTGCTGGGTGAGGGTGTGGAGATCGCCGCGGTCAACGGCCCGTCGTCGG    2250
 V  L  G  E  G  V  E  I  A  A  V  N  G  P  S  S

TGGTTCTCTCCGGTGATGAGGCCGCCGTGCTGCAGGCCGCGGAGGGGCTG    2300
 V  V  L  S  G  D  E  A  A  V  L  Q  A  A  E  G  L

GGGAAGTGGACGCGGCTGGCGACCAGCCACGCGTTCCATTCCGCCCGTAT    2350
 G  K  W  T  R  L  A  T  S  H  A  F  H  S  A  R  M

GGAACCCATGCTGGAGGAGTTCCGGGCGGTCGCCGAAGGCCTGACCTACC    2400
 E  P  M  L  E  E  F  R  A  V  A  E  G  L  T  Y

GGACGCCGCAGGTCTCCATGGCCGTTGGTGATCAGGTGACCACCGCTGAG    2450
 R  T  P  Q  V  S  M  A  V  G  D  Q  V  T  T  A  E

TACTGGGTGCGGCAGGTCCGGGACACGGTCCGGTTCGGCGAGCAGGTGGC    2500
 Y  W  V  R  Q  V  R  D  T  V  R  F  G  E  Q  V  A

CTCGTACGAGGACGCCGTGTTCGTCGAGCTGGGTGCCGACCGGTCACTGG    2550
 S  Y  E  D  A  V  F  V  E  L  G  A  D  R  S  L

CCCGCCTGGTCGACGGTGTCGCGATGCTGCACGGCGACCACGAAATCCAG    2600
 A  R  L  V  D  G  V  A  M  L  H  G  D  H  E  I  Q

GCCGCGATCGGCGCCCTGGCCCACCTGTATGTCAACGGCGTCACGGTCGA    2650
 A  A  I  G  A  L  A  H  L  Y  V  N  G  V  T  V  D

CTGGCCCGCGCTCCTGGGCGATGCTCCGGCAACACGGGTGCTGGACCTTC    2700
 W  P  A  L  L  G  D  A  P  A  T  R  V  L  D  L

CGACATACGCCTTCCAGCACCAGCGCTACTGGCTCGAGTCGGCACGCCCG    2750
 P  T  Y  A  F  Q  H  Q  R  Y  W  L  E  S  A  R  P

GCCGCATCCGACGCGGGCCACCCCGTGCTGGGCTCCGGTATCGCCCTCGC    2800
 A  A  S  D  A  G  H  P  V  L  G  S  G  I  A  L  A

CGGGTCGCCGGGCCGGGTGTTCACGGGTTCCGTGCCGACCGGTGCGGACC    2850
 G  S  P  G  R  V  F  T  G  S  V  P  T  G  A  D

GCGCGGTGTTCGTCGCCGAGCTGGCGCTGGCCGCCGCGGACGCGGTCGAC    2900
 R  A  V  F  V  A  E  L  A  L  A  A  A  D  A  V  D

TGCGCCACGGTCGAGCGGCTCGACATCGCCTCCGTGCCCGGCCGGCCGGG    2950
 C  A  T  V  E  R  L  D  I  A  S  V  P  G  R  P  G

CCATGGCCGGACGACCGTACAGACCTGGGTCGACGAGCCGGCGGACGACG    3000
 H  G  R  T  T  V  Q  T  W  V  D  E  P  A  D  D

GCCGGCGCCGGTTCACCGTGCACACCCGCACCGGCGACGCCCCGTGGACG    3050
 G  R  R  R  F  T  V  H  T  R  T  G  D  A  P  W  T
```

```
                      -continued
CTGCACGCCGAGGGGGTGCTGCGCCCCATGGCACGGCCCTGCCCGATGC    3100
 L  H  A  E  G  V  L  R  P  H  G  T  A  L  P  D  A GGCCGACGCCGAGTGGCCCCCACCGGGCGCGGTGCCCGCGGACGGGCTGC   3150
  A  D  A  E  W  P  P  P  G  A  V  P  A  D  G  L CGGGTGTGTGGCGCCGGGGGGACCAGGTCTTCGCCGAGGCCGAGGTGGAC   3200
 P  G  V  W  R  R  G  D  Q  V  F  A  E  A  E  V  D GGACCGGACGGTTTCGTGGTGCACCCCGACCTGCTCGACGCGGTCTTCTC   3250
 G  P  D  G  F  V  V  H  P  D  L  L  D  A  V  F  S CGCGGTCGGCGACGGAAGCCGCCAGCCGGCCGGATGGCGCGACCTGACGG   3300
  A  V  G  D  G  S  R  Q  P  A  G  W  R  D  L  T TGCACGCGTCGGACGCCACCGTACTGCGCGCCTGCCTCACCCGGCGCACC   3350
 V  H  A  S  D  A  T  V  L  R  A  C  L  T  R  R  T GACGGAGCCATGGGATTCGCCGCCTTCGACGGCGCCGGCCTGCCGGTACT   3400
  D  G  A  M  G  F  A  A  F  D  G  A  G  L  P  V  L CACCGCGGAGGCGGTGACGCTGCGGGAGGTGGCGTCACCGTCCGGCTCCG   3450
  T  A  E  A  V  T  L  R  E  V  A  S  P  S  G  S AGGAGTCGGACGGCCTGCACCGGTTGGAGTGGCTCGCGGTCGCCGAGGCG   3500
 E  E  S  D  G  L  H  R  L  E  W  L  A  V  A  E  A GTCTACGACGGTGACCTGCCCGAGGGACATGTCCTGATCACCGCCGCCCA   3550
 V  Y  D  G  D  L  P  E  G  H  V  L  I  T  A  A  H CCCCGACGACCCCGAGGACATACCCACCCGCGCCCACACCCGCGCCACCC   3600
  P  D  D  P  E  D  I  P  T  R  A  H  T  R  A  T GCGTCCTGACCGCCCTGCAACACCACCTCACCACCACCGACCACACCCTC   3650
 R  V  L  T  A  L  Q  H  H  L  T  T  T  D  H  T  L ATCGTCCACACCACCACCGACCCCGCCGGCGCCACCGTCACCGGCCTCAC   3700
 I  V  H  T  T  T  D  P  A  G  A  T  V  T  G  L  T CCGCACCGCCCAGAACGAACACCCCCACCGCATCCGCCTCATCGAAACCG   3750
  R  T  A  Q  N  E  H  P  H  R  I  R  L  I  E  T ACCACCCCCACACCCCCCTCCCCCTGGCCCAACTCGCCACCCTCGACCAC   3800
 D  H  P  H  T  P  L  P  L  A  Q  L  A  T  L  D  H CCCCACCTCCGCCTCACCCACCACACCCTCCACCACCCCACCTCACCCC    3850
  P  H  L  R  L  T  H  H  T  L  H  H  P  H  L  T  P CCTCCACACCACCACCCCACCCACCACCACCACCCCCCTCAACCCCGAACACG  3900
 L  H  T  T  T  P  P  T  T  T  P  L  N  P  E  H CCATCATCATCACCGGCGGCTCCGGCACCCTCGCCGGCATCCTCGCCCGC   3950
 A  I  I  I  T  G  G  S  G  T  L  A  G  I  L  A  R CACCTGAACCACCCCCACACCTACCTCCTCTCCCGCACCCCACCCCCCGA   4000
 H  L  N  H  P  H  T  Y  L  L  S  R  T  P  P  P  D CGCCACCCCCGGCACCCACCTCCCCTGCGACGTCGGCGACCCCCACCAAC   4050
  A  T  P  G  T  H  L  P  C  D  V  G  D  P  H  Q TCGCCACCACCCTCACCCACATCCCCCAACCCCTCACCGCCATCTTCCAC   4100
 L  A  T  T  L  T  H  I  P  Q  P  L  T  A  I  F  H ACCGCCGCCACCCTCGACGACGGCATCCTCCACGCCCTCACCCCCGACCG   4150
  T  A  A  T  L  D  D  G  I  L  H  A  L  T  P  D  R CCTCACCACCGTCCTCCACCCCAAAGCCAACGCCGCCTGGCACCTGCACC   4200
  L  T  T  V  L  H  P  K  A  N  A  A  W  H  L  H ACCTCACCCAAAACCAACCCCTCACCCACTTCGTCCTCTACTCCAGCGCC   4250
 H  L  T  Q  N  Q  P  L  T  H  F  V  L  Y  S  S  A GCCGCCGTCCTCGGCAGCCCCGGACAAGGAAACTACGCCGCCGCCAACGC   4300
  A  A  V  L  G  S  P  G  Q  G  N  Y  A  A  A  N  A CTTCCTCGACGCCCTCGCCACCCACCGCCACACCCTCGGCCAACCCGCCA   4350
  F  L  D  A  L  A  T  H  R  H  T  L  G  Q  P  A CCTCCATCGCCTGGGGCATGTGGCACACCACCAGCACCCTCACCGGACAA   4400
 T  S  I  A  W  G  M  W  H  T  T  S  T  L  T  G  Q
```

```
CTCGACGACGCCGACCGGGACCGCATCCGCCGCGGCGGTTTCCTCCCGAT   4450
 L  D  D  A  D  R  D  R  I  R  R  G  G  F  L  P  I

CACGGACGACGAGGGCATGGGGATGCAT
  T  D  D  E  G
```

The AvrII-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below (SEQ ID NOS:18–19).

```
AGATCTGGCAGCTCGCCGAAGCGCTGCTGACGCTCGTCCGGGAGAGCACC   50
  Q  L  A  E  A  L  L  T  L  V  R  E  S  T

GCCGCCGTGCTCGGCCACGTGGGTGGCGAGGACATCCCCGCGACGGCGGC   100
  A  A  V  L  G  H  V  G  G  E  D  I  P  A  T  A  A

GTTCAAGGACCTCGGCATCGACTCGCTCACCGCGGTCCAGCTGCGCAACG   150
   F  K  D  L  G  I  D  S  L  T  A  V  Q  L  R  N

CCCTCACCGAGGCGACCGGTGTGCGGCTGAACGCCACGGCGGTCTTCGAC   200
  A  L  T  E  A  T  G  V  R  L  N  A  T  A  V  F  D

TTCCCGACCCCGCACGTGCTCGCCGGGAAGCTCGGCGACGAACTGACCGG   250
   F  P  T  P  H  V  L  A  G  K  L  G  D  E  L  T  G

CACCCGCGCGCCCGTCGTGCCCCGGACCGCGGCCACGGCCGGTGCGCACG   300
    T  R  A  P  V  V  P  R  T  A  A  T  A  G  A  H

ACGAGCCGCTGGCGATCGTGGGAATGGCCTGCCGGCTGCCCGGCGGGGTC   350
  D  E  P  L  A  I  V  G  M  A  C  R  L  P  G  G  V

GCGTCACCCGAGGAGCTGTGGCACCTCGTGGCATCCGGCACCGACGCCAT   400
  A  S  P  E  E  L  W  H  L  V  A  S  G  T  D  A  I

CACGGAGTTCCCGACGGACCGCGGCTGGGACGTCGACGCGATCTACGACC   450
    T  E  F  P  T  D  R  G  W  D  V  D  A  I  Y  D

CGGACCCCGACGCGATCGGCAAGACCTTCGTCCGGCACGTGGCTTCCTC    500
  P  D  P  D  A  I  G  K  T  F  V  R  H  G  G  F  L

ACCGGCGCGACAGGCTTCGACGCGGCGTTCTTCGGCATCAGCCCGCGCGA   550
    T  G  A  T  G  F  D  A  A  F  F  G  I  S  P  R  E

GGCCCTCGCGATGGACCCGCAGCAGCGGGTGCTCCTGGAGACGTCGTGGG   600
    A  L  A  M  D  P  Q  Q  R  V  L  L  E  T  S  W

AGGCGTTCGAAAGCGCCGGCATCACCCCGGACTCGACCCGCGGCAGCGAC   650
  E  A  F  E  S  A  G  I  T  P  D  S  T  R  G  S  D

ACCGGCGTGTTCGTCGGCGCCTTCTCCTACGGTTACGGCACCGGTGCGGA   700
    T  G  V  F  V  G  A  F  S  Y  G  Y  G  T  G  A  D

CACCGACGGCTTCGGCGCGACCGGCTCGCAGACCAGTGTGCTCTCCGGCC   750
     T  D  G  F  G  A  T  G  S  Q  T  S  V  L  S  G

GGCTGTCGTACTTCTACGGTCTGGAGGGTCCGGCGGTCACGGTCGACACG   800
  R  L  S  Y  F  Y  G  L  E  G  P  A  V  T  V  D  T

GCGTGTTCGTCGTCGCTGGTGGCGCTGCACCAGGCCGGGCAGTCGCTGCG   850
   A  C  S  S  S  L  V  A  L  H  Q  A  G  Q  S  L  R

CTCCGGCGAATGCTCGCTCGCCCTGGTCGGCGGCGTCACGGTGATGGCGT   900
     S  G  E  C  S  L  A  L  V  G  G  V  T  V  M  A

CTCCCGGCGGCTTCGTGGAGTTCTCCCGGCAGCGCGGCCTCGCGCCGGAC   950
   S  P  G  G  F  V  E  F  S  R  Q  R  G  L  A  P  D

GGCCGGGCGAAGGCGTTCGGCGCGGGTGCGGACGGCACGAGCTTCGCCGA   1000
  G  R  A  K  A  F  G  A  G  A  D  G  T  S  F  A  E

GGGTGCCGGTGTGCTGATCGTCGAGAGGCTCTCCGACGCCGAACGCAACG   1050
   G  A  G  V  L  I  V  E  R  L  S  D  A  E  R  N

GTCACACCGTCCTGGCGGTCGTCCGTGGTTCGGCGGTCAACCAGGATGGT   1100
  G  H  T  V  L  A  V  V  R  G  S  A  V  N  Q  D  G
```

-continued

```
GCCTCCAACGGGCTGTCGGCGCCGAACCGGCCGTCGCAGGAGCGGGTGAT    1150
 A  S  N  G  L  S  A  P  N  G  P  S  Q  E  R  V  I

CCGGCAGGCCCTGGCCAACGCCGGGCTCACCCCGGCGGACGTGGACGCCG    1200
 R  Q  A  L  A  N  A  G  L  T  P  A  D  V  D  A

TCGAGGCCCACGGCACCGGCACCAGGCTGGGCGACCCCATCGAGGCACAG    1250
 V  E  A  H  G  T  G  T  R  L  G  D  P  I  E  A  Q

GCGGTACTGGCCACCTACGGACAGGAGCGCGCCACCCCCCTGCTGCTGGG    1300
 A  V  L  A  T  Y  G  Q  E  R  A  T  P  L  L  L  G

CTCGCTGAAGTCCAACATCGGCCACGCCCAGGCCGCGTCCGGCGTCGCCG    1350
 S  L  K  S  N  I  G  H  A  Q  A  A  S  G  V  A

GCATCATCAAGATGGTGCAGGCCCTCCGGCACGGGGAGCTGCCGCCGACG    1400
 G  I  I  K  M  V  Q  A  L  R  H  G  E  L  P  P  T

CTGCACGCCGACGAGCCGTCGCCGCACGTCGACTGGACGGCCGGCGCCGT    1450
 L  H  A  D  E  P  S  P  H  V  D  W  T  A  G  A  V

CGAACTGCTGACGTCGGCCCGGCCGTGGCCCGAGACCGACCGGCCTAGGC    1500
 E  L  L  T  S  A  R  P  W  P  E  T  D  R  P  R

GGGCGGGCGTGTCGTCCTTCGGAGTCAGCGGCACCAACGCCCACGTCATC    1550
 R  A  G  V  S  S  F  G  V  S  G  T  N  A  H  V  I

CTGGAGAGCGCACCCCCCGCTCAGCCCGCGGAGGAGGCGCAGCCTGTTGA    1600
 L  E  S  A  P  P  A  Q  P  A  E  E  A  Q  P  V  E

GACGCCGGTGGTGGCCTCGGATGTGCTGCCGCTGGTGATATCGGCCAAGA    1650
 T  P  V  V  A  S  D  V  L  P  L  V  I  S  A  K

CCCAGCCCGCCCTGACCGAACACGAAGACCGGCTGCGCGCCTACCTGGCG    1700
 T  Q  P  A  L  T  E  H  E  D  R  L  R  A  Y  L  A

GCGTCGCCCGGGGCGGATATACGGGCTGTGGCATCGACGCTGGCGGTGAC    1750
 A  S  P  G  A  D  I  R  A  V  A  S  T  L  A  V  T

ACGGTCGGTGTTCGAGCACCGCGCCGTACTCCTTGGAGATGACACCGTCA    1800
 R  S  V  F  E  H  R  A  V  L  L  G  D  D  T  V

CCGGCACCGCGGTGACCGACCCCAGGATCGTGTTTGTCTTTCCCGGGCAG    1850
 T  G  T  A  V  T  D  P  R  I  V  F  V  F  P  G  Q

GGGTGGCAGTGGCTGGGGATGGGCAGTGCACTGCGCGATTCGTCGGTGGT    1900
 G  W  Q  W  L  G  M  G  S  A  L  R  D  S  S  V  V

GTTCGCCGAGCGGATGGCCGAGTGTGCGGCGGCGTTGCGCGAGTTCGTGG    1950
 F  A  E  R  M  A  E  C  A  A  A  L  R  E  F  V

ACTGGGATCTGTTCACGGTTCTGGATGATCCGGCGGTGGTGGACCGGGTT    2000
 D  W  D  L  F  T  V  L  D  D  P  A  V  V  D  R  V

GATGTGGTCCAGCCCGCTTCCTGGGCGATGATGGTTTCCCTGGCCGCGGT    2050
 D  V  V  Q  P  A  S  W  A  M  M  V  S  L  A  A  V

GTGGCAGGCGGCCGGTGTGCGGCCGGATGCGGTGATCGGCCATTCGCAGG    2100
 W  Q  A  A  G  V  R  P  D  A  V  I  G  H  S  Q

GTGAGATCGCCGCAGCTTGTGTGGCGGGTGCGGTGTCACTACGCGATGCC    2150
 G  E  I  A  A  A  C  V  A  G  A  V  S  L  R  D  A

GCCCGGATCGTGACCTTGCGCAGCCAGGCGATCGCCCGGGGCCTGGCGGG    2200
 A  R  I  V  T  L  R  S  Q  A  I  A  R  G  L  A  G

CCGGGGCGCGATGGCATCCGTCGCCCTGCCCGCGCAGGATGTCGAGCTGG    2250
 R  G  A  M  A  S  V  A  L  P  A  Q  D  V  E  L

TCGACGGGGCCTGGATCGCCGCCCACAACGGGCCCGCCTCCACCGTGATC    2300
 V  D  G  A  W  I  A  A  H  N  G  P  A  S  T  V  I

GCGGGCACCCCGGAAGCGGTCGACCATGTCCTCACCGCTCATGAGGCACA    2350
 A  G  T  P  E  A  V  D  H  V  L  T  A  H  E  A  Q

AGGGGTGCGGGTGCGGCGGATCACCGTCGACTATGCCTCGCACACCCCGC    2400
 G  V  R  V  R  R  I  T  V  D  Y  A  S  H  T  P

ACGTCGAGCTGATCCGCGACGAACTACTCGACATCACTAGCGACAGCAGC    2450
 H  V  E  L  I  R  D  E  L  L  D  I  T  S  D  S  S
```

```
TCGCAGACCCCGCTCGTGCCGTGGCTGTCGACCGTGGACGGCACCTGGGT         2500
  S  Q  T  P  L  V  P  W  L  S  T  V  D  G  T  W  V

CGACAGCCCGCTGGACGGGAGTACTGGTACCGGAACCTGCGTGAACCGG          2550
   D  S  P  L  D  G  E  Y  W  Y  R  N  L  R  E  P

TCGGTTTCCACCCCGCCGTCAGCCAGTTGCAGGCCCAGGGCGACACCGTG         2600
  V  G  F  H  P  A  V  S  Q  L  Q  A  Q  G  D  T  V

TTCGTCGAGGTCAGCGCCAGCCCGGTGTTGTTGCAGGCGATGGACGACGA         2650
   F  V  E  V  S  A  S  P  V  L  L  Q  A  M  D  D  D

TGTCGTCACGGTTGCCACGCTGCGTCGTGACGACGGCGACGCCACCCGGA         2700
     V  V  T  V  A  T  L  R  R  D  D  G  D  A  T  R

TGCTCACCGCCCTGGCACAGGCCTATGTCCACGGCGTCACCGTCGACTGG         2750
  M  L  T  A  L  A  Q  A  Y  V  H  G  V  T  V  D  W

CCCGCCATCCTCGGCACCACCACAACCCGGGTACTGGACCTTCCGACCTA         2800
  P  A  I  L  G  T  T  T  T  R  V  L  D  L  P  T  Y

CGCCTTCCAACACCAGCGGTACTGGCTCGAGTCGGCACGCCCGGCCGCAT         2850
   A  F  Q  H  Q  R  Y  W  L  E  S  A  R  P  A  A

CCGACGCGGGCCACCCCGTGCTGGGCTCCGGTATCGCCCTCGCCGGGTCG         2900
  S  D  A  G  H  P  V  L  G  S  G  I  A  L  A  G  S

CCGGGCCGGGTGTTCACGGGTTCCGTGCCGACCGGTGCGGACCGCGCGGT         2950
  P  G  R  V  F  T  G  S  V  P  T  G  A  D  R  A  V

GTTCGTCGCCGAGCTGGCGCTGGCCGCCGCGGACGCGGTCGACTGCGCCA         3000
   F  V  A  E  L  A  L  A  A  A  D  A  V  D  C  A

CGGTCGAGCGGCTCGACATCGCCTCCGTGCCCGGCCGGCCGGGCCATGGC         3050
  T  V  E  R  L  D  I  A  S  V  P  G  R  P  G  H  G

CGGACGACCGTACAGACCTGGGTCGACGAGCCGGCGGACGACGGCCGGCG         3100
  R  T  T  V  Q  T  W  V  D  E  P  A  D  D  G  R  R

CCGGTTCACCGTGCACACCCGCACCGGCGACGCCCCGTGGACGCTGCACG         3150
   R  F  T  V  H  T  R  T  G  D  A  P  W  T  L  H

CCGAGGGGGTGCTGCGCCCCCATGGCACGGCCCTGCCCGATGCGGCCGAC         3200
  A  E  G  V  L  R  P  H  G  T  A  L  P  D  A  A  D

GCCGAGTGGCCCCCACCGGGCGCGGTGCCCGCGGACGGGCTGCCGGGTGT         3250
  A  E  W  P  P  P  G  A  V  P  A  D  G  L  P  G  V

GTGGCGCCGGGGGGACCAGGTCTTCGCCGAGGCCGAGGTGGACGGACCGG         3300
   W  R  R  G  D  Q  V  F  A  E  A  E  V  D  G  P

ACGGTTTCGTGGTGCACCCCGACCTGCTCGACGCGGTCTTCTCCGCGGTC         3350
  D  G  F  V  V  H  P  D  L  L  D  A  V  F  S  A  V

GGCGACGGAAGCCGCCAGCCGGCCGGATGGCGCGACCTGACGGTGCACGC         3400
  G  D  G  S  R  Q  P  A  G  W  R  D  L  T  V  H  A

GTCGGACGCCACCGTACTGCGCGCCTGCCTCACCCGGCGCACCGACGGAG         3450
   S  D  A  T  V  L  R  A  C  L  T  R  R  T  D  G

CCATGGGATTCGCCGCCTTCGACGGCGCCGGCCTGCCGGTACTCACCGCG         3500
  A  M  G  F  A  A  F  D  G  A  G  L  P  V  L  T  A

GAGGCGGTGACGCTGCGGGAGGTGGCGTCACCGTCCGGCTCCGAGGAGTC         3550
  E  A  V  T  L  R  E  V  A  S  P  S  G  S  E  E  S

GGACGGCCTGCACCGGTTGGAGTGGCTCGCGGTCGCCGAGGCGGTCTACG         3600
   D  G  L  H  R  L  E  W  L  A  V  A  E  A  V  Y

ACGGTGACCTGCCCGAGGGACATGTCCTGATCACCGCCGCCCACCCCGAC         3650
  D  G  D  L  P  E  G  H  V  L  I  T  A  A  H  P  D

GACCCCGAGGACATACCCACCCGCGCCCACACCCGCGCCACCCGCGTCCT         3700
   D  P  R  D  I  P  T  R  A  H  T  R  A  T  R  V  L

GACCGCCCTGCAACACCACCTCACCACCACCGACCACACCCTCATCGTCC         3750
   T  A  L  Q  H  H  L  T  T  T  D  H  T  L  I  V
```

```
                                           -continued
ACACCACCACCGACCCCGCCGGCGCCACCGTCACCGGCCTCACCCGCACC   3800
  H  T  T  T  D  P  A  G  A  T  V  T  G  L  T  R  T GCCCAGAACGAACACCCCCACCGCATCCGCCTCATCGAAACCGACCACCC   3850
  A  Q  N  E  H  P  H  R  I  R  L  I  E  T  D  H  P CCACACCCCCCTCCCCCTGGCCCAACTCGCCACCCTCGACCACCCCCACC   3900
   H  T  P  L  P  L  A  Q  L  A  T  L  D  H  P  H TCCGCCTCACCCACCACACCCTCCACCACCCCCACCTCACCCCCCTCCAC   3950
  L  R  L  T  H  H  T  L  H  H  P  H  L  T  P  L  H ACCACCACCCCACCCACCACCACCCCCCTCAACCCCGAACACGCCATCAT   4000
  T  T  T  P  P  T  T  T  P  L  N  P  E  H  A  I  I CATCACCGGCGGCTCCGGCACCCTCGCCGGCATCCTCGCCCGCCACCTGA   4050
   I  T  G  G  S  G  T  L  A  G  I  L  A  R  H  L ACCACCCCCACACCTACCTCCTCTCCCGCACCCCACCCCCCGACGCCACC   4100
 N  H  P  H  T  Y  L  L  S  R  T  P  P  P  D  A  T CCCGGCACCCACCTCCCCTGCGACGTCGGCGACCCCCACCAACTCGCCAC   4150
  P  G  T  H  L  P  C  D  V  G  D  P  H  Q  L  A  T CACCCTCACCCACATCCCCCAACCCCTCACCGCCATCTTCCACACCGCCG   4200
   T  L  T  H  I  P  Q  P  L  T  A  I  F  H  T  A CCACCCTCGACGACGGCATCCTCCACGCCCTCACCCCCGACCGCCTCACC   4250
  A  T  L  D  D  G  I  L  H  A  L  T  P  D  R  L  T ACCGTCCTCCACCCCAAAGCCAACGCCGCCTGGCACCTGCACCACCTCAC   4300
  T  V  L  H  P  K  A  N  A  A  W  H  L  H  H  L  T CCAAAACCAACCCCTCACCCACTTCGTCCTCTACTCCAGCGCCGCCGCCG   4350
   Q  N  Q  P  L  T  H  F  V  L  Y  S  S  A  A  A TCCTCGGCAGCCCCGGACAAGGAAACTACGCCGCCGCCAACGCCTTCCTC   4400
  V  L  G  S  P  G  Q  G  N  Y  A  A  A  N  A  F  L GACGCCCTCGCCACCCACCGCCACACCCTCGGCCAACCCGCCACCTCCAT   4450
   D  A  L  A  T  H  R  H  T  L  G  Q  P  A  T  S  I CGCCTGGGGCATGTGGCACACCACCAGCACCCTCACCGGACAACTCGACG   4500
   A  W  G  M  W  H  T  T  S  T  L  T  G  Q  L  D ACGCCGACCGGGACCGCATCCGCCGCGGCGGTTTCCTCCCGATCACGGAC   4550
  D  A  D  R  D  R  I  R  R  G  G  F  L  P  I  T  D

GACGAGGGCATGGGGATGCAT
  D  E  G
```

The NheII-XhoI restriction fragment that encodes module 8 of the FK-520 PKS with the endogenous AT domain replaced by the AT domain of module 12 (specific for malonyl CoA) of the rapamycin PKS has the DNA sequence and encodes the amino acid sequence shown below (SEQ ID NOS:20–21).

```
AGATCTGGCAGCTCGCCGAAGCGCTGCTGACGCTCGTCCGGGAGAGCACC   50
  Q  L  A  E  A  L  L  T  L  V  R  E  S  T

GCCGCCGTGCTCGGCCACGTGGGTGGCGAGGACATCCCCGCGACGGCGGC   100
  A  A  V  L  G  H  V  G  G  E  D  I  P  A  T  A  A

GTTCAAGGACCTCGGCATCGACTCGCTCACCGCGGTCCAGCTGCGCAACG   150
    F  K  D  L  G  I  D  S  L  T  A  V  Q  L  R  N

CCCTCACCGAGGCGACCGGTGTGCGGCTGAACGCCACGGCGGTCTTCGAC   200
  A  L  T  E  A  T  G  V  R  L  N  A  T  A  V  F  D

TTCCCGACCCCGCACGTGCTCGCCGGGAAGCTCGGCGACGAACTGACCGG   250
   F  P  T  P  H  V  L  A  G  K  L  G  D  E  L  T  G

CACCCGCGCGCCCGTCGTGCCCCGGACCGCGGCCACGGCCGGTGCGCACG   300
      T  R  A  P  V  V  P  R  T  A  A  T  A  G  A  H

ACGAGCCGCTGGCGATCGTGGGAATGGCCTGCCGGCTGCCCGGCGGGGTC   350
  D  E  P  L  A  I  V  G  M  A  C  R  L  P  G  G  V
```

-continued

```
GCGTCACCCGAGGAGCTGTGGCACCTCGTGGCATCCGGCACCGACGCCAT      400
 A  S  P  E  E  L  W  H  L  V  A  S  G  T  D  A  I

CACGGAGTTCCCGACGGACCGCGGCTGGGACGTCGACGCGATCTACGACC      450
 T  E  F  P  T  D  R  G  W  D  V  D  A  I  Y  D

CGGACCCCGACGCGATCGGCAAGACCTTCGTCCGGCACGGTGGCTTCCTC      500
 P  D  P  D  A  I  G  K  T  F  V  R  H  G  G  F  L

ACCGGCGCGACAGGCTTCGACGCGGCGTTCTTCGGCATCAGCCCGCGCGA      550
 T  G  A  T  G  F  D  A  A  F  F  G  I  S  P  R  E

GGCCCTCGCGATGGACCCGCAGCAGCGGGTGCTCCTGGAGACGTCGTGGG      600
 A  L  A  M  D  P  Q  Q  R  V  L  L  E  T  S  W

AGGCGTTCGAAAGCGCCGGCATCACCCCGGACTCGACCCGCGGCAGCGAC      650
 E  A  F  E  S  A  G  I  T  P  D  S  T  R  G  S  D

ACCGGCGTGTTCGTCGGCGCCTTCTCCTACGGTTACGGCACCGGTGCGGA      700
 T  G  V  F  V  G  A  F  S  Y  G  Y  G  T  G  A  D

CACCGACGGCTTCGGCGCGACCGGCTCGCAGACCAGTGTGCTCTCCGGCC      750
 T  D  G  F  G  A  T  G  S  Q  T  S  V  L  S  G

GGCTGTCGTACTTCTACGGTCTGGAGGGTCCGGCGGTCACGGTCGACACG      800
 R  L  S  Y  F  Y  G  L  E  G  P  A  V  T  V  D  T

GCGTGTTCGTCGTCGCTGGTGGCGCTGCACCAGGCCGGGCAGTCGCTGCG      850
 A  C  S  S  S  L  V  A  L  H  Q  A  G  Q  S  L  R

CTCCGGCGAATGCTCGCTCGCCCTGGTCGGCGGCGTCACGGTGATGGCGT      900
 S  G  E  C  S  L  A  L  V  G  G  V  T  V  M  A

CTCCCGGCGGCTTCGTGGAGTTCTCCCGGCAGCGCGGCCTCGCGCCGGAC      950
 S  P  G  G  F  V  E  F  S  R  Q  R  G  L  A  P  D

GGCCGGGCGAAGGCGTTCGGCGCGGGTGCGGACGGCACGAGCTTCGCCGA      1000
 G  R  A  K  A  F  G  A  G  A  D  G  T  S  F  A  E

GGGTGCCGGTGTGCTGATCGTCGAGAGGCTCTCCGACGCCGAACGCAACG      1050
 G  A  G  V  L  I  V  E  R  L  S  D  A  E  R  N

GTCACACCGTCCTGGCGGTCGTCCGTGGTTCGGCGGTCAACCAGGATGGT      1100
 G  H  T  V  L  A  V  V  R  G  S  A  V  N  Q  D  G

GCCTCCAACGGGCTGTCGGCGCCGAACGGGCCGTCGCAGGAGCGGGTGAT      1150
 A  S  N  G  L  S  A  P  N  G  P  S  Q  E  R  V  I

CCGGCAGGCCCTGGCCAACGCCGGGCTCACCCCGGCGGACGTGGACGCCG      1200
 R  Q  A  L  A  N  A  G  L  T  P  A  D  V  D  A

TCGAGGCCCACGGCACCGGCACCAGGCTGGGCGACCCCATCGAGGCACAG      1250
 V  E  A  H  G  T  G  T  R  L  G  D  P  I  E  A  Q

GCGGTACTGGCCACCTACGGACAGGAGCGCGCCACCCCCCTGCTGCTGGG      1300
 A  V  L  A  T  Y  G  Q  E  R  A  T  P  L  L  L  G

CTCGCTGAAGTCCAACATCGGCCACGCCCAGGCCGCGTCCGGCGTCGCCG      1350
 S  L  K  S  N  I  G  H  A  Q  A  A  S  G  V  A

GCATCATCAAGATGGTGCAGGCCCTCCGGCACGGGGAGCTGCCGCCGACG      1400
 G  I  I  K  M  V  Q  A  L  R  H  G  E  L  P  P  T

CTGCACGCCGACGAGCCGTCGCCGCACGTCGACTGGACGGCCGGCGCCGT      1450
 L  H  A  D  E  P  S  P  H  V  D  W  T  A  G  A  V

CGAACTGCTGACGTCGGCCCGGCCGTGGCCCGAGACCGACCGGCCACGGC      1500
 E  L  L  T  S  A  R  P  W  P  E  T  D  R  P  R

GTGCCGCCGTCTCCTCGTTCGGGGTGAGCGGCACCAACGCCCACGTCATC      1550
 R  A  A  V  S  S  F  G  V  S  G  T  N  A  H  V  I

CTGGAGGCCGGACCGGTAACGGAGACGCCCGCGGCATCGCCTTCCGGTGA      1600
 L  E  A  G  P  V  T  E  T  P  A  A  S  P  S  G  D

CCTTCCCCTGCTGGTGTCGGCACGCTCACCGGAAGCGCTCGACGAGCAGA      1650
 L  P  L  L  V  S  A  R  S  P  E  A  L  D  E  Q

TCCGCCGACTGCGCGCCTACCTGGACACCACCCCGGACGTCGACCGGGTG      1700
 I  R  R  L  R  A  Y  L  D  T  T  P  D  V  D  R  V
```

```
GCCGTGGCACAGACGCTGGCCCGGCGCACACACTTCGCCCACCGCGCCGT    1750
 A  V  A  Q  T  L  A  R  R  R  T  H  F  A  H  R  A  V

GCTGCTCGGTGACACCGTCATCACCACACCCCCGCGGACCGGCCCGACG     1800
 L  L  G  D  T  V  I  T  T  P  P  A  D  R  P  D

AACTCGTCTTCGTCTACTCCGGCCAGGGCACCCAGCATCCCGCGATGGGC    1850
 E  L  V  F  V  Y  S  G  Q  G  T  Q  H  P  A  M  G

GAGCAGCTAGCCGCCGCGTTCCCCGTCTTCGCGCGGATCCATCAGCAGGT    1900
 E  Q  L  A  A  A  F  P  V  F  A  R  I  H  Q  Q  V

GTGGGACCTGCTCGATGTGCCCGATCTCGAGGTGAACGAGACCGGTTACG    1950
 W  D  L  L  D  V  P  D  L  E  V  N  E  T  G  Y

CCCAGCCGGCCCTGTTCGCAATGCAGGTGGCTCTGTTCGGGCTGCTGGAA    2000
 A  Q  P  A  L  F  A  M  Q  V  A  L  F  G  L  L  E

TCGTGGGGTGTACGACCGGACGCGGTGATCGGCCATTCGGTGGGTGAGCT    2050
 S  W  G  V  R  P  D  A  V  I  G  H  S  V  G  E  L

TGCGGCTGCGTATGTGTCCGGGGTGTGGTCGTTGGAGGATGCCTGCACTT    2100
 A  A  A  Y  V  S  G  V  W  S  L  E  D  A  C  T

TGGTGTCGGCGCGGGCTCGTCTGATGCAGGCTCTGCCCGCGGGTGGGGTG    2150
 L  V  S  A  R  A  R  L  M  Q  A  L  P  A  G  G  V

ATGGTCGCTGTCCCGGTCTCGGAGGATGAGGCCCGGGCCGTGCTGGGTGA    2200
 M  V  A  V  P  V  S  E  D  E  A  R  A  V  L  G  E

GGGTGTGGAGATCGCCGCGGTCAACGGCCCGTCGTCGGTGGTTCTCTCCG    2250
 G  V  E  I  A  A  V  N  G  P  S  S  V  V  L  S

GTGATGAGGCCGCCGTGCTGCAGGCCGCGGAGGGGCTGGGGAAGTGGACG    2300
 G  D  E  A  A  V  L  Q  A  A  E  G  L  G  K  W  T

CGGCTGGCGACCAGCCACGCGTTCCATTCCGCCCGTATGGAACCCATGCT    2350
 R  L  A  T  S  H  A  F  H  S  A  R  M  E  P  M  L

GGAGGAGTTCCGGGCGGTCGCCGAAGGCCTGACCTACCGGACGCCGCAGG    2400
 E  E  F  R  A  V  A  E  G  L  T  Y  R  T  P  Q

TCTCCATGGCCGTTGGTGATCAGGTGACCACCGCTGAGTACTGGGTGCGG    2450
 V  S  M  A  V  G  D  Q  V  T  T  A  E  Y  W  V  R

CAGGTCCGGGACACGGTCCGGTTCGGCGAGCAGGTGGCCTCGTACGAGGA    2500
 Q  V  R  D  T  V  R  F  G  E  Q  V  A  S  Y  E  D

CGCCGTGTTCGTCGAGCTGGGTGCCGACCGGTCACTGGCCCGCCTGGTCG    2550
 A  V  F  V  E  L  G  A  D  R  S  L  A  R  L  V

ACGGTGTCGCGATGCTGCACGGCGACCACGAAATCCAGGCCGCGATCGGC    2600
 D  G  V  A  M  L  H  G  D  H  E  I  Q  A  A  I  G

GCCCTGGCCCACCTGTATGTCAACGGCGTCACGGTCGACTGGCCCGCGCT    2650
 A  L  A  H  L  Y  V  N  G  V  T  V  D  W  P  A  L

CCTGGGCGATGCTCCGGCAACACGGGTGCTGGACCTTCCGACATACGCCT    2700
 L  G  D  A  P  A  T  R  V  L  D  L  P  T  Y  A

TCCAGCACCAGCGCTACTGGCTCGAGTCGGCACGCCCGGCCGCATCCGAC    2750
 F  Q  H  Q  R  Y  W  L  E  S  A  R  P  A  A  S  D

GCGGGCCACCCCGTGCTGGGCTCCGGTATCGCCCTCGCCGGGTCGCCGGG    2800
 A  G  H  P  V  L  G  S  G  I  A  L  A  G  S  P  G

CCGGGTGTTCACGGGTTCCGTGCCGACCGGTGCGGACCGCGCGGTGTTCG    2850
 R  V  F  T  G  S  V  P  T  G  A  D  R  A  V  F

TCGCCGAGCTGGCGCTGGCCGCCGCGGACGCGGTCGACTGCGCCACGGTC    2900
 V  A  E  L  A  L  A  A  A  D  A  V  D  C  A  T  V

GAGCGGCTCGACATCGCCTCCGTGCCCGGCCGGCCGCGGCATGGCCGGAC    2950
 E  R  L  D  I  A  S  V  P  G  R  P  G  H  G  R  T

GACCGTACAGACCTGGGTCGACGAGCCGGCGGACGACGGCCGGCGCCGT    3000
 T  V  Q  T  W  V  D  E  P  A  D  D  G  R  R  R
```

```
TCACCGTGCACACCCGCACCGGCGACGCCCCGTGGACGCTGCACGCCGAG     3050
 F  T  V  H  T  R  T  G  D  A  P  W  T  L  H  A  E

GGGGTGCTGCGCCCCCATGGCACGGCCCTGCCCGATGCGGCCGACGCCGA     3100
 G  V  L  R  P  H  G  T  A  L  P  D  A  A  D  A  E

GTGGCCCCCACCGGGCGCGGTGCCCGCGGACGGGCTGCCGGGTGTGTGGC     3150
 W  P  P  P  G  A  V  P  A  D  G  L  P  G  V  W

GCCGGGGGACCAGGTCTTCGCCGAGGCCGAGGTGGACGGACCGGACGGT     3200
 R  R  G  D  Q  V  F  A  E  A  E  V  D  G  P  D  G

TTCGTGGTGCACCCCGACCTGCTCGACGCGGTCTTCTCCGCGGTCGGCGA     3250
 F  V  V  H  P  D  L  L  D  A  V  F  S  A  V  G  D

CGGAAGCCGCCAGCCGGCCGGATGGCGCGACCTGACGGTGCACGCGTCGG     3300
  G  S  R  Q  P  A  G  W  R  D  L  T  V  H  A  S

ACGCCACCGTACTGCGCGCCTGCCTCACCCGGCGCACCGACGGAGCCATG     3350
 D  A  T  V  L  R  A  C  L  T  R  R  T  D  G  A  M

GGATTCGCCGCCTTCGACGGCGCCGGCCTGCCGGTACTCACCGCGGAGGC     3400
  G  F  A  A  F  D  G  A  G  L  P  V  L  T  A  E  A

GGTGACGCTGCGGGAGGTGGCGTCACCGTCCGGCTCCGAGGAGTCGGACG     3450
  V  T  L  R  E  V  A  S  P  S  G  S  E  E  S  D

GCCTGCACCGGTTGGAGTGGCTCGCGGTCGCCGAGGCGGTCTACGACGGT     3500
 G  L  H  R  L  E  W  L  A  V  A  E  A  V  Y  D  G

GACCTGCCCGAGGGACATGTCCTGATCACCGCCGCCCACCCCGACGACCC     3550
  D  L  P  E  G  H  V  L  I  T  A  A  H  P  D  D  P

CGAGGACATACCCACCCGCGCCCACACCCGCGCCACCCGCGTCCTGACCG     3600
  E  D  I  P  T  R  A  H  T  R  A  T  R  V  L  T

CCCTGCAACACCACCTCACCACCACCGACCACACCCTCATCGTCCACACC     3650
 A  L  Q  H  H  L  T  T  T  D  H  T  L  I  V  H  T

ACCACCGACCCCGCCGGCGCCACCGTCACCGGCCTCACCCGCACCGCCCA     3700
 T  T  D  P  A  G  A  T  V  T  G  L  T  R  T  A  Q

GAACGAACACCCCCACCGCATCCGCCTCATCGAAACCGACCACCCCCACA     3750
  N  E  H  P  H  R  I  R  L  I  E  T  D  H  P  H

CCCCCCTCCCCCTGGCCCAACTCGCCACCCTCGACCACCCCCACCTCCGC     3800
 T  P  L  P  L  A  Q  L  A  T  L  D  H  P  H  L  R

CTCACCCACCACACCCTCCACCACCCCCACCTCACCCCCCTCCACACCAC     3850
 L  T  H  H  T  L  H  H  P  H  L  T  P  L  H  T  T

CACCCCACCCACCACCACCCCCCTCAACCCCGAACACGCCATCATCATCA     3900
  T  P  P  T  T  T  P  L  N  P  E  H  A  I  I  I

CCGGCGGCTCCGGCACCCTCGCCGGCATCCTCGCCCGCCACCTGAACCAC     3950
 T  G  G  S  G  T  L  A  G  I  L  A  R  H  L  N  H

CCCCACACCTACCTCCTCTCCCGCACCCCACCCCCCGACGCCACCCCCGG     4000
 P  H  T  Y  L  L  S  R  T  P  P  P  D  A  T  P  G

CACCCACCTCCCCTGCGACGTCGGCGACCCCCACCAACTCGCCACCACCC     4050
  T  H  L  P  C  D  V  G  D  P  H  Q  L  A  T  T

TCACCCACATCCCCCAACCCCTCACCGCCATCTTCCACACCGCCGCCACC     4100
 L  T  H  I  P  Q  P  L  T  A  I  F  H  T  A  A  T

CTCGACGACGGCATCCTCCACGCCCTCACCCCCGACCGCCTCACCACCGT     4150
 L  D  D  G  I  L  H  A  L  T  P  D  R  L  T  T  V

CCTCCACCCCAAAGCCAACGCCGCCTGGCACCTGCACCACCTCACCCAAA     4200
  L  H  P  K  A  N  A  A  W  H  L  H  H  L  T  Q

ACCAACCCCTCACCCACTTCGTCCTCTACTCCAGCGCCGCCGCCGTCCTC     4250
 N  Q  P  L  T  H  F  V  L  Y  S  S  A  A  A  V  L

GGCAGCCCCGGACAAGGAAACTACGCCGCCGCCAACGCCTTCCTCGACGC     4300
 G  S  P  G  Q  G  N  Y  A  A  A  N  A  F  L  D  A
```

```
CCTCGCCACCCACCGCCACACCCTCGGCCAACCCGCCACCTCCATCGCCT    4350
  L  A  T  H  R  H  T  L  G  Q  P  A  T  S  I  A

GGGGCATGTGGCACACCACCAGCACCCTCACCGGACAACTCGACGACGCC    4400
  W  G  M  W  H  T  T  S  T  L  T  G  Q  L  D  D  A

GACCGGGACCGCATCCGCCGCGGCGGTTTCCTCCCGATCACGGACGACGA    4450
  D  R  D  R  I  R  R  G  G  F  L  P  I  T  D  D  E

GGGCATGGGGATGCAT
  G
```

The NheII-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below (SEQ ID NOS:22–23).

```
AGATCTGGCAGCTCGCCGAAGCGCTGCTGACGCTCGTCCGGGAGAGCACC    50
  Q  L  A  E  A  L  L  T  L  V  R  E  S  T

GCCGCCGTGCTCGGCCACGTGGGTGGCGAGGACATCCCCGCGACGGCGGC    100
  A  A  V  L  G  H  V  G  G  E  D  I  P  A  T  A  A

GTTCAAGGACCTCGGCATCGACTCGCTCACCGCGGTCCAGCTGCGCAACG    150
  F  K  D  L  G  I  D  S  L  T  A  V  Q  L  R  N

CCCTCACCGAGGCGACCGGTGTGCGGCTGAACGCCACGGCGGTCTTCGAC    200
  A  L  T  E  A  T  G  V  R  L  N  A  T  A  V  F  D

TTCCCGACCCCGCACGTGCTCGCCGGGAAGCTCGGCGACGAACTGACCGG    250
  F  P  T  P  H  V  L  A  G  K  L  G  D  E  L  T  G

CACCCGCGCGCCCGTCGTGCCCCGGACCGCGGCCACGGCCGGTGCGCACG    300
  T  R  A  P  V  V  P  R  T  A  A  T  A  G  A  H

ACGAGCCGCTGGCGATCGTGGGAATGGCCTGCCGGCTGCCCGGCGGGGTC    350
  D  E  P  L  A  I  V  G  M  A  C  R  L  P  G  G  V

GCGTCACCCGAGGAGCTGTGGCACCTCGTGGCATCCGGCACCGACGCCAT    400
  A  S  P  E  E  L  W  H  L  V  A  S  G  T  D  A  I

CACGGAGTTCCCGACGGACCGCGGCTGGGACGTCGACGCGATCTACGACC    450
  T  E  F  P  T  D  R  G  W  D  V  D  A  I  Y  D

CGGACCCCGACGCGATCGGCAAGACCTTCGTCCGGCACGGTGGCTTCCTC    500
  P  D  P  D  A  I  G  K  T  F  V  R  H  G  G  F  L

ACCGGCGCGACAGGCTTCGACGCGGCGTTCTTCGGCATCAGCCCGCGCGA    550
  T  G  A  T  G  F  D  A  A  F  F  G  I  S  P  R  E

GGCCCTCGCGATGGACCCGCAGCAGCGGGTGCTCCTGGAGACGTCGTGGG    600
  A  L  A  M  D  P  Q  Q  R  V  L  L  E  T  S  W

AGGCGTTCGAAAGCGCCGGCATCACCCCGGACTCGACCCGCGGCAGCGAC    650
  E  A  F  E  S  A  G  I  T  P  D  S  T  R  G  S  D

ACCGGCGTGTTCGTCGGCGCCTTCTCCTACGGTTACGGCACCGGTGCGGA    700
  T  G  V  F  V  G  A  F  S  Y  G  Y  G  T  G  A  D

CACCGACGGCTTCGGCGCGACCGGCTCGCAGACCAGTGTGCTCTCCGGCC    750
  T  D  G  F  G  A  T  G  S  Q  T  S  V  L  S  G

GGCTGTCGTACTTCTACGGTCTGGAGGGTCCGGCGGTCACGGTCGACACG    800
  R  L  S  Y  F  Y  G  L  E  G  P  A  V  T  V  D  T

GCGTGTTCGTCGTCGCTGGTGGCGCTGCACCAGGCCGGGCAGTCGCTGCG    850
  A  C  S  S  S  L  V  A  L  H  Q  A  G  Q  S  L  R

CTCCGGCGAATGCTCGCTCGCCCTGGTCGGCGGCGTCACGGTGATGGCGT    900
  S  G  E  C  S  L  A  L  V  G  G  V  T  V  M  A

CTCCCGGCGGCTTCGTGGAGTTCTCCCGGCAGCGCGGCCTCGCGCCGGAC    950
  S  P  G  G  F  V  E  F  S  R  Q  R  G  L  A  P  D

GGCCGGGCGAAGGCGTTCGGCGCGGGTGCGGACGGCACGAGCTTCGCCGA    1000
  G  R  A  K  A  F  G  A  G  A  D  G  T  S  F  A  E
```

-continued

```
GGGTGCCGGTGTGCTGATCGTCGAGAGGCTCTCCGACGCCGAACGCAACG      1050
  G  A  G  V  L  I  V  E  R  L  S  D  A  E  R  N

GTCACACCGTCCTGGCGGTCGTCCGTGGTTCGGCGGTCAACCAGGATGGT      1100
G  H  T  V  L  A  V  V  R  G  S  A  V  N  Q  D  G

GCCTCCAACGGGCTGTCGGCGCCGAACGGGCCGTCGCAGGAGCGGGTGAT      1150
 A  S  N  G  L  S  A  P  N  G  P  S  Q  E  R  V  I

CCGGCAGGCCCTGGCCAACGCCGGGCTCACCCCGGCGGACGTGGACGCCG      1200
  R  Q  A  L  A  N  A  G  L  T  P  A  D  V  D  A

TCGAGGCCCACGGCACCGGCACCAGGCTGGGCGACCCCATCGAGGCACAG      1250
V  E  A  H  G  T  G  T  R  L  G  D  P  I  E  A  Q

GCGGTACTGGCCACCTACGGACAGGAGCGCGCCACCCCCCTGCTGCTGGG      1300
 A  V  L  A  T  Y  G  Q  E  R  A  T  P  L  L  G

CTCGCTGAAGTCCAACATCGGCCACGCCCAGGCCGCGTCCGGCGTCGCCG      1350
  S  L  K  S  N  I  G  H  A  Q  A  A  S  G  V  A

GCATCATCAAGATGGTGCAGGCCCTCCGGCACGGGGAGCTGCCGCCGACG      1400
 G  I  I  K  M  V  Q  A  L  R  H  G  E  L  P  P  T

CTGCACGCCGACGAGCCGTCGCCGACGTCGACTGGACGGCCGGCGCCGT       1450
  L  H  A  D  E  P  S  P  H  V  D  W  T  A  G  A  V

CGAACTGCTGACGTCGGCCCGGCCGTGGCCCGAGACCGACCGGCCACGGC      1500
  E  L  L  T  S  A  R  P  W  P  E  T  D  R  P  R

GTGCCGCCGTCTCCTCGTTCGGGGTGAGCGGCACCAACGCCCACGTCATC      1550
R  A  A  V  S  S  F  G  V  S  G  T  N  A  H  V  I

CTGGAGGCCGGACCGGTAACGGAGACGCCCGCGGCATCGCCTTCCGGTGA      1600
L  E  A  G  P  V  T  E  T  P  A  A  S  P  S  G  D

CCTTCCCCTGCTGGTGTCGGCACGCTCACCGGAAGCGCTCGACGAGCAGA      1650
  L  P  L  L  V  S  A  R  S  P  E  A  L  D  E  Q

TCCGCCGACTGCGCGCCTACCTGGACACCACCCCGGACGTCGACCGGGTG      1700
I  R  R  L  R  A  Y  L  D  T  T  P  D  V  D  R  V

GCCGTGGCACAGACGCTGGCCCGGCGCACACACTTCGCCCACCGCGCCGT      1750
 A  V  A  Q  T  L  A  R  R  T  H  F  A  H  R  A  V

GCTGCTCGGTGACACCGTCATCACCACACCCCCCGCGGACCGGCCCGACG      1800
  L  L  G  D  T  V  I  T  T  P  P  A  D  R  P  D

AACTCGTCTTCGTCTACTCCGGCCAGGGCACCCAGCATCCCGCGATGGGC      1850
 E  L  V  F  V  Y  S  G  Q  G  T  Q  H  P  A  M  G

GAGCAGCTAGCCGATTCGTCGGTGGTGTTCGCCGAGCGGATGGCCGAGTG      1900
 E  Q  L  A  D  S  S  V  V  F  A  E  R  M  A  E  C

TGCGGCGGCGTTGCGCGAGTTCGTGGACTGGGATCTGTTCACGGTTCTGG      1950
  A  A  A  L  R  E  F  V  D  W  D  L  F  T  V  L

ATGATCCGGCGGTGGTGGACCGGGTTGATGTGGTCCAGCCCGCTTCCTGG      2000
D  D  P  A  V  V  D  R  V  D  V  V  Q  P  A  S  W

GCGATGATGGTTTCCCTGGCCGCGGTGTGGCAGGCGGCCGGTGTGCGGCC      2050
 A  M  M  V  S  L  A  A  V  W  Q  A  A  G  V  R  P

GGATGCGGTGATCGGCCATTCGCAGGGTGAGATCGCCGCAGCTTGTGTGG      2100
  D  A  V  I  G  H  S  Q  G  E  I  A  A  A  C  V

CGGGTGCGGTGTCACTACGCGATGCCGCCCGGATCGTGACCTTGCGCAGC      2150
 A  G  A  V  S  L  R  D  A  A  R  I  V  T  L  R  S

CAGGCGATCGCCCGGGGCCTGGCGGGCCGGGGCGCGATGGCATCCGTCGC      2200
 Q  A  I  A  R  G  L  A  G  R  G  A  M  A  S  V  A

CCTGCCCGCGCAGGATGTCGAGCTGGTCGACGGGGCCTGGATCGCCGCCC      2250
  L  P  A  Q  D  V  E  L  V  D  G  A  W  I  A  A

ACAACGGGCCCGCCTCCACCGTGATCGCGGGCACCCCGGAAGCGGTCGAC      2300
H  N  G  P  A  S  T  V  I  A  G  T  P  E  A  V  D
```

```
CATGTCCTCACCGCTCATGAGGCACAAGGGGTGCGGGTGCGGCGGATCAC    2350
 H  V  L  T  A  H  E  A  Q  G  V  R  V  R  R  I  I

CGTCGACTATGCCTCGCACACCCCGCACGTCGAGCTGATCCGCGACGAAC    2400
 V  D  Y  A  S  H  T  P  H  V  E  L  I  R  D  R

TACTCGACATCACTAGCGACAGCAGCTCGCAGACCCCGCTCGTGCCGTGG    2450
 L  L  D  I  T  S  D  S  S  Q  T  P  L  V  P  W

CTGTCGACCGTGGACGGCACCTGGGTCGACAGCCCGCTGGACGGGGAGTA    2500
 L  S  T  V  D  G  T  W  V  D  S  P  L  D  G  E  Y

CTGGTACCGGAACCTGCGTGAACCGGTCGGTTTCCACCCCGCCGTCAGCC    2550
 W  Y  R  N  L  R  E  P  V  G  F  H  P  A  V  S

AGTTGCAGGCCCAGGGCGACACCGTGTTCGTCGAGGTCAGCGCCAGCCCG    2600
 Q  L  Q  A  Q  G  D  T  V  F  V  E  V  S  A  S  P

GTGTTGTTGCAGGCGATGGACGACGATGTCGTCACGGTTGCCACGCTGCG    2650
 V  L  L  Q  A  M  D  D  D  V  V  T  V  A  T  L  R

TCGTGACGACGGCGACGCCACCCGGATGCTCACCGCCCTGGCACAGGCCT    2700
 R  D  D  G  D  A  T  R  M  L  T  A  L  A  Q  A

ATGTCCACGGCGTCACCGTCGACTGGCCCGCCATCCTCGGCACCACCACA    2750
 Y  V  H  G  V  T  V  D  W  P  A  I  L  G  T  T  T

ACCCGGGTACTGGACCTTCCGACCTACGCCTTCCAACACCAGCGGTACTG    2800
 T  R  V  L  D  L  P  T  Y  A  F  Q  H  Q  R  Y  W

GCTCGAGTCGGCACGCCCGGCCGCATCCGACGCGGGCCACCCCGTGCTGG    2850
 L  E  S  A  R  P  A  A  S  D  A  G  H  P  V  L

GCTCCGGTATCGCCCTCGCCGGGTCGCCGGGCCGGGTGTTCACGGGTTCC    2900
 G  S  G  I  A  L  A  G  S  P  G  R  V  F  T  G  S

GTGCCGACCGGTGCGGACCGCGCGGTGTTCGTCGCCGAGCTGGCGCTGGC    2950
 V  P  T  G  A  D  R  A  V  F  V  A  E  L  A  L  A

CGCCGCGGACGCGGTCGACTGCGCCACGGTCGAGCGGCTCGACATCGCCT    3000
 A  A  D  A  V  D  C  A  T  V  E  R  L  D  I  A

CCGTGCCCGGCCGGCCGGGCCATGGCCGGACGACCGTACAGACCTGGGTC    3050
 S  V  P  G  R  P  G  H  G  R  T  T  V  Q  T  W  V

GACGAGCCGGCGGACGACGGCCGGCGCCGGTTCACCGTGCACACCCGCAC    3100
 D  E  P  A  D  D  G  R  R  R  F  T  V  H  T  R  T

CGGCGACGCCCCGTGGACGCTGCACGCCGAGGGGTGCTGCGCCCCCATG    3150
 G  D  A  P  W  T  L  H  A  E  G  V  L  R  P  H

GCACGGCCCTGCCCGATGCGGCCGACGCCGAGTGGCCCCACCGGGCGCG    3200
 G  T  A  L  P  D  A  A  D  A  E  W  P  P  P  G  A

GTGCCCGCGGACGGGCTGCCGGGTGTGTGGCGCCGGGGGACCAGGTCTT    3250
 V  P  A  D  G  L  P  G  V  W  R  R  G  D  Q  V  F

CGCCGAGGCCGAGGTGGACGGACCGGACGGTTTCGTGGTGCACCCCGACC    3300
 A  E  A  E  V  D  G  P  D  G  F  V  V  H  P  D

TGCTCGACGCGGTCTTCTCCGCGGTCGGCGACGGAAGCCGCCAGCCGGCC    3350
 L  L  D  A  V  F  S  A  V  G  D  G  S  R  Q  P  A

GGATGGCGCGACCTGACGGTGCACGCGTCGGACGCCACCGTACTGCGCGC    3400
 G  W  R  D  L  T  V  H  A  S  D  A  T  V  L  R  A

CTGCCTCACCCGGCGCACCGACGGAGCCATGGGATTCGCCGCCTTCGACG    3450
 C  L  T  R  R  T  D  G  A  M  G  F  A  A  F  D

GCGCCGGCCTGCCGGTACTCACCGCGGAGGCGGTGACGCTGCGGGAGGTG    3500
 G  A  G  L  P  V  L  T  A  E  A  V  T  L  R  E  V

GCGTCACCGTCCGGCTCCGAGGAGTCGGACGCCTGCACCGGTTGGAGTG    3550
 A  S  P  S  G  S  E  E  S  D  G  L  H  R  L  E  W

GCTCGCGGTCGCCGAGGCGGTCTACGACGGTGACCTGCCCGAGGGACATG    3600
 L  A  V  A  E  A  V  Y  D  G  D  L  P  E  G  H
```

-continued

```
TCCTGATCACCGCCGCCCACCCCGACGACCCCGAGGACATACCCACCCGC    3650
 V  L  I  T  A  A  H  P  D  D  P  E  D  I  P  T  R

GCCCACACCCGCGCCACCCGCGTCCTGACCGCCCTGCAACACCACCTCAC    3700
 A  H  T  R  A  T  R  V  L  T  A  L  Q  H  H  L  T

CACCACCGACCACACCCTCATCGTCCACACCACCACCGACCCCGCCGGCG    3750
   T  T  D  H  T  L  I  V  H  T  T  T  D  P  A  G

CCACCGTCACCGGCCTCACCCGCACCGCCCAGAACGAACACCCCCACCGC    3800
 A  T  V  T  G  L  T  R  T  A  Q  N  E  H  P  H  R

ATCCGCCTCATCGAAACCGACCACCCCCACACCCCCCTCCCCCTGGCCCA    3850
 I  R  L  I  E  T  D  H  P  H  T  P  L  P  L  A  Q

ACTCGCCACCCTCGACCACCCCCACCTCCGCCTCACCCACCACACCCTCC    3900
   L  A  T  L  D  H  P  H  L  R  L  T  H  H  T  L

ACCACCCCCACCTCACCCCCCTCCACACCACCACCCCACCCACCACCACC    3950
 H  H  P  H  L  T  P  L  H  T  T  T  P  P  T  T  T

CCCCTCAACCCCGAACACGCCATCATCATCACCGGCGGCTCCGGCACCCT    4000
   P  L  N  P  E  H  A  I  I  I  T  G  G  S  G  T  L

CGCCGGCATCCTCGCCCGCCACCTGAACCACCCCCACACCTACCTCCTCT    4050
   A  G  I  L  A  R  H  L  N  H  P  H  T  Y  L  L

CCCGCACCCCACCCCCCGACGCCACCCCCGGCACCCACCTCCCCTGCGAC    4100
 S  R  T  P  P  P  D  A  T  P  G  T  H  L  P  C  D

GTCGGCGACCCCCACCAACTCGCCACCACCCTCACCCACATCCCCCAACC    4150
 V  G  D  P  H  Q  L  A  T  T  L  T  H  I  P  Q  P

CCTCACCGCCATCTTCCACACCGCCGCCACCCTCGACGACGGCATCCTCC    4200
   L  T  A  I  F  H  T  A  A  T  L  D  D  G  I  L

ACGCCCTCACCCCCGACCGCCTCACCACCGTCCTCCACCCCAAAGCCAAC    4250
 H  A  L  T  P  D  R  L  T  T  V  L  H  P  K  A  N

GCCGCCTGGCACCTGCACCACCTCACCCAAAACCAACCCCTCACCCACTT    4300
 A  A  W  H  L  H  H  L  T  Q  N  Q  P  L  T  H  F

CGTCCTCTACTCCAGCGCCGCCGCCGTCCTCGGCAGCCCCGGACAAGGAA    4350
   V  L  Y  S  S  A  A  A  V  L  G  S  P  G  Q  G

ACTACGCCGCCGCCAACGCCTTCCTCGACGCCCTCGCCACCCACCGCCAC    4400
 N  Y  A  A  A  N  A  F  L  D  A  L  A  T  H  R  H

ACCCTCGGCCAACCCGCCACCTCCATCGCCTGGGGCATGTGGCACACCAC    4450
 T  L  G  Q  P  A  T  S  I  A  W  G  M  W  H  T  T

CAGCACCCTCACCGGACAACTCGACGACGCCGACCGGGACCGCATCCGCC    4500
   S  T  L  T  G  Q  L  D  D  A  D  R  D  R  I  R

GCGGCGGTTTCCTCCCGATCACGGACGACGAGGGCATGGGGATGCAT
 R  G  G  F  L  P  I  T  D  D  E  G
```

Phage KC515 DNA was prepared using the procedure described in Genetic Manipulation of Streptomyces, A Laboratory Manual, edited by D. Hopwood et al. A phage suspension prepared from 10 plates (100 mm) of confluent plaques of KC515 on S. lividans TK24 generally gave about 3 μg of phage DNA. The DNA was ligated to circularize at the cos site, subsequently digested with restriction enzymes BamHI and PstI, and dephosphorylated with SAP.

Each module 8 cassette described above was excised with restriction enzymes BglII and NsiI and ligated into the compatible BamHI and PstI sites of KC515 phage DNA prepared as described above. The ligation mixture containing KC515 and various cassettes was transfected into protoplasts of Streptomyces lividans TK24 using the procedure described in Genetic Manipulation of Streptomyces, A Laboratory Manual edited by D. Hopwood et al. and overlaid with TK24 spores. After 16–24 hr, the plaques were restreaked on plates overlaid with TK24 spores. Single plaques were picked and resuspended in 200 μL of nutrient broth. Phage DNA was prepared by the boiling method (Hopwood et al., supra). The PCR with primers spanning the left and right boundaries of the recombinant phage was used to verify the correct phage had been isolated. In most cases, at least 80% of the plaques contained the expected insert. To confirm the presence of the resistance marker (thiostrepton), a spot test is used, as described in Lomovskaya et al. (1997), in which a plate with spots of phage is overlaid with mixture of spores of TK24 and phiC31 TK24 lysogen. After overnight incubation, the plate is overlaid with antibiotic in soft agar. A working stock is made of all phage containing desired constructs.

Streptomyces hygroscopicus ATCC 14891 (see U.S. Pat. No. 3,244,592, issued Apr. 5, 1966, incorporated herein by reference) mycelia were infected with the recombinant phage by mixing the spores and phage ($1 \times 10^8$ of each), and incubating on R2YE agar (Genetic Manipulation of Streptomyces, A Laboratory Manual, edited by D. Hopwood et al.) at 30° C. for 10 days. Recombinant clones were selected and plated on minimal medium containing thiostrepton (50 µg/ml) to select for the thiostrepton resistance-conferring gene. Primary thiostrepton resistant clones were isolated and purified through a second round of single colony isolation, as necessary. To obtain thiostrepton-sensitive revertants that underwent a second recombination event to evict the phage genome, primary recombinants were propagated in liquid media for two to three days in the absence of thiostrepton and then spread on agar medium without thiostrepton to obtain spores. Spores were plated to obtain about 50 colonies per plate, and thiostrepton sensitive colonies were identified by replica plating onto thiostrepton containing agar medium. The PCR was used to determine which of the thiostrepton sensitive colonies reverted to the wild type (reversal of the initial integration event), and which contain the desired AT swap at module 8 in the ATCC 14891-derived cells. The PCR primers used amplified either the KS/AT junction or the AT/DH junction of the wild-type and the desired recombinant strains. Fermentation of the recombinant strains, followed by isolation of the metabolites and analysis by LCMS, and NMR is used to characterize the novel polyketide compounds.

Example 2

Replacement of Methoxyl with Hydrogen or Methyl at C-13 of FK-506

The present invention also provides the 13-desmethoxy derivatives of FK-506 and the novel PKS enzymes that produce them. A variety of Streptomyces strains that produce FK-506 are known in the art, including *S. tsukubaensis* No. 9993 (FERM BP-927), described in U.S. Pat. No. 5,624,852, incorporated herein by reference; *S. hygroscopicus* subsp. *yakushimaensis* No. 7238, described in U.S. Pat. No. 4,894,366, incorporated herein by reference; S. sp. MA6858 (ATCC 55098), described in U.S. Pat. No. 5,116,756, incorporated herein by reference; and S. sp. MA 6548, described in Motamedi et al., 1998, "The biosynthetic gene cluster for the macrolactone ring of the immunosuppressant FK-506," *Eur. J. Biochem.* 256: 528–534, and Motamedi et al., 1997, "Structural organization of a multifunctional polyketide synthase involved in the biosynthesis of the macrolide immunosuppressant FK-506," *Eur. J. Biochem.* 244: 74–80, each of which is incorporated herein by reference.

The complete sequence of the FK-506 gene cluster from Streptomyces sp. MA6548 is known, and the sequences of the corresponding gene clusters from other FK-506-producing organisms is highly homologous thereto. The novel FK-506 recombinant gene clusters of the present invention differ from the naturally occurring gene clusters in that the AT domain of module 8 of the naturally occurring PKSs is replaced by an AT domain specific for malonyl CoA or methylmalonyl CoA. These AT domain replacements are made at the DNA level, following the methodology described in Example 1.

The naturally occurring module 8 sequence for the MA6548 strain is shown below, followed by the illustrative hybrid module 8 sequences for the MA6548 strains (SEQ ID NOS:24–25).

```
GCATGCGGCTGTACGAGGCGGCACGGCGCACCGGAAGTCCCGTGGTGGTG    50
   M  R  L  Y  E  A  A  R  R  T  G  S  P  V  V  V

GCGGCCGCGCTCGACGACGCGCCGGACGTGCCGCTGCTGCGCGGGCTGCG   100
 A  A  A  L  D  D  A  P  D  V  P  L  L  R  C  L  R

GCGTACGACCGTCCGGCGTGCCGCCGTCCGGGAACGCTCTCTCGCCGACC   150
   R  T  T  V  R  R  A  A  V  R  E  R  S  L  A  D

GCTCGCCGTGCTGCCCGACGACGAGCGCGCCGACGCCTCCCTCGCGTTCG   200
 R  S  P  C  C  P  T  T  S  A  P  T  P  P  S  R  S

TCCTGGAACAGCACCGCCACCGTGCTCGGCCACCTGGGCGCCGAAGACAT   250
   S  W  N  S  T  A  T  V  L  G  H  L  G  A  E  D  I

CCCGGCGACGACGACGTTCAAGGAACTCGGCATCGACTCGCTCACCGCGG   300
    P  A  T  T  T  F  K  E  L  G  I  D  S  L  T  A

TCCAGCTGCGCAACGCGCTGACCACGGCGACCGGCGTACGCCTCAACGCC   350
 V  Q  L  R  N  A  L  T  T  A  T  G  V  R  L  N  A

ACAGCGGTCTTCGACTTTCCGACGCCGCGCGCGCTCGCCGCGAGACTCGG   400
    T  A  V  F  D  F  P  T  P  R  A  L  A  A  R  L  G

CGACGAGCTGGCCGGTACCCGCGCGCCCGTCGCGGCCCGGACCGCGGCCA   450
    D  E  L  A  G  T  R  A  P  V  A  A  R  T  A  A

CCGCGGCCGCGCACGACGAACCGCTGGCGATCGTGGGCATGGCCTGCCGT   500
 T  A  A  A  H  D  E  P  L  A  I  V  G  M  A  C  R

CTGCCGGGCGGGGTCGCGTCGCCACAGGAGCTGTGGCGTCTCGTCGCGTC   550
  L  P  G  G  V  A  S  P  Q  E  L  W  R  L  V  A  S

CGGCACCGACGCCATCACGGAGTTCCCCGCGGACCGCGGCTGGGACGTGG   600
    G  T  D  A  I  T  E  F  P  A  D  R  G  W  D  V

ACGCGCTCTACGACCCGGACCCCGACGCGATCGGCAAGACCTTCGTCCGG   650
 D  A  L  Y  D  P  D  P  D  A  I  G  K  T  F  V  R
```

-continued

```
CACGGCGGCTTCCTCGACGGTGCGACCGGCTTCGACGCGGCGTTCTTCGG    700
 H  G  G  F  L  D  G  A  T  G  F  D  A  A  F  F  G

GATCAGCCCGCGCGAGGCCCTGGCCATGGACCCGCAGCAACGGGTGCTCC    750
 I  S  P  R  E  A  L  A  M  D  P  Q  Q  R  V  L

TGGAGACGTCCTGGGAGGCGTTCGAAAGCGCGGGCATCACCCCGGACGCG    800
 L  E  T  S  W  E  A  F  E  S  A  G  I  T  P  D  A

GCGCGGGGCAGCGACACCGGCGTGTTCATCGGCGCGTTCTCCTACGGGTA    850
 A  R  G  S  D  T  G  V  F  I  G  A  F  S  Y  G  Y

CGGCACGGGTGCGGATACCAACGGCTTCGGCGCGACAGGGTCGCAGACCA    900
 G  T  G  A  D  T  N  G  F  G  A  T  G  S  Q  T

GCGTGCTCTCCGGCCGCCTCTCGTACTTCTACGGTCTGGAGGGCCCTTCG    950
 S  V  L  S  G  R  L  S  Y  F  Y  G  L  E  G  P  S

GTCACGGTCGACACCGCCTGCTCGTCGTCACTGGTCGCCCTGCACCAGGC    1000
 V  T  V  D  T  A  C  S  S  S  L  V  A  L  H  Q  A

AGGGCAGTCCCTGCGCTCGGGCGAATGCTCGCTCGCCCTGGTCGGCGGTG    1050
 G  Q  S  L  R  S  G  E  C  S  L  A  L  V  G  G

TCACGGTGATGGCGTCGCCCGGCGGATTCGTCGAGTTCTCCCGGCAGCGC    1100
 V  T  V  M  A  S  P  G  G  F  V  E  F  S  R  Q  R

GGGCTCGCGCCGGACGGGCGGGCGAAGGCGTTCGGCGCGGGCGCGGACGG    1150
 G  L  A  P  D  G  R  A  K  A  F  G  A  G  A  D  G

TACGAGCTTCGCCGAGGGCGCCGGTGCCCTGGTGGTCGAGCGGCTCTCCG    1200
 T  S  F  A  E  G  A  G  A  L  V  V  E  R  L  S

ACGCGGAGCGCCACGGCCACACCGTCCTCGCCCTCGTACGCGGCTCCGCG    1250
 D  A  E  R  H  G  H  T  V  L  A  L  V  R  G  S  A

GCTAACTCCGACGGCGCGTCGAACGGTCTGTCGGCGCCGAACGGCCCCTC    1300
 A  N  S  D  G  A  S  N  G  L  S  A  P  N  G  P  S

CCAGGAACGCGTCATCCACCAGGCCCTCGCGAACGCGAAACTCACCCCCG    1350
 Q  E  R  V  I  H  Q  A  L  A  N  A  K  L  T  P

CCGATGTCGACGCGGTCGAGGCGCACGGCACCGGCACCCGCCTCGGCGAC    1400
 A  D  V  D  A  V  E  A  H  G  T  G  T  R  L  G  D

CCCATCGAGGCGCAGGCGCTGCTCGCGACGTACGGACAGGACCGGGCGAC    1450
 P  I  E  A  Q  A  L  L  A  T  Y  G  Q  D  R  A  T

GCCCCTGCTGCTCGGCTCGCTGAAGTCGAACATCGGGCACGCCCAGGCCG    1500
 P  L  L  L  G  S  L  K  S  N  I  G  H  A  Q  A

CGTCAGGGGTCGCCGGGATCATCAAGATGGTGCAGGCCATCCGGCACGGG    1550
 A  S  G  V  A  G  I  I  K  M  V  Q  A  I  R  H  G

GAACTGCCGCCGACACTGCACGCGGACGAGCCGTCGCCGCACGTCGACTG    1600
 E  L  P  P  T  L  H  A  D  E  P  S  P  H  V  D  W

GACGGCCGGTGCCGTCGAGCTCCTGACGTCGGCCCGGCCGTGGCCGGGGA    1650
 T  A  G  A  V  E  L  L  T  S  A  R  P  W  P  G

CCGGTCGCCCGCGCCGCGCTGCCGTCTCGTCGTTCGGCGTGAGCGGCACG    1700
 T  G  R  P  R  R  A  A  V  S  S  F  G  V  S  G  T

AACGCCCACATCATCCTTGAGGCAGGACCGGTCAAAACGGGACCGGTCGA    1750
 N  A  H  I  I  L  E  A  G  P  V  K  T  G  P  V  E

GGCAGGAGCGATCGAGGCAGGACCGGTCGAAGTAGGACCGGTCGAGGCTG    1800
 A  G  A  I  E  A  G  P  V  E  V  G  P  V  E  A

GACCGCTCCCCGCGGCGCCGCCGTCAGCACCGGGCGAAGACCTTCCGCTG    1850
 G  P  L  P  A  A  P  P  S  A  P  G  E  D  L  P  L

CTCGTGTCGGCGCGTTCCCCGGAGGCACTCGACGAGCAGATCGGGCGCCT    1900
 L  V  S  A  R  S  P  E  A  L  D  E  Q  I  G  R  L

GCGCGCCTATCTCGACACCGGCCCGGGCGTCGACCGGGCGGCCGTGGCGC    1950
 R  A  Y  L  D  T  G  P  G  V  D  R  A  A  V  A
```

```
AGACACTGGCCCGGCGTACGCACTTCACCCACCGGGCCGTACTGCTCGGG    2000
 Q  T  L  A  R  R  T  H  F  T  H  R  A  V  L  L  G

GACACCGTCATCGGCGCTCCCCCCGCGGACCAGGCCGACGAACTCGTCTT    2050
 D  T  V  I  G  A  P  P  A  D  Q  A  D  E  L  V  F

CGTCTACTCCGGTCAGGGCACCCAGCATCCCGCGATGGGCGAGCAACTCG    2100
  V  Y  S  G  Q  G  T  Q  H  P  A  M  G  E  Q  L

CGGCCGCGTTCCCCGTGTTCGCCGATGCCTGGCACGACGCGCTCCGACGG    2150
 A  A  A  F  P  V  F  A  D  A  W  H  D  A  L  R  R

CTCGACGACCCCGACCCGCACGACCCCACACGGAGCCAGCACACGCTCTT    2200
 L  D  D  P  D  P  H  D  P  T  R  S  Q  H  T  L  F

CGCCCACCAGGCGGCGTTCACCGCCCTCCTGAGGTCCTGGGACATCACGC    2250
  A  H  Q  A  A  F  T  A  L  L  R  S  W  D  I  T

CGCACGCCGTCATCGGCCACTCGCTCGGCGAGATCACCGCCGCGTACGCC    2300
 P  H  A  V  I  G  H  S  L  G  E  I  T  A  A  Y  A

GGCGGGATCCTGTCGCTCGACGACGCCTGCACCCTGATCACCACGCGTGC    2350
  A  G  I  L  S  L  D  D  A  C  T  L  I  T  T  R  A

CCGCCTCATGCACACGCTTCCGCCGCCCGGCGCCATGGTCACCGTGCTGA    2400
  R  L  M  H  T  L  P  P  P  G  A  M  V  T  V  L

CCAGCGAGGAGGAGGCCCGTCAGGCGCTGCGGCCGGGCGTGGAGATCGCC    2450
 T  S  E  E  E  A  R  Q  A  L  R  P  G  V  E  I  A

GCGGTCTTCGGCCCGCACTCCGTCGTGCTCTCGGGCGACGAGGACGCCGT    2500
 A  V  F  G  P  H  S  V  V  L  S  G  D  E  D  A  V

GCTCGACGTCGCACAGCGGCTCGGCATCCACCACCGTCTGCCCGCGCCGC    2550
  L  D  V  A  Q  R  L  G  I  H  H  R  L  P  A  P

ACGCGGGCCACTCCGCGCACATGGAACCCGTGGCCGCCGAGCTGCTCGCC    2600
 H  A  G  H  S  A  H  M  E  P  V  A  A  E  L  L  A

ACCACTCGCGAGCTCCGTTACGACCGGCCCCACACCGCCATCCCGAACGA    2650
  T  T  R  E  L  R  Y  D  R  P  H  T  A  I  P  N  D

CCCCACCACCGCCGAGTACTGGGCCGAGCAGGTCCGCAACCCCGTGCTGT    2700
  P  T  T  A  E  Y  W  A  E  Q  V  R  N  P  V  L

TCCACGCCCACACCCAGCGGTACCCCGACGCCGTGTTCGTCGAGATCGGC    2750
 F  H  A  H  T  Q  R  Y  P  D  A  V  F  V  E  I  G

CCCGGCCAGGACCTCTCACCGCTGGTCGACGGCATCGCCCTGCAGAACGG    2800
  P  G  Q  D  L  S  P  L  V  D  G  I  A  L  Q  N  G

CACGGCGGACGAGGTGCACGCGCTGCACACCGCGCTCGCCCGCCTCTTCA    2850
  T  A  D  E  V  H  A  L  H  T  A  L  A  R  L  F

CACGCGGCGCCACGCTCGACTGGTCCCGCATCCTCGGCGGTGCTTCGCGG    2900
 T  R  G  A  T  L  D  W  S  R  I  L  G  G  A  S  R

CACGACCCTGACGTCCCCTCGTACGCGTTCCAGCGGCGTCCCTACTGGAT    2950
  H  D  P  D  V  P  S  Y  A  F  Q  R  R  P  Y  W  I

CGAGTCGGCTCCCCCGGCCACGGCCGACTCGGGCCACCCCGTCCTCGGCA    3000
  E  S  A  P  P  A  T  A  D  S  G  H  P  V  L  G

CCGGAGTCGCCGTCGCCGGGTCGCCGGGCCGGGTGTTCACGGGTCCCGTG    3050
 T  G  V  A  V  A  G  S  P  G  R  V  F  T  G  P  V

CCCGCCGGTGCGGACCGCGCGGTGTTCATCGCCGAACTGGCGCTCGCCGC    3100
  P  A  G  A  D  R  A  V  F  I  A  E  L  A  L  A  A

CGCCGACGCCACCGACTGCGCCACGGTCGAACAGCTCGACGTCACCTCCG    3150
  A  D  A  T  D  C  A  T  V  E  Q  L  D  V  T  S

TGCCCGGCGGATCCGCCCGCGGCAGGGCCACCGCGCAGACCTGGGTCGAT    3200
 V  P  G  G  S  A  R  G  R  A  T  A  Q  T  W  V  D

GAACCCGCCGCCGACGGGCGGCGCCGCTTCACCGTCCACACCCGCGTCGG    3250
  E  P  A  A  D  G  R  R  R  F  T  V  H  T  R  V  G
```

-continued

```
CGACGCCCCGTGGACGCTGCACGCCGAGGGGTTCTCCGCCCCGGCCGCG     3300
  D  A  P  W  T  L  H  A  E  G  V  L  R  P  G  R

TGCCCCAGCCCGAAGCCGTCGACACCGCTGGCCCCCGCCGGGCGCGGTG     3350
 V  P  Q  P  E  A  V  D  T  A  W  P  P  P  G  A  V

CCCGCGGACGGGCTGCCCGGGGCGTGGCGACGCGCGGACCAGGTCTTCGT    3400
 P  A  D  G  L  P  G  A  W  R  R  A  D  Q  V  F  V

CGAAGCCGAAGTCGACAGCCCTGACGGCTTCGTGGCACACCCCGACCTGC    3450
  E  A  E  V  D  S  P  D  G  F  V  A  H  P  D  L

TCGACGCGGTCTTCTCCGCGGTCGGCGACGGGAGCCGCCAGCCGACCGGA    3500
  L  D  A  V  F  S  A  V  G  D  G  S  R  Q  P  T  G

TGGCGCGACCTCGCGGTGCACGCGTCGGACGCCACCGTGCTGCGCGCCTG    3550
  W  R  D  L  A  V  H  A  S  D  A  T  V  L  R  A  C

CCTCACCCGCCGCGACAGTGGTGTCGTGGAGCTCGCCGCCTTCGACGGTG    3600
  L  T  R  R  D  S  G  V  V  E  L  A  A  F  D  G

CCGGAATGCCGGTGCTCACCGCGGAGTCGGTGACGCTGGGCGAGGTCGCG    3650
 A  G  M  P  V  L  T  A  E  S  V  T  L  G  E  V  A

TCGGCAGGCGGATCCGACGAGTCGGACGGTCTGCTTCGGCTTGAGTGGTT    3700
  S  A  G  G  S  D  E  S  D  G  L  L  R  L  E  W  L

GCCGGTGGCGGAGGCCCACTACGACGGTGCCGACGAGCTGCCCGAGGGCT    3750
  P  V  A  E  A  H  Y  D  G  A  D  E  L  P  E  G

ACACCCTCATCACCGCCACACACCCCGACGACCCCGACGACCCCACCAAC    3800
 Y  T  L  I  T  A  T  H  P  D  D  P  D  D  P  T  N

CCCCACAACACACCCACACGCACCCACACACAAACCACACGCGTCCTCAC    3850
 P  H  N  T  P  T  R  T  H  T  Q  T  T  R  V  L  T

CGCCCTCCAACACCACCTCATCACCACCAACCACACCCTCATCGTCCACA    3900
  A  L  Q  H  H  L  I  T  T  N  H  T  L  I  V  H

CCACCACCGACCCCCCAGGCGCCGCCGTCACCGGCCTCACCCGCACCGCA    3950
 T  T  T  D  P  P  G  A  A  V  T  G  L  T  R  T  A

CAAAACGAACACCCCGGCCGCATCCACCTCATCGAAACCCACCACCCCCA    4000
  Q  N  E  H  P  G  R  I  H  L  I  E  T  H  H  P  H

CACCCCACTCCCCCTCACCCAACTCACCACCCTCCACCAACCCCACCTAC    4050
  T  P  L  P  L  T  Q  L  T  T  L  H  Q  P  H  L

GCCTCACCAACAACACCCTCCACACCCCCCACCTCACCCCCATCACCACC    4100
 R  L  T  N  N  T  L  H  T  P  H  L  T  P  I  T  T

CACCACAACACCACCACAACCACCCCCAACACCCCACCCCTCAACCCCAA    4150
  H  H  N  T  T  T  T  T  P  N  T  P  P  L  N  P  N

CCACGCCATCCTCATCACCGGCGGCTCCGGCACCCTCGCCGGCATCCTCG    4200
  H  A  I  L  I  T  G  G  S  G  T  L  A  G  I  L

CCCGCCACCTCAACCACCCCCACACCTACCTCCTCTCCCGCACACCACCA    4250
 A  R  H  L  N  H  P  H  T  Y  L  L  S  R  T  P  P

CCCCCCACCACACCCGGCACCCACATCCCCTGCGACCTCACCGACCCCAC    4300
  P  P  T  T  P  G  T  H  I  P  C  D  L  T  D  P  T

CCAAATCACCCAAGCCCTCACCCACATACCACAACCCCTCACCGGCATCT    4350
   Q  I  T  Q  A  L  T  H  I  P  Q  P  L  T  G  I

TCCACACCGCCGCCACCCTCGACGACGCCACCCTCACCAACCTCACCCCC    4400
 F  H  T  A  A  T  L  D  D  A  T  L  T  N  L  T  P

CAACACCTCACCACCACCCTCCAACCCAAAGCCGACGCCGCCTGGCACCT    4450
  Q  H  L  T  T  T  L  Q  P  K  A  D  A  A  W  H  L

CCACCACCACACCCAAAACCAACCCCTCACCCACTTCGTCCTCTACTCCA    4500
  H  H  H  T  Q  N  Q  P  L  T  H  F  V  L  Y  S

GCGCCGCCGCCACCCTCGGCAGCCCCGGCCAAGCCAACTACGCCGCCGCC    4550
 S  A  A  A  T  L  G  S  P  G  Q  A  N  Y  A  A  A
```

-continued

```
AACGCCTTCCTCGACGCCCTCGCCACCCACCGCCACACCCAAGGACAACC    4600
 N  A  F  L  D  A  L  A  T  H  R  H  T  Q  G  Q  P

CGCCACCACCATCGCCTGGGGCATGTGGCACACCACCACCACACTCACCA    4650
 A  T  T  I  A  W  G  M  W  H  T  T  T  T  L  T

GCCAACTCACCGACAGCGACCGCGACCGCATCCGCCGCGGCGGCTTCCTG    4700
 S  Q  L  T  D  S  D  R  D  R  I  R  R  G  G  F  L

CCGATCTCGGACGACGAGGGCATGC
 P  I  S  D  D  E  G  M
```

AvrII-AlzoI hybrid FK-506 PKS module 8 containing the AT domain of module 12 of rapamycin is shown below (SEQ ID NOS:26–27).

```
GCATGCGGCTGTACGAGGCGGCACGGCGCACCGGAAGTCCCGTGGTGGTG    50
    M  R  L  Y  E  A  A  R  R  T  G  S  P  V  V  V

GCGGCCGCGCTCGACGACGCGCCGGACGTGCCGCTGCTGCGCGGGCTGCG    100
 A  A  A  L  D  D  A  P  D  V  P  L  L  R  G  L  R

GCGTACGACCGTCCGGCGTGCCGCCGTCCGGGAACGCTCTCTCGCCGACC    150
    R  T  T  V  R  R  A  A  V  R  E  R  S  L  A  D

GCTCGCCGTGCTGCCCGACGACGAGCGCGCCGACGCCTCCCTCGCGTTCG    200
 R  S  P  C  C  P  T  T  S  A  P  T  P  P  S  R  S

TCCTGGAACAGCACCGCCACCGTGCTCGGCCACCTGGGCGCCGAAGACAT    250
 S  W  N  S  T  A  T  V  L  G  H  L  G  A  E  D  I

CCCGGCGACGACGACGTTCAAGGAACTCGGCATCGACTCGCTCACCGCGG    300
    P  A  T  T  T  F  K  E  L  G  I  D  S  L  T  A

TCCAGCTGCGCAACGCGCTGACCACGGCGACCGGCGTACGCCTCAACGCC    350
 V  Q  L  R  N  A  L  T  T  A  T  G  V  R  L  N  A

ACAGCGGTCTTCGACTTTCCGACGCCGCGCGCGCTCGCCGCGAGACTCGG    400
    T  A  V  F  D  F  P  T  P  R  A  L  A  A  R  L  G

CGACGAGCTGGCCGGTACCCGCGCGCCCGTCGCGGCCCGGACCGCGGCCA    450
    D  E  L  A  G  T  R  A  P  V  A  A  R  T  A  A

CCGCGGCCGCGCACGACGAACCGCTGGCGATCGTGGGCATGGCCTGCCGT    500
 T  A  A  A  H  D  E  P  L  A  I  V  G  M  A  C  R

CTGCCGGGCGGGGTCGCGTCGCCACAGGAGCTGTGGCGTCTCGTCGCGTC    550
 L  P  G  G  V  A  S  P  Q  E  L  W  R  L  V  A  S

CGGCACCGACGCCATCACGGAGTTCCCCGCGGACCGCGGCTGGGACGTGG    600
    G  T  D  A  I  T  E  F  P  A  D  R  G  W  D  V

ACGCGCTCTACGACCCGGACCCCGACGCGATCGGCAAGACCTTCGTCCGG    650
 D  A  L  Y  D  P  D  P  D  A  I  G  K  T  F  V  R

CACGGCGGCTTCCTCGACGGTGCGACCGGCTTCGACGCGGCGTTCTTCGG    700
 H  G  D  F  L  D  G  A  T  G  F  D  A  A  F  F  G

GATCAGCCCGCGCGAGGCCCTGGCCATGGACCCGCAGCAACGGGTGCTCC    750
    I  S  P  R  E  A  L  A  M  D  P  Q  Q  R  V  L

TGGAGACGTCCTGGGAGGCGTTCGAAAGCGCGGGCATCACCCCGGACGCG    800
 L  E  T  S  W  E  A  F  E  S  A  G  I  T  P  D  A

GCGCGGGGCAGCGACACCGGCGTGTTCATCGGCGCGTTCTCCTACGGGTA    850
 A  R  G  S  D  T  G  V  F  T  G  A  F  S  Y  G  Y

CGGCACGGGTGCGGATACCAACGGCTTCGGCGCGACAGGGTCGCAGACCA    900
    G  T  G  A  D  T  N  G  F  G  A  T  G  S  Q  T

GCGTGCTCTCCGGCCGCCTCTCGTACTTCTACGGTCTGGAGGGCCCTTCG    950
 S  V  L  S  G  R  L  S  Y  F  Y  G  L  E  G  P  S

GTCACGGTCGACACCGCCTGCTCGTCGTCACTGGTCGCCCTGCACCAGGC    1000
    V  T  V  D  T  A  C  S  S  S  L  V  A  L  H  Q  A
```

-continued

```
AGGGCAGTCCCTGCGCTCGGGCGAATGCTCGCTCGCCCTGGTCGGCGGTG        1050
  G  Q  S  L  R  S  G  E  C  S  L  A  L  V  G  G

TCACGGTGATGGCGTCGCCCGGCCGATTCGTCGAGTTCTCCCGGCAGCGC        1100
  V  T  V  M  A  S  P  G  G  F  V  E  F  S  R  Q  R

GGGCTCGCGCCGGACGGGCGGGCGAAGGCGTTCGGCGCGGGCGCGGACGG        1150
  G  L  A  P  D  G  R  A  K  A  F  G  A  G  A  D  G

TACGAGCTTCGCCGAGGGCGCCGGTGCCCTGGTGGTCGAGCGGCTCTCCG        1200
  T  S  F  A  E  G  A  G  A  L  V  V  E  R  L  S

ACGCGGAGCGCCACGGCCACACCGTCCTCGCCCTCGTACGCGGCTCCGCG        1250
  D  A  E  R  H  G  H  T  V  L  A  L  V  R  G  S  A

GCTAACTCCGACGGCGCGTCGAACGGTCTGTCGGCGCCGAACGGCCCCTC        1300
  A  N  S  D  G  A  S  N  G  L  S  A  P  N  G  P  S

CCAGGAACGCGTCATCCACCAGGCCCTCGCGAACGCGAAACTCACCCCCG        1350
  Q  E  R  V  I  H  Q  A  L  A  N  A  K  L  T  P

CCGATCTCGACGCGGTCGAGGCGCACGGCACCGGCACCCGCCTCGGCGAC        1400
  A  D  V  D  A  V  E  A  H  G  T  G  T  R  L  G  D

CCCATCGAGGCGCAGGCGCTGCTCGCGACGTACGGACAGGACCGGGCGAC        1450
  P  I  E  A  Q  A  L  L  A  T  Y  G  Q  D  R  A  T

GCCCCTGCTGCTCGGCTCGCTGAAGTCGAACATCGGGCACGCCCAGGCCG        1500
  P  L  L  L  G  S  L  K  S  N  I  G  H  A  Q  A

CGTCAGGGGTCGCCGGGATCATCAAGATGGTGCAGGCCATCCGGCACGGG        1550
  A  S  G  V  A  G  I  I  K  M  V  Q  A  I  R  H  G

GAACTGCCGCCGACACTGCACGCGGACGAGCCGTCGCCGCACGTCGACTG        1600
  E  L  P  P  T  L  H  A  D  E  P  S  P  H  V  D  W

GACGGCCGGTGCCGTCGAGCTCCTGACGTCGGCCCGGCCGTGGCCGGGGA        1650
  T  A  G  A  V  E  L  L  T  S  A  R  P  W  P  G

CCGGTCGCCCTAGGCGGGCAGGCGTGTCGTCCTTCGGGATCAGTGGCACC        1700
  T  G  R  P  R  R  A  G  V  S  S  F  G  I  S  G  T

AACGCCCACGTCATCCTGGAAAGCGCACCCCCCACTCAGCCTGCGGACAA        1750
  N  A  H  V  I  L  E  S  A  P  P  T  Q  P  A  D  N

CGCGGTGATCGAGCGGGCACCGGAGTGGGTGCCGTTGGTGATTTCGGCCA        1800
  A  V  I  E  R  A  P  E  W  V  P  L  V  I  S  A

GGACCCAGTCGGCTTTGACTGAGCACGAGGGCCGGTTGCGTGCGTATCTG        1850
  R  T  Q  S  A  L  T  E  H  E  G  R  L  R  A  Y  L

GCGGCGTCGCCCGGGGTGGATATGCGGGCTGTGGCATCGACGCTGGCGAT        1900
  A  A  S  P  G  V  D  M  R  A  V  A  S  T  L  A  M

GACACGGTCGCTGTTCGAGCACCGTGCCGTGCTGCTGGGAGATGACACCG        1950
  T  R  S  V  F  E  H  R  A  V  L  L  G  D  D  T

TCACCGGCACCGCTGTGTCTGACCCTCGGGCGGTGTTCGTCTTCCCGGGA        2000
  V  T  G  T  A  V  S  D  P  R  A  V  F  V  F  P  G

CAGGGGTCGCAGCGTGCTGGCATGGGTGAGGAACTGGCCGCCGCGTTCCC        2050
  Q  G  S  Q  R  A  G  M  G  E  E  L  A  A  A  F  P

CGTCTTCGCGCGGATCCATCAGCAGGTGTGGGACCTGCTCGATGTGCCCG        2100
  V  F  A  R  I  H  Q  Q  V  W  D  L  L  D  V  P

ATCTGGAGGTGAACGAGACCGGTTACGCCCAGCCGGCCCTGTTCGCAATG        2150
  D  L  E  V  N  E  T  G  Y  A  Q  P  A  L  F  A  M

CAGGTGGCTCTGTTCGGGCTGCTGGAATCGTGGGGTGTACGACCGGACGC        2200
  Q  V  A  L  F  G  L  L  E  S  W  G  V  R  P  D  A

GGTGATCGGCCATTCGGTGGGTGAGCTTGCGGCTGCGTATGTGTCCGGG         2250
  V  I  G  H  S  V  G  E  L  A  A  A  Y  V  S  G

TGTGGTCGTTGGAGGATGCCTGCACTTTGGTGTCGGCGCGGGCTCGTCTG        2300
  V  W  S  L  E  D  A  C  T  L  V  S  A  R  A  R  L

ATGCAGGCTCTGCCCGCGGGTGGGGTGATGGTCGCTGTCCCGGTCTCGGA        2350
  M  Q  A  L  P  A  G  G  V  M  V  A  V  P  V  S  E
```

-continued

```
GGATGAGGCCCGGGCCGTGCTGGGTGAGGGTGTGGAGATCGCCGCGGTCA      2400
  D  E  A  R  A  V  L  G  E  D  V  E  T  A  A  V

ACGGCCCGTCGTCGGTGGTTCTCTCCGGTGATGAGGCCGCCGTGCTGCAG      2450
 N  G  P  S  S  V  V  L  S  G  D  E  A  A  V  L  Q

GCCGCGGAGGGGCTGGGGAAGTGGACGCGGCTGGCGACCAGCCACGCGTT      2500
  A  A  E  G  L  G  K  W  T  R  L  A  T  S  H  A  F

CCATTCCGCCCGTATGGAACCCATGCTGGAGGAGTTCCGGGCGGTCGCCG      2550
   H  S  A  R  M  E  P  M  L  E  E  F  R  A  V  A

AAGGCCTGACCTACCGGACGCCGCAGGTCTCCATGGCCGTTGGTGATCAG      2600
 E  G  L  T  Y  R  T  P  Q  V  S  M  A  V  G  D  Q

GTGACCACCGCTGAGTACTGGGTGCGGCAGGTCCGGGACACGGTCCGGTT      2650
  V  T  T  A  E  Y  W  V  R  Q  V  R  D  T  V  R  F

CGGCGAGCAGGTGGCCTCGTACGAGGACGCCGTGTTCGTCGAGCTGGGTG      2700
   G  E  Q  V  A  S  Y  E  D  A  V  F  V  E  L  G

CCGACCGGTCACTGGCCCGCCTGGTCGACGGTGTCGCGATGCTGCACGGC      2750
  A  D  R  S  L  A  R  L  V  D  G  V  A  M  L  H  G

GACCACGAAATCCAGGCCGCGATCGGCGCCCTGGCCCACCTGTATGTCAA      2800
  D  H  E  I  Q  A  A  I  G  A  L  A  H  L  Y  V  N

CGGCGTCACGGTCGACTGGCCCGCGCTCCTGGGCGATGCTCCGGCAACAC      2850
   G  V  T  V  D  W  P  A  L  L  G  D  A  P  A  T

GGGTGCTGGACCTTCCGACATACGCCTTCCAGCACCAGCGCTACTGGCTC      2900
 R  V  L  D  L  P  T  Y  A  F  Q  H  Q  R  Y  W  L

GAGTCGGCTCCCCCGGCCACGGCCGACTCGGGCCACCCCGTCCTCGGCAC      2950
  E  S  A  P  P  A  T  A  D  S  G  H  P  V  L  G  T

CGGAGTCGCCGTCGCCGGGTCGCCGGGCCGGGTGTTCACGGGTCCCGTGC      3000
   G  V  A  V  A  G  S  P  G  R  V  F  T  G  P  V

CCGCCGGTGCGGACCGCGCGGTGTTCATCGCCGAACTGGCGCTCGCCGCC      3050
  P  A  G  A  D  R  A  V  F  I  A  E  L  A  L  A  A

GCCGACGCCACCGACTGCGCCACGGTCGAACAGCTCGACGTCACCTCCGT      3100
  A  D  A  T  D  C  A  T  V  E  Q  L  D  V  T  S  V

GCCCGGCGGATCCGCCCGCGGCAGGGCCACCGCGCAGACCTGGGTCGATG      3150
   P  G  G  S  A  R  G  R  A  T  A  Q  T  W  V  D

AACCCGCCGCCGACGGGCGGCGCCGCTTCACCGTCCACACCCGCGTCGGC      3200
 E  P  A  A  D  G  R  R  R  F  T  V  H  T  R  V  G

GACGCCCCGTGGACGCTGCACGCCGAGGGGGTTCTCCGCCCCGGCCGCGT      3250
  D  A  P  W  T  L  H  A  E  G  V  L  R  P  G  R  V

GCCCCAGCCCGAAGCCGTCGACACCGCCTGGCCCCCGCCGGGCGCGGTGC      3300
   P  Q  P  E  A  V  D  T  A  W  P  P  P  G  A  V

CCGCGGACGGGCTGCCCGGGGCGTGGCGACGCGCGGACCAGGTCTTCGTC      3350
  P  A  D  G  L  P  G  A  W  R  R  A  D  Q  V  F  V

GAAGCCGAAGTCGACAGCCCTGACGGCTTCGTGGCACACCCCGACCTGCT      3400
  E  A  E  V  D  S  P  D  G  F  V  A  H  P  D  L  L

CGACGCGGTCTTCTCCGCGGTCGGCGACGGGAGCCGCCAGCCGACCGGAT      3450
   D  A  V  F  S  A  V  G  D  G  S  R  Q  P  T  G

GGCGCGACCTCGCGGTGCACGCGTCGGACGCCACCGTGCTGCGCGCCTGC      3500
 W  R  D  L  A  V  H  A  S  D  A  T  V  L  R  A  C

CTCACCCGCCGCGACAGTGGTGTCGTGGAGCTCGCCGCCTTCGACGGTGC      3550
   L  T  R  R  D  S  G  V  V  S  L  A  A  F  D  G  A

CGGAATGCCGGTGCTCACCGCGGAGTCGGTGACGCTGGGCGAGGTCGCGT      3600
   G  M  P  V  L  T  A  E  S  V  T  L  G  S  V  A

CGGCAGGCGGATCCGACGAGTCGGACGGTCTGCTTCGGCTTGAGTGGTTG      3650
 S  A  G  G  S  D  E  S  D  G  L  L  R  L  E  W  L
```

```
CCGGTGGCGGAGGCCCACTACGACGGTGCCGACGAGCTGCCCGAGGGCTA       3700
 P  V  A  E  A  H  Y  D  G  A  D  E  L  P  E  G  Y

CACCCTCATCACCGCCACACACCCCGACGACCCCGACGACCCCACCAACC       3750
 T  L  I  T  A  T  H  P  D  D  P  D  D  P  T  N

CCCACAACACACCCACACGCACCCACACACAAACCACACGCGTCCTCACC       3800
 P  H  N  T  P  T  R  T  H  T  Q  T  T  R  V  L  T

GCCCTCCAACACCACCTCATCACCACCAACCACACCCTCATCGTCCACAC       3850
 A  L  Q  H  H  L  I  T  T  N  H  T  L  I  V  H  T

CACCACCGACCCCCAGGCGCCGCCGTCACCGGCCTCACCCGCACCGCAC        3900
 T  T  D  P  P  G  A  A  V  T  G  L  T  R  T  A

AAAACGAACACCCCGGCCGCATCCACCTCATCGAAACCCACCACCCCCAC       3950
 Q  N  E  H  P  G  R  I  H  L  I  E  T  H  H  P  H

ACCCCACTCCCCCTCACCCAACTCACCACCCTCCACCAACCCCACCTACG       4000
 T  P  L  P  L  T  Q  L  T  T  L  H  Q  P  H  L  R

CCTCACCAACAACACCCTCCACACCCCCCACCTCACCCCCATCACCACCC       4050
 L  T  N  N  T  L  H  T  P  H  L  T  P  I  T  T

ACCACCACACCACCACAACCACCCCCAACACCCCACCCGTCAACCCCAAC       4100
 H  H  N  T  T  T  T  P  N  T  P  P  L  N  P  N

CACGCCATCCTCATCACCGGCGGCTCCGGCACCCTCGCCGGCATCCTCGC       4150
 H  A  I  L  I  T  G  G  S  G  T  L  A  G  I  L  A

CCGCCACCTCAACCACCCCCACACCTACCTCCTCTCCCGCACACCACCAC       4200
 R  H  L  N  H  P  H  T  Y  L  L  S  R  T  P  P

CCCCCACCACACCCGGCACCCACATCCCCTGCGACCTCACCGACCCCACC       4250
 P  P  T  T  P  G  T  H  I  P  C  D  L  T  D  P  T

CAAATCACCCAAGCCCTCACCCACATACCACAACCCCTCACCGGCATCTT       4300
 Q  I  T  Q  A  L  T  H  I  P  Q  P  L  T  G  I  F

CCACACCGCCGCCACCCTCGACGACGCCACCCTCACCAACCTCACCCCCC       4350
 H  T  A  A  T  L  D  D  A  T  L  T  N  L  T  P

AACACCTCACCACCACCCTCCAACCCAAAGCCGACGCCGCCTGGCACCTC       4400
 Q  H  L  T  T  T  L  Q  P  K  A  D  A  A  W  H  L

CACCACCACACCCAAAACCAACCCCTCACCCACTTCGTCCTCTACTCCAG       4450
 H  H  H  T  Q  N  Q  P  L  T  H  F  V  L  Y  S  S

CGCCGCCGCCACCCTCGGCAGCCCCGGCCAAGCCAACTACGCCGCCGCCA       4500
 A  A  A  T  L  G  S  P  G  Q  A  N  Y  A  A  A

ACGCCTTCCTCGACGCCCTCGCCACCCACCGCCACACCCAAGGACAACCC       4550
 N  A  F  L  D  A  L  A  T  H  R  H  T  Q  G  Q  P

GCCACCACCATCGCCTGGGGCATGTGGCACACCACCACCACACTCACCAG       4600
 A  T  T  I  A  W  G  M  W  H  T  T  T  L  T  S

CCAACTCACCGACAGCGACCGCGACCGCATCCGCCGCGGCGGCTTCCTGC       4650
 Q  L  T  D  S  D  R  D  R  I  R  R  G  G  F  L

CGATCTCGGACGACGAGGGCATGC
 P  I  S  D  D  E  G  M
```

The AvrII-XhoI hybrid FK-506 PKS module 8 containing the AT domain of module 13 of rapamycin is shown below (SEQ ID NOS:28–29).

```
GCATGCGGCTGTACGAGGCGGCACGGCGCACCGGAAGTCCCGTGGTGGTG       50
   M  R  L  Y  E  A  A  R  R  T  G  S  P  V  V  V

GCGGCCGCGCTCGACGACGCGCCGGACGTGCCGCTGCTGCGCGGGCTGCG       100
 A  A  A  L  D  D  A  P  D  V  P  L  L  R  G  L  R

GCGTACGACCGTCCGGCGTGCCGCCGTCCGGGAACGCTCTCTCGCCGACC       150
   R  T  T  V  R  R  A  A  V  R  E  R  S  L  A  D
```

-continued

```
GCTCGCCGTGCTGCCCGACGACGAGCGCGCCGACGCCTCCCTCGCGTTCG      200
 R   S   P   C   C   P   T   T   S   A   P   T   P   P   S   R   S

TCCTGGAACAGCACCGCCACCGTGCTCGGCCACCTGGGCGCCGAAGACAT      250
 S   W   N   S   T   A   T   V   L   G   H   L   G   A   E   D   I

CCCGGCGACGACGACGTTCAAGGAACTCGGCATCGACTCGCTCACCGCGG      300
  P   A   T   T   T   F   K   E   L   G   I   D   S   L   T   A

TCCAGCTGCGCAACGCGCTGACCACGGCGACCGGCGTACGCCTCAACGCC      350
 V   Q   L   R   N   A   L   T   T   A   T   G   V   R   L   N   A

ACAGCGGTCTTCGACTTTCCGACGCCGCGCGCGCTCGCCGCGAGACTCGG      400
  T   A   V   F   D   F   P   T   P   R   A   L   A   A   R   L   G

CGACGAGCTGGCCGGTACCCGCGCGCCCGTCGCGGCCCGGACCGCGGCCA      450
  D   E   L   A   G   T   R   A   P   V   A   A   R   T   A   A

CCGCGGCCGCGCACGACGAACCGCTGGCGATCGTGGGCATGGCCTGCCGT      500
 T   A   A   A   H   D   E   P   L   A   I   V   G   M   A   C   R

CTGCCGGGCGGGGTCGCGTCGCCACAGGAGCTGTGGCGTCTCGTCGCGTC      550
  L   P   G   G   V   A   S   P   Q   E   L   W   H   L   V   A   S

CGGCACCGACGCCATCACGGAGTTCCCCGCGGACCGCGGCTGGGACGTGG      600
   G   T   D   A   I   T   E   F   P   A   D   R   G   W   D   V

ACGCGCTCTACGACCCGGACCCCGACGCGATCGGCAAGACCTTCGTCCGG      650
 D   A   L   Y   D   P   D   P   D   A   I   G   K   T   F   V   R

CACGGCGGCTTCCTCGACGGTGCGACCGGCTTCGACGCGGCGTTCTTCGG      700
 H   G   G   F   L   D   G   A   T   G   F   D   A   A   F   F   G

GATCAGCCCGCGCGAGGCCCTGGCCATGGACCCGCAGCAACGGGTGCTCC      750
  I   S   P   R   E   A   L   A   M   D   P   Q   Q   R   V   L

TGGAGACGTCCTGGGAGGCGTTCGAAAGCGCGGGCATCACCCCGGACGCG      800
 L   E   T   S   W   E   A   F   E   S   A   G   I   T   P   D   A

GCGCGGGGCAGCGACACCGGCGTGTTCATCGGCGCGTTCTCCTACGGGTA      850
  A   R   G   S   D   T   G   V   F   I   G   A   F   S   Y   G   Y

CGGCACGGGTGCGGATACCAACGGCTTCGGCGCGACAGGGTCGCAGACCA      900
   G   T   G   A   D   T   N   G   F   G   A   T   G   S   Q   T

GCGTGCTCTCCGGCCGCCTCTCGTACTTCTACGGTCTGGAGGGCCCTTCG      950
  S   V   L   S   G   H   L   S   Y   F   Y   G   L   E   G   P   S

GTCACGGTCGACACCGCCTGCTCGTCGTCACTGGTCGCCCTGCACCAGGC      1000
  V   T   V   D   T   A   C   S   S   S   L   V   A   L   H   Q   A

AGGGCAGTCCCTGCGCTCGGGCGAATGCTCGCTCGCCCTGGTCGGCGGTG      1050
   G   Q   S   L   H   S   G   E   C   S   L   A   L   V   G   G

TCACGGTGATGGCGTCGCCCGGCGGATTCGTCGAGTTCTCCCGGCAGCGC      1100
  V   T   V   M   A   S   P   G   G   F   V   E   F   S   R   Q   R

GGGCTCGCGCCGGACGGGCGGGCGAAGGCGTTCGGCGCGGGCGCGGACGG      1150
   G   L   A   P   D   G   R   A   K   A   F   G   A   G   A   D   G

TACGAGCTTCGCCGAGGGCGCCGGTGCCCTGGTGGTCGAGCGGCTCTCCG      1200
  T   S   F   A   H   G   A   G   A   L   V   V   H   H   L   S

ACGCGGAGCGCCACGGCCACACCGTCCTCGCCCTCGTACGCGGCTCCGCG      1250
 D   A   E   R   H   G   H   T   V   L   A   L   V   R   G   S   A

GCTAACTCCGACGGCGCGTCGAACGGTCTGTCGGCGCCGAACGGCCCCTC      1300
 A   N   S   D   G   A   S   N   G   L   S   A   P   N   G   P   S

CCAGGAACGCGTCATCCACCAGGCCCTCGCGAACGCGAAACTCACCCCCG      1350
  Q   E   R   V   T   H   Q   A   L   A   N   A   K   L   T   P

CCGATGTCGACGCGGTCGAGGCGCACGGCACCGGCACCCGCCTCGGCGAC      1400
  A   D   V   D   A   V   E   A   H   G   T   G   T   R   L   G   D

CCCATCGAGGCGCAGGCGCTGCTCGCGACGTACGGACAGGACCGGGCGAC      1450
  P   I   E   A   Q   A   L   L   A   T   Y   G   Q   D   R   A   T
```

```
GCCCCTGCTGCTCGGCTCGCTGAAGTCGAACATCGGGCACGCCCAGGCCG    1500
  P  L  L  L  G  S  L  K  S  N  I  G  H  A  Q  A

CGTCAGGGGTCGCCGGGATCATCAAGATGGTGCAGGCCATCCGGCACGGG    1550
A  S  C  V  A  G  I  I  K  M  V  Q  A  I  R  H  G

GAACTGCCGCCGACACTGCACGCGGACGAGCCGTCGCCGCACGTCGACTG    1600
 E  L  P  P  T  L  H  A  D  E  P  S  P  H  V  D  W

GACGGCCGGTGCCGTCGAGCTCCTGACGTCGGCCCGGCCGTGGCCGGGGA    1650
  T  A  G  A  V  E  L  L  T  S  A  R  P  W  P  G

CCGGTCGCCCTAGGCGGGCGGGCGTGTCGTCCTTCGGAGTCAGCGGCACC    1700
T  G  R  P  R  R  A  G  V  S  S  F  G  V  S  G  T

AACGCCCACGTCATCCTGGAGAGCGCACCCCCCGCTCAGCCCGCGGAGGA    1750
 N  A  H  V  I  L  E  S  A  P  P  A  Q  P  A  E  E

GGCGCAGCCTGTTGAGACGCCGGTGGTGGCCTCGGATGTGCTGCCGCTGG    1800
  A  Q  P  V  E  T  P  V  V  A  S  D  V  L  P  L

TGATATCGGCCAAGACCCAGCCCGCCCTGACCGAACACGAAGACCGGCTG    1850
V  I  S  A  K  T  Q  P  A  L  T  E  H  E  D  R  L

CGCGCCTACCTGGCGGCGTCGCCCGGGGCGGATATACGGGCTGTGGCATC    1900
 R  A  Y  L  A  A  S  P  G  A  D  I  R  A  V  A  S

GACGCTGGCGGTGACACGGTCGGTGTTCGAGCACCGCGCCGTACTCCTTG    1950
  T  L  A  V  T  R  S  V  F  E  H  R  A  V  L  L

GAGATGACACCGTCACCGGCACCGCGGTGACCGACCCCAGGATCGTGTTT    2000
G  D  D  T  V  T  G  T  A  V  T  D  P  R  I  V  F

GTCTTTCCCGGGCAGGGGTGGCAGTGGCTGGGGATGGGCAGTGCACTGCG    2050
 V  F  P  G  Q  G  W  Q  W  L  G  M  G  S  A  L  R

CGATTCGTCGGTGGTGTTCGCCGAGCGGATGGCCGAGTGTGCGGCGGCGT    2100
  D  S  S  V  V  F  A  E  R  M  A  E  C  A  A  A

TGCGCGAGTTCGTGGACTGGGATCTGTTCACGGTTCTGGATGATCCGGCG    2150
L  R  E  F  V  D  W  D  L  F  T  V  L  D  D  P  A

GTGGTGGACCGGGTTGATGTGGTCCAGCCCGCTTCCTGGGCGATGATGGT    2200
 V  V  D  R  V  D  V  V  Q  P  A  S  W  A  M  M  V

TTCCCTGGCCGCGGTGTGGCAGGCGGCCGGTGTGCGGCCGGATGCGGTGA    2250
  S  L  A  A  V  W  Q  A  A  G  V  R  P  D  A  V

TCGGCCATTCGCAGGGTGAGATCGCCGCAGCTTGTGTGGCGGGTGCGGTG    2300
I  G  H  S  Q  G  E  I  A  A  A  C  V  A  G  A  V

TCACTACGCGATGCCGCCCGGATCGTGACCTTGCGCAGCCAGGCGATCGC    2350
 S  L  R  D  A  A  R  I  V  T  L  R  S  Q  A  I  A

CCGGGGCCTGGCGGGCCGGGGCGCGATGGCATCCGTCGCCCTGCCCGCGC    2400
  R  G  L  A  G  R  G  A  M  A  S  V  A  L  P  A

AGGATGTCGAGCTGGTCGACGGGGCCTGGATCGCCGCCCACAACGGGCCC    2450
Q  D  V  E  L  V  D  G  A  W  I  A  A  H  N  G  P

GCCTCCACCGTGATCGCGGGCACCCCGGAAGCGGTCGACCATGTCCTCAC    2500
 A  S  T  V  I  A  G  T  P  E  A  V  D  H  V  L  T

CGCTCATGAGGCACAAGGGGTGCGGGTGCGGCGGATCACCGTCGACTATG    2550
  A  H  E  A  Q  G  V  R  V  R  R  I  T  V  D  Y

CCTCGCACACCCCGCACGTCGAGCTGATCCGCGACGAACTACTCGACATC    2600
A  S  H  T  P  H  V  E  L  I  R  D  E  L  L  D  I

ACTAGCGACAGCAGCTCGCAGACCCCGCTCGTGCCGTGGCTGTCGACCGT    2650
 T  S  D  S  S  Q  T  P  L  V  P  W  L  S  T  V

GGACGGCACCTGGGTCGACACCCCGCTGGACGGGGAGTACTGGTACCGGA    2700
  D  G  T  W  V  D  S  P  L  D  G  E  Y  W  Y  R

ACCTGCGTGAACCGGTCGGTTTCCACCCCGCCGTCAGCCAGTTGCAGGCC    2750
N  L  R  E  P  V  G  F  H  P  A  V  S  Q  L  Q  A
```

```
CAGGGCGACACCGTGTTCGTCGAGGTCAGCGCCAGCCCGGTGTTGTTGCA     2800
 Q  G  D  T  V  F  V  E  V  S  A  S  P  V  L  L  Q

GGCGATGGACGACGATGTCGTCACGGTTGCCACGCTGCGTCGTGACGACG     2850
 A  M  D  D  D  V  V  T  V  A  T  L  R  R  D  D

GCGACGCCACCCGGATGCTCACCGCCCTGGCACAGGCCTATGTCCACGGC     2900
 G  D  A  T  R  M  L  T  A  L  A  Q  A  Y  V  H  G

GTCACCGTCGACTGGCCCGCCATCCTCGGCACCACCACAACCCGGGTACT     2950
 V  T  V  D  W  P  A  I  L  G  T  T  T  T  R  V  L

GGACCTTCCGACCTACGCCTTCCAACACCAGCGGTACTGGCTCGAGTCGG     3000
 D  L  P  T  Y  A  F  Q  H  Q  R  Y  W  L  E  S

CTCCCCCGGCCACGGCCGACTCGGGCCACCCCGTCCTCGGCACCGGAGTC     3050
 A  P  P  A  T  A  D  S  G  H  P  V  L  G  T  G  V

GCCGTCGCCGGGTCGCCGGGCCGGGTGTTCACGGGTCCCGTGCCCGCCGG     3100
 A  V  A  G  S  P  G  R  V  F  T  G  P  V  P  A  G

TGCGGACCGCGCGGTGTTCATCGCCGAACTGGCGCTCGCCGCCGCCGACG     3150
 A  D  R  A  V  F  I  A  E  L  A  L  A  A  A  D

CCACCGACTGCGCCACGGTCGAACAGCTCGACGTCACCTCCGTGCCCGGC     3200
 A  T  D  C  A  T  V  E  Q  L  D  V  T  S  V  P  G

GGATCCGCCCGCGGCAGGGCCACCGCGCAGACCTGGGTCGATGAACCCGC     3250
 G  S  A  R  G  R  A  T  A  Q  T  W  V  D  E  P  A

CGCCGACGGGCGGCGCCGCTTCACCGTCCACACCCGCGTCGGCGACGCCC     3300
 A  D  G  R  R  R  F  T  V  H  T  R  V  G  D  A

CGTGGACGCTGCACGCCGAGGGGGTTCTCCGCCCCGGCCGCGTGCCCCAG     3350
 P  W  T  L  H  A  E  G  V  L  R  P  G  R  V  P  Q

CCCGAAGCCGTCGACACCGCCTGGCCCCCGCCGGGCGCGGTGCCCGCGGA     3400
 P  E  A  V  D  T  A  W  P  P  P  G  A  V  P  A  D

CGGGCTGCCCGGGGCGTGGCGACGCGCGGACCAGGTCTTCGTCGAAGCCG     3450
 G  L  P  G  A  W  R  R  A  D  Q  V  F  V  E  A

AAGTCGACAGCCCTGACGGCTTCGTGGCACACCCCGACCTGCTCGACGCG     3500
 E  V  D  S  P  D  G  F  V  A  H  P  D  L  L  D  A

GTCTTCTCCGCGGTCGGCGACGGGAGCCGCCAGCCGACCGGATGGCGCGA     3550
 V  F  S  A  V  G  D  G  S  R  Q  P  T  G  W  R  D

CCTCGCGGTGCACGCGTCGGACGCCACCGTGCTGCGCGCCTGCCTCACCC     3600
 L  A  V  H  A  S  D  A  T  V  L  R  A  C  L  T

GCCGCGACAGTGGTGTCGTGGAGCTCGCCGCCTTCGACGGTGCCGGAATG     3650
 R  R  D  S  G  V  V  E  L  A  A  F  D  G  A  G  M

CCGGTGCTCACCGCGGAGTCGGTGACGCTGGGCGAGGTCGCGTCGGCAGG     3700
 P  V  L  T  A  E  S  V  T  L  G  E  V  A  S  A  G

CGGATCCGACGAGTCGGACGGTCTGCTTCGGCTTGAGTGGTTGCCGGTGG     3750
 G  S  D  E  S  D  G  L  L  R  L  E  W  L  P  V

CGGAGGCCCACTACGACGGTGCCGACGAGCTGCCCGAGGGCTACACCCTC     3800
 A  E  A  H  Y  D  G  A  D  E  L  P  E  G  Y  T  L

ATCACCGCCACACACCCCGACGACCCCGACGACCCCACCAACCCCCACAA     3850
 I  T  A  T  H  P  D  D  P  D  D  P  T  N  P  H  N

CACACCCACACGCACCCACACACAAACCACACGCGTCCTCACCGCCCTCC     3900
 T  P  T  R  T  H  T  Q  T  T  R  V  L  T  A  L

AACACCACCTCATCACCACCAACCACACCCTCATCGTCCACACCACCACC     3950
 Q  H  H  L  I  T  T  N  H  T  L  I  V  H  T  T  T

GACCCCCCAGGCGCCGCCGTCACCGGCCTCACCCGCACCGCACAAAACGA     4000
 D  P  P  G  A  A  V  T  G  L  T  R  T  A  Q  N  E

ACACCCCGGCCGCATCCACCTCATCGAAACCCACCACCCCCACACCCCAC     4050
 H  P  G  R  I  H  L  I  E  T  H  E  P  H  T  P
```

-continued

```
TCCCCCTCACCCAACTCACCACCCTCCACCAACCCCACCTACGCCTCACC    4100
 L  P  L  T  Q  L  T  T  L  H  Q  P  H  L  R  L  T

AACAACACCCTCCACACCCCCCACCTCACCCCCATCACCACCCACCACAA    4150
 N  N  T  L  H  T  P  H  L  T  P  I  T  T  H  H  N

CACCACCACAACCACCCCCAACACCCCACCCCTCAACCCCAACCACGCCA    4200
    T  T  T  T  P  N  T  P  P  L  N  P  N  H  A

TCCTCATCACCGGCGGCTCCGGCACCCTCGCCGGCATCCTCGCCCGCCAC    4250
 I  L  I  T  G  G  S  G  T  L  A  G  I  L  A  R  H

CTCAACCACCCCCACACCTACCTCCTCTCCCGCACACCACCACCCCCCAC    4300
 L  N  H  P  H  T  Y  L  L  S  R  T  P  P  P  P  T

CACACCCGGCACCCACATCCCCTGCGACCTCACCGACCCCACCCAAATCA    4350
    T  P  G  T  H  I  P  C  D  L  T  D  P  T  Q  I

CCCAAGCCCTCACCCACATACCACAACCCCTCACCGGCATCTTCCACACC    4400
 T  Q  A  L  T  H  I  P  Q  P  L  T  G  I  F  H  T

GCCGCCACCCTCGACGACGCCACCCTCACCAACCTCACCCCCCAACACCT    4450
    A  A  T  L  D  D  A  T  L  T  N  L  T  P  Q  H  L

CACCACCACCCTCCAACCCAAAGCCGACGCCGCCTGGCACCTCCACCACC    4500
    T  T  T  L  Q  P  K  A  D  A  A  W  H  L  H  H

ACACCCAAAACCAACCCCTCACCCACTTCGTCCTCTACTCCAGCGCCGCC    4550
 H  T  Q  N  Q  P  L  T  H  F  V  L  Y  S  S  A  A

GCCACCCTCGGCAGCCCCGGCCAAGCCAACTACGCCGCCGCCAACGCCTT    4600
    A  T  L  G  S  P  G  Q  A  N  Y  A  A  A  N  A  F

CCTCGACGCCCTCGCCACCCACCGCCACACCCAAGGACAACCCGCCACCA    4600
    L  D  A  L  A  T  H  R  H  T  Q  G  Q  P  A  T

CCATCGCCTGGGGCATGTGGCACACCACCACCACACTCACCAGCCAACTC    4700
 T  I  A  W  G  M  W  H  T  T  T  T  L  T  S  Q  L

ACCGACAGCGACCGCGACCGCATCCGCCGCGGCGGCTTCCTGCCGATCTC    4750
    T  D  S  D  R  D  R  I  R  R  G  G  F  L  P  I  S

GGACGACGAGGGCATGC
    D  D  E  G  M
```

The NheI-XhoI hybrid FK-506 PKS module 8 containing the AT domain of module 12 of rapamycin is shown below (SEQ ID NOS:30–31).

```
GCATGCGGCTGTACGAGGCGGCACGGCGCACCGGAAGTCCCGTGGTGGTG    50
       M  R  L  Y  E  A  A  R  R  T  G  S  P  V  V  V

GCGGCCGCGCTCGACGACGCGCCGGACGTGCCGCTGCTGCGCGGGCTGCG    100
 A  A  A  L  D  D  A  P  D  V  P  L  L  R  G  L  R

GCGTACGACCGTCCGGCGTGCCGCCGTCCGGGAACGCTCTCTCGCCGACC    150
    R  T  T  V  R  R  A  A  V  R  E  R  S  L  A  D

GCTCGCCGTGCTGCCCGACGACGAGCGCGCCGACGCCTCCCTCGCGTTCG    200
 R  S  P  C  C  P  T  T  S  A  P  T  P  P  S  R  S

TCCTGGAACAGCACCGCCACCGTGCTCGGCCACCTGGGCGCCGAAGACAT    250
 S  W  N  S  T  A  T  V  L  G  H  L  G  A  E  D  I

CCCGGCGACGACGACGTTCAAGGAACTCGGCATCGACTCGCTCACCGCGG    300
    P  A  T  T  T  F  K  E  L  G  I  D  S  L  T  A

TCCAGCTGCGCAACGCGCTGACCACGGCGACCGGCGTACGCCTCAACGCC    350
 V  Q  L  R  N  A  L  T  T  A  T  G  V  R  L  N  A

ACAGCGGTCTTCGACTTTCCGACGCCGCGCGCGCTCGCCGCGAGACTCGG    400
    T  A  V  F  D  F  P  T  P  R  A  L  A  A  R  L  G

CGACGAGCTGGCCGGTACCCGCGCGCCCGTCGCGGCCCGGACCGCGGCCA    450
    D  E  L  A  G  T  R  A  P  V  A  A  R  T  A  A
```

```
CCGCGGCCGCGCACGACGAACCGCTGGCGATCGTGGGCATGGCCTGCCGT    500
 T  A  A  A  H  D  S  P  L  A  I  V  G  M  A  C  R

CTGCCGGGCGGGGTCGCGTCGCCACAGGAGCTGTGGCGTCTCGTCGCGTC    550
 L  P  G  G  V  A  S  P  Q  E  L  W  R  L  V  A  S

CGGCACCGACGCCATCACGGAGTTCCCCGCGGACCGCGGCTGGGACGTGG    600
  G  T  D  A  I  T  E  F  P  A  D  R  G  W  D  V

ACGCGCTCTACGACCCGGACCCCGACGCGATCGGCAAGACCTTCGTCCGG    650
 D  A  L  Y  D  P  D  P  D  A  I  G  K  T  F  V  R

CACGGCGGCTTCCTCGACGGTGCGACCGGCTTCGACGCGGCGTTCTTCGG    700
 H  G  G  F  L  D  G  A  T  G  F  D  A  A  F  F  G

GATCAGCCCGCGCGAGGCCCTGGCCATGGACCCGCAGCAACGGGTGCTCC    750
  I  S  P  R  E  A  L  A  M  D  P  Q  Q  R  V  L

TGGAGACGTCCTGGGAGGCGTTCGAAAGCGCGGGCATCACCCCGGACGCG    800
 L  E  T  S  W  E  A  F  E  S  A  G  I  T  P  D  A

GCGCGGGGCAGCGACACCGGCGTGTTCATCGGCGCGTTCTCCTACGGGTA    850
 A  R  G  S  D  T  G  V  F  I  G  A  F  S  Y  G  Y

CGGCACGGGTGCGGATACCAACGGCTTCGGCGCGACAGGGTCGCAGACCA    900
  G  T  G  A  D  T  N  G  F  G  A  T  G  S  Q  T

GCGTGCTCTCCGGCCGCCTCTCGTACTTCTACGGTCTGGAGGGCCCTTCG    950
 S  V  L  S  G  R  L  S  Y  F  Y  G  L  E  G  P  S

GTCACGGTCGACACCGCCTGCTCGTCGTCACTGGTCGCCCTGCACCAGGC    1000
 V  T  V  D  T  A  C  S  S  S  L  V  A  L  H  Q  A

AGGGCAGTCCCTGCGCTCGGGCGAATGCTCGCTCGCCCTGGTCGGCGGTG    1050
  G  Q  S  L  R  S  G  E  C  S  L  A  L  V  G  G

TCACGGTGATGGCGTCGCCCGGCGGATTCGTCGAGTTCTCCCGGCAGCGC    1100
 V  T  V  M  A  S  P  G  G  F  V  B  F  S  R  Q  R

GGGCTCGCGCCGGACGGGCGGGCGAAGGCGTTCGGCGCGGGCGCGGACGG    1150
  G  L  A  P  D  G  R  A  K  A  F  G  A  G  A  D  G

TACGAGCTTCGCCGAGGGCGCCGGTGCCCTGGTGGTCGAGCGGCTCTCCG    1200
  T  S  F  A  B  G  A  G  A  L  V  V  B  R  L  S

ACGCGGAGCGCCACGGCCACACCGTCCTCGCCCTCGTACGCGGCTCCGCG    1250
 D  A  E  R  H  G  H  T  V  L  A  L  V  R  G  S  A

GCTAACTCCGACGGCGCGTCGAACGGTCTGTCGGCGCCGAACGGCCCCTC    1300
 A  N  S  D  G  A  S  N  G  L  S  A  P  N  G  P  S

CCAGGAACGCGTCATCCACCAGGCCCTCGCGAACGCGAAACTCACCCCCG    1350
  Q  E  R  V  I  H  Q  A  L  A  N  A  K  L  T  P

CCGATGTCGACGCGGTCGAGGCGCACGGCACCGGCACCCGCCTCGGCGAC    1400
 A  D  V  D  A  V  E  A  H  G  T  G  T  R  L  G  D

CCCATCGAGGCGCAGGCGCTGCTCGCGACGTACGGACAGGACCGGGCGAC    1450
  P  I  E  A  Q  A  L  L  A  T  Y  G  Q  D  R  A  T

GCCCCTGCTGCTCGGCTCGCTGAAGTCGAACATCGGGCACGCCCAGGCCG    1500
  P  L  L  L  G  S  L  K  S  N  T  G  H  A  Q  A

CGTCAGGGGTCGCCGGGATCATCAAGATGGTGCAGGCCATCCGGCACGGG    1550
 A  S  G  V  A  G  I  I  K  M  V  Q  A  I  R  H  G

GAACTGCCGCCGACACTGCACGCGGACGAGCCGTCGCCGCACGTCGACTG    1600
 E  L  P  P  T  L  H  A  D  E  P  S  P  H  V  D  W

GACGGCCGGTGCCGTCGAGCTCCTGACGTCGGCCCGGCCGTGGCCGGGGA    1650
  T  A  G  A  V  E  L  L  T  S  A  R  P  W  P  G

CCGGTCGCCCGCGCCGCGCTGCCGTCTCGTCGTTCGGCGTGAGCGGCACG    1700
 T  G  R  P  R  R  A  A  V  S  S  F  G  V  S  G  T

AACGCCCACATCATCCTTGAGGCAGGACCGGTCAAAACGGGACCGGTCGA    1750
  N  A  H  I  I  L  E  A  G  P  V  K  T  G  P  V  E
```

-continued

```
GGCAGGAGCGATCGAGGCAGGACCGGTCGAAGTAGGACCGGTCGAGGCTG      1800
  A  G  A  I  E  A  G  P  V  E  V  G  P  V  E  A

GACCGCTCCCCGCGGCGCCGCCGTCAGCACCGGGCGAAGACCTTCCGCTG      1850
G  P  L  P  A  A  P  P  S  A  P  G  E  D  L  P  L

CTCGTGTCGGCGCGTTCCCCGGAGGCACTCGACGAGCAGATCGGGCGCCT      1900
 L  V  S  A  R  S  P  E  A  L  D  E  Q  I  G  R  L

GCGCGCCTATCTCGACACCCGCCCGGGCGTCGACCGGGCGGCCGTGGCGC      1950
  R  A  Y  L  D  T  G  P  G  V  D  R  A  A  V  A

AGACACTGGCCCGGCGTACGCACTTCACCCACCGGGCCGTACTGCTCGGG      2000
Q  T  L  A  R  R  T  H  F  T  H  R  A  V  L  L  G

GACACCGTCATCGGCGCTCCCCCCGCGGACCAGGCCGACGAACTCGTCTT      2050
 D  T  V  T  G  A  P  P  A  D  Q  A  D  E  L  V  F

CGTCTACTCCGGTCAGGGCACCCAGCATCCCGCGATGGGCGAGCAGCTAG      2100
  V  Y  S  G  Q  G  T  Q  H  P  A  M  G  E  Q  L

CCGCCGCGTTCCCCGTCTTCGCGCGGATCCATCAGCAGGTGTGGGACCTG      2150
A  A  A  F  P  V  F  A  R  I  H  Q  Q  V  W  D  L

CTCGATGTGCCCGATCTGGAGGTGAACGAGACCGGTTACGCCCAGCCGGC      2200
 L  D  V  P  D  L  E  V  N  E  T  G  Y  A  Q  P  A

CCTGTTCGCAATGCAGGTGGCTGTGTTCGGGCTGCTGGAATCGTGGGGTG      2250
  L  F  A  M  Q  V  A  L  F  G  L  L  E  S  W  G

TACGACCGGACGCGGTGATCGGCCATTCGGTGGGTGAGCTTGCGGCTGCG      2300
V  R  P  D  A  V  I  G  H  S  V  G  E  L  A  A  A

TATGTGTCCGGGGTGTGGTCGTTGGAGGATGCCTGCACTTTGGTGTCGGC      2350
 Y  V  S  G  V  W  S  L  E  D  A  C  T  L  V  S  A

GCGGGCTCGTCTGATGCAGGCTCTGCCCGCGGGTGGGGTGATGGTCGCTG      2400
  R  A  R  L  M  Q  A  L  P  A  G  G  V  M  V  A

TCCCGGTCTCGGAGGATGAGGCCCGGGCCGTGCTGGGTGAGGGTGTGGAG      2450
V  P  V  S  E  D  E  A  R  A  V  L  G  E  G  V  E

ATCGCCGCGGTCAACGGCCCGTCGTCGGTGGTTCTCTCCGGTGATGAGGC      2500
 I  A  A  V  N  G  P  S  S  V  V  L  S  G  D  E  A

CGCCGTGCTGCAGGCCGCGGAGGGGCTGGGGAAGTGGACGCGGCTGGCGA      2550
  A  V  L  Q  A  A  E  G  L  G  K  W  T  R  L  A

CCAGCCACGCGTTCCATTCCGCCCGTATGGAACCCATGCTGGAGGAGTTC      2600
T  S  H  A  F  H  S  A  R  M  E  P  M  L  E  E  F

CGGGCGGTCGCCGAAGGCCTGACCTACCGGACGCCGCAGGTCTCCATGGC      2650
 R  A  V  A  E  G  L  T  Y  R  T  P  Q  V  S  M  A

CGTTGGTGATCAGGTGACCACCGCTGAGTACTGGGTGCGGCAGGTCCGGG      2700
  V  G  D  Q  V  T  T  A  E  Y  W  V  R  Q  V  R

ACACGGTCCGGTTCGGCGAGCAGGTGGCCTCGTACGAGGACGCCGTGTTC      2750
D  T  V  R  F  G  E  Q  V  A  S  Y  E  D  A  V  F

GTCGAGCTGGGTGCCGACCGGTCACTGGCCCGCCTGGTCGACGGTGTCGC      2800
 V  E  L  G  A  D  R  S  L  A  R  L  V  D  G  V  A

GATGCTGCACGGCGACCACGAAATCCAGGCCGCGATCGGCGCCCTGGCCC      2850
  M  L  H  G  D  H  E  I  Q  A  A  I  G  A  L  A

ACCTGTATGTCAACGGCGTCACGGTCGACTGGCCCGCGCTCCTGGGCGAT      2900
H  L  Y  V  N  G  V  T  V  D  W  P  A  L  L  G  D

GCTCCGGCAACACGGGTGCTGGACCTTCCGACATACGCCTTCCAGCACCA      2950
 A  P  A  T  R  V  L  D  L  P  T  Y  A  F  Q  H  Q

GCGCTACTGGCTCGAGTCGGCTCCCCCGGCCACGGCCGACTCGGGCCACC      3000
  R  Y  W  L  E  S  A  P  P  A  T  A  D  S  G  H

CCGTCCTCGGCACCGGAGTCGCCGTCGCCGGGTCGCCGGGCCGGGTGTTC      3050
P  V  L  G  T  G  V  A  V  A  G  S  P  G  R  V  F
```

```
ACGGGTCCCGTGCCCGCCGGTGCGGACCGCGCGGTGTTCATCGCCGAACT    3100
  T  G  P  V  P  A  G  A  D  R  A  V  F  I  A  E  L

GGCGCTCGCCGCCGCCGACGCCACCGACTGCGCCACGGTCGAACAGCTCG    3150
   A  L  A  A  A  D  A  T  D  C  A  T  V  E  Q  L

ACGTCACCTCCGTGCCCGGCGGATCCGCCCGCGGCAGGGCCACCGCGCAG    3200
  D  V  T  S  V  P  G  G  S  A  R  G  R  A  T  A  Q

ACCTGGGTCGATGAACCCGCCGCCGACGGGCGGCGCCGCTTCACCGTCCA    3250
  T  W  V  D  E  P  A  A  D  G  R  R  R  F  T  V  H

CACCCGCGTCGGCGACGCCCCGTGGACGCTGCACGCCGAGGGGGTTCTCC    3300
  T  R  V  G  D  A  P  W  T  L  H  A  E  G  V  L

GCCCCGGCCGCGTGCCCCAGCCCGAAGCCGTCGACACCGCCTGGCCCCCG    3350
  R  P  G  R  V  P  Q  P  E  A  V  D  T  A  W  P  P

CCGGGCGCGGTGCCCGCGGACGGGCTGCCCGGGGCGTGGCGACGCGCGGA    3400
   P  G  A  V  P  A  D  G  L  P  G  A  W  R  R  A  D

CCAGGTCTTCGTCGAAGCCGAAGTCGACAGCCCTGACGGCTTCGTGGCAC    3450
   Q  V  F  V  E  A  E  V  D  S  P  D  G  F  V  A

ACCCCGACCTGCTCGACGCGGTCTTCTCCGCGGTCGGCGACGGGAGCCGC    3500
  H  P  D  L  L  D  A  V  F  S  A  V  G  D  G  S  R

CAGCCGACCGGATGGCGCGACCTCGCGGTGCACGCGTCGGACGCCACCGT    3550
  Q  P  T  G  W  R  D  L  A  V  H  A  S  D  A  T  V

GCTGCGCGCCTGCCTCACCCGCCGCGACAGTGGTGTCGTGGAGCTCGCCG    3600
   L  R  A  C  L  T  R  R  D  S  G  V  V  E  L  A

CCTTCGACGGTGCCGGAATGCCGGTGCTGACCGCGGAGTCGGTGACGCTG    3650
  A  F  D  G  A  G  M  P  V  L  T  A  E  S  V  T  L

GGCGAGGTCGCGTCGGCAGGCGGATCCGACGAGTCGGACGGTCTGCTTCG    3700
  G  E  V  A  S  A  G  G  S  D  E  S  D  G  L  L  R

GCTTGAGTGGTTGCCGGTGGCGGAGGCCCACTACGACGGTGCCGACGAGC    3750
   L  E  W  L  P  V  A  E  A  H  Y  D  G  A  D  E

TGCCCGAGGGCTACACCCTCATCACCGCCACACACCCCGACGACCCCGAC    3800
  L  P  E  G  Y  T  L  I  T  A  T  H  P  D  D  P  D

GACCCCACCAACCCCCACAACACACCCACACGCACCCACACACAAACCAC    3850
  D  P  T  N  P  H  N  T  P  T  R  T  H  T  Q  T  T

ACGCGTCCTCACCGCCCTCCAACACCACCTCATCACCACCAACCACACCC    3900
   R  V  L  T  A  L  Q  H  H  L  I  T  T  N  H  T

TCATCGTCCACACCACCACCGACCCCCCAGGCGCCGCCGTCACCGGCCTC    3950
  L  I  V  H  T  T  T  D  P  P  G  A  A  V  T  G  L

ACCCGCACCGCACAAAACGAACACCCCGGCCGCATCCACCTCATCGAAAC    4000
  T  R  T  A  Q  N  E  S  P  G  R  I  H  L  I  E  T

CCACCACCCCCACACCCCACTCCCCCTCACCCAACTCACCACCCTCCACC    4050
  H  H  P  H  T  P  L  P  L  T  Q  L  T  T  L  H

AACCCCACCTACGCCTCACCAACAACACCCTCCACACCCCCCACCTCACC    4100
  Q  P  H  L  R  L  T  N  N  T  L  H  T  P  H  L  T

CCCATCACCACCCACCACAACACCACCACAACCACCCCCAACACCCCACC    4150
   P  I  T  T  H  H  N  T  T  T  T  T  P  N  T  P  P

CCTCAACCCCAACCACGCCATCCTCATCACCGGCGGCTCCGGCACCCTCG    4200
   L  N  P  N  H  A  I  L  I  T  G  G  S  G  T  L

CCGGCATCCTCGCCCGCCACCTCAACCACCCCCACACCTACCTCCTCTCC    4250
  A  G  I  L  A  R  H  L  N  H  P  H  T  Y  L  L  S

CGCACACCACCACCCCCACCACACCCGGCACCCACATCCCCTGCGACCT    4300
  R  T  P  P  P  P  T  T  P  G  T  H  I  P  C  D  L

CACCGACCCCACCCAAATCACCCAAGCCCTCACCCACATACCACAACCCC    4350
  T  D  P  T  Q  I  T  Q  A  L  T  H  I  P  Q  P
```

-continued

```
TCACCGGCATCTTCCACACCGCCGCCACCCTCGACGACGCCACCCTCACC     4400
 L  T  G  I  F  H  T  A  A  T  L  D  D  A  T  L  T

AACCTCACCCCCCAACACCTCACCACCACCCTCCAACCCAAAGCCGACGC     4450
 N  L  T  P  Q  H  L  T  T  T  L  Q  P  K  A  D  A

CGCCTGGCACCTCCACCACCACACCCAAAACCAACCCCTCACCCACTTCG     4500
  A  W  H  L  H  H  H  T  Q  N  Q  P  L  T  H  F

TCCTCTACTCCAGCGCCGCCGCCACCCTCGGCAGCCCCGGCCAAGCCAAC     4550
 V  L  Y  S  S  A  A  A  T  L  G  S  P  G  Q  A  N

TACGCCGCCGCCAACGCCTTCCTCGACGCCCTCGCCACCCACCGCCACAC     4600
 Y  A  A  A  N  A  F  L  D  A  L  A  T  H  R  H  T

CCAAGGACAACCCGCCACCACCATCGCCTGGGGCATGTGGCACACCACCA     4650
  Q  G  Q  P  A  T  T  I  A  W  G  M  W  H  T  T

CCACACTCACCAGCCAACTCACCGACAGCGACCGCGACCGCATCCGCCGC     4700
 T  T  L  T  S  Q  L  T  D  S  D  R  D  R  I  R  R

GGCGGCTTCCTGCCGATCTCGGACGACGAGGGCATGC
 G  G  F  L  P  I  S  D  D  E  G  M
```

The NheI-XhoI hybrid FK-506 PKS module 8 containing the AT domain of module 13 of rapamycin is shown below (SEQ ID NOS:32–33).

```
GCATGCGGCTGTACGAGGCGGCACGGCGCACCGGAACTCCCGTGGTGGTG     50
   M  R  L  Y  E  A  A  R  R  T  G  S  P  V  V  V

GCGGCCGCGCTCGACGACGCGCCGGACGTGCCGCTGCTGCGCGGGCTGCG    100
  A  A  A  L  D  D  A  P  D  V  P  L  L  R  G  L  R

GCGTACGACCGTCCGGCGTGCCGCCGTCCGGGAACGCTCTCTCGCCGACC    150
   R  T  T  V  R  R  A  A  V  R  E  R  S  L  A  D

GCTCGCCGTGCTGCCCGACGACGAGCGCGCCGACGCCTCCCTCGCGTTCG    200
  R  S  P  C  C  P  T  T  S  A  P  T  P  P  S  R  S

TCCTGGAACAGCACCGCCACCGTGCTCGGCCACCTGGGCGCCGAAGACAT    250
  S  W  N  S  T  A  T  V  L  G  H  L  G  A  E  D  I

CCCGGCGACGACGACGTTCAAGGAACTCGGCATCGACTCGCTCACCGCGG    300
   P  A  T  T  T  F  K  E  L  G  I  D  S  L  T  A

TCCAGCTGCGCAACGCGCTGACCACGGCGACCGGCGTACGCCTCAACGCC    350
 V  Q  L  R  N  A  L  T  T  A  T  G  V  R  L  N  A

ACAGCGGTCTTCGACTTTCCGACGCCGCGCGCGCTCGCCGCGAGACTCGG    400
  T  A  V  F  D  F  P  T  P  R  A  L  A  A  R  L  G

CGACGAGCTGGCCGGTACCCGCGCGCCCGTCGCGGCCCGGACCGCGGCCA    450
   D  E  L  A  G  T  R  A  P  V  A  A  R  T  A  A

CCGCGGCCGCGCACGACGAACCGCTGGCGATCGTGGGCATGGCCTGCCGT    500
 T  A  A  A  H  D  E  P  L  A  I  V  G  M  A  C  R

CTGCCGGGCGGGGTCGCGTCGCCACAGGACGTGTGGCGTCTCGTCGCGTC    550
 L  P  G  G  V  A  S  P  Q  E  L  W  R  L  V  A  S

CGGCACCGACGCCATCACGGAGTTCCCCGCGGACCGCGGCTGGGACGTGG    600
   G  T  D  A  I  T  E  F  P  A  D  R  G  W  D  V

ACGCGCTCTACGACCCGGACCCCGACGCGATCGGCAAGACCTTCGTCCGG    650
 D  A  L  Y  D  P  D  P  D  A  I  G  K  T  F  V  R

CACGGCGGCTTCCTCGACGGTGCGACCGGCTTCGACGCGGCGTTCTTCGG    700
  H  G  G  F  L  D  G  A  T  G  F  D  A  A  F  F  G

GATCAGCCCGCGCGAGGCCCTGGCCATGGACCCGCAGCAACGGGTGCTCC    750
   I  S  P  R  E  A  L  A  M  D  P  Q  Q  R  V  L

TGGAGACGTCCTGGGAGGCGTTCGAAAGCGCGGGCATCACCCCGGACGCG    800
  L  E  T  S  W  E  A  F  E  S  A  G  I  T  P  D  A
```

```
GCGCGGGGCAGCGACACCGGCGTGTTCATCGGCGCGTTCTCCTACGGGTA    850
 A  R  G  S  D  T  G  V  F  I  G  A  F  S  Y  G  Y

CGGCACGGGTGCGGATACCAACGGCTTCGGCGCGACAGGGTCGCAGACCA    900
  G  T  G  A  D  T  N  G  F  G  A  T  G  S  Q  T

GCGTGCTCTCCGGCCGCCTCTCGTACTTCTACGGTCTGGAGGGCCCTTCG    950
 S  V  L  S  G  R  L  S  Y  F  Y  G  L  E  G  P  S

GTCACGGTCGACACCGCCTGCTCGTCGTCACTGGTCGCCCTGCACCAGGC   1000
 V  T  V  D  T  A  C  S  S  S  L  V  A  L  H  Q  A

AGGGCAGTCCCTGCGCTCGGGCGAATGCTCGCTCGCCCTGGTCGGCGGTG   1050
  G  Q  S  L  R  S  G  E  C  S  L  A  L  V  G  G

TCACGGTGATGGCGTCGCCCGGCGGATTCGTCGAGTTCTCCCGGCAGCGC   1100
 V  T  V  M  A  S  P  G  G  F  V  E  F  S  R  Q  R

GGGCTCGCGCCGGACGGGCGGGCGAAGGCGTTCGGCGCGGGCGCGGACGG   1150
  G  L  A  P  D  G  R  A  K  A  F  G  A  G  A  D  G

TACGAGCTTCGCCGAGGGCGCCGGTGCCCTGGTGGTCGAGCGGCTCTCCG   1200
  T  S  F  A  E  G  A  G  A  L  V  V  E  R  L  S

ACGCGCAGCGCCACGCCCACACCGTCCTCGCCCTCGTACGCGGCTCCGCG   1250
 D  A  E  R  H  G  H  T  V  L  A  L  V  R  G  S  A

GCTAACTCCGACGGCGCGTCGAACGGTCTGTCGGCGCCGAACGGCCCCTC   1300
 A  N  S  D  G  A  S  N  G  L  S  A  P  N  G  P  S

CCAGGAACGCGTCATCCACCAGGCCCTCGCGAACGCGAAACTCACCCCCG   1350
  Q  E  R  V  I  H  Q  A  L  A  N  A  K  L  T  P

CCGATGTCGACGCGGTCGAGGCGCACGGCACCGGCACCCGCCTCGGCGAC   1400
 A  D  V  D  A  V  E  A  H  G  T  G  T  R  L  G  D

CCCATCGAGGCGCAGGCGCTGCTCGCGACGTACGGACAGGACCGGGCGAC   1450
  P  I  E  A  Q  A  L  L  A  T  Y  G  Q  D  R  A  T

GCCCCTGCTGCTCGGCTCGCTGAAGTCGAACATCGGGCACGCCCAGGCCG   1500
  P  L  L  L  G  S  L  K  S  N  I  G  H  A  Q  A

CGTCAGGGGTCGCCGGGATCATCAAGATGGTGCAGGCCATCCGGCACGGG   1550
 A  S  G  V  A  G  I  I  K  M  V  Q  A  I  R  H  G

GAACTGCCGCCGACACTGCACGCGGACGAGCCGTCGCCGCACGTCGACTG   1600
 E  L  P  P  T  L  H  A  D  F  P  S  P  H  V  D  W

GACGGCCGGTGCCGTCGAGCTCCTGACGTCGGCCCGGCCGTGGCCGGGGA   1650
  T  A  G  A  V  E  L  L  T  S  A  R  P  W  P  G

CCGGTCGCCCGCCGCGCTGCCGTCTCGTCGTTCGGCGTGAGCGGCACG    1700
 T  G  R  P  R  R  A  A  V  S  S  F  G  V  S  G  T

AACGCCCACATCATCCTTGAGGCAGGACCGGTCAAAACGGGACCGGTCGA   1750
 N  A  H  I  I  L  E  A  G  P  V  K  T  G  P  V  E

GGCAGGAGCGATCGAGGCAGGACCGGTCGAAGTAGGACCGGTCGAGGCTG   1800
  A  G  A  I  E  A  G  P  V  E  V  G  P  V  E  A

GACCGCTCCCCGCGGCGCCGCCGTCAGCACCGGGCGAAGACCTTCCGCTG   1850
  G  P  L  P  A  A  P  P  S  A  P  G  E  D  L  P  L

CTCGTGTCGGCGCGTTCCCCGGAGGCACTCGACGAGCAGATCGGGCGCCT   1900
  L  V  S  A  R  S  P  E  A  L  D  E  Q  I  G  R  L

GCGCGCCTATCTCGACACCGGCCCGGGCGTCGACCGGGCGGCCGTGGCGC   1950
  R  A  Y  L  D  T  G  P  G  V  D  R  A  A  V  A

AGACACTGGCCCGGCGTACGCACTTCACCCACCGGGCCGTACTGCTCGGG   2000
  Q  T  L  A  R  R  T  H  F  T  H  R  A  V  L  L  G

GACACCGTCATCGGCGCTCCCCCCGCGGACCAGGCCGACGAACTCGTCTT   2050
  D  T  V  I  G  A  P  P  A  D  Q  A  D  E  L  V  F

CGTCTACTCCGGTCAGGGCACCCAGCATCCCGCGATGGGCGAGCAGCTAG   2100
  V  Y  S  G  Q  G  T  Q  H  P  A  M  G  E  Q  L
```

```
CCGATTCGTCGGTGGTGTTCGCCGAGCGGATGGCCGAGTGTGCGGCGGCG    2150
 A  D  S  S  V  V  F  A  E  R  M  A  E  C  A  A  A

TTGCGCGAGTTCGTGGACTGGGATCTGTTCACGGTTCTGGATGATCCGGC    2200
 L  R  E  F  V  D  W  D  L  F  T  V  L  D  D  P  A

GGTGGTGGACCGGGTTGATGTGGTCCAGCCCGCTTCCTGGGCGATGATGG    2250
  V  V  D  R  V  D  V  V  Q  P  A  S  W  A  M  M

TTTCCCTGGCCGCGGTGTGGCAGGCGGCCGGTGTGCGGCCGGATGCGGTG    2300
 V  S  L  A  A  V  W  Q  A  A  G  V  R  P  D  A  V

ATCGGCCATTCGCAGGGTGAGATCGCCGCAGCTTGTGTGGCGGGTGCGGT    2350
 I  G  H  S  Q  G  E  I  A  A  A  C  V  A  G  A  V

GTCACTACGCGATGCCGCCCGGATCGTGACCTTGCGCAGCCAGGCGATCG    2400
  S  L  R  D  A  A  R  I  V  T  L  R  S  Q  A  I

CCCGGGGCCTGGCGGGCCGGGGCGCGATGGCATCCGTCGCCCTGCCCGCG    2450
 A  R  C  L  A  G  R  D  A  M  A  S  V  A  L  P  A

CAGGATGTCGAGCTGGTCGACGGGGCCTGGATCGCCGCCCACAACGGGCC    2500
  Q  D  V  E  L  V  D  G  A  W  I  A  A  H  N  G  P

CGCCTCCACCGTGATCGCGGGCACCCCGGAAGCGGTCGACCATGTCCTCA    2550
  A  S  T  V  T  A  G  T  P  E  A  V  D  H  V  L

CCGCTCATGAGGCACAAGGGGTGCGGGTGCGGCGGATCACCGTCGACTAT    2600
 T  A  H  E  A  Q  G  V  R  V  R  R  I  T  V  D  Y

GCCTCGCACACCCCGCACGTCGAGCTGATCCGCGACGAACTACTCGACAT    2650
 A  S  H  T  P  H  V  E  L  I  R  D  E  L  L  D  I

CACTAGCGACAGCAGCTCGCAGACCCCGCTCGTGCCGTGGCTGTCGACCG    2700
  T  S  D  S  S  S  Q  T  P  L  V  P  W  L  S  T

TGGACGGCACCTGGGTCGACAGCCCGCTGGACGGGGAGTACTGGTACCGG    2750
 V  D  G  T  W  V  D  S  P  L  D  G  E  Y  W  Y  R

AACCTGCGTGAACCGGTCGGTTTCCACCCCGCCGTCAGCCAGTTGCAGGC    2800
 N  L  R  E  P  V  G  F  H  P  A  V  S  Q  L  Q  A

CCAGGGCGACACCGTGTTCGTCGAGGTCAGCGCCAGCCCGGTGTTGTTGC    2850
  Q  G  D  T  V  F  V  E  V  S  A  S  P  V  L  L

AGGCGATGGACGACGATGTCGTCACGGTTCGGACGCTGCGTCGTGACGAC    2900
 Q  A  M  D  D  D  V  V  T  V  A  T  L  R  R  D  D

GGCGACGCCACCCGGATGCTCACCGCCCTGGCACAGGCCTATGTCCACGG    2950
  G  D  A  T  R  M  L  T  A  L  A  Q  A  Y  V  H  G

CGTCACCGTCGACTGGCCCGCCATCCTCGGCACCACCACAACCCGGGTAC    3000
  V  T  V  D  W  P  A  I  L  G  T  T  T  T  R  V

TGGACCTTCCGACCTACGCCTTCCAACACCAGCGGTACTGGCTCGAGTCG    3050
 L  D  L  F  T  Y  A  F  Q  H  Q  R  Y  W  L  E  S

GCTCCCCCGGCCACGGCCGACTCGGGCCACCCCGTCCTCGGCACCGGAGT    3100
  A  P  P  A  T  A  D  S  C  H  P  V  L  G  T  G  V

CGCCGTCGCCGGGTCGCCGGGCCGGGTGTTCACGGGTCCCGTGCCCGCCG    3150
  A  V  A  G  S  P  G  R  V  F  T  G  P  V  P  A

GTGCGGACCGCGCGGTGTTCATCGCCGAACTGGCGCTCGCCGCCGCCGAC    3200
  G  A  D  R  A  V  F  I  A  E  L  A  L  A  A  A  D

GCCACCGACTGCGCCACGGTCGAACAGCTCGACGTCACCTCCGTGCCCGG    3250
  A  T  D  C  A  T  V  E  Q  L  D  V  T  S  V  P  G

CGGATCCGCCCGCGGCAGGGCCACCGCGCAGACCTGGGTCGATGAACCCG    3300
  G  S  A  R  G  R  A  T  A  Q  T  W  V  D  E  P

CCGCCGACGGGCGGCGCCGCTTCACCGTCCACACCCGCGTCGGCGACGCC    3350
  A  A  D  G  R  R  R  F  T  V  H  T  R  V  G  D  A

CCGTGGACGCTGCACGCCGACCCCCTTCTCCGCCCCGGCCGCGTGCCCCA    3400
  P  W  T  L  H  A  E  G  V  L  R  P  G  R  V  P  Q
```

```
GCCCGAAGCCGTCGACACCGCCTGGCCCCCGCCGGGCGCGGTGCCCGCGG      3450
  P  E  A  V  D  T  A  W  P  P  P  G  A  V  P  A

ACGGGCTGCCCGGGGCGTGGCGACGCGCGGACCAGGTCTTCGTCGAAGCC      3500
 D  G  L  P  G  A  W  R  R  A  D  Q  V  F  V  E  A

GAAGTCGACAGCCCTGACGGCTTCGTGGCACACCCCGACCTGCTCGACGC      3550
  E  V  D  S  P  D  G  F  V  A  H  P  D  L  L  D  A

GGTCTTCTCCGCGGTCGGCGACGGGAGCCGCCAGCCGACCGGATGGCGCG      3600
  V  F  S  A  V  G  D  G  S  R  Q  P  T  G  W  R

ACCTCGCGGTGCACGCGTCGGACGCCACCGTGCTGCGCGCCTGCCTCACC      3650
 D  L  A  V  H  A  S  D  A  T  V  L  R  A  C  L  T

CGCCGCGACAGTGGTGTCGTGGAGCTCGCCGCCTTCGACGGTGCCGGAAT      3700
 R  R  D  S  G  V  V  E  L  A  A  F  D  G  A  G  M

GCCGGTGCTCACCGCGGAGTCGGTGACGCTGGGCGAGGTCGCGTCGGCAG      3750
  P  V  L  T  A  E  S  V  T  L  G  E  V  A  S  A

GCGGATCCGACGAGTCGGACGGTCTGCTTCGGCTTGAGTGGTTGCCGGTG      3800
 G  G  S  D  E  S  D  G  L  L  R  L  E  W  L  P  V

GCGGAGGCCCACTACGACGGTGCCGACGAGCTGCCCGAGGGCTACACCCT      3850
 A  E  A  H  Y  D  G  A  D  E  L  P  E  G  Y  T  L

CATCACCGCCACACACCCCGACGACCCCGACGACCCCACCAACCCCCACA      3900
  I  T  A  T  H  P  D  D  P  D  D  P  T  N  P  H

ACACACCCACACGCACCCACACACAAACCACACGCGTCCTCACCGCCCTC      3950
 N  T  P  T  R  T  H  T  Q  T  T  R  V  L  T  A  L

CAACACCACCTCATCACCACCAACCACACCCTCATCGTCCACACCACCAC      4000
  Q  H  H  L  I  T  T  N  H  T  L  I  V  H  T  T  T

CGACCCCCCAGGCGCCGCCGTCACCGGCCTCACCCGCACCGCACAAAACG      4050
  D  P  P  G  A  A  V  T  G  L  T  R  T  A  Q  N

AACACCCCGGCCGCATCCACCTCATCGAAACCCACCACCCCCACACCCCA      4100
 E  H  P  G  R  I  H  L  I  E  T  H  H  P  H  T  P

CTCCCCCTCACCCAACTCACCACCCTCCACCAACCCCACCTACGCCTCAC      4150
 L  P  L  T  Q  L  T  T  L  H  Q  P  H  L  R  L  T

CAACAACACCCTCCACACCCCCCACCTCACCCCCATCACCACCCACCACA      4200
  N  N  T  L  H  T  P  H  L  T  P  I  T  T  H  H

ACACCACCACAACCACCCCCAACACCCCACCCCTCAACCCCAACCACGCC      4250
 N  T  T  T  T  T  P  N  T  P  P  L  N  P  N  H  A

ATCCTCATCACCGGCGGCTCCGGCACCCTCGCCGGCATCCTCGCCCGCCA      4300
  I  L  I  T  G  G  S  G  T  L  A  G  I  L  A  R  H

CCTCAACCACCCCCACACCTACCTCCTCTCCCGCACACCACCACCCCCCA      4350
 L  N  H  P  H  T  Y  L  L  S  R  T  P  P  P  P

CCACACCCGGCACCCACATCCCCTGCGACCTCACCGACCCCACCCAAATC      4400
 T  T  P  G  T  H  I  P  C  D  L  T  D  P  T  Q  I

ACCCAAGCCCTCACCCAGATACCACAACCCCTCACCGGCATCTTCCACAC      4450
  T  Q  A  L  T  H  I  P  Q  P  L  T  G  I  F  H  T

CGCCGCCACCCTCGACGACGCCACCCTCACCAACCTCACCCCCCAACACC      4500
 A  A  T  L  D  D  A  T  L  T  N  L  T  P  Q  H

TCACCACCACCCTCCAACCCAAAGCCGACGCCGCCTGGCACCTCCACCAC      4550
 L  T  T  T  L  Q  P  K  A  D  A  A  W  H  L  H  H

CACACCCAAAACCAACCCCTCACCCACTTCGTCCTCTACTCCAGCGCCGC      4600
  H  T  Q  N  Q  P  L  T  H  F  V  L  Y  S  S  A  A

CGCCACCCTCGGCAGCCCCGGCCAAGCCAACTACGCCGCCGCCAACGCCT      4650
  A  T  L  G  S  P  G  Q  A  N  Y  A  A  A  N  A

TCCTCGACGCCCTCGCCACCCACCGCCACACCCAAGGACAACCCGCCACC      4700
 F  L  D  A  L  A  T  H  R  H  T  Q  C  Q  P  A  T
```

-continued

```
ACCATCGCCTGGGGCATGTGGCACACCACCACCACACTCACCAGCCAACT    4750
 T  I  A  W  G  M  W  H  T  T  T  T  L  T  S  Q  L

CACCGACAGCGACCGCGACCGCATCCGCCGCGGCGGCTTCCTGCCGATCT    4800
 T  D  S  D  R  D  R  I  R  R  D  C  F  L  P  I

CGGACGACGAGGGCATGC
 S  D  D  E  D  M
```

Example 3

Recombinant PKS Genes for 13-desmethoxy FK-506 and FK-520

The present invention provides a variety of recombinant PKS genes in addition to those described in Examples 1 and 2 for producing 13-desmethoxy FK-506 and FK-520 compounds. This Example provides the construction protocols for recombinant FK-520 and FK-506 (from Streptomyces sp. MA6858 (ATCC 55098), described in U.S. Pat. No. 5,116,756, incorporated herein by reference) PKS genes in which the module 8 AT coding sequences have been replaced by either the rapAT3 (the AT domain from module 3 of the rapamycin PKS), rapAT12, eryAT1 (the AT domain from module 1 of the erythromycin (DEBS) PKS), or eryAT2 coding sequences. Each of these constructs provides a PKS that produces the 13-desmethoxy-13-methyl derivative, except for the rapAT12 replacement, which provides the 13-desmethoxy derivative, i.e., it has a hydrogen where the other derivatives have methyl.

FIG. 7 shows the process used to generate the AT replacement constructs. First, a fragment of ~4.5 kb containing module 8 coding sequences from the FK-520 cluster of ATCC 14891 was cloned using the convenient restriction sites SacI and SphI (Step A in FIG. 7). The choice of restriction sites used to clone a 4.0–4.5 kb fragment comprising module 8 coding sequences from other FK-520 or FK-506 clusters can be different depending on the DNA sequence, but the overall scheme is identical. The unique SacI and SphI restriction sites at the ends of the FK-520 module 8 fragment were then changed to unique Bgl II and NsiI sites by ligation to synthetic linkers (described in the preceding Examples, see Step B of FIG. 7). Fragments containing sequences 5' and 3' of the AT8 sequences were then amplified using primers, described above, that introduced either an AvrII site or an NheI site at two different KS/AT boundaries and an XhoI site at the AT/DH boundary (Step C of FIG. 7). Heterologous AT domains from the rapamycin and erythromycin gene clusters were amplified using primers, as described above, that introduced the same sites as just described (Step D of FIG. 7). The fragments were ligated to give hybrid modules with in-frame fusions at the KS/AT and AT/DH boundaries (Step E of FIG. 7). Finally, these hybrid modules were ligated into the BamHI and PstI sites of the KC515 vector. The resulting recombinant phage were used to transform the FK-506 and FK-520 producer strains to yield the desired recombinant cells, as described in the preceding Examples.

The following table shows the location and sequences surrounding the engineered site of each of the heterologous AT domains employed (SEQ ID NOS:34–63, in order of appearance). The FK-506 hybrid construct was used as a control for the FK-520 recombinant cells produced, and a similar FK-520 hybrid construct was used as a control for the FK-506 recombinant cells.

| Heterologous AT | Enzyme | Location of Engineered Site |
|---|---|---|
| FK-506 AT8 (hydroxy-malonyl) | AvrII | GGCCGTccgcgcCGTGCGGCGGTCTCGTCGTTC<br>G R P R R A A V S S F |
| | NheI | ACCCAGCATCCCGCGATGGGTGAGCGgctcgcC<br>T Q H PAM G ER LA |
| | XhoI | TACGCCTTCCAGCGGCGGCCCTACTGGatcgag<br>Y A F Q R R P Y W I H |
| rapamycin AT3 (methyl-malonyl) | AvrII | GACCGGccccgtCGGGCGGGCGTGTCGTCCTTC<br>D R P R R A G V S S F |
| | NheI | TGGCAGTGGCTGGGGATGGGCAGTGCcctgcgG<br>W Q W L GM C SAL R |
| | XhoI | TACGCCTTCCAACACCAGCGGTACTGGgtcgag<br>Y A F Q H Q R Y W V B |
| rapamycin AT12 (malonyl) | AvrII | GGCCGAgcgcgcCGGGCAGGCGTGTCGTCCTTC<br>G R A R R A G V S S F |
| | NheI | TCGCAGCGTGCTGGCATGGGTGAGGAactggcC<br>SQ RAG MG EEL A |
| | XhoI | TACGCCTTCCAGCACCAGCGCTACTGGctcgag<br>Y A F Q H Q R Y W L H |
| DEBS AT1 (methyl-malonyl) | AvrII | GCGCGAccgcgcCGGGCGGGGGTCTCGTCGTTC<br>A R P R R A C V S S F |
| | NheI | TGGCAGTGGGCGGGCATGGCCGTCGActgctC<br>W Q WAG MA V DL L |
| | XhoI | TACCCGTTCCAGCGCGAGCGCGTCTGGctcgaa<br>Y P F Q R E R V W L E |
| DEBS AT2 (methyl-malonyl) | AvrII | GACGGGgtgcgcCGGGCAGGTGTGTCGGCGTTC<br>D G V R R A G V S A F |
| | NheI | GCCCAGTGGGAAGGCATGGCGCGGGAgttgttG<br>A Q WE G MAR EL L |
| | XhoI | TATCCTTTCCAGGGCAAGCGGTTCTGGctgctg<br>P″ F″ Q″ G″ K″ R″ F″ W″ L″ L |

The sequences shown below provide the location of the KS/AT boundaries chosen in the FK-520 module 8 coding sequences. Regions where AvrII and NheI sites were engineered are indicated by lower case and underlining (SEQ ID NOS:64–65).

```
CCGGCGCCGTCGAACTGCTGACGTCGGCCCGGCCGTGGCCCGAGACCGAC
 A  G  A  V  E  L  L  T  S  A  R  P  W  P  E  T  D

CGGccacggCGTGCCGCCGTCTCCTCGTTCGGGGTGAGCGGCACCAACGC
 R  P  R  R  A  A  V  S  S  F  G  V  S  G  T  N  A CCACGTCATCCTGGAGGCCGGACCGGTAACGGAGACGCCCGCGGCATCGC
  H  V  I  L  E  A  G  P  V  T  E  T  P  A  A  S CTTCCGGTGACCTTCCCCTGCTGGTGTCGGCACGCTCACCGGAAGCGCTC
 P  S  G  D  L  P  L  L  V  S  A  R  S  R  E  A  L GACGAGCAGATCCGCCGACTGCGCGCCTACCTGGACACCACCCCGGACGT
  D  E  Q  I  R  R  L  R  A  Y  L  D  T  T  P  D  V CGACCGGGTGGCCGTGGCACAGACGCTGGCCCGGCGCACACACTTCGCCC
  D  R  V  A  V  A  Q  T  L  A  R  R  T  H  F  A ACCGCGCCGTGCTGCTCGGTGACACCGTCATCACCACACCCCCCGCGGAC
 H  R  A  V  L  L  G  D  T  V  I  T  T  P  P  A  D
```

-continued
```
CGGCCCGACGAACTCGTCTTCGTCTACTCCGGCCAGGGCACCCAGCATCC
 R   P   D   E   L   V   F   V   Y   S   G   Q   G   T   Q   H   P CGCGATGGGCGAGCAgctcgCCGCCGCCCATCCCGTGTTCGCCGACGCCT
 A   M   G   E   Q   L   A   A   A   H   P   V   F   A   D   A

GGCATGAAGCGCTCCGCCGCCTTGAACCCC
 W   H   E   A   L   R   R   L   D   N
```

The sequences shown below provide the location of the AT/DH boundary chosen in the FK-520 module 8 coding sequences. The region where an XhoI site was engineered is indicated by lower case and underlining (SEQ ID NOS:66–67).

```
TCCTCGGGGCTGGGTCACGGCACGACGCGGATGTGCCCGCGTACGCGTTC
 I   L   G   A   G   S   R   H   D   A   D   V   P   A   Y   A   F

CAACGGCGGCACTACTGGatCGagTCGGCACGCCCGGCCGCATCCGACGC
 Q   R   R   H   Y   W   I   E   S   A   R   P   A   A   S   D   A

GGGCCACCCCGTGCTGGGCT
 G   H   P   V   L   G
```

The sequences shown below provide the location of the KS/AT boundaries chosen in the FK-506 module 8 coding sequences. Regions where AvrII and NheI sites were engineered are indicated by lower case and underlining (SEQ ID NOS:68–69).

```
TCGGCCAGGCCGTGGCCGCGGACCGGCCGTccgcgcCGTGCGGCGGTCTC
 S   A   R   P   W   P   R   T   G   R   P   R   R   A   A   V   S GTCGTTCGGGGTGAGCGGCACCAACGCCCACATCATCCTGGAGGCCGGAC
 S   F   C   V   S   G   T   N   A   H   I   I   L   E   A   G CCGACCAGGAGGAGCCGTCGGCAGAACCGGCCGGTGACCTCCCGCTGCTC
 P   D   Q   E   E   P   S   A   E   P   A   G   D   L   P   L   L GTGTCGGCACGGTCCCCGGAGGCACTGGACGAGCAGATCGGGCGCCTGCG
 V   S   A   R   S   P   E   A   L   D   E   Q   I   G   R   L   R CGACTATCTCGACGCCGCCCCCGGCGTGGACCTGGCGGCCGTGGCGCGGA
 D   Y   L   D   A   A   P   G   V   D   L   A   A   V   A   R CACTGGCCACGCGTACGCACTTCTCCCACCGCGCCGTACTGCTCGGTGAC
 T   L   A   T   R   T   H   F   S   H   R   A   V   L   L   G   D ACCGTCATCACCGCTCCCCCCGTGGPJCAGCCGGGCGAGCTCGTCTTCGT
 T   V   I   T   A   P   P   V   E   Q   P   G   E   L   V   F   V CTACTCGGGACAGGGCACCCAGCATCCCGCGATGGGTGAGCGgctcgcCG
 Y   S   G   Q   G   T   Q   H   P   A   M   G   E   R   L   A CAGCCTTCCCCGTGTTCGCCGACCCGGACGTACCCGCCTACGCCTTCCAG
 A   A   F   P   V   F   A   D   P   D   V   P   A   Y   A   F   Q

CGGCGGCCCTACTGGATCGAGTCCGCGCCG
 R   R   P   Y   W   I   E   S   A   P
```

The sequences shown below provide the location of the AT/DH boundary chosen in the FK-506 module 8 coding sequences. The region where an XhoI site was engineered is indicated by lower case and underlining (SEQ ID NOS:70–71).

```
GACCCGGACGTACCCGCCTACGCCTTCCAGCGGCGGCCCTACTGGatcga
 D   P   D   V   P   A   Y   A   F   Q   R   R   P   Y   W   T   E gTCCGCGCCG
 S   A   P
```

Example 4

Replacement of Methoxyl with Hydrogen or Methyl at C-15 of FK-506 and FK-520

The methods and reagents of the present invention also provide novel FK-506 and FK-520 derivatives in which the methoxy group at C-15 is replaced by a hydrogen or methyl. These derivatives are produced in recombinant host cells of the invention that express recombinant PKS enzymes the produce the derivatives. These recombinant PKS enzymes are prepared in accordance with the methodology of Examples 1 and 2, with the exception that AT domain of module 7, instead of module 8, is replaced. Moreover, the present invention provides recombinant PKS enzymes in which the AT domains of both modules 7 and 8 have been changed. The table below summarizes the various compounds provided by the present invention.

| Compound | C-13 | C-15 | Derivative Provided |
|---|---|---|---|
| FK-506 | hydrogen | hydrogen | 13,15-didesmethoxy-FK-506 |
| FK-506 | hydrogen | methoxy | 13-desmethoxy-FK-506 |
| FK-506 | hydrogen | methyl | 13,15-didesmethoxy-15-methyl-FK-506 |
| FK-506 | methoxy | hydrogen | 15-desmethoxy-FK-506 |
| FK-506 | methoxy | methoxy | Original Compound--FK-506 |
| FK-506 | methoxy | methyl | 15-desmethoxy-15-methyl-FK-506 |
| FK-506 | methyl | hydrogen | 13,15-didesmethoxy-13-methyl-FK-506 |
| FK-506 | methyl | methoxy | 13-desmethoxy-13-methyl-FK-506 |
| FK-506 | methyl | methyl | 13,15-didesmethoxy-13,15-dimethyl-FK-506 |
| FK-520 | hydrogen | hydrogen | 13,15-didesmethoxy FK-520 |
| FK-520 | hydrogen | methoxy | 13-desmethoxy FK-520 |
| FK-520 | hydrogen | methyl | 13,15-didesmethoxy-15-methyl-FK-520 |
| FK-520 | methoxy | hydrogen | 15-desmethoxy-FK-520 |
| FK-520 | methoxy | methoxy | Original Compound--FK-520 |
| FK-520 | methoxy | methyl | 15-desmethoxy-15-methyl-FK-520 |
| FK-520 | methyl | hydrogen | 13,15-didesmethoxy-13-methyl-FK-520 |
| FK-520 | methyl | methoxy | 13-desmethoxy-13-methyl-FK-520 |
| FK-520 | methyl | methyl | 13,15-didesmethoxy-13,15-dimethyl-FK-520 |

Example 5

Replacement of Methoxyl with Ethyl at C-13 and/or C-15 of FK-506 and FK-520

The present invention also provides novel FK-506 and FK-520 derivative compounds in which the methoxy groups at either or both the C-13 and C-15 positions are instead ethyl groups. These compounds are produced by novel PKS enzymes of the invention in which the AT domains of modules 8 and/or 7 are converted to ethylmalonyl specific AT domains by modification of the PKS gene that encodes the module. Ethylmalonyl specific AT domain coding sequences can be obtained from, for example, the FK-520 PKS genes, the niddamycin PKS genes, and the tylosin PKS genes. The novel PKS genes of the invention include not only those in which either or both of the AT domains of modules 7 and 8 have been converted to ethylmalonyl specific AT domains but also those in which one of the modules is converted to an ethylmalonyl specific AT domain and the other is converted to a malonyl specific or a methylmalonyl specific AT domain.

Example 6

Neurotrophic Compounds

The compounds described in Examples 1–4, inclusive have immunosuppressant activity and can be employed as immunosuppressants in a manner and in formulations similar to those employed for FK-506. The compounds of the invention are generally effective for the prevention of organ rejection in patients receiving organ transplants and in particular can be used for immunosuppression following orthotopic liver transplantation. These compounds also have pharmacokinetic properties and metabolism that are more advantageous for certain applications relative to those of FK-506 or FK-520. These compounds are also neurotrophic; however, for use as neurotrophins, it is desirable to modify the compounds to diminish or abolish their immunosuppressant activity. This can be readily accomplished by hydroxylating the compounds at the C-18 position using established chemical methodology or novel FK-520 PKS genes provided by the present invention.

Thus, in one aspect, the present invention provides a method for stimulating nerve growth that comprises administering a therapeutically effective dose of 18-hydroxy-FK-520. In another embodiment, the compound administered is a C-18,20-dihydroxy-FK-520 derivative. In another embodiment, the compound administered is a C-13-desmethoxy and/or C-15-desmethoxy 18-hydroxy-FK-520 derivative. In another embodiment, the compound administered is a C-13-desmethoxy and/or C-15-desmethoxy 18,20-dihydroxy-FK-520 derivative. In other embodiments, the compounds are the corresponding analogs of FK-506. The 18-hydroxy compounds of the invention can be prepared chemically, as described in U.S. Pat. No. 5,189,042, incorporated herein by reference, or by fermentation of a recombinant host cell provided by the present invention that expresses a recombinant PKS in which the module 5 DH domain has been deleted or rendered non-functional.

The chemical methodology is as follows. A compound of the invention (~200 mg) is dissolved in 3 mL of dry methylene chloride and added to 45 µL of 2,6-lutidine, and the mixture stirred at room temperature. After 10 minutes, tert-butyldimethylsilyl trifluoromethanesulfonate (64 µL) is added by syringe. After 15 minutes, the reaction mixture is diluted with ethyl acetate, washed with saturated bicarbonate, washed with brine, and the organic phase dried over magnesium sulfate. Removal of solvent in vacuo and flash chromatography on silica gel (ethyl acetate:hexane (1:2) plus 1% methanol) gives the protected compound, which is dissolved in 95% ethanol (2.2 mL) and to which is added 53 µL of pyridine, followed by selenium dioxide (58 mg). The flask is fitted with a water condenser and heated to 70° C. on a mantle. After 20 hours, the mixture is cooled to room temperature, filtered through diatomaceous earth, and the filtrate poured into a saturated sodium bicarbonate solution. This is extracted with ethyl acetate, and the organic phase is washed with brine and dried over magnesium sulfate. The solution is concentrated and purified by flash chromatography on silica gel (ethyl acetate:hexane (1:2) plus 1% methanol) to give the protected 18-hydroxy compound. This compound is dissolved in acetonitrile and treated with aqueous HF to remove the protecting groups. After dilution with ethyl acetate, the mixture is washed with saturated bicarbonate and brine, dried over magnesium sulfate, filtered, and evaporated to yield the 18-hydroxy compound. Thus, the present invention provides the C-18-hydroxyl derivatives of the compounds described in Examples 1–4.

Those of skill in the art will recognize that other suitable chemical procedures can be used to prepare the novel 18-hydroxy compounds of the invention. See, e.g., Kawai et al., January 1993, Structure-activity profiles of macrolactam immunosuppressant FK-506 analogues, *FEBS Letters* 316 (2): 107–113, incorporated herein by reference These methods can be used to prepare both the C18-[S]-OH and C18-[R]-OH enantiomers, with the R enantiomer showing a somewhat lower $IC_{50}$, which may be preferred in some applications. See Kawai et al., supra. Another preferred protocol is described in Umbreit and Sharpless, 1977, JACS 99(16): 1526–28, although it may be preferable to use 30 equivalents each of $SeO_2$ and t-BuOOH rather than the 0.02 and 3–4 equivalents, respectively, described in that reference.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A polyketide having the structure

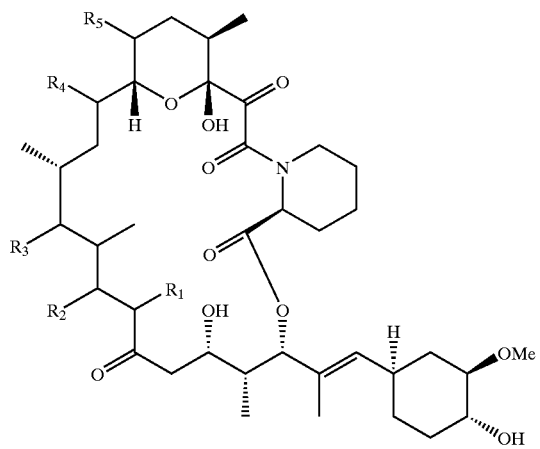

wherein, $R_1$ is hydrogen, methyl, ethyl, or allyl; $R_2$ is hydrogen or hydroxyl, provided that when $R_2$ is hydrogen, there is a double bond between C-20 and C-19; $R_3$ is hydrogen or hydroxyl; $R_4$ is methoxyl, hydrogen, methyl, or ethyl; and $R_5$ is hydrogen.

2. The polyketide of claim 1 that is 13-desmethoxy-FK-506.

3. The polyketide of claim 1 that is 13-desmethoxy-18-hydroxy-FK-520.

4. The polyketide of claim 1, wherein $R_1$ is allyl.

5. The polyketide of claim 1, wherein $R_1$ is ethyl.

6. The polyketide of claim 1, wherein $R_2$ is hydrogen.

7. The polyketide of claim 1, wherein $R_3$ is hydrogen.

8. The polyketide of claim 1, wherein each of $R_2$ and $R_3$ is hydrogen.

9. The polyketide of claim 1, wherein $R_4$ is methoxyl.

10. A polyketide having the structure

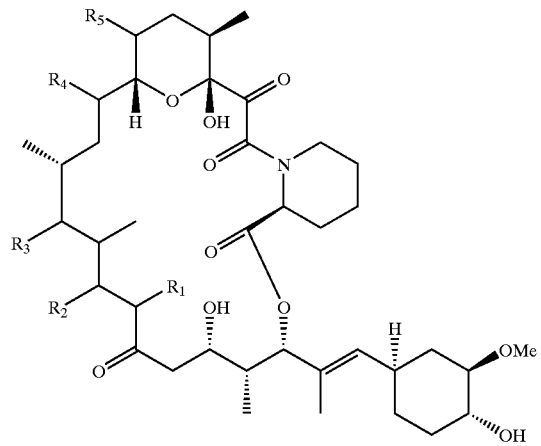

wherein, $R_1$ is ethyl or allyl; each of $R_2$ and $R_3$ is hydrogen and there is a double bond between C-20 and C-19; $R_4$ is methoxyl; and $R_5$ is hydrogen, wherein said polyketide is 13-desmethoxy-FK-506 or 13-desmethoxy-18-hydroxy-FK-520.

* * * * *